(12) United States Patent
Hanna et al.

(10) Patent No.: US 11,959,097 B2
(45) Date of Patent: Apr. 16, 2024

(54) METHODS OF GENERATING A SYNTHETIC EMBRYO

(71) Applicant: Yeda Research and Development Co. Ltd., Rehovot (IL)

(72) Inventors: Yaqub Hanna, Tel Aviv-Jaffa (IL); Sergey Viukov, Rehovot (IL); Emilie Wildschutz, Rehovot (IL); Noa Novershtern, Rehovot (IL); Carine Joubran, Rehovot (IL); Segev Naveh Tassa, Rehovot (IL); Alejandro Castrejon Aguilera, Rehovot (IL); Bernardo Oldak, Rehovot (IL); Shadi Tarazi, Rehovot (IL); Francesco Roncato, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 18/226,877

(22) Filed: Jul. 27, 2023

(65) Prior Publication Data
US 2024/0010973 A1    Jan. 11, 2024

Related U.S. Application Data

(63) Continuation of application No. PCT/IL2023/050235, filed on Mar. 6, 2023.

(60) Provisional application No. 63/390,695, filed on Jul. 20, 2022, provisional application No. 63/317,036, filed on Mar. 6, 2022.

(51) Int. Cl.
*C12N 5/073* (2010.01)

(52) U.S. Cl.
CPC ........ *C12N 5/0604* (2013.01); *C12N 2500/02* (2013.01); *C12N 2501/115* (2013.01); *C12N 2501/119* (2013.01); *C12N 2501/155* (2013.01); *C12N 2501/415* (2013.01); *C12N 2501/91* (2013.01); *C12N 2501/999* (2013.01); *C12N 2506/03* (2013.01)

(58) Field of Classification Search
CPC .............. C12N 5/0604; C12N 2500/02; C12N 2501/115; C12N 2501/119; C12N 2501/155; C12N 2501/415; C12N 2501/91; C12N 2501/999; C12N 2506/03
See application file for complete search history.

(56) References Cited

U.S. PATENT DOCUMENTS

2022/0308041 A1  9/2022  Zernicka-Goetz et al.
2023/0236171 A1  7/2023  Zernicka-Goetz et al.

FOREIGN PATENT DOCUMENTS

| CN | 109749987 | 5/2019 |
| WO | WO 2018/046929 | 3/2018 |
| WO | WO 2023/114754 | 6/2023 |
| WO | WO 2023/170682 | 9/2023 |

OTHER PUBLICATIONS

Amadei et al., (2021) Inducible stem-cell-derived embryos capture mouse morphogenetic events in vitro. 56(3) 336-382.e9 (Year: 2021).*
International Search Report and the Written Opinion dated Jun. 21, 2023 From the International Searching Authority Re. Application No. PCT/IL2023/050235 (17 Pages).
Invitation to Pay Additional Fees and Communication Relating to the Results of the Partial International Search dated May 15, 2023 From the International Searching Authority Re. Application No. PCT/IL2023/050235. (4 Pages).
Aguilera-Castrejon et al. "Ex Utero Mouse Embryogenesis From Pre-Gastrulation to Late Organogenesis", Nature, 593(7857): 119-124 & Methods , Published Online Mar. 17, 2021.
Amadei et al. "Embryo Model Completes Gastrulation to Neurulation and Organogenesis", Nature, 610(7930): 143-153, Published Online Aug. 25, 2022.
Amadei et al. "Inducible Stem-Cell-Derived Embryos Capture Mouse Morphogenetic Events In Vitro", Developmental Cell, 56(3): 366-382, Published Online Dec. 29, 2020.
Anderson et al. "Insulin Fine-Tunes Self-Renewal Pathways Governing Naive Pluripotency and Extra-Embryonic Endoderm", Nature Cell Biology, 19:1164-1177, Sep. 25, 2017. Abstract.
Bayerl et al. "Principles of Signaling Pathway Modulation for Enhancing Human Naive Pluripotency Induction", Cell Stem Cell, 28(9): 1549-1565, Published Online Apr. 28, 2021.
Choi et al. "Prolonged Mek1/2 Suppression Impairs the Developmental Potential of Embryonic Stem Cells", Nature, 548(7666): 219-223, Aug. 10, 2017.

(Continued)

*Primary Examiner* — Kara D Johnson

(57) ABSTRACT

Methods of generating a synthetic embryo are provided. Accordingly, there is provided a method of generating a synthetic embryo comprising inducing expression of a factor that induces differentiation to trophectoderm cells in a subpopulation of naïve pluripotent stem cells (PSCs) to obtain a trophectoderm primed cells; inducing expression of a factor that induces differentiation to extra embryonic primitive endodermal cells in a second subpopulation of naïve PSCs to obtain extra embryonic primitive endodermal primed cells; and mixing said trophectoderm primed cells and said extra embryonic primitive endodermal primed cells with naïve PSCs under conditions that allow formation of aggregated cells. Also provided are articles of manufactures, mixtures and aggregates of cells and methods of using same.

18 Claims, 113 Drawing Sheets
(97 of 113 Drawing Sheet(s) Filed in Color)
Specification includes a Sequence Listing.

(56) References Cited

OTHER PUBLICATIONS

Dupont et al. "Efficient Generation of ETX Embryoids That Recapitulate the Entire Window of Murine Egg Cylinder Developmen", Science Advances, 9(3): eadd2913-1-eadd2913-18, Jan. 18, 2023.
Gafni et al. "Derivation of Novel Human Ground State Naive Pluripotent Stem Cells", Nature, 504(7479): 282-286, Published Online Oct. 30, 2013.
Garcia "Embryo Manipulation Techniques in the Rabbit", New Insights Into Theriogenology, 1st Ed., Chap.7: 113-133, Nov. 5, 2018.
Geula et al. "M6 mRNA Methylation Facilitates Resolution of Naive Pluripotency Toward Differentiation", Science, 347(6225): 1002-1006, Published Online Jan. 1, 2015.
Harrison et al. "Assembly of Embryonic and Extraembryonic Stem Cells to Mimic Embryogenesis In Vitro", Science, 356(6334): eaal1810-1-eaal1810-12, Published Online Mar. 2, 2017.
Manor et al. "Establishing the Human Naive Pluripotent State", Current Opinion in Genetics & Development, 34: 35-45, Published Online Aug. 24, 2015.
Nichols et al. "Naive and Primed Pluripotent States", Cell Stem Cell, 4(6): 487-492, Jun. 5, 2009.
Oldak et al. "Recent Insights Into Mammalian Natural and Synthetic Ex Utero Embryogenesis", Current Opinion in Genetics & Development, 77: 101988-1-101988-7, Available Online Sep. 28, 2022.
Posfai et al. "Evaluating Totipotency Using Criteria of Increasing Stringency", Nature Cell Biology, 23(1): 49-60, Published Online Jan. 8, 2021.
Shakiba et al. "CD24 Tracks Divergent Pluripotent States in Mouse and Human Cells", Nature Communications, 6(1): 7329-1-7329-11, Jun. 16, 2015.
Sozen et al. "Self-Assembly of Embryonic and Two Extra-Embryonic Stem Cell Types Into Gastrulating Embryo-Like Structures", Nature Cell Biology, 20(8): 979-989, Published Online Jul. 23, 2018.
Tarazi et al. "Post-Gastrulation Synthetic Embryos Generated Ex Utero From Mouse Naive ESCs", Cell, 185(18): 3290-3306, Published Online Aug. 1, 2022.
Viukov et al. "Human Primed and Naïve PSCs Are Both Able to Differentiate Into Trophoblast Stem Cells", Stem Cell Reports, 17(11): 2484-2500, Published Online Oct. 20, 2022.
Weinberger et al. "Dynamic Stem Cell States: Naive to Primed Pluripotency in Rodents and Humans", Nature Reviews. Molecular Cell Biology, 17(3): 155-169, Published Online Feb. 10, 2016.
Zhang et al. "Generation of Artificial Gamete and Embryo From Stem Cells in Reproductive Medicine", Frontiers in Bioengineering and Biotechnology, 8(Art.781): 1-12, Jul. 22, 2020.
Zhang et al. "Implantation Initiation of Self-Assembled Embryo-Like Structures Generated Using Three Types of Mouse Blastocyst-Derived Stem Cells", Nature Communications, 10(1): 496-1-496-18, Jan. 30, 2019.
Amadei et al. "Stem Cell-Derived Mouse Embryos Develop Within An Extra-Embryonic Yolk Sac to Form Anterior Brain Regions and A Beating Heart", BioRxiv Preprint, 26 P., Posted Aug. 2, 2022.
Lau et al. "Mouse Embryo Model Derived Exclusively From Embryonic Stem Cells Undergo Neurulation and Heart Development", Cell Stem Cell, 29(10): 1445-1458, Published Online Sep. 8, 2022.

* cited by examiner

FIG. 3A ZHBTC4 Serum-LIF P3

FIG. 3B ZHBTC4 P3 + DOX in mTSC

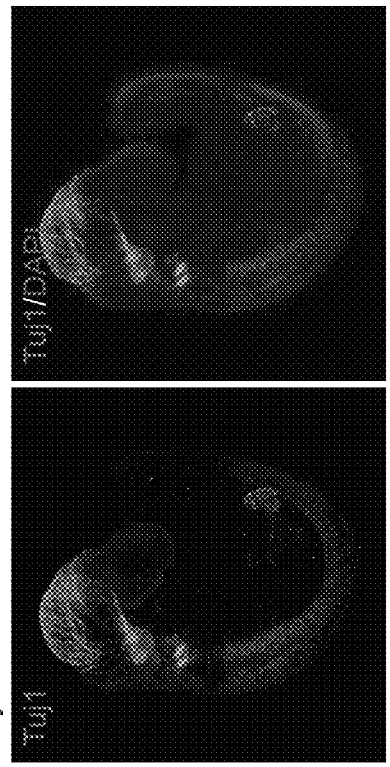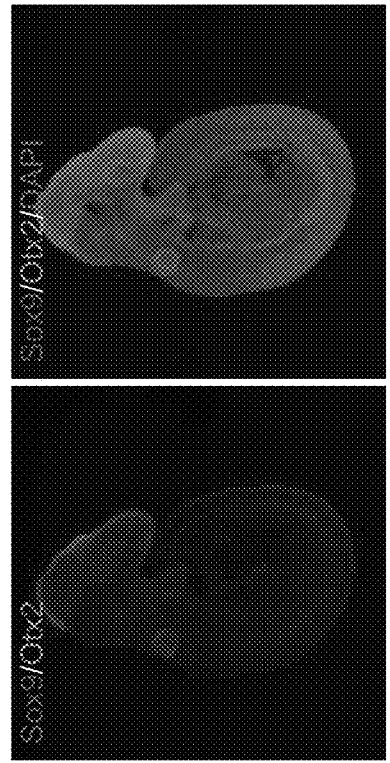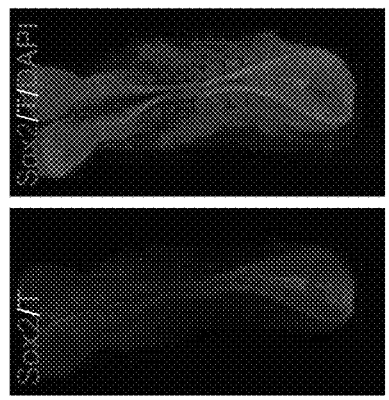
FIG. 15C Day 7 - ~E8.5
FIG. 15D Day 7 - ~E8.5
FIG. 15E Day 8 - ~E9.5
FIG. 15F Day 8 - ~E9.5

FIG. 18B
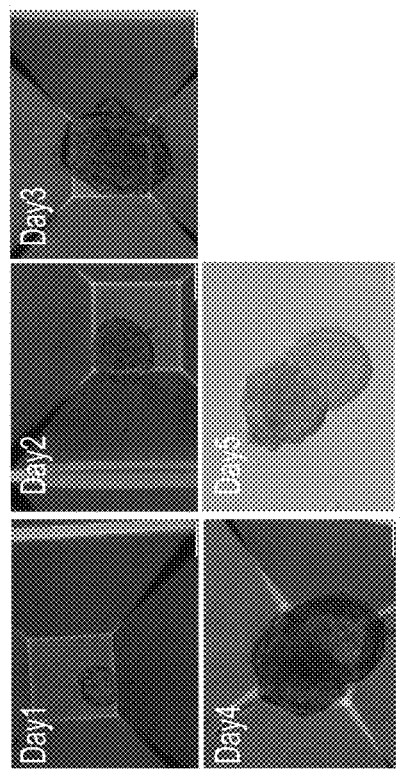
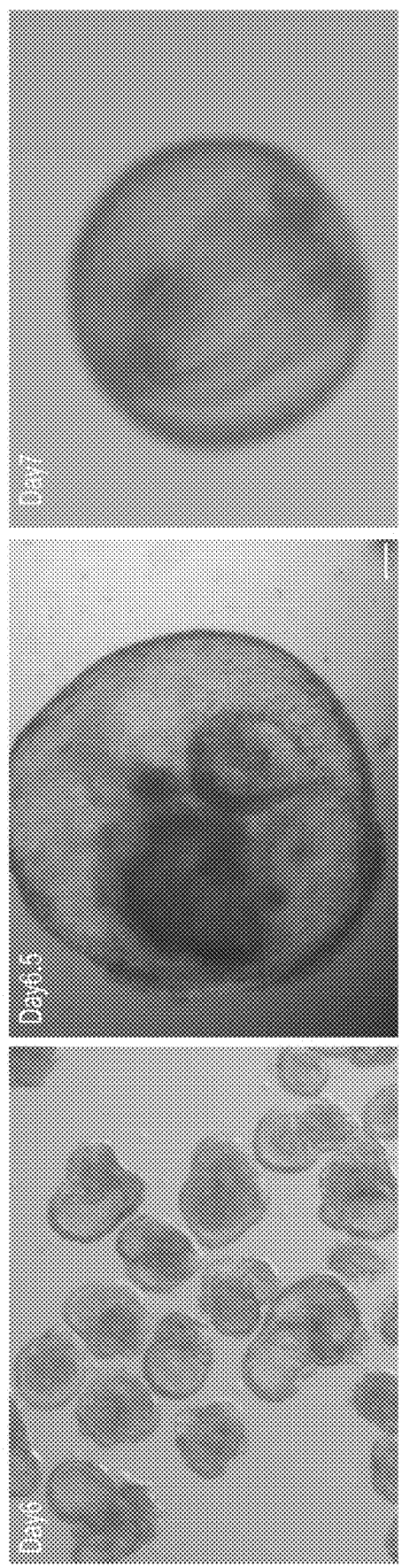

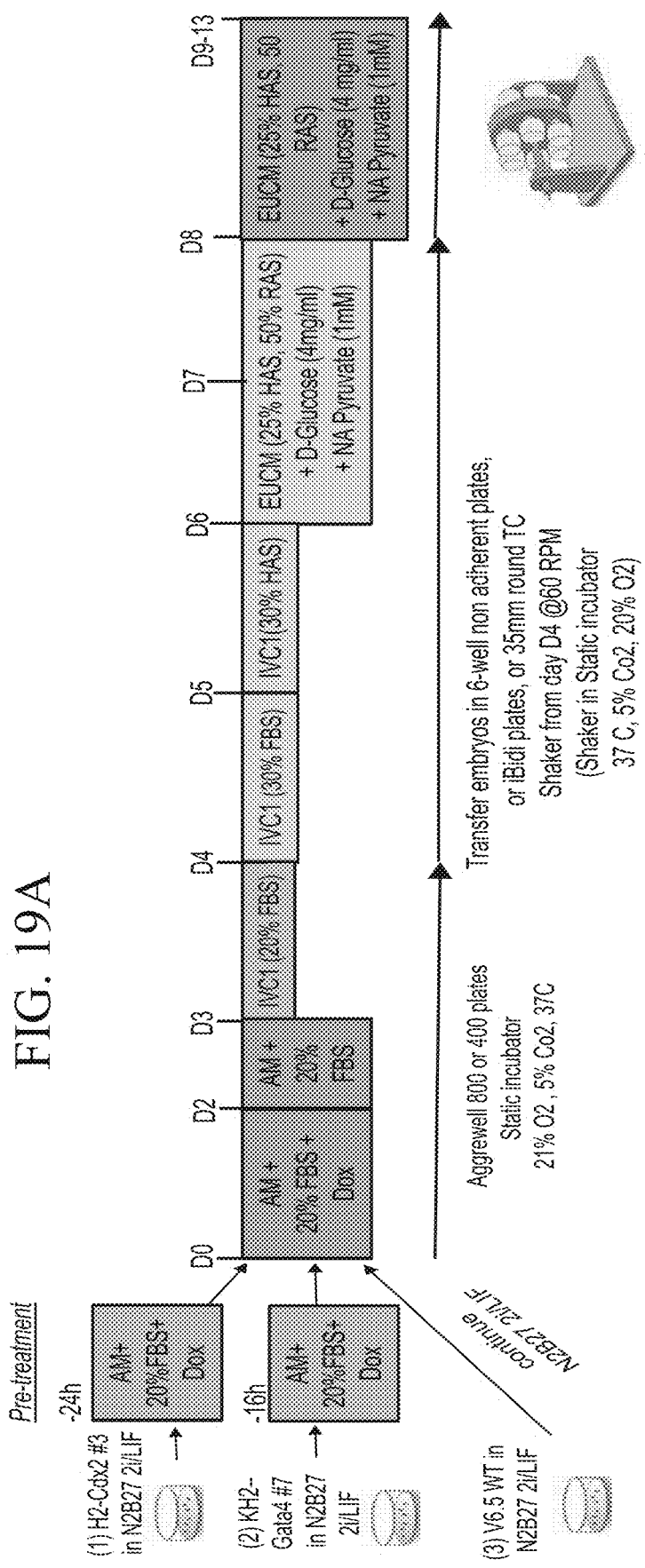
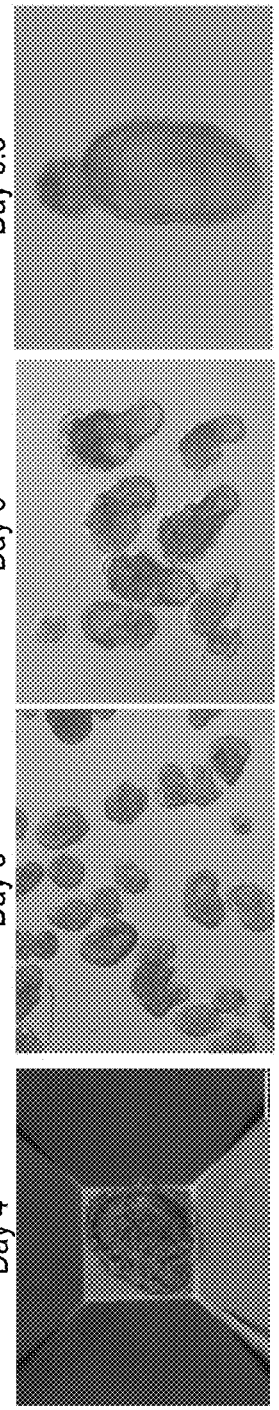
FIG. 19A
FIG. 19B

FIG. 41D
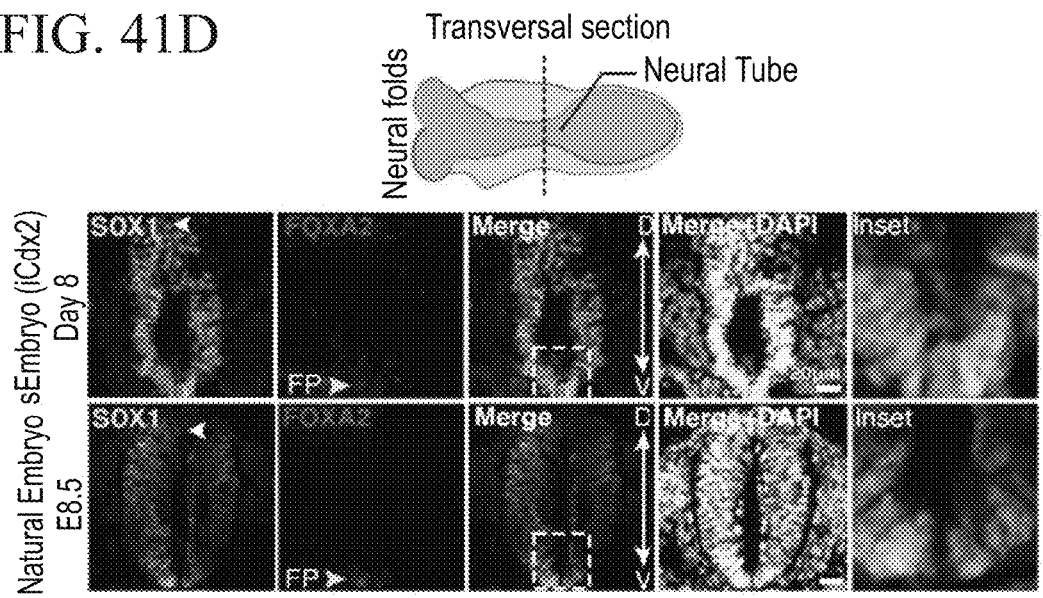
FIG. 41E
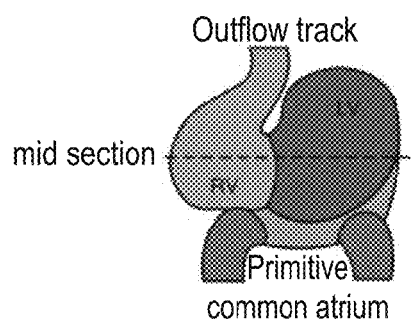
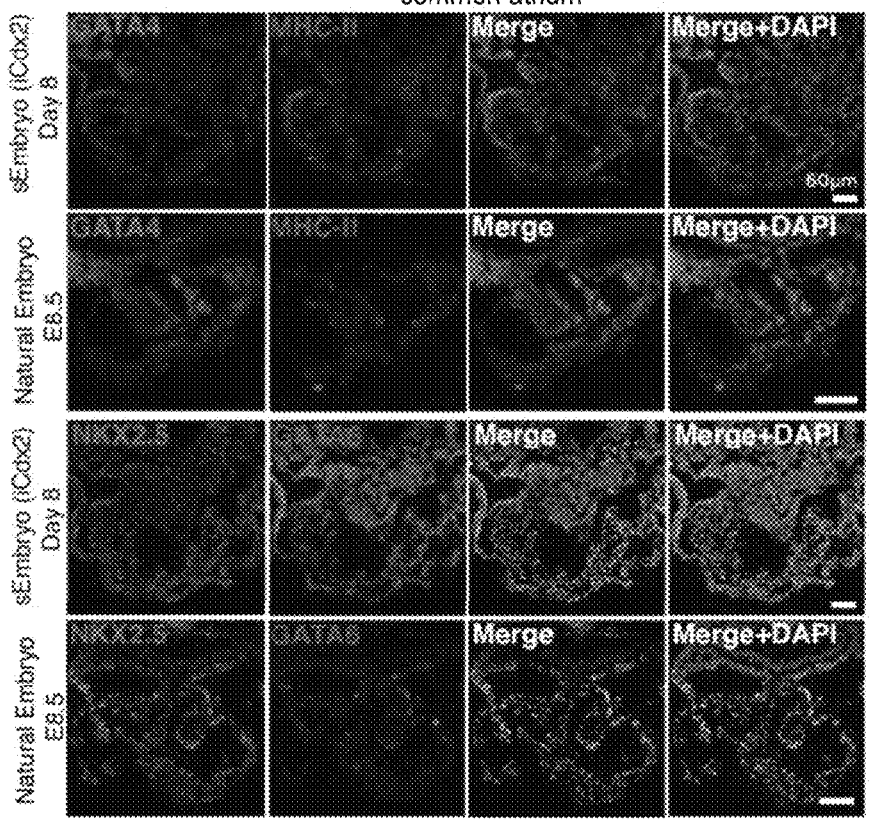

FIG. 42A
FIG. 42B
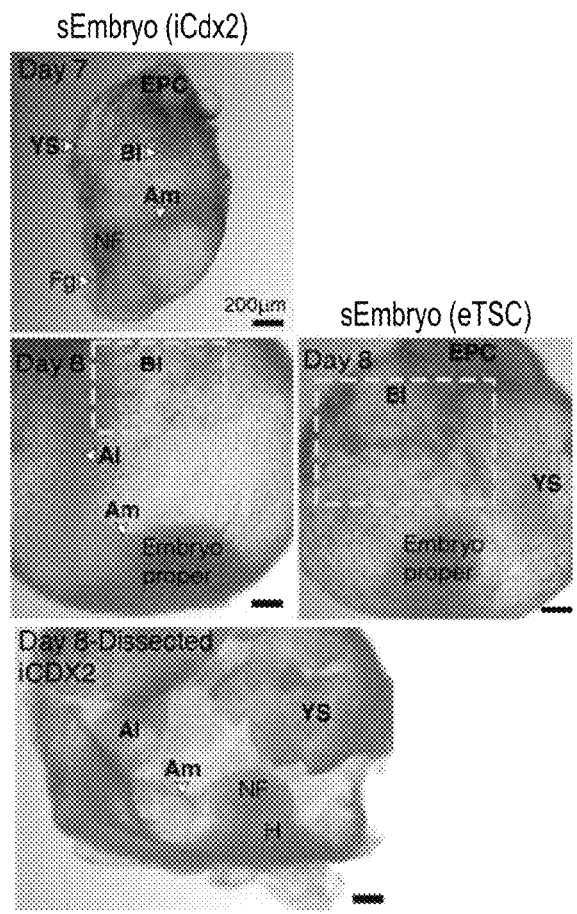
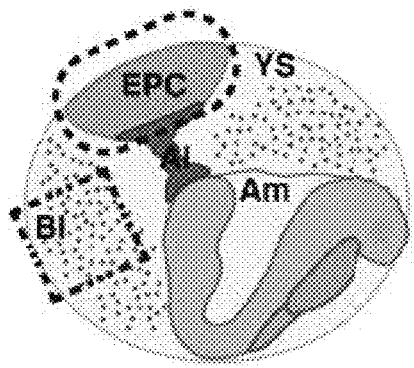
FIG. 42C
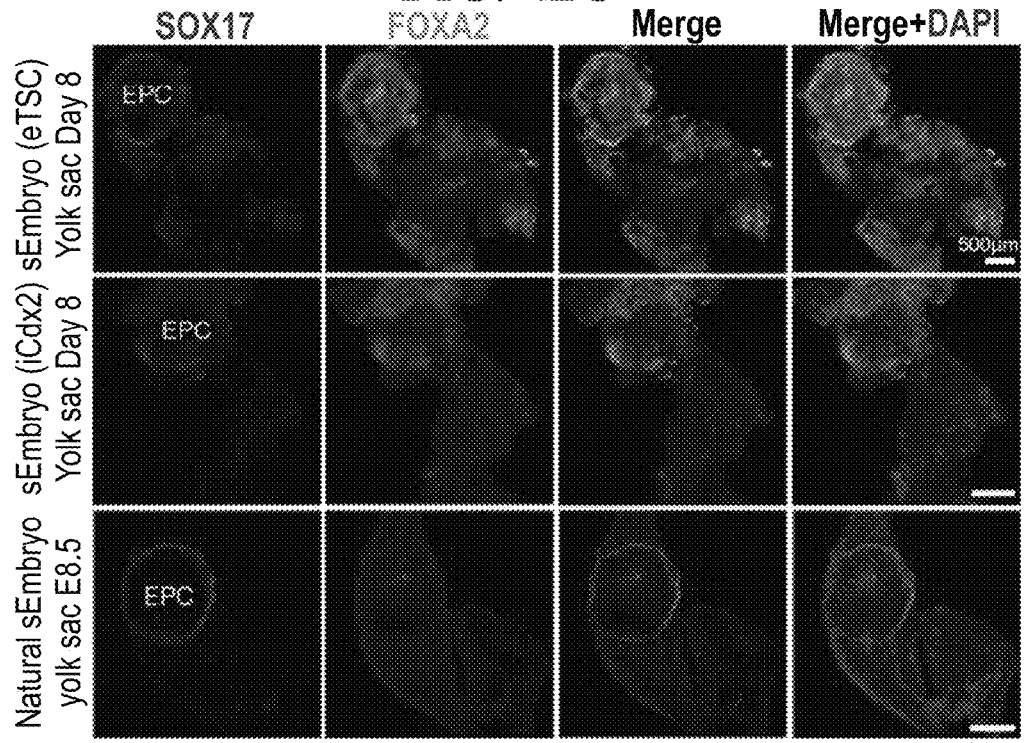

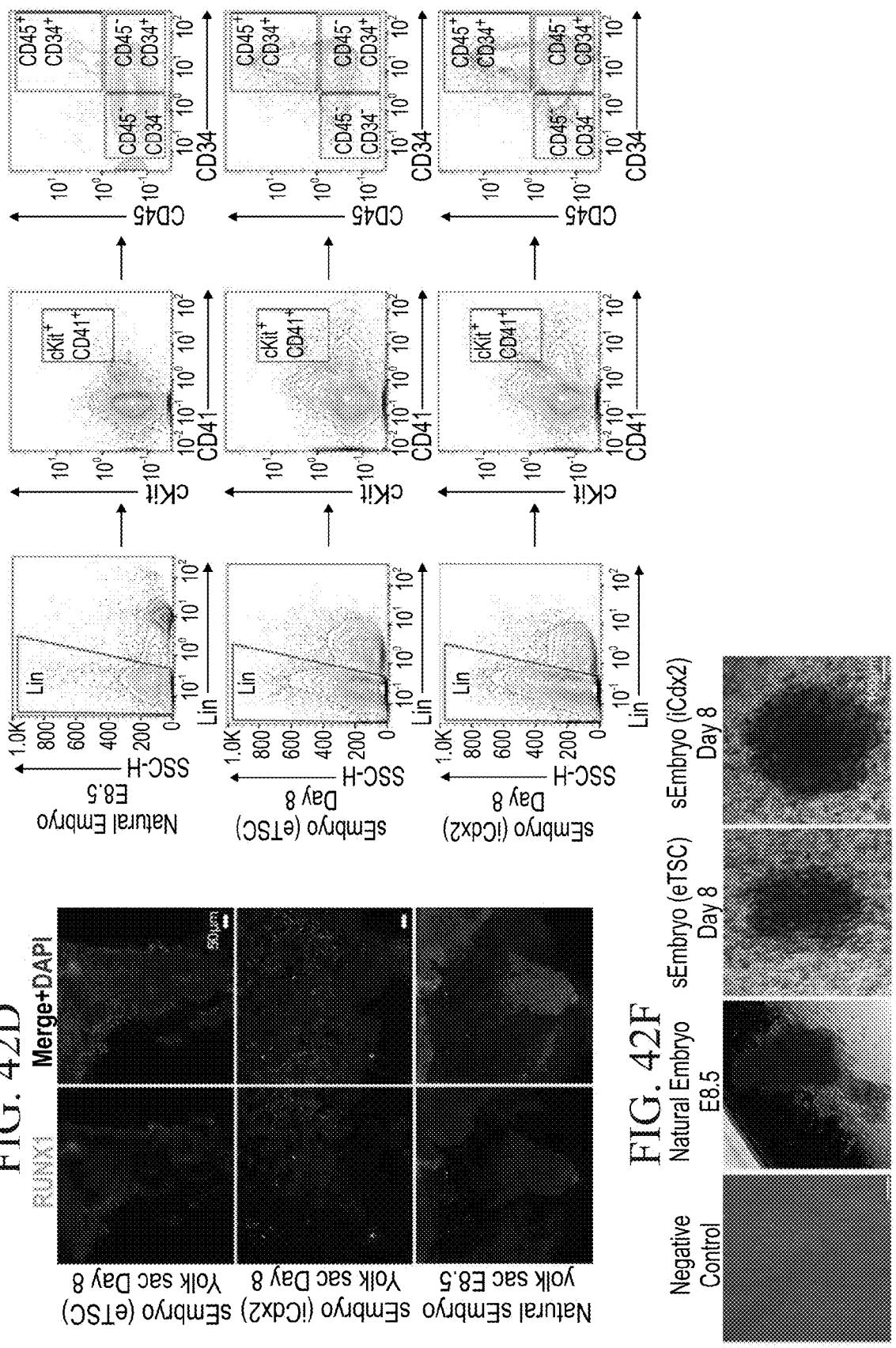

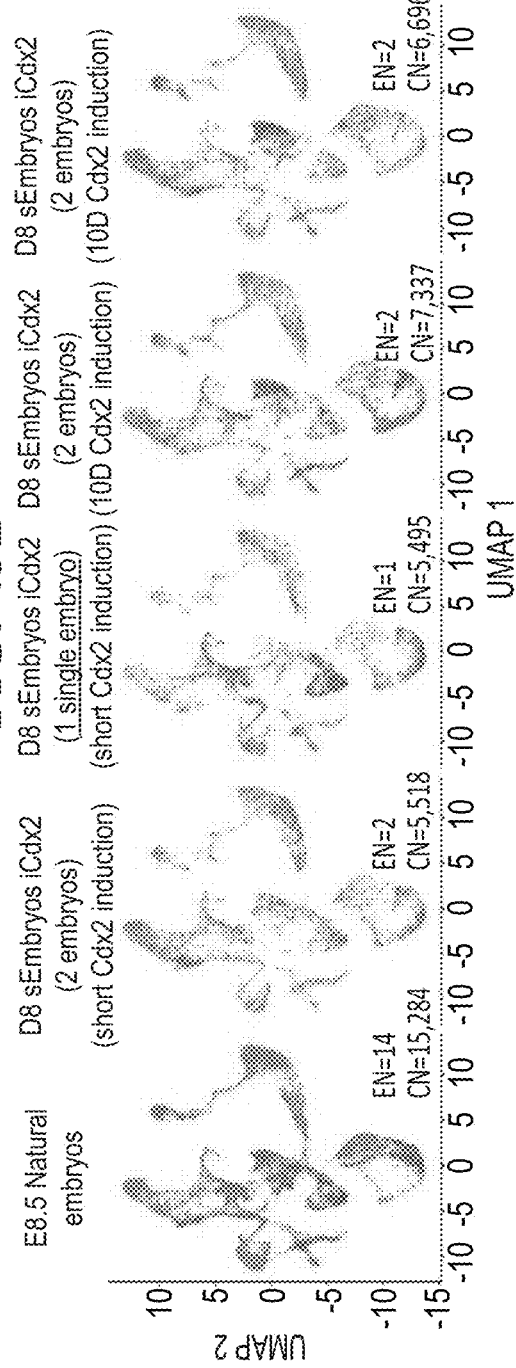
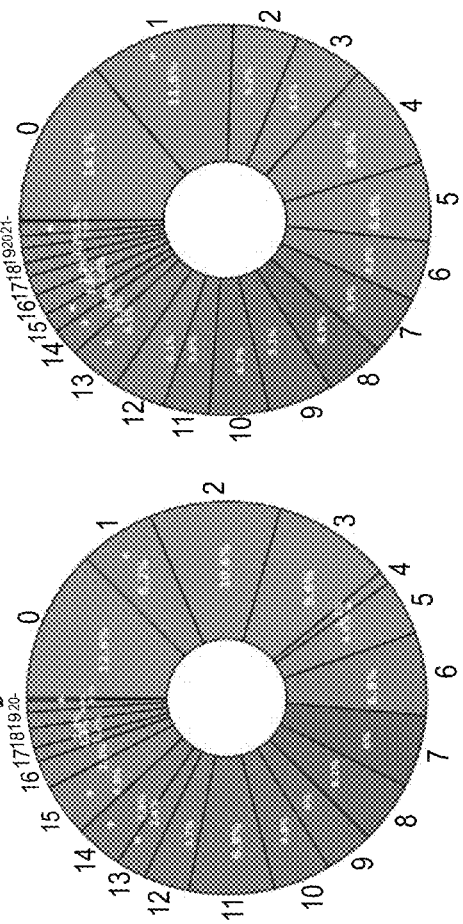
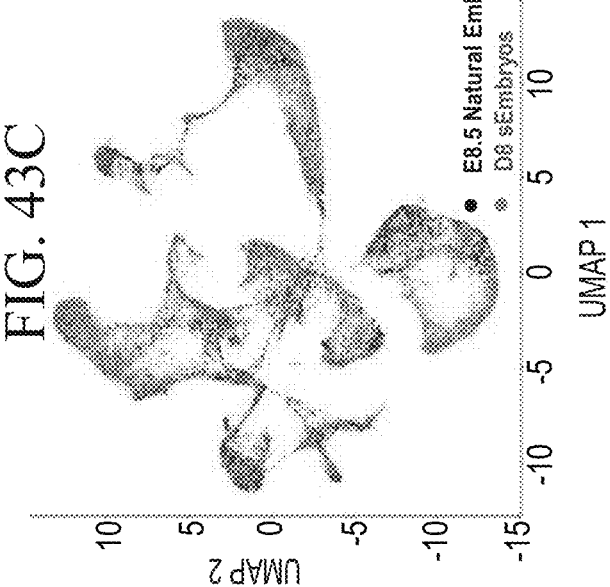
FIG. 43B
FIG. 43C
FIG. 43D

Different Naïve Culture Media For ESCs donor cells (i) N2B27 2i/LIF (ii) 2i/LIFAlternative 2i-LIF with CHIR & SRCi (iii) Extented potential media- LCDM (iv) DMEM 15% Serum-LIF (serum/Lif)

1500 cell/well BVSC ESC
1500 cell/well iGATA4 KH2-ESC
4800 cell/well iCdx2 KH2-ESC

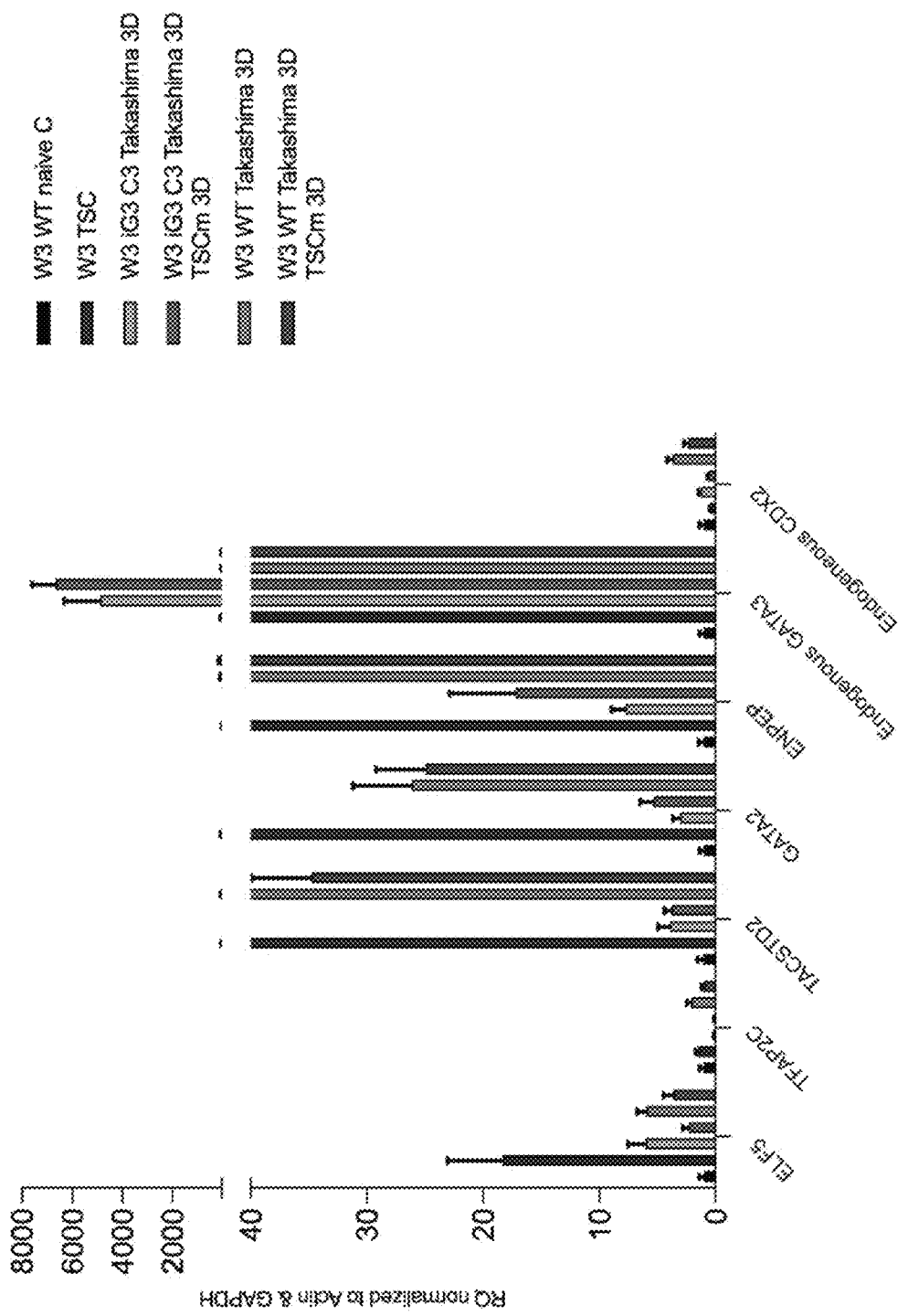

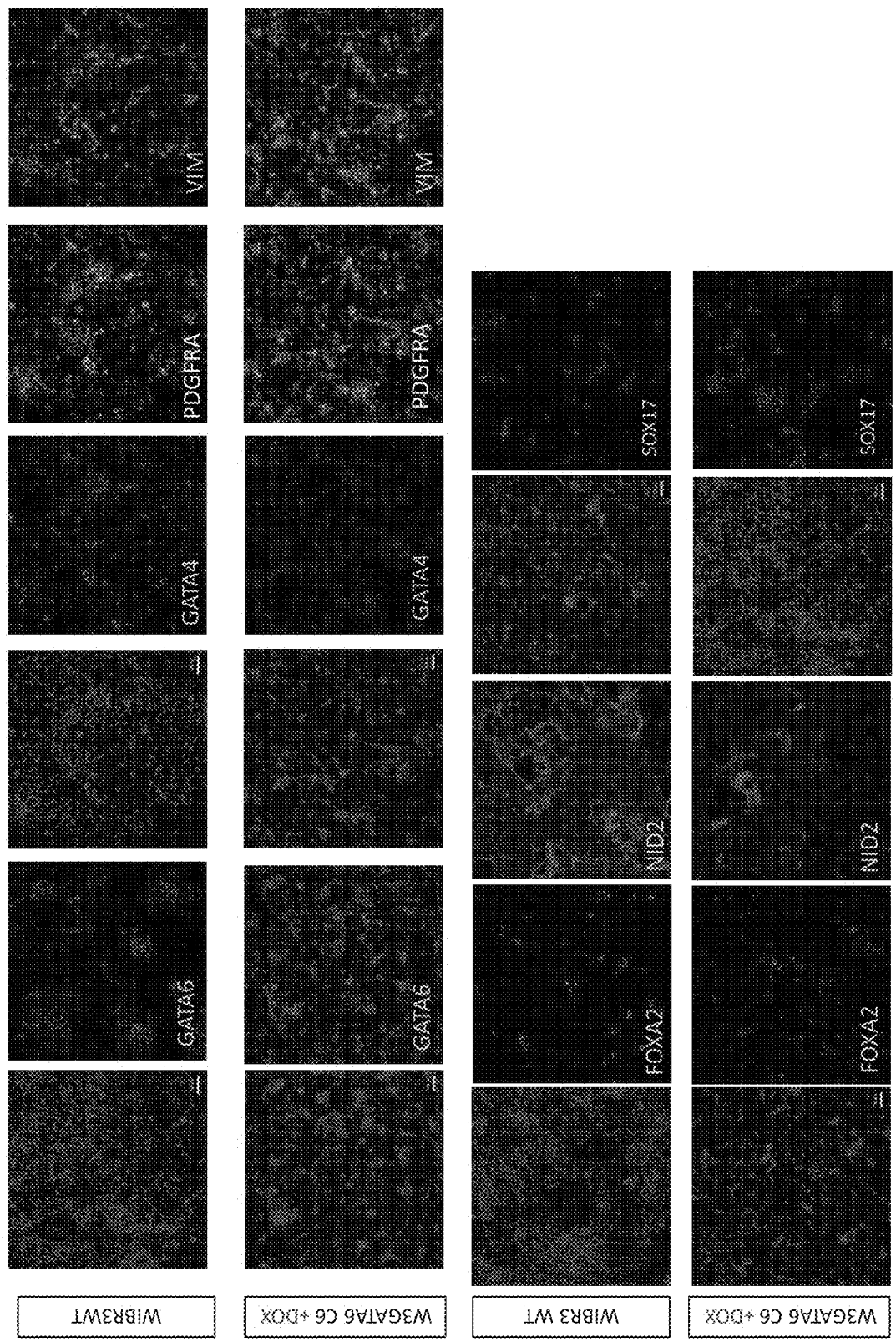

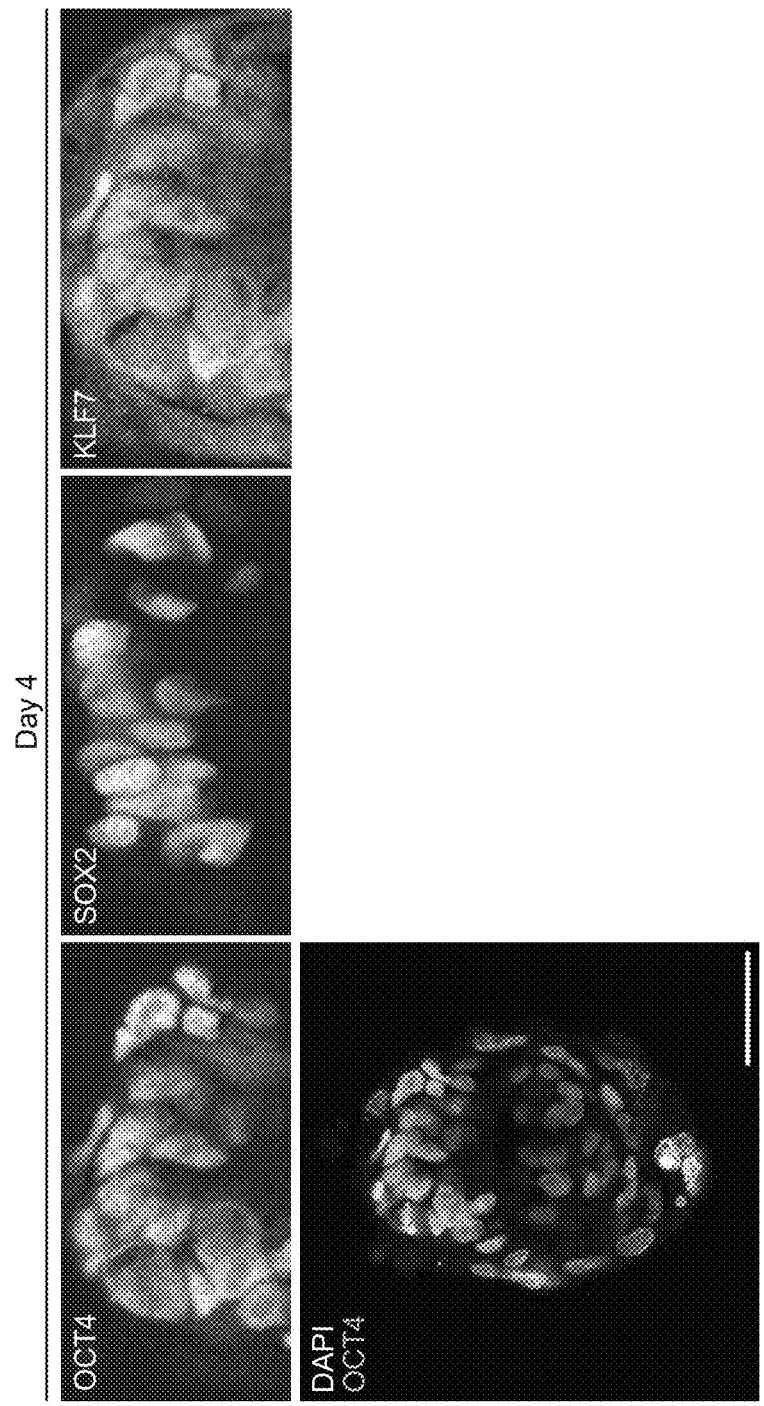

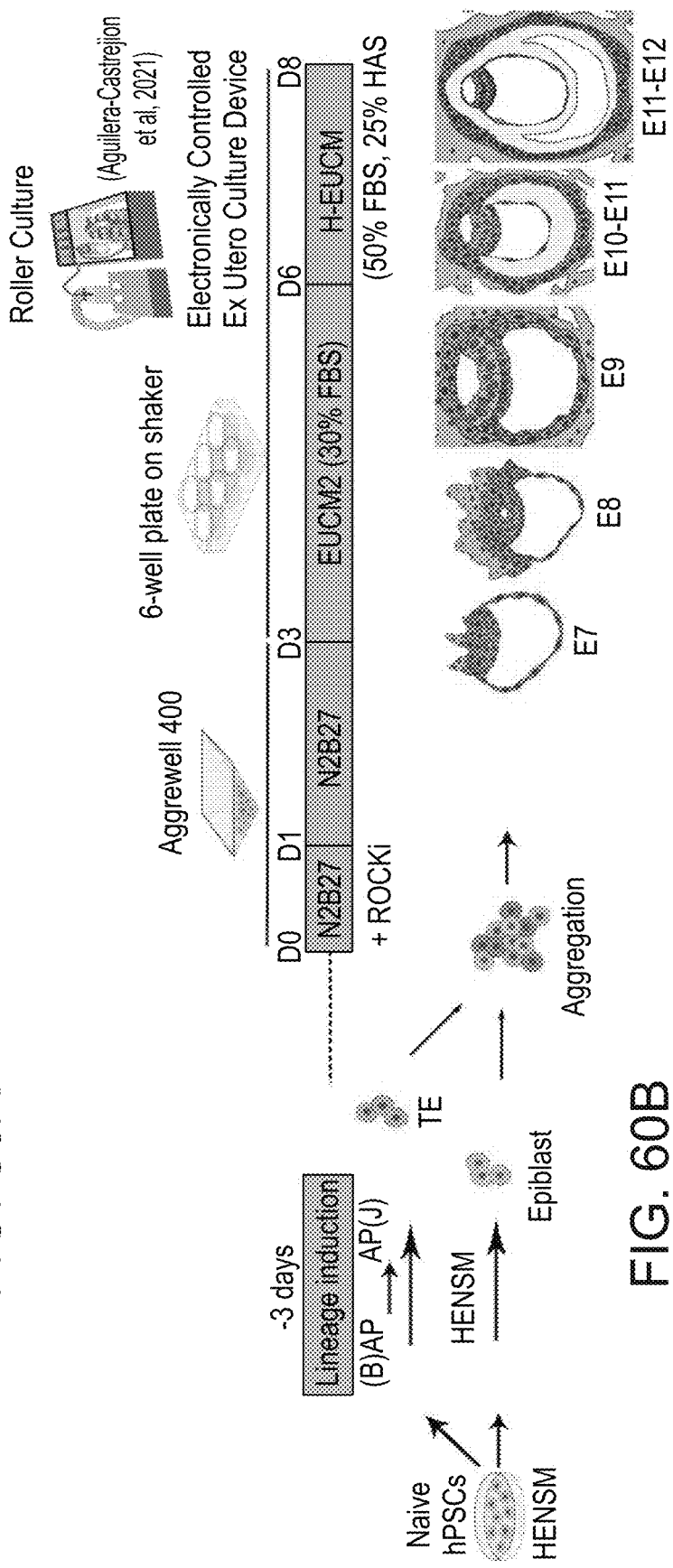
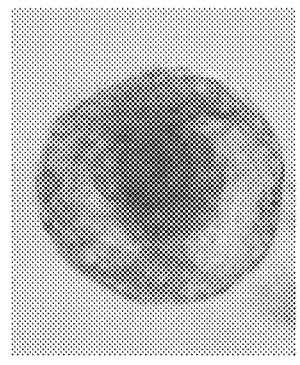
FIG. 60A
FIG. 60B
Day 8 hSEM

METHODS OF GENERATING A SYNTHETIC EMBRYO

RELATED APPLICATIONS

This application is a Continuation of PCT Patent Application No. PCT/IL2023/050235 having International filing date of Mar. 6, 2023, which claims the benefit of priority under 35 USC § 119(e) of U.S. Provisional Patent Application No. 63/317,036 filed on Mar. 6, 2022 and 63/390,695 filed on Jul. 20, 2022. The contents of the above applications are all incorporated by reference as if fully set forth herein in their entirety.

SEQUENCE LISTING STATEMENT

The XML file, entitled 96226ReplacementSequenceListing.xml, created on Aug. 23, 2023, comprising 319,668 bytes, is incorporated herein by reference. The sequence listing submitted herewith is identical to the sequence listing forming part of the international application.

FIELD AND BACKGROUND OF THE INVENTION

The present invention, in some embodiments thereof, relates to methods of generating a synthetic embryo.

Advanced artificial embryogenesis utilizing in vitro established embryonic stem cell lines and induced pluripotent stem cell lines (iPSCs) while bypassing the use of oocytes and zygotes or blastocysts has been a desired goal in the fields of developmental biology and reproductive medicine. The establishment of methods and systems for producing such synthetic embryos (abbreviated as sEmbryo or sEmbryoids; also could be referred to as Stem Cell-Derived Embryo or Embryoid Model (SEMs) or Stem Cell-Derived Whole Embryoid Model (SWEM)) ex utero may constitute a powerful tool in basic research e.g. as a framework to investigate the emergence of cellular diversity, cell fate decisions and how tissues and organs emerge from a single pluripotent cell; as well as a source of cells, tissue, embryos and organs for transplantation, testing the effect of drugs on embryonic development and possibly the bioengineering of embryos.

The blastocyst (the early mammalian embryo) forms all embryonic and extraembryonic tissues, including the placenta. This structure occurs at the 64-cell stage, which is shortly after the embryo loses its "ball of cells" shape and forms a cavity. In this structure, the inner cell mass (ICM) will develop into the embryo proper, and is placed above the blastocoel cavity which is the hallmark of the blastocyst stage. Cells enveloped around the ICM are trophectoderm (TE) cells, which will later contribute to trophoblast extraembryonic placental tissue (fetal placenta). Part of the ICM further differentiates into the primitive endoderm (PRE) which gives rise later on to the extraembryonic yolk sac and membranes, while preparing for implantation [Zhang et al. (2020) Front. Bioeng. Biotechnol. 8:781].

Different pluripotent states of embryonic stem cell lines (ESCs) and iPSCs can be expanded in vitro and can contribute to embryonic and/or extraembryonic tissues when injected into host embryos. For example, upon microinjection into mouse blastocysts, mouse naïve ESCs or iPSCs (Bayerl et al. Cell Stem Cell (2021) 28(9): 1549-1565.e12; Weinberger et al. Nat Rev Mol Cell Biol (2016) 17(3): 155-69; Manor et al. Curr Opin Genet Dev (2015) 34: 35-45; Shakiba et al. Nat Commun (2015) 16 6:7329; Gafni et al. Nature (2013) 504(7479): 282-6; Geula et al. Science (2015) 347(6225): 1002-6) can function like the resident pluripotent cells and equally contribute to the embryos being formed (Nicols and Smith Cell Stem Cell (2009) 4(6): 487-92). To the contrary, mouse primed pluripotent stem cells (also known as Epiblast stem cells (EpiSCs)), expanded in N2B27 FGF2/ACTIVIN conditions are extremely inefficient at making chimeric embryos and not able to significantly contribute to such embryos when injected into host blastocysts or E7.5 embryos (Alejandro-Castrejon et al. Nature (2021) 593(7857): 119-124).

Mouse trophoblast stem cells (TSCs) can be derived from early mouse embryos (E5.5-E7.5 post-implantation mouse embryos) or directly from mouse ESCs in vitro (through a process that takes few passages of growth and selection to establish stable mouse TSC lines and typically alongside overexpression of transgene like Cdx2). Upon microinjection of conventional stabilized mouse TSC lines into blastocysts they can mildly contribute to advanced embryonic placental development, but have never been shown to be able to reconstitute the entire placental and trophectoderm progeny (Posfai et al. Nat Cell Biol (2021) 23(1): 49-60). Injecting mouse naïve ESCs or iPSCs in the tetraploid embryo complementation microinjection approach can generate unique "all ESC/iPSC" chimeras in which all the embryonic cells are derived only from the injected mouse stem cells, and the extraembryonic cells are derived only from the electrofused cells of the host embryo (Choi et al. Nature (2017) 548(7666): 219-223).

However, the goal of artificial synthetic embryos is to establish embryo-like structures without any donated germ cells, zygotes or blastocysts. Several studies attempted to make synthetic embryos by co-aggregations of two or three different cell types [see e.g. Zhang et al. (2020) Front. Bioeng. Biotechnol. 8:781]. For example, Harrison et al. [Science (2017) DOI:10.1126/science.aal1810] used in vitro expanded mouse PSCs, non-pluripotent conventional trophoblast stem cells (TSCs), Sozen et al. (Nature Cell Biology volume 20, pages 979-989 (2018)) used in vitro expanded mouse PSCs, non-pluripotent conventional trophoblast stem cells (TSCs) and non-pluripotent extra embryonic endodermal cells (referred to as XEN cells); while Amadei et al. [Developmental Cell (2021) 56, 366-382] used naïve iPSCs, non-pluripotent conventional TSC lines and mouse ES cells that transiently overexpress Gata4 transcription factor that helps promote primitive endoderm fate (instead of using stable mouse XEN lines). However, the embryos obtained were heavily aberrant and could not proceed through or complete gastrulation or initiate organogenesis and had aberrant morphology and missing key embryo defining features (DOI: 10.1126/sciadv.add2913).

SUMMARY OF THE INVENTION

According to an aspect of some embodiments of the present invention there is provided a method of generating a synthetic embryo, the method comprising:
(a) inducing expression of a factor that induces differentiation to trophectoderm cells in a subpopulation of naïve pluripotent stem cells (PSCs) to obtain trophectoderm primed cells; and
(b) mixing the trophectoderm primed cells with naïve PSCs under conditions that allow formation of aggregated cells,
wherein when the factor that induces differentiation to trophectoderm cells is an exogenous factor the inducing the expression comprises inducing transient expression starting within 14 days—0 hours prior to the mixing and ending no later than 120 hours following the mixing; and wherein the factor that induces differentiation to trophectoderm cells is an endogenous factor the inducing the expression comprises culturing the subpopulation of naïve PSCs under conditions enabling expression of the factor starting within 14 days—6 hours prior to the mixing, thereby generating the synthetic embryo.

According to some embodiments of the invention, the method further comprising inducing expression of a factor that induces differentiation to extra embryonic primitive endodermal cells in a second subpopulation of naïve PSCs to obtain extra embryonic primitive endodermal primed cells in the (a); and mixing the extra embryonic primitive endodermal primed cells with the cells in the (b).

According to some embodiments of the invention, the wherein when the factor that induces differentiation to extra embryonic primitive endodermal cells is an exogenous factor the inducing the expression comprises inducing transient expression starting within 14 days—0 hours prior to the mixing and ending no later than 120 hours following the mixing; and wherein the factor that induces differentiation to extra embryonic primitive endodermal cells is an endogenous factor the inducing the expression comprises culturing the subpopulation of naïve PSCs under conditions enabling expression of the factor starting within 14 days—6 hours prior to the mixing.

According to an aspect of some embodiments of the present invention there is provided a method of generating a synthetic embryo, the method comprising:
  (a) inducing transient expression of an exogenous factor that induces differentiation to trophectoderm cells in a subpopulation of naïve pluripotent stem cells (PSCs) to obtain trophectoderm primed cells; and
  (b) mixing the trophectoderm primed cells with naïve PSCs under conditions that allow formation of aggregated cells,
  wherein the inducing the transient expression starts within 14 days—0 hours prior to the mixing and ends no later than 120 hours following the mixing,
  thereby generating the synthetic embryo.

According to some embodiments of the invention, the method further comprising inducing transient expression of an exogenous factor that induces differentiation to extra embryonic primitive endodermal cells in a second subpopulation of naïve PSCs to obtain extra embryonic primitive endodermal primed cells in the (a); and mixing the extra embryonic primitive endodermal primed cells with the cells in the (b).

According to some embodiments of the invention, mixing the naïve PSCs, the trophectoderm primed cells and the extra embryonic primitive endodermal primed cells is effected concomitantly.

According to some embodiments of the invention, mixing the naïve PSCs and the extra embryonic primitive endodermal primed cells is effected prior to the mixing with the trophectoderm primed cells.

According to some embodiments of the invention, the trophectoderm cells and/or the extra embryonic primitive endodermal primed cells express a pluripotency marker at the 0 hours.

According to some embodiments of the invention, the trophectoderm cells and/or the extra embryonic primitive endodermal primed cells express a pluripotency marker at the mixing.

According to some embodiments of the invention, the trophectoderm primed cells express a trophectoderm marker at the 0 hours.

According to some embodiments of the invention, the trophectoderm primed cells express a trophectoderm marker at the mixing.

According to some embodiments of the invention, the extra embryonic endodermal primed cells express an extra embryonic primitive endoderm marker at the 0 hours.

According to some embodiments of the invention, the extra embryonic endodermal primed cells express an extra embryonic primitive endoderm marker at the mixing.

According to an aspect of some embodiments of the present invention there is provided an article of manufacture comprising:
  (i) trophectoderm primed cells, wherein the trophectoderm primed cells comprise naïve pluripotent stem cell (PSCs) comprising an exogenous polynucleotide suitable for transient expression of a factor that induces differentiation to trophectoderm cells; and
  (ii) naïve PSCs.

According to some embodiments of the invention, the article of manufacture further comprising:
  (iii) extra embryonic primitive endodermal primed cells, wherein the extra embryonic primitive endodermal primed cells comprise naïve pluripotent stem cells (PSCs) comprising an exogenous polynucleotide suitable for transient expression of factor that induces differentiation to extra embryonic primitive endodermal cells.

According to an aspect of some embodiments of the present invention there is provided an article of manufacture comprising:
  (i) trophectoderm primed cells, wherein the trophectoderm primed cells comprise naïve pluripotent stem cells (PSCs) comprising an exogenous polynucleotide suitable for transient expression of a factor that induces differentiation to trophectoderm cells; and
  (ii) extra embryonic primitive endodermal primed cells, wherein the extra embryonic primitive endodermal primed cells comprise naïve pluripotent stem cells (PSCs) comprising an exogenous polynucleotide suitable for transient expression of factor that induces differentiation to extra embryonic primitive endodermal cells.

According to some embodiments of the invention, the (i) the (ii) and the (iii) are in a single container.

According to some embodiments of the invention, the (i) the (ii) and the (iii) are in separate containers.

According to an aspect of some embodiments of the present invention there is provided a method of ex-utero culturing a synthetic embryo, the method comprising mixing the cells of the article of manufacture under conditions the allow formation of aggregated cells, wherein the method comprises inducing transient expression of the factor starting within 14 days—0 hours prior to the mixing and ending no later than 120 hours following the mixing, thereby generating the synthetic embryo.

According to an aspect of some embodiments of the present invention there is provided a mixture or aggregate, obtainable by the method.

According to an aspect of some embodiments of the present invention there is provided a mixture or aggregate comprising:
(i) naïve pluripotent stem cell (PSCs);
(ii) trophectoderm primed cells, wherein the trophectoderm primed cells comprise stem cells expressing an endogenous trophectoderm marker and an endogenous pluripotent marker; and
(iii) extra embryonic primitive endodermal primed cells, wherein the extra embryonic primitive endodermal primed cells comprise stem cells expressing an endogenous extra embryonic primitive endoderm marker and an endogenous pluripotency marker,
wherein the mixture or aggregate is not structurally organized as a native embryo at any developmental stage; and
wherein the mixture or aggregate is capable of forming a synthetic embryo structurally organized as a native embryo of at least a post-implantation egg cylinder or a bilaminar disc developmental stage.

According to an aspect of some embodiments of the present invention there is provided a mixture or aggregate, comprising:
(i) trophectoderm primed cells, wherein the trophectoderm primed cells comprise stem cells expressing an exogenous factor that induces differentiation to trophectoderm cells, an endogenous trophectoderm marker and an endogenous pluripotent marker; and
(ii) naïve pluripotent stem cell (PSCs).

According to some embodiments of the invention, the mixture or aggregate further comprising:
(iii) extra embryonic primitive endodermal primed cells, wherein the extra embryonic primitive endodermal primed cells comprise stem cells expressing an exogenous factor that induces differentiation to extra embryonic primitive endodermal cells, an endogenous extra embryonic primitive endoderm marker and an endogenous pluripotency marker.

According to some embodiments of the invention, the factor that induces differentiation to extra embryonic primitive endodermal cells comprises Gata4, Gata6 and/or SOX17.

According to some embodiments of the invention, the factor that induces differentiation to extra embryonic primitive endodermal cells comprises Gata4 and/or Gata6.

According to some embodiments of the invention, inducing expression of a factor that induces differentiation to extra embryonic primitive endodermal cells comprises culturing the second subpopulation of naïve PSCs with a factor that induces differentiation to extra embryonic primitive endodermal cells starting within 14 days—6 hours prior to the mixing.

According to some embodiments of the invention, the method further comprises contacting the second subpopulation of naïve PSCs with a factor that induces differentiation to extra embryonic primitive endodermal cells within 14 days—0 hours prior to the mixing.

According to some embodiments of the invention, the factor that induces differentiation to extra embryonic primitive endodermal cells is selected from the group consisting of a GSK-3 inhibitor, WNT ligand, heparin, FGF2, FGF4, PDGF, leukemia inhibitory factor (LIF) and insulin.

According to some embodiments of the invention, the factor that induces differentiation to extra embryonic primitive endodermal cells is selected from the group consisting of a GSK-3 inhibitor, WNT ligand, heparin, FGF2 and FGF4.

According to some embodiments of the invention, the factor that induces differentiation to trophectoderm cells is selected from the group consisting of Cdx2, Gata3 and Gata2.

According to some embodiments of the invention, inducing expression of a factor that induces differentiation to trophectoderm cells comprises culturing the subpopulation of naïve PSCs with a factor that induces differentiation to trophectoderm cells starting within 14 days—6 hours prior to the mixing.

According to some embodiments of the invention, the method further comprises contacting the subpopulation of naïve PSCs with a factor that induces differentiation to trophectoderm cells within 14 days—0 hours prior to the mixing.

According to some embodiments of the invention, the factor that induces differentiation to trophectoderm cells is selected from the group consisting of TGFR inhibitor, FGFR inhibitor, MEK/ERK inhibitor, BMP4, JAK inhibitor, a ROCK pathway inhibitor, FGF4, FGF2, heparin, a SUMOylation inhibitor, a Histone Deacetylase inhibitor, a HIPPO signaling pathway inhibitor and a factor that induces YAP nuclear translocation.

According to some embodiments of the invention, the factor that induces differentiation to trophectoderm cells is selected from the group consisting of FGF4, FGF2, heparin, a SUMOylation inhibitor, a Histone Deacetylase inhibitor, a HIPPO signaling pathway inhibitor and a factor that induces YAP nuclear translocation.

According to some embodiments of the invention, the transient expression is effected by introducing a polynucleotide encoding the factor.

According to some embodiments of the invention, the polynucleotide is a DNA.

According to some embodiments of the invention, the expression of the polynucleotide is regulated by an inducible promoter.

According to some embodiments of the invention, the introducing is by transient transfection.

According to some embodiments of the invention, the polynucleotide is a RNA.

According to some embodiments of the invention, the inducing the transient expression starts within 120-0 hours prior to the mixing.

According to some embodiments of the invention, the inducing the transient expression starts within 48-0 hours prior to the mixing.

According to some embodiments of the invention, the inducing the transient expression starts within 24-0 hours prior to the mixing.

According to some embodiments of the invention, the inducing the transient expression starts within 48-12 hours prior to the mixing.

According to some embodiments of the invention, the inducing the transient expression ends no later than 48 hours following the mixing.

According to some embodiments of the invention, the inducing the transient expression is effected for no more than 96 hours.

According to some embodiments of the invention, the inducing the expression of the endogenous factor starts within 10-1 days prior to the mixing.

According to some embodiments of the invention, a ratio between the naïve PSCs and the trophectoderm primed cells is between 1:1 and 1:5.

According to some embodiments of the invention, a ratio between the naïve PSCs and the trophectoderm primed cells is 1:3.

According to some embodiments of the invention, a ratio between the naïve PSCs and the primitive endodermal primed cells is between 1:1 and 2:1.

According to some embodiments of the invention, a ratio between the naïve PSCs and the primitive endodermal primed cells is 1:1.

According to some embodiments of the invention, the method further comprising ex-utero culturing the aggregated cells following the (b).

According to an aspect of some embodiments of the present invention there is provided a method of ex-utero culturing a synthetic embryo, the method comprising ex-utero culturing the mixture or aggregate.

According to some embodiments of the invention, the culturing is effected in a static culture followed by a dynamic culture.

According to some embodiments of the invention, the static culture is effected until the embryo reaches at least an early post-implantation egg-cylinder or bilaminar discstage.

According to some embodiments of the invention, the dynamic culture starts the latest when the embryo reaches an early somite stage.

According to an aspect of some embodiments of the present invention there is provided a method of ex-utero culturing a synthetic embryo, the method comprising ex-utero culturing a synthetic embryo at an aggregate stage in a static culture followed by a dynamic culture, wherein the static culture is effected until the embryo reaches at least an early post-implantation egg-cylinder or bilaminar disc stage; and the dynamic culture starts the latest when the embryo reaches an early somite stage.

According to some embodiments of the invention, the dynamic culture comprises a shaker culture, a roller culture or a sequential combination thereof.

According to some embodiments of the invention, the dynamic culture is effected under a hyperbaric pressure of more than 0.1 and less than 10.2 pounds per square inch (psi).

According to some embodiments of the invention, the dynamic culture is effected under a hyperbaric pressure of more than 5 and less than 10.2 pounds per square inch (psi).

According to some embodiments of the invention, the culturing is effected in an atmosphere comprising 10-40% oxygen.

According to some embodiments of the invention, the culturing is effected with a medium comprising increasing concentrations of serum or serum replacement throughout the culturing.

According to some embodiments of the invention, the culturing is effected with a medium comprising at least 15% serum or serum replacement from the beginning until the embryo reaches an early post-implantation egg-cylinder or bilaminar disc stage and at least 30% serum or serum replacement thereafter.

According to some embodiments of the invention, the culturing is effected with a medium comprising a human serum for at least part of the culturing.

According to some embodiments of the invention, the method further comprising transferring the synthetic embryo in-utero.

According to some embodiments of the invention, the cells are mammalian cells.

According to some embodiments of the invention, the mammalian cells are mouse cells.

According to some embodiments of the invention, the mammalian cells are human cells.

According to some embodiments of the invention, the mammalian cells are non-human primate cells.

According to some embodiments of the invention, the mammalian cells are live stock cells.

According to an aspect of some embodiments of the present invention there is provided a synthetic embryo obtainable by the method.

According to an aspect of some embodiments of the present invention there is provided a method of obtaining extra embryonic primitive endodermal primed cells, the method comprising culturing naïve PSCs in a base medium devoid of Activin A under conditions that allow differentiation of the naïve PSCs to GATA4$^+$GATA6$^+$OCT4$^+$Nanog$^-$ extra embryonic primitive endodermal primed cells, thereby obtaining the extra embryonic primitive endodermal primed cells.

According to some embodiments of the invention, the culturing is effected for at least 1 day.

According to some embodiments of the invention, the culturing is effected for up to 10 days.

According to some embodiments of the invention, the cells can be expanded in culture for at least five passages while maintaining the GATA4$^+$GATA6$^+$OCT4$^+$Nanog$^-$ phenotype.

According to some embodiments of the invention, the base medium is supplemented with at least one of a GSK-3 inhibitor, leukemia inhibitory factor (LIF) and insulin.

According to some embodiments of the invention, the base medium is supplemented with at least one of GSK-3 inhibitor, heparin, FGF4, PDGF and BSA.

According to some embodiments of the invention, the cells are human cells.

According to some embodiments of the invention, the cells are mouse cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows immunostaining images of E6.5 mouse embryo derived mouse TSC line #1 at passage 3 (day 14 since derivation), demonstrating expression of the TSC markers Cdx2 and Gata3. DAPI was used for counterstaining.

Figure 2:
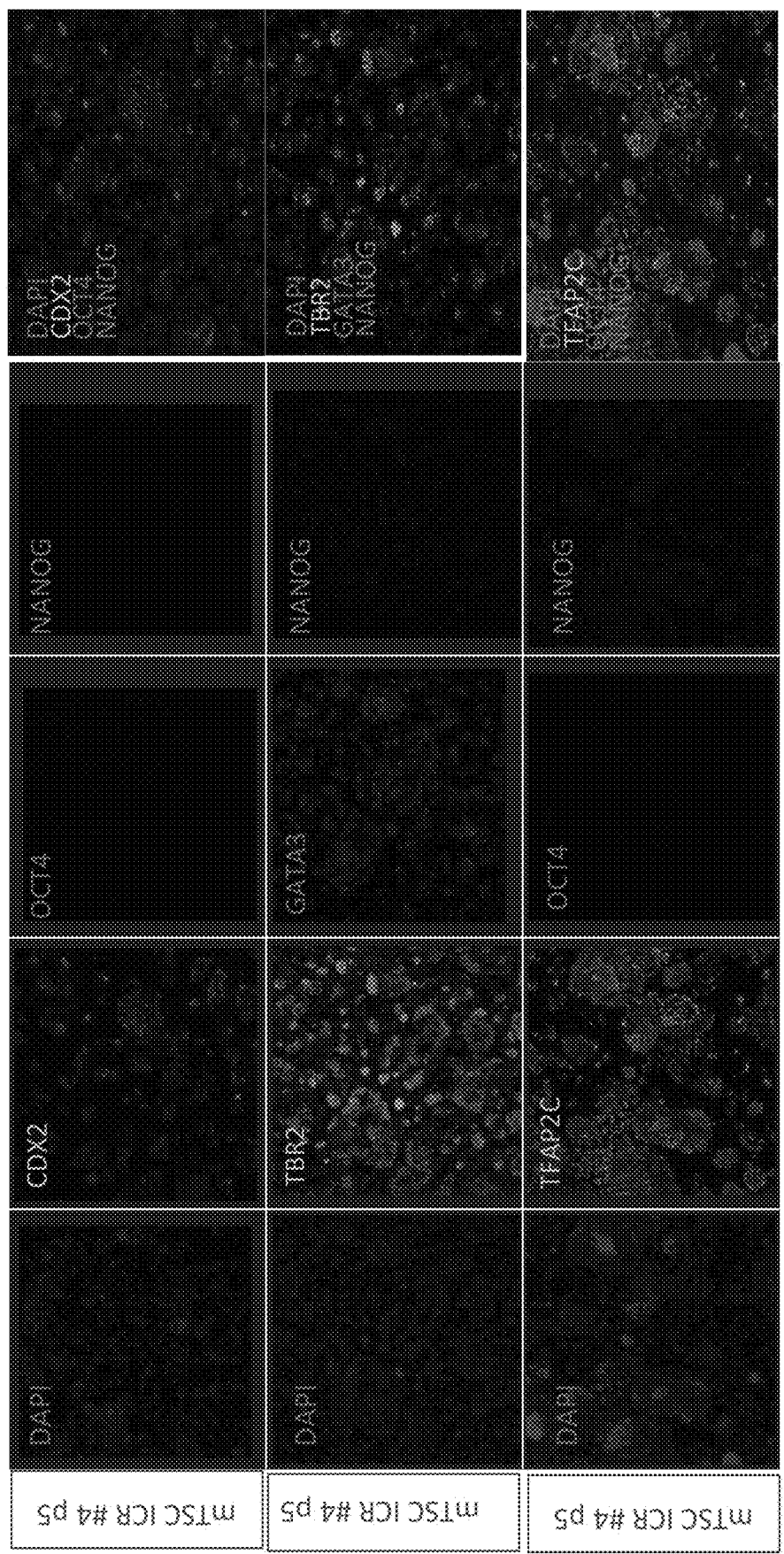

FIG. 2 shows immunostaining images of mouse TSC line #1 at passage 5 (day 25 since derivation), demonstrating expression of the TSC markers Cdx2, TBR2, Gata3 and TFAP2C and no expression of Oct4 and Nanog. DAPI was used for counterstaining.

Figure 3:
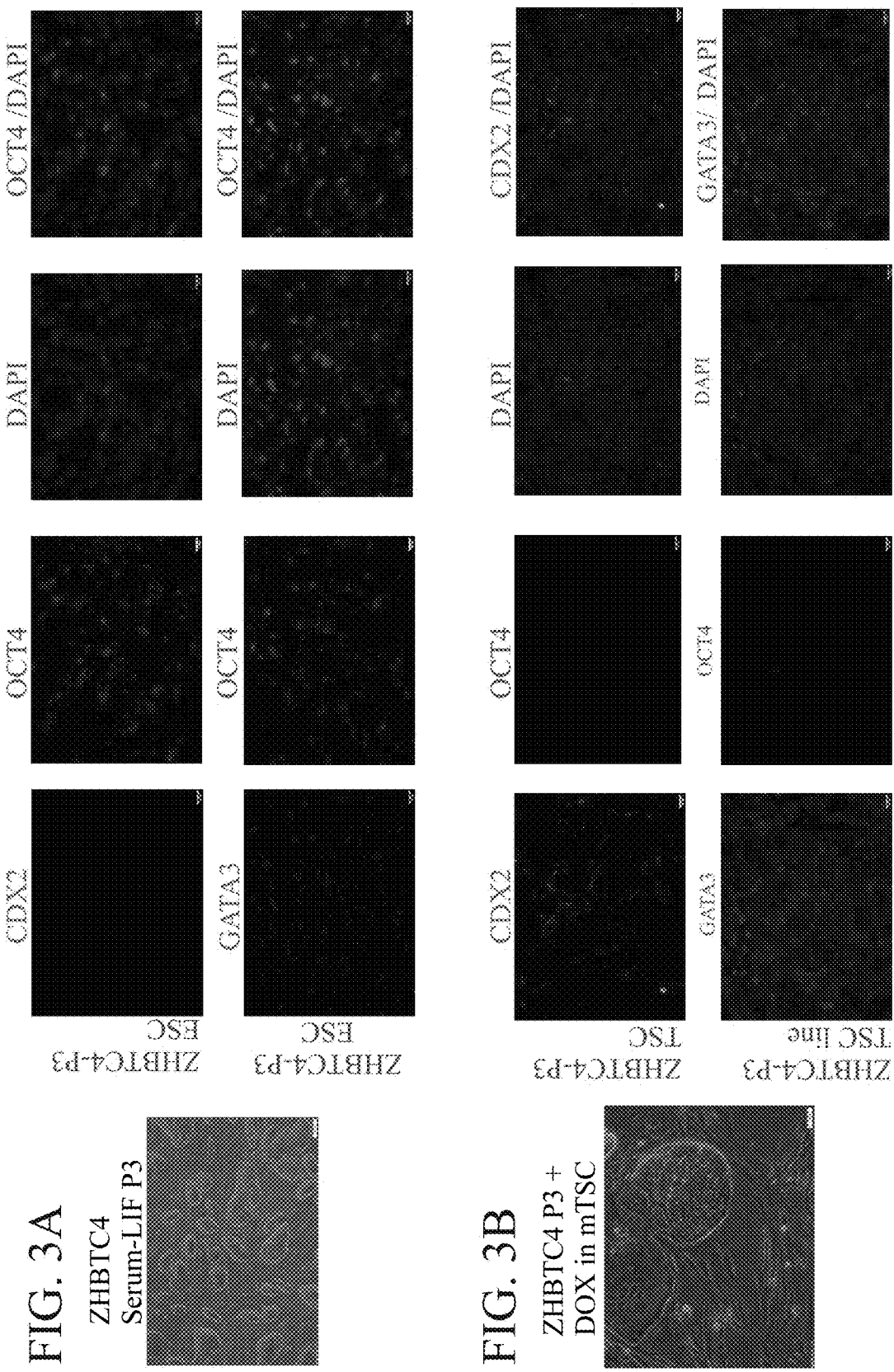

FIGS. 3A-B show immunostaining images of parental ESC line (FIG. 3A) and mouse TSC line #2 at passage 3 (approximately day 12 since protocol initiation) (FIG. 3B) which was derived after transient Oct4 knockdown to the parental ES lines, demonstrating expression of the TSC marker Cdx2 and Gata3 and no expression of Oct4 in the established TSC line. DAPI was used for counterstaining.

Figure 4:
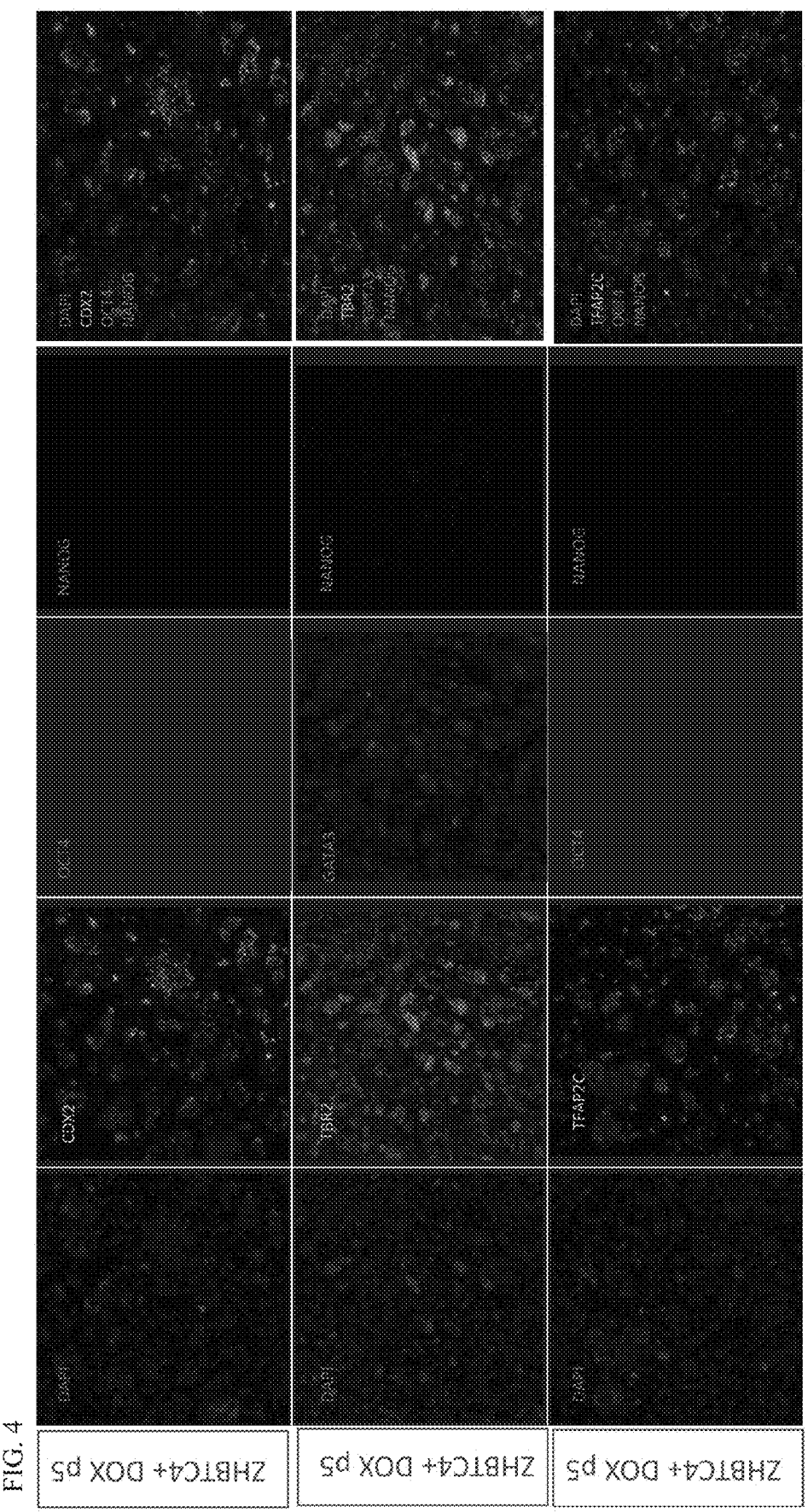

FIG. 4 shows immunostaining images of mouse TSC line #2 at passage 5 (day 30 since protocol initiation), demonstrating expression of the TSC markers Cdx2, TBR2, Gata3 and TFAP2C and no expression of Oct4 and Nanog. DAPI was used for counterstaining.

Figure 5:
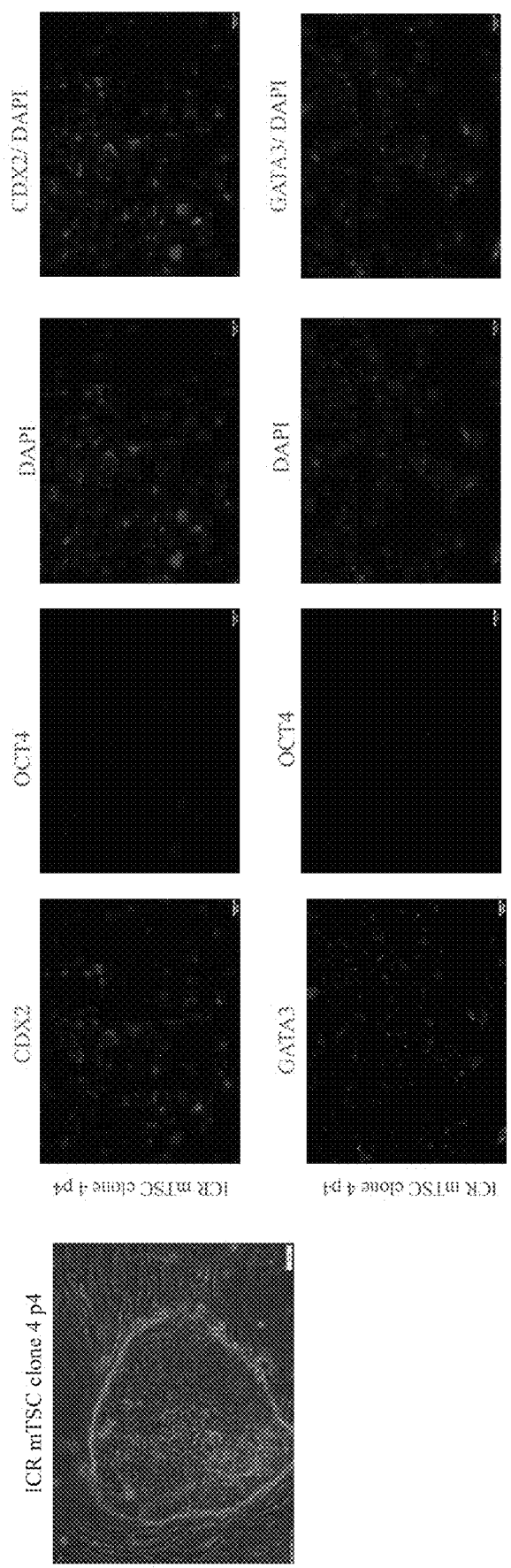

FIG. 5 shows immunostaining images of mouse TSC line #3 at passage 4 (approximately day 24 since protocol initiation and transfection), demonstrating expression of the TSC markers Cdx2 and Gata3 and TFAP2C and no expression of Oct4. DAPI was used for counterstaining.

Figure 6A:
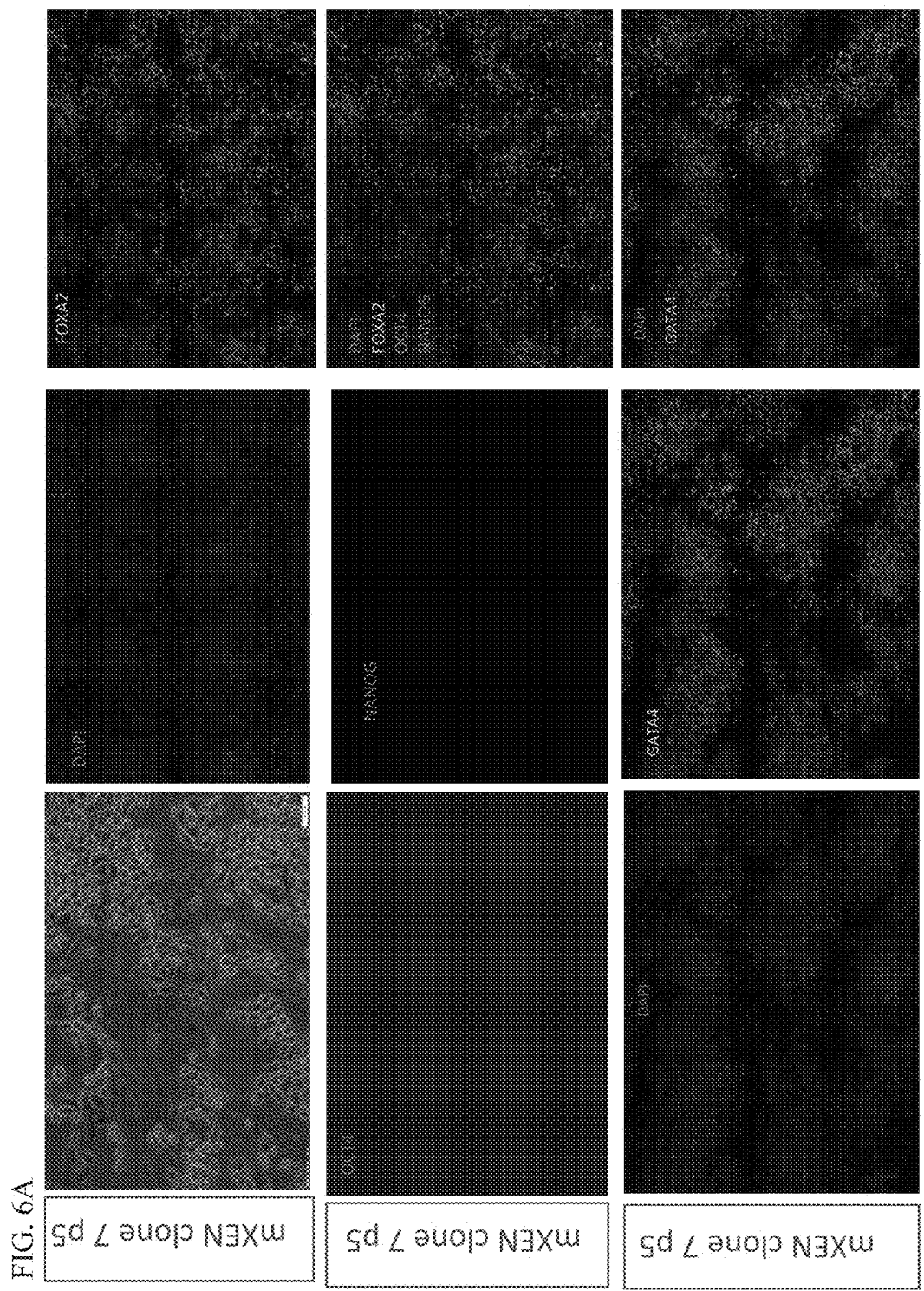

FIG. 6A shows immunostaining images of mouse XEN line #7 at passage 5, demonstrating expression of the XEN markers Foxa2 and Gata4 and no expression of Oct4 and Nanog. DAPI was used for counterstaining.

Figure 6B:
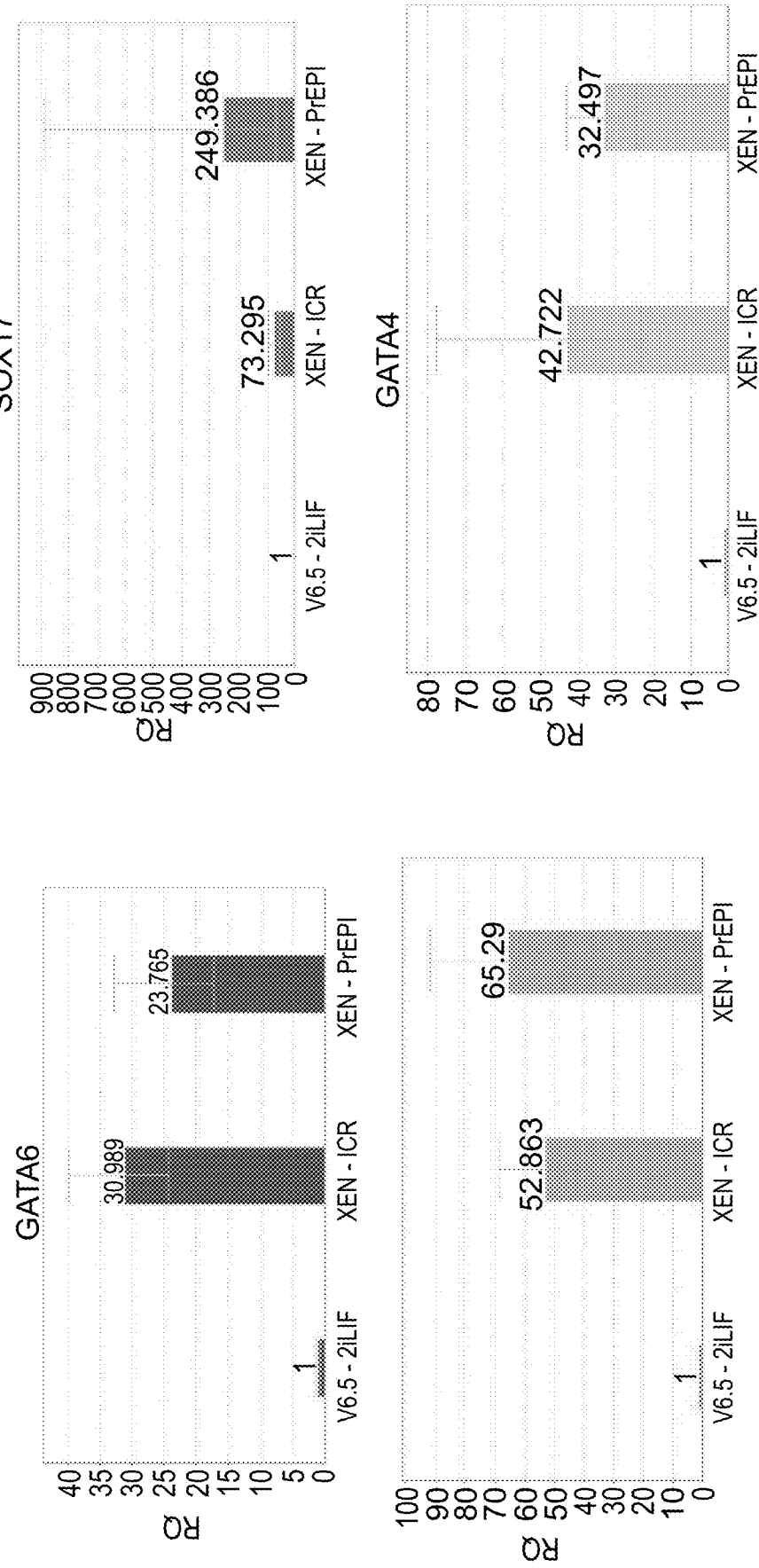

FIG. 6B shows RNA expression levels of the XEN markers Gata6, PDGFRA, Sox17 and Gata4 in the mouse XEN lines XEN-ICR clone #7 and XEN-Prep1, as determined by real-time PCR analysis. Mouse V6.5 naïve ESCs expanded in 2i-LIF conditions were used as a reference control (value set as 1).

Figure 7A:
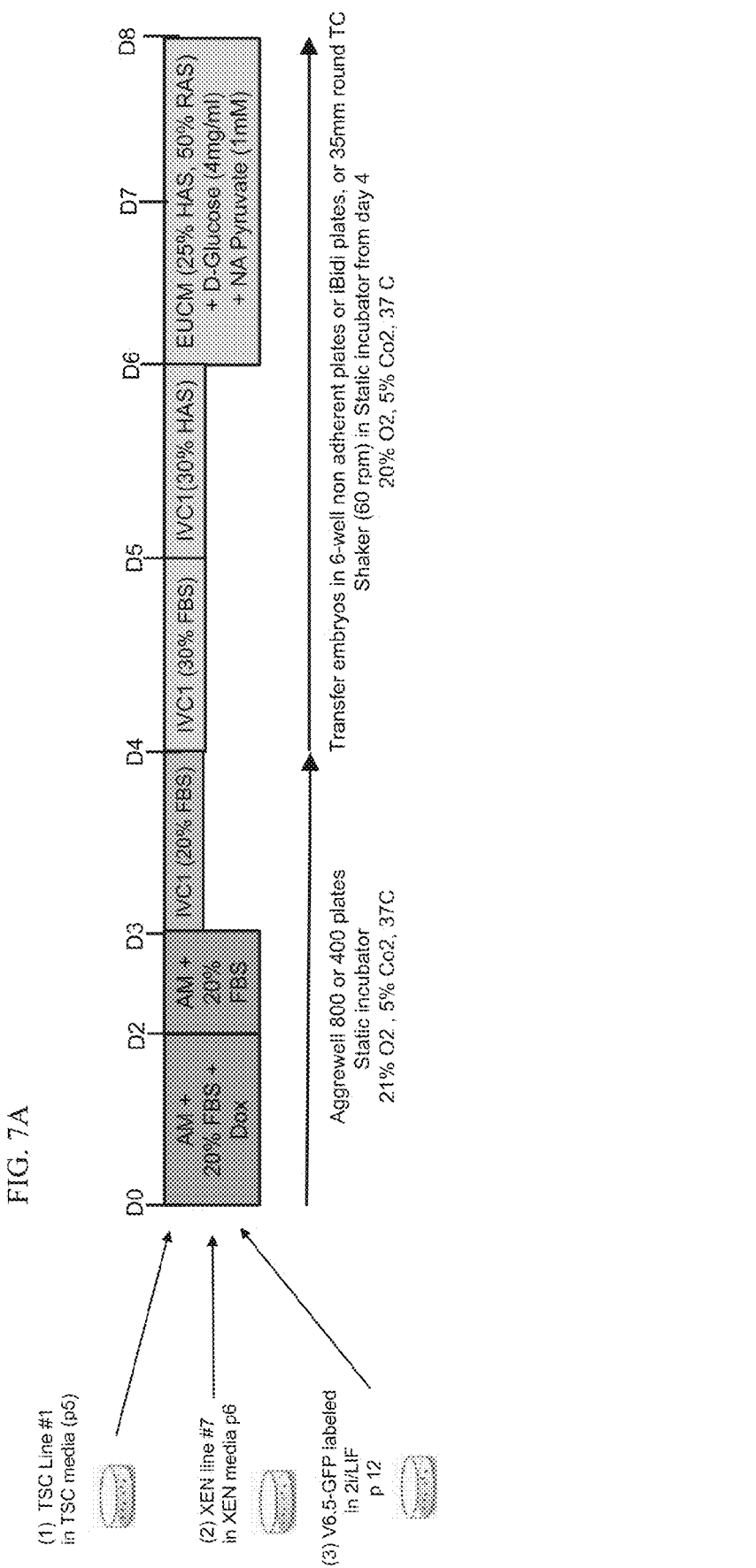
Figure 7B:
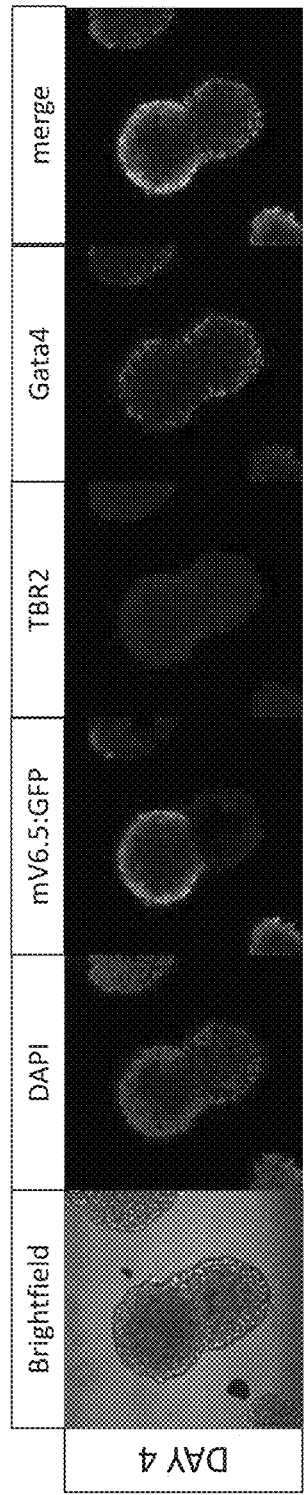
Figure 7C:
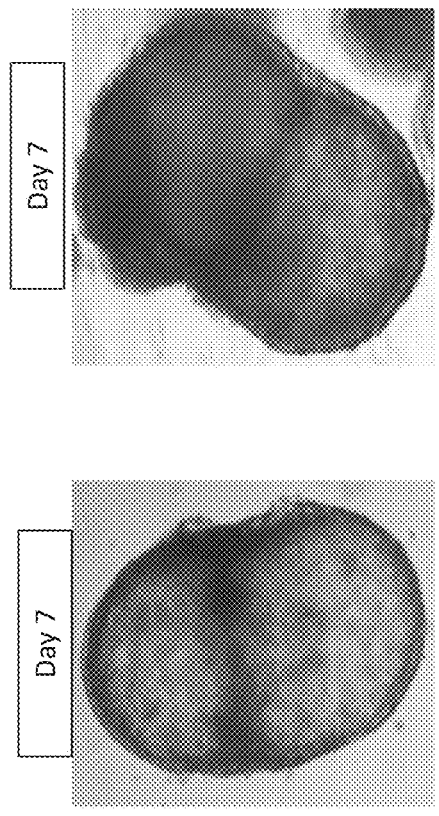

FIGS. 7A-C demonstrate that co-aggregation of naïve mouse PSCs (V6.5-GFP), mouse XEN cells (mouse XEN line #7 cells) and mouse TSCs (mouse TSC line #1 cells) followed by ex-utero culturing does not lead to generation of an organized embryo. FIG. 7A is a schematic representation of the protocol. Aggregation medium (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010) and 0.45% BSA (Sigma Aldrich A7979) (For 500 ml Total). IVC1 medium—Advanced DMEM/F12 (Gibco 12634010) Glutamax 1×, Pen/Strep 1×, ITS-X 1× (Gibco 51500056), beta-Estradiol 8 nM, Progesterone 20 ng/ml, N-acetyl-L-cysteine 25 μM and serum as indicated in the scheme [For 500 ml total]. EUCM—25% DMEM (GIBCO 11880), 25% HAS (Human Adult Serum or Human cord serum), 50% Rat Serum (RAS), Glutamax 1× (GIBCO 35050038), HEPES 2 mM (GIBCO 15630056), Pen/Strep 1×. FIG. 7B shows images of representative embryoid aggregates at Day 4 of the protocol immunostained for TBR2 (red) which marks trophectoderm lineage, Gata4 which marks primitive endoderm lineage, and GFP signals marked the labeled ESCs contributing to the epiblast. FIG. 7C shows images or representative structures at Day 7 of the protocol demonstrating no organized embryos in the yolk sac with no signs of emergence of neural folds and cardiac regions.

Figure 7D:
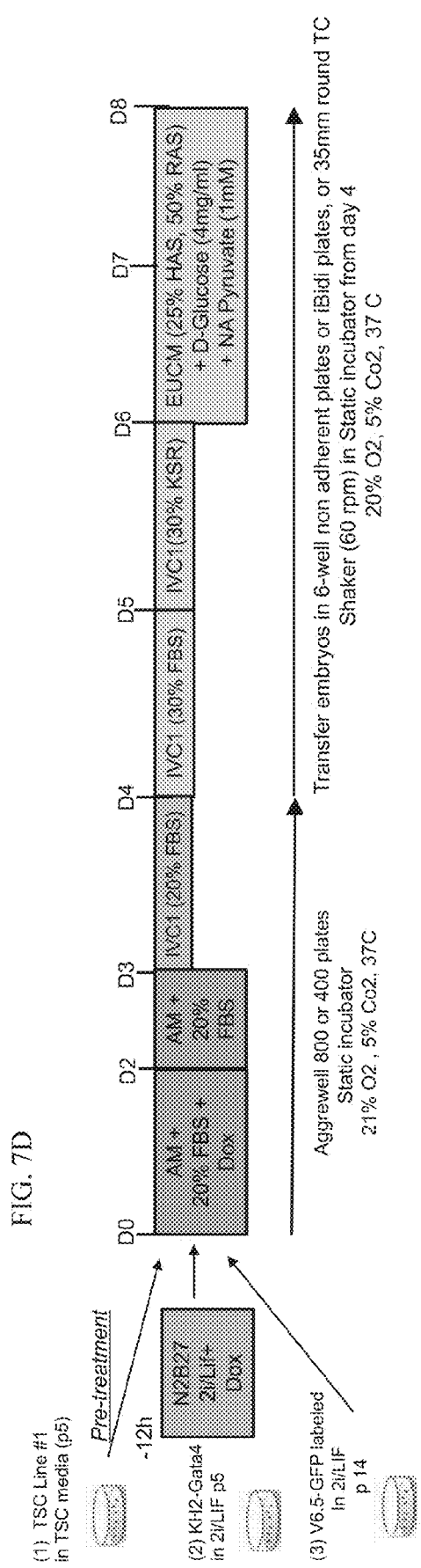
Figure 7E:
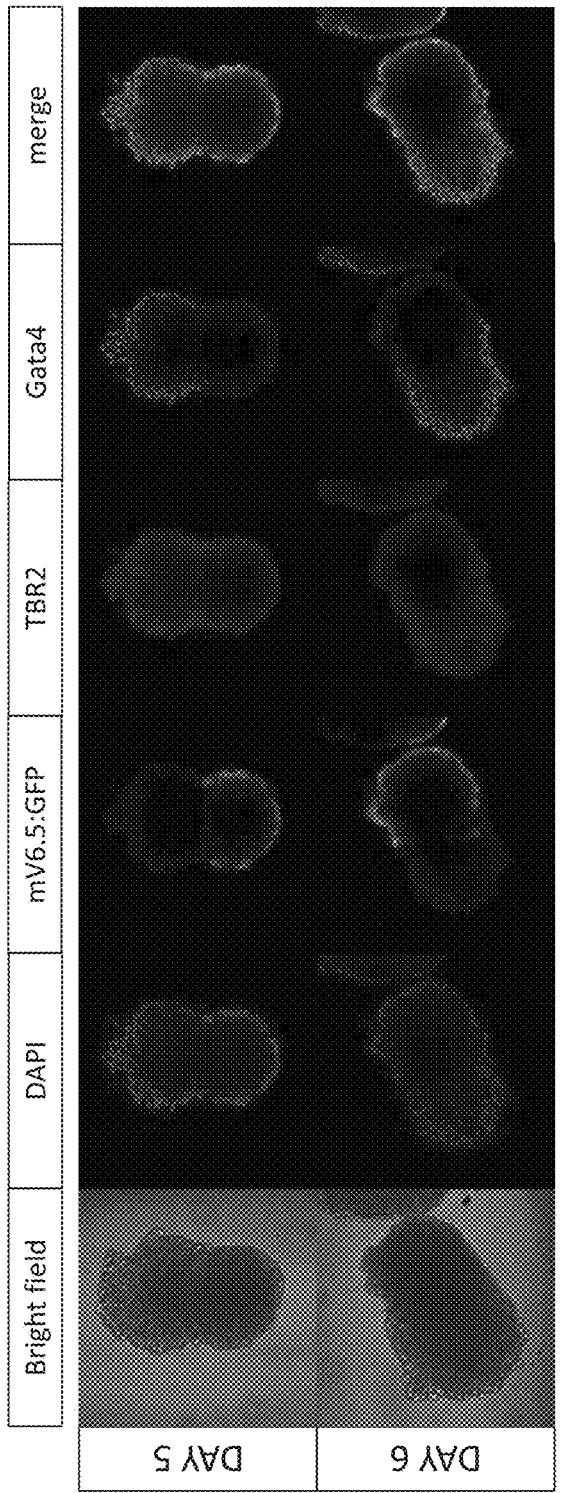
Figure 7F:
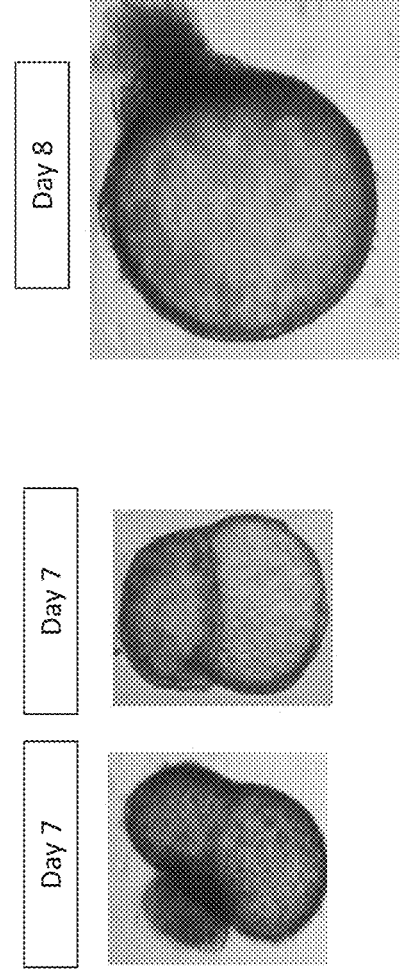

FIGS. 7D-F demonstrate that co-aggregation of naïve mouse PSCs (V6.5-GFP), mouse KH2-Gata4 Dox inducible ES cells and mouse TSCs (mouse TSC line #1 cells) followed by ex-utero culturing does not lead to generation of an organized embryo. FIG. 7D is a schematic representation of the protocol. Aggregation medium (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), Beta-mercaptoethanol 0.1 mM (Thermo 31350010), 0.45% BSA (SigmaAldrich A7979) (For 500 ml Total). IVC1 medium—Advanced DMEM/F12 (Gibco 12634010) Glutamax 1×, Pen/Strep 1×, ITS-X 1× (Gibco 51500056), beta-Estradiol 8 nM, Progesterone 20 ng/ml, N-acetyl-L-cysteine 25 μM and serum or KSR as indicated in the scheme (For 500 ml total). EUCM—25% DMEM (GIBCO 11880), 25% HAS (Human Adult Serum or Human cord serum), 50% Rat Serum (RAS), Glutamax 1× (GIBCO 35050038), HEPES 2 mM (GIBCO 15630056), Pen/Strep 1×. FIG. 7E shows images of representative embryoid aggregates at Days 5 and 6 of the protocol immunostained for TBR2 (red) which marks trophectoderm lineage, Gata4 which marks primitive endoderm lineage, and GFP signals marked the labeled ESCs contributing to the epiblast. FIG. 7F shows images or representative structures at Days 7 and 8 of the protocol demonstrating no organized embryos in the yolk sac with no signs of emergence of neural folds and cardiac regions.

Figure 8:
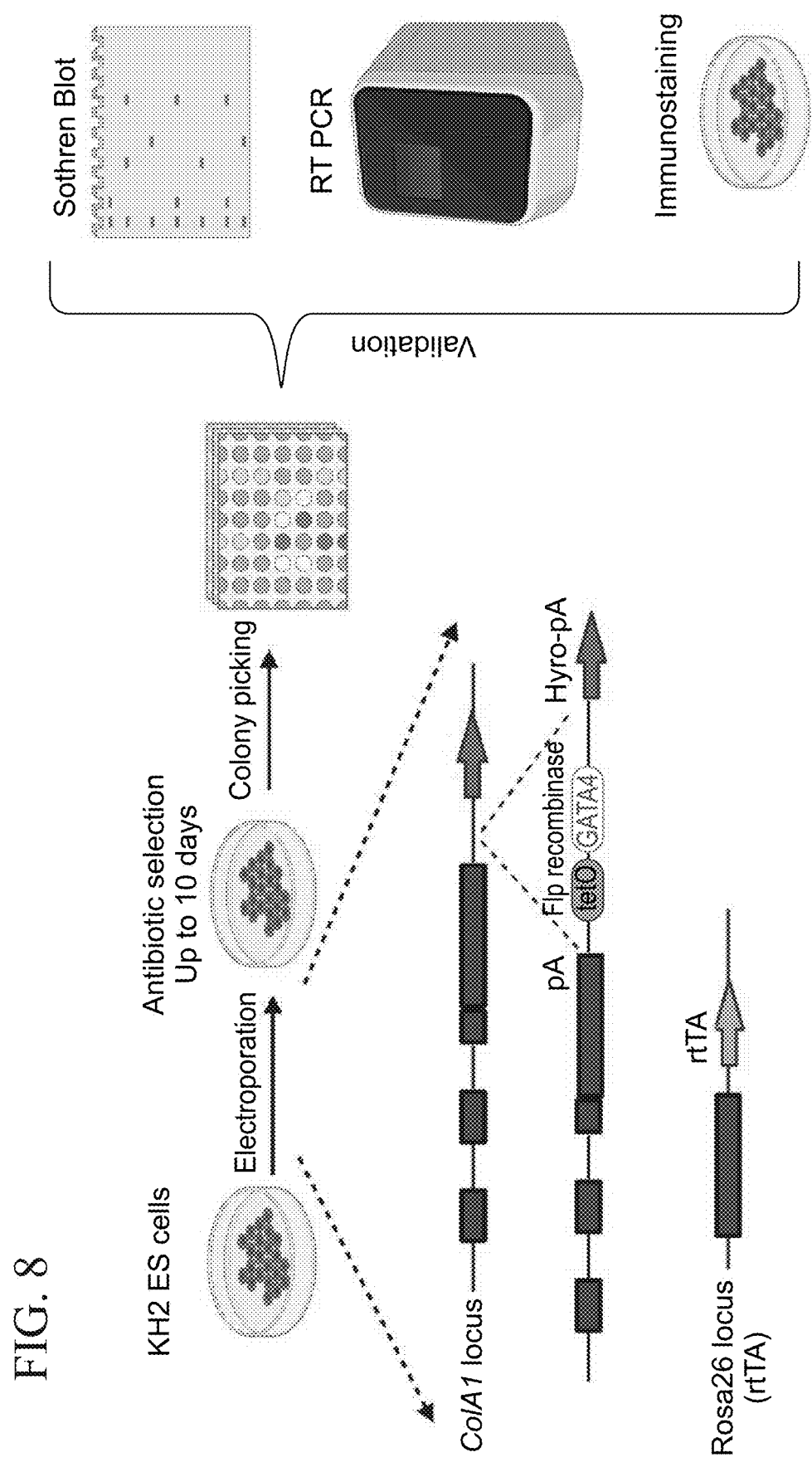

FIG. 8 shows a schematic representation of the generation and validation of KH2-Gata4 Dox inducible naïve ES cells.

Figure 9:
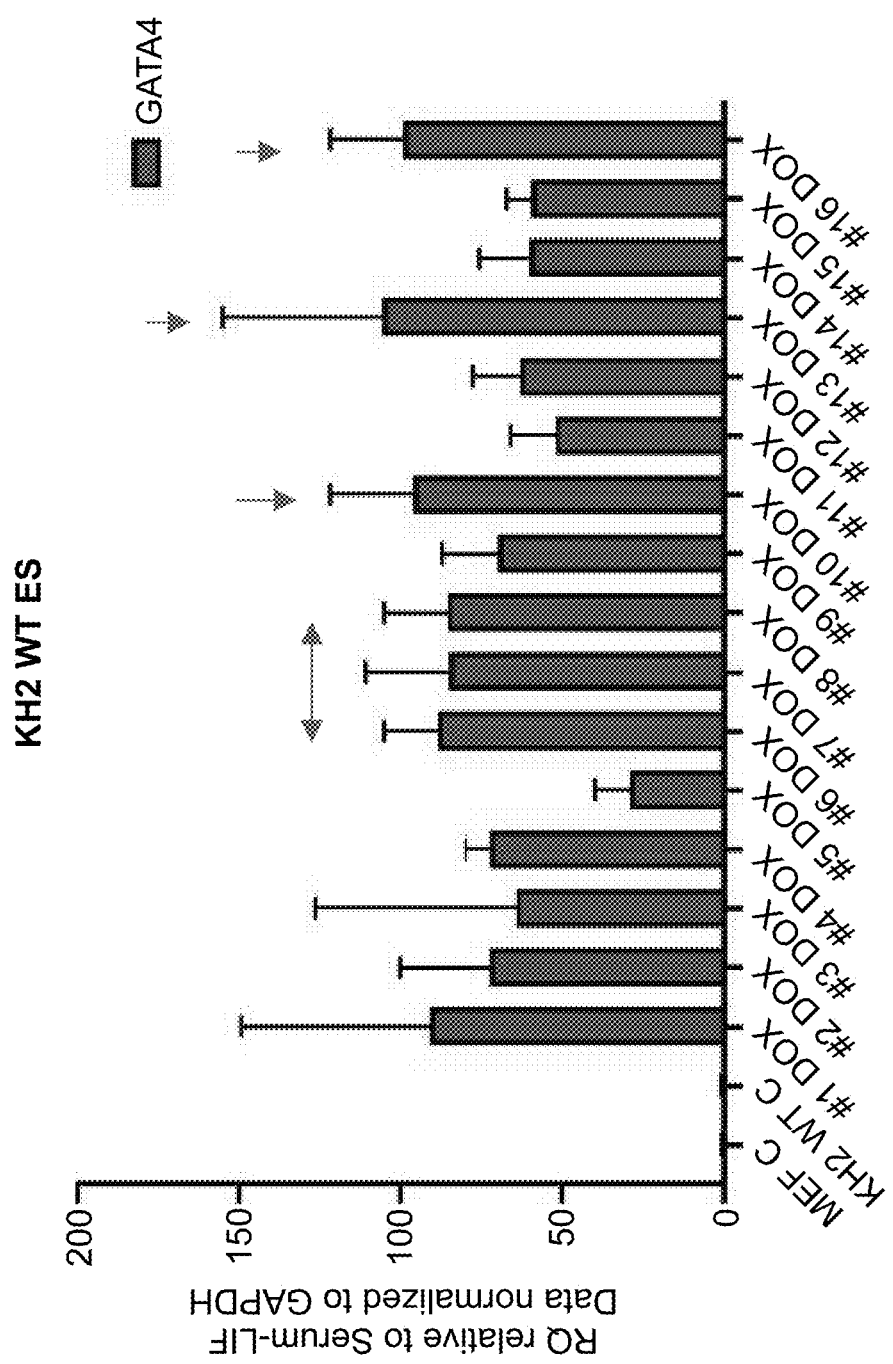

FIG. 9 shows Real-Time PCR analysis of exogenous GATA4 expression in different KH2-Gata4 mouse ES clones targeted with TetOn-Gata4 in the collagen locus after treatment with DOX. KH2-WT and mouse irradiated fibroblast cells (MEFs) were used as negative control.

Figure 10:
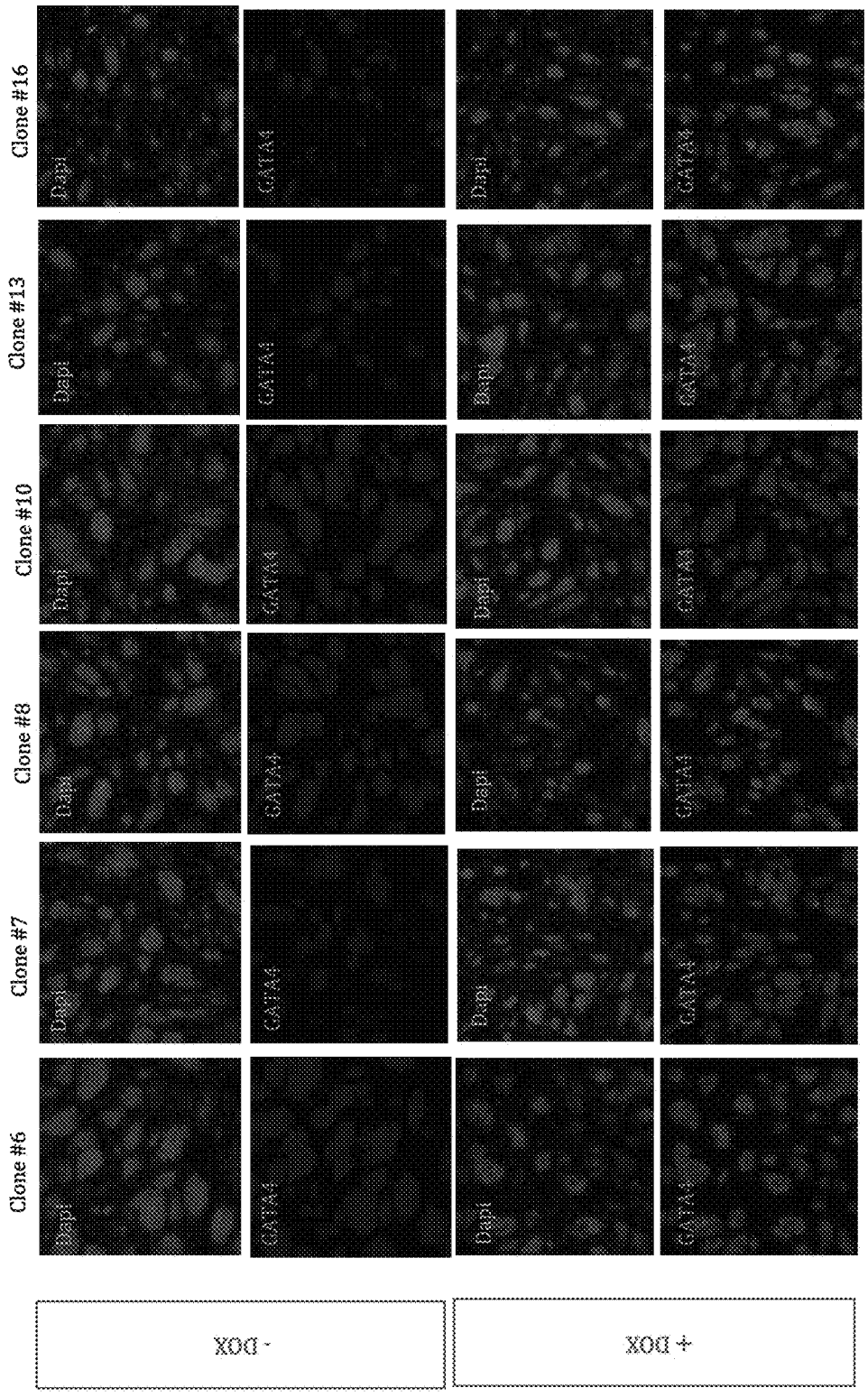

FIG. 10 shows immunostaining images of different KH2 mouse naïve ES clones targeted with TetOn-Gata4 (KH2-Gata4) in the collagen locus before and after treatment with DOX in naïve 2i/LIF conditions. Gata4 was robustly expressed in the tested clones only after DOX treatment. DAPI was used for counterstaining.

Figure 11:
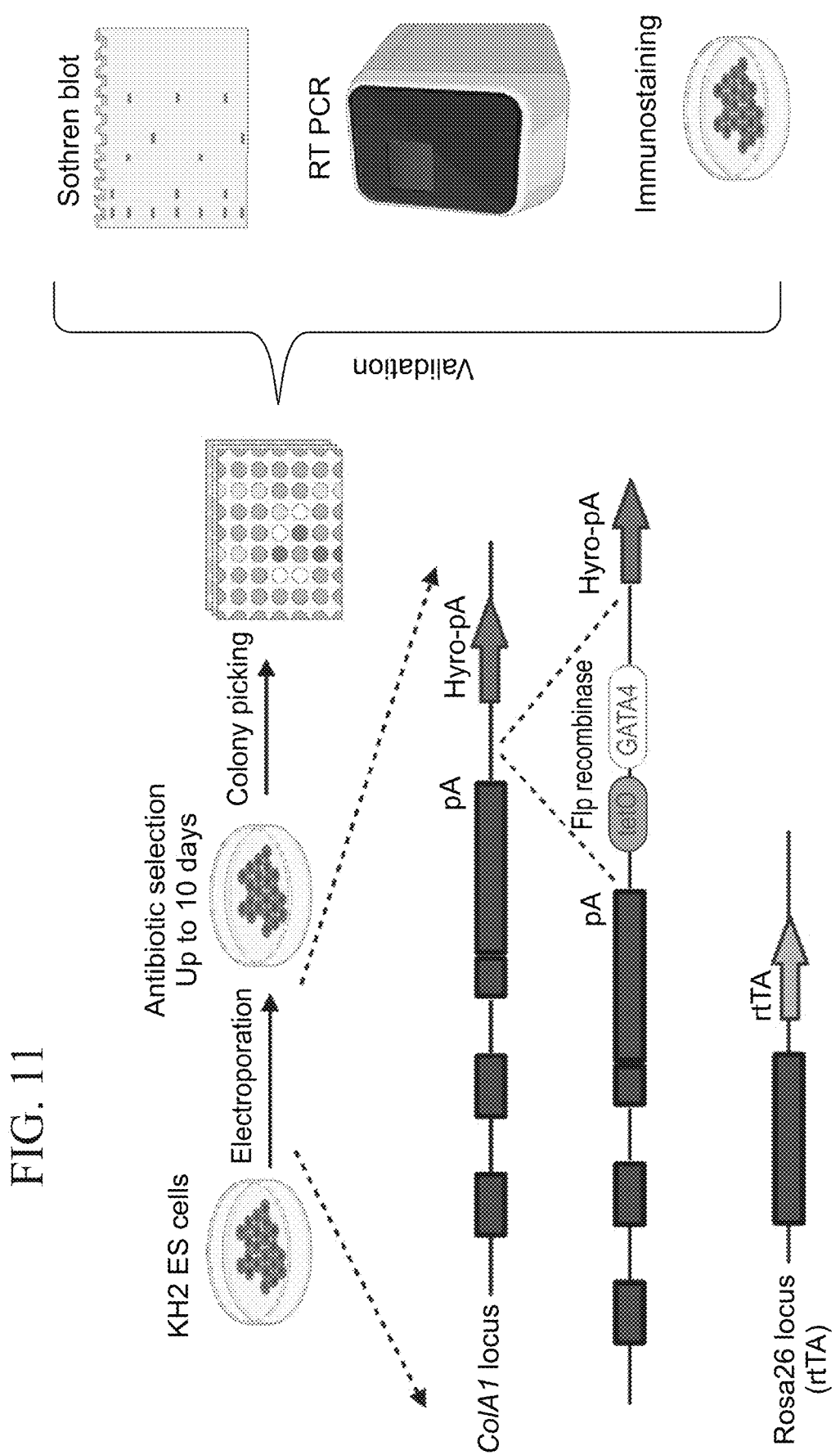

FIG. 11 shows a schematic representation of the generation and validation of KH2-Cdx2 Dox inducible cells.

Figure 12:
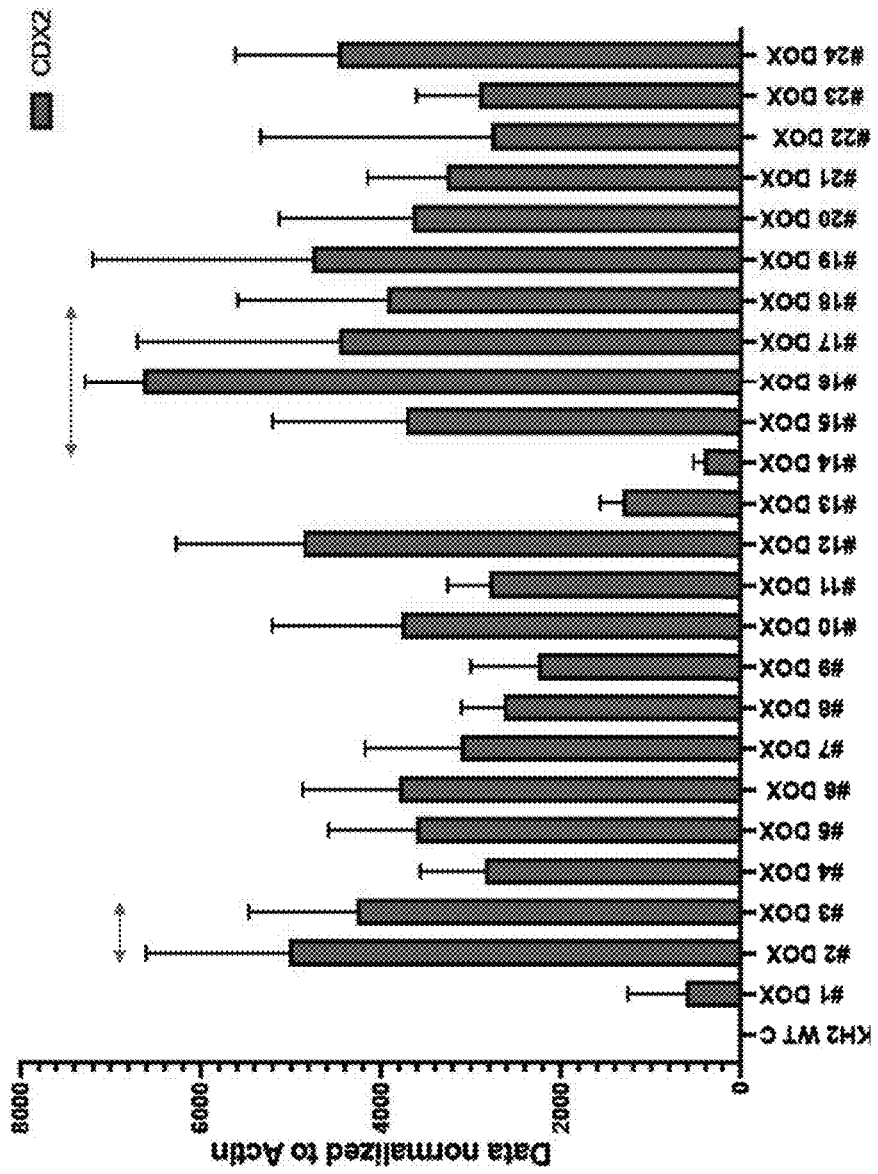

FIG. 12 shows Real-Time PCR analysis of exogenous Cdx2 expression in different KH2-Cdx2 mouse ES clones targeted with TetOn-Cdx2 in the collagen locus after treatment with DOX. KH2-WT cells were used as negative control.

Figure 13:
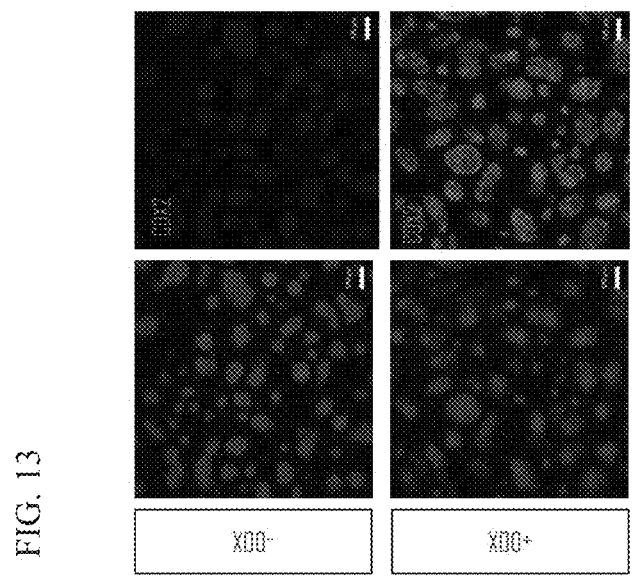

FIG. 13 shows immunostaining KH2 mouse naïve ES clone #3 targeted with TetOn-Cdx2 (KH2-Cdx2) in the collagen locus before and after treatment with DOX in naïve 2i/LIF conditions. Cdx2 was robustly expressed in the tested clone only after DOX treatment. DAPI was used for counterstaining.

Figure 14:
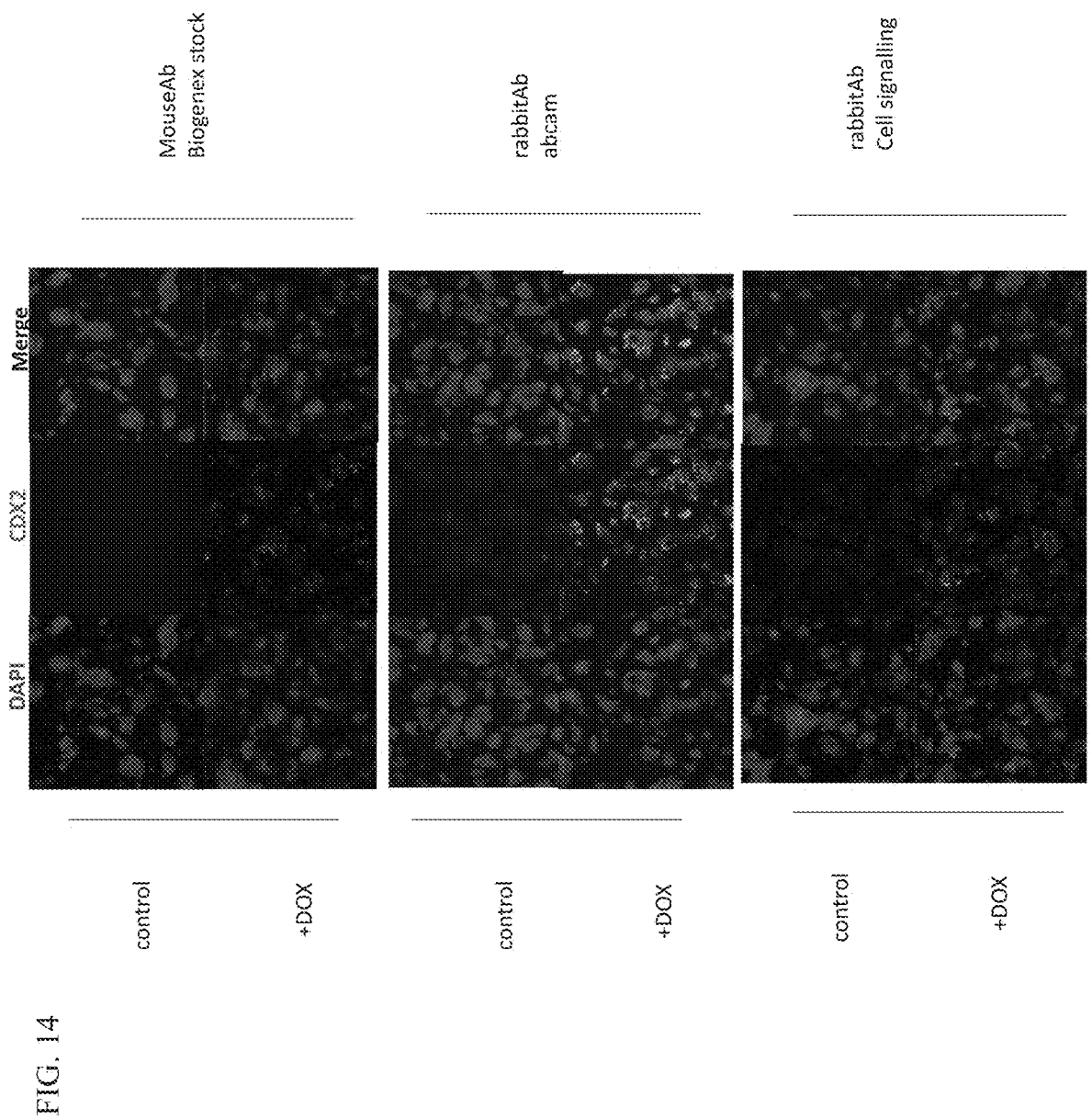

FIG. 14 shows immunostaining KH2 mouse naïve ES clone #7 targeted with TetOn-Cdx2 (KH2-Cdx2) in the collagen locus before and after treatment with DOX in naïve 2i/LIF conditions. Cdx2 was robustly expressed in the tested clone only after DOX treatment. DAPI was used for counterstaining.

Figure 15A:
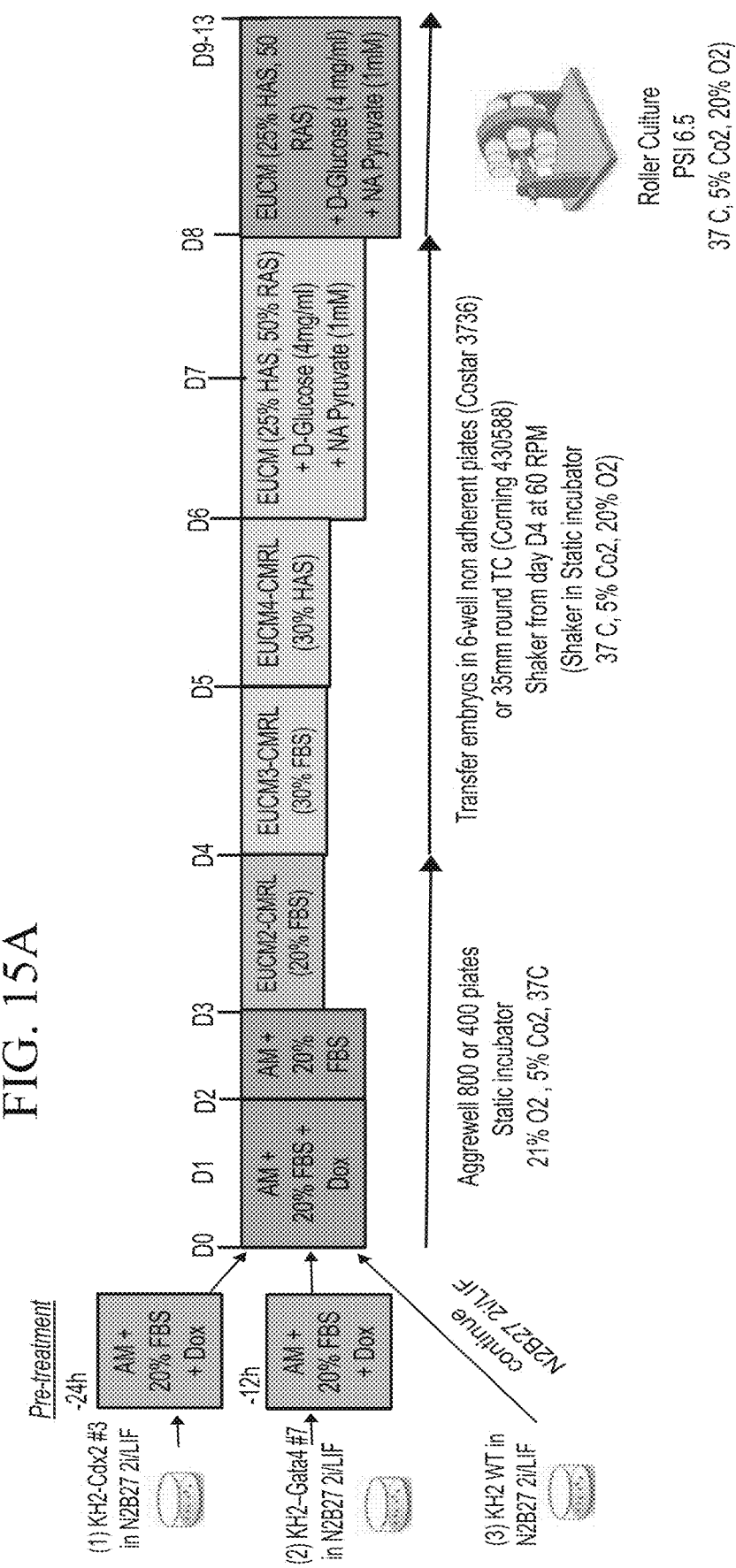

FIGS. 15A-F demonstrate that co-aggregation of naïve KH2-WT ES cells with DOX pre-treated KH2-Gata4 naïve ES cells and DOX pre-treated KH2-Cdx2 naïve ES cells, followed by ex-utero culturing leads to generation of an organized embryo. FIG. 15A is a schematic representation of the protocol. Aggregation medium (AM)—1:1 DMEM-F12 (Thermo 21331-020) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010), 0.45% BSA (SigmaAldrich A7979)

Figure 15B:
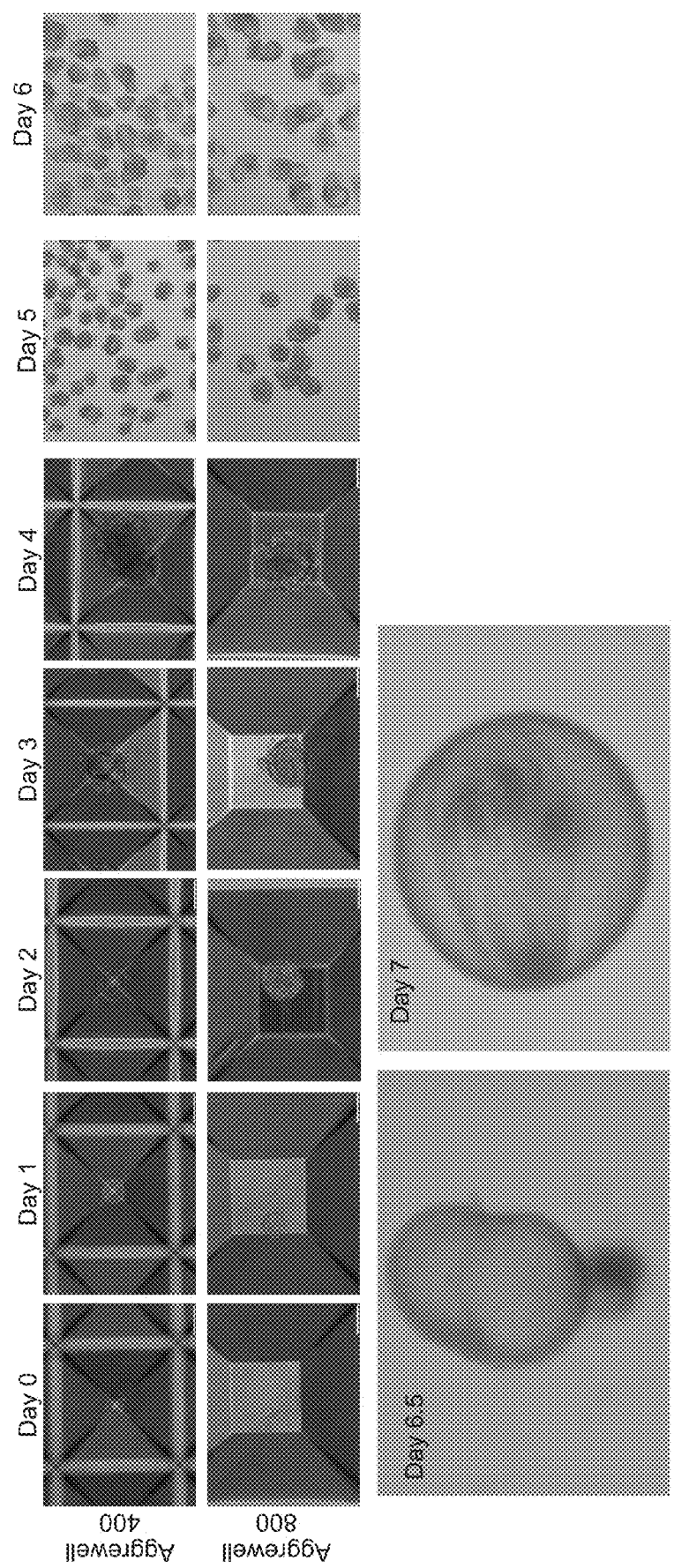

(For 500 ml Total), EUCM2-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 20% FBS (For 500 ml total). EUCM3-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% FBS (For 500 ml total). EUCM4-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% HAS (For 500 ml total). EUCM—25% DMEM (GIBCO 11880), 25% HAS, 50% Rat Serum, Glutamax 1× (GIBCO 35050038), HEPES 2 mM (GIBCO 15630056), Pen/Strep 1×. FIG. 15B shows phase contrast images of the synthetic embryos obtained at the indicated time points. At Days 4 and 5, embryos with clear egg cylinder shape are evident, with extra embryonic ectoderm (EXE) appearing on the opposite side. At Day 6.5, Yolk sac and ectoplacental cone are evident with embryo-like structure engulfed inside). At Day 7, an embryo that completed gastrulation with evident neural folds and somite formation and beating heart was evident. FIGS. 15C-F show immunostaining images of the synthetic embryos obtained. The embryo obtained at Day 7 of the protocol corresponds to an E8.5 stage embryo (FIGS. 15C-D). In FIG. 15C, the embryo demonstrates neural folds staining positive for Sox2 marker (red) and brachyury (green) staining for mesoderm. In FIG. 15D, the embryo demonstrates neural folds staining positive for Pax6 marker (green), and Sox17 marker (red) that marks the developing endodermal gut. The embryo obtained at Day 8 of the protocol corresponds to an E9.5 stage embryo (FIGS. 15E-F). In FIG. 15E, the embryo demonstrates neural tube closure and somite formation (positively stained for Sox9 in Red). Otx2 (magenta) marks forebrain region. In FIG. 15F, the embryo demonstrates advanced organ formation and normal morphology with adequate distribution of neural brain cells positively stained with Tuj1 marker (green).

Figure 16A:
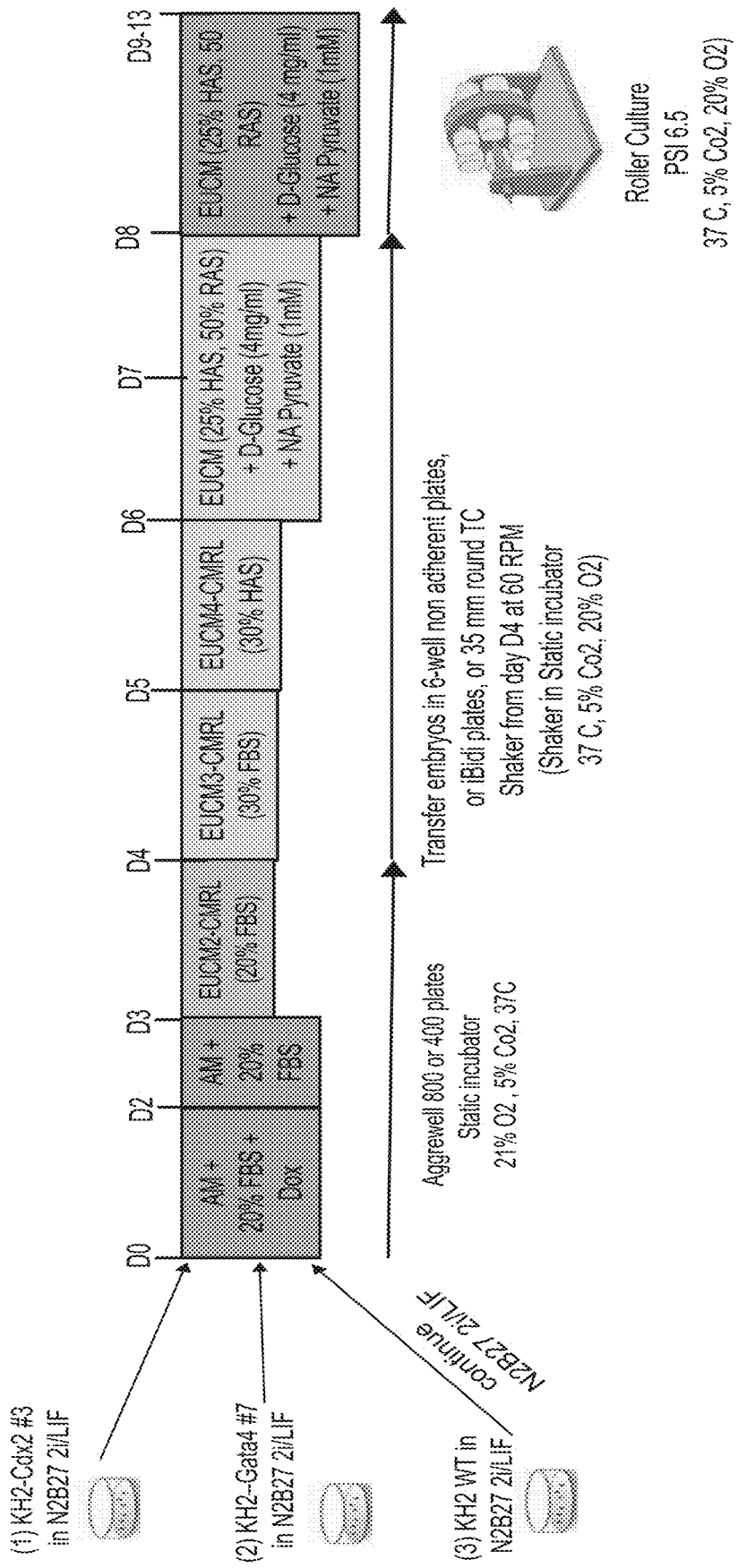
Figure 16B:
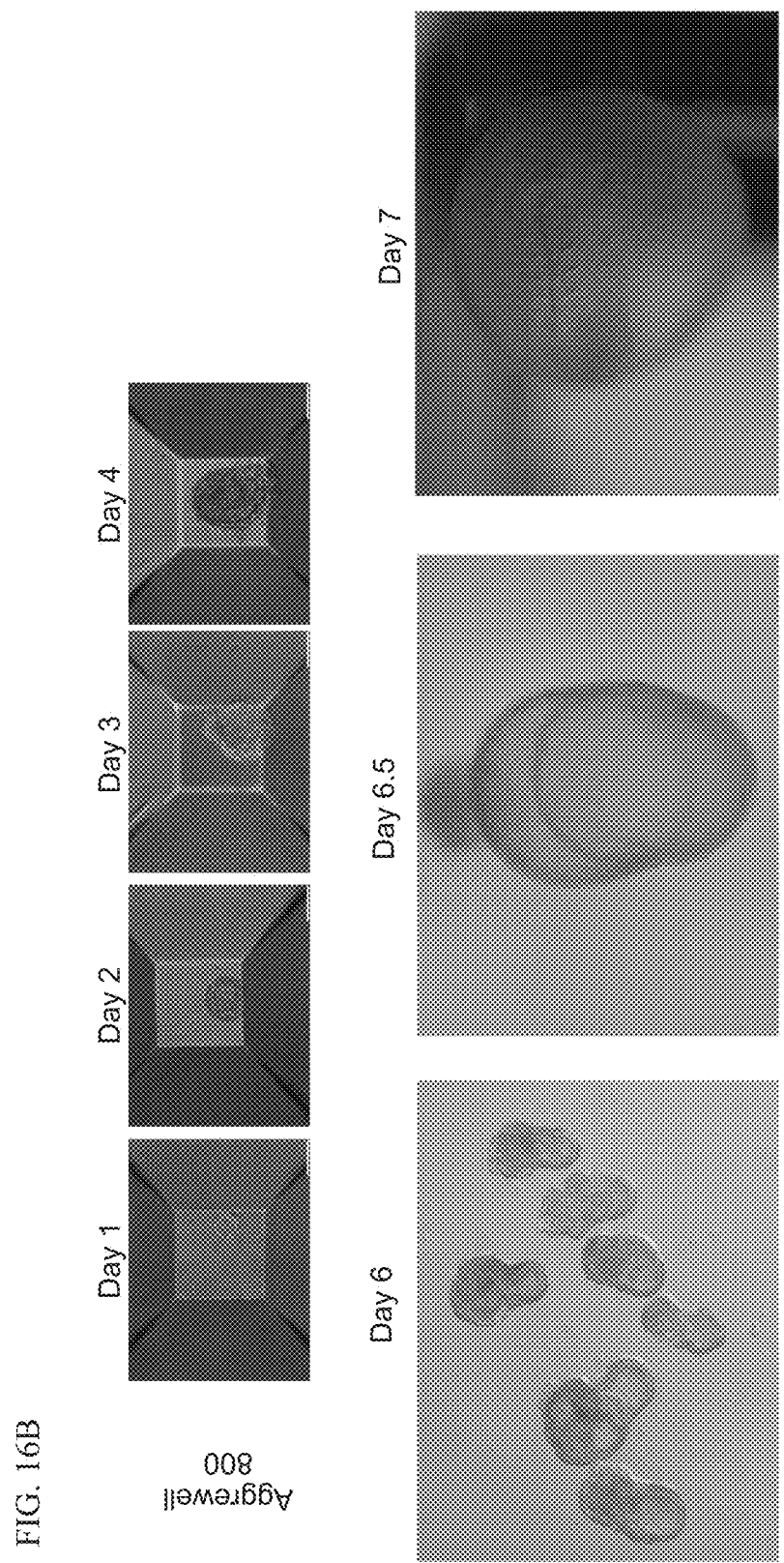

FIGS. 16A-B demonstrate that co-aggregation of KH2-WT naïve ES cells with naïve KH2-Gata4 and KH2-Cdx2 naïve cells in the presence of Dox, followed by ex-utero culturing leads to generation of an organized embryo. FIG. 16A is a schematic representation of the protocol. Aggregation media (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010), 0.45% BSA (SigmaAldrich A7979) (For 500 ml Total). EUCM2-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 20% FBS (For 500 ml total). EUCM3-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% FBS (For 500 ml total). EUCM4-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% HAS (For 500 ml total). EUCM—25% DMEM (GIBCO 11880), 25% HAS, 50% Rat Serum (RAS), Glutamax 1× (GIBCO 35050038), HEPES 2 mM (GIBCO 15630056), Pen/Strep 1×. FIG. 16B shows phase contrast images of the synthetic embryos obtained at the indicated time points. At Days 4 and 6, embryos with clear egg cylinder shape were evident, and with extra embryonic ectoderm (EXE) appearing on the opposite side. At Day 6.5, Yolk sac and ectoplacental cone were evident with embryo-like structure engulfed in side. At Day 7, an embryo that completed gastrulation with evident neural folds and early somite formation and beating heart was evident.

Figure 17A:
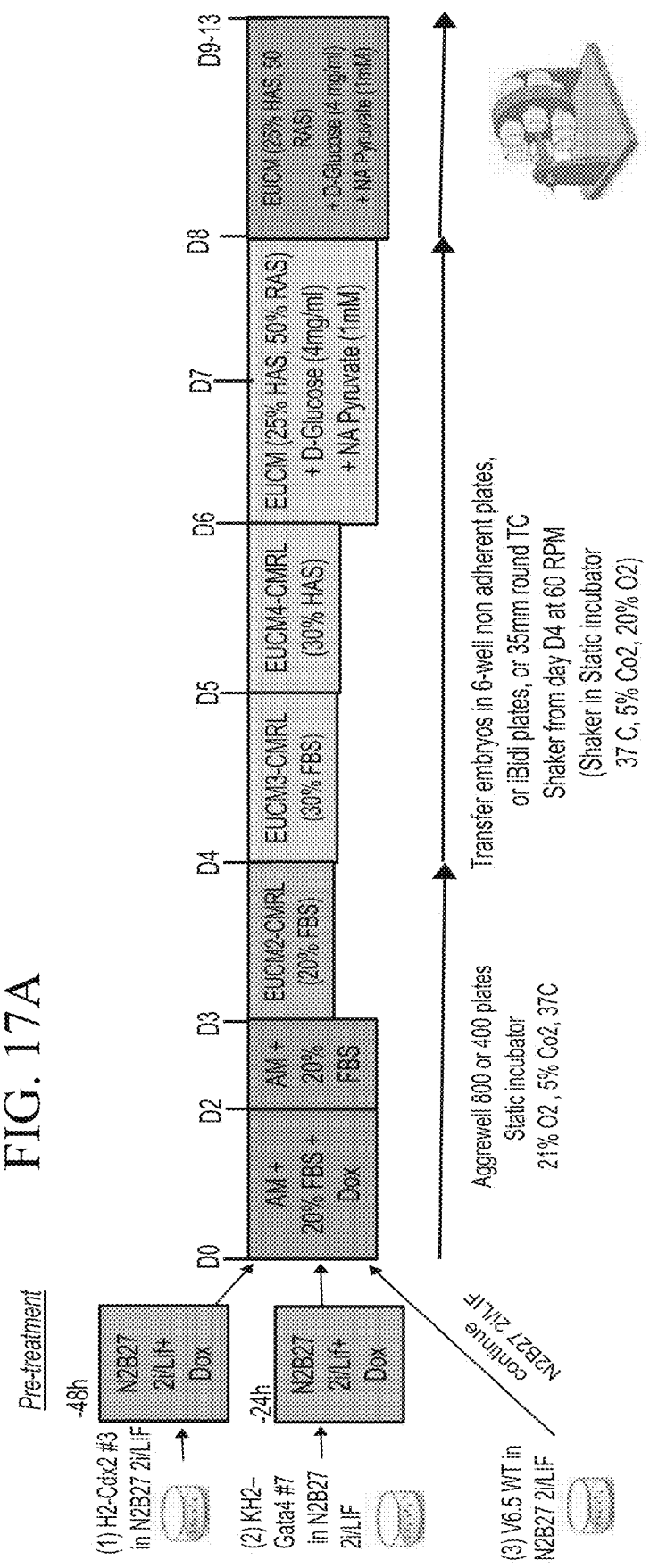
Figure 17B:
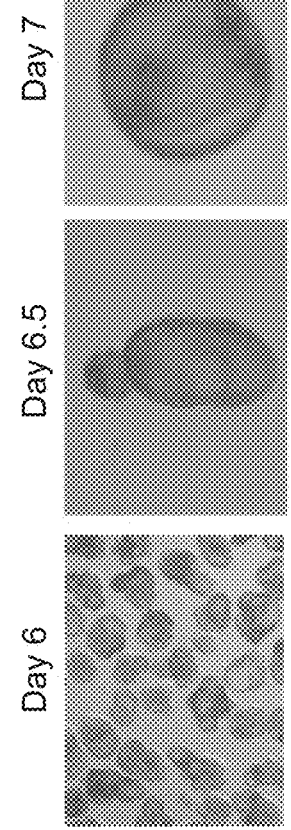

FIGS. 17A-B demonstrate that co-aggregation of KH2-WT naïve ES cells with Dox pre-treated naïve KH2-Gata4 ES cells and Dox pre-treated KH2-Cdx2 naïve ES cells, followed by ex-utero culturing leads to generation of an organized embryo. FIG. 17A is a schematic representation of the protocol. Aggregation media (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010), 0.45% BSA (SigmaAldrich A7979) (For 500 ml Total). EUCM2-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 20% FBS (For 500 ml total). EUCM3-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% FBS (For 500 ml total). EUCM4-CMRL—CMRL (Gibco 11530037), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% HAS (For 500 ml total). EUCM—25% DMEM (GIBCO 11880), 25% HAS, 50% RAS, Glutamax 1× (GIBCO 35050038), HEPES 10 mM (GIBCO 15630056), Pen/Strep 1×. FIG. 17B shows phase contrast images of the synthetic embryos obtained at the indicated time points. At Day 6, embryos with clear egg cylinder shape were evident, and with extra embryonic ectoderm (EXE) appearing on the opposite side. At Day 6.5, Yolk sac and ectoplacental cone were evident with embryo-like structure engulfed inside. At Day 7, an embryo that completed gastrulation with evident neural folds and early somite formation and beating heart was evident equivalent to E8.5.

Figure 18A:
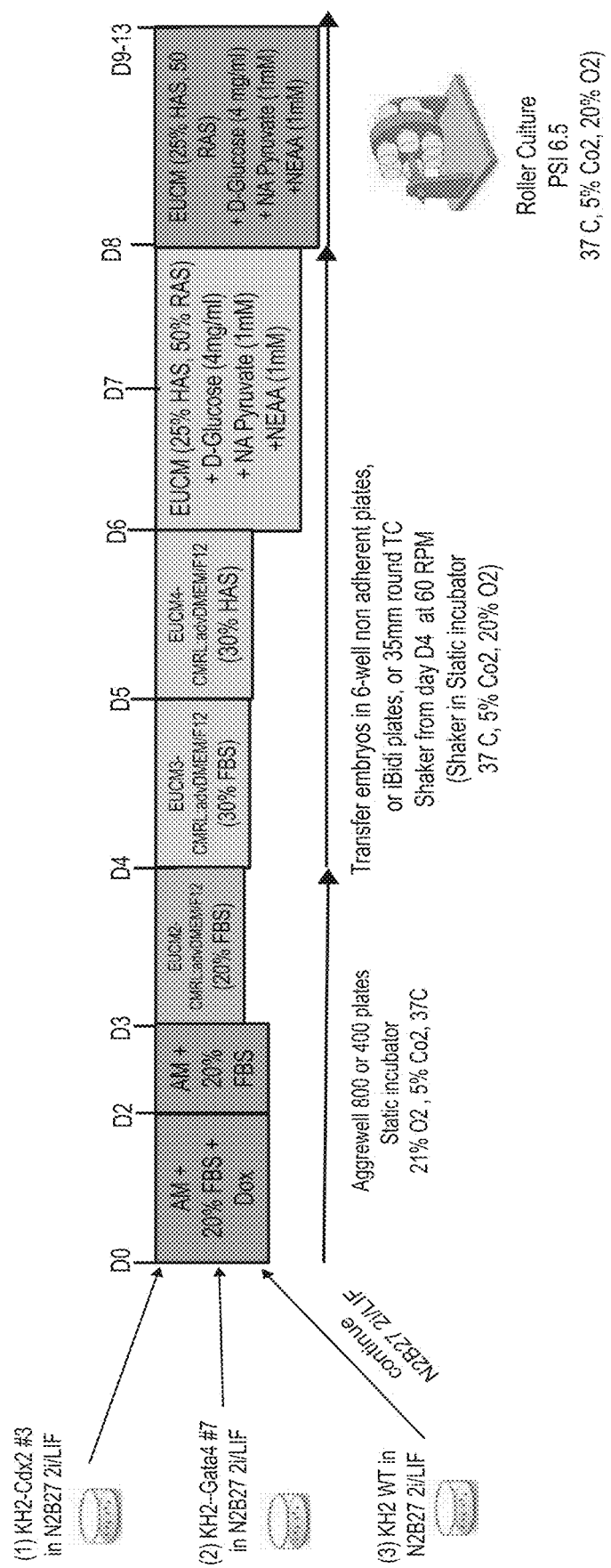

FIGS. 18A-B demonstrate that co-aggregation of KH2-WT naïve ES, cells with KH2-Gata4 naïve ES cells and KH2-Cdx2 naïve ES cells in the presence of Dox, followed by ex-utero culturing leads to generation of an organized embryo. FIG. 18A is a schematic representation of the protocol. Aggregation media (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010), 0.45% BSA (SigmaAldrich A7979) (For 500 ml Total). EUCM2-CMRL-advDMEM/F12—1:1 mix of CMRL (Gibco 11530037) & Advanced DMEM/F12 (Thermo 12634010), Glutamax 1×, Sodium pyruvate 1 mM, Pen/Strep 1×+NEAA 1×, D-Glucose 1 mg/mL, ITS-X 1× (Gibco 51500056), beta-Estradiol 8 nM, Progesterone 20 ng/ml, 20% FBS (For 500 ml total). EUCM3-CMRL-advDMEM/F12—1:1 mix of CMRL (Gibco 11530037) & Advanced DMEM/F12 (Thermo 12634010), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% FBS (For 500 ml total). EUCM4-CMRL-advDMEM/F12—1:1 mix of CMRL (Gibco 11530037) & Advanced DMEM/F12 (Thermo 12634010), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% HAS (For 500 ml total). EUCM—25% DMEM (GIBCO 11880), 25% HAS, 50% RAS, Glutamax 1× (GIBCO 35050038), HEPES 10 mM (GIBCO 15630056), Pen/Strep 1×. FIG. 18B shows phase contrast images of the synthetic embryos obtained at the indicated time points. At Days 4, and 6, embryos with clear egg cylinder shape were evident, and with extra embryonic ectoderm (EXE) appearing on the opposite side. At Day 6.5, Yolk sac, ectoplacental cone and umbilical cord invagination were evident with embryo-like structure engulfed inside. At Day 7, an embryo that completed gastrulation with evident neural folds and early somite formation and beating heart was evident.

FIGS. 19A-B demonstrate that co-aggregation of KH2-WT naïve ES cells with Dox pre-treated KH2-Gata4 naïve ES and Dox pre-treated KH2-Cdx2 naïve ES cells, followed by ex-utero culturing leads to generation of an organized embryo. FIG. 19A is a schematic representation of the protocol. Aggregation media (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010), 0.45% BSA (SigmaAldrich A7979) (For 500 ml Total). IVC1—Advanced DMEM/F12 (Gibco 12634010) Glutamax 1×, Pen/Strep 1×, ITS-X 1× (Gibco 51500056), beta-Estradiol 8 nM, Progesterone 20 ng/ml, N-acetyl-L-cysteine 25 µM and FBS or HAS as indicated (For 500 ml total). EUCM—25% DMEM (GIBCO 11880), 25% HAS, 50% RAS, Glutamax 1× (GIBCO 35050038), HEPES 2 mM (GIBCO 15630056), Pen/Strep 1×. FIG. 19B shows phase contrast images of the synthetic embryos obtained at the indicated time points. At Day 6, embryos with clear egg cylinder shape were evident, and with extra embryonic ectoderm (EXE) appearing on the opposite side. At Day 6.5, Yolk sac and ectoplacental cone were evident with embryo-like structure engulfed in side.

Figure 20A:
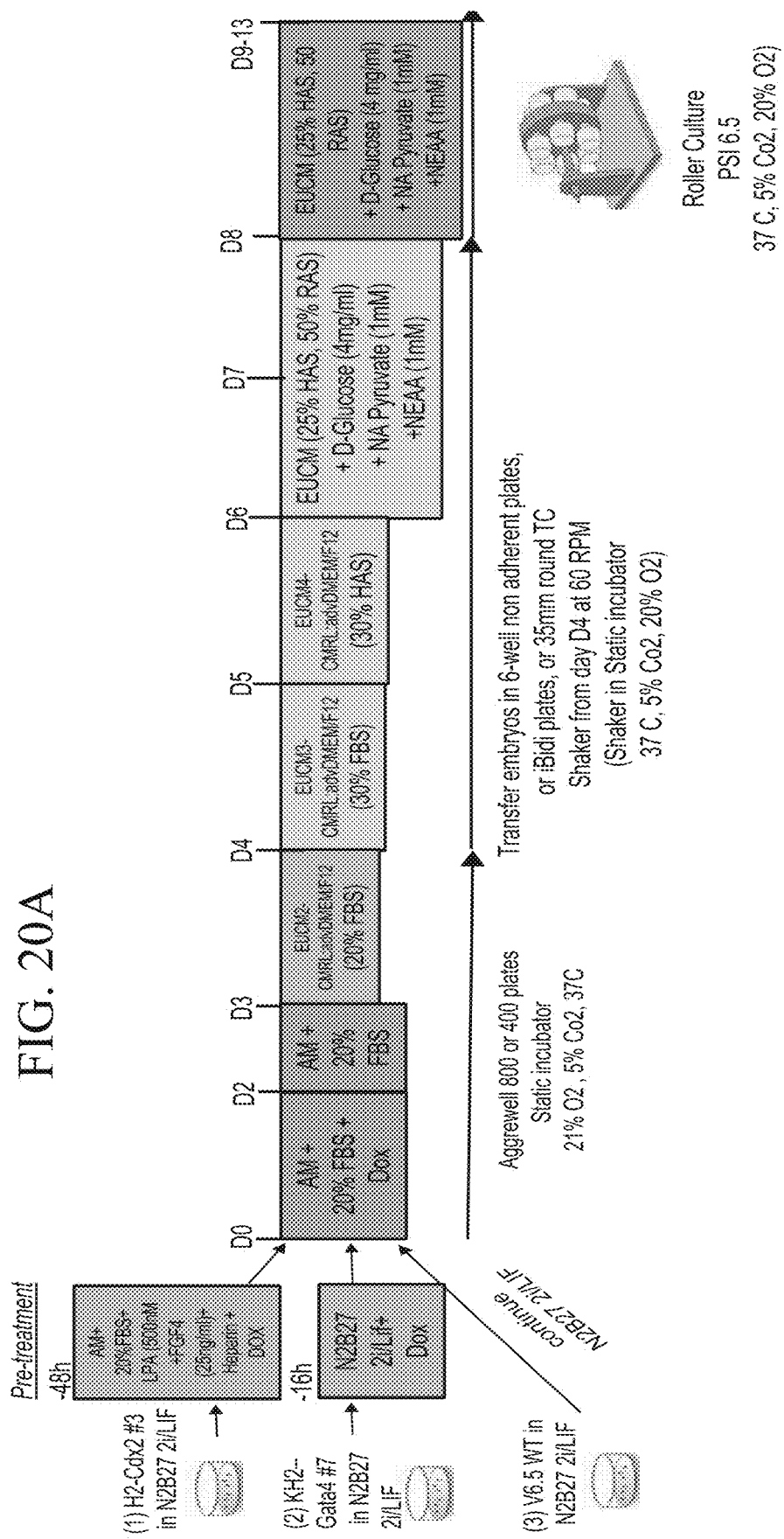
Figure 20B:
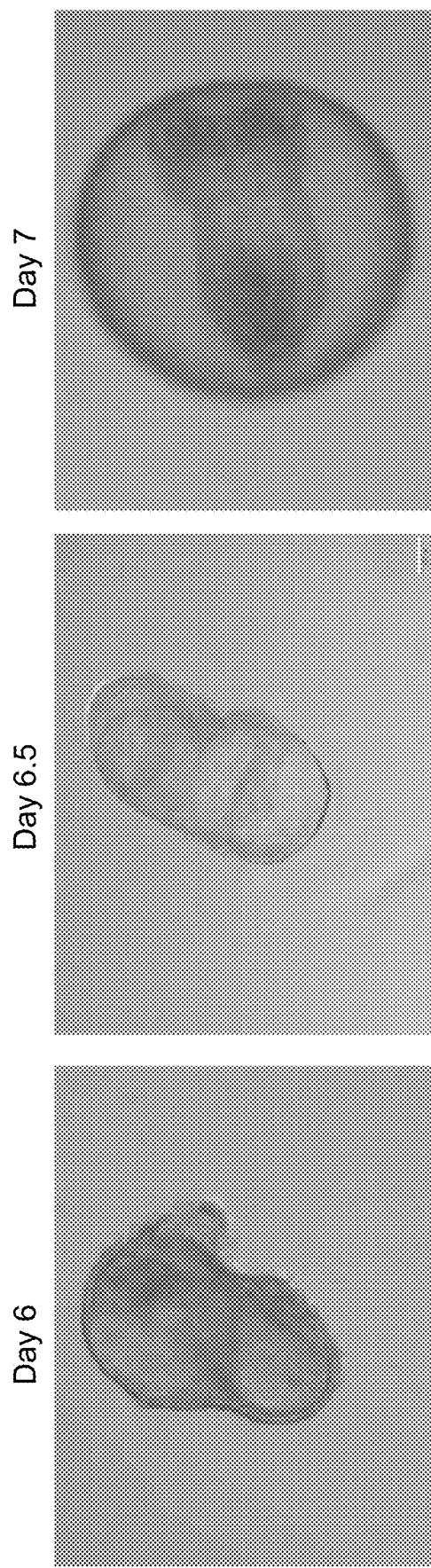

FIGS. 20A-B demonstrate that co-aggregation of KH2-WT naïve ES cells with Dox pre-treated KH2-Gata4 and Dox+FGF4+LPA pre-treated KH2-Cdx2 naïve ES cells, followed by ex-utero culturing leads to generation of an organized embryo. FIG. 20A is a schematic representation of the protocol. Aggregation media (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010), 0.45% BSA (SigmaAldrich A7979) (For 500 ml Total). EUCM2-CMRL-advDMEM/F12—1:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, D-Glucose 4 mg/mL, ITS-X 1× (Gibco 51500056), beta-Estradiol 8 nM, Progesterone 20 ng/ml, 20% FBS (For 500 ml total). EUCM3-CMRL-advDMEM/F12—1:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, D-Glucose 4 mg/mL, ITS-X 1× (Gibco 51500056), beta-Estradiol 8 nM, Progesterone 20 ng/ml, 30% FBS (For 500 ml total). EUCM4-CMRL-advDMEM/F12—1:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, D-Glucose 4 mg/mL, ITS-X 1× (Gibco 51500056), beta-Estradiol 8 nM, Progesterone 20 ng/ml, 30% HAS (For 500 ml total). EUCM—25% DMEM (GIBCO 11880), % HAS, 50% RAS, Glutamax 1× (GIBCO 35050038), HEPES 2 mM (GIBCO 15630056), Pen/Strep 1×. FIG. 20B shows phase contrast images of the synthetic embryos obtained at the indicated time points. At Day 6, embryos with clear egg cylinder shape and amnion were evident, and with extra embryonic ectoderm (EXE) appearing on the opposite side. At Day 6.5, Yolk sac and ectoplacental cone and umbilical cord invagination were evident with embryo-like structure engulfed inside. At Day 7, an embryo that completed gastrulation with evident neural folds and early somite formation and beating heart was evident.

Figure 21:
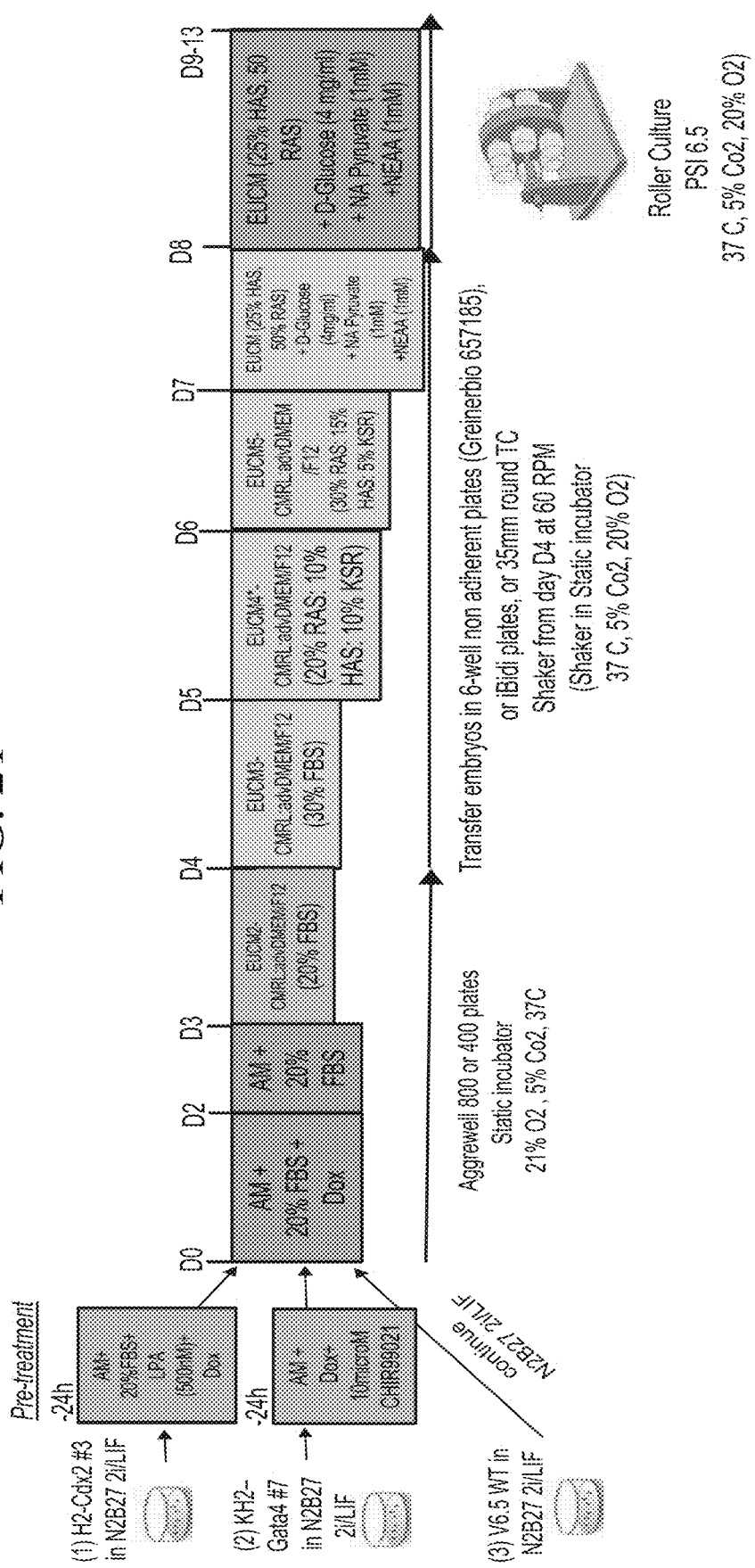

FIG. 21 shows a schematic protocol for co-aggregation of KH2-WT naïve cells with Dox+CHIR99021 pre-treated KH2-Gata4 naïve cells and Dox+LPA pre-treated KH2-Cdx2 naïve cells, followed by ex-utero culturing that leads to generation of an organized embryo. Aggregation media (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010), 0.45% BSA (SigmaAldrich A7979) (For 500 ml Total). EUCM2-CMRL-advDMEM/F12—1:4 mix of CMRL (Gibco 11530037) & Advanced DMEM/F12 (Thermo 12634010), Glutamax 1×, Sodium pyruvate 0.5 mM, Pen/Strep 1×+NEAA 0.5×, extra D-Glucose 2 mg/mL, ITS-X 1× (Gibco 51500056), beta-Estradiol 8 nM, Progesterone 20 ng/ml, % FBS (For 500 ml total). EUCM3-CMRL-advDMEM/F12—4:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, +Extra D-Glucose 2 mg/mL, ITS-X 1× (Gibco 51500056), beta-Estradiol 8 nM, Progesterone 20 ng/ml, 30% FBS (For 500 ml total). EUCM4*-CMRL-advDMEM/F12—4:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, extra D-Glucose 3 mg/mL, ITS-X 1× (Gibco 51500056), beta-Estradiol 8 nM, Progesterone 20 ng/ml, % RAS, 10% HAS, 10% KSR, HEPES 2 mM (GIBCO 15630056) (For 500 ml total). EUCM5-CMRL-advDMEM/F12—4:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, +extra D-Glucose 3 mg/mL, ITS-X 1× (Gibco 51500056), beta-Estradiol 8 nM, Progesterone 20 ng/ml, 30% RAS, 15% HAS, 5% KSR, HEPES 2 mM (GIBCO 15630056) (For 500 ml total). EUCM—25% Advanced DMEM/F12 (Thermo 12634010), 25% HAS, 50% RAS, Glutamax 1× (GIBCO 35050038), HEPES 2 mM (GIBCO 15630056), Pen/Strep 1×.

Figure 22:
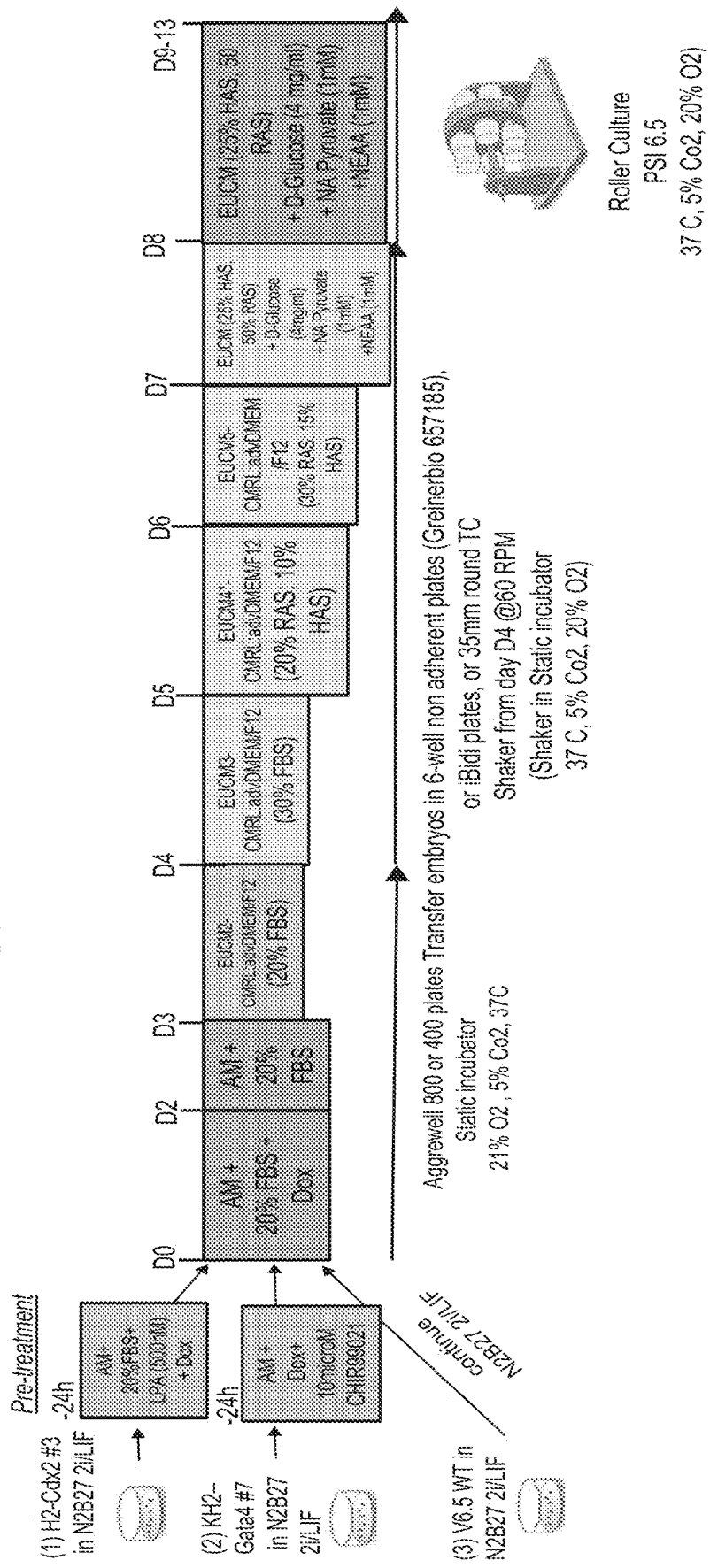

FIG. 22 shows a schematic protocol for co-aggregation of KH2-WT naïve ES cells with Dox+CHIR99021 pre-treated KH2-Gata4 naïve ES cells and Dox+LPA pre-treated KH2-Cdx2 naïve cells, followed by ex-utero culturing that leads to generation of an organized embryo. Aggregation media (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010), 0.45% BSA (SigmaAldrich A7979) (For 500 ml Total). EUCM2-CMRL-advDMEM/F12:1:4 mix of CMRL (Gibco 11530037) & Advanced DMEM/F12 (Thermo 12634010), Glutamax 1×, Sodium pyruvate 0.5 mM, Pen/Strep 1×+NEAA 0.5×, extra D-Glucose 2 mg/mL, ITS-X 1× (Gibco 51500056), beta-Estradiol 8 nM, Progesterone 20 ng/ml, % FBS (For 500 ml total). EUCM3-CMRL-advDMEM/F12: 4:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, +Extra D-Glucose 2 mg/mL, ITS-X 1× (Gibco 51500056), beta-Estradiol 8 nM, Progesterone 20 ng/ml, 30% FBS (For 500 ml total). EUCM4*-CMRL-advDMEM/F12—4:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, extra D-Glucose 3 mg/mL, ITS-X 1× (Gibco 51500056), beta-Estradiol 8 nM, Progesterone 20 ng/ml, % RAS, 10% HAS+HEPES 2 mM (GIBCO 15630056) (For 500 ml total). EUCM5-CMRL-advDMEM/F12—4:1 mix of CMRL (Gibco 11530037) & Advanced DMEM/F12 (Thermo 12634010), Glutamax 1×, Sodium pyruvate 0.5 mM, Pen/Strep 1×+NEAA 0.5×, +extra D-Glucose 3 mg/mL, ITS-X 1× (Gibco 51500056), beta-Estradiol 8 nM, Progesterone 20 ng/ml, 30% RAS, 15% HAS, HEPES 2 mM (GIBCO 15630056) (For 50 0 ml total). EUCM—25% Advanced DMEM/F12 (Thermo 12634010), 25% HAS, 50% RAS, Glutamax 1× (GIBCO 35050038), HEPES 2 mM (GIBCO 15630056), Pen/Strep 1×.

Figure 23A:
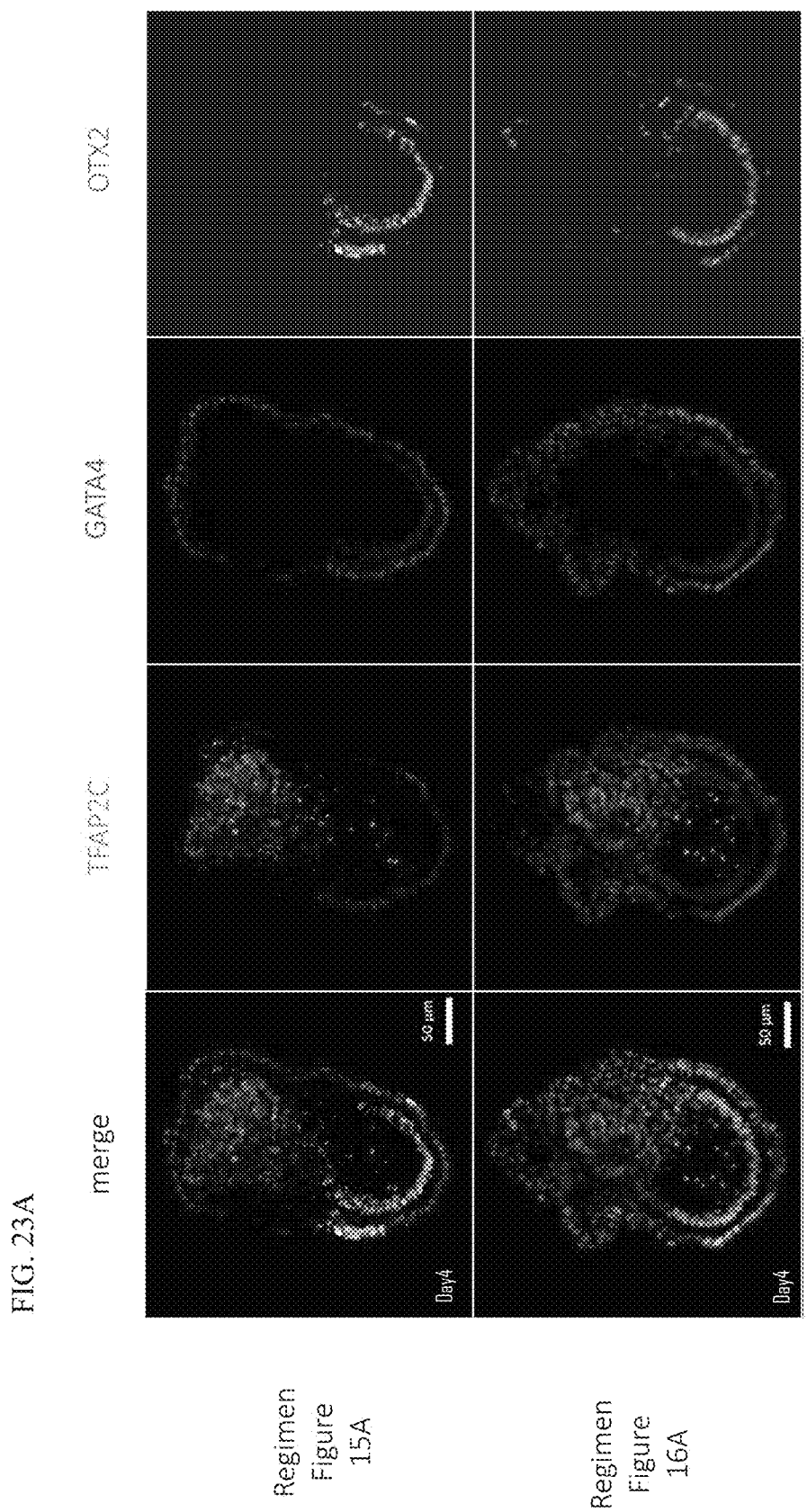
Figure 23B:
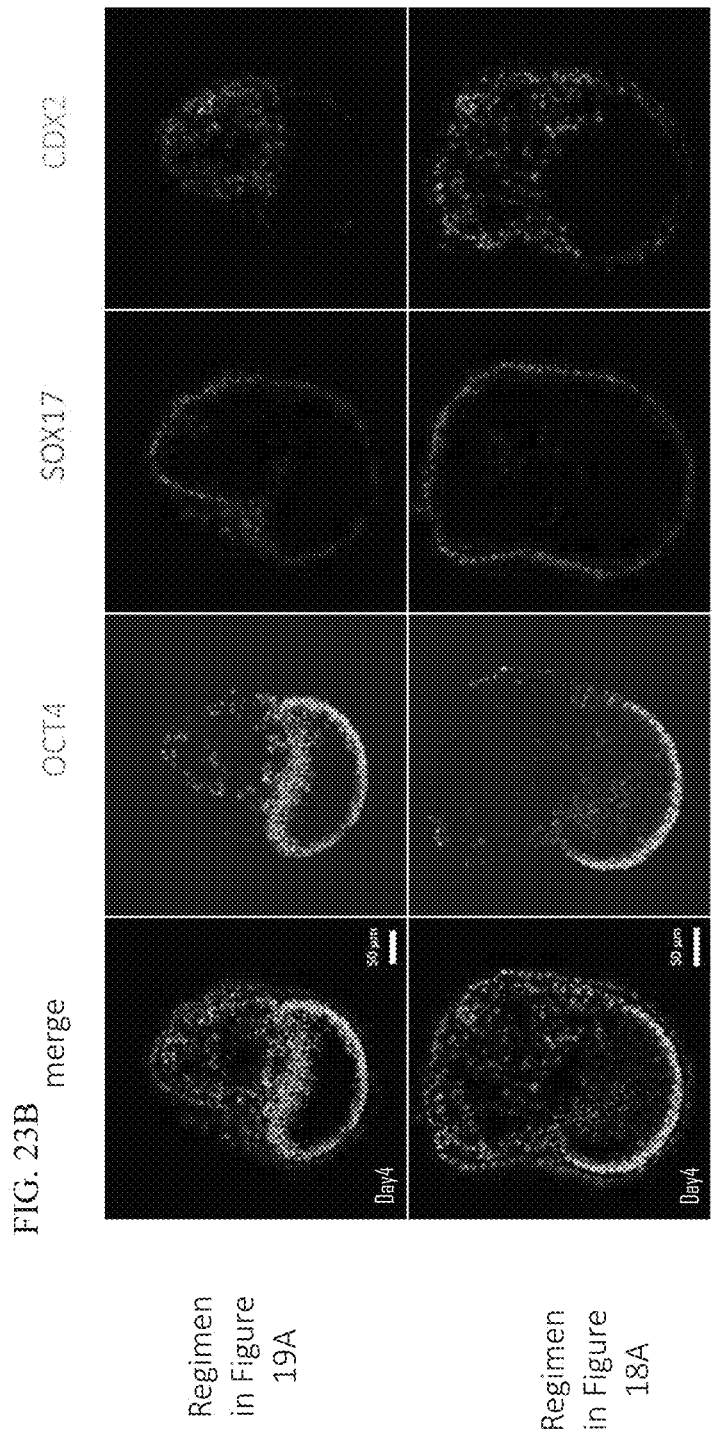
Figure 23C:
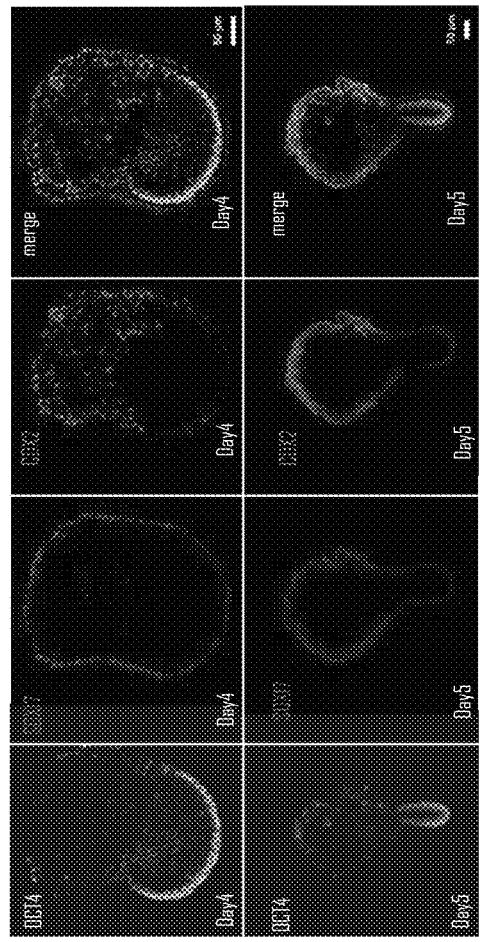
Figure 23D:
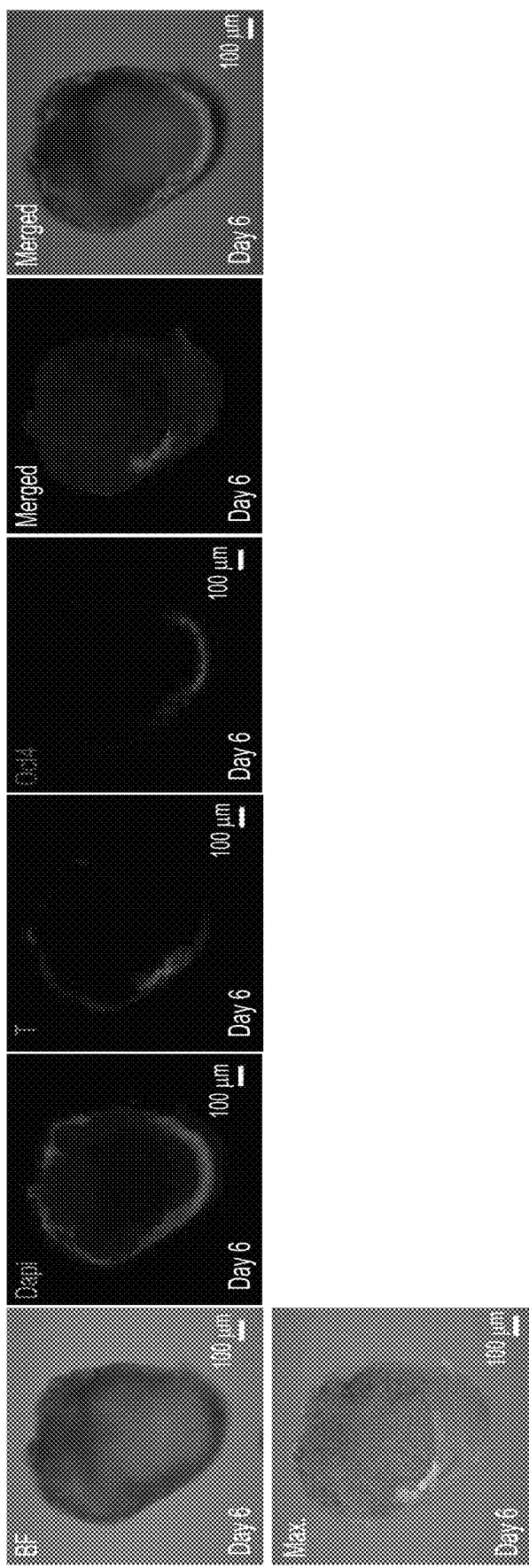

FIGS. 23A-D shows immunostaining images of representative synthetic embryos obtained according to the protocols described in Example 2 demonstrating generation of organized synthetic embryos. FIG. 23A shows immunostaining of representative day 4 mouse synthetic embryos from the indicated regimens. OTX2 (grey) was used to stain the primed pluripotent epiblast, Gata4 (red) was used to stain extraembryonic primitive endoderm progeny, and TFAP2C (green) to mark trophoblast lineage. Images show normal embryo structure with egg cylinder morphology, in which the trophoblast EXE and pluripotent epiblast self-organize on opposite sides pf the embryo as expected, and that Gata4 primitive endoderm cells surround the embryo. FIG. 23B shows immunostaining of representative day 4 mouse synthetic embryos from the indicated regimens. Oct4 (grey) was used to stain the primed pluripotent epiblast in the egg cylinder shaped epiblast, Sox17 (red) was used to stain extraembryonic primitive endoderm progeny, and Cdx2 to mark trophoblast lineage. Images show normal embryo structure with egg cylinder morphology, in which the trophoblast EXE and pluripotent epiblast (Oct4+ region) self-organize to opposite sides of the Cdx2+ region, and that Sox17+ primitive endoderm cells surround the embryos. FIG. 23C shows immunostaining of representative day 4 or day 5 mouse synthetic embryos from the indicated regimens. Oct4 (grey) was used to stain the primed pluripotent epiblast in the egg cylinder shaped epiblast, Sox17 (red) was used to stain extraembryonic primitive endoderm progeny, and Cdx2 to mark trophoblast lineage. Images show normal embryo structure with egg cylinder morphology, in which the trophoblast EXE and pluripotent epiblast (Oct4+ region) self-organize to opposite sides of the Cdx2+ region, and that Sox17+ primitive endoderm cells surround the embryos. FIG. 23D shows immunostaining of representative mouse synthetic embryos from the regimen shown in FIG. 21). Oct4 (Magenta) was used to stain the primed pluripotent epiblast in the egg cylinder shaped epiblast. T/Brachyury which marks the emergence of the primitive streak that is stained in Green. DAPI is in blue for counterstain. Day 6 egg cylinder shaped mouse embryoids show primitive streak formation and imitation of gastrulation at day 7 of the protocol as evident by specific immunostaining.

Figure 24:
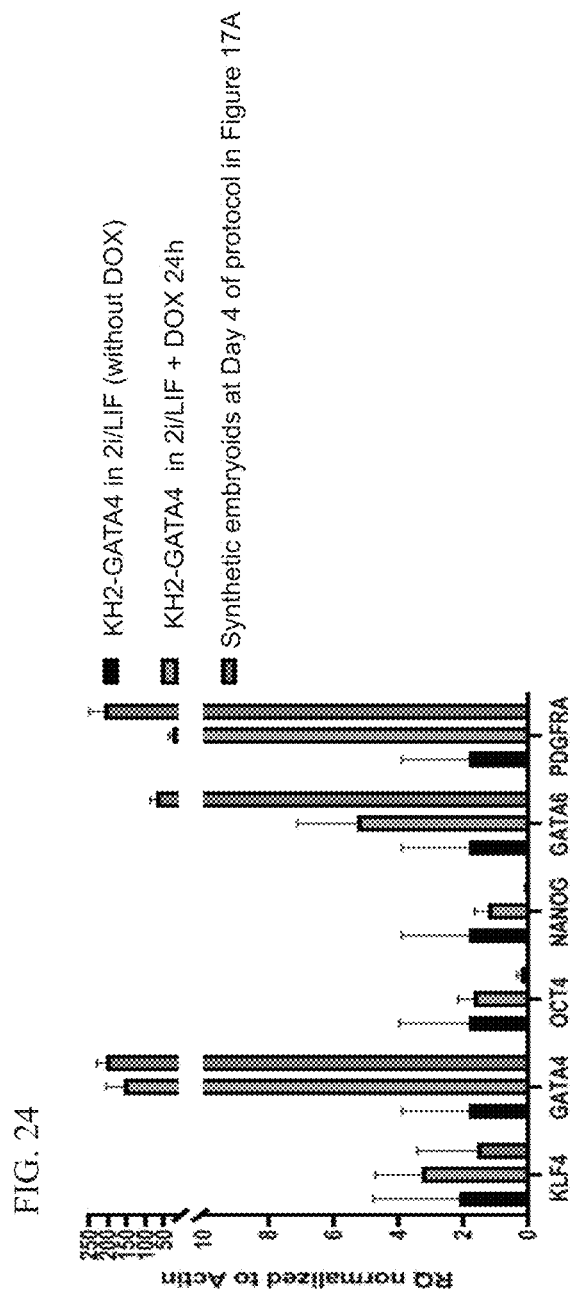

FIG. 24 demonstrates endogenous expression of the indicated markers in KH2-Gata4 naïve ES cells prior to and following Dox administration and in 4 Days synthetic embryos obtained according to the protocol described in FIG. 17A, as determined by Real-time PCR.

Figure 25:
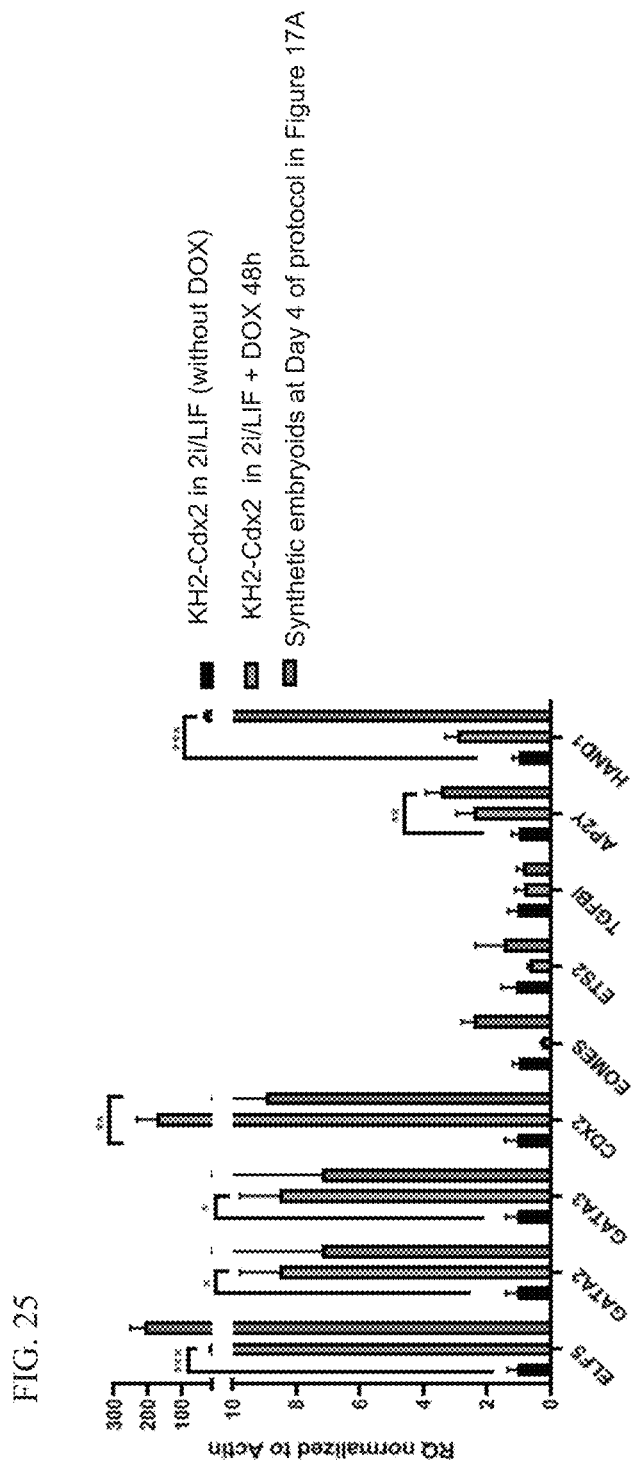

FIG. 25 demonstrates endogenous expression of the indicated markers in KH2-Cdx2 naïve ES cells prior to and following Dox administration and in 4 Days synthetic embryos obtained according to the protocol described in FIG. 17A, as determined by Real-time PCR.

Figure 26:
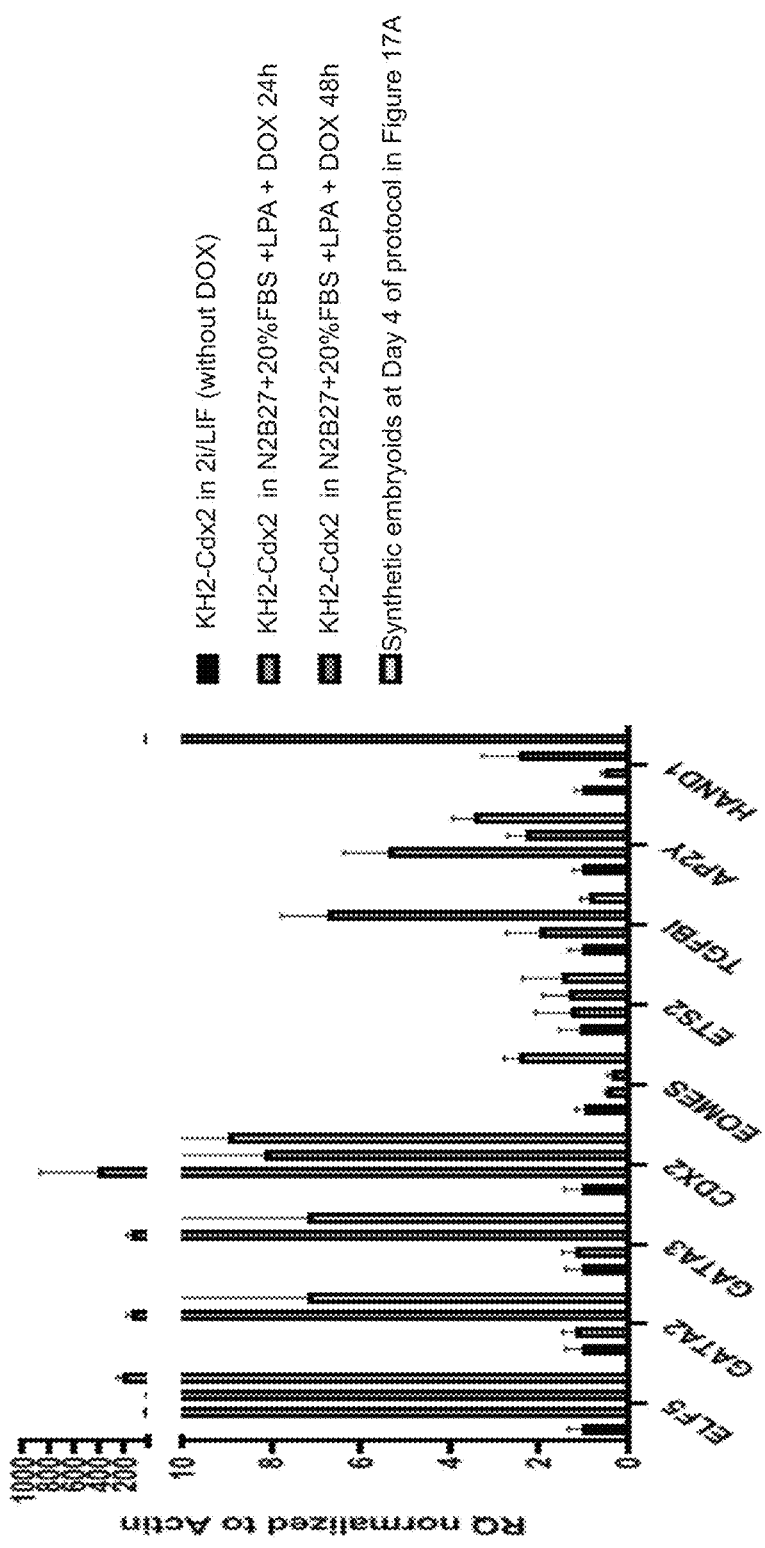

FIG. 26 demonstrates endogenous expression of the indicated markers in KH2-Cdx2 naïve cells prior to and following Dox and LPA administration and in 4 Days synthetic embryos obtained according to the protocol described in FIG. 19A), as determined by Real-time PCR.

Figure 27:
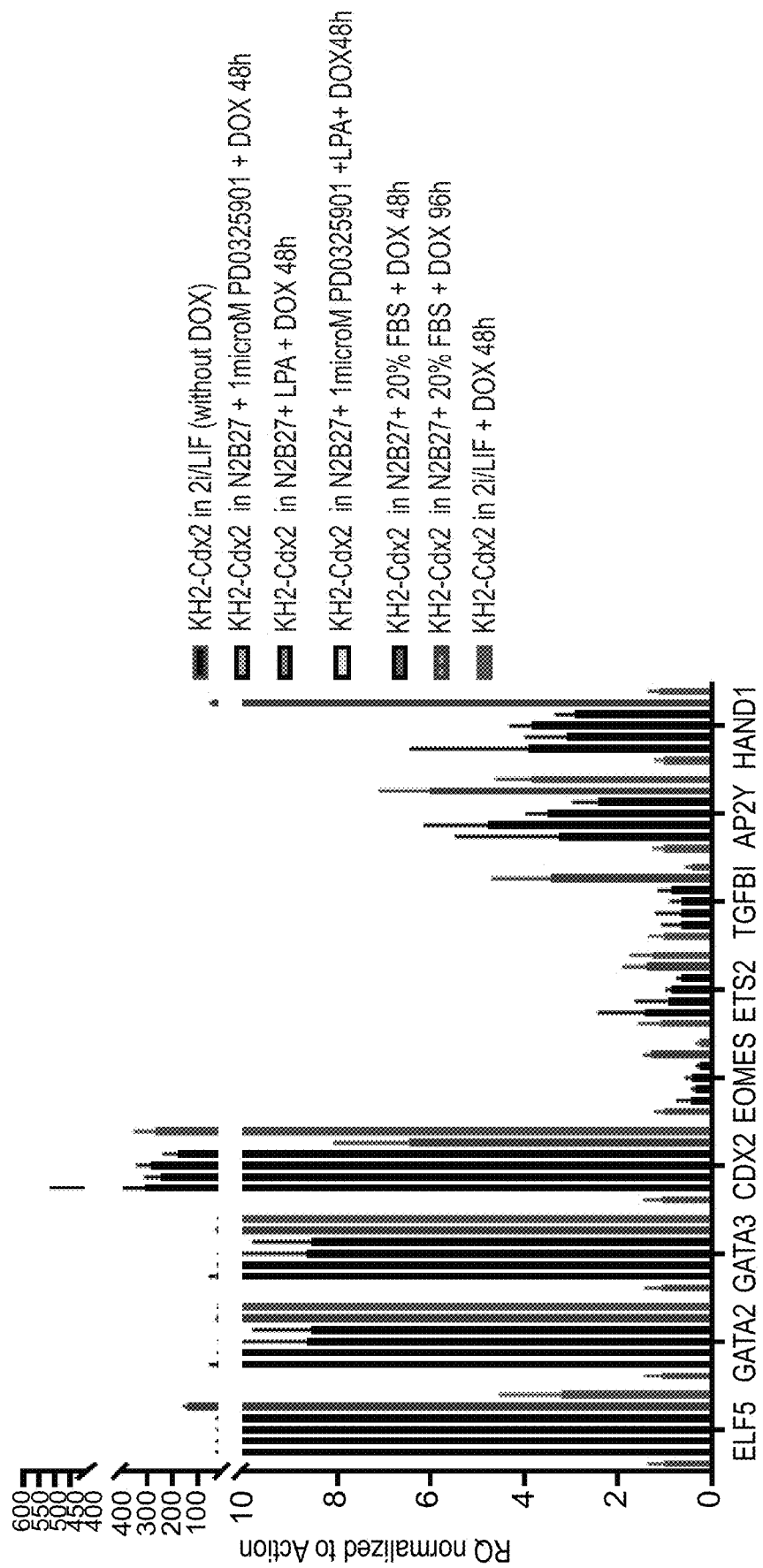

FIG. 27 demonstrates endogenous expression of the indicated markers in KH2-Cdx2 naïve ES cells prior to and following treatment with Dox and the indicated media and factors, as determined by Real-time PCR.

Figure 28:
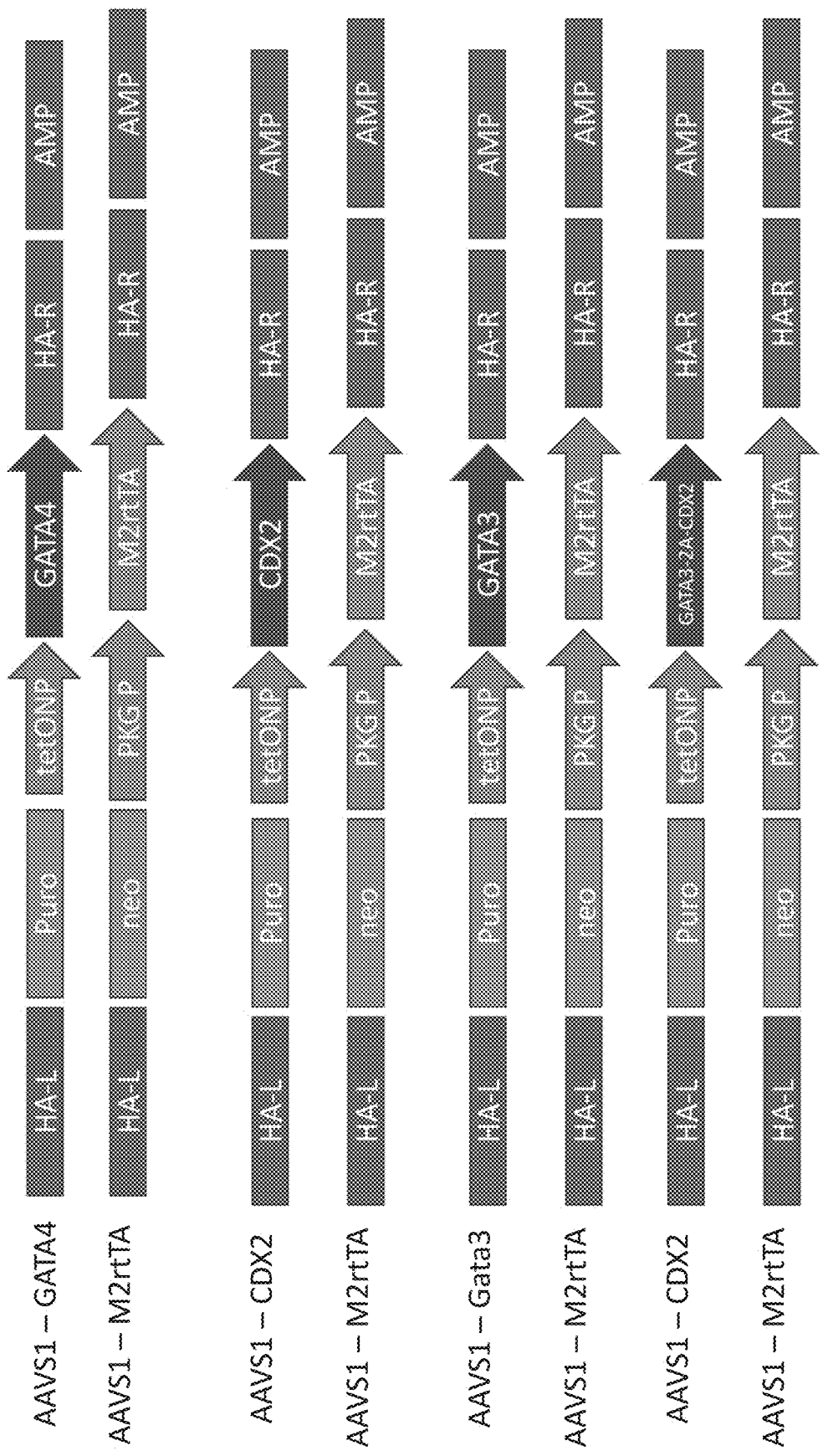

FIG. 28 shows schematic representations of targeting vectors designed to generate human TetON inducible Gata4, or Cdx2 or Gata3 of Gata3-2A-Cdx2 overexpression inserts.

Figure 29:
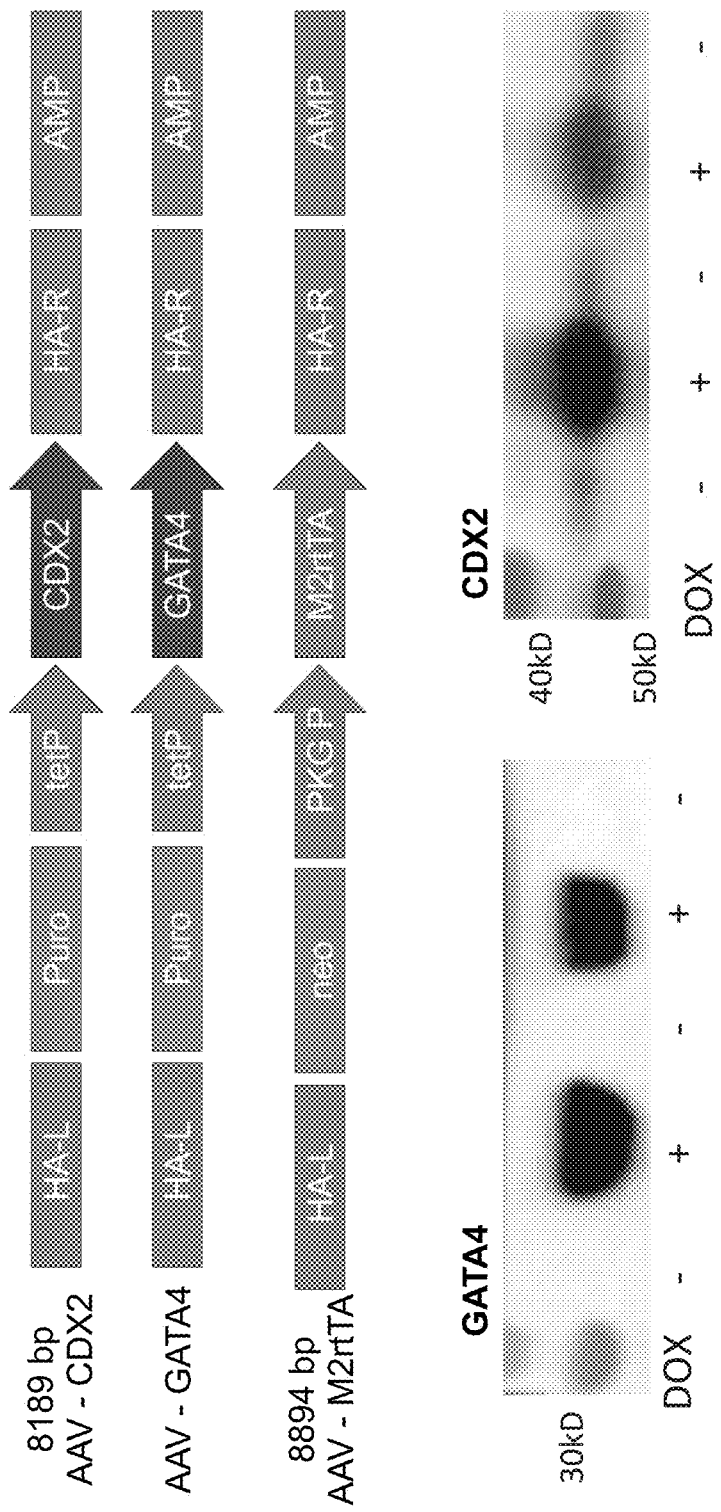

FIG. 29 demonstrates human naïve PSC clones correctly targeted for either GATA4 or CDX2 overexpression. Shown the targeting schemes and western blot analysis before and after DOX treatment which showed specific overexpression of the respective TF following DOX.

Figure 30:
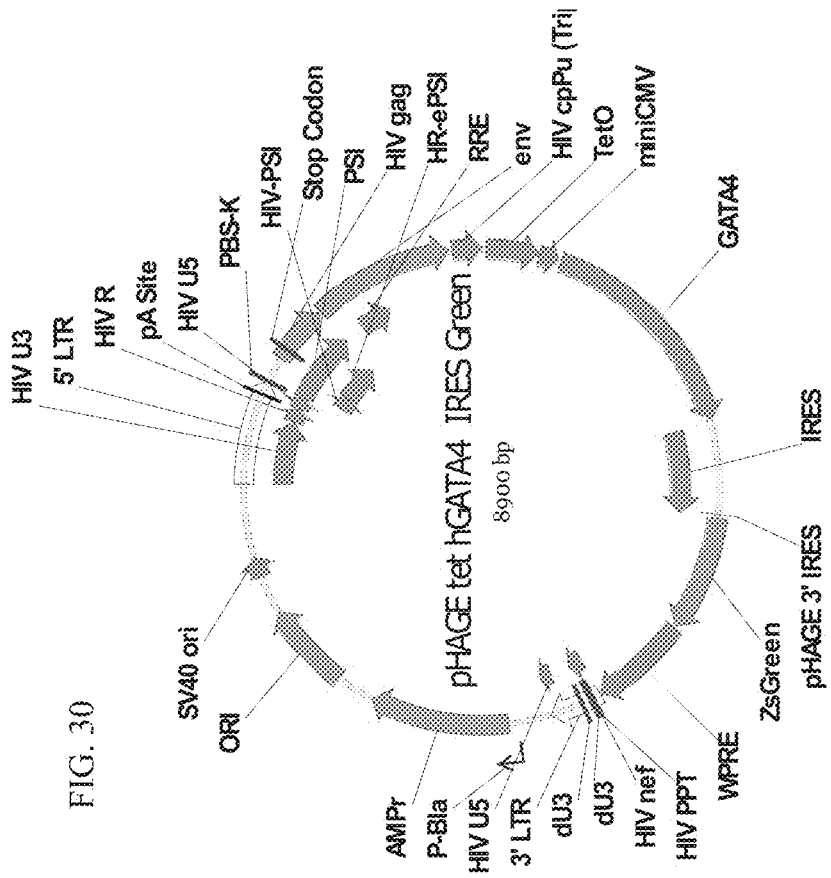

FIG. 30 shows plasmid design for generating a lentivirus allowing TetOn inducible Gata4 overexpression after Dox treatment of lentiviral infected mouse or human PSCs. Green reporter is also DOX responsive. This lentivirus can be used with PSCs already expressing M2RTTA or by co-infecting with FUW-CAGGS-M2Rtta encoding lentivirus.

Figure 31:
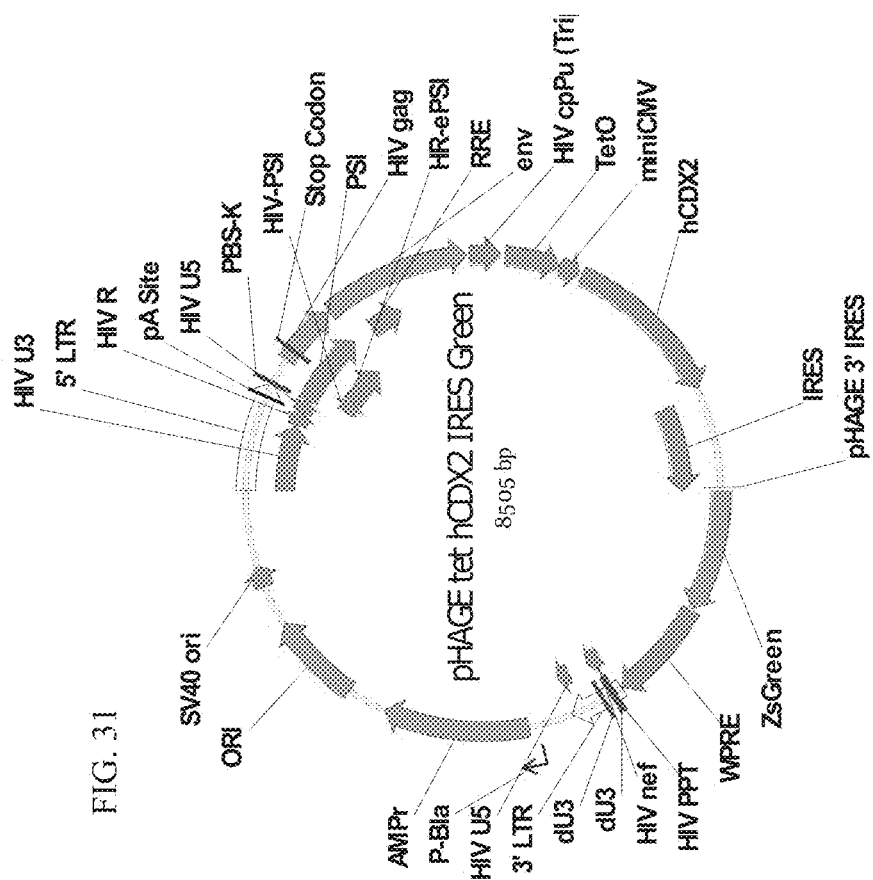

FIG. 31 shows plasmid design for generating a lentivirus allowing TetOn inducible CDX2 overexpression after Dox treatment of lentiviral infected mouse or human PSCs. Green reporter is also DOX responsive. This lentivirus can be used with PSCs already expressing M2RTTA or by co-infecting with FUW-CAGGS-M2Rtta encoding lentivirus.

Figure 32:
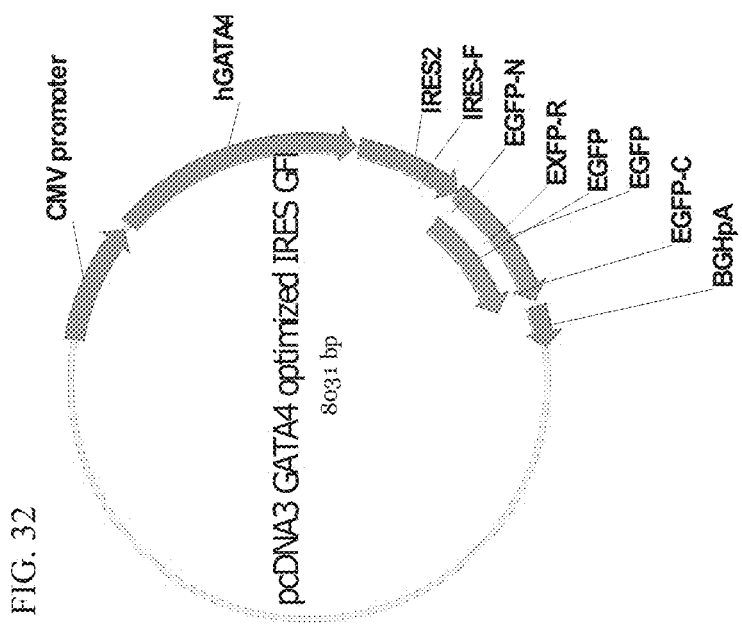

FIG. 32 shows plasmid design of pcDNA3 plasmid that is used for transient transfection of mouse or human naïve PSCs. It encodes GATA4-IRES-Green fluorescence under a CMV promoter.

Figure 33:
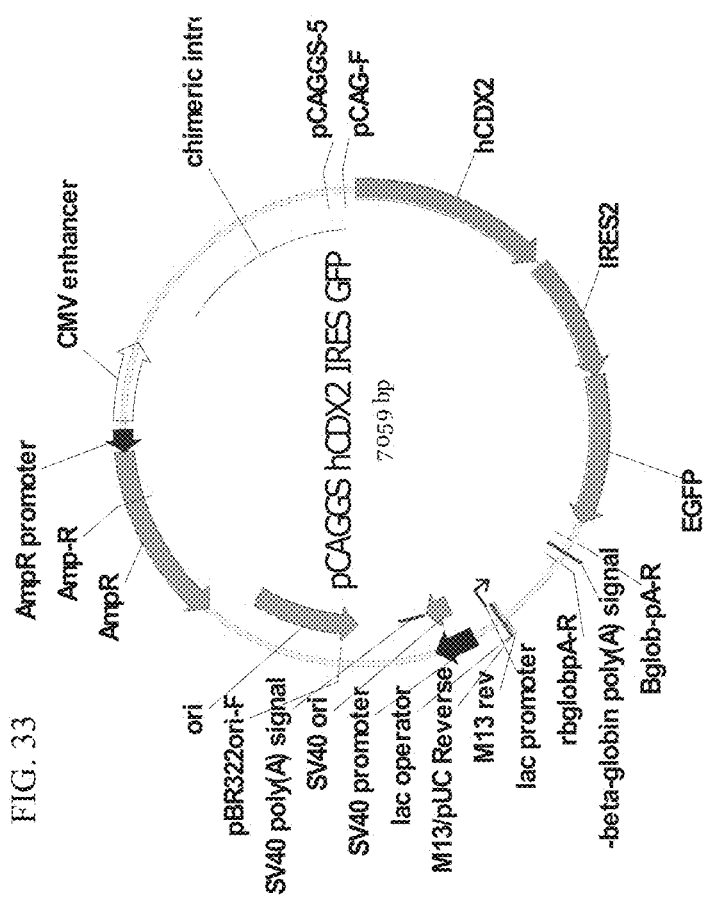

FIG. 33 shows plasmid design that is used for transient transfection of human naïve PSCs. It encodes human CDX2-IRES-Green fluorescence under a CAGGS promoter.

Figure 34:
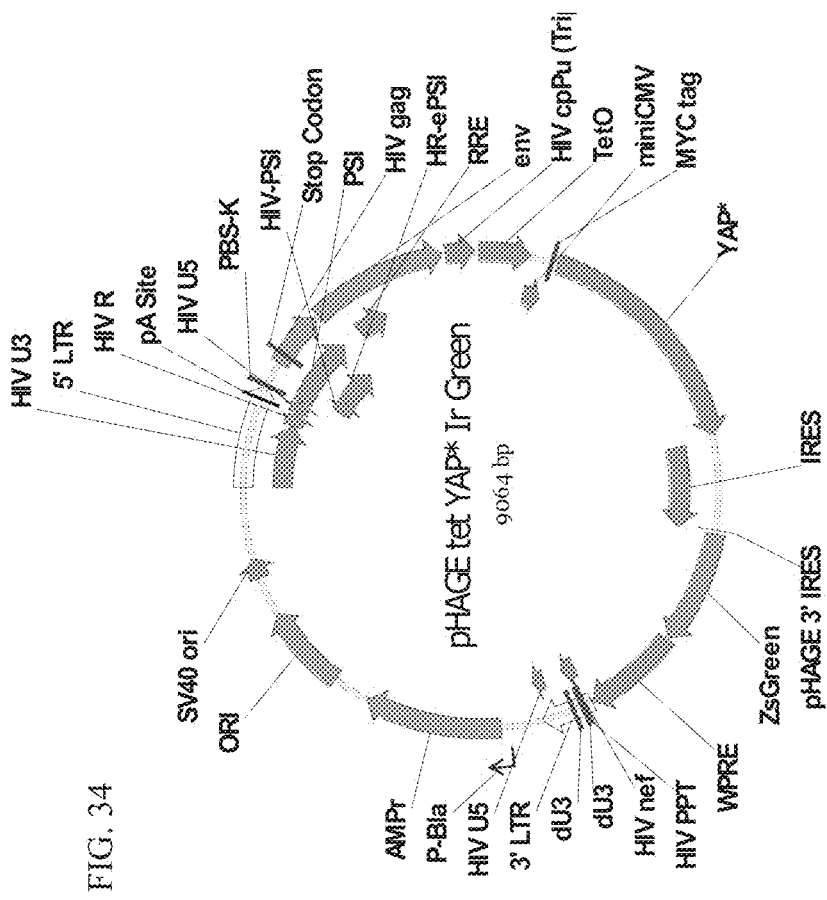

FIG. 34 shows plasmid design for generating a human lentivirus allowing TetOn inducible YAP*mut (carries a mutant that it enforces YAP nuclear localization) overexpression after Dox treatment of lentiviral infected mouse or human PSCs. Green GFP reporter is also DOX responsive. This lentivirus can be used with PSCs already expressing M2RTTA or by co-infecting with FUW-CAGGS-M2Rtta encoding lentivirus. For this construct the constitutively active(mut) human YAP was used—Serines at positions 61, 109, 127, 128, 131, 163, 164, and 381 changed to Alanine (phosphorylation sites), see addgene entry #27371 from which the insert was taken (Yap-mut).

Figure 35:
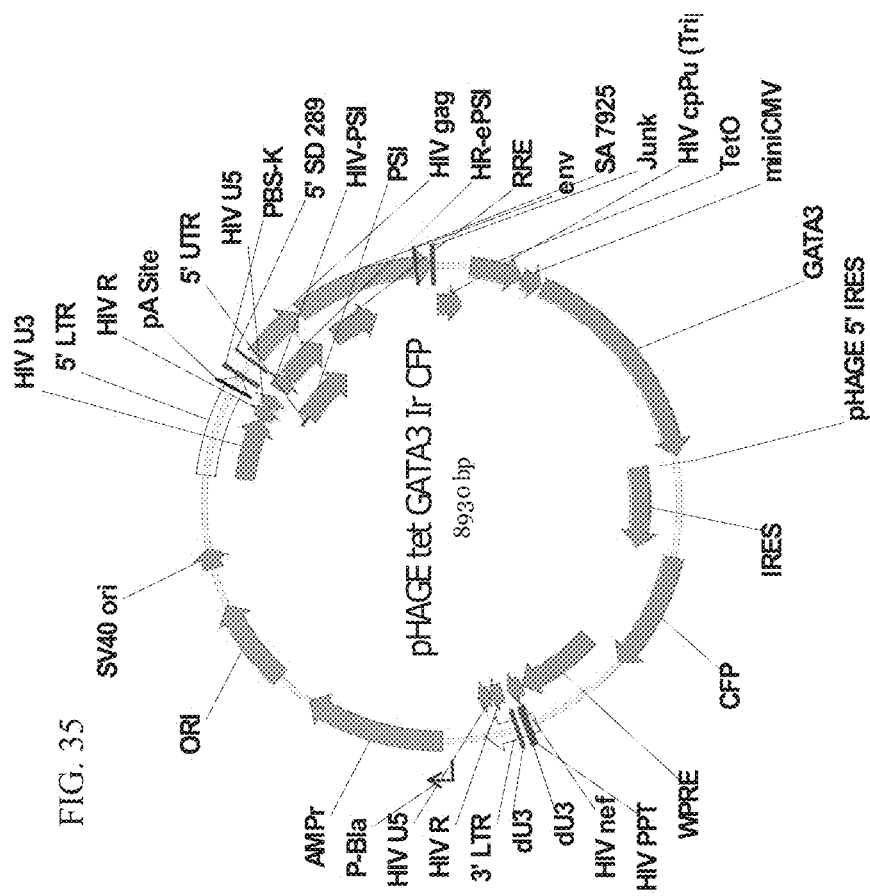

FIG. 35 shows plasmid design for generating a lentivirus allowing TetOn inducible Gata3 overexpression after Dox treatment of lentiviral infected mouse or human PSCs. CFP reporter is also DOX responsive. This lentivirus can be used with PSCs already expressing M2RTTA or by co-infecting with FUW-CAGGS-M2Rtta encoding lentivirus.

Figure 36:
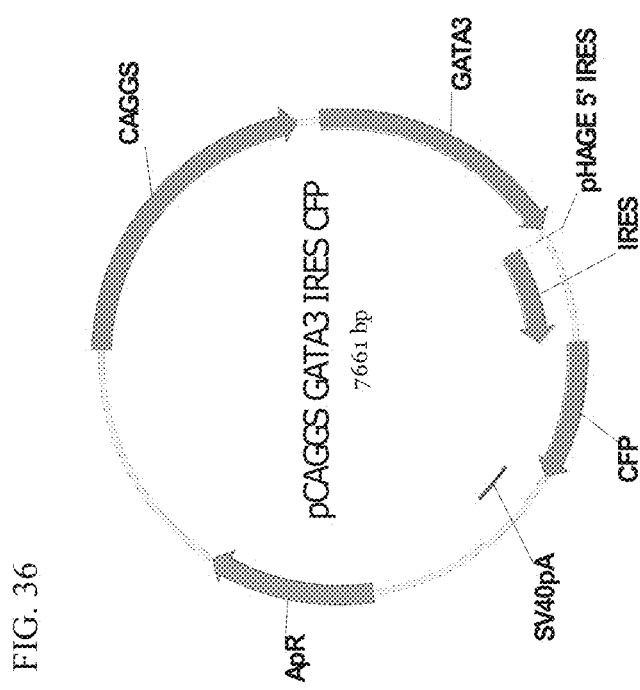

FIG. 36 shows plasmid design of plasmid that is used for transient transfection of mouse or human naïve PSCs. It encodes GATA3-IRES-CFP fluorescence under a CAGGS promoter.

Figure 37:
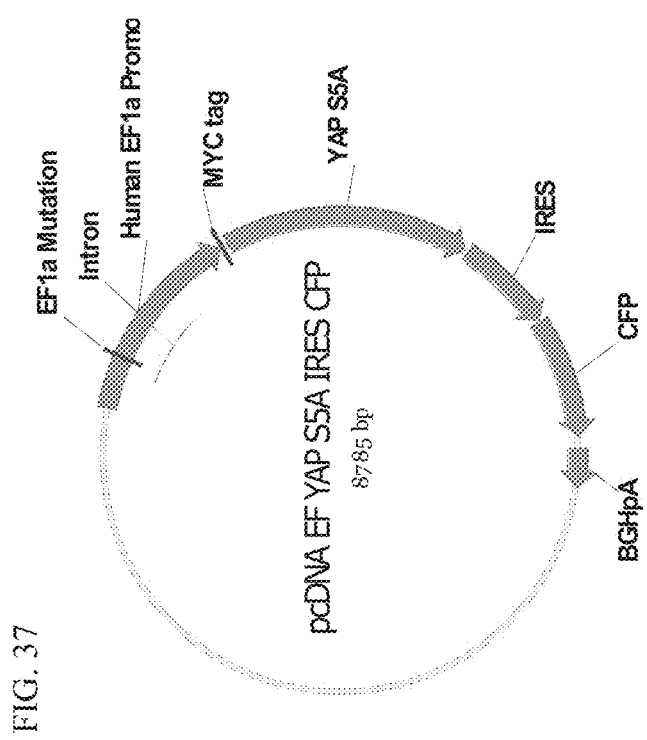

FIG. 37 shows plasmid design of pcDNA3 plasmid that is used for transient transfection of mouse or human naïve PSCs. It encodes YAP*mut-IRES-CFP fluorescence under a CMV promoter. Yap-mut: carries a mutant that it enforces YAP nuclear localization. For this construct the constitutively active(mut) human YAP was used—Serines at positions 61, 109, 127, 128, 131, 163, 164, and 381 changed to Alanine (phosphorylation sites), see addgene entry #27371 from which the insert was taken (Yap-mut).

Figure 38A:
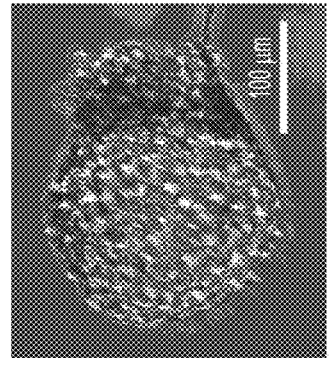
Figure 38B:
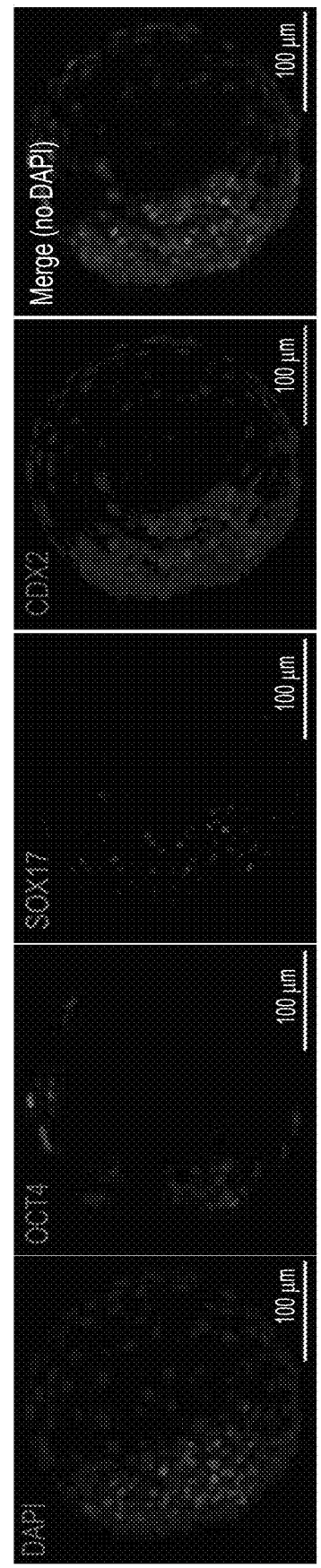

FIGS. 38A-B shows images of representative synthetic embryoids obtained according to the protocols described in Example 3 demonstrating generation of human day 4.5 synthetic embryos. FIG. 38A shows a phase contrast image of day 4.5 synthetic human embryoid. FIG. 38B shows images of a representative day 4.5 synthetic human embryoid immunostained for Oct4 pluripotency marker, Sox17 primitive endoderm (hypoblast) marker and CDX2 Trophectoderm marker. The images demonstrate a typic human embryo with an aggregate of OCT4+ pluripotent cells surrounded by a sphere of trophectoderm CDX2+ cells, and SOX17+ primitive endoderm—hypoblast region lying just below the OCT4+ cell mass.

Figure 39A:
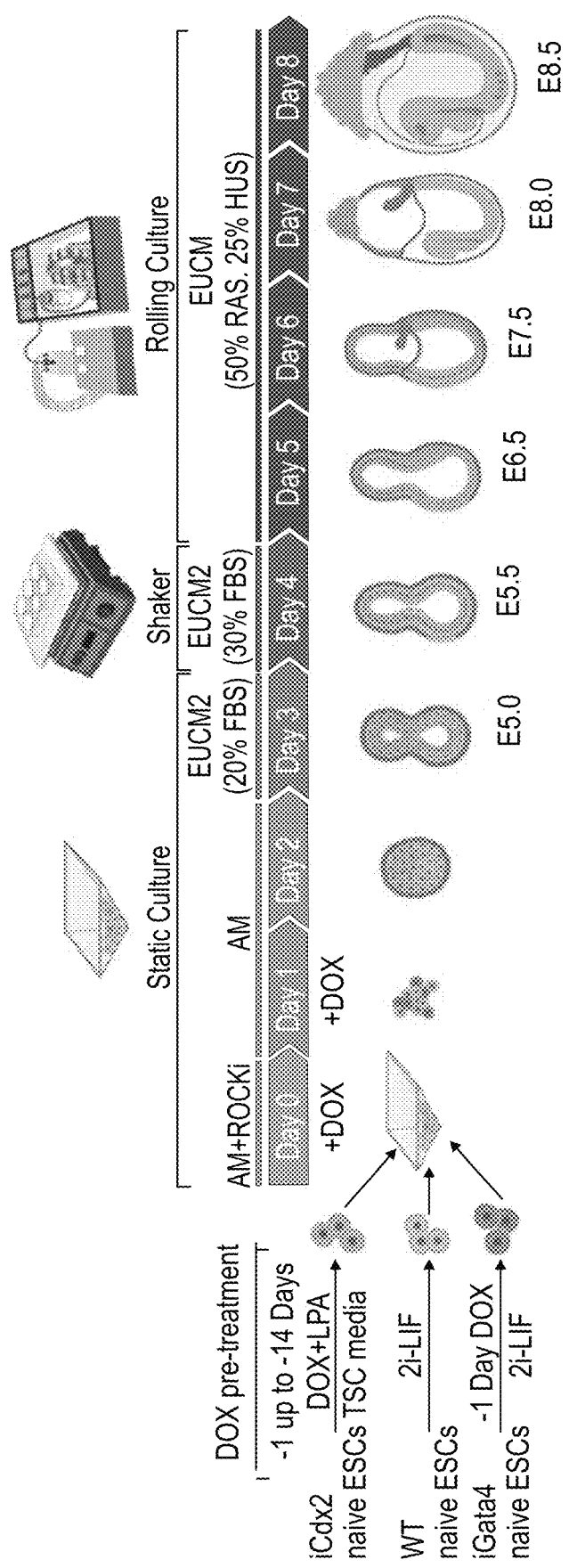
Figure 39B:
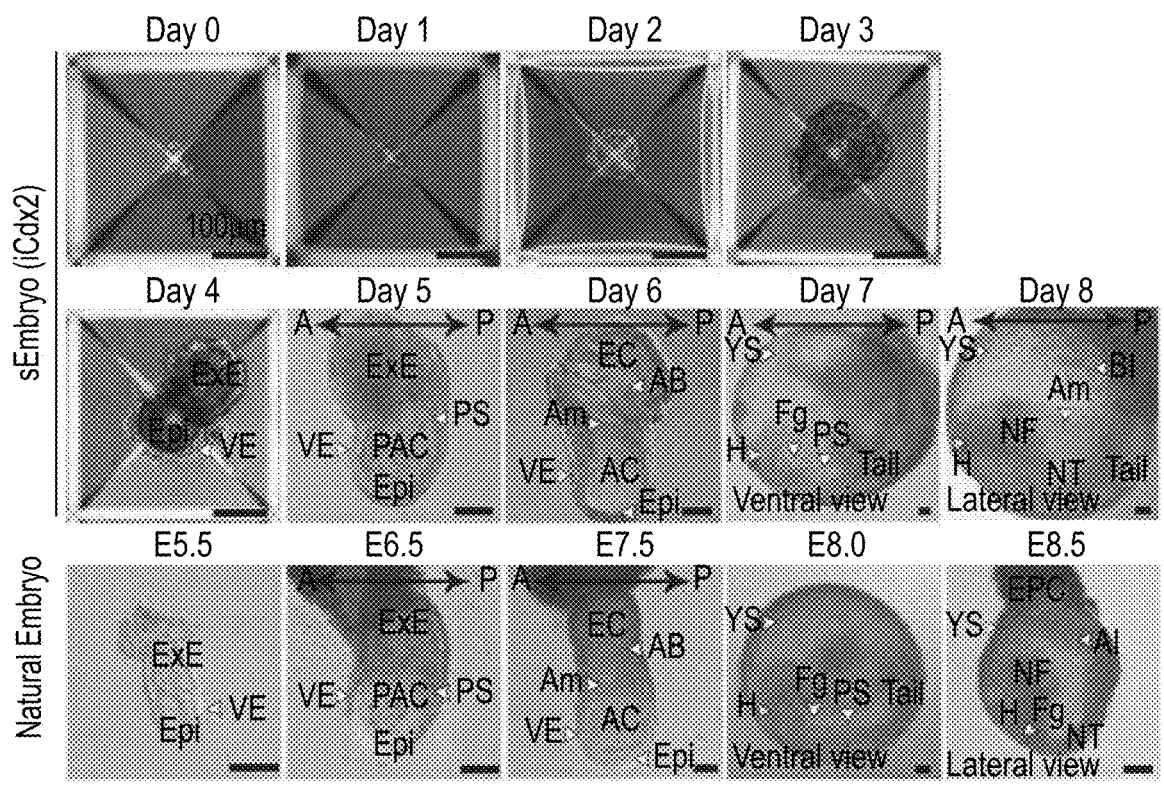
Figure 39C:
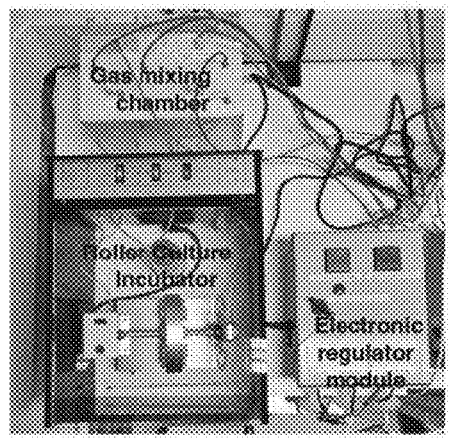
Figure 39D:
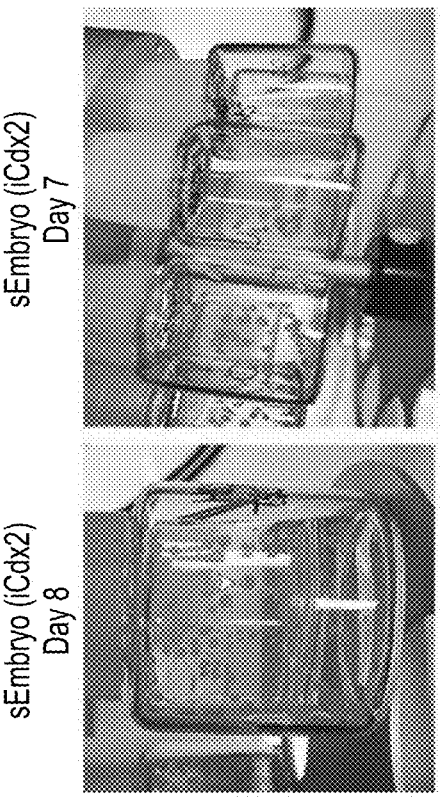
Figure 39E:
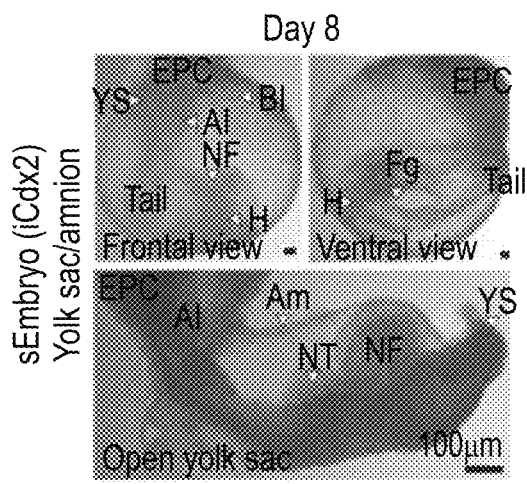
Figure 39G:
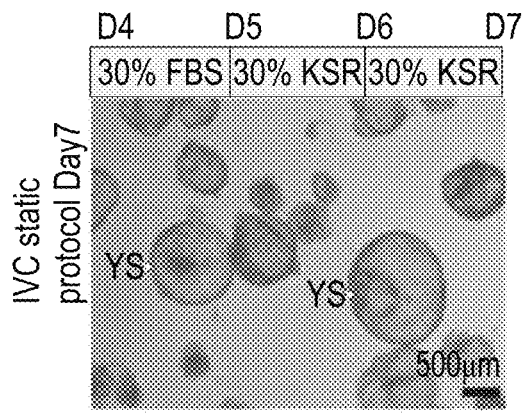
Figure 39F:
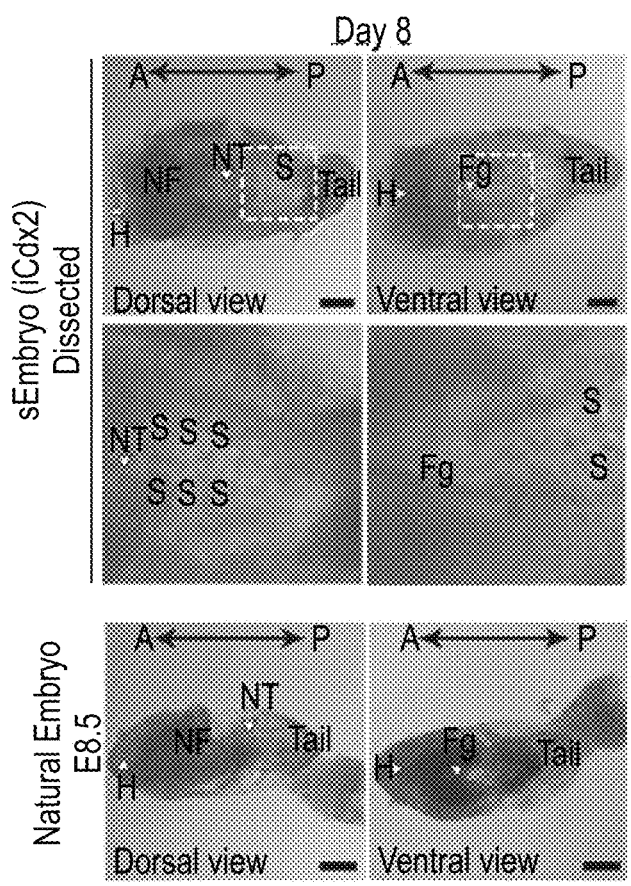

FIGS. 39A-G demonstrate that the naïve ESC-derived synthetic embryos complete gastrulation and reach organogenesis stages within extraembryonic membranes. FIG. 39A shows a schematic depiction of the synthetic embryo generation and culture protocol. DOX Pre-induction (−1 day for Gata4 in 2iLIF and −14 up to −1 days for Cdx2 in TSC-LPA media) and aggregation of the 3 types of naïve ESCs derived populations followed by culture in AM (with DOX in first 2 days), EUCM2 (20-30% FBS), EUCM2 (30% FBS), and EUCM for 8 days generates self-organized synthetic embryo ["sEmbryos (iCdx2)] that grow to early organogenesis. FIG. 39B shows bright field images of representative embryos at each day of the culture protocol compared to stage-matched natural embryos. FIG. 39C shows the electronically controlled roller bottle ex utero culture platform set-up used for sEmbryo propagation. FIG. 39D shows images of day 7 and day 8 sEmbryos cultured ex utero inside the roller culture bottles. FIG. 39E shows bright-field images of day 8 sEmbryos growing ex utero within extraembryonic membranes (yolk sac and amnion). FIG. 39F shows images of day 8 sEmbryo (iCdx2) and E8.5 natural embryos after dissection and removal of extraembryonic membranes. Insets are enlargements of the dashed boxes. FIG. 39G is a representative image of empty yolk sacs obtained after continuous culture in IVC—static culture based protocol. All images represent a minimum of three biological replicates. Scale bars, 100 µM in FIGS. 39B-C, 500 µm in FIG. 39G. A—anterior; AC—amniotic cavity; Am—amnion; A—allantois; AB—allantoic bud; BI—blood islands; Epi—epiblast; EC—exocoelomic cavity; EPC—ectoplacental cone; ExE—extraembryonic ectoderm; Fg—foregut pocket; H—heart; NF—neural folds; NT—neural tube; P—posterior; PAC—pro-amniotic cavity; PS—primitive streak; S—somites; VE—visceral endoderm; YS—yolk sac.

Figure 40C:
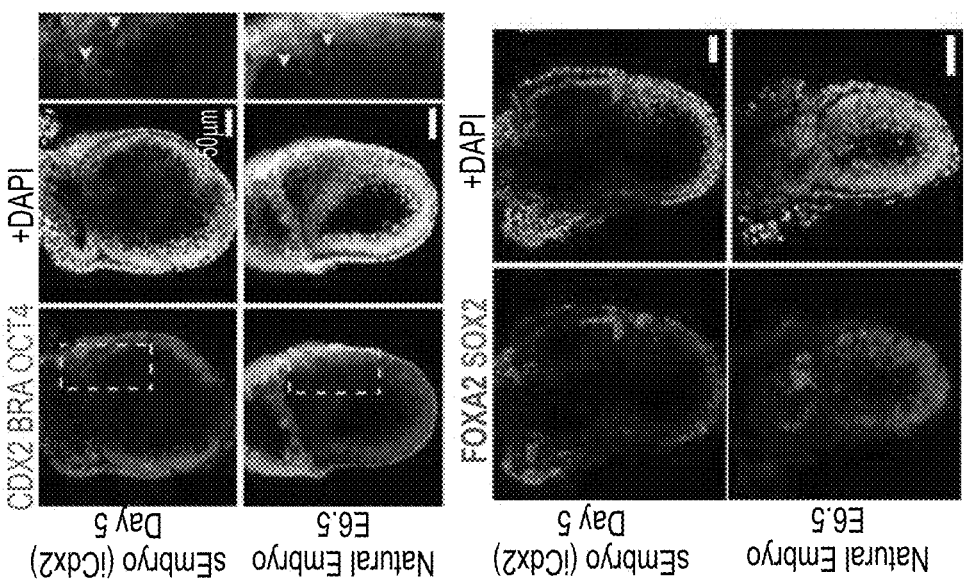
Figure 40B:
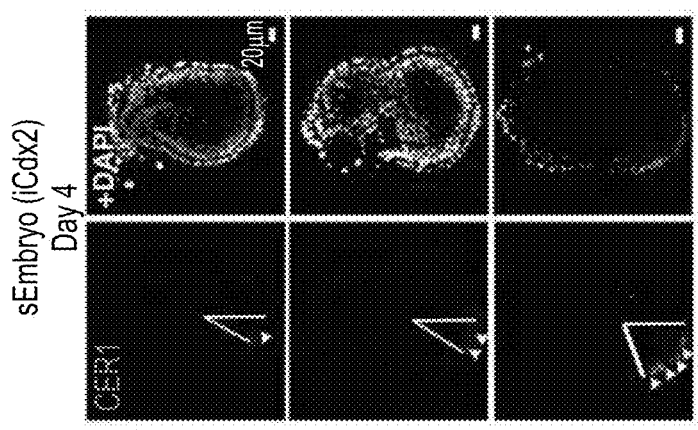
Figure 40A:
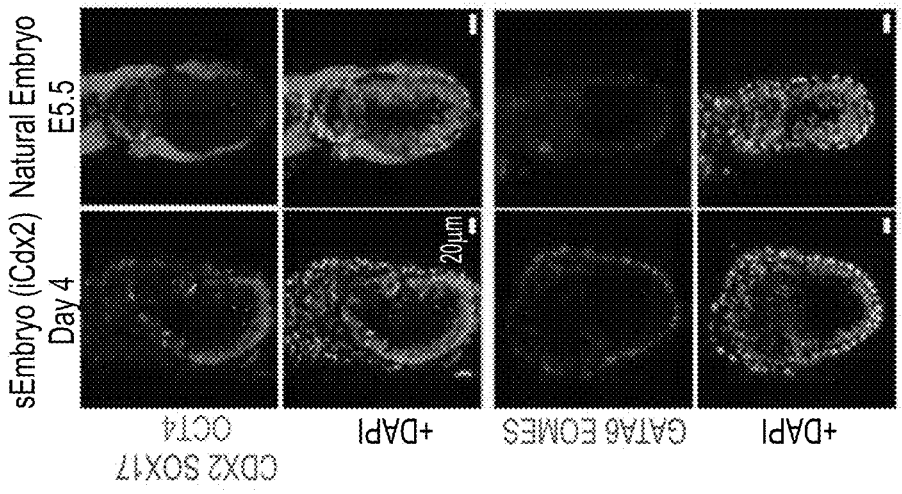
Figure 40E:
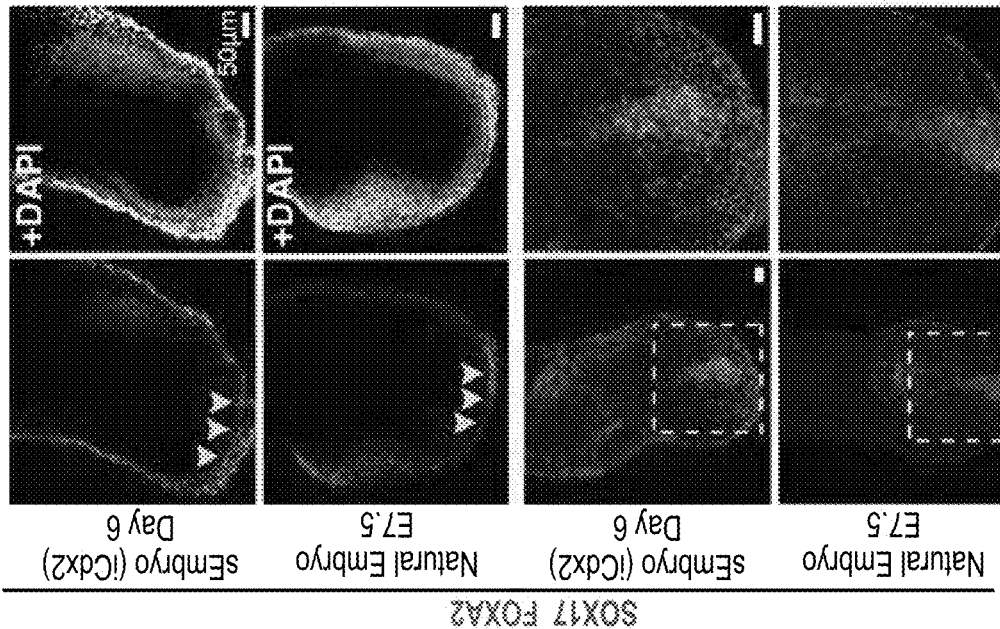
Figure 40D:
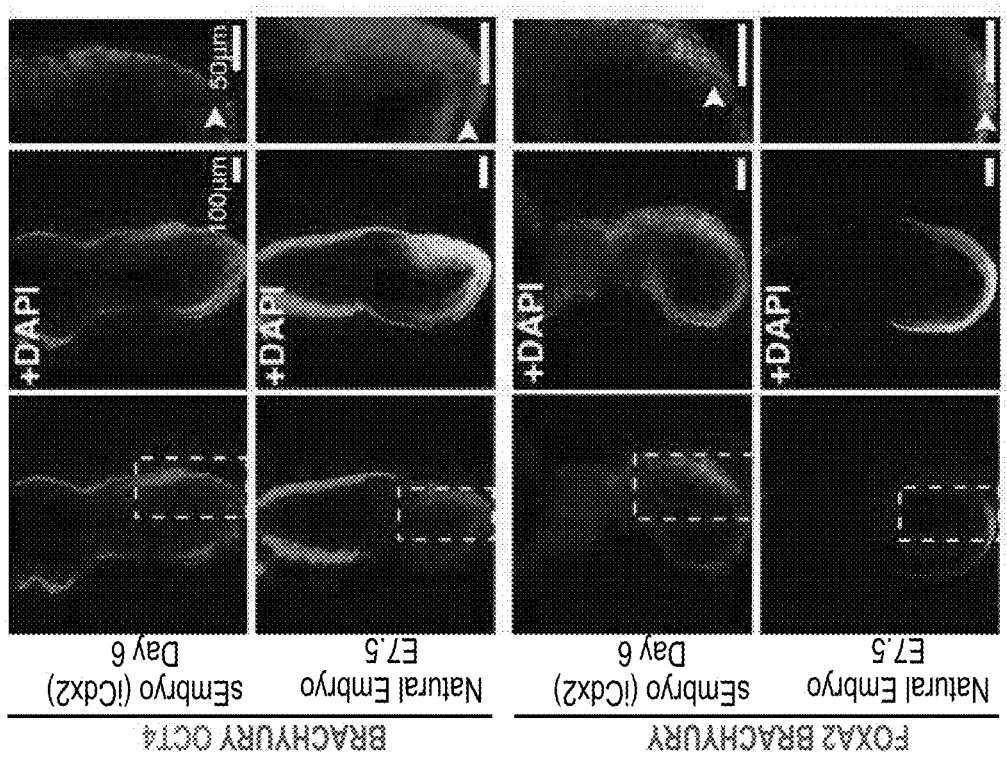
Figure 40F:
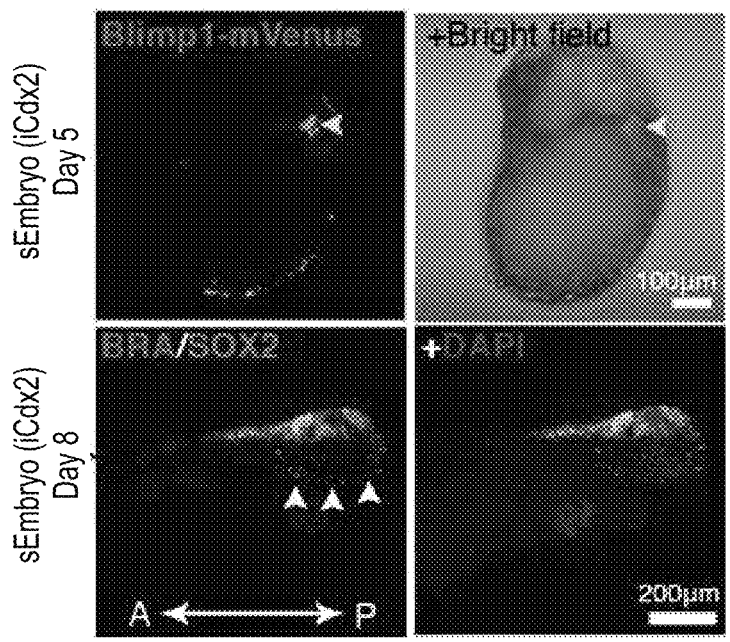
Figure 40G:
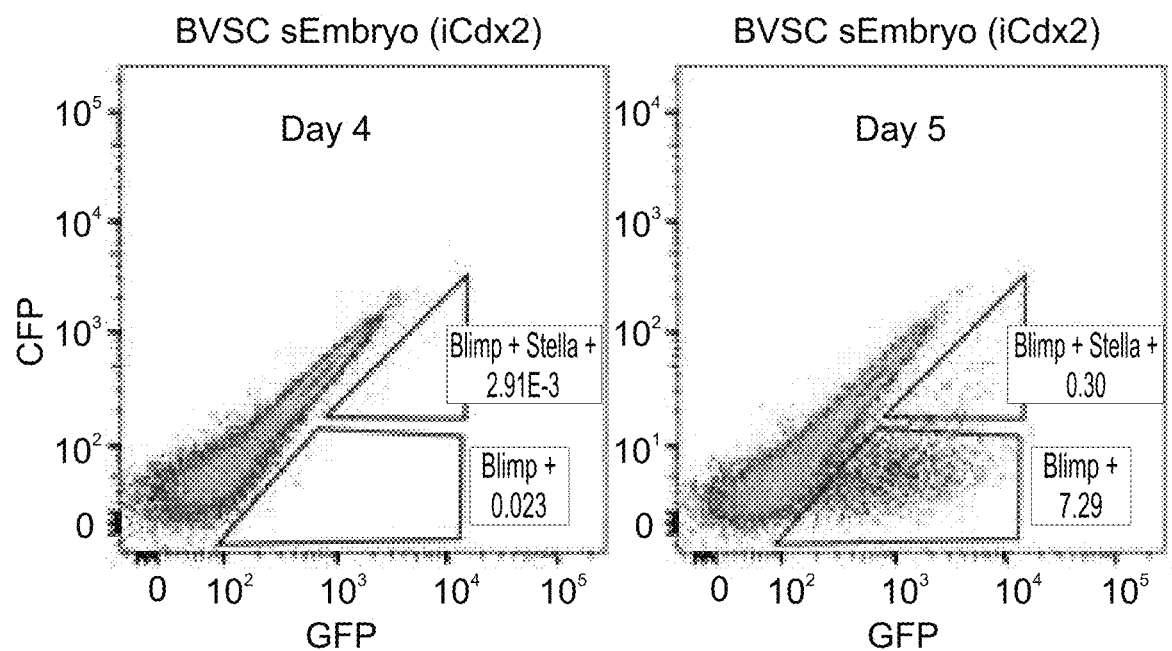

FIGS. 40A-G demonstrate that expression patterns of lineage markers in egg-cylinder shaped sEmbryos (iCdx2) resemble those of natural embryos. FIG. 40A shows middle section confocal images of day 4 egg cylinder sEmbryos (iCdx2) and natural E5.5 embryos immunostained for extraembryonic ectoderm, visceral endoderm and epiblast markers. Figure shows migration of the Anterior Visceral Endoderm (AVE) from the distal to the future anterior part revealed by CER1 staining (magenta) in day 4 sEmbryo (iCdx2). FIG. 40C shows representative immunofluorescence images (middle section) of visceral endoderm, trophoblast, epiblast and gastrulation markers (Brachyury, yellow arrows) in day 5 sEmbryos (iCdx2) compared to matched E6.5 natural embryos. FIGS. 40D-E demonstrate migration of the primitive streak and establishment of the definitive endoderm in sEmbryos (iCdx2) at day 6 and control E7.5 natural embryos. FIG. 40D shows immunofluorescence images showing migration of BRACHYURY+ cells and presence of Brachyury/Foxa2 double positive cells. FIG. 40E shows SOX17/FOXA2 immunostaining exposing invaginating definitive endoderm cells; FOXA2+/SOX17- cells along the epiblast reveal a node-like organizer in sEmbryos (iCdx2). Insets are enlargements of the dashed boxes. FIG. 40F shows middle section images of Blimp1-mVenus fluorescence at day 5 sEmbryos (iCdx2) detected by live imaging marking PGC specification (upper panel). Sox2+ PGCs show proper allocation to the anterior ventral side of the sEmbryos (iCdx2) at day 8 (lower panel). FIG. 40G shows flow cytometry plots for Blimp1-Venus/Stella-CFP in sEmbryos (iCdx2) at day 4 and day 5, marking their emergence at day 5 as expected (equivalent to E6.5). Scale bars are indicated on each panel.

Figure 41A:
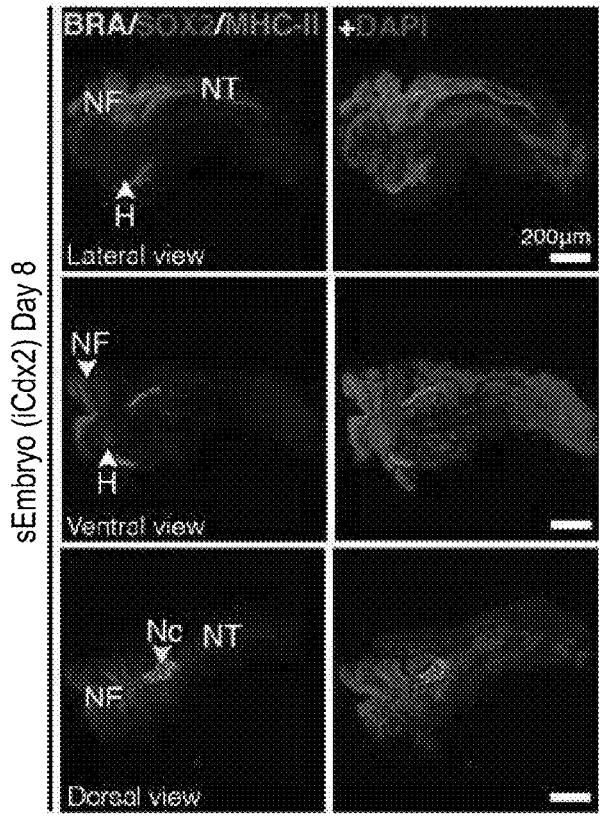
Figure 41B:
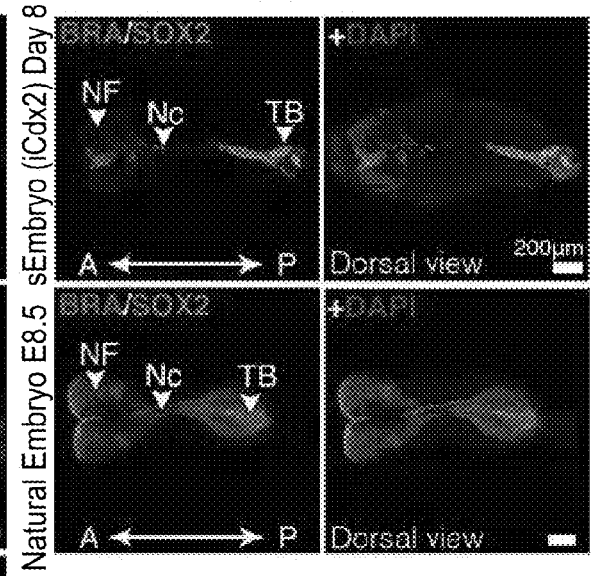
Figure 41C:
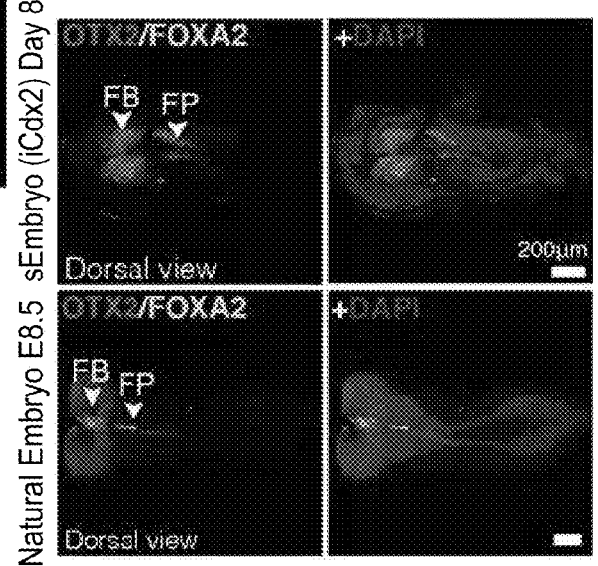

FIGS. 41A-E demonstrate that day 8 post-gastrulation sEmbryos (iCdx2) properly recapitulate spatial expression patterns of tissues derived from all three germ-layers. FIG. 41A shows representative whole-mount immunofluorescence images of day 8 sEmbryos (iCdx2) showing proper expression of neural (Sox2), heart (MHC-II) and notochord (Brachyury) lineage markers. Scale bars, 200 µM. FIG. 41B shows day 8 sEmbryo (iCdx2) maximum intensity projection confocal images for Sox2 and Brachyury compared to natural in utero E8.5 embryo. Scale bars, 200 µM. FIG. 41C shows day 8 sEmbryo (iCdx2) maximum intensity projection confocal images for OTX2 and FOXA2 compared to natural in utero grown E8.5 embryo. Scale bars, 200 µM. FIG. 41D shows schematic representation of the cutting planes for neural tube section (upper panel). Representative immunosection confocal images (mid-section, transversal plane) of the closed neural tube in day 8 sEmbryos (iCdx2) compared to natural in utero E8.5 embryos (lower panel). Scale bars, 20 µM. FIG. 41E shows schematic representation of the cutting plane for heart sections (upper panel). Representative immunohistochemistry images (mid-section, transversal plane) of the heart tube in day 8 sEmbryos (iCdx2) (lower panel). Scale bars, 50 µM. Images are representative of a minimum of 3 biological replicates. FB—forebrain; FP—floor plate; H—heart; LV—left ventricle; Nc—notochord; NF—neural folds; NT—neural tube; RV—right ventricle; TB—tail bud.

FIGS. 42A-F demonstrate that sEmbryos (iCdx2) grow within the extraembryonic membranes and develop allantois, blood islands and ectoplacental cone. FIG. 42A shows representative images of day 7 and day 8 sEmbryos (iCdx2) showing the presence of amnion, yolk sac, allantois, ectoplacental cone and blood islands. Scale bars, 200 µM. FIG. 42B is a schematic illustration of the extraembryonic compartments present in day 8 sEmbryos (iCdx2). FIG. 42C shows representative whole-mount immunofluorescence images of canonical markers in yolk sacs isolated from sEmbryos (iCdx2) at day 8 and E8.5 in utero natural embryos. Scale bars, 500 µM. FIG. 42D shows representative images of RUNX1 immunostaining in yolk sacs obtained from sEmbryos (iCdx2) at day 8 and equivalent to E8.5 natural embryos. Scale bars, 50 µM. FIG. 42E shows representative flow cytometry contour plots for CD45 and CD34 expression among Kit+ CD41+ progenitor cells, and Kit and CD41 expression among lineage negative population from E8.5 in the yolk sac (Upper panel) and sEmbryo (iCdx2) (bottom panel). Gates were set based on the fluorescence minus one (FMO) of each cell surface marker antibody. FIG. 42F shows methylcellulose based in vitro culture, colony forming potential and morphology of erythroid progenitors derived from day 8 sEmbryo (iCDX2) along with natural in utero control E8.5 derived ones. Data represents a minimum of 3 biological replicates. Scale bars are indicated on each panel.

Figure 43A:
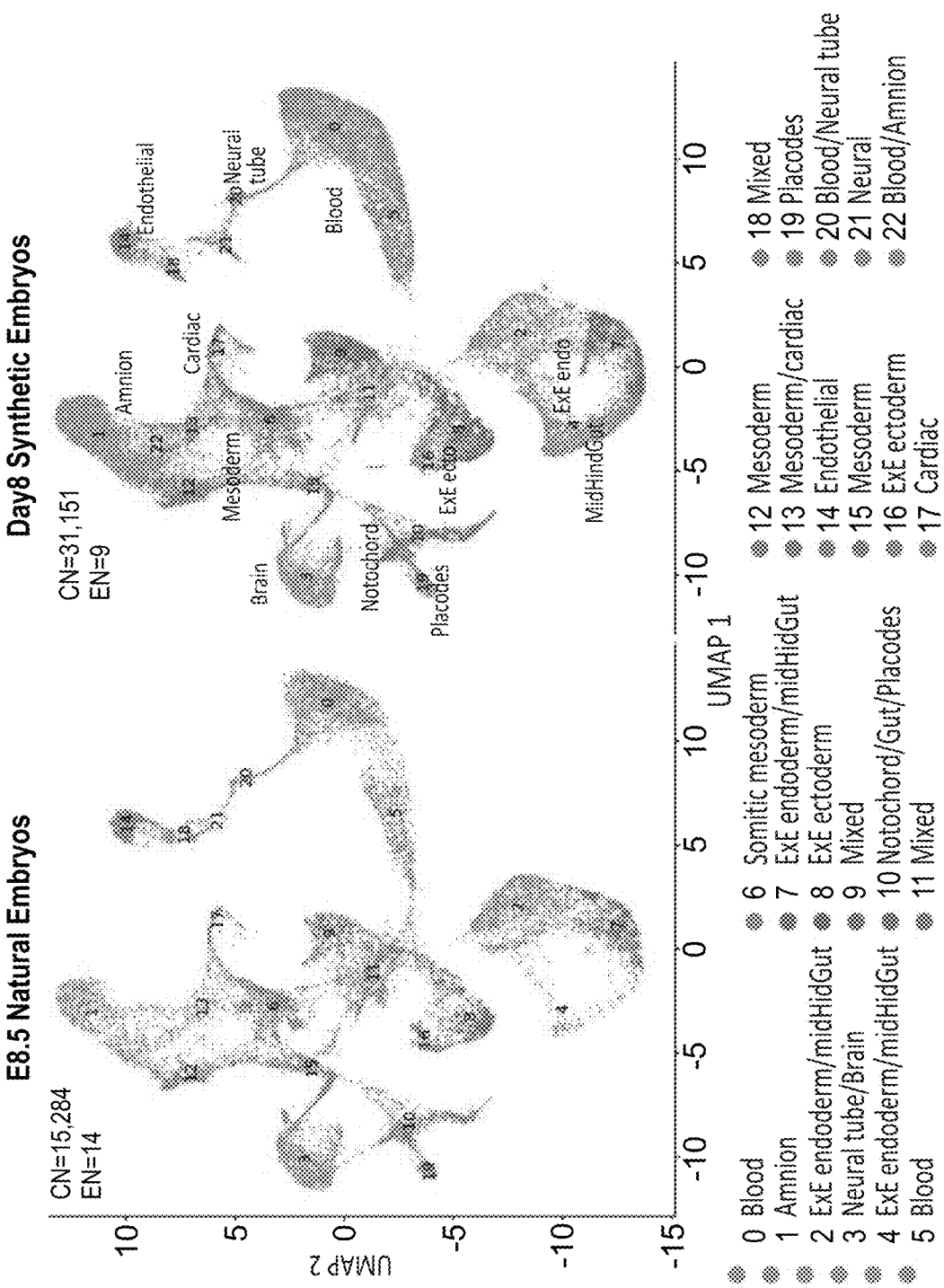

FIGS. 43A-D demonstrate scRNA-seq analysis of natural embryos versus synthetic embryos. FIG. 43A is a UMAP plot displaying individual cells (n=15,284 Natural E8.5 embryos; n=31,151 Synthetic day 8 embryos). Points are colored according to their assigned cell cluster. Cell lineage annotation of clusters based on marker genes of the major cell types identified in E8.5 mouse embryos. EN=total Embryo Number; CN=total Cell Number. FIG. 43B is a UMAP plot displaying individual cells of the different samples as indicated. Colors as in FIG. 43A. FIG. 43C shows natural embryo cells (black) and synthetic embryo cells (red) projected on the same UMAP plot. FIG. 43D shows pie charts depicting the proportional abundance of each cell cluster in both natural and synthetic embryos. Asterisks denote clusters with statistically significant differences between the two groups.*T-test p<0.05.

Figure 44A:
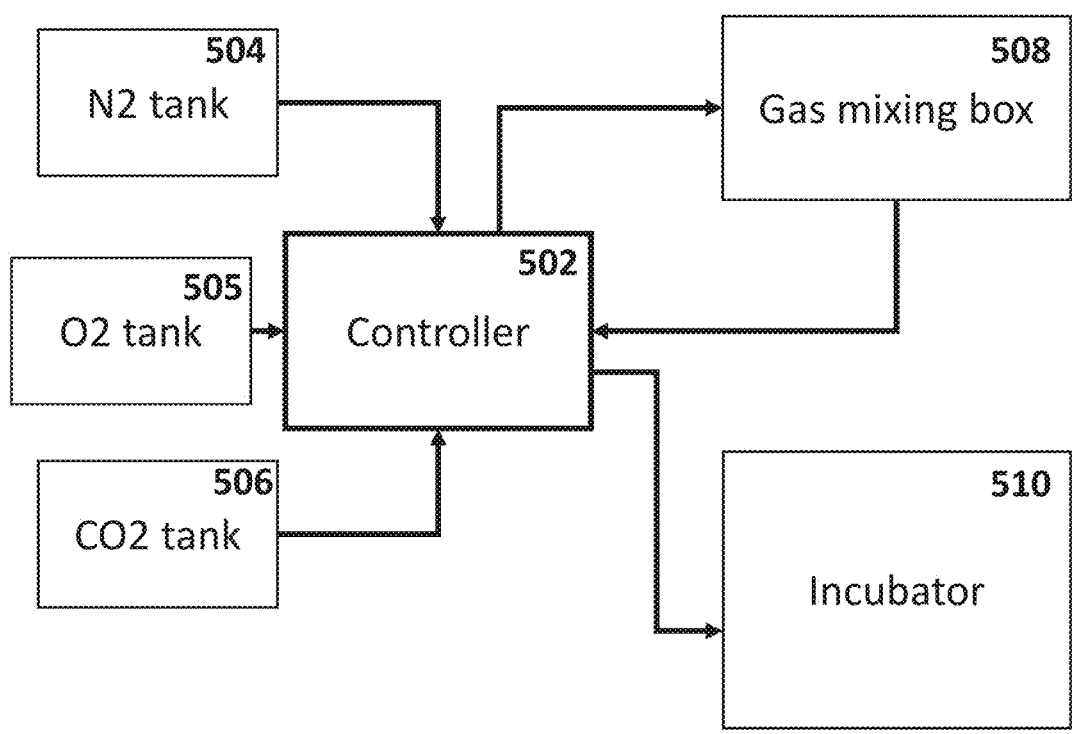
Figure 44B:
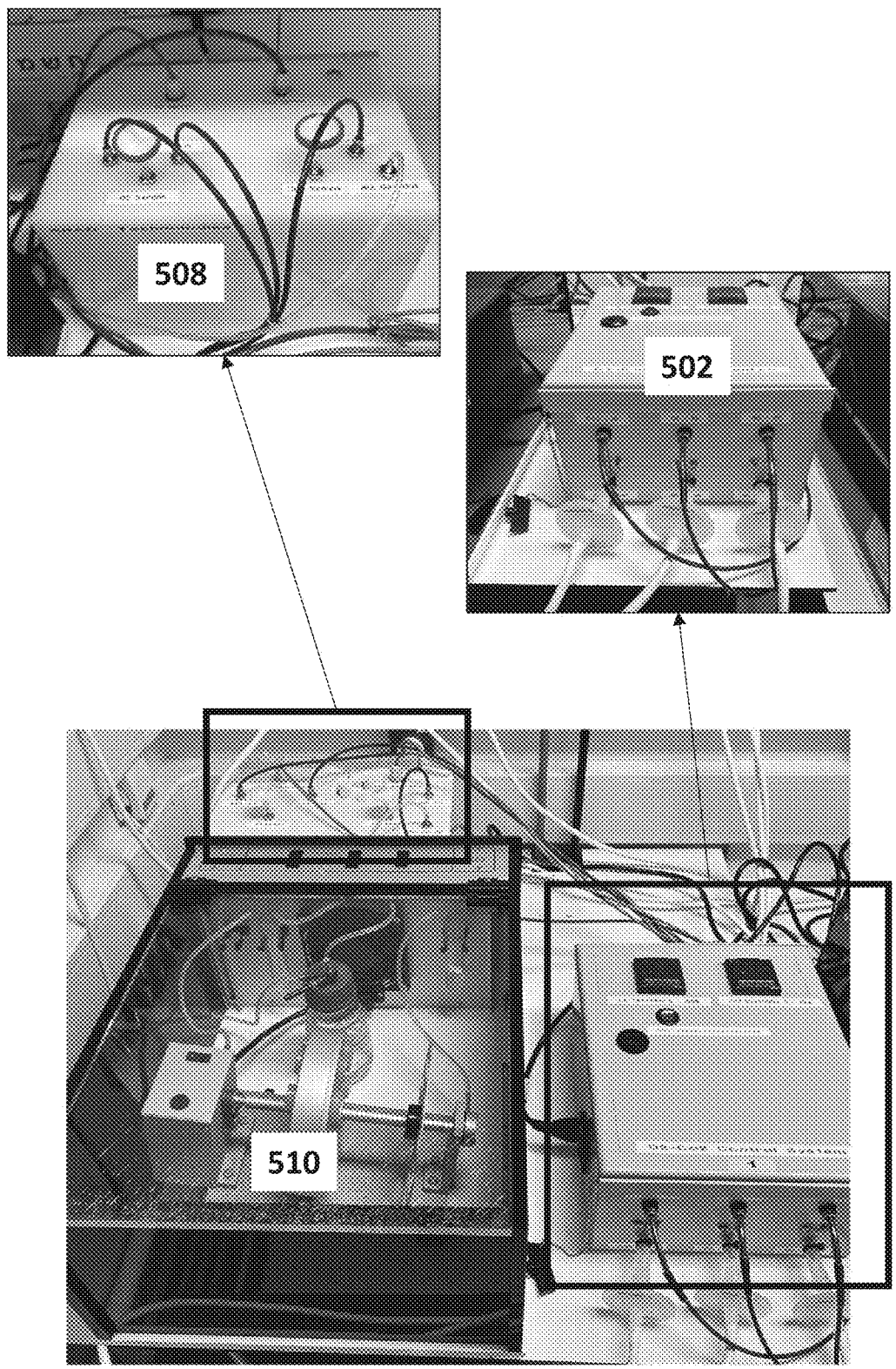
Figure 44C:
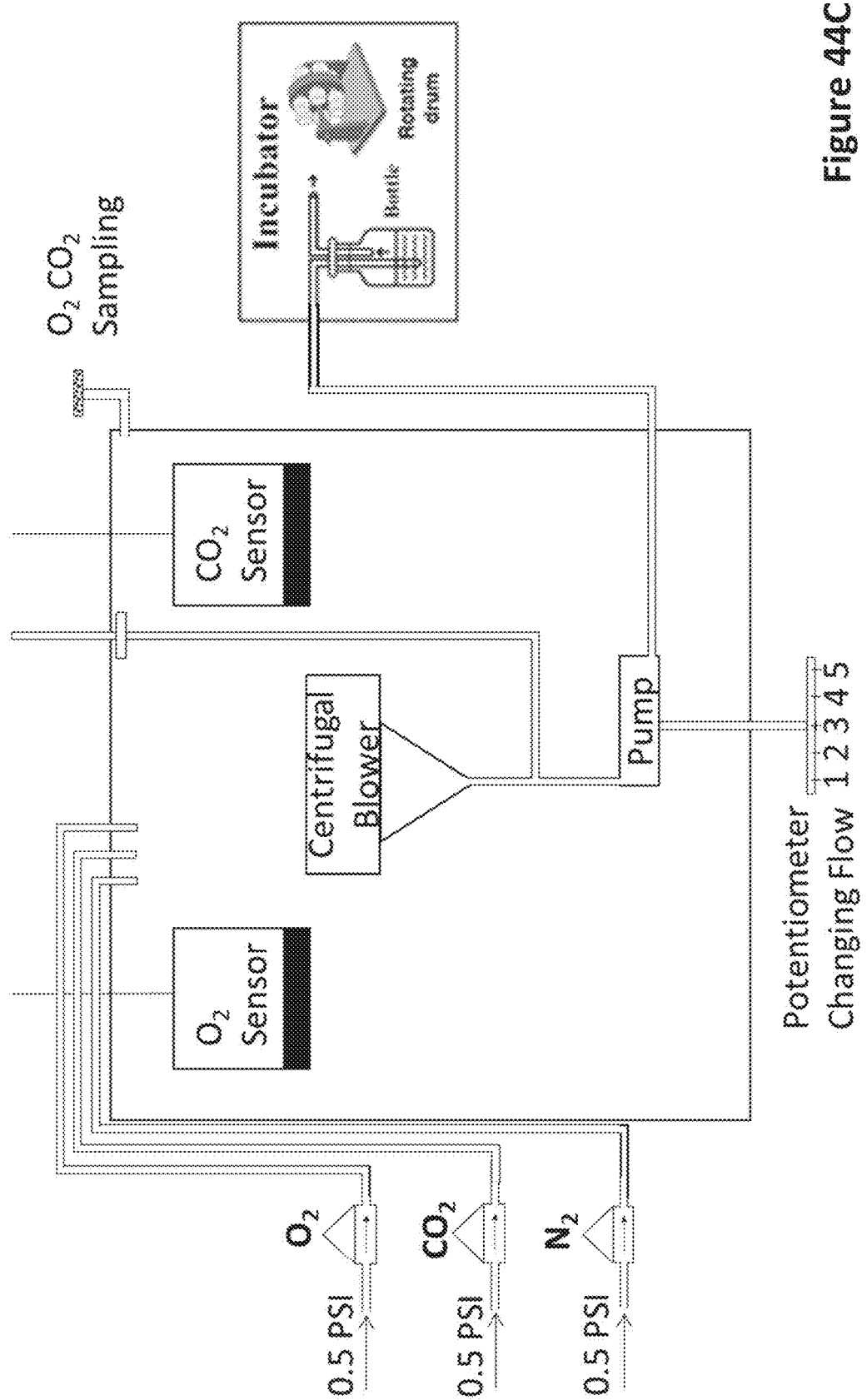
Figure 44D:
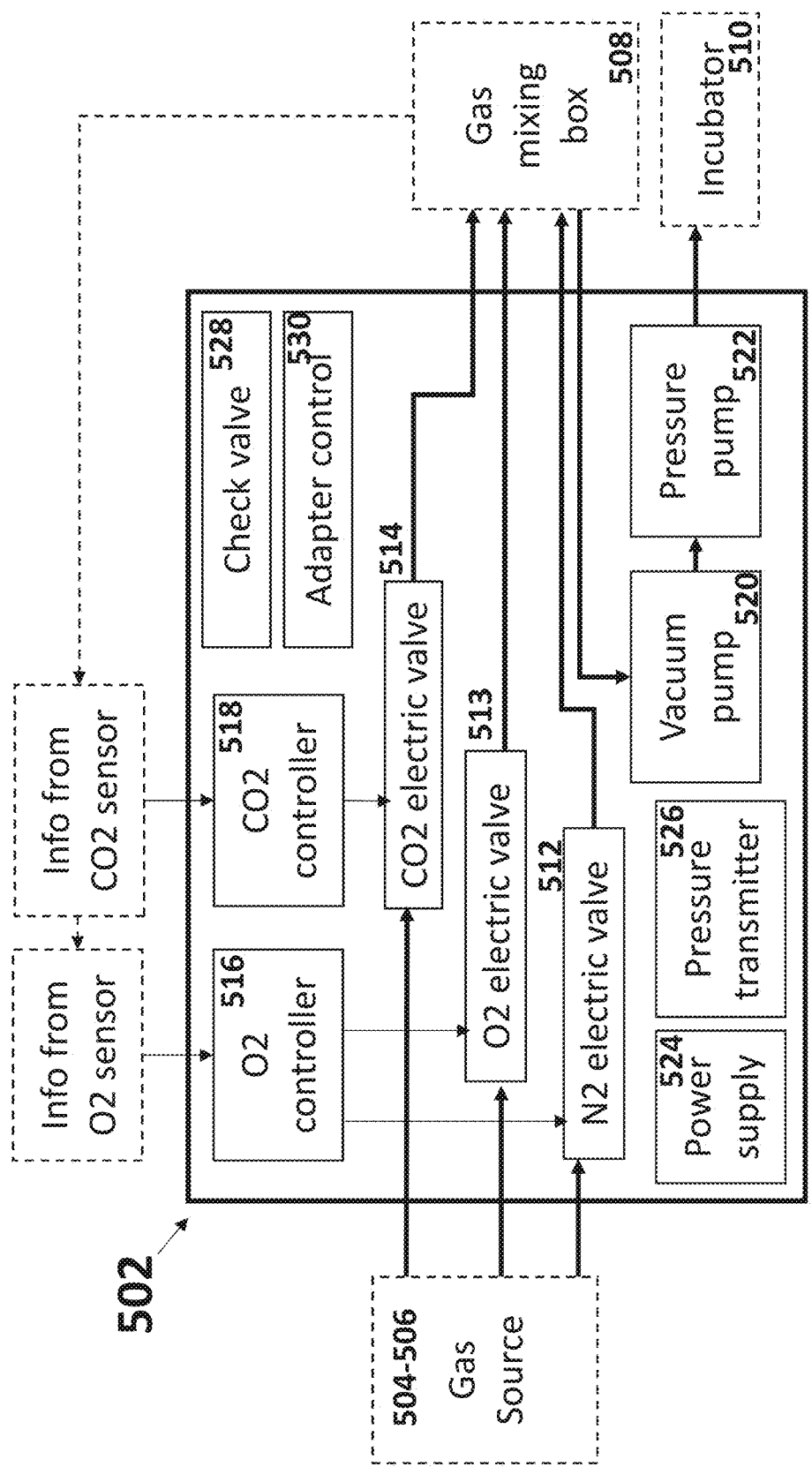
Figure 44E:
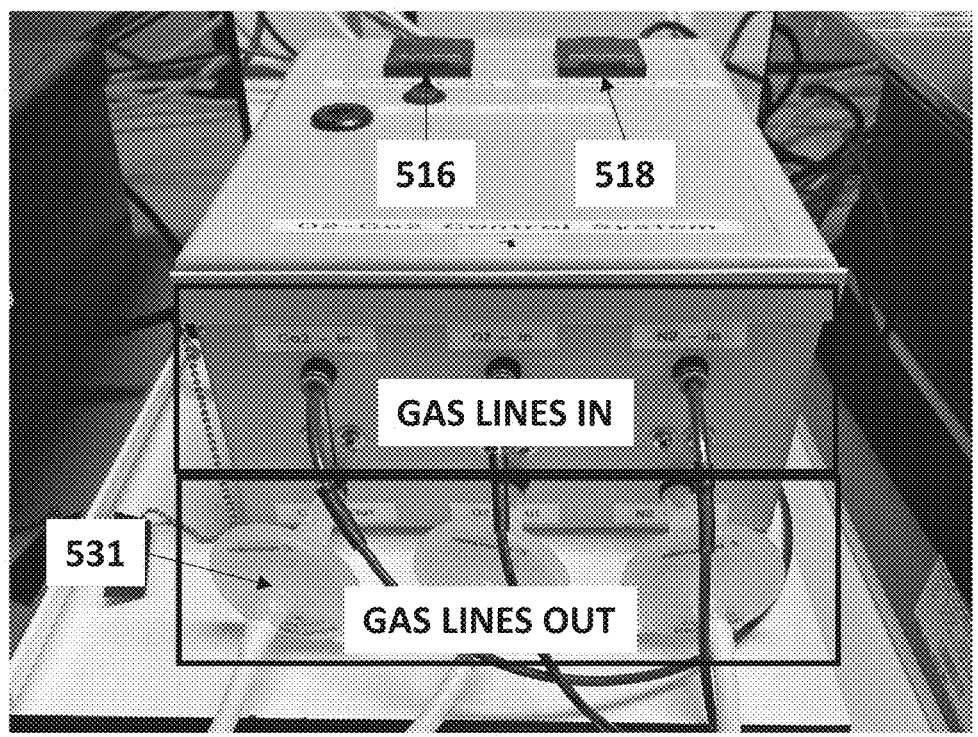
Figure 44F:
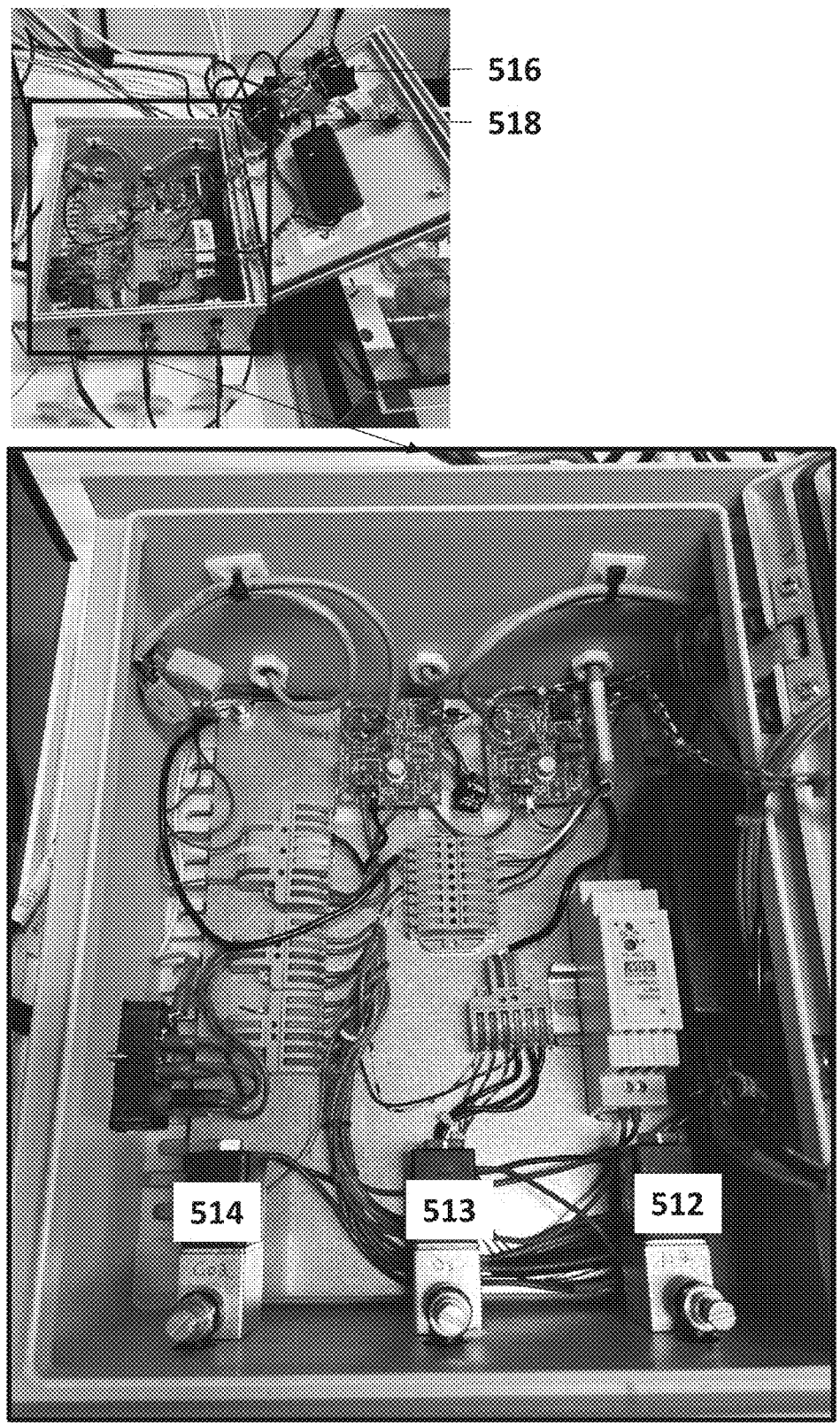
Figure 44G:
Figure 44H:
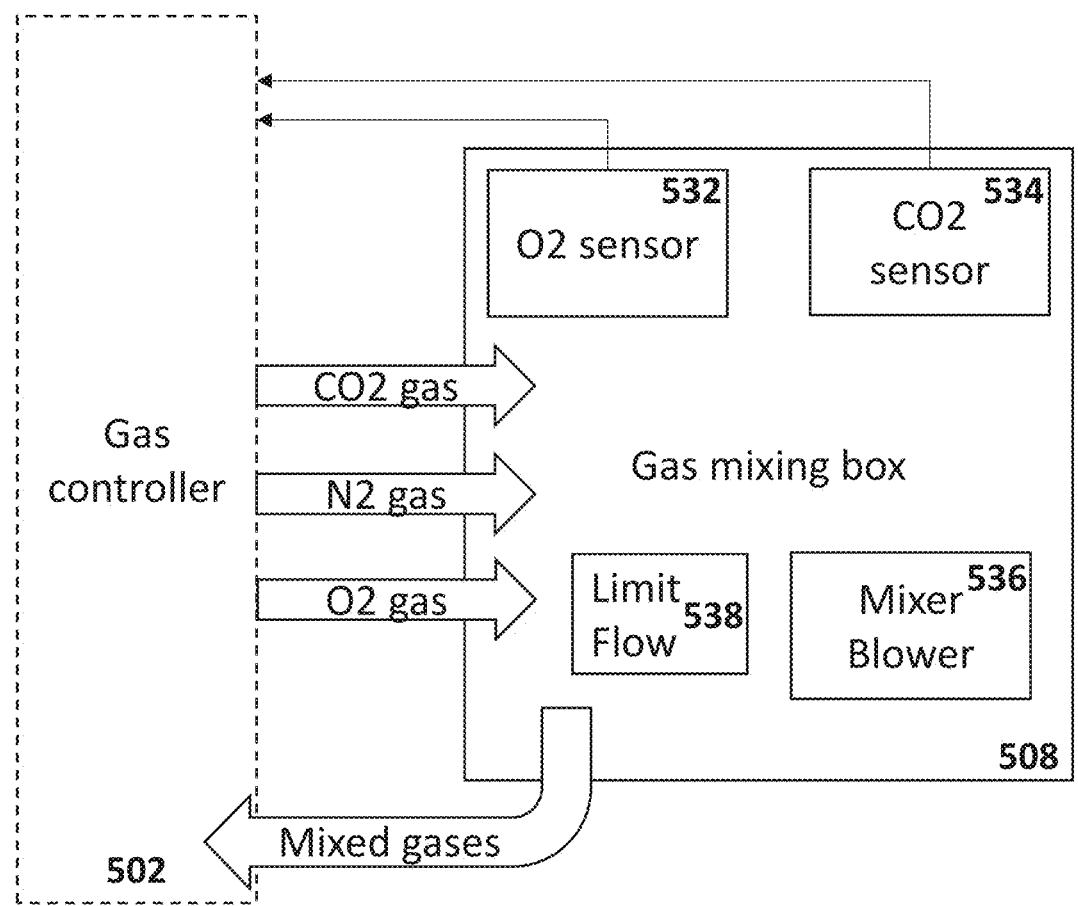
Figure 44I:
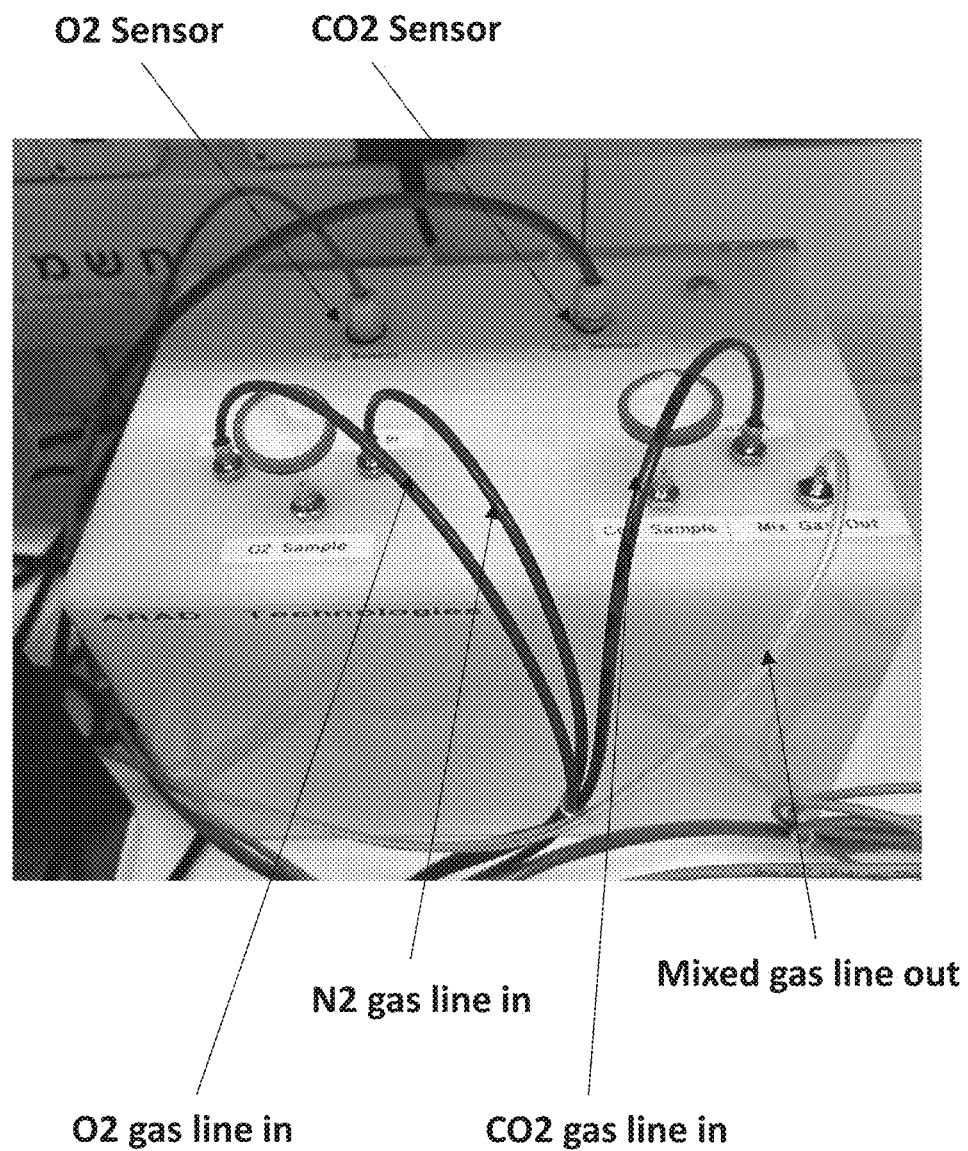
Figure 44J:
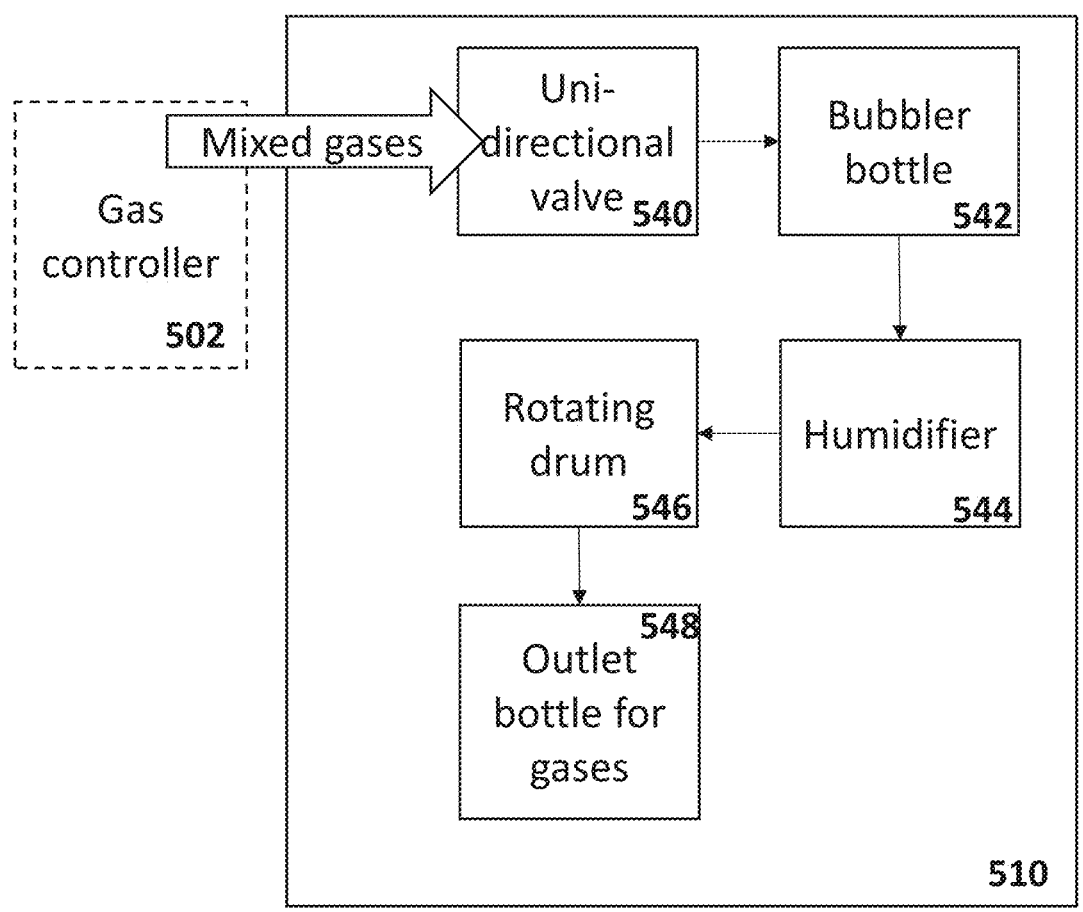
Figure 44K:
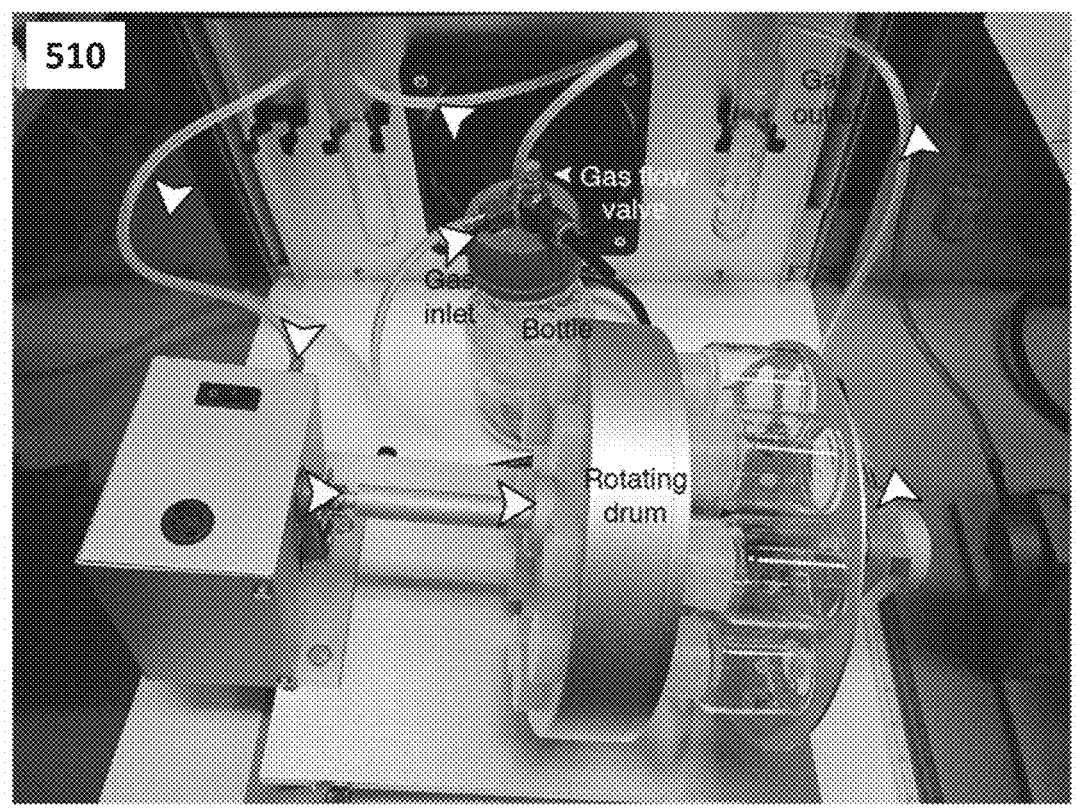
Figure 44L:
Figure 44M:
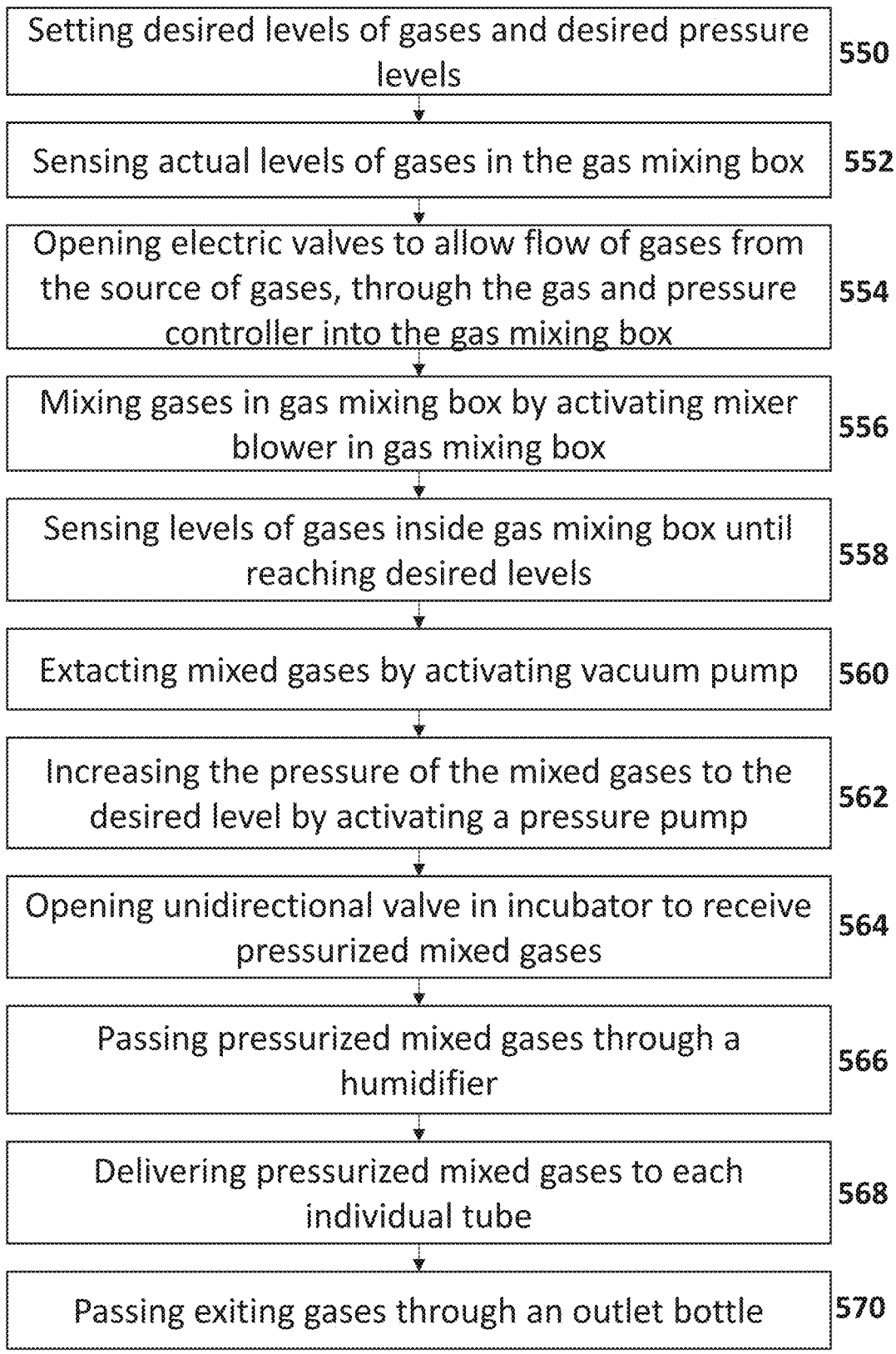

FIGS. 44A-M demonstrate an optimized gas and pressure regulating controller for roller culture incubators. FIG. 44A is a schematic representation of a fetal incubation system. FIG. 44B is an image of an exemplary fetal incubation system. FIG. 44C is a diagram depicting the configuration of the electronic module for gas and pressure regulation. $O_2$, $N_2$ and $CO_2$ enter into the system at a pressure of 0.1-0.5 psi and are mixed into by a centrifugal blower. Gases are then injected into a water bottle inside the incubator by a pump that allows control of the gas pressure (hyperbaric conditions). Lph=liters per hour. FIG. 44D is a schematic representation of an exemplary gas and pressure controller. FIG. 44E shows a perspective view of an exemplary gas and pressure controller configured to monitor and manipulate $CO_2$ and $O_2$ levels by providing $CO_2$ and/or $N_2$. FIG. 44F shows a top view of the gas and pressure controller open and showing internal components. FIG. 44G is a front view of the gas and pressure controller. FIG. 44H is a schematic representation of an exemplary gas mixing box. FIG. 44I is an image of an exemplary gas mixing box. FIG. 44J is a schematic representation of an exemplary incubator. FIG. 44K is an image of the interior of the precision incubator system (B.T.C. Engineering) showing the direction of the gas flow (indicated by the white arrowheads). FIG. 44L is an image of embryos cultured in rotating bottles (yellow arrowheads). FIG. 44M is a flowchart of an exemplary method related to the fetal incubation system.

Figure 45A:
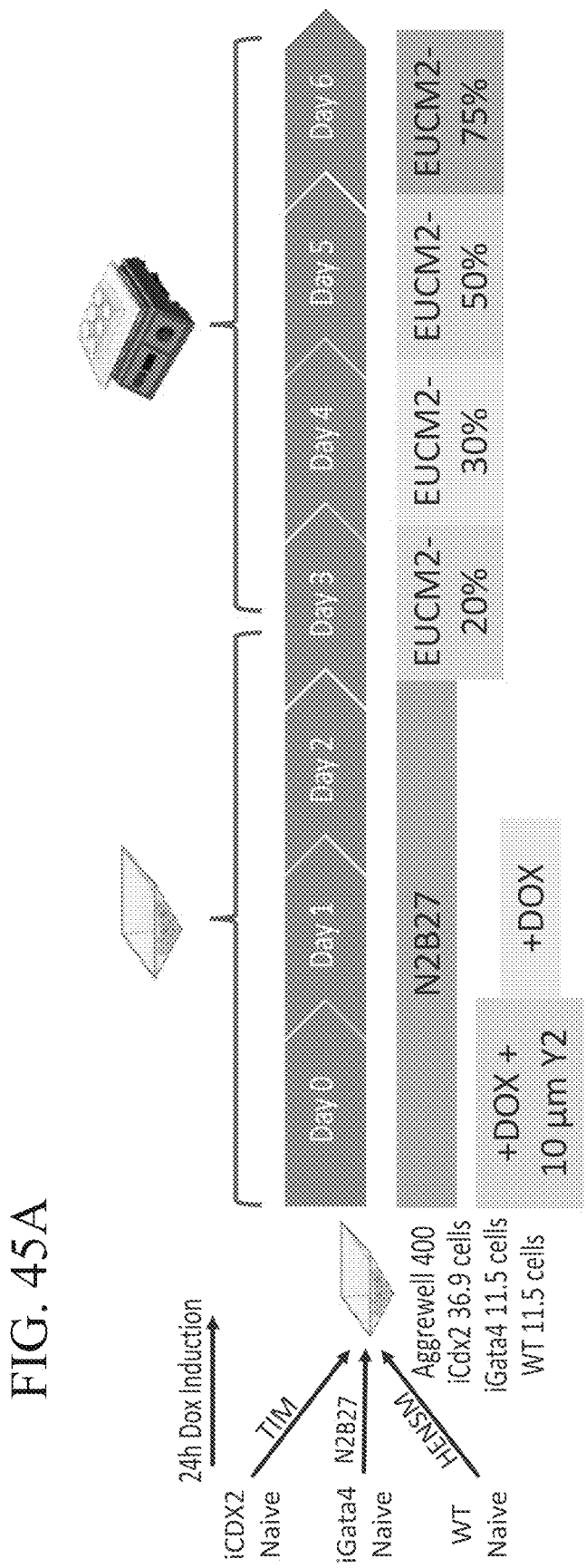
Figure 45B:
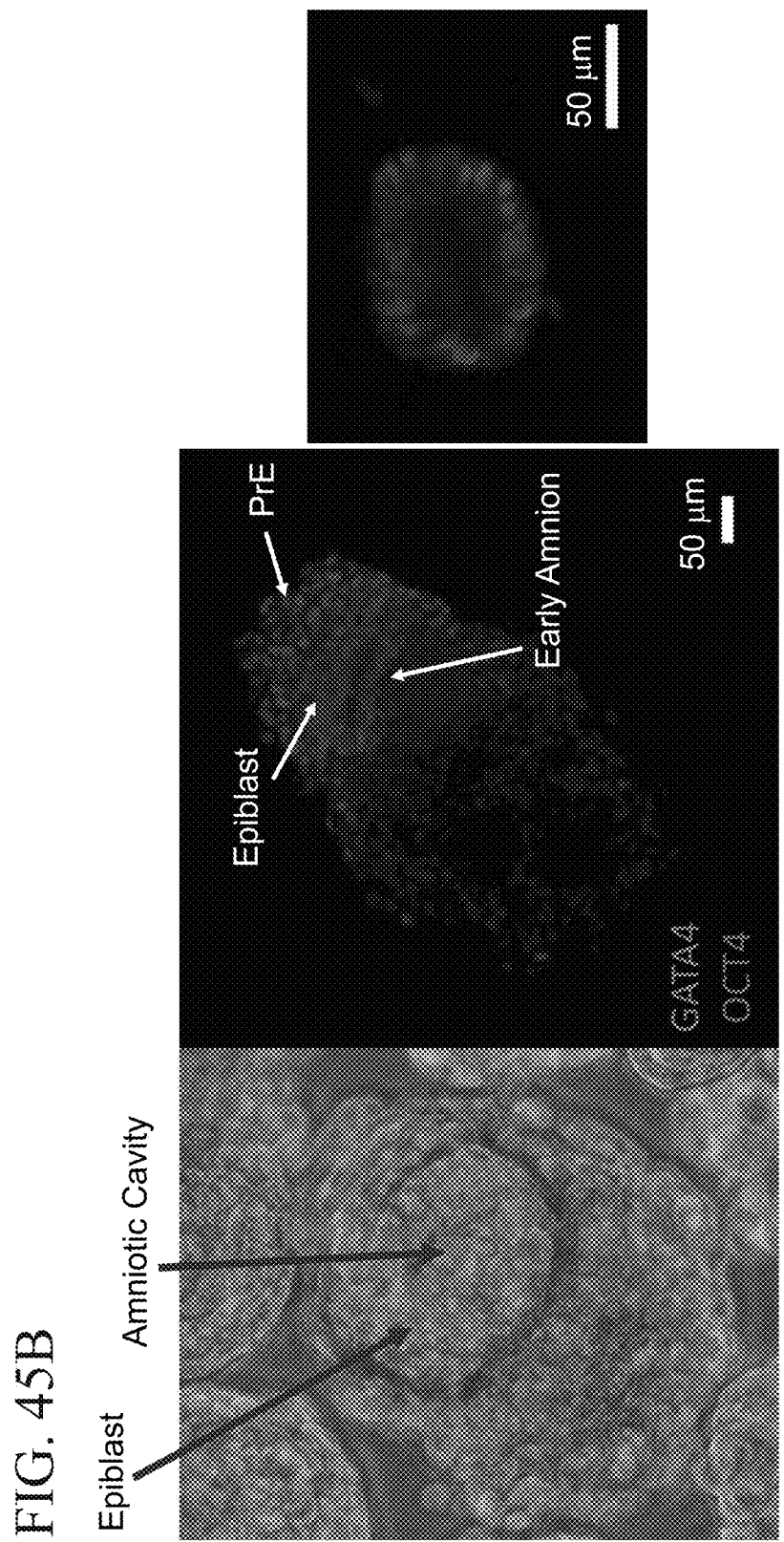
Figure 45C:
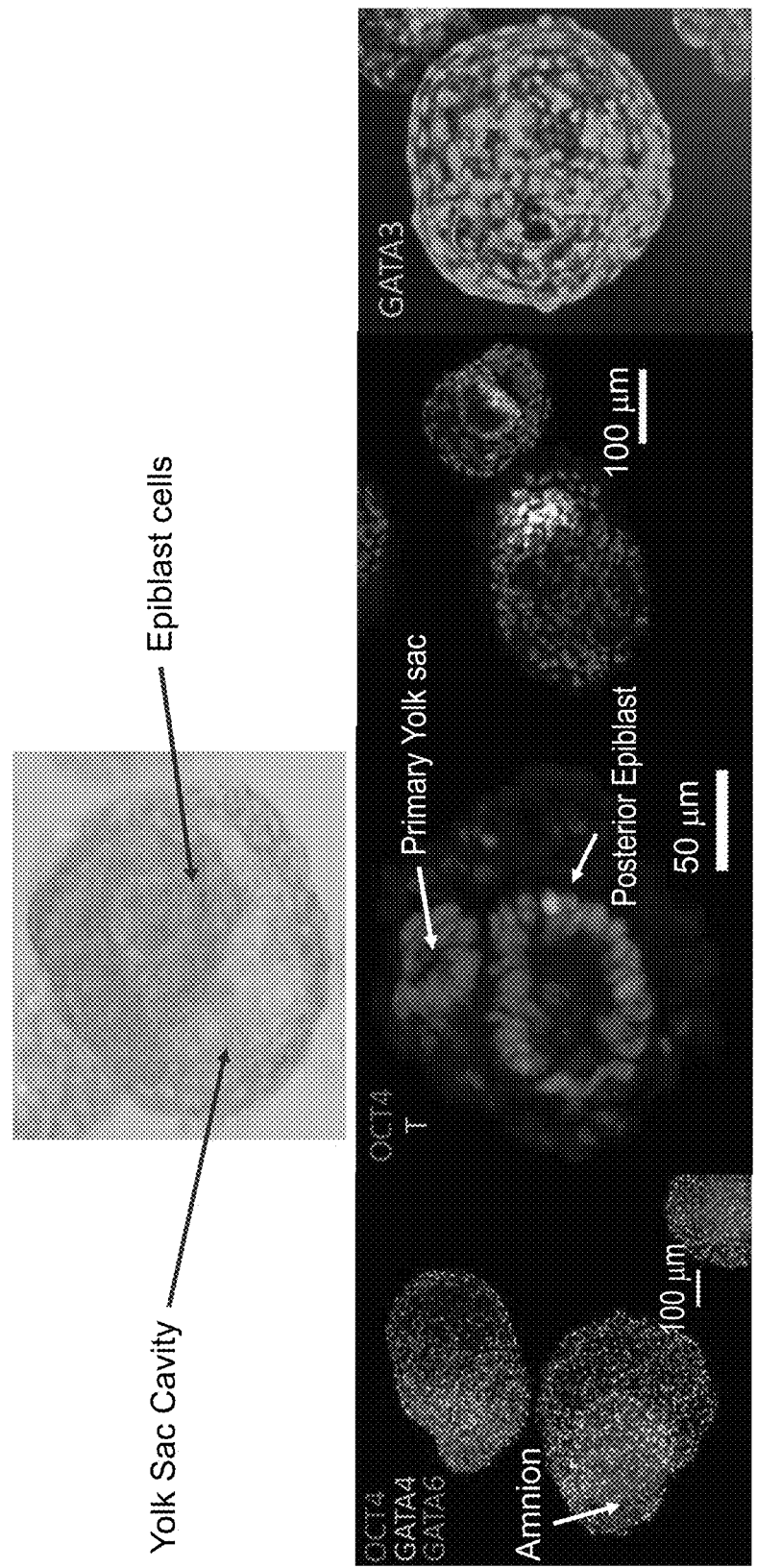
Figure 45D:
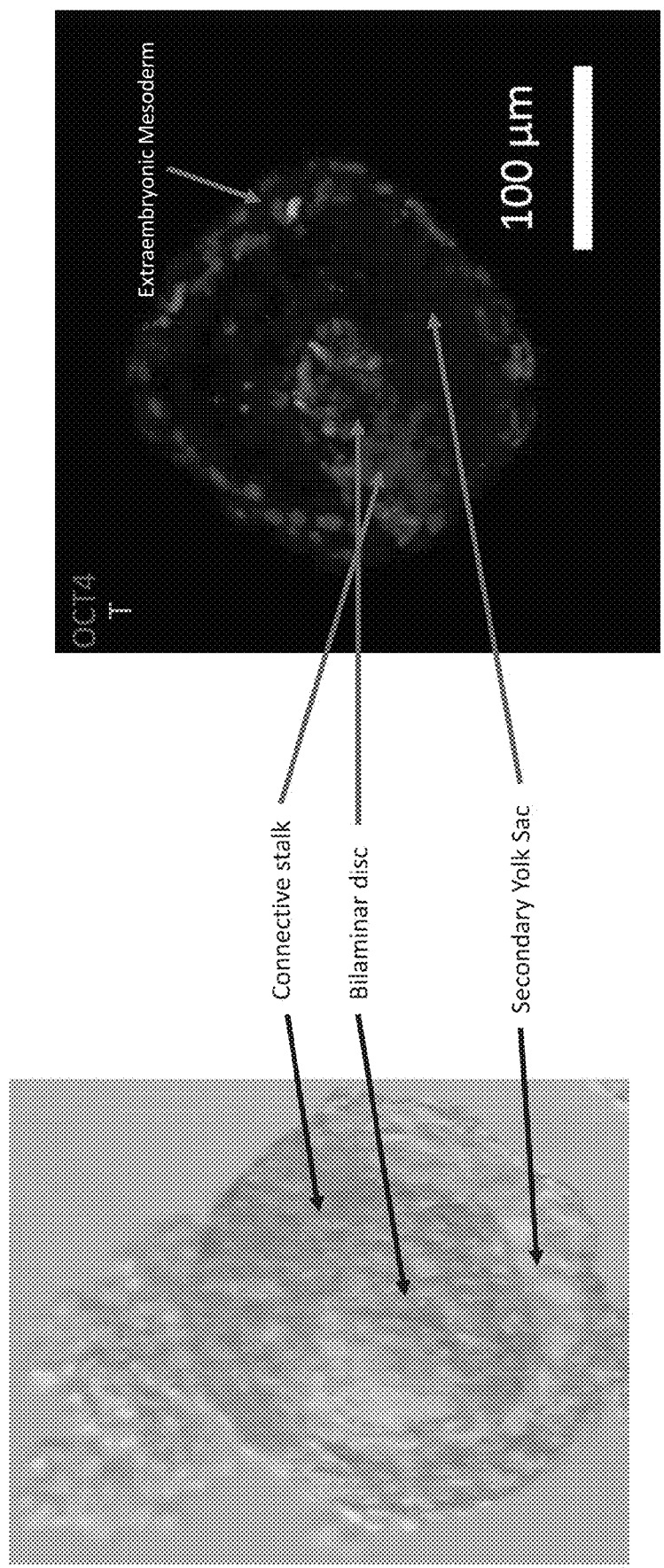
Figure 45E:
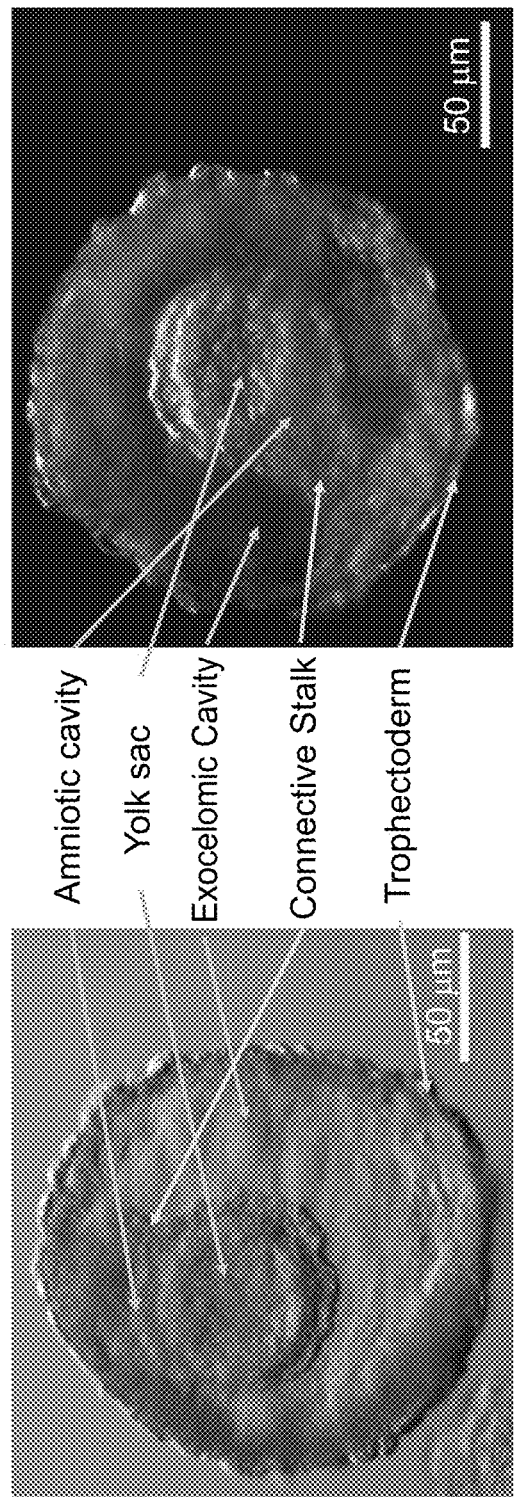

FIGS. 45A-E demonstrate that co-aggregation of human naïve PSCs cells with DOX pre-treated iGata4 human naïve PSCs and DOX pre-treated iCdx2 human naïve PSCs, followed by ex-uteru culturing leads to generation of an organized embryo. FIG. 45A is a schematic representation of the protocol. FIG. 45B-E show phase contrast and immunostaining images of the synthetic embryos obtained at the indicated time points after aggregation. FIG. 45B demonstrates appearance of the bilaminar disc on day+4. FIG. 45C demonstrates the formation of the primary yolk sac on day+5. FIG. 45D demonstrates the formation of the Secondary Yolk sac day+6 after co-aggregation. FIG. 45E demonstrates the consolidation of the bilaminar disc on day+7 human synthetic-embryo.

Figure 45F:
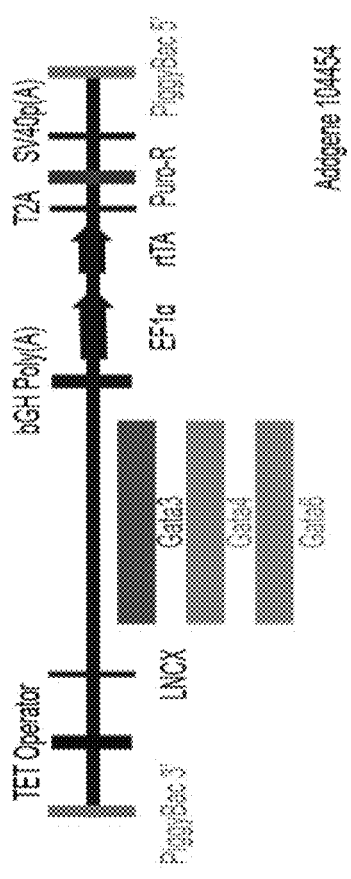

FIG. 45F shows a schematic representation of an inducible plasmid for transient expression of human CDX2, GATA3 GATA4 or GATA6. Shown is a PiggyBac plasmid expressing a cDNA insert of choice under the control of a doxycycline-inducible promotor. The Piggybac vector used (www (dot)addgene (dot)org/104454/), carries M2Rtta and a cite for cDNA insert of transcription factor of interest. This vector was used to generate 4 different plasmids: human CDX2 or Gata3 (to promote human PSC differentiation towards trophectoderm) and human GATA4 or GATA6 (to promote human primitive endoderm priming from human PSCs.

Figure 46A:
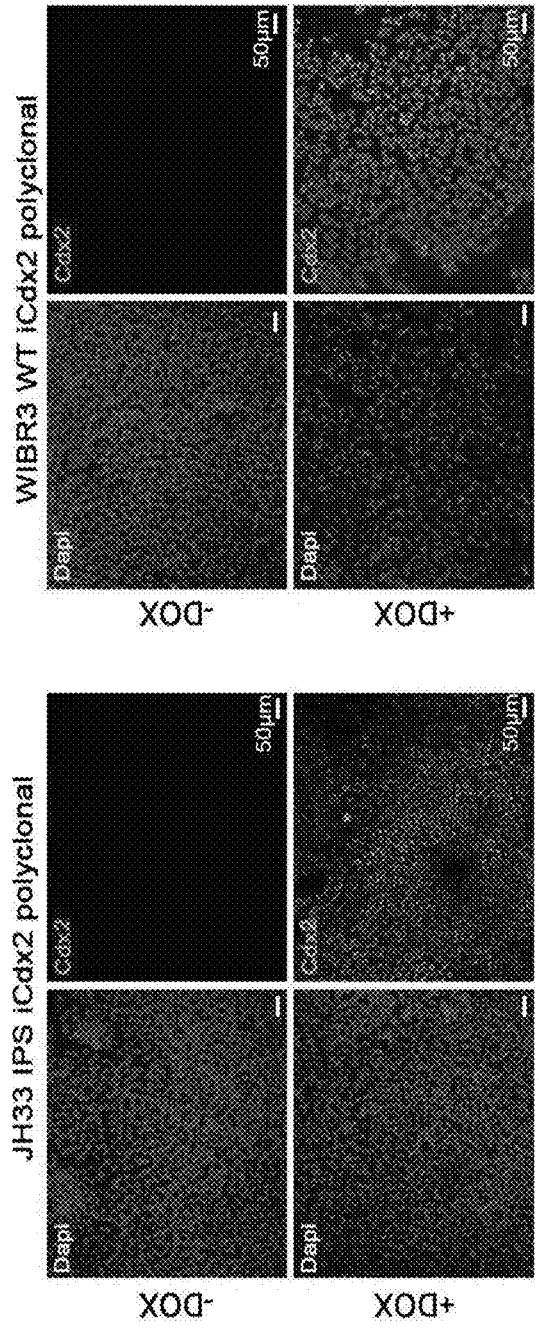
Figure 46B:
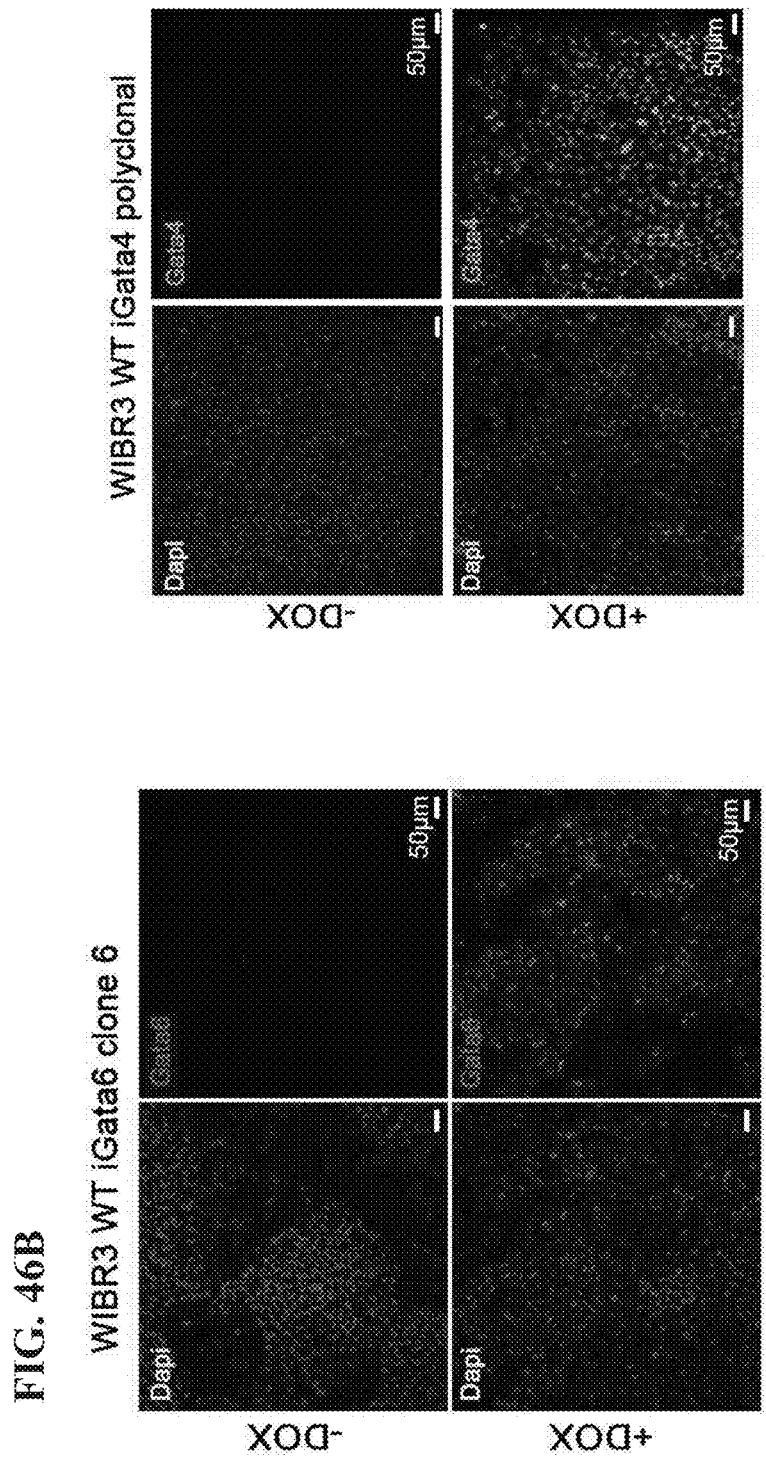
Figure 46C:
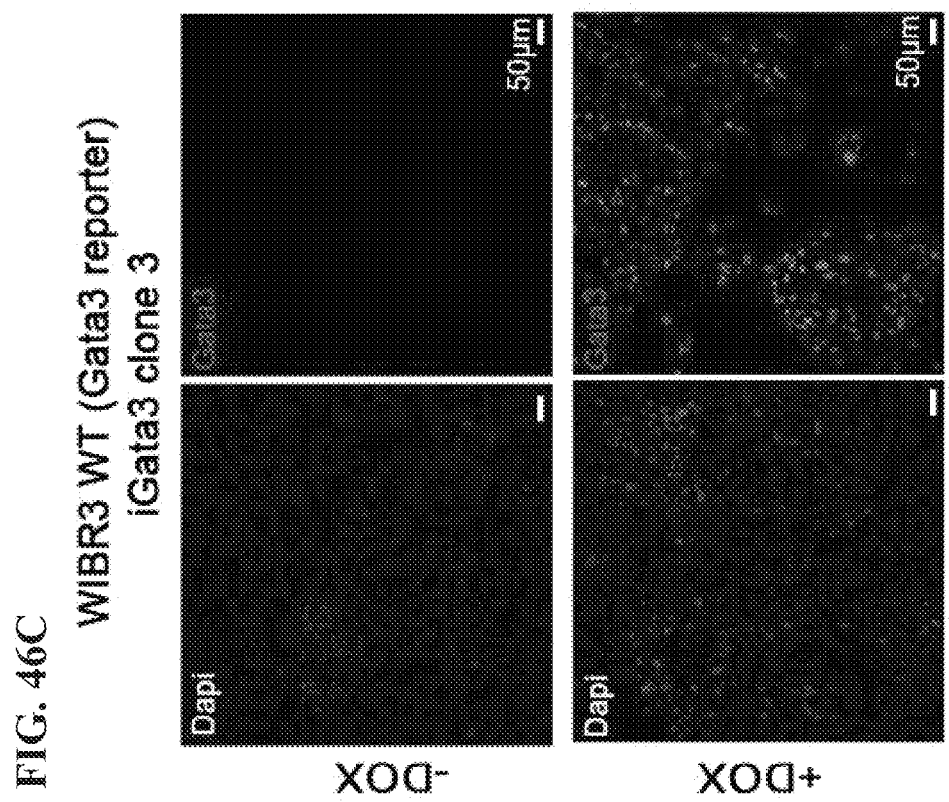

FIGS. 46A-C show immunostaining images of human PSC lines expressing the inducible plasmid demonstrated in FIG. 45F. FIG. 46A shows JH33 iPSs (a genetically unmodified human iPSC lines made from a healthy adult Caucasian male), and WIBR3 WT human female ESCs used to generate CDX2 inducible lines (iCDX2) using a Piggybac plasmid with CDX2 insert. Shown is immunostaining analysis for CDX2 protein expression of the human primed PSCs grown in mTESR conditions with and without DOX addition (2 μg/ml Dox). CDX2 expression was specifically detected only after DOX addition. FIG. 46B shows WIBR3 WT human female ESCs used to generate GATA4 or GATA6 DOX inducible lines (iGATA4 or iGATA6) using a Piggybac plasmid with human GATA4 or GATA6 as indicated. Shown is immunostaining analysis for GATA6 or GATA4 protein expression of the human primed PSCs (iGATA6 or iGATA4, respectively) grown in mTESR conditions with and without DOX addition (2 μg/ml final concentration of Dox). GATA4 or GATA6 expression was specifically detected only after DOX addition in the corresponding lines as shown. FIG. 46C shows WIBR3 WT human female ESCs used to generate GATA3 inducible lines (iGATA3) using a Piggybac plasmid with a GATA3 insert. Shown is immunostaining analysis for GATA3 protein expression of the human primed PSCs grown in mTESR conditions with and without DOX addition (2 μg/ml final Dox concentration in growth media). GATA3 expression was specifically detected only after DOX addition.

Figure 47A:
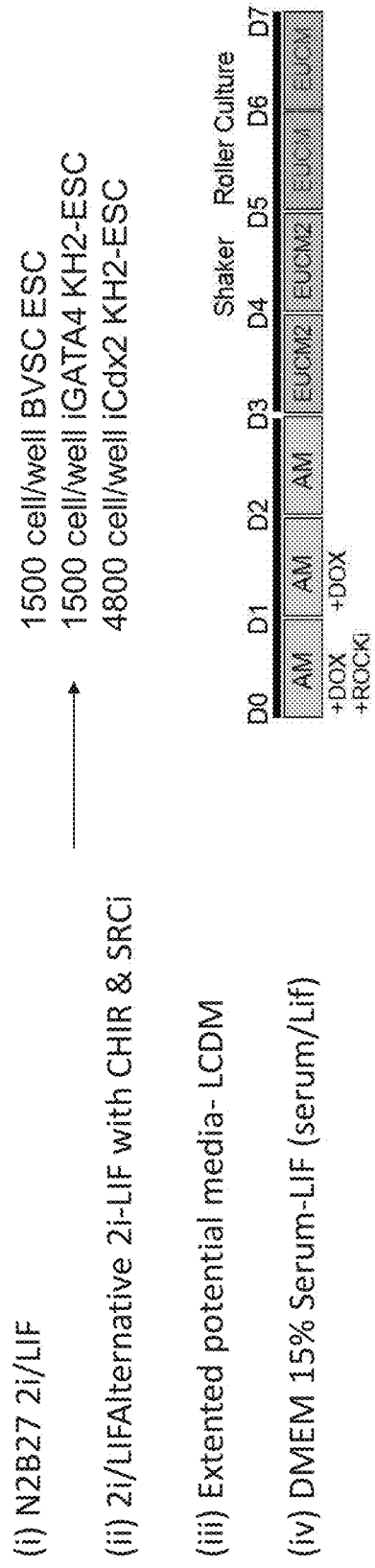
Figure 47B:
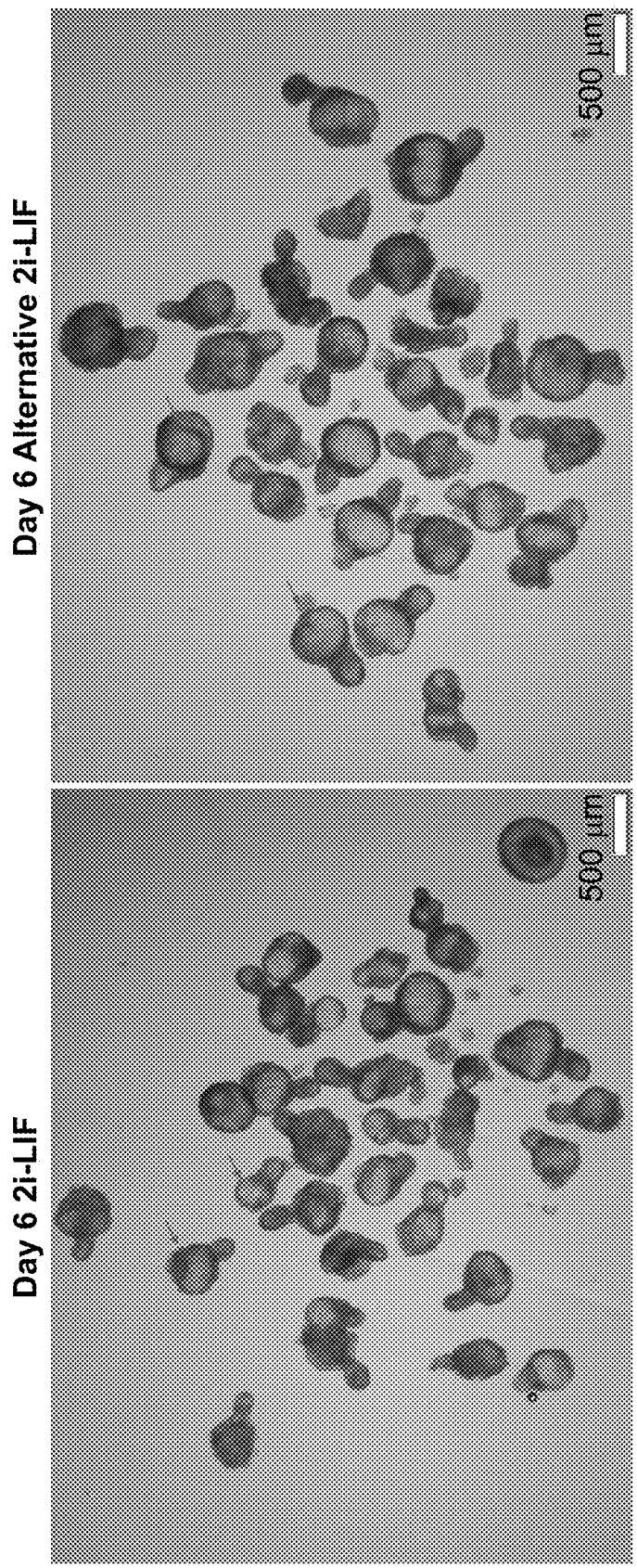
Figure 47C:
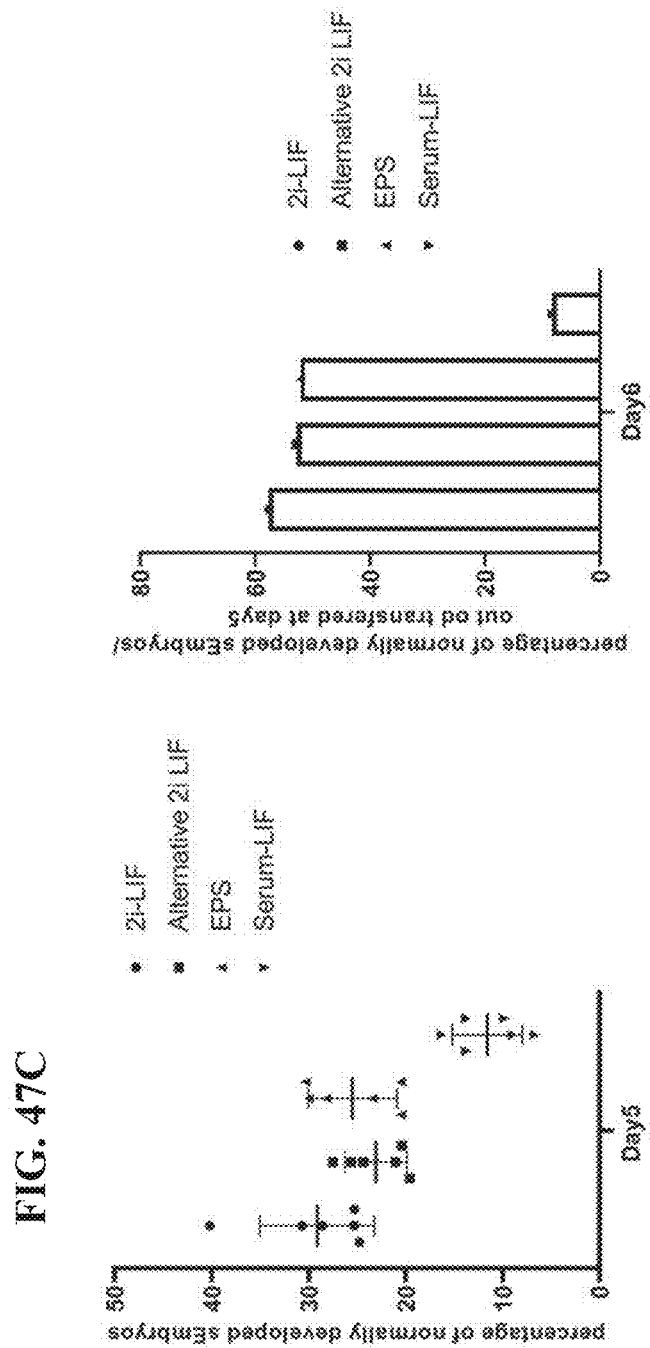

FIGS. 47A-C demonstrate the ability of alternative conditions to generate naïve PSCs as the starting population for generating organized embryos. FIG. 47A shows a schematic representation of the protocol. FIG. 47B demonstrates egg-cylinder shaped sEmbryos obtained at day 6 of the protocol from BVSC, KH2-iGata4 and Kh2-iCDX2 cells expanded in 2i/LIF and a2i/LIF (alternative 2i/Lif) conditions (blue arrows highlight normal day 6 sEmbryo morphology). FIG. 47C is a graph demonstrating efficiency of egg-cylinder shaped sEmbryos obtained at day 5 of the protocol from BVSC, KH2-iGata4 and Kh2-iCDX2 cells expanded in 2i/LIF and a2i/LIF (alternative 2i/LIF) conditions, EPS (LCDM naïve conditions) and serum-LIF conditions. Error bars indicate SEM from average.

Figure 48:
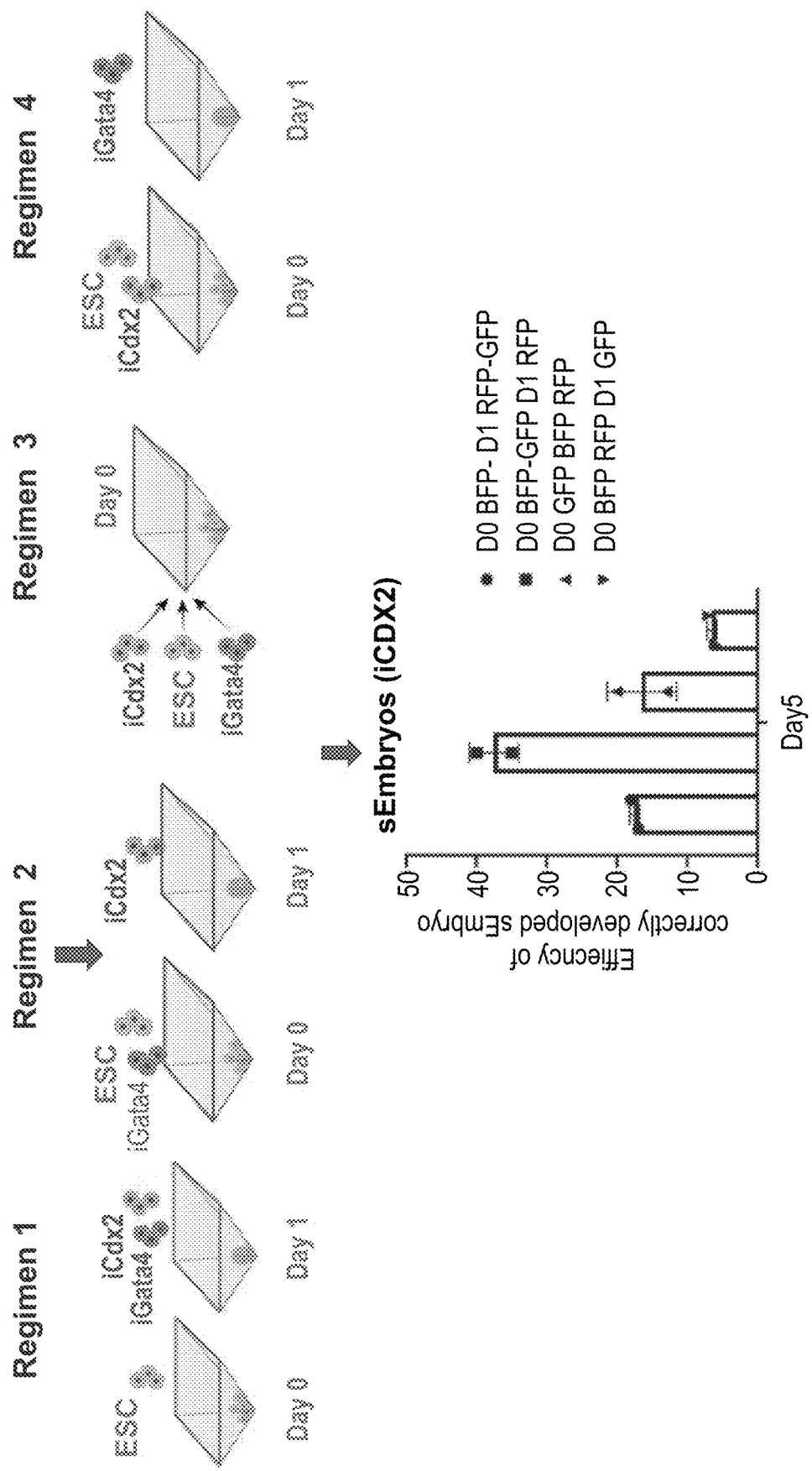

FIG. 48 demonstrates that a two steps aggregation protocol enhances sEmbryo formation efficiency. Shown is a schematic representation of the protocol and different regimens and a graph demonstrating efficiency of egg-cylinder shaped sEmbryos obtained at day 5 of the protocol.

Figure 49A:
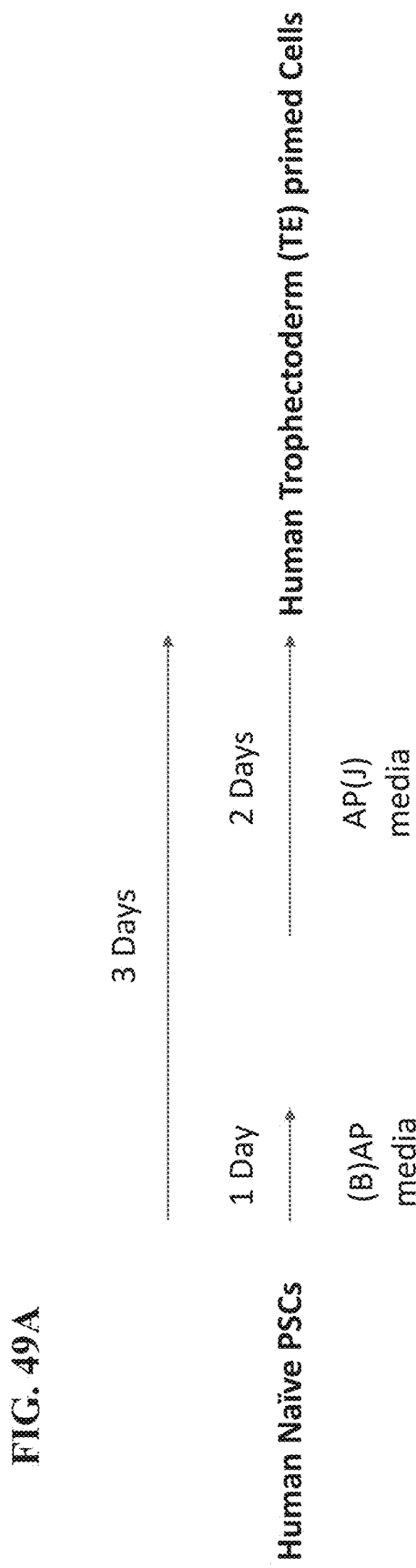
Figure 49B:
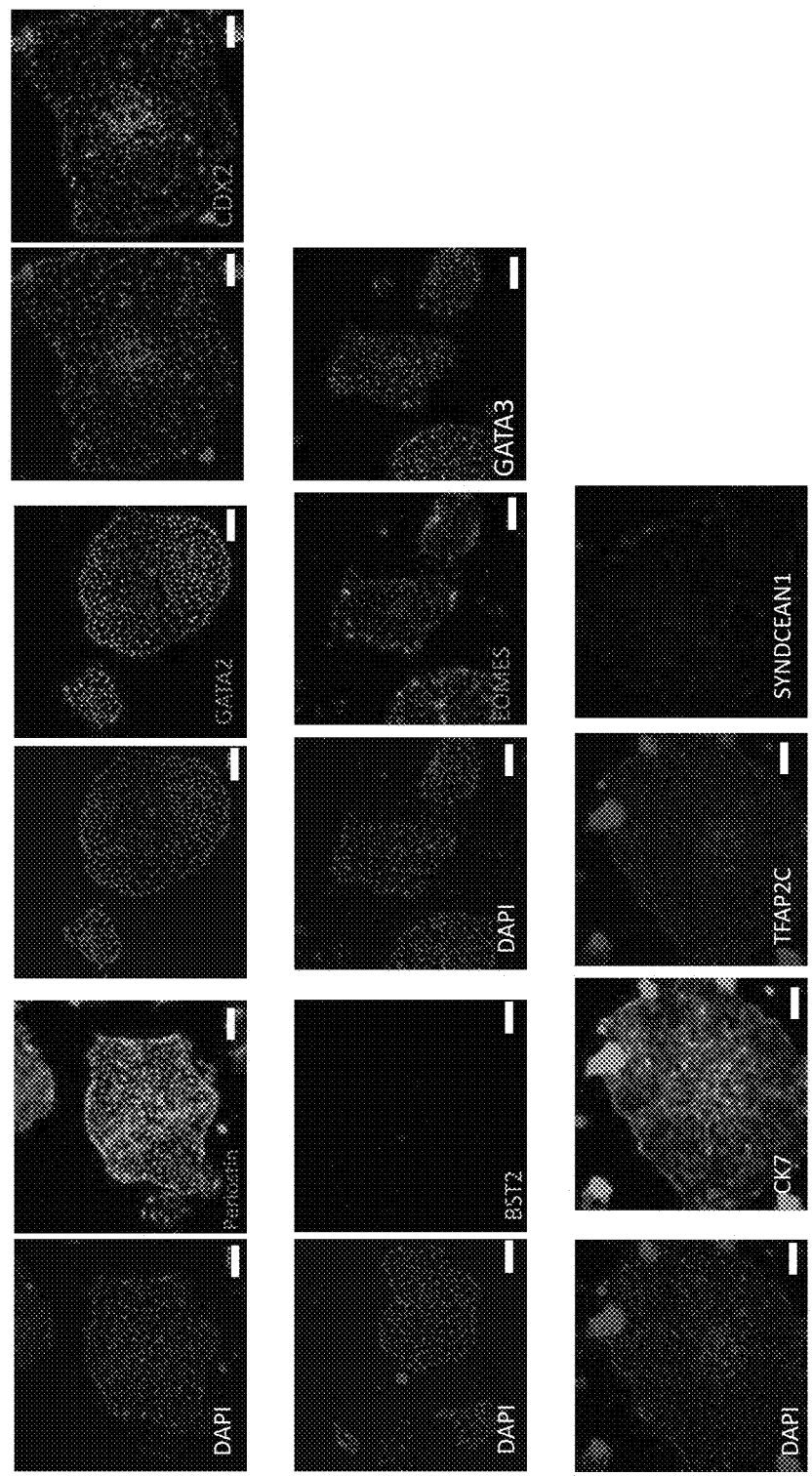
Figure 49C:
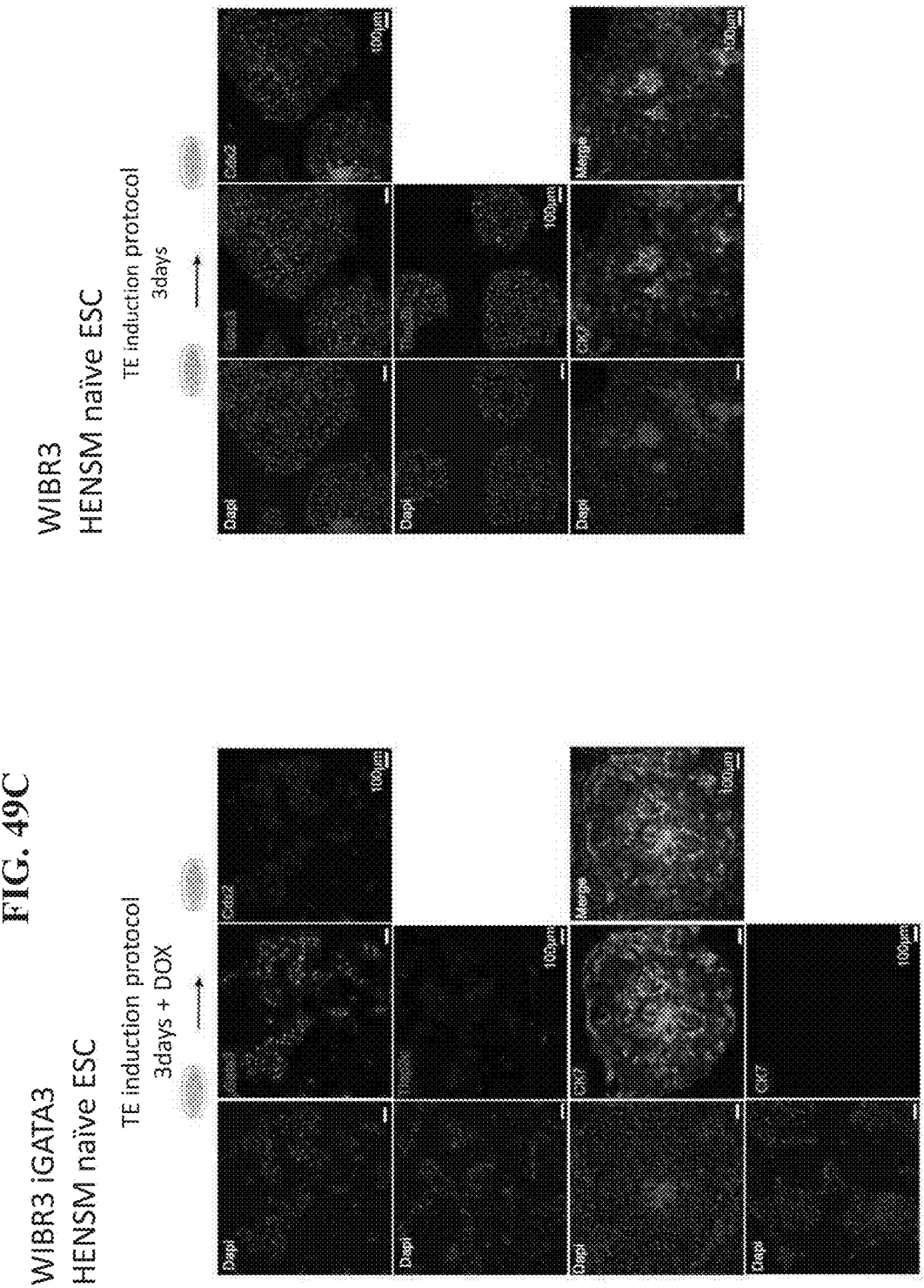

FIGS. 49A-D demonstrate generation of human trophectoderm (TE) primed cells by inducing expression of endogenous expression of differentiation factors. FIG. 49A is a schematic representation of the culture conditions. FIG. 49B shows immunostaining characterization of the human trophectoderm (TE) primed cells. Staining was conducted in day 3 of the trophectoderm induction regimen (TE). FIG. 49C shows immunostaining characterization of the human trophectoderm primed cells with or without transgenic iGATA3 expression. Staining was conducted in day 3 of the trophectoderm induction regimen (TE). FIG. 49D demonstrates RT PCR expression of different trophectoderm markers in the WT and iGATA3 WIBR3 cells.

Figure 50A:
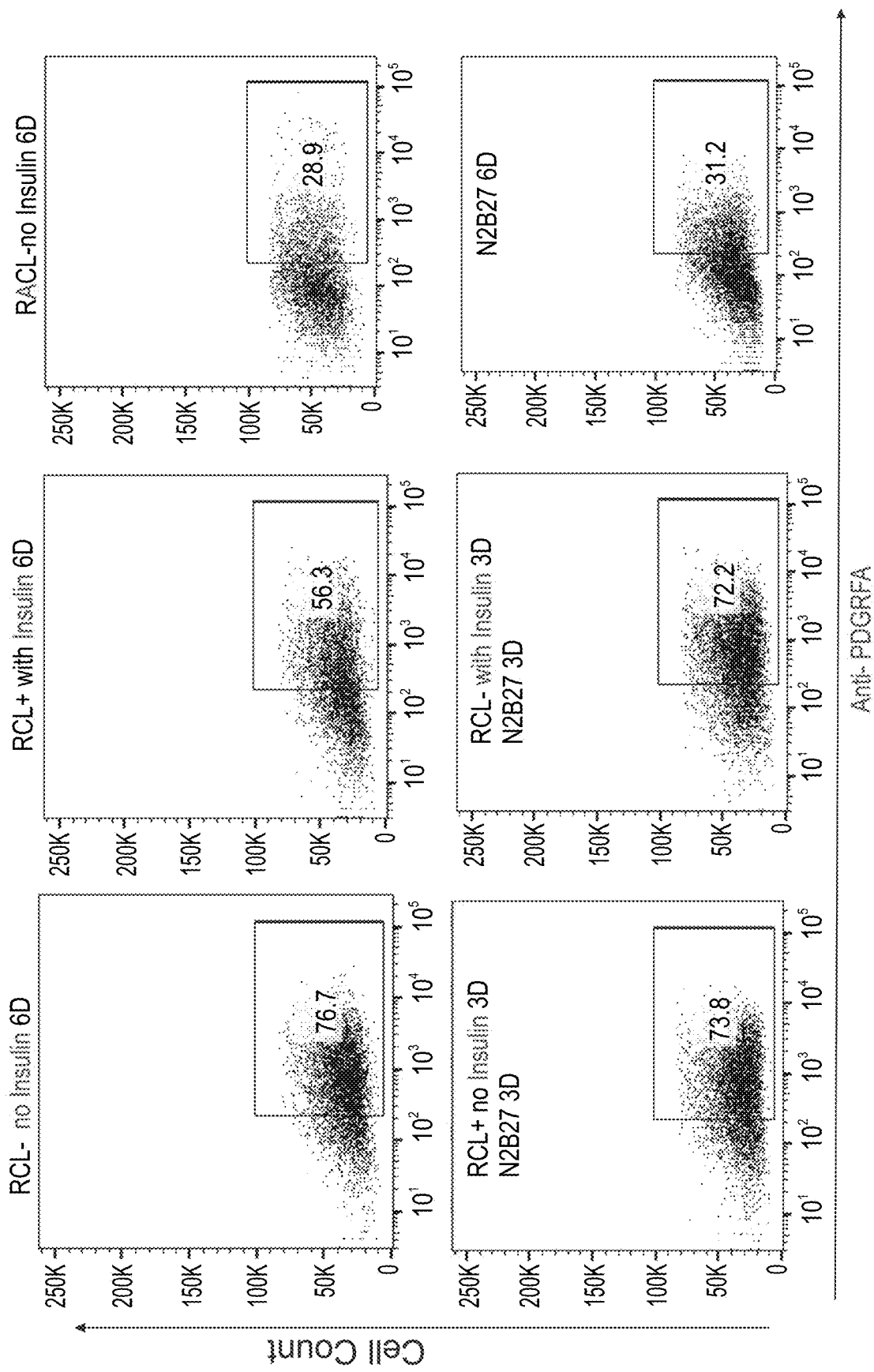
Figure 50B:
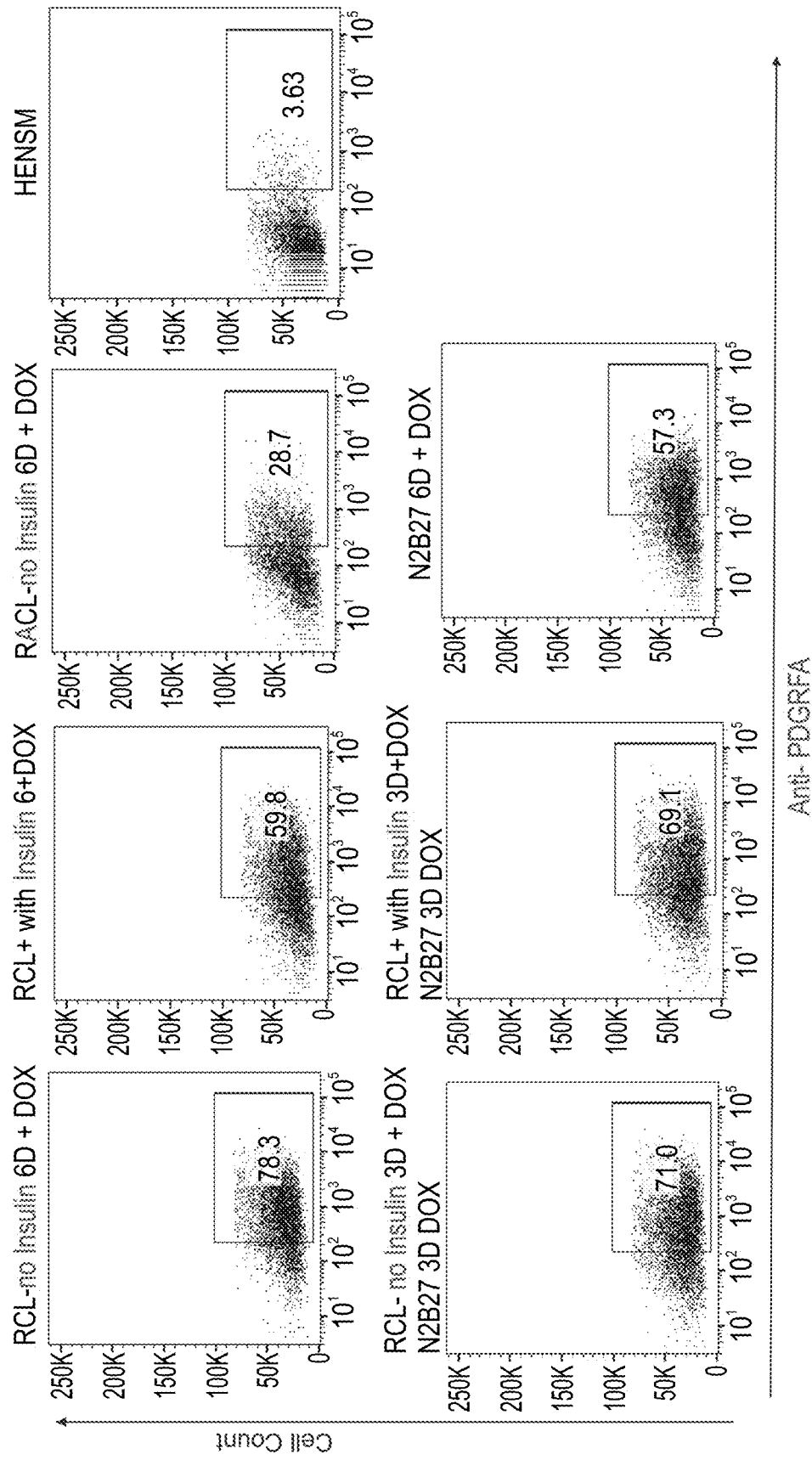
Figure 50C:
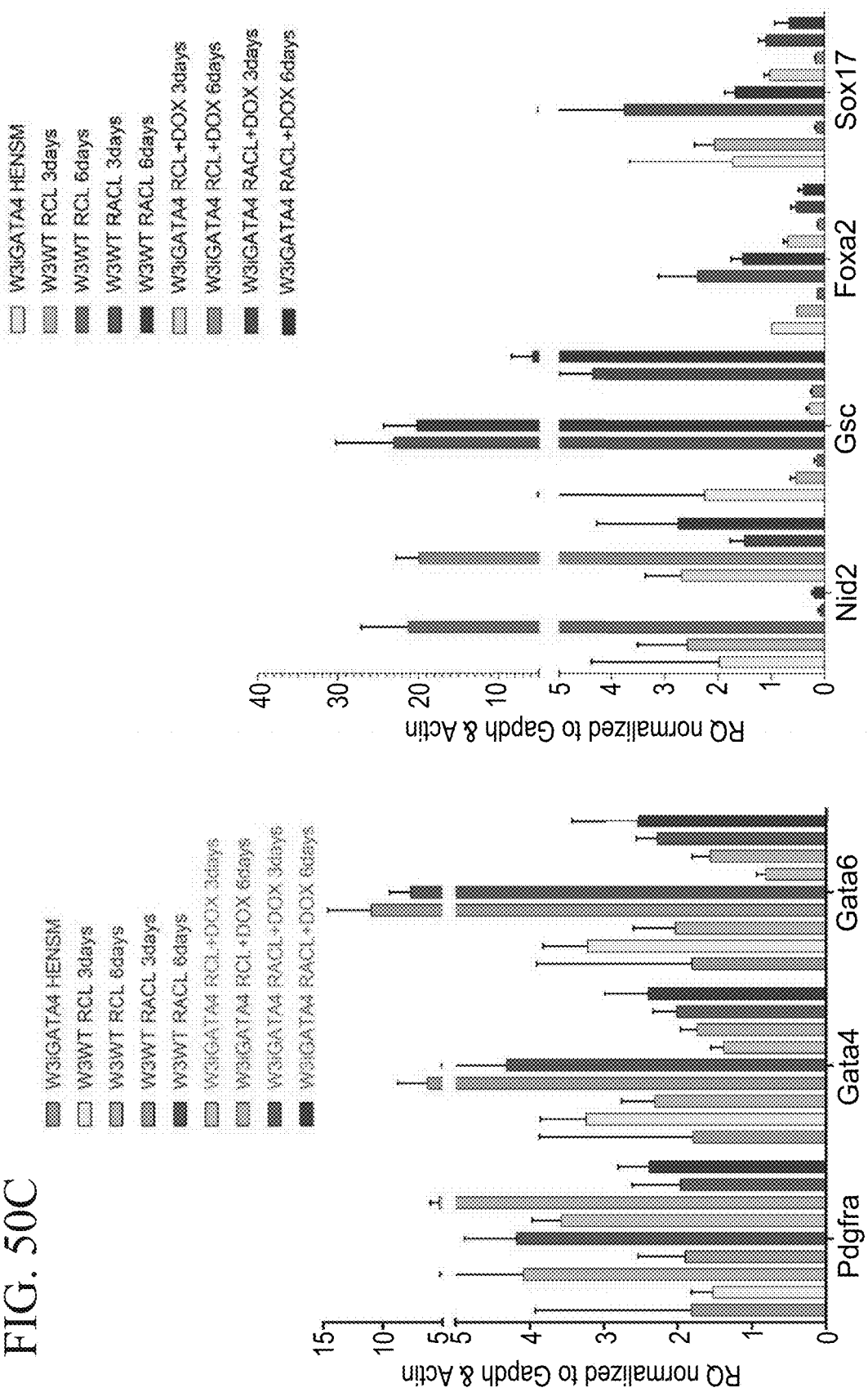

FIGS. 50A-D demonstrate generation of extra embryonic primitive endodermal primed cells (PRE) by inducing expression of endogenous expression of differentiation factors. Figure shows FACS analysis of PDGFRa expression after 6 days of induction in the indicated media. FIG. 50B shows FACS analysis of PDGFRa expression in iGATA6 cells after 6 days of induction in the indicated media. FIG. 50C demonstrates RT PCR expression of PRE markers (PDGFRa, GATA4, GATA6, Nid2, SOX17) and definitive endoderm markers (Gsc and Foxa2) in the WT and iGATA6 WIBR3 cells. FIG. 50D shows immunostaining characterization of the human PRE cells with or without transgenic iGATA3 expression. Staining was conducted in day 6 of the PRE induction regimen.

Figure 51A:
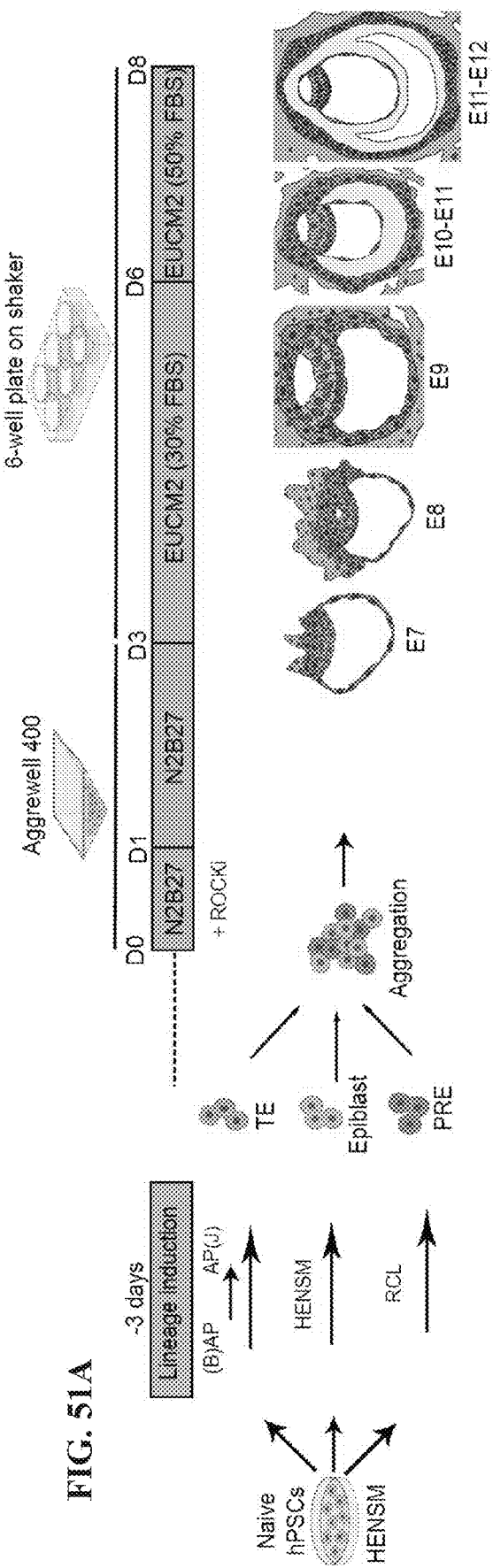
Figure 51B:
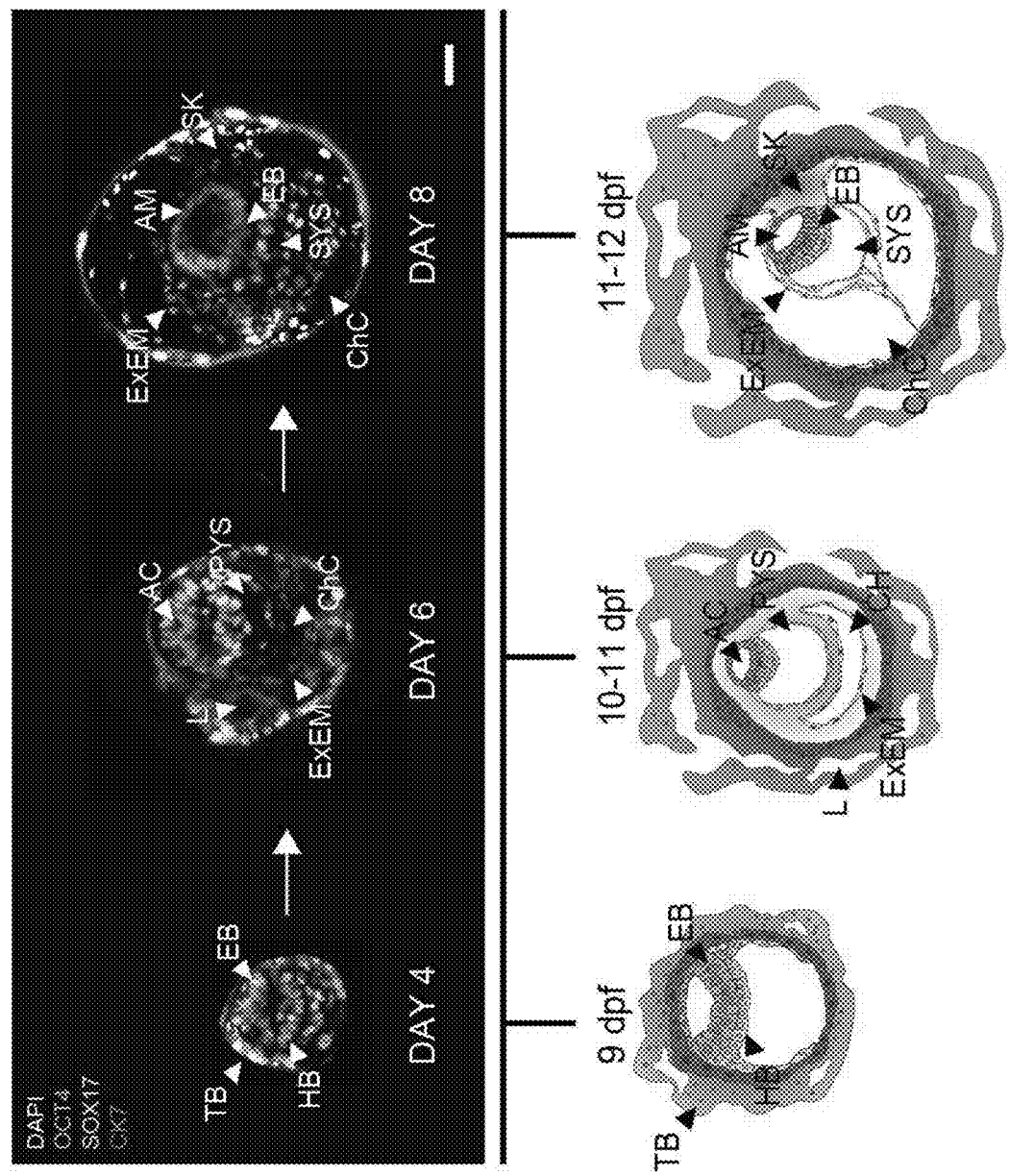
Figure 51E:
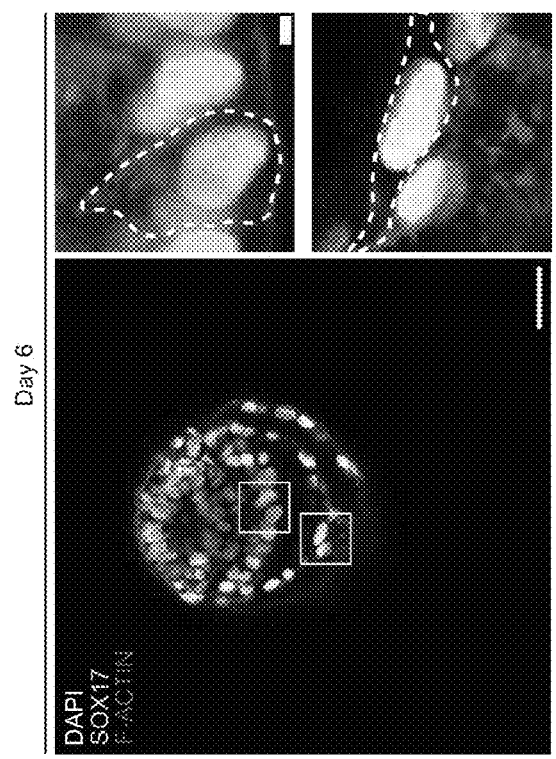
Figure 51D:
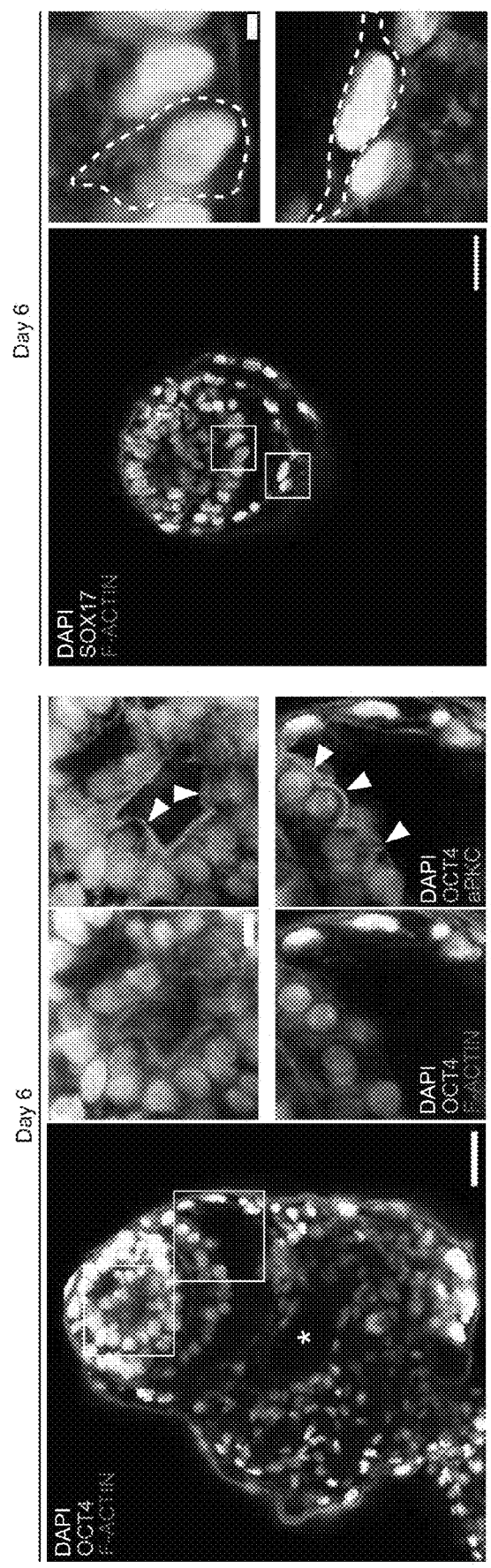
Figures 51F, 51G:
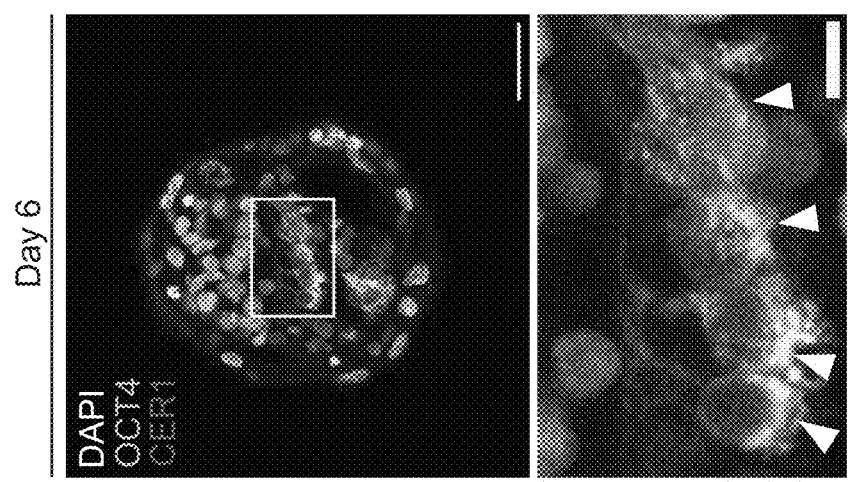
Figure 51J:
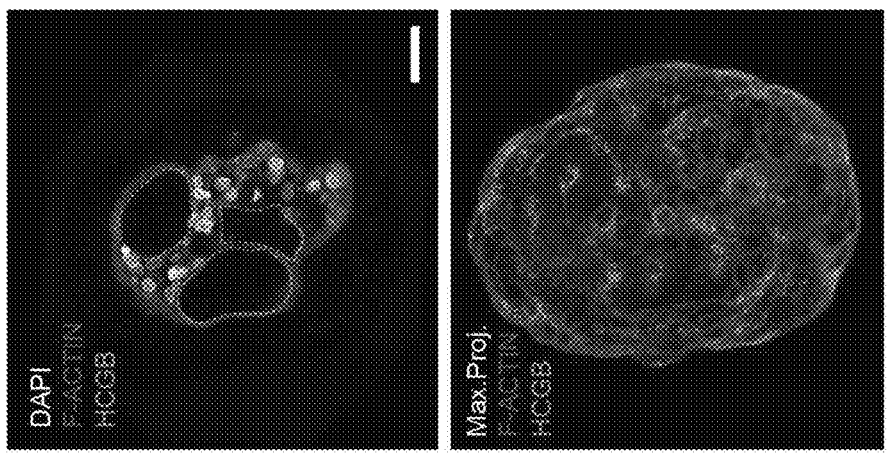
Figure 51I:
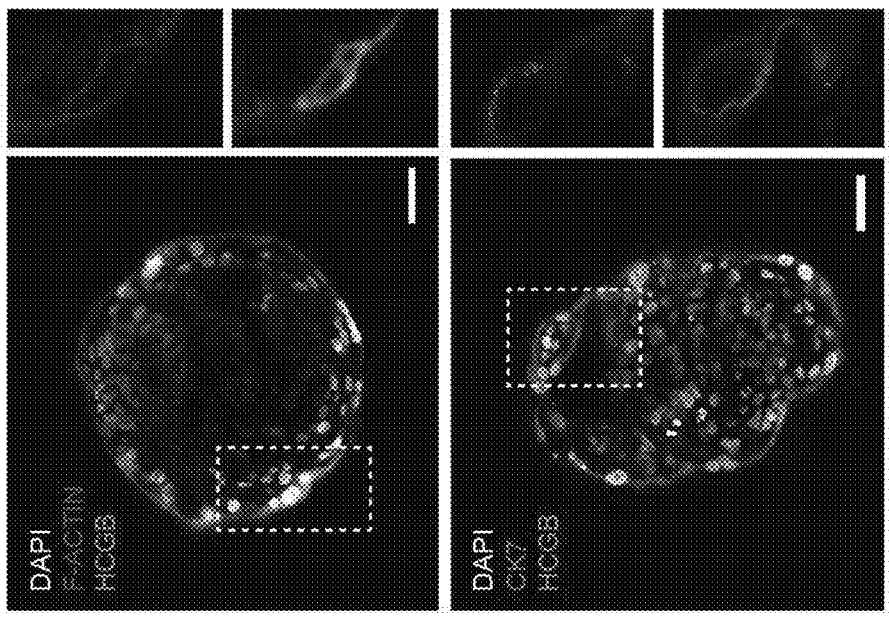
Figure 51H:
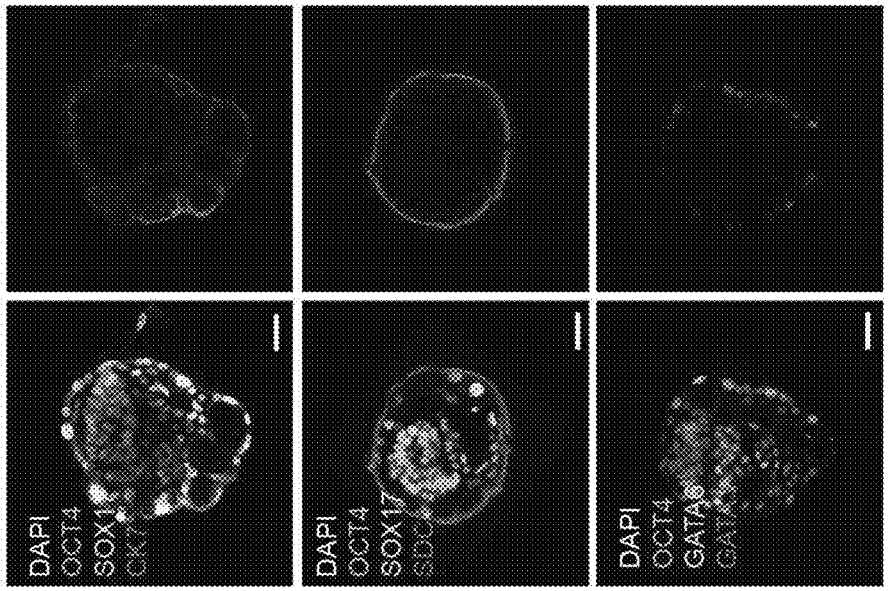
Figure 51L:
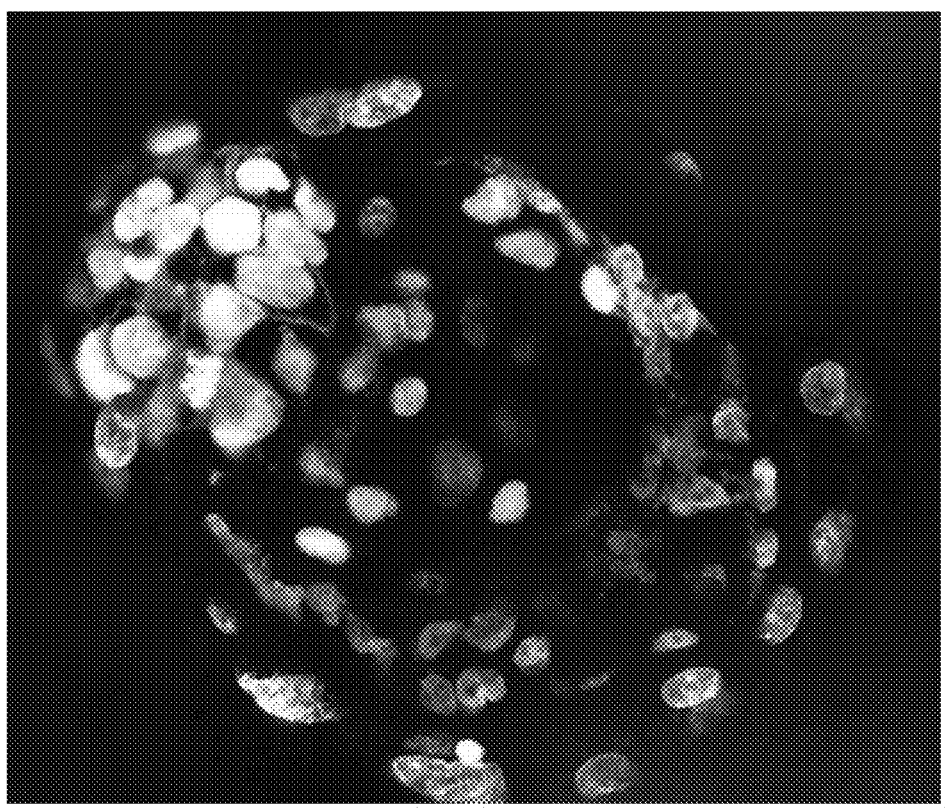
Figure 51K:
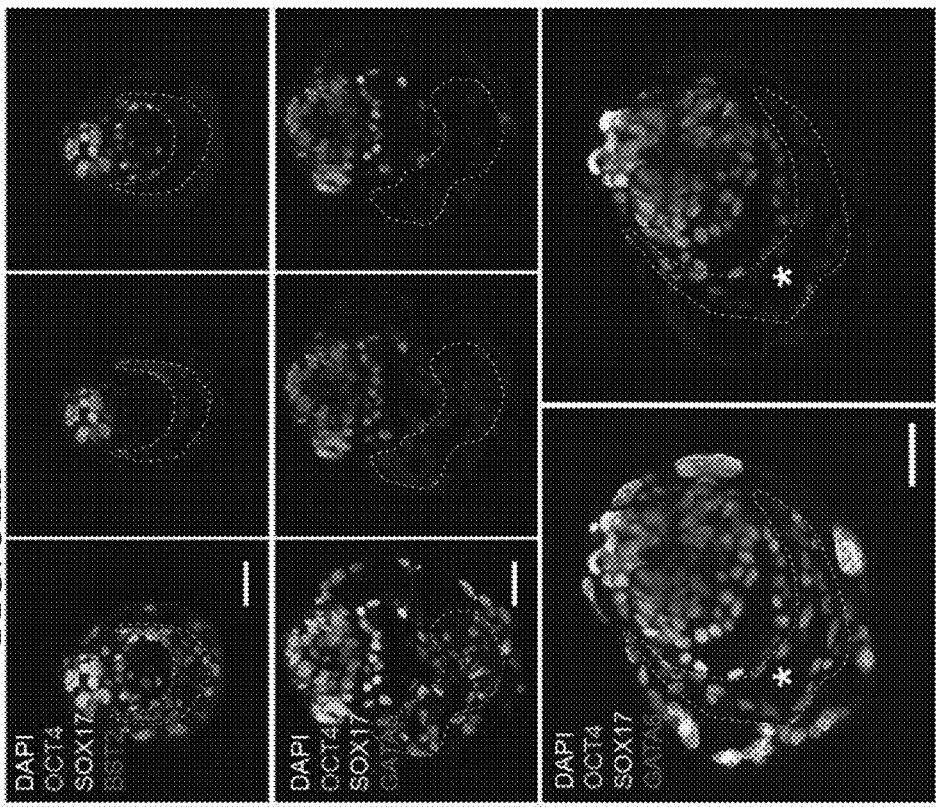

FIGS. 51A-L demonstrate that co-aggregation of human naïve PSCs cells with trophectoderm (TE) primed cells described in FIG. 49A-D and the extra embryonic primitive endodermal primed cells described in FIGS. 50A-D, followed by ex-utero culturing leads to generation of an organized embryo. FIG. 51A shows a schematic representation of the protocol. FIG. 51B demonstrates progression of human sEmbryos from D4 to D8 of the protocol (top panel) compared to 9-12 dpf of human embryos (schematically shown at the bottom). The top panel shows images of human days 4-8 sEmbryos immunostained for OCT4 (Cyan), SOX17 (Yellow) and CK7 (Magenta), which are markers for epiblast, hypoblast and trophoblast, respectively. Scale bar: 50 μm. Abbreviations: TB, Trophoblast; EB, Epiblast; HB, Hypoblast; L, Lacuna; AC, Amniotic cavity; PYS, Primary Yolk Sac; ChC, Chorionic Cavity; ExEM, Extraembryonic Mesoderm; SK, Stalk; dpf, days post fertilization. FIG. 51C shows characterization of epiblast pluripotency in human sEmbryos. Shown are image of D4 sEmbryos immunostained for OCT4, SOX2, KLf17 and DNA (DAPI). Scale bar: 25 μm. Top panel—2× zoom into the epiblast region. FIGS. 51D-E shows apical cell polarity and lumenogenesis in human sEmbryos. FIG. 51D shows images of D6 sEmbryos immunostained for OCT4 (cyan), F-actin (red), and DNA (DAPI, grey). Scale bar: 50 μm. Asterisk indicates putative chorionic cavity. Right top, 2× zoom into the amniotic lumen. Right bottom, 2× zoom into the yolk sac lumen. Arrows mark apical cell surfaces with aPKC (green). Scale bar: 12.5 μm. FIG. 51E shows images of D6 sEmbryos immunostained for SOX17 (yellow), F-actin (red), and DNA (DAPI, grey). Scale bar: 50 μm. Right, zoom into the yolk sac lumen showing yolk sac layers with cylindrical (top) and a squamous cell (bottom). Cell perimeters are outlined with dashed lines. Scale bar: 5 μm. OCT4 and SOX17 mark epiblast and hypoblast, respectively. FIGS. 51F-G show Anterior-posterior symmetry breaking in the human sEmbryos. FIG. 51F shows images of D6 sEmbryos immunostained for OCT4 (cyan), CER1 (red), and DNA (DAPI, grey). Scale bar: 50 μm. Bottom, 4× zoom into the hypoblast region enriched for apical vesicles with CER1 (marked with arrows) which makes the AVE (anterior visceral endoderm). FIG. 51G shows images of D6 sEmbryos immunostained for OCT4 (cyan), Brachyury (BRA, red), and DNA (DAPI, grey). Scale bar: 50 μm. Right, 4× zoom into the BRA-positive epiblast cells (marked with arrows). OCT4 marks pluripotent epiblast whereas BRA and CER1 are early markers of epiblast and hypoblast differentiation, respectively, associated with anterior-posterior symmetry breaking in the early post-implantation human embryo. FIGS. 51H-J show trophoblast compartment characterization of the sEmbryos. FIG. 51H shows images of D6 sEmbryos immunostained for epiblast (OCT4, Cyan), hypoblast (SOX17, Yellow) and three different markers for trophoblast (CK7, SDC1, GATA3, Magenta). All three trophoblast are present in and form a surrounding layer covering the structure. FIG. 51I top panel shows images of D6 sEmbryos immunostained for F-ACTIN (Red) and HCGB (Green), demonstrating the membranes and syncytiotrophoblast. Zoom in shows multinucleated cell expressing HCGB, characteristic of syncytiotrophoblast. FIG. 51I bottom panel shows images of D6 sEmbryos immunostained for CK7 (Magenta) and HCGB (Green) demonstrating partial, but not complete overlap of the two markers, indicating the presence of cyto-(CK7+ only) and syncytiotrophoblast (CK7+ and HCGB+). FIG. 51J top panel shows images of D6 sEmbryos immunostained for F-ACTIN and HCGB. Single stack of membrane marker F-actin and HCGB show the formation of lacuna (dotted line) by syncytiotrophoblast. FIG. 51J bottom panel shows maximum projection demonstrating that syncytiotrophoblast surround the whole structure. Scale bar: 50 μm. FIGS. 51K-L demonstrate presence and organization of Extraembryonic mesoderm (ExEm) in the sEmbryos. FIG. 51K shows images of D6 sEmbryos immunostained for epiblast (OCT4, Cyan), PYS (SOX17, Yellow) and ExEm markers (BST2, GATA6, Red). The top panel demonstrates that BST2+ cells invade the space between the yolk sac (SOX17+) and the outer trophoblast layer (DAPI, SOX17−, OCT4−, BST2−) showing the presence of ExEM cells. The middle panel demonstrates that the ExEM are also express GATA6, a shared marker for HB/PYS, but in a lower level then in the PYS. The bottom panel demonstrates that the ExEM cells organize and form a cavity between PYS and trophoblast cells, indicating the formation of chorionic cavity (asterix). FIG. 51L shows a zoom in of the middle-section of immunofluorescent image stained for OCT4 (Cyan), SOX17 (Green) and BST2 (Red). BST2 is expressed in between the yolk sac (SOX17+) and the outer trophoblast cells (DAPI, SOX17−, OCT4−, BST2−) and in the epiblast (OCT4+). ExEM cells are characterized here by expression of BST2 and lack of expression of SOX17 and OCT4. Scale bar: 50 μm. Abbreviations: Max.Proj., Maximum intensity projection of z-stacks.

Figure 52A:
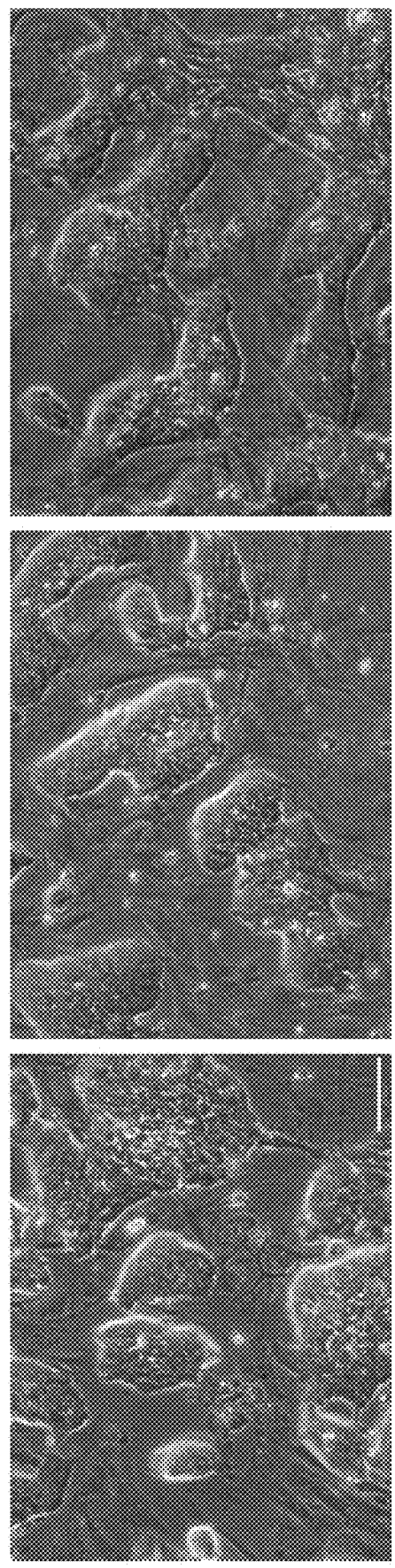
Figure 52B:
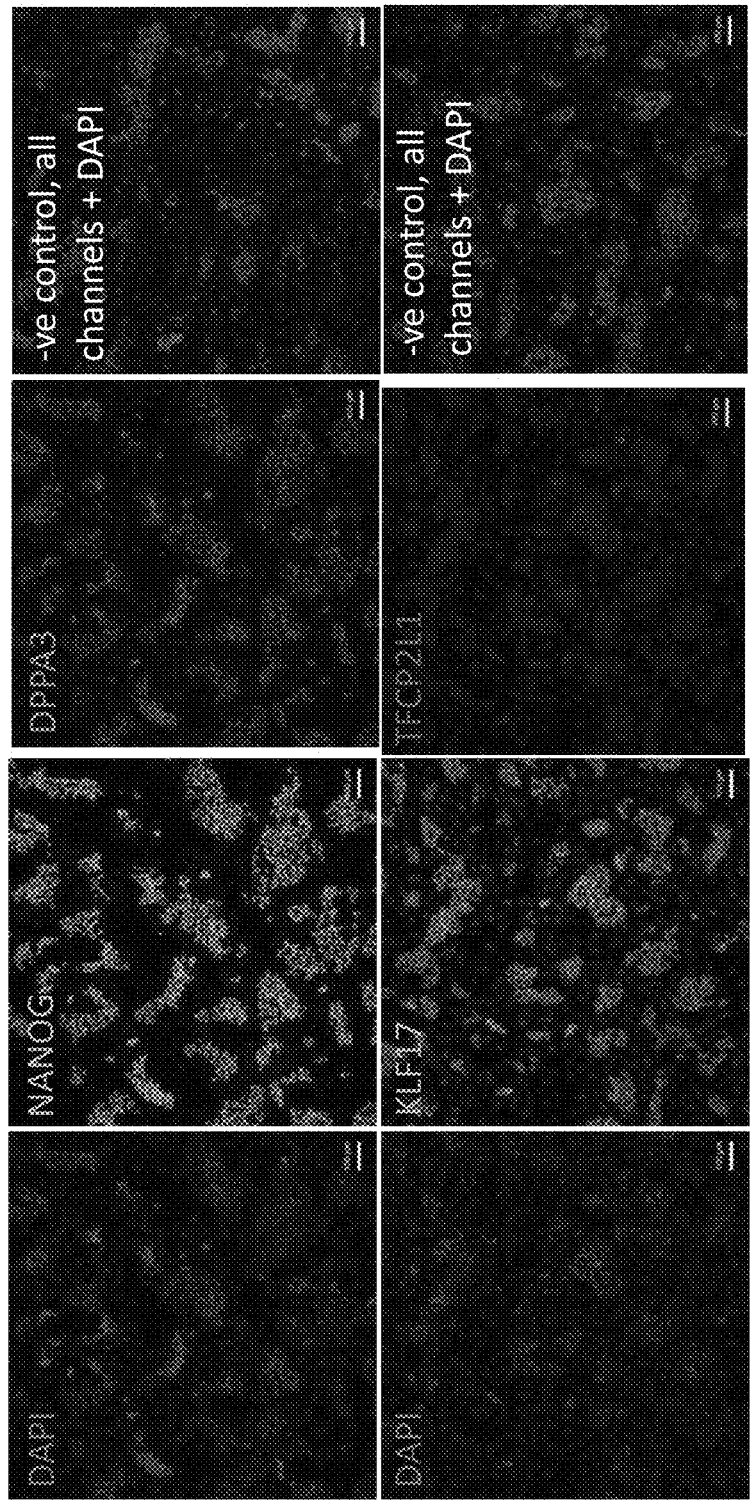

FIGS. 52A-B demonstrate generation of naïve Rhesus Macaque (RM) PSCs. FIG. 52A shows phase images demonstrating typical domed like morphology of RM-1 naïve hESCs expanded in NENSM conditions at the indicated passages. FIG. 52B shows images of the monkey naïve RM1-ESCs immunostained for several naïve pluripotency markers: DPPA3, TFCP2L1, KLF17 and NANOG. DAPI was used for counterstain.

Figure 53:
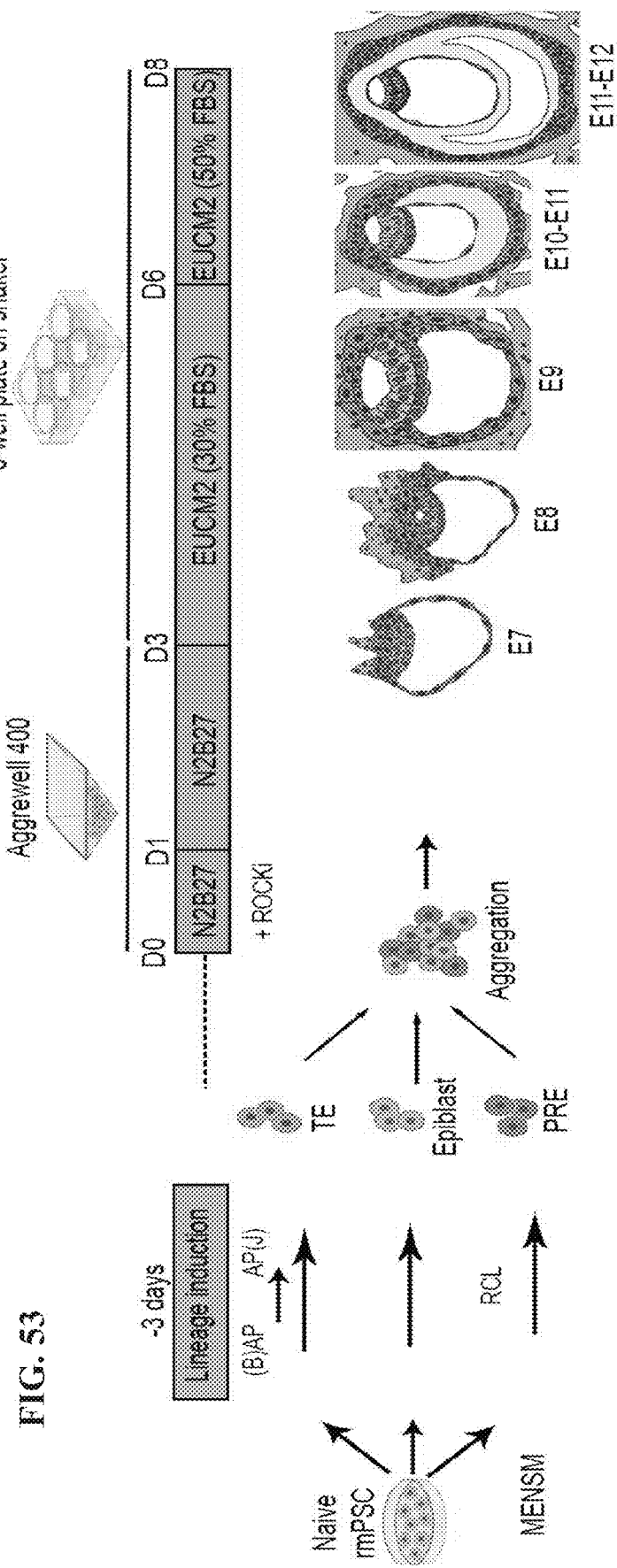

FIG. 53 is a schematic representation of the protocol for the generation of RM synthetic embryos.

Figure 54:
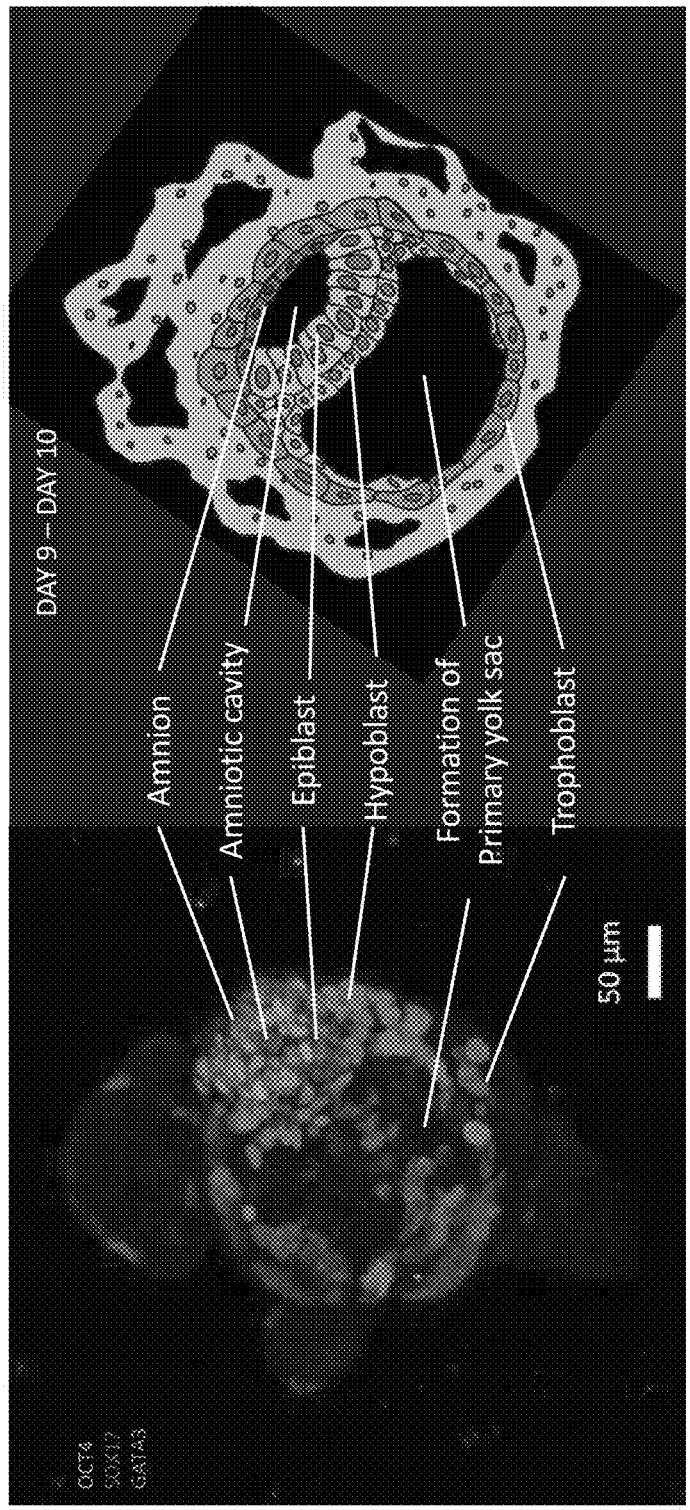

FIG. 54 demonstrates that co-aggregation of RM naïve PSCs cells with human trophectoderm (TE) primed cells and the human extra embryonic primitive endodermal primed cells described in Example 12, followed by ex-utero culturing leads to generation of an organized embryo. The Figure demonstrates progression of human sEmbryos from D6 of the protocol (left panel) compared to 9-12 dpf of RM embryos (schematically shown on the right). The sEmbryo was immunostained for OCT4 (Green), SOX17 (Red) and Gata3 (Magenta), which are markers for epiblast, hypoblast and trophoblast, respectively. Scale bar: 50 μm.

Figure 55:
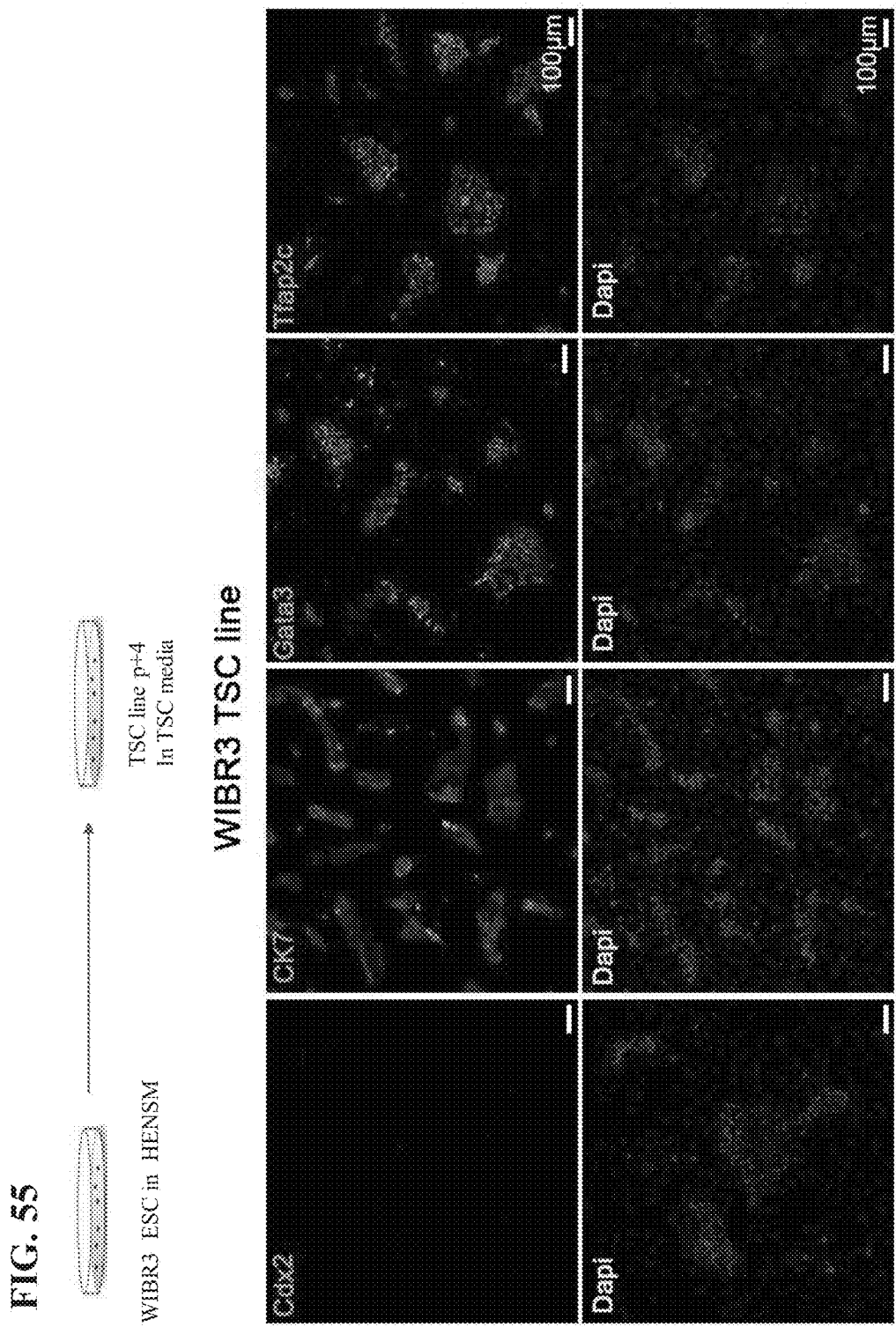

FIG. 55 demonstrates formation of a stable human TSC line. Shown are images of cells immunostained for CDX2, Cytokeratin7 (CK7), GATA3 and TFAP2C. DAPI was used for counterstain.

Figure 56:
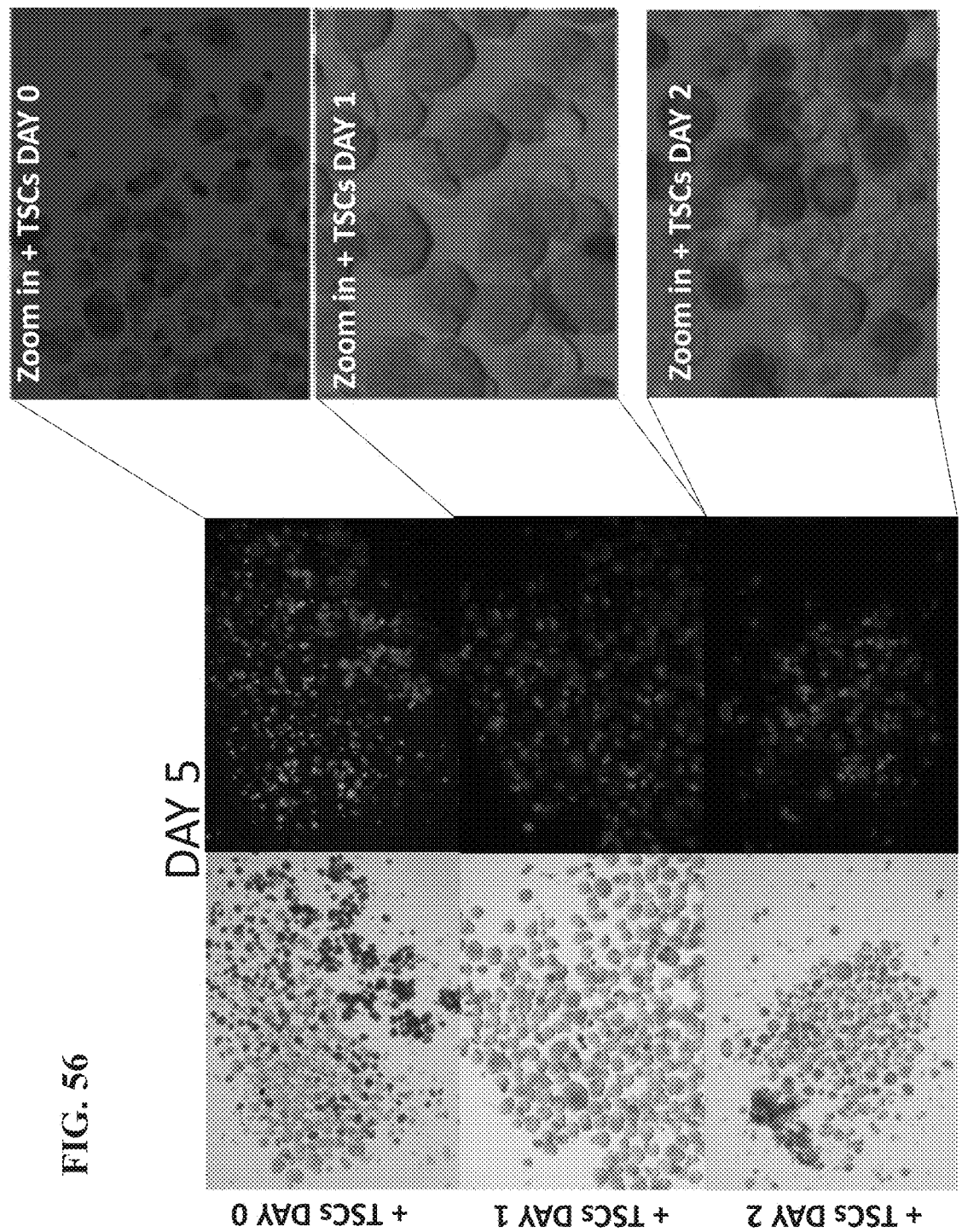

FIG. 56 demonstrates that human stable derived TSC lines are not capable of forming normal sEmbryos. Three starting cell types were co-aggregated, naïve WT hESCs cultured in HENSM medium; for the primitive endoderm compartment Naïve WT cells were plated on mouse embryonic fibroblast conditions on HENSM supplemented with ROCKi 10 μM (Axon Medchem 1683), next day medium was replaced by RCL medium, RCL was kept for 72 h with 24-hour medium exchanges; and for the Trophoblast compartment, a human TSC line derived from WIBR3 naïve ESCs at (Passage 5) was used. The latter was generated by transferring human naïve WIBR3 expanded in HENSM conditions into TSC media on MEF coated plates and serially passaged in TSC media and validated as TSC line. The TSC line was constitutively labeled with RFP coding lentivirus (labeling it as RED). Human TSCs were introduced in day 0, day 1 and day 2 of the sEmbryo protocol. In all cases it could be appreciated that the cells co-localize in one side of the aggregate (as appreciated by their RED label) without surrounding the entire sEmbryo at Day 5, which does not correspond with the expected morphology and does not yield normally developed embryos that are surrounded by trophoblast lineage only on the outside periphery.

Figure 57A:
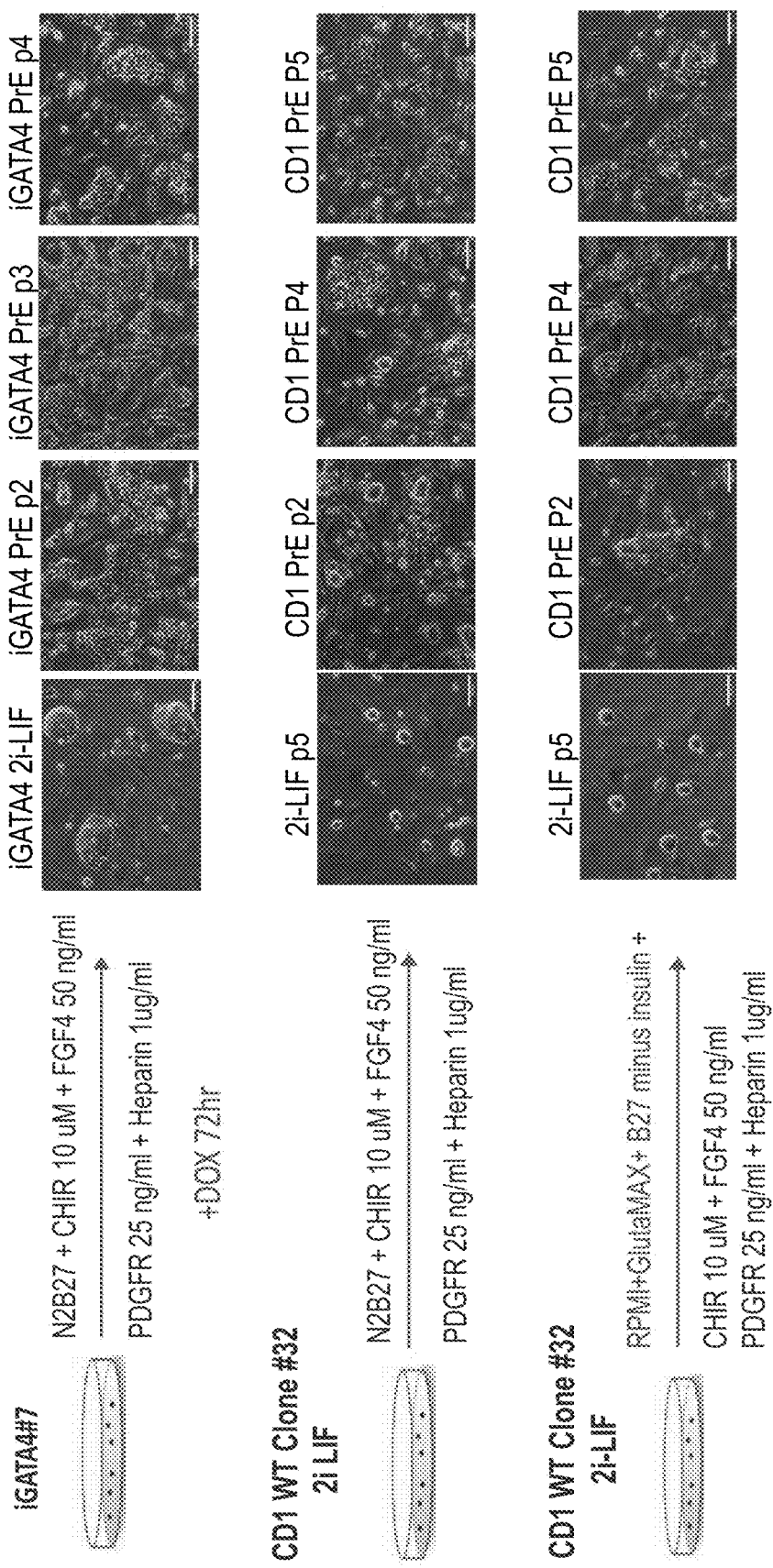
Figure 57B:
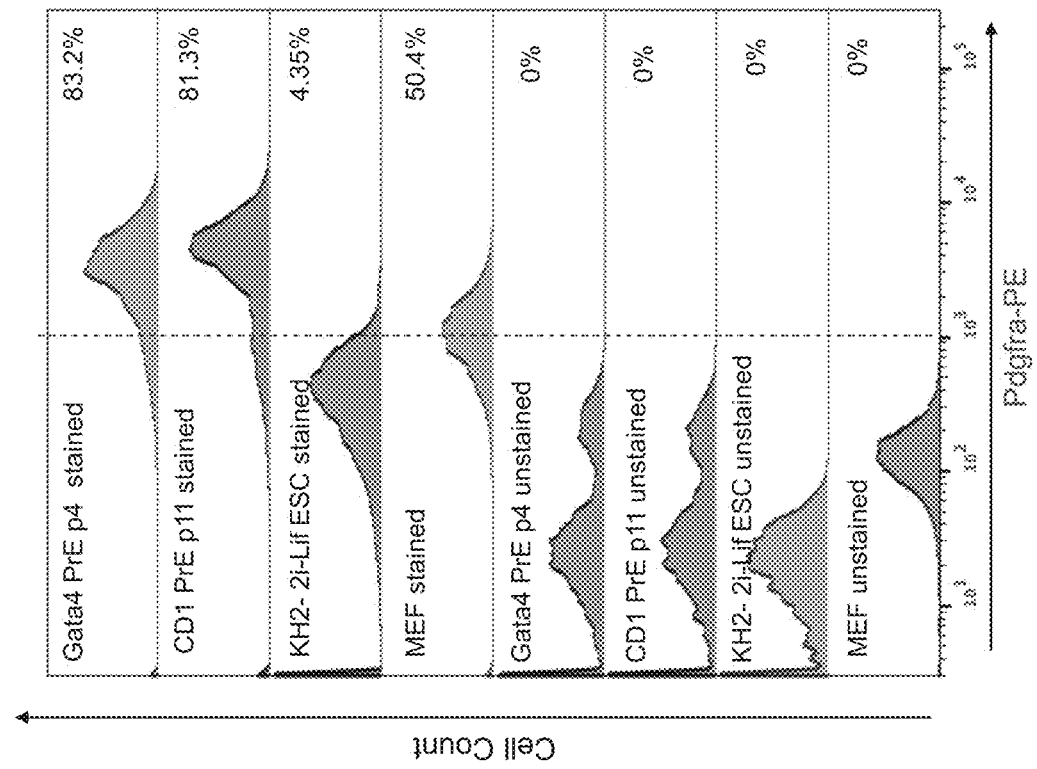
Figure 57C:
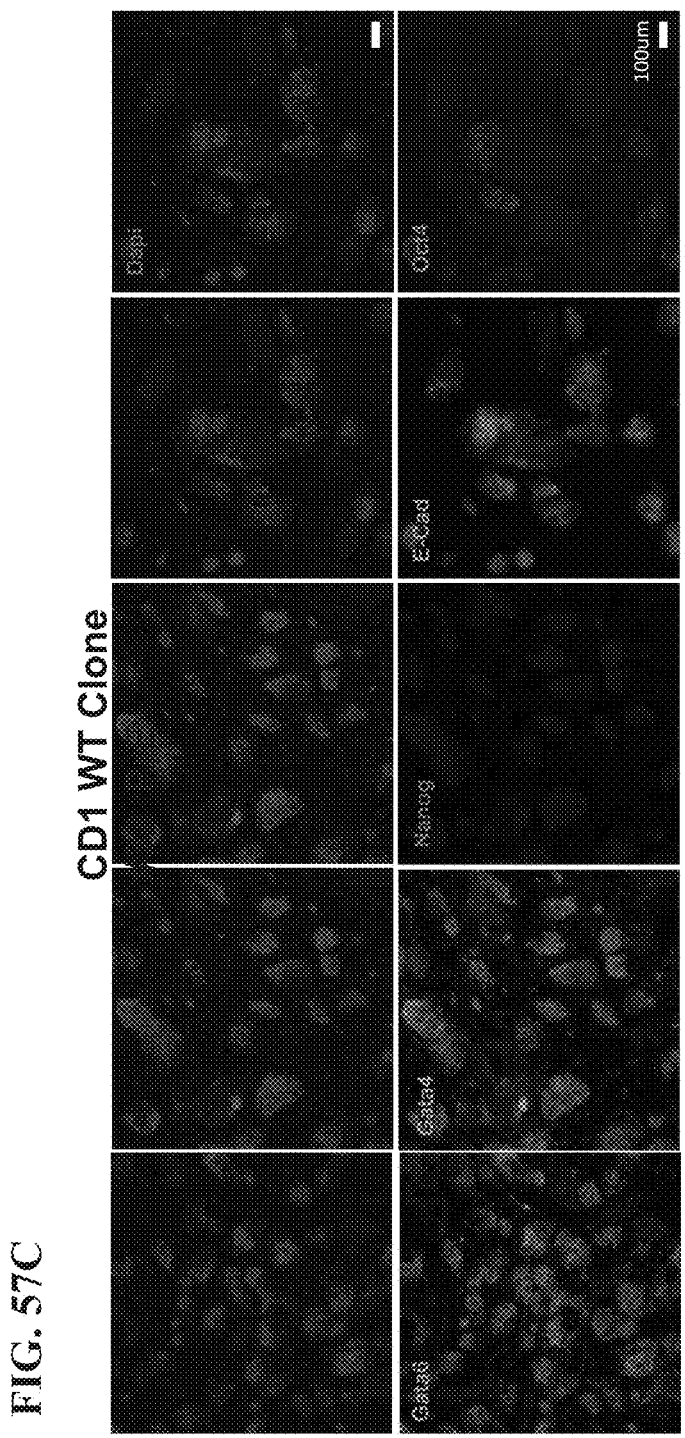

FIGS. 57A-C demonstrate derivation of novel stable mouse extra embryonic primitive endodermal primed cells (mouse PRE) from WT mouse naïve ESCs/iPSCs or following transient overexpression of Gata4 in mouse ESCs. FIG. 57A shows three strategies used to derive the mouse PRE cells that can be permanently expanded in mouse PRE indicated media. Images were taken at time 0 (naïve ESC in 2i/LIF stage) and after differentiation start. DOX was used for 72 hours in the first regimen as indicated. FIG. 57B shows FACS analysis of the cells using an anti-PDGFRa antibody. The parental ESC lines are shown as controls. Unstained samples are shown as negative controls. It is noted that MEFs are known to express PDGFRA as well, but at lower levels than mouse PRE cells. FIG. 57C shows representative images of the cells immunostained for the indicated markers. Immunostaining was effected on genetically unmodified CD1 iPSC derived mouse PRE cells expanded in PRE media. DAPI was used as counterstain.

Figure 58:
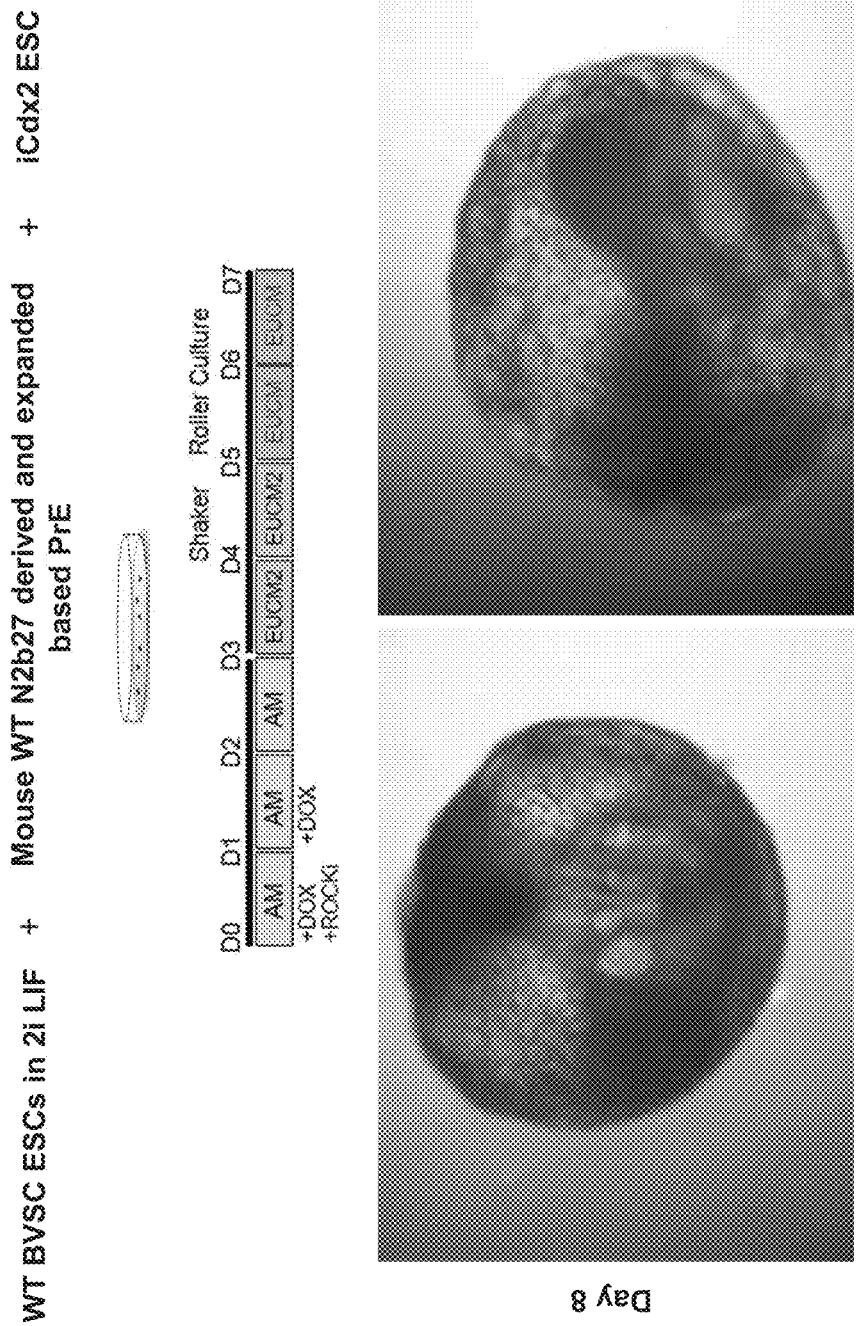

FIG. 58 demonstrates that co-aggregation of naïve mouse PSCs with the mouse PRE cells described in FIGS. 57A-C and mouse iCDX2 trophectoderm primed cells, followed by ex-utero culturing enabled generation of organized embryos. The Figure shows images of Day 8 mouse sEmbryos generated according to protocol shown in the Figures.

Figure 59A:
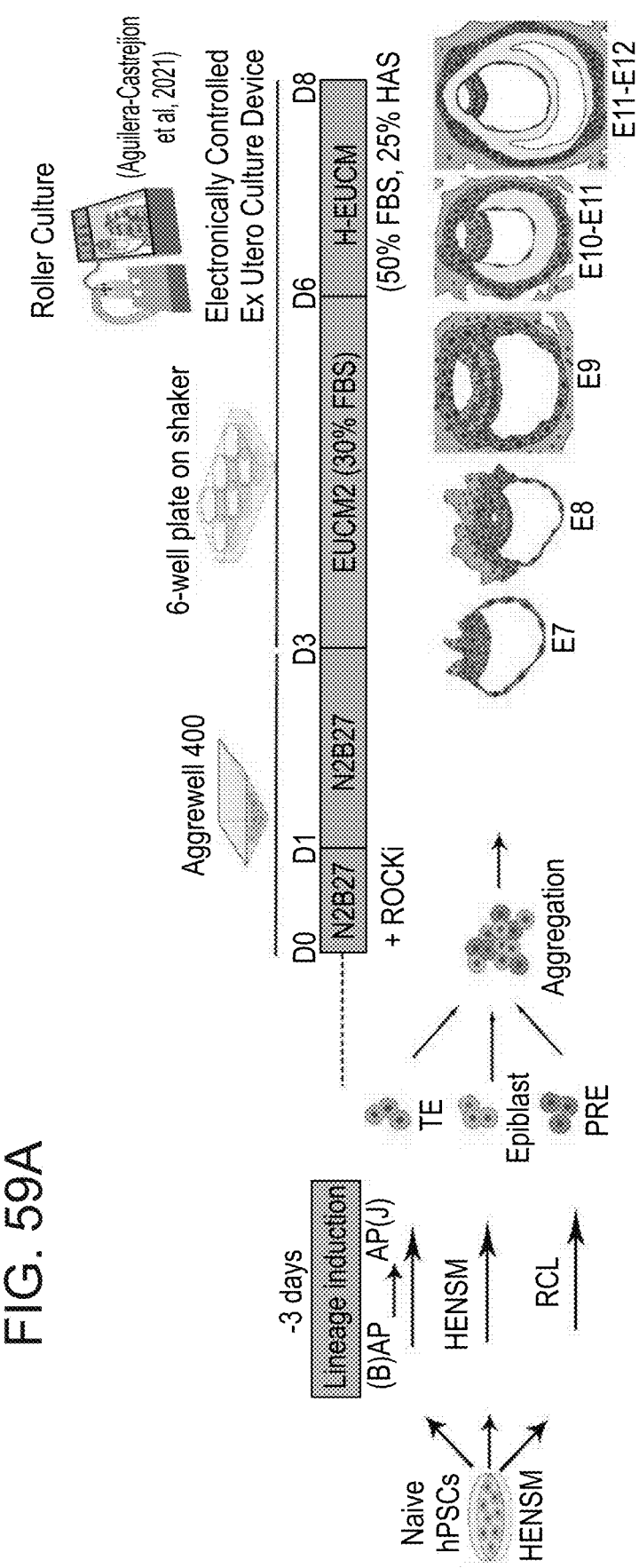
Figure 59B:

FIGS. 59A-B demonstrate that co-aggregation of human naïve PSCs cells with trophectoderm (TE) primed cells and extra embryonic primitive endodermal primed cells as described in Example 15 hereinbelow, followed by ex-utero culturing leads to generation of an organized embryo. FIG. 59A shows a schematic representation of the protocol. FIG. 59B is a representative phase image demonstrating bilaminar disc formation, amniotic cavity and yolk sac cavity, all surrounded by trophoblast compartment.

FIGS. 60A-B demonstrate that co-aggregation of human naïve PSCs cells with trophectoderm (TE) primed cells as described in Example 16 hereinbelow, followed by ex-utero culturing leads to generation of an organized embryo. FIG. 60A shows a schematic representation of the protocol. FIG. 60B is a representative phase image demonstrating bilaminar disc formation, amniotic cavity and yolk sac cavity, all surrounded by trophoblast compartment.

DESCRIPTION OF SPECIFIC EMBODIMENTS OF THE INVENTION

The present invention, in some embodiments thereof, relates to methods of generating a synthetic embryo.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Advanced artificial embryogenesis utilizing in vitro established embryonic stem cell lines (ESCs) and induced pluripotent stem cell lines (iPSCs) while bypassing the use of oocytes and zygotes or blastocysts has been a desired goal in the fields of developmental biology and reproductive medicine. While different pluripotent states of stem cells can be expanded in vitro and can contribute to embryonic and/or extraembryonic tissues when injected into host embryos, obtaining advanced gastrulating whole embryo-like structures with both embryonic and extra-embryonic compartments without relying on a micro-injected host embryo, has failed to date (see e.g., Zhang et al. (2020) Front. Bioeng. Biotechnol. 8:781; Harrison et al. Science (2017) DOI: 10.1126/science.aal1810; Amadei et al. Developmental Cell (2021) 56, 366-382; as also exemplified by Example 1 of the Examples section which follows).

Whilst reducing specific embodiments of the present invention to practice, the present inventors have now developed a method for generation of synthetic embryos, with both embryonic and extra-embryonic compartments, by starting solely from naïve ESCs followed by culturing under a controlled ex-utero embryo culture platform.

As is illustrated hereinunder and in the examples section, which follows, the present inventors show that co-aggregating three populations of mouse stem cells, namely non-transduced naïve PSCs, naïve PSCs that transiently overexpress a master regulatory transcription factor for trophectoderm cells (Cdx2) and naïve ESCs that transiently overexpress a master regulatory transcription factor for an extra embryonic primitive endodermal cells (Gata4) followed by ex-utero culturing the aggregate in a recently described controlled platform and growth conditions (Aguilera-Castrejon et al., 2021a), resulted in assembly into complete synthetic mouse embryos that accomplish gastrulation, develop brain, neural folds, neural tube, beating heart, somites, and progenitors of other organs (Examples 2-3 and 7-8 of the Examples section which follows). The synthetic embryos developed within extraembryonic membranes as natural embryos. Further, thorough analysis of both embryonic and extra embryonic compartments showed that these synthetic embryos achieved equivalent level of lineage complexity seen in natural in-utero embryos, where all annotated cell types were represented in synthetic embryos at E8.5 equivalent developmental stage. Furthermore, for each tissue a very high level of correlation in gene expression was seen between natural in-utero embryos and the synthetic mouse embryos. In a similar manner, the present inventors show that co-aggregating the same three populations of stem cells but of human origin, followed by ex-utero culturing the aggregate, resulted in assembly into complete synthetic human embryos with both embryonic and extra embryonic compartments (Examples 4-6 of the Examples section which follows). Following, the present inventors show that various culturing conditions can also support differentiation of naïve PSCs (of mouse, human or Rhesus Macaque origin) into trophectoderm (TE)-primed or extra embryonic primitive endodermal (PRE)-primed cells; and the co-aggregation of these stem cell populations followed by ex-utero culturing the aggregate resulted in assembly into complete synthetic embryos (Examples 9-12 and 14-16 of the Examples section which follows).

The establishment of methods and systems for producing such synthetic embryos ex utero may constitute a powerful tool in basic research e.g. as a framework to investigate the emergence of cellular diversity, cell fate decisions and how tissues and organs emerge from a single pluripotent cell; as well as a source of cells, tissues, embryos and organs for transplantation, testing the effect of drugs on embryonic development and possibly the bioengineering of embryos etc.

Thus, according to an aspect of the present invention, there is provided a method of generating a synthetic embryo, the method comprising:
(a) inducing expression of a factor that induces differentiation to trophectoderm cells in a subpopulation of naïve pluripotent stem cells (PSCs) to obtain trophectoderm primed cells; and
(b) mixing said trophectoderm primed cells with naïve PSCs under conditions that allow formation of aggregated cells,
wherein when said factor that induces differentiation to trophectoderm cells is an exogenous factor said inducing said expression comprises inducing transient expression starting within 14 days—0 hours prior to said mixing and ending no later than 120 hours following said mixing; and
wherein said factor that induces differentiation to trophectoderm cells is an endogenous factor said inducing said expression comprises culturing said subpopulation of naïve PSCs under conditions enabling expression of said factor starting within 14 days—6 hours prior to said mixing,
thereby generating the synthetic embryo.

According to an additional or an alternative aspect of the present invention, there is provided a method of generating a synthetic embryo, the method comprising:
(a) inducing transient expression of an exogenous factor that induces differentiation to trophectoderm cells in a subpopulation of naïve pluripotent stem cells (PSCs) to obtain a trophectoderm primed cells; and
(b) mixing said trophectoderm primed cells with naïve PSCs under conditions that allow formation of aggregated cells,
wherein said inducing said transient expression starts within 14 days—0 hours prior to said mixing and ends no later than 120 hours following said mixing,
thereby generating the synthetic embryo.

According to specific embodiments, the method further comprising inducing expression of a factor that induces differentiation to extra embryonic primitive endodermal cells in a second subpopulation of naïve PSCs to obtain extra embryonic primitive endodermal primed cells in said (a); and mixing said extra embryonic primitive endodermal primed cells with said cells in said (b).

According to specific embodiments, the method further comprising inducing transient expression of an exogenous factor that induces differentiation to extra embryonic primitive endodermal cells in a second subpopulation of naïve PSCs to obtain an extra embryonic primitive endodermal primed cells in said (a); and mixing said extra embryonic primitive endodermal primed cells with said cells in said (b).

According to an additional or an alternative aspect of the present invention there is provided a mixture or aggregate of cells obtainable by the methods disclosed herein, as further described infra.

According to an additional or an alternative aspect of the present invention there is provided a synthetic embryo obtainable by the methods disclosed herein.

As used herein, the term "synthetic embryo" refers to at least a collection of distinct cells generated ex-vivo using pluripotent stem cells without any donated germ cells, zygotes or blastocysts. When cultured, the synthetic embryo undergoes self-organization and differentiation that give rise to multiple tissue types which are organized as a native embryo or exhibit embryonic-like properties.

According to specific embodiments, the synthetic embryo structure mimics the developmental stages of a native or naturally occurring embryo, at least in the early stages of embryonic development post the blastocyst developmental stage.

According to specific embodiments, the synthetic embryo is not a blastocyst (e.g. a structure having characteristic of E3.5/4-5 of an in-utero natural mouse embryo or PFD6/PFD7 of an in-utero natural human embryo).

According to specific embodiments, the synthetic embryo mimics at least the Carnegie 5, Carnegie 6, Carnegie 8 or later developmental stages (relates to humans), embryo with primary and secondary yolk sac, bilaminar disc stage surrounded by trophoblast surround and formation of amnion, yolk and chorionic cavity including the formation of extra-embryonic mesoderm cells.

According to specific embodiments, the mouse synthetic embryo mimics at least the formation of egg-cylinder stage, completion of gastrulation (E7.5) and beginning of organogenesis (E8.0 in mouse embryos or later).

According to specific embodiments, the synthetic embryo is generated solely ex-utero.

As used herein the phrase "pluripotent stem cell (PSC)" refers to an undifferentiated cell (e.g., a mammalian cell, a primate cell) capable of differentiating into all three embryonic germ cell layers, i.e., to the mesoderm, ectoderm and endoderm embryonic germ layers; or remaining in an undifferentiated state.

Methods of determining ability of stem cells to differentiate into the endodermal, mesodermal and ectodermal embryonic germ layers are known in the art and disclosed e.g. in International Patent Application Publication No. WO2014/174470, the contents of which is fully incorporated herein by reference in its entirety, and include for example generation of embryoid bodies (in vitro) or teratomas (in vivo).

According to some embodiments of the invention, the pluripotent stem cell is selected from the group consisting of embryonic stem cell (ESC), induced pluripotent stem cells (iPSCs), and embryonic germ cell (EGC).

According to specific embodiments, the cell is a mammalian cell e.g., rodent (e.g. mouse, rat), human (*Homo sapiens*), monkey (e.g. chimpanzee, Gorillas, Rhesus and/or Baboon), livestock animal (e.g. cattle, sheep, pigs, goats, horses, donkeys, mules).

According to specific embodiments, the cell is a mouse cell.

According to specific embodiments, the cell is a human cell.

According to other specific embodiments, the cell is of a non-human primate (e.g. Macaques).

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting.

The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

It will be appreciated that commercially available stem cells can also be used according to some embodiments of the invention. Human ES cells can be purchased from the NIH human embryonic stem cells registry [Hypertext Transfer Protocol://grants(dot)nih(dot)gov/stem_cells/registry/current(dot)htm]. Non-limiting examples of commercially available embryonic stem cell lines are BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Non-limiting examples of commercially available mouse embryonic stem cell lines are v6.5, KH2, BVSC ES line, NGFP1 iPSC line, NGFP2 iPSC lines.

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other combinations of pluripotency factor overexpression generated iPSCs are included as well (Buganim et al. Cell (2012) 150(6): 1209-1222 www(dot)doi(dot)org/10.1016/j.cell.2012.08.023) Other embryonic-like stem cells can be generated by nuclear transfer to oocytes, fusion with embryonic stem cells or nuclear transfer into zygotes if the recipient cells are arrested in mitosis.

The methods of some embodiments of the invention utilize PSCs in their naïve state.

The phrase "naïve pluripotent stem cells (PSCs)" refers to PSCs that express pluripotent markers (such as Oct4, Nanog and Klf4), lack of extraembryonic endoderm, trophectoderm and somatic early lineage specific markers. The cells retain a non-restricted developmental potential as they can robustly differentiate into all cell types in vitro and, upon injection into the blastocyst, they efficiently contribute to the three germ layers and to the germ-line of chimeric animals.

Human and non-human primate naïve PSCs also a pre X-inactivation state.

Chromosome X inactivation is an early developmental process in mammalian females that transcriptionally silences one of the pair of X chromosomes, thus providing dosage equivalence between males and females. The process is regulated by several factors, including a region of chromosome X called the X inactivation center (XIC). The XIC comprises several non-coding and protein-coding genes, and XIST gene was the first non-coding gene identified within the XIC.

When XIST bodies are present, then XIST is exclusively expressed from the XIC of the inactive X chromosome, and is essential for the spread of X-inactivation.

The pre-X-inactivation state according to some embodiments of the invention is characterized by presence of two unmethylated alleles of the promoter of the X-inactive specific transcript (XIST) gene in the female cell, and presence an unmethylated allele of the promoter of the XIST gene in a male cell.

This is contrary to human and non-human primate "primed PSC" or "conventional PSC" which are characterized by one methylated allele of XIST and one unmethylated allele of XIST in the female cell, and by one methylated allele in the male cell.

The XIST gene is located on human Xq13.2 chromosome and has the sequence depicted in clone NC_000023.10 (73040486.73072588, complement, based on GenBank version GRCh37.p10). The XIST gene has a non-coding RNA which is provided in GenBank Accession NO. NR_001564.2.

Methods of determining the methylation status of the XIST gene are known in the art and disclosed e.g. in Lengner Cell 141, 872-883 (2010); Hanna et al., Cell 143, 508-525; (2010); TAKASHI SADO et al., DEVELOPMENTAL DYNAMICS 205: 421-434 (1996); and International Patent Application Publication No. WO2016/016894 and WO2014/174470, each of which is fully incorporated herein by reference in its entirety, and include e.g. bisulfite sequencing and Southern blot analysis.

According to some embodiments of the invention, presence of two unmethylated alleles of XIST gene in a female cell refers to having below about 20% of CpG methylated reads sequenced in the XIST promoter, e.g., below about 19%, below about 18%, below about 17%, below about 16%, below about 15%, below about 14%, below about 13%, below about 12%, below about 11%, below about 10%, below about 9%, below about 8%, below about 7%, below about 6%, below about 5%, below about 4%, below about 3%, below about 2%, below about 1%, e.g., 0% (e.g., complete absence) of CpG methylated reads sequenced in the XIST promoter.

According to some embodiments of the invention, presence of one unmethylated allele of XIST gene in a male cell refers to having below about 20% of CpG methylated reads sequenced in the XIST promoter, e.g., below about 19%, below about 18%, below about 17%, below about 16%, below about 15%, below about 14%, below about 13%, below about 12%, below about 11%, below about 10%, below about 9%, below about 8%, below about 7%, below about 6%, below about 5%, below about 4%, below about 3%, below about 2%, below about 1%, e.g., 0% of CpG methylated reads sequenced in the XIST promoter.

A non-limited example of the XIST promoter which includes CpG islands which can be either methylated or unmethylated is provided in the XIST promoter amplicon set forth by SEQ ID NO: 65.

According to some embodiments of the invention, the naïve PSC exhibits a pre-X inactivation status similar to the pre-X inactivation status of a human Inner cell mass (ICM).

According to some embodiments of the invention, the naïve PSC is characterized by a reduced methylation of CpG islands as compared to a level of methylation of the CpG islands in a primed PSC.

According to some embodiments of the invention, naïve PSCs are characterized by significantly low levels of total methylated cytosine out of the total guanine nucleotides in each cell (e.g., 1-2%) as determined by Liquid Chromatography—Mass Spectrometry (LC-MS) quantitative analysis.

According to some embodiments of the invention, the naïve PSC is characterized by 0-3% of total methylated cytosine out of the total Guanine nucleotides in the naïve PSC cell. For comparison, the primed PSC or a somatic cell has between 3.5%-5% of total methylated cytosine out of the total Guanine nucleotides in the primed PSC cell.

According to some embodiments of the invention, the human naïve PSC expresses XIST.

Methods of detecting XIST expression are known in the art and include for example reverse transcriptase—polymerase chain reaction (RT-PCR) analysis using XIST specific PCR primers, e.g., the forward primer: 5'-AGGGAGCAGTTTGCCCTACT (SEQ ID NO: 66), and the reverse primer: 5'-CACATGCAGCGTGGTATCTT (SEQ ID NO: 67).

According to some embodiments of the invention, the naïve PSC is devoid of XIST bodies.

As used herein the phrase "XIST bodies" refers to a XIST-coated inactive X chromosome.

Methods of detecting XIST bodies are known in the art and include for example RNA fluorescent in situ hybridization. RNA fluorescence in situ hybridization (FISH) is carried out as previously described [Hanna J., et al., Cell 143, 508-525]. Briefly, human pluripotent stem cells are harvested, MEF-depleted, and cytospun onto glass slides before fixation. cDNA probes are generated to XIST exon 1 (GenBank Accession No. U80460: 61251-69449, SEQ ID NO: 26) and exon 6 (GenBank Accession No. U80460: 75081-78658, SEQ ID NO: 27) and labeled by nick translation (Roche) with Cy3—dUTP (Amersham), and Cot-1 DNA is labeled with fluorescein-12-dUTP using the Prime-It Fluor Labeling Kit (Stratagene).

According to some embodiments of the invention, the naïve PSC is devoid of an H3K27me3/polycomb focus.

As used herein the phrase "H3K27me3/polycomb focus" refers to nuclear focus obtained following immuno-staining that corresponds to condensed inactive X chromosome.

Methods of detecting H3K27me3/polycomb focus are known in the art and include for example, the use of immuno-fluorescence analysis using anti H3K27me3 antibodies (e.g., Rabbit anti H3K27me3, Millipore, CA, USA Catalogue number 07-449), as shown for example in FIGS. 23C-D.

According to some embodiments of the invention, the naïve PSC has a low XIST expression level while being in the naïve state, without inactivation of any of the X chromosomes and without presence of XIST bodies.

It should be noted that the naïve PSCs of some embodiments of the invention (which are in a pre-X inactivation and a naïve state) can upon differentiation inactivate one of the X chromosome alleles and methylate one of the XIST genes.

According to specific embodiments, expression level of the transcription factor E3 (TFE3) in the naïve PSC is characterized by a nucleus to cytoplasm expression ratio which is equal to or higher than 1, as determined by e.g. an immunostaining assay.

According to specific embodiments, the naïve cells express c-Kit on their cell surface, as determined by e.g. flow cytometry or immunostaining assay.

Contrary to the known primed PSC, the naïve PSC of some embodiments of the invention is "resistant" to induction of differentiation by FGFR/MEK/ERK inhibitor, JNK inhibitor, and/or P38 inhibitor. Thus, according to some embodiments of the invention, when the isolated naïve PSC is incubated in the presence of an agent selected from the group consisting of FGFR/MEK/ERK inhibitor, JNK inhibitor, and P38 inhibitor, the naïve PSC remains in the pluripotent state.

According to some embodiments of the invention, the naïve PSC has an inhibited p38 pathway as compared to a primed PSC. For example, p38 activity is inhibited in the naïve PSC.

According to some embodiments of the invention, the level of p38 RNA and/or phosphorylated p38 protein in the naïve PSC is less than about 30%, e.g., less than about 20%, e.g., less than about 5%, e.g., less than about 0.5%, e.g., less than about 0.1% as compared to the level of p38 RNA and/or phosphorylated p38 protein, respectively, in a non-naïve PSC incubated and/or cultured under the same conditions, yet without being subject to p38 inhibition.

According to some embodiments of the invention, the naïve PSC has an inhibited JNK pathway as compared to a primed PSC. For example, JNK activity is inhibited in the naïve PSC.

According to some embodiments of the invention, the level of JNK RNA and/or phosphorylated JNK protein in the naïve PSC is less than about 30%, e.g., less than about 20%, e.g., less than about 5%, e.g., less than about 0.5%, e.g., less than about 0.1% as compared to the level of JNK RNA and/or phosphorylated JNK protein, respectively, in a non-naïve PSC incubated and/or cultured under the same conditions, yet without being subject to JNK inhibition.

According to some embodiments of the invention, the naïve PSC has an inhibited ROCK pathway as compared to a primed PSC. For example, ROCK activity is inhibited in the naïve PSC.

According to some embodiments of the invention, the level of ROCK RNA and/or phosphorylated ROCK protein in the naïve PSC is less than about 30%, e.g., less than about 20%, e.g., less than about 5%, e.g., less than about 0.5%, e.g., less than about 0.1% as compared to the level of ROCK RNA and/or phosphorylated ROCK protein, respectively, in a non-naïve PSC incubated and/or cultured under the same conditions, yet without being subject to ROCK inhibition.

According to some embodiments of the invention, the naïve PSC which is maintained in the undifferentiated, pluripotent and naïve state (as defined above), expresses significantly lower levels SOX1 as compared to the level of expression present in primed PSC (e.g., primed ESC) under identical SOX1 assay conditions, and wherein the primed PSC exhibits one methylated and one unmethylated allele of XIST (in a female cell) or one methylated allele of XIST (in a male cell); expresses XIST; exhibits XIST bodies; and exhibits a H3K27me3/polycomb focus.

According to some embodiments of the invention, the naïve PSC expresses a lower level of MHC class I as compared to a primed PSC under identical detection assay conditions, and wherein the primed PSC exhibits one methylated and one unmethylated allele of XIST (in a female cell) or one methylated allele of XIST (in a male cell); expresses XIST; exhibits XIST bodies; and exhibits a H3K27me3/polycomb focus.

The level of MHC class I can be determined by various methods known in the art such as FACS analysis using specific antibodies to detect the surface expression of the MHC class I molecules, and using fluorescently labeled anti HLA-A,B,C antibody (BD Biosciences).

According to some embodiments of the invention, the naïve PSC is characterized by at least about 10%, at least about 20%, at least about 30%, at least about 40%, at least about 50%, at least about 60%, at least about 70%, at least about 80%, at least about 90% more RNA polymerase II pausing on chromosomes as compared to a primed PSC under identical assay conditions, and wherein the primed PSC exhibits one methylated and one unmethylated allele of XIST (in a female cell) or one methylated allele of XIST (in a male cell); expresses XIST; exhibits XIST bodies; and exhibits a H3K27me3/polycomb focus.

According to specific embodiments, the naïve PSCs express a pluripotency marker, i.e., positive for one or more pluripotency markers.

According to specific embodiments, the expression is of an endogenous protein.

Positive is also abbreviated by (+). Positive for a marker means that at least about 70%, 80%, 85%, 90%, 95%, or 100% of the cells in the population present detectable levels of the marker assayed by a method known to those of skill in the art. Developmental markers can be detected using immunological techniques well known in the art [described e.g. in Thomson J A et al., (1998). *Science* 282: 1145-7]. Examples include, but are not limited to, immunostaining, microscopy, flow cytometry, western blot, and enzymatic immunoassays. Other non-limiting methods include PCR analysis, RNA fluorescence in situ hybridization (FISH), northern blot, single cell RNA sequencing.

Pluripotency markers are well known in the art and include, but not limited to Oct4, NANOG, KLF4, KLF17, SUSD2, TFCP2L1.

The naïve PSC of some embodiments of the invention is characterized by a positive expression of the C-KIT protein (also known as CD117) on the cell surface.

According to specific embodiments, the naïve PSCs can be obtained in culture in the naïve state without the need of exogenous expression of Oct4, Sox2, Klf4 and/or c-Myc factors.

According to specific embodiments, the naïve PSCs are negative for a differentiation marker.

Negative is also abbreviated by (−). Negative for a marker means that no more than about 30%, no more than about 25%, no more than about 20%, no more than about 15%, no more than about 10%, no more than about 5%, no more than about 4%, no more than about 3%, no more than about 2%, no more than about 1%, of the cells in the population present detectable levels of the marker assayed by a method known to those of skill in the art such as FACS, immunofluorescence, immunohistochemistry, Western blot analysis, RT-PCR. Non-limiting examples of differentiation markers include Gata3, Gata2, tbr2, tfap2c, Cdx2, Elf5, Hand1, EOMES, ETS2, Foxa2, Gata4, Gata6, PDGFRA, Sox17.

Determination of PSC differentiation can also be effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, California, USA).

According to specific embodiments, the naïve PSCs can be obtained in culture in the naïve state under feeder layer free conditions [e.g., on a Matrigel, Laminin, and/or fibronectin-coated surface and not on feeder cell e.g., fibroblast feeder cells, e.g., mouse embryonic fibroblasts (MEFs)].

According to specific embodiments, the naïve PSCs can be obtained in culture in the naïve pluripotent state in the absence of exogenous L-glutamine in the culture medium.

According to specific embodiments, the naïve PSCs can be obtained in culture in the naïve pluripotent state in the absence of expression of DNA methyltransferase 1 (DNMT1).

Methods of obtaining naïve PSCs and maintaining them in a naïve and pluripotent state are known in the art and are further disclosed in the Examples section which follows which serve as an integral part of the specification and in e.g. Choi, J., Huebner, A., Clement, K. et al. Nature 548, 219-223 (2017), www(dot)doi(dot)org/10.1038/nature23274; Yang et al. Cell (2017) 169(2): 243-257, www(dot)cell(dot)com/fulltext/50092-8674%2817%2930183-6; Bayerl et al. 2021, Cell Stem Cell 28, 1549-1565 and International Patent Application Publication No. WO2016/016894 and WO2014/174470, the contents or which are fully incorporated herein by reference.

Multiple naïve PSCs cell lines are also known, for example, V6.5 mouse ESC line, BVSc ES line, NGFP1 iPSC line, WIBR3 line, WIS1 ES line and WIS ES line, and are commercially available from public cell line repositories.

As used herein, the term "trophectoderm (TE) primed cell" refers to a stem cell originating from a naïve PSC that comprises an exogenous nucleic acid sequence encoding a factor that induces differentiation to a trophectoderm cell and/or a cell originating from a naïve PSC that is committed to the trophectoderm lineage (e.g. trophectoderm cell). It will be appreciated that prior to induction of expression of the factor (i.e. the protein product expressed from the exogenous nucleic acid sequence or the endogenous factor) the cell is in a naïve and undifferentiated state (i.e. naïve PSC) and following induction of expression of the factor the cell acquires characteristics of a trophectoderm cell.

According to specific embodiments, the trophectoderm primed cell comprises an exogenous polynucleotide suitable for transient expression of the factor that induces differentiation to trophectoderm cells, as further described hereinbelow.

According to specific embodiments, the trophectoderm primed cell comprises the protein product expressed from the exogenous nucleic acid sequence encoding the factor.

According to other specific embodiments, the trophectoderm primed cell does not comprise the protein product expressed from the exogenous nucleic acid sequence encoding the factor.

As used herein, "trophectoderm cell" refers to a cell having a restricted potential to generate all placental lineages but not other cell lineages.

According to some embodiment, the trophectoderm cells gives rise to the ecto-placental cone, and/or extra-embryonic ectoderm (ExE), and/or the umbilical cord and/or the chorion.

Non-limiting examples of trophectoderm cell markers include Gata3, Gata2, tbr2, tfap2c, Cdx2, Elf5, Hand1, EOMES, KLF5 and ETS2.

According to specific embodiments, the trophectoderm cell expresses Cdx2, i.e. positive for Cdx2.

According to specific embodiments, the trophectoderm primed cell expresses a trophectoderm marker. According to specific embodiments, the trophectoderm primed cell expresses at least one trophectoderm marker selected from the group consisting of Gata3, Gata2, Cdx2 and Elf5.

According to specific embodiments, the trophectoderm primed cell expresses pluripotency marker. Such markers are known in the art and are further described hereinabove and below. According to specific embodiments, the trophectoderm primed cell expresses (positive for) at least one pluripotency marker selected from the group consisting of Oct4, Tfap2c, Susd2, Sox2, SSEA1, SSEA3, SSEA4, TRA1-60. According to specific embodiments, the trophectoderm primed cell expresses Oct4. According to specific embodiments, the trophectoderm primed cell is negative for a pluripotency marker selected from the group consisting of Klf17, Klf4 and Nanog.

According to specific embodiments, the trophectoderm primed cell expresses a trophectoderm marker and a pluripotency marker.

According to specific embodiments, the marker is endogenous to the cell.

Thus, according to specific embodiments, the trophectoderm primed cell expresses an exogenous factor that induces differentiation to trophectoderm cells, an endogenous trophectoderm marker and an endogenous pluripotency marker.

According to specific embodiments, the trophectoderm primed cell expresses a trophectoderm marker upon mixing (i.e., at time 0 hours), in the mixture or in the aggregate.

According to specific embodiments, the trophectoderm primed cell expresses a pluripotency marker upon mixing (i.e., at time 0 hours), in the mixture or in the aggregate.

According to specific embodiments, the trophectoderm primed cell does not express Oct4 and Nanog upon mixing (i.e., at time 0 hours), in the mixture or in the aggregate.

According to specific embodiments, the trophectoderm primed cell (e.g., upon mixing, in the mixture, in the aggregate) is not in a differentiation stage of a trophoblast stem cell (TSC). In other words, it does not have a phenotypic signature of a TSC (derived from the trophectoderm or an induced TSC or obtained by de-differentiation or reprogramming of a cell).

According to specific embodiments, the TSC (e.g., human TSC) has a $CDX2^-TFAP2C^+GATA3\pm SIGLE6^+$ phenotype.

In comparison, the human trophectoderm primed cell or some embodiments of the invention has a $CDX2^+TFAP2c^+GATA3^+SIGLEC6^-$ phenotype.

According to specific embodiments, the TSC (e.g., mouse TSC) has a $CDX2^+TFAP2C^+MHC$ class $1\pm OCT4^-$ phenotype.

In comparison, the mouse trophectoderm primed cell or some embodiments of the invention has a $CDX2^+TFAP2C^+$ MHC class $1^-Oct4^{+(low)}$ phenotype.

The factor which expression induces differentiation of the naïve PSCs of some embodiments of the invention may be endogenous and/or exogenous to the cell.

According to specific embodiments, the method comprises inducing expression of an exogenous factor that induces differentiation to (towards) trophectoderm cells.

As used herein, the term "exogenous" refers to a heterologous polynucleotide or polypeptide which is not naturally expressed within the cell or which overexpression in the cell is desired. It should be noted that the exogenous polynucleotide and/or polypeptide may comprise a nucleic acid sequence and/or an amino acid sequence, respectively, which is identical or partially homologous to an endogenous nucleic acid sequence and/or an endogenous amino acid sequence of the cell.

According to additional or alternative embodiments, the method comprises inducing expression of an endogenous factor that induces differentiation to (toward) trophectoderm cells. Hence, according to specific embodiments, the cell is cultured under conditions enabling expression of an endogenous factor that induces differentiation to the trophectoderm primed cell. Such conditions include for example an appropriate temperature (e.g., 37° C.), atmosphere (e.g., % $O_2$, % $CO_2$), pressure, pH, light, medium, supplements (e.g. a differentiation factor as disclosed herein) and the like. Further description on culturing conditions are provided hereinbelow. Hence, according to specific embodiments, the naïve PSC cell or the trophectoderm primed cell is contacted with the factor. Under this culturing scenario the cells may further comprise or be devoid of an exogenous polynucleotide suitable for expression of a factor that induces differentiation to trophectoderm cells. According to a specific embodiment, the cell does not comprise an exogenous polynucleotide suitable for expression of a factor that induces differentiation to trophectoderm cells. In this case inducing expression of the endogenous factor, the culturing or the contacting is typically effected prior to mixing the subpopulations of cells (e.g. starting within 14 days—0 hours prior to the mixing, within 13 days—0 hours prior to the mixing, within 12 days—0 hours prior to the mixing, within 11 days—0 hours prior to the mixing, within 10 days—0 hours prior to the mixing, within 9 days—0 hours prior to the mixing, within 8 days—0 hours prior to the mixing, within 7 days—0 hours prior to the mixing, within 6 days—0 hours prior to the mixing within 5 days—0 hours prior to the mixing, within 120 hours—0 hours prior to the mixing, within 100 hours—0 hours prior to the mixing, within 80 hours—0 hours prior to the mixing, within 60 hours—0 hours prior to the mixing, within 48 hours—0 hours prior to the mixing, within 36 hours—0 hours prior to the mixing, within 24 hours—0 hours prior to the mixing, within 12 hours—0 hours prior to the mixing, within 14—1 days prior to the mixing, within 13—1 days prior to the mixing, within 12—1 days prior to the mixing, within 11—1 days prior to the mixing, within 10—1 days prior to the mixing, within 9—1 days prior to the mixing, within 8—1 days prior to the mixing, within 7—1 days prior to the mixing, within 6—1 days prior to the mixing within 5—1 days prior to the mixing, within 120—20 hours prior to the mixing, within 100—20 hours prior to the mixing, within 80-20 hours prior to the mixing, within 60-20 hours prior to the mixing, within 48-20 hours prior to the mixing, within 14 days—12 hours prior to the mixing, within 13 days—12 hours prior to the mixing, within 12 days—12 hours prior to the mixing, within 11 days—12 hours prior to the mixing, within 10 days—12 hours prior to the mixing, within 9 days—12 hours prior to the mixing, within 8 days—12 hours prior to the mixing, within 7 days—12 hours prior to the mixing, within 6 days—12 hours prior to the mixing within 5 days—12 hours prior to the mixing, within 120-12 hours prior to the mixing, within 100-12 hours prior to the mixing, within 80-12 hours prior to the mixing, within 60-12 hours prior to the mixing, within 48-12 hours prior to the mixing, within 14 days—6 hours prior to the mixing, within 13 days—6 hours prior to the mixing, within 12 days—6 hours prior to the mixing, within 11 days—6 hours prior to the mixing, within 10 days—6 hours prior to the mixing, within 9 days—6 hours prior to the mixing, within 8 days—6 hours prior to the mixing, within 7 days—6 hours prior to the mixing, within 6 days—6 hours prior to the mixing within 5 days—6 hours prior to the mixing, within 120 hours-6 hours prior to the mixing, within 100 hours-6 hours prior to the mixing, within 80 hours-6 hours prior to the mixing, within 60 hours-6 hours prior to the mixing, within 48 hours-6 hours prior to the mixing, within 36 hours-6 hours prior to the mixing, within 24 hours-6 hours prior to the mixing, or within 12 hours-6 hours prior to the mixing, each possibility represents a separate embodiment of the invention).

According to specific embodiments, the culturing or the contacting starts at least 6 hours, at least 10 hours, at least 12 hours, at least 16 hours, at least 24 hours, at least 36 hours, at least 48 hours, at least 72 hours, or at least 96 hours prior to the mixing.

According to specific embodiments, the culturing or the contacting starts no more than 3 days, no more than 4 days, no more than 5 days, no more than 6 days, no more that 7 days, no more than 8 days, no more than 9 days, no more than 10 days, not more that 14 days, no more than 16 days, or no more than 20 days prior to the mixing.

According to specific embodiments, the culturing or the contacting starts within about 6-3 days prior to the mixing.

According to specific embodiments, the culturing or the contacting starts about 3 days prior to the mixing.

Factors that induce differentiation towards trophectoderm cells are well known in the art, and include factor expressed in the cells and factor that are contacted with the cells. Non-limiting examples of such factors include Cdx2, Gata3, Gata2, TGFR inhibitor, FGFR inhibitor, MEK/ERK inhibitor, BMP4, JAK inhibitor, FGF4, FGF2, heparin, a SUMOylation inhibitor, a Histone Deacetylase inhibitor, a HIPPO signaling pathway inhibitor and a factor that induces YAP nuclear translocation.

According to specific embodiments, the factor that induces differentiation to trophectoderm cells is Cdx2.

As used herein, the term "Cdx2", refers to the polynucleotide and expression product e.g., polypeptide of the CDX2 gene (corresponding to human gene ID NO: 1045) or homolog or ortholog of same. According to specific embodiments the Cdx2 refers to the human Cdx2, such as provided in the following GeneBank Numbers NP_001256, NP_001341629, NM_001265, NM_001354700 (SEQ ID NO: 68-70). According to specific embodiments the Cdx2 refers to the mouse Cdx2, such as provided in the following GeneBank Numbers NP_031699 and NM_007673 and (SEQ ID NO: 72-73). A homolog (as further defined hereinbelow) refers to a functional expression product of Cdx2 capable of inducing the differentiation of naïve PSCs to trophectoderm cells.

Thus, as mentioned any of the polynucleotides and expression products described herein (e.g., Cdx2, Gata4 etc.), also refer to homologues which exhibit the desired activity as defined herein. Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polypeptide or polynucleotide sequences provided herein.

The homolog may also refer to an ortholog, a deletion, insertion, or substitution variant, including an amino acid substitution, as long as it retains the activity.

Sequence identity or homology can be determined using any protein or nucleic acid sequence alignment algorithm such as Blast, ClustalW, and MUSCLE.

According to specific embodiments, the factor that induces differentiation to trophectoderm cells is Gata3.

As used herein, the term "Gata3", also known as GATA Binding Protein 3 and HDRS, refers to the polynucleotide and expression product e.g., polypeptide of the GATA3 gene (corresponding to human gene ID NO: 2625) or homolog or ortholog of same. According to specific embodiments the Gata3 refers to the human Gata3, such as provided in the following GeneBank Numbers NP_001002295 and NM_001002295 (SEQ ID NO: 74). According to specific embodiments the Gata3 refers to the mouse Gata3, such as provided in the following GeneBank Numbers NP_032117, NP_001342039, NP_001342040, NP_001342041, NM_008091, NM_001355110, NM_001355111 and NM_001355112 (SEQ ID NO: 76-83). A homolog (as further defined hereinabove) refers to a functional expression product of Gata3 capable of inducing the differentiation of naïve PSCs to trophectoderm cells.

According to specific embodiments, the factor that induces differentiation to trophectoderm cells is Gata2.

As used herein, the term "Gata2", also known as GATA Binding Protein 2, refers to the polynucleotide and expression product e.g., polypeptide of the GATA2 gene (corresponding to human gene ID NO: 2624) or homolog or ortholog of same. According to specific embodiments the Gata2 refers to the human Gata2, such as provided in the following GeneBank Numbers NP_001139133, NP_001139134, NP_116027, NM_032638, NM_001145661 and NM_001145662 (SEQ ID NO: 84-89). According to specific embodiments the Gata2 refers to the mouse Gata2, such as provided in the following GeneBank Numbers NP_032116, NP_001342182, NM_008090 and NM_001355253 (SEQ ID NO: 90-93). A homolog (as further defined hereinabove) refer to a functional expression product of Gata2 capable of inducing the differentiation of naïve PSCs to trophectoderm cells.

According to specific embodiments, the factor that induces differentiation to trophectoderm cells is a TGFR inhibitor.

As used herein the term "transforming growth factor receptor (TGFR)" (also known as "TGFβR") refers to TGF-β type I receptor ALK5, type I activin/nodal receptor ALK4 and type I nodal receptor ALK7.

As used herein the term "TGFR inhibitor (or TGFRi)" refers to a molecule capable of inhibiting TGFR expression and/or activity level as determined by phosphorylated ALK4, 5 and 7. Non-limiting examples of TGFR inhibitors include SB431542 and A 83-01 small molecule compound.

According to specific embodiments, the factor that induces differentiation to trophectoderm cells is a FGFR inhibitor.

As used herein the term "fibroblast growth factor receptor (FGFR)" refers to FGFR1, FGFR2 and FGFR3.

As used herein the term "FGFR inhibitor (or FGFRi)" refers to a molecule capable of inhibiting FGFR expression and/or activity level as determined by levels of phosphorylated FGFR1, 2, and 3. Non-limiting examples of FGFR inhibitors include PD173074, SU5401 and PD0325901.

According to specific embodiments, the factor that induces differentiation to trophectoderm cells is ROCK inhibitor.

As used herein the term "ROCK", also known as Rho-associated protein kinase and includes ROCK1 and ROCK2 having a serine/threonine kinase activity.

As used herein the term "ROCK inhibitor" refers to any molecule capable of inhibiting the activity of ROCK as determined by inhibition of ROCK phosphorylation levels (e.g. detected by western blot analysis).

Non-limiting examples of ROCK inhibitors include Y27632 (TOCRIS, Catalogue number 1254), Blebbistatin (TOCRIS Catalogue number 1760) and Thiazovivin (Axon Medchem—Axon 1535). Blebbistatin is a selective inhibitor of myosin II ATpase, a downstream effector of ROCK pathway, and thus effectively leads to ROCK pathway inhibition (Chen G1, Hou Z et al. Actin-myosin contractility is responsible for the reduced viability of dissociated human embryonic stem cells. *Cell Stem Cell*. 2010; 7(2):240-8, which is fully incorporated herein by reference in its entirety).

According to specific embodiments, the factor that induces differentiation to trophectoderm cells is a MEK/ERK inhibitor (as further defined infra).

According to specific embodiments, the factor that induces differentiation to trophectoderm cells is BMP4.

As used herein, the term "BMP4", also known as Bone morphogenic protein 4, refers to the polynucleotide and expression product e.g., polypeptide of the BMP4 gene (corresponding to human gene ID NO: 652) or a homolog or ortholog of same. According to specific embodiments the BMP4 refers to the human BMP4, such as provided in the following UniProt Number P12644 (SEQ ID NO: 195). According to specific embodiments the BMP4 refers to the mouse BMP4, such as provided in the following UniProt Number P21275 (SEQ ID NO: 196). A homolog (as further defined hereinabove) refers to a functional expression product of BMP4 capable of inducing the differentiation of naïve PSCs to trophectoderm cells.

According to specific embodiments, the factor that induces differentiation to trophectoderm cells is a JAK inhibitor.

As used herein the term "JAK" refers to a Janus kinase and includes JAK1, JAK2, JAK3 and TYK2.

As used herein the term "JAK inhibitor (or JAKi)" refers to a molecule capable of inhibiting JAK expression and/or activity level as determined by levels of phosphorylated STAT (signal transducer and activator of transcription). Non-limiting examples of JAK inhibitors include Calbiochem 420099, Tofacitinib, Baricitinib, Ruxolitinib, Fedratinib, Upadacitinib, Cedulatinib, Gandotinib, Lesraurtinib, Momelotinib, Pacritinib, Curuebitacin I, CHZ868.

According to specific embodiments, the factor that induces differentiation to trophectoderm cells is FGF4.

As used herein, the term "FGF4", also known as Fibroblast growth factor 4, refers to the polynucleotide and expression product e.g., polypeptide of the FGF4 gene (corresponding to human gene ID NO: 2249) or homolog or ortholog of same. According to specific embodiments the FGF4 refers to the human FGF4, such as provided in the following GeneBank Numbers NP_001998 and NM_002007 (SEQ ID NO: 94-95). According to specific embodiments the FGF4 refers to the mouse FGF4, such as provided in the following GeneBank Numbers NP_034332 and NM_010202 (SEQ ID NO: 96-97). A homolog (as further defined hereinabove) refers to a functional expression product of FGF4 capable of inducing the differentiation of naïve PSCs to trophectoderm cells and/or extra embryonic primitive endodermal cells.

According to specific embodiments, the factor that induces differentiation to trophectoderm cells is FGF2.

As used herein, the term "FGF2", also known as basic fibroblast growth factor (bFGF) and FGF-β, refers to the polynucleotide and expression product e.g., polypeptide of the FGF2 gene (corresponding to human gene ID NO: 2247)

or homolog or ortholog of same. According to specific embodiments the FGF2 refers to the human FGF2, such as provided in the following GeneBank Numbers NP_001997, NP_001348594, NM_002006 and NM_001361665 (SEQ ID NO: 98-101). According to specific embodiments the FGF2 refers to the mouse FGF2, such as provided in the following GeneBank Numbers NP_032032 and NM_008006 (SEQ ID NO: 102-103). A homolog (as further defined hereinabove) refers to a functional expression product of FGF2 capable of inducing the differentiation of naïve PSCs to trophectoderm cells and/or extra embryonic primitive endodermal cells.

According to specific embodiments, the factor that induces differentiation to trophectoderm cells is a SUMOylation inhibitor, such as but not limited to DC 2-D08 (2',3',4'-trihydroxy flavone).

According to specific embodiments, the factor that induces differentiation to trophectoderm cells is a Histone Deacetylase inhibitor (HDACi), such as but not limited to VPA (valproic acid), Trichostatin A, sodium butyrate or UF010 small molecule inhibitor.

According to specific embodiments, the factor that induces differentiation to trophectoderm cells is a HIPPO signaling pathway inhibitor or a factor that induces YAP nuclear translocation.

The HIPPO signaling pathway, also known as the Salvador/Warts/Hippo (SWH) pathway, comprise a complex cascade of serine/threonine-protein kinases that eventually regulates phosphorylation of Yap/Taz. Specifically, when the Hippo pathway is 'off', the phosphorylated YAP/TAZ is retained in the cytoplasm and may also undergo proteolytic degradation. When the Hippo pathway is 'on', the unphosphorylated YAP/TAZ moves into the nucleus and binds to transcription factors called TEA DNA-binding proteins (TEAD1-4). Non-limiting examples of components of the HIPPO signaling pathway include Hpo, Serine threonine kinase 3 (STK3) and STK4 (also known as MST1 and MST2), salvador homolog 1 (SAV1), large tumor suppressor 1/2 (LATS1/2). MAP4K, TAOK, MOB kinase activator 1A/B (MOB1A/B), yes-associated protein (YAP1), transcriptional co-activator with PDZ-binding motif (TAZ or WWTR1) and Neurofibromin 2 (NF2).

The HIPPO signaling pathway inhibitor disclosed herein binds a component of the HIPPO signaling pathway and inhibits expression and/or activity of same. Such inhibitors are known in the art and include, but not limited to LPA and XMU-MP-1.

As used herein, the term "extra embryonic primitive endodermal (PRE) primed cell" refers to a stem cell originating from a naïve PSC that comprises an exogenous nucleic acid sequence encoding a factor that induces differentiation to an extra embryonic primitive endodermal cell and/or a cell originating from a naïve PSC that is committed to the extra embryonic primitive endoderm lineage (e.g. extra embryonic primitive endodermal cell).

It will be appreciated that prior to induction of expression of the exogenous factor (i.e. the protein product expressed from the exogenous nucleic acid sequence or the endogenous factor) the cell is in a naïve and undifferentiated state (i.e. naïve PSC) and following induction of expression of the exogenous factor the cell acquires characteristics of an extra embryonic primitive endodermal cell.

According to specific embodiments, the extra embryonic primitive endodermal primed cell comprises an exogenous polynucleotide suitable for transient expression of the factor that induces differentiation to extra embryonic primitive endodermal cells, as further described hereinbelow.

According to specific embodiments, the extra embryonic primitive endodermal primed cell comprises the protein product expressed from the exogenous nucleic acid sequence encoding the factor.

According to other specific embodiments, the extra embryonic primitive endodermal primed cell does not comprise the protein product expressed from the exogenous nucleic acid sequence encoding the factor.

As used herein, "extra embryonic primitive endodermal cell" refers to a cell having a restricted potential to generate all primitive endoderm lineages but not other cell lineages.

Non-limiting examples of extra embryonic primitive endodermal cell markers include Foxa2, Gata4, Gata6, PDGFRA and Sox17.

According to specific embodiments, the extra embryonic primitive endodermal cell expresses Gata4, i.e. positive for Gata4.

According to specific embodiments, the extra embryonic primitive endodermal primed cell expresses an extra embryonic primitive endoderm marker. According to specific embodiments, the extra embryonic primitive endodermal primed cell expresses at least one extra embryonic primitive endoderm marker selected from the group consisting of PDGFRA, GATA4, SOX17, NID2 and GATA6.

According to specific embodiments, the extra embryonic primitive endodermal primed cell expresses a pluripotency marker. Such markers are known in the art and are further described hereinabove and below. According to specific embodiments, the extra embryonic primitive endodermal primed cell expresses (positive for) at least one pluripotency marker selected from the group consisting of OCT4, SSEA1 and SSEA4. According to specific embodiments, the extra embryonic primitive endodermal primed cell is negative for a pluripotency marker selected from the group consisting of NANOG, KLF17, NANOG-NB and, TFCP2L1.

According to specific embodiments, the extra embryonic primitive endodermal primed cell expresses an extra embryonic primitive endoderm marker and a pluripotency marker.

According to specific embodiments, the marker is endogenous to the cell.

Thus, according to specific embodiments, the extra embryonic primitive endodermal primed cell expresses an exogenous factor that induces differentiation to extra embryonic primitive endodermal cells, an endogenous extra embryonic primitive endoderm marker and an endogenous pluripotency marker.

According to specific embodiments, the extra embryonic primitive endodermal primed cell expresses an extra embryonic primitive endoderm marker upon mixing (i.e. at time 0 hours), in the mixture or in the aggregate.

According to specific embodiments, the extra embryonic primitive endodermal primed cell expresses a pluripotency marker upon mixing (i.e. at time 0 hours), in the mixture or in the aggregate.

According to specific embodiments, the extra embryonic primitive endodermal primed cell expresses Oct4 upon mixing (i.e. at time 0 hours), in the mixture or in the aggregate According to other specific embodiments, the extra embryonic primitive endodermal primed cell does not express Oct4 upon mixing (i.e. at time 0 hours), in the mixture or in the aggregate.

According to specific embodiments, the extra embryonic primitive endodermal primed cell (e.g. upon mixing, in the mixture, in the aggregate) is not in a differentiation stage of a XEN cell. In other words, it does not have a phenotypic signature of a XEN (which can be obtained from blastocysts, early post-implantation embryo or an induced XEN obtained by de-differentiation or re-programming of a cell).

According to specific embodiments, the XEN has an OCT4−GATA6+GATA4+SOX17+PDGFRa+ phenotype.

In comparison the extra embryonic primitive endodermal primed cell of some embodiments of the invention has an OCT4+GATA6+GATA4+SOX17+PDGFRa+ phenotype.

As mentioned, the factor which expression induces differentiation of the naïve PSCs of some embodiments of the invention may be endogenous and/or exogenous to the cell.

According to specific embodiments, the method comprises inducing expression of an exogenous factor that induces differentiation to (towards) extra embryonic primitive endodermal cells.

According to additional or alternative embodiments, the method comprises inducing expression of an endogenous factor that induces differentiation to (towards) extra embryonic primitive endodermal cells. Hence, according to specific embodiments, the cell is cultured under conditions enabling expression of an endogenous factor that induces differentiation to the extra embryonic primitive endodermal primed cell. Such conditions include for example an appropriate temperature (e.g., 37° C.), atmosphere (e.g., % $O_2$, % $CO_2$), pressure, pH, light, medium, supplements (e.g. a differentiation factor as disclosed herein) and the like. Further description on culturing conditions are provided hereinbelow. Hence, according to specific embodiments, the naïve PSC cell or the extra embryonic primitive endodermal primed cell is contacted with the factor. Under this culturing scenario the cells may further comprise or be devoid of an exogenous polynucleotide suitable for expression of a factor that induces differentiation to extra embryonic primitive endodermal cells. According to a specific embodiment, the cell does not comprise an exogenous polynucleotide suitable for expression of a factor that induces differentiation to extra embryonic primitive endodermal. In this case inducing expression of the endogenous factor, the culturing or the contacting is typically effected prior to mixing the subpopulations of cells (e.g. starting within 14 days—0 hours prior to the mixing, within 13 days—0 hours prior to the mixing, within 12 days—0 hours prior to the mixing, within 11 days—0 hours prior to the mixing, within 10 days—0 hours prior to the mixing, within 9 days—0 hours prior to the mixing, within 8 days—0 hours prior to the mixing, within 7 days—0 hours prior to the mixing, within 6 days—0 hours prior to the mixing within 5 days—0 hours prior to the mixing, within 120 hours—0 hours prior to the mixing, within 100 hours—0 hours prior to the mixing, within 80 hours—0 hours prior to the mixing, within 60 hours—0 hours prior to the mixing, within 48 hours—0 hours prior to the mixing, within 36 hours—0 hours prior to the mixing, within 24 hours—0 hours prior to the mixing, within 12 hours—0 hours prior to the mixing, within 14-1 days prior to the mixing, within 13-1 days prior to the mixing, within 12-1 days prior to the mixing, within 11-1 days prior to the mixing, within 10-1 days prior to the mixing, within 9-1 days prior to the mixing, within 8-1 days prior to the mixing, within 7-1 days prior to the mixing, within 6-1 days prior to the mixing within 5-1 days prior to the mixing, within 120-20 hours prior to the mixing, within 100-20 hours prior to the mixing, within 80-20 hours prior to the mixing, within 60-20 hours prior to the mixing, within 48-20 hours prior to the mixing, within 14 days-12 hours prior to the mixing, within 13 days-12 hours prior to the mixing, within 12 days-12 hours prior to the mixing, within 11 days-12 hours prior to the mixing, within 10 days-12 hours prior to the mixing, within 9 days-12 hours prior to the mixing, within 8 days-12 hours prior to the mixing, within 7 days-12 hours prior to the mixing, within 6 days-12 hours prior to the mixing within 5 days-12 hours prior to the mixing, within 120-12 hours prior to the mixing, within 100-12 hours prior to the mixing, within 80-12 hours prior to the mixing, within 60-12 hours prior to the mixing, or within 48-12 hours prior to the mixing, within 14 days-6 hours prior to the mixing, within 13 days-6 hours prior to the mixing, within 12 days-6 hours prior to the mixing, within 11 days-6 hours prior to the mixing, within 10 days-6 hours prior to the mixing, within 9 days-6 hours prior to the mixing, within 8 days-6 hours prior to the mixing, within 7 days-6 hours prior to the mixing, within 6 days-6 hours prior to the mixing within 5 days-6 hours prior to the mixing, within 120 hours-6 hours prior to the mixing, within 100 hours-6 hours prior to the mixing, within 80 hours-6 hours prior to the mixing, within 60 hours-6 hours prior to the mixing, within 48 hours-6 hours prior to the mixing, within 36 hours-6 hours prior to the mixing, within 24 hours-6 hours prior to the mixing, or within 12 hours-6 hours prior to the mixing, each possibility represents a separate embodiment of the invention).

According to specific embodiments, the culturing or the contacting starts at least 6 hours, at least 10 hours, at least 12 hours, at least 16 hours, at least 24 hours, at least 36 hours, at least 48 hours, at least 72 hours, or at least 96 hours prior to the mixing.

According to specific embodiments, the culturing or the contacting starts no more than 3 days, no more than 4 days, no more than 5 days, no more than 6 days, no more that 7 days, no more than 8 days, no more than 9 days, no more than 10 days, not more that 14 days, no more than 16 days, or no more than 20 days prior to the mixing.

According to specific embodiments, the culturing or the contacting starts within about 6-3 days prior to the mixing.

According to specific embodiments, the culturing or the contacting starts about 3 days prior to the mixing.

Factors that induce differentiation to extra embryonic primitive endodermal cells are well known in the art, and include factor expressed in the cells and factor that are contacted with the cells. Non-limiting examples of such factors include Gata4, Gata6, a GSK-3 inhibitor, WNT ligand, heparin, FGF2, FGF4, PDGFRA, leukemia inhibitory factor (LIF) and insulin.

According to specific embodiments, the factor that induces differentiation to extra embryonic primitive endodermal cells is Gata4.

As used herein, the term "Gata4", also known as GATA Binding Protein 4 and Transcription factor Gata4, refers to the polynucleotide and expression product e.g., polypeptide of the GATA4 gene (corresponding to human gene ID NO: 2626) or homolog or ortholog of same. According to specific embodiments the Gata4 refers to the human Gata4, such as provided in the following GeneBank Numbers NP_001295022, NP_001295023, NP_002043, NP_001361202, NP_001361203, NM_001308093, NM_001308094, NM_002052, NM_001374273 and NM_001374274 (SEQ ID NO: 104-113). According to specific embodiments the Gata4 refers to the mouse Gata4, such as provided in the following GeneBank Numbers NP_001297539, NP_032118, NM_008092 and NM_001310610 (SEQ ID NO: 114-117). A homolog (as further defined hereinabove) refers to a functional expression product of Gata4 capable of inducing the differentiation of naïve PSCs to extra embryonic primitive endodermal cells.

According to specific embodiments, the factor that induces differentiation to extra embryonic primitive endodermal cells is Gata6.

As used herein, the term "Gata6", also known as GATA Binding Protein 6 and Transcription factor Gata6, refers to the polynucleotide and expression product e.g., polypeptide of the GATA6 gene (corresponding to human gene ID NO: 2627) or homolog or ortholog of same. According to specific embodiments the Gata6 refers to the human Gata6, such as provided in the following GeneBank Numbers NP_005248 and NP_005257 (SEQ ID NO: 118-119). According to specific embodiments the Gata6 refers to the mouse Gata6, such as provided in the following GeneBank Numbers NP_034388 and NM_010258 (SEQ ID NO: 120-121). A homolog (as further defined hereinabove) refers to a functional expression product of Gata6 capable of inducing the differentiation of naïve PSCs to extra embryonic primitive endodermal cells.

According to specific embodiments, the factor that induces differentiation to extra embryonic primitive endodermal cells is SOX17.

As used herein, the term "SOX17", also known as SRY-box 17, refers to the polynucleotide and expression product e.g., polypeptide of the SOX17 gene (corresponding to human gene ID NO: 64321) or homolog or ortholog of same. According to specific embodiments the SOX17 refers to the human SOX17, such as provided in the following GeneBank Numbers NP_071899 and NM $O_{22454}$ (SEQ ID NO: 197-198). According to specific embodiments the SOX17 refers to the mouse SOX17, such as provided in the following UniProt No. Q61473 (SEQ ID NO: 199). A homolog (as further defined hereinabove) refers to a functional expression product of SOX17 capable of inducing the differentiation of naïve PSCs to extra embryonic primitive endodermal cells.

According to specific embodiments, the factor that induces differentiation to extra embryonic primitive endodermal cells is a GSK-3 inhibitor.

As used herein the term "GSK-3" refers to the glycogen synthase kinase 3 beta protein set forth by GenBank Accession Nos. NP_002084 (SEQ ID NO: 122) and/or NP_001139628 (SEQ ID NO: 123) having the WNT signaling regulatory activity via its kinase activity.

As used herein the term "GSK-3 inhibitor" refers to any molecule capable of inhibiting the activity of GSK-3 as determined by specifically inhibiting levels of phosphorylated GSK3b (out of total GSK3b present in a cell).

Non-limiting examples of GSK-3 inhibitors include CHIR99021 (AXON MEDCHEM—AXON 1386), BIO (AXONMEDCHEM—Axon 1693), and Kenpaullone (TOCRIS—cat no. 1398).

According to specific embodiments, the factor that induces differentiation to extra embryonic primitive endodermal cells is a WNT ligand.

Wnt ligands are a large family of secreted glycoproteins that are cysteine-rich and highly hydrophobic. Non-limiting examples of Wnt ligands that can be used with specific embodiments of the invention include Wnt-1, Wnt-2, Wnt-2b, Wnt-3a, Wnt-4, Wnt-5a, Wnt-5b, Wnt-6, Wnt-7a, Wnt-7b, Wnt8a, Wnt-8b, Wnt-9a, Wnt-9b, Wnt-10a, Wnt-10b, Wnt-11 and Wnt16b.

According to specific embodiments, the factor that induces differentiation to extra embryonic primitive endodermal cells is FGF2.

According to specific embodiments, the factor that induces differentiation to extra embryonic primitive endodermal cells is FGF4.

According to specific embodiments, the factor that induces differentiation to extra embryonic primitive endodermal cells is PDGF.

As used herein, the term "PDGF", refers to a platelet-derived growth factor, and includes the various subtypes of PDGF including PDGF-B (e.g. GenBank Accession Nos. X02811 and CAA26579), PDGF-A (e.g. GenBank Accession nos. X06374 and CAA29677), PDGF-C (e.g. GenBank Accession Nos. NM 016205 and NP 057289), PDGF-D, variants 1 and 2 (e.g. GenBank Accession Nos. NM 025208, NP 079484, NM 033135, NP 149126), and dimerized forms thereof, including PDGF-AA, PDGF-AB, PDGF-BB, PDGF-CC, and PDGF-DD. Typically, platelet-derived growth factors includes homo- or heterodimers of A-chain and B-chain that exert their action via binding to and dimerization of two related receptor tyrosine kinase platelet-derived growth factor cell surface receptors PDGFR-α (also known as PDGFRA, e.g. GenBank Accession Nos. NM 006206 and NP 006197) and PDGFR-β (e.g. GenBank Accession Nos. NM 002609 and NP 002600). See also PCT Application Publication No. WO2010/127029 and US Application Publication No. US20150182623, which are incorporated herein in its entirety, for PDGF sequences. According to specific embodiments, the PDGF is capable of inducing the differentiation of naïve PSCs to extra embryonic primitive endodermal cells.

According to specific embodiments, the factor that induces differentiation to extra embryonic primitive endodermal cells is LIF (as further defined infra).

According to specific embodiments, the factor that induces differentiation to extra embryonic primitive endodermal cells is insulin.

As the present inventors developed culture conditions which enabled the generation of extra embryonic primitive endodermal primed cells from naïve PSCs which can be used for example for generating synthetic embryos (Examples 10 and 14 of the Examples section which follows), embodiments of the invention also contemplate methods of obtaining these cells.

Thus, according to an aspect of the present invention, there is provided a method of obtaining extra embryonic primitive endodermal primed cells, the method comprising culturing naïve PSCs in a base medium devoid of Activin A under conditions that allow differentiation of said naïve PSCs to GATA4$^+$GATA6$^+$OCT4$^+$Nanog$^-$ extra embryonic primitive endodermal primed cells, thereby obtaining the extra embryonic primitive endodermal primed cells.

According to specific embodiments, the GATA4$^+$GATA6$^+$OCT4$^+$Nanog$^-$ cells are also positive for PDGFRA and NID2.

According to specific embodiments of this aspect of the present invention, the method further comprising inducing expression (e.g. transient expression) of an exogenous factor that induces differentiation to extra embryonic primitive endodermal cells.

According to other specific embodiments of this aspect of the present invention, the method does not comprise inducing expression (e.g. transient expression) of an exogenous factor that induces differentiation to extra embryonic primitive endodermal cells.

According to specific embodiments, the culturing is effected for at least 6 hours, at least 12 hours, at least 16 hours, at least 1 day (or at least 24 hours), at least 2 days or at least 3 days.

According to specific embodiments, the culturing is effected for up to 14 days, up to 13 days, up to 12 days, up to 11 days, up to 10 days, up to 9 days, up to 8 days, up to 7 days or up to 6 days.

According to specific embodiments, the culturing is effected for 1-10 days.

According to specific embodiments, the culturing is effected for about 3-6 days.

According to specific embodiments, the culturing is effected from about 3 days.

According to specific embodiments, the obtained cells are a stable line maintaining the extra embryonic primitive endodermal primed cells phenotype (e.g. GATA4$^+$GATA6$^+$OCT4$^+$Nanog$^-$ phenotype) over multiple generations/passages. Thus, according to specific embodiments, the cells can be expanded in culture for at least 3, at least 4, at least 5, at least 6, at least 7, at least 8, at least 9, at least 10, at least 20, or at least 30 passages while maintaining the extra embryonic primitive endodermal primed cells phenotype (e.g. GATA4$^+$GATA6$^+$OCT4$^+$Nanog$^-$ phenotype).

The exogenous factors of some embodiments of the invention are transiently expressed in the cells.

Methods of expressing an exogenous nucleic acid sequence and/or amino acid sequence are known in the art and include those described for example in the materials and methods of the Examples section which follows and in Mansour et al. 2012; Warren et al. 2010 and Hongyan Zhou al. Cell Stem Cell (2009) 4(6): 581; Rabinovich and Weissman (2013) *Methods Mol Biol.* 969:3-28; International Application Publication No. WO 2013049389 and U.S. Pat. No. 8,557,972, which are fully incorporated herein by reference in their entirety.

Further, methods of transient expression are well known in the art and include, but not limited to, expression under the control of an inducible promoter, by introduction of mRNA into the cells (in this way the mRNA will be translated in the cells and degraded after a relatively short time) or by transfecting with the protein, as further described infra.

Distinguishing a cell expressing an exogenous polynucleotide and/or polypeptide from a cell not expressing the exogenous polynucleotide and/or polypeptide can be effected by e.g. determining the level and/or distribution of the RNA and/or protein molecules in the cell, the location of DNA integration in the genome of the cell and/or the number of gene copy number. Methods of determining the presence of an exogenous polynucleotide and/or polypeptide in a cell are well known in the art and include e.g. PCR, DNA and RNA sequencing, Southern blot, Western blot, immunoprecipitation, immunocytochemistry, flow cytometry and imaging.

According to specific embodiments, the expression is affected by introducing to the cells a polynucleotide encoding the factor.

According to specific embodiments, expressing is not in the natural location (i.e., gene locus) and/or expression level (e.g., copy number and/or cellular localization) of the native gene of the factor.

Alternatively or additionally, exogenous expression of a factor may be facilitated by activation of the endogenous locus of these genes such that the factor is overexpressed in the cell. Methods of activating and overexpressing an endogenous gene are well known in the art [see for example Menke D. Genesis (2013) 51: -618; Capecchi, *Science* (1989) 244:1288-1292; Santiago et al. *Proc Natl Acad Sci USA* (2008) 105:5809-5814; International Patent Application Nos. WO 2014085593, WO 2009071334 and WO 2011146121; U.S. Pat. Nos. 8,771,945, 8,586,526, 6,774,279 and US Patent Application Publication Nos. 20030232410, 20050026157, US20060014264; the contents of which are incorporated by reference in their entireties] and include, but not limited to and include targeted homologous recombination (e.g. "Hit and run", "double-replacement"), site specific recombinases (e.g. the Cre recombinase and the Flp recombinase), PB transposases (e.g. Sleeping Beauty, piggyBac, Tol2 or Frog Prince), genome editing by engineered nucleases (e.g. meganucleases, Zinc finger nucleases (ZFNs), transcription-activator like effector nucleases (TALENs) and CRISPR/Cas system) and genome editing using recombinant adeno-associated virus (rAAV) platform, and small molecules. Agents for introducing nucleic acid alterations to a gene of interest can be designed publically available sources or obtained commercially from Transposagen, Addgene and Sangamo Biosciences.

As used herein the term "polynucleotide" refers to a single or double stranded nucleic acid sequence in the form of an RNA sequence (e.g. mRNA), a complementary polynucleotide sequence (cDNA), a genomic polynucleotide sequence (e.g. sequence isolated from a chromosome), a composite polynucleotide sequences (e.g., a combination of the above) or mimetic or analog thereof. This term includes polynucleotides and/or oligonucleotides derived from naturally occurring nucleic acids molecules (e.g., RNA or DNA), synthetic polynucleotide and/or oligonucleotide molecules composed of naturally occurring bases, sugars, and covalent internucleoside linkages (e.g., backbone), as well as synthetic polynucleotides and/or oligonucleotides having non-naturally occurring portions, which function similarly to the respective naturally occurring portions.

According to specific embodiments, the polynucleotide is a modified polynucleotide e.g. modified RNA.

Such a modified polynucleotide may comprise a modification in either backbone, internucleoside linkages or bases. The modified polynucleotide may comprise naturally modified nucleotides or synthetic nucleoside analogous. Modified polynucleotides may be preferred over native forms according to specific embodiments, because of desirable properties such as, for example, enhanced cellular uptake, enhanced affinity for nucleic acid target, increased stability in the presence of nucleases and decreased immunogenicity.

Such modifications include, but are not limited to 5-methoxyuridine, Pseudouridine, 5-methyl cytidine, N6-methyladenosine, 2'-O-methyl, 2'-O-methyl 3'phosphorothioate, 2'-O-methyl 3'thiophosphonoacetate, Locked nucleic acid (LNA).

Methods of stabilizing mRNA are known in the art and include modulation of the length of the polyadenine tail found at the 3" end of the mRNA transcript. Alternatively or additionally, the RNA cap found at the molecule's 5' end can be modified. The naturally occurring cap structure typical in mammalian cells has a tendency to be improperly incorporated into RNAs synthesized in vitro, rendering them less effective. Synthetic "anti-reverse cap analogs" (e.g. those commercially available at Thermo Fisher Scientific) can prevent this misincorporation, which results in more stable RNA with improved translational efficiency. In order to reduce immunogenicity, substitution of particular nucleotides can be exchanged with chemically modified alternatives such as 5-methylcytosine or pseudoruidine. Such substitutions can mute the immune response whilst also bolstering the stability of the mRNA and efficiency of translation. Other exemplary chemically modified nucleotides are described herein above.

Alternatively, or additionally, the mRNA may be encapsulated in lipid-based particles to enhance fusion with the lipid cell membrane.

Polynucleotides designed according to the teachings of some embodiments of the invention can be generated according to any polynucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The term "polypeptide" or "protein" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH-NNAïve-CO—), wherein R is any alkyl (e.g., methyl), amine bonds (—CH2-NH—), sulfide bonds (—CH2-S—), ethylene bonds (—CH2-CH2—), hydroxyethylene bonds (—CH(OH)—CH2—), thioamide bonds (—CS—NH—), olefinic double bonds (—CH=CH—), fluorinated olefinic double bonds (—CF=CH—), retro amide bonds (—NH—CO—), peptide derivatives Naïve(R)—CH2-CO—), wherein R is the "normal" side chain, naturally present on the carbon atom.

These modifications can occur at any of the bonds along the polypeptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The polypeptides of some embodiments of the invention may also include one or more modified amino acids or one or more non-amino acid monomers (e.g. fatty acids, complex carbohydrates etc.).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The polypeptides of some embodiments of the invention may be synthesized by any techniques known to those skilled in the art of peptide synthesis, for example but not limited to recombinant DNA techniques or solid phase peptide synthesis.

Following is a non-limiting description of expression vectors and modes of administering thereof into cells which can be used to express a polypeptide-of-interest (e.g., any of the factors described hereinabove and below, e.g. Cdx2, Gata4) in a cell.

According to specific embodiments, expressing comprises introducing into the cell a polynucleotide encoding the polypeptide-of-interest (e.g. the factor).

According to specific embodiments, the polynucleotide is a DNA.

According to specific embodiments, the polynucleotide is a RNA. Typically, mRNA introduced into cells exists only in the cytoplasm, does not cause genome perturbations and is essentially transient. Unless expression of the mRNA changes the cell epigenetically, transient transfection is limited by the time of mRNA and cognate protein persistence in the cell, and does not continue after degradation of cognate proteins.

To express an exogenous protein in mammalian cells, a polynucleotide sequence encoding the polypeptide-of-interest is preferably ligated into a nucleic acid construct suitable for mammalian cell expression.

It will be appreciated that over-expression of genes can be effected using knock-in and/or knock-out constructs [see for example, Fukushige, S. and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62].

Such a nucleic acid construct or system includes at least one cis-acting regulatory element for directing expression of the nucleic acid sequence. Cis-acting regulatory sequences include those that direct constitutive expression of a nucleotide sequence as well as those that direct inducible expression of the nucleotide sequence only under certain conditions.

According to specific embodiments, an inducible promoter sequence for directing transcription of the polynucleotide sequence in the cell in an inducible manner is included in the nucleic acid construct. Inducible mammalian promoters are known to those of skill in the art (see, e.g. Bitter et al. (1987) *Methods in Enzymology* 153: 516-544). Inducible promoters can be activated by external signals or agents (i.e. inducer). The inducer may directly activate a promoter or inactivate a repressor of that promoter. For example, inducible systems endogenous to mammalian cells include promoters induced by heavy-metals (Brinster et al. Nature (1982) 296:39-42; Mayo et al. Cell (1982) 29:99-108; and Searle et al. Molecular and Cellular Biology (1985) 5:1480-1489), steroid hormones (Hynes et al. Proc. Natl. Acad. Sci. USA (1981) 78:2038-2042; Lee et al. Nature (1981) 294:

228-232; and Klock et al. Nature (1987) 329:734-736), heat shock (Nouer, Heat Shock Response. Boca Raton, FL, Ed. CRC, 1991) (reviewed in Mullick, A. and B. Massie Encyclopedia of Cell Technology pp. 1 140-1 164, 2000)) are well characterized. PCT publication WO2002/088346 discloses a cumate-inducible promoter. Additional inducible promoters are known in the art, and include, but are not limited to inflammation and hypoxia induced promoters. Prokaryotic and insect inducible promoter systems have been adapted for regulated expression in mammalian cells. See, for example, Gossen et al. (1993) TIBS 18:471-475 and No et al. (1996) Proc. Natl. Acad. Sci. USA 93:3346-3351). The insect ecdysone-inducible promoter is tightly regulated with no detectable background expression in the absence of inducer. Ecdysone is suitable for use in vivo because it is a naturally occurring lipophilic steroid that can penetrate tissues, is inert in mammals and exhibits rapid clearance kinetics (No et al). Gupta et al. (*PNAS* (2004) 101: 1927-1932) discloses retroviral delivery of an ecdysone-inducible gene expression system under the control of a modified RNA polymerase Ill-specific U6 promoter.

The prokaryotic repressors from the lac and tet operons have been incorporated in eukaryotic inducible expression systems. Repression of expression is mediated by the repressor bound to operator sites placed downstream of the minimal promoter in the absence of inducer and repression is relieved on the addition of the inducer (Brown et al. (1987) Cell 49:603-612; Hu and Davidson (1987) Cell 48:555-566; Blau and Rossi, Proc. Natl. Acad. Sci. USA (1999) 96:797-799; and Gossen et al. (1995) Science 268:1766-1769).

According to specific embodiments, the inducible promoter is a Tet-on promoter induced by Tetracycline or Doxycycline.

Methods for construction of nucleic acid constructs or systems containing an inducible promoter operatively linked to a coding sequence of any polypeptide are known to those of skill in the art, as are methods for introducing such constructs of systems and vectors containing such expression cassette into cells.

In the case of mRNA, since gene expression from an RNA source does not require transcription, there is no need in a promoter sequence or the additional sequences involved in transcription described hereinbelow.

The nucleic acid construct or system (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vector may also contain a transcription and/or translation initiation sequence, transcription and/or translation terminator and a polyadenylation signal. By way of example, such constructs will typically include a 5' LTR, a tRNA binding site, a packaging signal, an origin of second-strand DNA synthesis, and a 3' LTR or a portion thereof.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding the protein-of-interest can be arranged in a "head-to-tail" configuration, may be present as an inverted complement, or in a complementary configuration, as an antiparallel strand. While such variety of configuration is more likely to occur with non-coding elements of the expression vector, alternative configurations of the coding sequence within the expression vector are also envisioned.

According to specific embodiments, the expression construct include labels for imaging in cells, such as fluorescent labels.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A$^+$, pMT010/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein.

Various methods can be used to introduce the polynucleotide or polypeptide of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation, nucleofection, microinjection, and infection with recombinant viral vectors. In addition, see U.S. Pat. Nos. 5,464,764 and 5,487,992 for positive-negative selection methods. Currently preferred in vivo nucleic acid transfer techniques include transfection with viral or non-viral constructs, such as adenovirus, lentivirus, Herpes simplex I virus, or adeno-associated virus (AAV) and lipid-based systems.

According to specific embodiments, introducing is by transient transfection.

Naked DNA or RNA, cell penetrating peptide or Viral and non-viral vectors (e.g. but not limited to liposomes, nanoparticles, mammalian vectors and the like) may be utilized as delivery vehicles in delivery of the polynucleotide or polypeptide as is known in the art. According to specific embodiments of the invention, the delivery system used is biocompatible and nontoxic.

Following are exemplary embodiments suitable for enhancing penetration of the exogenous polynucleotide or polypeptide to cells.

According to one exemplary embodiment, naked DNA or RNA [e.g., naked plasmid DNA (pDNA)] is non-viral vector, which can be produced in bacteria and manipulated using standard recombinant DNA techniques. It does not induce antibody response against itself (i.e., no anti-DNA or RNA antibodies generated) and enables long-term gene expression even without chromosome integration. Naked DNA or RNA can be introduced by numerous means, for example but not limited to, intravascular and electroporation techniques [Wolff J A, Budker V, 2005, Adv. Genet. 54: 3-20], or by jet injection [Walther W, et al., 2004, Mol. Biotechnol. 28: 121-8].

According to another exemplary embodiment, mammalian vectors are used, as further described hereinabove.

According to specific embodiments, the polynucleotide is comprised in a viral vector. Introduction of nucleic acids by viral infection offers several advantages over other methods such as lipofection and electroporation, since higher transfection efficiency can be obtained due to the infectious nature of viruses. The viral vector may be a virus with DNA based genome of a virus with RNA based genome (i.e. positive single stranded and negative single stranded RNA viruses). Examples of viral vectors include, but are not limited to, Lentivirus, Adenovirus and Retrovirus.

A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. Protocols for producing recombinant retroviruses and for infecting cells in-vitro or in-vivo with such viruses can be found in, for example, Ausubel et al., reds, *Current Protocols in Molecular Biology*, Greene Publishing Associates, (1989)]. Other suitable expression vectors may be an adenovirus, a lentivirus, a Herpes simplex I virus or adeno-associated virus (AAV).

Regulatory elements that limit expression to particular cell types can also be included. Such features include, for example, promoter and regulatory elements that are specific for the desired cell type.

According to specific embodiments, expressing comprises introducing into the cell the polypeptide-of-interest (e.g. the factor).

According to specific embodiments, the polypeptide is provided in a formulation suitable for cell penetration that enhances intracellular delivery of the polypeptide as further described hereinbelow.

Cell-Penetrating Peptides (CPPs) are short peptides (≤40 amino acids), with the ability to gain access to the interior of almost any cell. They are highly cationic and usually rich in arginine and lysine amino acids. They have the exceptional property of carrying into the cells a wide variety of covalently and noncovalently conjugated cargoes such as proteins, oligonucleotides, and even 200 nm liposomes. Therefore, according to additional exemplary embodiment CPPs can be used to transport the polynucleotide or polypeptide to the interior of cells.

TAT (transcription activator from HIV-1), pAntp (also named penetratin, *Drosophila* antennapedia homeodomain transcription factor) and VP22 (from Herpes Simplex virus) are examples of CPPs that can enter cells in a non-toxic and efficient manner and may be suitable for use with some embodiments of the invention. Protocols for producing CPPs-cargos conjugates and for infecting cells with such conjugates can be found, for example L Theodore et al. [The Journal of Neuroscience, (1995) 15(11): 7158-7167], Fawell S, et al. [Proc Natl Acad Sci USA, (1994) 91:664-668], and Jing Bian et al. [Circulation Research. (2007) 100: 1626-1633].

The expression level and/or activity level of the exogenous polynucleotide and/or polypeptide expressed in the cells of some embodiments of the invention can be determined using methods known in the arts, e.g. but not limited to Northern blot analysis, PCR analysis, Western blot analysis, Immunohistochemistry, and Fluorescence activated cell sorting (FACS).

As mentioned, according to specific embodiments, expression of the exogenous factor is transient.

According to specific embodiments, inducing the transient expression starts within 14 days—0 hours prior to the mixing.

According to specific embodiments, inducing the transient expression starts within 13 days—0 hours prior to the mixing, within 12 days—0 hours prior to the mixing, within 11 days—hours prior to the mixing, within 10 days—0 hours prior to the mixing, within 9 days—0 hours prior to the mixing, within 8 days—0 hours prior to the mixing, within 7 days—0 hours prior to the mixing, within 6 days—0 hours prior to the mixing within 5 days—0 hours prior to the mixing, within 120 hours—0 hours prior to the mixing, within 100 hours—0 hours prior to the mixing, within 80 hours—0 hours prior to the mixing, within 60 hours—0 hours prior to the mixing, within 48 hours—0 hours prior to the mixing, within 36 hours—0 hours prior to the mixing, within 24 hours—0 hours prior to the mixing or within 12 hours—0 hours prior to the mixing, each possibility represents a separate embodiment of the invention.

According to a specific embodiment, inducing the transient expression starts within within 120-0 hours prior to the mixing.

According to a specific embodiment, inducing the transient expression starts within within 48-0 hours prior to the mixing.

According to a specific embodiment, inducing the transient expression starts within within 42-0 hours prior to the mixing.

According to specific embodiments, inducing the transient expression starts no later than 48, 24 or 12 hours prior to the mixing.

According to specific embodiments, inducing the transient expression starts within 14-1 days prior to the mixing, within 13-1 days prior to the mixing, within 12-1 days prior to the mixing, within 11-1 days prior to the mixing, within 10-1 days prior to the mixing, within 9-1 days prior to the mixing, within 8-1 days prior to the mixing, within 7-1 days prior to the mixing, within 6-1 days prior to the mixing within 5-1 days prior to the mixing, within 120—hours prior to the mixing, within 100-20 hours prior to the mixing, within 80-20 hours prior to the mixing, within 60-house prior to the mixing, or within 48-20 hours prior to the mixing, each possibility represents a separate embodiment of the invention.

According to specific embodiments, inducing the transient expression starts within 14 days—12 hours prior to the mixing, within 13 days—12 hours prior to the mixing, within 12 days—12 hours prior to the mixing, within 11 days—12 hours prior to the mixing, within 10 days—12 hours prior to the mixing, within 9 days—12 hours prior to the mixing, within 8 days—12 hours prior to the mixing, within 7 days—12 hours prior to the mixing, within 6 days—12 hours prior to the mixing within 5 days—12 hours prior to the mixing, within 120-12 hours prior to the mixing, within 100-12 hours prior to the mixing, within 80-12 hours prior to the mixing, within 60-12 hours prior to the mixing, or within 48-12 hours prior to the mixing, each possibility represents a separate embodiment of the invention.

According to a specific embodiment, inducing the transient expression starts within 48-12 hours prior to the mixing.

According to specific embodiments, inducing the transient expression ends no later than 120 hours following the mixing.

According to specific embodiments, inducing the transient expression ends no later than 110 hours, 100 hours, 90 hours, 80 hours, 70 hours, 60 hours, 50 hours, 48 hours, 36 hours, 24 hours, 20 hours or 12 hours following the mixing, each possibility represents a separate embodiment of the invention.

According to specific embodiments, inducing the transient expression ends no later than 48 hours following the mixing.

According to specific embodiments, inducing the transient expression is effected for no more than 19 days.

According to specific embodiments, inducing the transient expression is effected for no more than 18 days, 17 days, 16 days, 15 days, 14 days, 13 days, 12 days, 11 days, 10 days, 9 days, 8 days, 7 days, 6 days, 5 days.

According to a specific embodiment, inducing the transient expression is effected for no more than 16 days.

According to a specific embodiment, inducing the transient expression is effected for no more than 96 hours.

According to a specific embodiment, inducing the transient expression starts 24 hours prior to the mixing and is effected for 96 hours (i.e. ends 48 hours following the mixing).

It will be appreciated that the culturing conditions suitable for the maintenance of the naïve PSCs and trophectoderm- and extra embryonic primitive endodermal-primed cells prior to the mixing include various tissue culture medium composition, feeder cells, oxygen concentration, culture vessel and the like and it is within the capability of one skilled in the art to determine which conditions should be applied. Non-limiting examples of such are described in the Examples section that follows, which serves as an integral part of the specification and Choi, J., Huebner, A., Clement, K. et al. Nature 548, 219-223 (2017); Yang et al. Cell (2017) 169(2): 243-257, www(dot)cell(dot)com/fulltext/S0092-8674%2817%2930183-6; www(dot)doi(dot)org/10.1038/nature23274; www(dot)doi(dot)org/10.1242/dev.180620; DOI: DOI: 10.1016/j.stem.2017.11.004; Shingo Io et al. (2021) Cell Stem Cell, 28(6): 1023-1039 and Mitsuyoshi Amita et al. (2013) PNAS E1212-1221; and International Patent Application Publication No. WO2016/016894 and WO2014/174470, the contents of which are fully incorporated herein by reference.

According to specific embodiments, the medium comprises a STAT3 activator.

As used herein the term "STAT3" refers to the signal transducer and activator of transcription 3 gene product (acute-phase response factor) (Gene ID 6774). In response to cytokines and growth factors, STAT family members are phosphorylated by the receptor associated kinases, and then form homo—or heterodimers that translocate to the cell nucleus where they act as transcription activators. Known STAT3 activators include, but are not limited to, interferon (IFN), epidermal growth factor (EGF), interleukin 5 (IL5), interleukin 6 (IL6), hepatocyte growth factor (HGF), leukemia inhibitory factor (LIF) and bone morphogenetic protein 2 (BMP2).

According to some embodiments of the invention, the STAT3 activator, which is used in the medium of some embodiments of the invention, is selected from the group consisting of LIF, IL6 and EGF.

According to some embodiments of the invention, the STAT3 activator, which is used in the medium of some embodiments of the invention, is selected from the group consisting of LIF and IL6.

According to some embodiments of the invention, the STAT3 activator, which is used in the medium of some embodiments of the invention is LIF.

As used herein the term "leukemia inhibitor factor (LIF)" refers to the polynucleotide and expression product e.g. polypeptide of the LIF gene (e.g. human Gene ID NO: 3976). A non-limiting example of a human LIF polypeptide is provided in the following GenBank Accession No. NP_001244064 (SEQ ID NO: 124). Preferably, the LIF used by the method according to some embodiments of the invention is capable of supporting, along with other factors, the undifferentiated growth of naïve PSCs, while maintaining their pluripotent capacity. LIF can be obtained from various manufacturers such as Millipore, Peprotech, and R&D systems.

According to specific embodiments, the medium comprises a GSK-3 inhibitor.

According to specific embodiments, the medium comprises an ERK1/2 inhibitor.

As used herein the term "ERK1" refers to the mitogen-activated protein kinase 3 (MAPK3) isoform 1 e.g. as set forth by GeneBank Accession No. NP_002737 (SEQ ID NO: 125), the MAPK3 isoform 2 e.g., as set forth by GenBank Accession No. NP_001035145 (SEQ ID NO: 126), the MAPK3 isoform 3 e.g. as set forth by GenBank Accession No. NP_001103361 (SEQ ID NO: 127) and/or ERK1 set forth in GenBank Accession No. M84490 (SEQ ID NO: 128) having the MAPK signaling activity.

As used herein the term "ERK2" refers to the mitogen-activated protein kinase 1 (MAPK1) e.g. as set forth by GenBank Accession No. NP_002736 (SEQ ID NO: 129) and/or GenBank Accession No. NP_620407 (SEQ ID NO: 130) having the MAPK signaling activity.

As used herein the term "ERK1/2 inhibitor" refers to any molecule capable of inhibiting the activity of ERK1/2 as determined by Western blot protein detection of phosphorylated ERK1/2 proteins.

Non-limiting examples of ERK1/2 inhibitors (also known as MEK1/2 inhibitors) include PD0325901 (AXONMEDCHEM—AXON 1408), PD98059 (AXONMEDCHEM—Axon 1223), and PD184352 (AXONMEDCHEM—AXON 1368).

According to specific embodiments, the medium comprises at least one of a GSK-3 inhibitor, WNT ligand, heparin, FGF2, FGF4, PDGF, leukemia inhibitory factor (LIF) and insulin.

According to specific embodiments, the medium comprises at least one of a GSK-3 inhibitor, leukemia inhibitory factor (LIF) and insulin.

According to specific embodiments, the medium comprises with at least one of GSK-3 inhibitor, heparin, FGF4, PDGF and BSA.

According to specific embodiments, the medium is devoid of Activin A [also known as Inhibin beta A, a polynucleotide and expression product e.g., polypeptide of the INHBA gene (corresponding to human gene ID: 3624) or homolog or ortholog of same].

According to specific embodiments, the medium is devoid of REPROCELL.

According to specific embodiments, the medium comprises at least one of a TGFR inhibitor, FGFR inhibitor, MEK/ERK inhibitor, BMP4, JAK inhibitor, FGF4, FGF2, heparin, a SUMOylation inhibitor, a Histone Deacetylase inhibitor, a HIPPO signaling pathway inhibitor and a factor that induces YAP nuclear translocation.

According to specific embodiments, for the TSCs primed cell pre-induction the following components may be useful supplements together or each: TGFRi A-83, LIF, HIPPO inhibitor LPA, ROCK inhibitor Y27632, MEK/ERK inhibitor PD0325901, EGF, JAKi.

Additional description of media and supplements that can be used with specific embodiments of the invention is provided infra.

According to specific embodiments, the subpopulation of cells are mixed together under conditions that allow formation of aggregated cells.

These conditions may comprise culturing time, culture vessel, medium composition, oxygen concentration, cells amount and ratio etc. Determining such conditions is well within the capabilities of the skilled artisan. Non-limiting examples of aggregation protocols that can be used with specific embodiments of the invention are described in the Examples section that follows, which serves as an integral part of the specification.

According to specific embodiments, mixing the naïve PSCs, the trophectoderm primed cells and the extra embryonic primitive endodermal primed cells is effected concomitantly.

According to other specific embodiments, mixing the naïve PSCs, the trophectoderm primed cells and the extra embryonic primitive endodermal primed cells is effected sequentially.

Thus, for example, according to specific embodiments, mixing the naïve PSCs and the extra embryonic primitive endodermal primed cells is effected prior to mixing with the trophectoderm primed cells. According to specific embodiments, mixing the naïve PSCs and the trophectoderm primed cells is effected prior to mixing with the extra embryonic primitive endodermal primed cells.

According to specific embodiments, mixing the trophectoderm primed cells with the extra embryonic primitive endodermal primed cells is effected prior to mixing with the naïve PSCs.

According to specific embodiments, this difference in mixing times can be up to 48 hours, up to 40 hours, up to 35 hours, up to 30 hours, up to 24 hours, up to 16 hours or up to 12 hours, each possibility represented a separate embodiment of the invention.

According to specific embodiments, the ratio between the naïve PSCs and the trophectoderm primed cells is between 1:1 and 1:5.

According to specific embodiments, the ratio between the naïve PSCs and the trophectoderm primed cells is between 1:3-1:4.

According to a specific embodiment, the ratio between the naïve PSCs and the trophectoderm primed cells is about 1:3.3.

According to specific embodiments, the ratio between the naïve PSCs and the primitive endodermal primed cells is between 1:1 and 2:1.

According to specific embodiments, the ratio between the naïve PSCs and the primitive endodermal primed cells is about 1:1.

According to specific embodiments, the aggregation is effects in an aggregation plate. Such plates are known to the skilled in the art and can be commercially obtained from e.g. STEMCELL Technologies.

Non-limiting examples of protocols for culturing of naïve PSCs, induction of trophectoderm primed cells and primitive endodermal primed cells and aggregation of the three cell types are provided in the Examples section which follows.

Thus, for example, naïve KH2 ESCs comprising a nucleic acid sequence encoding Gata4 under the control of a TetOn promoter may be cultured in 2iLif media and treated with DOX (e.g. 2 μg/ml-Sigma D9891) in 2i/Lif for 24 hours before starting the experiment. Induction of Gata4 can be similarly effected in N2B27 media, MEF media, TSC media or Aggregation media. Naïve KH2 ESCs comprising a nucleic acid sequence encoding Cdx2 under the control of a TetOn promoter may be cultured in 2i/Lif are treated with DOX (2 μg/ml-Sigma D9891) for different time points (−1 day to −14 days e.g. 24 hours) in TSC media (25 ng/ml FGF4 (Peprotech), 1 μg/ml Heparin (Sigma)) supplemented with or without lysophosphatidic acid (EPA) 0.5-1 μM, which is a Hippo pathway inhibitor. TGFR and/or ERK inhibitors may be optionally added as well in this pre-induction step. The non-inducible ESC fraction does not undergo special pre-treatment and is maintained in 2i/Lif conditions or serum LIF conditions. Other naïve conditions that can be used instead of 2i/LIF conditions include a2i conditions: which use N2B27 supplemented base media with GSK3 inhibitor CHIR99021 (3 μM final concentration), Lif (20 ng/ml final concentration) and SRCI CGP77675 (1microM final concentration). Following, aggregation is effected in AggreWell 24-well plate 400 (STEMCELL Technologies 34415), or AggreWell 24-well plate 800 (STEMCELL Technologies 34815). Non adherent 96 well shaped wells (NUNC or THERMo) can also be used instead. AggreWell plate preparation may be effected according to manufacturer instructions; for example: 500 μl of anti-adherence rinsing solution (STEMCELL Technologies 07010) is added to each well. Plate is centrifuged at 2,000 g for 5 minutes and incubated 30 minutes at room temperature. After incubation, the rinsing solution is removed and the plate is washed twice with PBS. Following, 500 μl of aggregation media (AM) supplemented with DOX (2 μg/ml final concentration—Sigma D9891) and ROCKi Y27632 (5 nM-10 μM final concentration—Axon Medchem 1683) is added to each well. At the day of aggregation (day 0), the three cell populations may be trypsinized with 0.05% trypsin-EDTA solution (Biological Industries—Sartorius 03-053-1B) for 4-6 minutes at 37° C. Trypsin enzymatic reaction is stopped by adding Aggregation Media (AM). TrypleE or Accutase can be alternatively be used instead of trypsin. Cells are centrifuged at 1200 rpm for 3 minutes and re-suspended in AM with DOX (2 μg/ml-Sigma D9891) and ROCKi Y27632 (5 nM-10 microM final concentration—Axon Medchem 1683). Cells may be plated on gelatinized tissue culture plates for mouse embryonic fibroblast depletion for 20 minutes at 37° C. Following, supernatant is collected, centrifuged and cells are re-suspended. The three cell fractions are counted and re-suspended in AM with DOX (2 μg/ml-Sigma D9891) and ROCKi Y27632 (5 nM—Axon Medchem 1683). An exemplary ratio of (1 Naïve ESCs:1 iGata4 ESC:3.33 iCdx2 ESC) is maintained in aggregation experiments with the following exact number of cells depending on the aggregation plate used e.g.: A) AggreWell 800: Number of microwells per well in 24 well plate=300; Number of added cells per each well of a 24 well plate=iCdx2: 5000 cells+iGata4: 1500 cells+Naïve ESC 1500 cells; Number of Cells per single microwell=~27 cells. B) AggreWell 400: Number of microwells per well in 24 well plate=1200; Number of added cells per each well of a 24 well plate=iCdx2: 20000 cells+iGata4: 6000 cells+Naïve ESC 6000 cells; Number of Cells per single microwell=~27 cells.

As another example, naïve PSCs are used to generate the following three population of cells:
1) Naïve WT PSC cells cultured in HENSM medium.
2) For the primitive endoderm compartment—Naïve WT cells plated on mouse embryonic fibroblast conditions on HENSM supplemented with ROCKi followed by replacement with a RCL medium on the next day for 72 hours.
3) For the Trophectoderm lineage—Naïve WT cells plated on feeder free conditions on HENSM supplemented with ROCKi followed by medium replacement on the next day with a (B)AP medium for 24 hours, and then with an with AP(J) for another 48 hours.

All three cell types are supplemented with a ROCKi before harvesting for co-aggregation on the next day. At the day of aggregation (day 0), Aggrewell plates 400, 24 wells (Stemcell technologies) are prepared and prefilled with 500 μL of N2B27 media and kept at 37° C. for medium equilibration. The three cell populations are disaggregated with TrypLE (Thermo Fisher 12604054) for 3 minutes for the WT and Primitive endoderm cells and 5 minutes for the Trophectoderm cells at 37° C., next the enzyme is removed and cells are incubated for two minutes at room temperature, afterwards cells are collected with PBS. Cells are centrifuged at 1300 rpm for 3 minutes and resuspended in N2B27 ROCKi. Following, primitive endoderm cells are plated on gelatinized tissue culture plates for mouse embryonic fibroblast depletion for minutes at 37° C. Supernatant is collected, and all three elements are centrifuged separately and cells resuspended on N2B27 medium. The three cell fractions are counted and resuspended in N2B27 supplemented with ROCKi. A ratio of 1:1:3 (WT:PRE:TE) is maintained in the co-aggregation.

The present invention also contemplates composition and articles of manufactures comprising the cells and aggregates disclosed herein.

Thus, according to an aspect of the present invention there is provided an article of manufacture comprising:
(i) trophectoderm primed cells, wherein said trophectoderm primed cells comprise naïve pluripotent stem cell (PSCs) comprising an exogenous polynucleotide suitable for transient expression of a factor that induces differentiation to trophectoderm cells; and
(ii) naïve PSCs.

According to specific embodiments, the article of manufacture further comprising:
(iii) extra embryonic primitive endodermal primed cells, wherein said extra embryonic primitive endodermal primed cells comprise naïve pluripotent stem cells (PSCs) comprising an exogenous polynucleotide suitable for transient expression of factor that induces differentiation to extra embryonic primitive endodermal cells.

According to an additional or an alternative aspect of the present invention there is provided an article of manufacture comprising:

(i) trophectoderm primed cells, wherein said trophectoderm primed cells comprise naïve pluripotent stem cells (PSCs) comprising an exogenous polynucleotide suitable for transient expression of a factor that induces differentiation to trophectoderm cells; and (ii) extra embryonic primitive endodermal primed cells, wherein said extra embryonic primitive endodermal primed cells comprise naïve pluripotent stem cells (PSCs) comprising an exogenous polynucleotide suitable for transient expression of factor that induces differentiation to extra embryonic primitive endodermal cells.

According to specific embodiments, the different subpopulations of cells are in a single container.

According to other specific embodiments, the different subpopulations of cells are in separate containers.

According to an additional or an alternative aspect of the present invention there is provided a method of ex-utero culturing a synthetic embryo, the method comprising mixing the cells of the article of manufacture disclosed herein under conditions the allow formation of aggregated cells, wherein the method comprises inducing transient expression of said factor starting within 14 days—0 hours prior to said mixing and ending no later than 120 hours following said mixing, thereby generating the synthetic embryo.

According to an additional or an alternative aspect of the present invention there is provided a mixture or aggregate, generated according to or obtainable by the methods disclosed herein.

According to specific embodiments, the mixture or aggregate is not structurally organized as a native or naturally occurring embryo at any developmental stage. According to specific embodiments, the different cells in the mixture or aggregate are randomly scattered within the mixture of aggregate in an un-organized manner. According to specific embodiments, the mixture or aggregate does not form a blastocyst at any stage. According to specific embodiments, the mixture or aggregate does not comprise a cavity.

According to specific embodiments, the mixture or aggregate comprises at least 12, at least 16, at least 32, at least 40, at least 50 cells, or at least 64 cells.

According to specific embodiments, the mixture or aggregate comprises more than 64 cells.

According to specific embodiments, the mixture or aggregate comprises up to 500 cells, up to 450 cells, up to 400 cells, up to 350 cells, up to 300 cells, up to 250 cells, up to 200 cells, up to 150 cells, or up to 100 cells.

It will be appreciated that during culturing the mixture or aggregate of unorganized cells there is a process of re-organization of the cells to form a synthetic embryo having a structure or organization of a native one.

According to specific embodiments, the mixture or aggregate is capable of forming a synthetic embryo structurally organized as a native embryo of at least a post-implantation egg cylinder or a bilaminar disc developmental stage.

Thus, according to an additional or an alternative aspect of the present invention, there is provided a mixture or aggregate comprising:

(i) naïve pluripotent stem cell (PSCs);

(ii) trophectoderm primed cells, wherein said trophectoderm primed cells comprise stem cells expressing an endogenous trophectoderm marker and an endogenous pluripotency marker; and (iii) extra embryonic primitive endodermal primed cells, wherein said extra embryonic primitive endodermal primed cells comprise stem cells expressing an endogenous extra embryonic primitive endoderm marker and an endogenous pluripotency marker, wherein said mixture or aggregate is not structurally organized as a native embryo at any developmental stage; and wherein said mixture or aggregate is capable of forming a synthetic embryo structurally organized as a native embryo of at least a post-implantation egg cylinder of bilaminar disc developmental stage.

According to an additional or an alternative aspect of the present invention there is provided a mixture or aggregate comprising:

(i) trophectoderm primed cells, wherein said trophectoderm primed cells comprise stem cells expressing an exogenous factor that induces differentiation to trophectoderm cells, an endogenous trophectoderm marker and an endogenous pluripotent marker; and (ii) naïve pluripotent stem cell (PSCs).

According to specific embodiments, the mixture or aggregate further comprising:

(iii) extra embryonic primitive endodermal primed cells, wherein said extra embryonic primitive endodermal primed cells comprise stem cells expressing an exogenous factor that induces differentiation to extra embryonic primitive endodermal cells, an endogenous extra embryonic primitive endoderm marker and an endogenous pluripotency marker.

It will be appreciated that the mixture or aggregate of some embodiments of the invention comprises distinct populations of stem cells all starting from naïve pluripotent stem cells (PSCs).

According to some embodiments of the invention, the method further comprises allowing the synthetic embryo to grow ex vivo (ex utero) or in vivo (in utero).

Thus, according to an aspect of the present invention, there is provided a method of ex-utero culturing a synthetic embryo, the method comprising ex-utero culturing the mixture or aggregate disclosed herein.

As described in the Examples section which follows the present inventors were able to generate post gastrulation synthetic embryos by utilizing a controlled ex utero embryo culture platform and growth conditions that previously enabled capturing mouse natural embryos gastrulation and organogenesis ex utero (Aguilera-Castrejon et al., 2021a), indicating these platform and growth conditions can be used to culture ex-utero synthetic embryos generated by both the methods disclosed herein as well as by any other method.

Thus, according to an aspect of the present invention, there is provided a method of ex-utero culturing a synthetic embryo, the method comprising ex-utero culturing a synthetic embryo at an aggregate stage in a static culture followed by a dynamic culture, wherein said static culture is effected until said embryo reaches at least an early post-implantation egg-cylinder or bilaminar disc developmental stage; and said dynamic culture starts the latest when said embryo reaches an early somite stage.

According to specific embodiments, the method further comprises determining development of the embryo prior to, during and/or following the culturing. Methods of assessing development are well known in the art and are further described in details herein.

As used herein, the term "culturing a synthetic embryo" refers to at least a synthetic embryo and culture medium in an in-vitro or ex-vivo (ex-utero) environment. The culture is maintained under conditions (or set of conditions) capable of inducing development and growth of the synthetic embryos. Such conditions include for example an appropriate temperature (e.g., 37° C.), atmosphere (e.g., % $O_2$, % $CO_2$), pressure, pH, light, medium, supplements and the like.

The culture may be in a glass, plastic or metal vessel that can provide an aseptic environment for culturing. According to specific embodiments, the culture vessel includes dishes, plates, flasks, bottles, vials, bags, bioreactors or any device that can be used to grow cells.

According to specific embodiments, the culture is maintained under sterile conditions.

According to specific embodiments, the culture is maintained at 37-38° C.

According to specific embodiments, the culture is maintained at 38° C.

According to specific embodiments, the culture is maintained at 37° C.

As changes in temperature may affect embryo developments, according to specific embodiments, care should be taken not to keep the embryo in a temperature higher than 38° C. and lower than 35° C. for a long periods of time. Thus, for example, opening the culture incubator or keeping the embryo at room temperature for a long periods of time should be avoided.

According to specific embodiments, the culture is a static culture.

According to other specific embodiments, the culture is a dynamic culture.

According to specific embodiments, the culture is a static culture followed by a dynamic culture.

As used herein, the term "static culture" refers to a cell culture that is carried out without agitation of the culture.

According to specific embodiments, the static culture is effected for 3-4 days.

According to specific embodiments, the static culture is effected for about 3 days.

Embryonic stage and development may be assessed compared to an in-vivo embryo counterpart at the same developmental stage by multiple ways well known in the art, including, but not limited to, morphology, length, weight, expression of developmental marker genes using specific antibodies or primers, transcriptional profiling and the like, as further described in the Examples section which follows which serve as an integral part of the specification.

As used herein, the term "embryonic day (E)", "post fertilization day (PFD)" or "gestation day (GD)" refers to an embryo having developmental characteristic of an in vivo (in-uterine tube or in utero, depending on the day) embryo counterpart at the specified day following fertilization or mating, wherein E0/PFD0/GD0 is considered as the fertilized egg.

According to specific embodiments, the static culture is effected for 2-5 days.

According to specific embodiments, the static culture is effected for about 4 days.

According to specific embodiments, the static culture is effected for 10-20 days.

According to specific embodiments, the static culture is effected for about 12 days.

According to specific embodiments, the static culture ends the latest when the synthetic embryo reaches the egg cylinder stage (e.g. for mouse) or the bilaminar disc stage (e.g. for human).

As used herein, the term "egg cylinder stage" refers to a synthetic embryo post (and not including) the blastocyst stage and prior to the post-gastrulation stage and is characterized by expansion of yolk-sac surrounding the embryo and completion of gastrulation and emergence of somites.

According to specific embodiments, the egg cylinder stage refers a synthetic embryo having characteristic of E5-7 of an in-utero natural mouse embryo.

As used herein, the term "bilaminar disc stage" refers to a synthetic embryo post (and not including) the blastocyst stage and prior to the day 15 stage (Carnegie stage 6) and is characterized by two, dorsally convex cellular discs, one disc formed by a thick layer of pseudostratified columnar cells called epiblast, and the other by a thin layer of cuboidal cells called hypoblast. The disc-shaped epiblast is slightly convex dorsally, separated from the amnion by the amniotic cavity at the middle of the embryonic disc.

According to specific embodiments, the bilaminar disc stage refers a synthetic embryo having characteristic of PFD8-14 of an in-utero natural human embryo.

According to specific embodiments, to prevent sticking of the embryonic epiblast and yolk sac to the culture vessel during the static culture, the culture is examined to ensure that only the ectoplacental cone remains attached to the surface of the plate. According to specific embodiments, the embryos are carefully pushed away from the plate surface by using e.g. forceps, when needed.

As used herein, the term "dynamic culture" refers to a cell culture that is carried out with agitation (e.g. rolling, shaking, inverting) of the culture. To reiterate, in a dynamic culture the whole culture, including the embryo, is agitated. Non-limiting examples of dynamic cultures include a roller culture (a culture on a rolling device), a shaker culture (a culture on a shaker, e.g. orbital shaker).

According to specific embodiments, the dynamic culture is a roller culture.

According to specific embodiments, the rolling culture is rolled in 30 rpm.

Rotator culture units may be obtained commercially from e.g. B.T.C. Engineering,—Cullum Stan Precision Engineering Ltd—UK, but can be further modified and adapted.

According to other specific embodiments, the dynamic culture is a shaker culture.

According to specific embodiments, the shaker rotates at 30-80 rpm, 40-70 rpm, 50-70 rpm or 55-65 rpm.

According to a specific embodiment, the shaker rotates at about 60 rpm.

According to specific embodiments, the dynamic culture comprises a shaker culture, a roller culture or a sequential combination thereof.

According to specific embodiments, the dynamic culture starts when the embryo reaches a pre-gastrulation stage.

As used herein the term "pre-gastrulation" refers to a synthetic embryo following the egg cylinder stage or the bilaminar disc stage and prior to the early gastrulation stage and is characterized by presence of OCT4 and OTX2+ epiblast, pro-amniotic cavity formation and extra ectoderm embryo formation (ExE).

According to specific embodiments, the pre-gastrulation stage refers to a synthetic embryo having characteristics of E5-6 of an in-utero natural mouse embryo or PFD8-14 of an in-utero natural a human embryo.

According to specific embodiments, the dynamic culture starts with a shaker culture (for e.g. 1-4 days) followed by a roller culture.

According to specific embodiments, the roller culture starts when the embryo reaches at least the early gastrulation stage.

As used herein the term "early gastrulation" refers to a synthetic embryo following the pre-gastrulation stage and prior to the late gastrulation stage and is characterized e.g. in mice by egg cylinder shape with the primitive streak at the posterior side; in human by bilaminar disc cylinder shape with the primitive streak at the posterior side.

According to specific embodiments, the early gastrulation stage refers a synthetic embryo having characteristic of E6-7 of an in-utero natural mouse embryo or PFD12-18 of an in-utero natural a human embryo.

According to specific embodiments, the roller culture starts the latest when the embryo reaches an early somite stage.

According to specific embodiments, the dynamic culture starts the latest when the embryo reaches an early somite stage.

As used herein, the term "early somite" refers to a synthetic embryo following the late gastrulation stage and prior to the neural tube closure stage and is characterized by the appearance of the somites and formation of the first organs.

According to specific embodiments, the early somite stage refers a synthetic embryo having characteristic of E8-9 of an in-utero natural mouse embryo or PFD18-24 of an in-utero natural a human embryo.

As used herein the phrase "base medium" refers to a liquid substance used to support the growth/survival of stem cells and/or synthetic embryos and optionally induce their development.

The medium (cell or embryo culture medium, aggregation medium etc.) used according to some embodiments of the invention can be a water-based medium which includes a combination of substances such as salts, nutrients, minerals, vitamins, amino acids, nucleic acids, and/or proteins such as cytokines, growth factors and hormones, all of which are needed for cell growth and embryo development.

Preferably, all ingredients included in the culture medium of the present invention are substantially pure, i.e., a tissue culture grade.

For example, the culture medium may comprise a base medium such as a synthetic tissue culture medium, e.g. DMEM, DMEM/F12 or advanced DMEM/F12 (can be commercially obtained from e.g. GIBCO® or Biological Industries), Neurobasal (Invitrogen 21103-049 or ThermoFisher 21103049); KO-DMEM (can be commercially obtained from e.g. GIBCO®), CMRL (can be commercially obtained from e.g. GIBCO®), TCM199 (can be commercially obtained from e.g. Sigma), StemPro® (can be commercially obtained from e.g. Thermo Fisher Scientific), RPMI (can be commercially obtained from e.g. Biological Industries) or a combination thereof supplemented with the necessary additives as is further described herein.

Non-limiting examples of media than can be used with specific embodiments and specific stages of the disclosed methods are described in details in the Examples section which follows and in e.g. International Patent Application Publication No. WO2016/016894 and WO2014/174470, the contents or which are fully incorporated herein by reference.

Further, as the present inventors have identified novel culture media comprising specific factors which can be used to allow generation of trophectoderm- and extra embryonic primitive endodermal primed cells-primed cells and the development of a synthetic embryo (see the Examples section which follows), the present invention also envisages aspects related to media as described in the Examples section which follows, wherein components of the media are provided in concentrations of ±20%.

According to specific embodiments, the base medium is devoid of phenol red.

According to a specific embodiment, the base medium comprises DMEM having the same components as the DMEM of GIBCO® Cat. No. 11880.

According to a specific embodiment, the base medium comprises DMEM/F12 having the same components as the DMEM/F12 of GIBCO® Cat. No. 12634-010.

According to a specific embodiment, the base medium comprises CMRL having the same components as the CMRL of GIBCO® Cat. No. 11530037.

According to a specific embodiment, the base medium comprises TCM199 having the same components as the TCM199 of Sigma Cat. No. M4530.

According to specific embodiments, the medium comprises serum or serum replacement.

According to specific embodiments, the medium comprises 10-80% 15-80%, 20-80%, 15-75%, or 20-75% [volume/volume (v/v)] serum or serum replacement.

According to specific embodiments, the medium comprises 15-60%, 15-40% or 15-30% (v/v) serum or serum replacement.

According to a specific embodiment, the medium comprises 20-40% or 20-30% (v/v) serum or serum replacement.

According to other specific embodiments, the medium comprises at least 20% (v/v) serum or serum replacement.

According to a specific embodiment, the medium comprises about 20% (v/v) serum or serum replacement.

According to a specific embodiment, the medium comprises about 30% (v/v) serum or serum replacement.

According to other specific embodiments, the medium comprises at least 30% (v/v) serum or serum replacement.

According to other specific embodiments, the medium comprises at least 35% (v/v), at least 40% (v/v), at least 45% (v/v), at least 50% (v/v), at least 55% (v/v), at least 60% (v/v), at least 65% (v/v), at least 70% (v/v) serum or serum replacement.

According to other specific embodiments, the medium comprises 40-80%, 50-80%, 60-80%, 70-80% (v/v) serum or serum replacement.

According to other specific embodiments, the medium comprises 70-80% (v/v) serum or serum replacement.

According to a specific embodiment, the medium comprises about 75% (v/v) serum or serum replacement.

According to a specific embodiment, the medium comprises increasing concentrations of serum or serum replacement throughout the culturing of the embryo.

According to a specific embodiment, the medium comprises at least 15% serum or serum replacement from the beginning until the embryo reaches an early post-implantation egg-cylinder or bilaminar disc stage and at least 30% serum or serum replacement thereafter.

The serum may be obtained from a rodent (e.g. rat, mouse) or a mammal (e.g. bovine, human).

According to specific embodiments, care should be taken that the serum (e.g. human serum) is devoid of any traces of hemolysis.

According to specific embodiments, the serum is obtained from an adult animal.

According to other specific embodiments, the serum is obtained from a fetal animal.

According to specific embodiments, the serum comprises a cord blood serum. Methods of obtaining cord blood serum (e.g. human cord blood serum) are well known in the art and are further described in the Examples section which follows.

According to specific embodiments, the serum comprises bovine serum (e.g. FCS).

According to specific embodiments, the serum comprises rat serum.

According to specific embodiments, the serum comprises human serum.

According to specific embodiments, the serum comprises human serum for at least part of the culturing.

According to specific embodiments, the human serum comprises umbilical cord serum (HCS).

According to other specific embodiments, the human serum comprises adult blood serum (HBS).

According to specific embodiments, the serum comprises rat serum and human serum.

According to specific embodiments, the ratio between the rat serum and the human serum in the medium is between 1:1-5:1 (v/v).

According to specific embodiments, the ratio between the rat serum and the human serum in the medium is between 1:1-3:1 (v/v).

According to specific embodiments, the ratio between the rat serum and the human serum in the medium is about 2:1 (v/v).

According to specific embodiments, the ratio between the rat serum and the human serum in the medium is 2:1 (v/v).

In some embodiments, optionally, the medium comprises knockout serum replacement (KSR) instead of an animal serum.

In some embodiments, optionally, the medium comprises knockout serum replacement (KSR) in addition to the animal serum e.g. the rat serum and the human serum.

In some embodiments, optionally, the KSR partially replaces one of either the human serum, the rat serum or partially replaces a quantity of both.

According to specific embodiments, the ratio between the serum and the base medium in the culture medium is between 1:0.5-10:1, 1:1-10:1 or 1:1-8:1 (v/v).

According to specific embodiments, the ratio between the serum and the base medium in the culture medium is between 1:1-5:1 (v/v).

According to specific embodiments, the ratio between the serum and the base medium in the culture medium is about 3:1 (v/v).

According to specific embodiments, the ratio between the serum and the base medium in the culture medium is 3:1 (v/v).

According to specific embodiments, the culture medium comprises 20-30% base medium, 40-60% rat serum and 20-30% human serum (v/v).

According to a specific embodiment, the culture medium comprises 25% base medium, % rat serum and 25% human serum (v/v).

According to specific embodiments, the serum is heat inactivated (e.g. in 55° C. 30-45 minutes).

According to specific embodiments, the serum is added to the medium just prior to use.

According to some embodiments of the invention, the medium can further include additional supplements including, but not limited to antibiotics (e.g., PEN-STREP), L-glutamine (e.g., GlutaMAX™), sodium pyruvate, non-essential amino acids (NEAA), Insulin-Transferrin-Selenium-Ethanolamine (ITS-X), β-Estradiol, progesterone, N-acetyl L-Cysteine, 3,3',5-Triiodo-L-thyronine sodium salt (T3), sodium lactate, glucose, serum replacement and/or HEPES.

According to some embodiments of the invention, the medium comprises $N_2$ and B27.

According to specific embodiments, the medium comprises glucose.

According to specific embodiments, the medium comprises at least 1 mg/ml, at least 2 mg/ml, at least 3 mg/ml or at least 4 mg/ml glucose.

According to specific embodiments, the medium comprises at least 4 mg/ml, at least 5 mg/ml, at least 6 mg/ml, at least 7 mg/ml or at least 8 mg/ml glucose.

According to specific embodiments, the medium comprises 2-12 mg/ml glucose, 3-12 mg/ml glucose, 4-12 mg/ml glucose or 4-8 mg/ml glucose.

According to specific embodiments, the glucose is provided in the medium in a constant or increasing concentrations throughout the culturing.

Thus, according to specific embodiments, throughout the culturing there is no decrease in the glucose concentration provided in the medium throughout the culturing (e.g. while passing from one set of conditions to a following set of conditions).

According to specific embodiments, the culture medium is devoid of MATRIGEL®.

According to specific embodiments, the conditions comprise replacement of at least half of the medium every 1-2 days of the culturing (e.g. in the static culture).

According to specific embodiments, the conditions comprise replacement of all the medium every 1-2 days of the culturing (e.g. in the dynamic culture).

According to specific embodiments, the culture is maintained under a hyperbaric pressure.

According to specific embodiments, the dynamic culture is maintained under a hyperbaric pressure.

According to specific embodiments, the roller culture is maintained under a hyperbaric pressure.

As used herein, the term "hyperbaric pressure" refers to a pressure greater than atmospheric pressure, wherein atmospheric pressure is generally regarded as 14.7 pounds per square inch (psi). Hence, wherein a specific hyperbaric pressure is indicated herein, it refers to the indicated pressure above the atmospheric pressure and not the value indicated per-se. For example, a hyperbaric pressure of 5 psi refers to a pressure of 19.7 psi, a hyperbaric pressure of 6.5 psi refers to a pressure of 21.2 psi and a hyperbaric pressure of 10.2 refers to a pressure of 24.7 psi.

According to specific embodiments, the hyperbaric pressure is more than 2.5 psi, more than 4 psi, more than 5 psi, more than 6 psi.

According to specific embodiments, the hyperbaric pressure is more than 5 psi.

According to specific embodiments, the hyperbaric pressure is less than 10.2 psi, less than 9 psi, less than 8 psi, less than 7 psi.

According to specific embodiments, the hyperbaric pressure is less than 10.2 psi.

According to specific embodiments, the hyperbaric pressure is more than 5 psi and less than 10.2 psi.

According to specific embodiments, the hyperbaric pressure is 6-7 psi.

According to specific embodiments, the hyperbaric pressure is 6.5 psi.

According to specific embodiments, the hyperbaric pressure is 0.1-0.5 psi.

According to other specific embodiments, the culture is maintained under atmospheric pressure.

According to specific embodiments, the static culture is maintained under atmospheric pressure.

According to specific embodiments, the culture is maintained in an atmosphere comprising a controlled level of $O_2$, $N_2$ and/or $CO_2$.

According to specific embodiments, the culturing is effected in an atmosphere comprising 5% $CO_2$.

According to specific embodiments, the culturing is effected in an atmosphere comprising 5-40% oxygen.

According to specific embodiments, the culturing is effected in an atmosphere comprising 5-30%, 5-25% or 5-21% oxygen.

According to specific embodiments, the culturing is effected in an atmosphere comprising 10-40%, 10-30% or 15-30% oxygen.

According to specific embodiments, the culturing is effected in an atmosphere comprising 15-30% oxygen.

According to specific embodiments, the culturing is effected in an atmosphere comprising 18-23% oxygen.

According to specific embodiments, the culturing is effected in an atmosphere comprising constant or increasing oxygen concentrations throughout the culturing.

Thus, according to specific embodiments, throughout the culturing there is no decrease in the oxygen concentration throughout the culturing (e.g. while passing from one set of conditions to a following set of conditions).

According to specific embodiments, in order to control the pressure and oxygen level in the culture the following fetal incubation system comprising a gas and pressure controller and a static and/or rotating incubator is used.

Exemplary Fetal Incubation System

Referring now to FIG. 44A, showing a schematic representation of a fetal incubation system, according to some embodiments of the invention. In some embodiments, the system comprises a gas and pressure controller 502, one or more sources of gas 504, 505 and 506 (in FIG. 44A—Carbon dioxide ($CO_2$) 506, Oxygen ($O_2$) 505 and Nitrogen ($N_2$) 504 tanks are shown), a gas mixing box 508 and an incubator 510. In some embodiments, gases from the gas sources 504, 505, 506 are delivered into the gas and pressure controller 502, which delivers the gases into the gas mixing box 508. In some embodiments, once the mix of gases have reached the required concentrations, the gas is returned into the gas and pressure controller 502, which is then controlled-delivered into the incubator 510. In some embodiments, the incubator 510 optionally comprises an internal rotating incubator module configured to hold one or more vials in which the embryos are kept. In some embodiments, the mixed gases are delivered into the internal rotating incubator module, where the gases are equally delivered into each of the vials (see below for more information).

FIG. 44B shows an image of an exemplary fetal incubation system comprising the gas and pressure controller 502, the gas mixing box 508 and the incubator 510, according to some embodiments of the invention.

FIG. 44C shows a schematic general representation of an exemplary configuration of a principle of the electronic module for gas (gas and pressure controller 502 together with the gas mixing box 508) and pressure regulation. In some embodiments, $N_2$, $O_2$ and/or $CO_2$ enter into the system at a pressure of 0.5 psi and are mixed by a mixing centrifugal blower (see below). In some embodiments, gases are then optionally injected into a water bottle inside the incubator by a pump that allows control of the gas pressure, therefore allowing for hyperbaric conditions. In some embodiments, the system comprises one or more sampling ports (for example for $O_2$ and/or $CO_2$), which allow additional monitoring of the levels of the gases in the system.

Exemplary Gas and Pressure Controller

Referring now to FIGS. 44D, showing a schematic representation of an exemplary gas and pressure controller 502, according to some embodiments of the invention. In some embodiments, as mentioned before one or more sources of gas 504, 505, 506 are connected to the gas and pressure controller 502. In some embodiments, each source of gas is connected to a dedicated electric valve 512, 513 and 514 in the gas and pressure controller 502. For example, gas from a source (for example a tank) of $CO_2$ 506 is connected to a dedicated $CO_2$ electric valve 514, and gas from a source (for example a tank) of $N_2$ 504 is connected to a dedicated $N_2$ electric valve 512, and gas from a source (for example a tank) of $O_2$ 505 is connected to a dedicated $O_2$ electric valve 513. In some embodiments, the gas and pressure controller 502 comprises dedicated 'individual gas controllers 516/518' for the manipulation and monitoring of the gases in the system (referred hereinafter as $CO_2$ controller 518 or $O_2$ controller 516—which are different from the main gas and pressure controller 502 of the fetal incubation system). For example, when the levels of $CO_2$ in the fetal incubation system are needed to be manipulated, a user accesses the $CO_2$ controller 518 to set up the required levels of $CO_2$ in the system, and for example when the levels of $O_2$ in the fetal incubation system are needed to be manipulated, a user accesses the $O_2$ controller 516 to set up the required levels of $O_2$ in the system by the addition or non-addition of $N_2$ gas into the system and/or by the addition or non-addition of $O_2$ gas into the system. It should be noted that in regular air there is about 21% oxygen, and when lower levels of oxygen are required inside the fetal incubation system, for example 5% or 10%, then nitrogen gas is inserted in order to reduce the levels of oxygen in the system. In some embodiments, when higher concentrations of oxygen are required, $N_2$ gases are stopped, and pure $O_2$ is provided, for example, to provide a 95%/5% $O_2/CO_2$ level inside the vials. In some embodiments, the system is configured to provide any combination of mixture of gases, for example from a mixture of gases that comprises 0% of $O_2$ to providing 100% of $O_2$; or for example any combination of $O_2/CO_2$ ratios, for example from about 1%/99% ratio to a 99%/1% ratio. In some embodiments, the gas and pressure controller 502, provides and ensures gases with a margin of error of about 0.2% for any of the gases provided to the fetal incubation system. In some embodiments, the margin of error is from about 0.1% to about 1% for $CO_2$ gases, from about 0.1% to about 2% for $O_2$ gases and from about 0.1% to about 2% for $N_2$ gases. In some embodiments, margins of error are not above 2% for $CO_2$. In some embodiments, margins of error are not above 5% for $N_2$. In some embodiments, margins of error are not above 5% for $O_2$. In some embodiments, each specific gas controller 516/518 controls the opening and closing of the specific electric valves 512, 513 and 514, according to the needs. In some embodiments, the needs, which are set by the user using the individual gas controllers 516/518, are monitored by dedicated sensors in the gas mixing box 508 (see below information about gas mixing box 508). Therefore, in some embodiments, information from the gas sensors in the gas mixing box 508 are delivered to the dedicated gas controllers 516/518. In some embodiments, the dedicated gas controllers 516/518 utilize the information from the gas sensors in the gas mixing box 508 to either open or close the specific electric valves 512, 513, 514, again according to the predetermined needs set by the user. In some embodiments, the gas and pressure controller 502 comprises a vacuum pump 520 and a pressure pump 522. In some embodiments, after the gases have been mixed in the gas mixing box 508 (see below information about gas mixing box 508), a vacuum pump 520 is activated to force out the mixed gases from the gas mixing box 508. In some embodiments, the gases are then accumulated in a pressure pump 522 until a predetermined level of pressure is reached before it is delivered into the incubator 510. In some embodiments, the pressure pump is configured to provide the mixed gases at a pressure of from about 1 psi to about 6 psi, optionally of from about 0.5 psi to about 8 psi, optionally from about to about 12 psi. Preferably at 6.5 psi, when needed. In some embodiments, the user manually sets the pressure levels on which the pressure pump 522 will delivered the mixed gases. In some embodiments, the gas and pressure controller 502 comprises a power supply unit 524 configured to provide the dedicated power to the different parts of the gas and pressure controller 502. In some embodiments, the gas and pressure controller 502 optionally comprises a pressure transmitter 526 configured to monitor the pressure in the system/gas and pressure controller 502. In some embodiments, the gas and pressure controller 502 optionally comprises a check valve 528 configured to ensure that mixed gases exiting the gas and pressure controller 502 do not return (flow back) into the gas and pressure controller 502. In some embodiments, the gas and pressure controller 502 optionally comprises an adapter control for gases 530 configured to control the flow rate in the system. In some embodiments, the gas and pressure controller 502 comprises one or more filters— shown in FIG. 44E (531)—(for example 1μ filters) mounted on the tubes flowing gases for ensuring purity of the gases and potentially avoid contaminations.

FIGS. 44E, 44F and 44G show different images of an exemplary gas and pressure controller 502, according to some embodiments of the invention. Specifically, FIG. 44E shows a perspective view of the gas and pressure controller 502, showing the gas lines that go into the gas and pressure controller 502, and the gas lines that go out from the gas and pressure controller 502. Additionally, gas controllers 516/518 and optional filters 531 are shown. FIG. 44F shows the internal arrangement of the gas and pressure controller 502, showing exemplary electric valves 512, 513, 514, according to some embodiments of the invention. FIG. 44G shows an exemplary gas and pressure controller 502 that is configured to monitor and deliver only $CO_2$ and/or $N_2$, according to some embodiments of the invention.

Exemplary Gas Mixing Box

Referring now to FIG. 44H, showing a schematic representation of an exemplary gas mixing box 508, according to some embodiments of the invention. In some embodiments, the gas mixing box 508 is used to ensure complete and uniform mixing of the different gases that are required to provide the necessary environment in the vials in the incubator. In some embodiments, the gas mixing box 508 comprises an internal volume of from about 250,000 $cm^3$ to about 260,000 $cm^3$. In some embodiments, different sizes may be used to provide different quantities of mixed gases as necessary. In some embodiments, the gas mixing box 508 is made of plastic, for example Perspex. In some embodiments, the gas mixing box 508 is made of a material other than plastic. In some embodiments, the gas mixing box 508 comprises dedicated gas sensors 532/534 configured to monitor the content percentage of those gases inside the gas mixing box 508. Following the previous description, in FIG. 44H two sensors are shown, an $O_2$ sensor 532 and a CO2 sensor 534. In some embodiments, the sensors comprise a sensitivity for accuracy of from about 95% accuracy to about a 100% accuracy. In some embodiments, the gas mixing box 508 comprises a mixer blower 536 configured to thoroughly mix the gases coming from the gas and pressure controller 502. In some embodiments, once the levels of the gases detected inside the gas mixing box 508 by the sensors 532/534 arrive at the desired level, the mixed gases are sucked away by the vacuum pump 520 in the gas and pressure controller 502. In some embodiments, the gas and pressure controller 502 optionally comprises a limit flow 538 configured to maintain a uniform flow rate in the system, therefore potentially avoiding the possibility of changes in the flow rate. In some embodiments, the gas mixing box 508 comprises one or more filters—not shown— (for example 1μ filters) mounted on the tubes flowing gases for ensuring purity of the gases and potentially avoid contaminations.

FIG. 44I shows an image of an exemplary gas mixing box 508, according to some embodiments of the invention.

Exemplary Incubator

In some embodiments, the incubator is a static incubator. In some embodiments, the incubator is a rotating incubator. In some embodiments, the incubator is a static incubator comprising a rotating module inside of it. In some embodiments, the static incubator comprises one or more temperature modulators configured to preserve the temperature inside the static incubator, including the rotating module allocated inside of it. In some embodiments, the temperatures inside the incubator are modulated to be from 4° C. to about 60° C. In some embodiments, the incubator is, for example, a "precision" incubator system (BTC01 model with gas bubbler kit—by B.T.C. Engineering,—Cullum Stan Precision Engineering Ltd—UK).

Referring now to FIG. 44J, showing a schematic representation of an exemplary incubator 510, according to some embodiments of the invention. In some embodiments, mixed gases are delivered from the gas and pressure controller 502 into the incubator 510. In some embodiments, the incubator comprises a unidirectional valve 540 connected to a tube, from which the mixed gases are delivered from the gas and pressure controller 502. In some embodiments, the unidirectional valve 540 is a manual unidirectional valve, which is opened and closed manually by a user. In some embodiments, the unidirectional valve 540 is an automatic unidirectional valve controlled by a master controller (see below). In some embodiments, the mixed gases are optionally delivered into a bubbler bottle 542. In some embodiments, the bubbler bottle 542 is partially filled with a liquid. In some embodiments, the liquid is water. In some embodiments, the gases are delivered into the liquid in the bubbler bottle 542, thereby creating bubbles in the liquid. In some embodiments, the bubbler bottle 542 allows a user to see that the system is delivering mixed gases by visually assessing: 1. If there are bubbles; and 2. The rate of creation of bubbles. In some embodiments, additionally, bubbler bottle 542 works as a humidifier for the gases (see below). In some embodiments, the bubbler bottle 542 provides a safeguard from pressure coming from the delivered mixed gases into the incubator 510, for example, in case of a malfunction if mixed gases are delivered at higher pressure than the desired one, the extra pressure will be contained and dissipated in the bubbler bottle 542. In some embodiments, the mixed gases are optionally then delivered into an additional humidifier 544. In some embodiments, the inventors have discovered that in certain cases dry mixed gases could be harmful to the samples in the incubator, therefore, the addition of the humidifier 544 overcomes this issue. In some embodiments, the additional humidifier reduces excess humidity from the gases coming from bubbler bottle 542. In some embodiments, from the humidifier 544, the mixed gases are delivered into the rotating drum 546 of the rotation module, which comprises all containers (vials) comprising the samples located in the incubator. In some embodiments, the rotating drum 546 is configured to deliver mixed gases equally between the containers, optionally while rotating the samples. In some embodiments, the containers (vials) in the rotating drum 546 comprise the medium necessary for the growth and/or maintenance of the embryos. In some embodiments, the delivery of the gases is provided into the containers (vials) and absorbed/used via the medium. It should be noted that, in some embodiments, since the embryos are left in suspension in the medium, continuous delivery of new medium with already mixed gases is problematic, because these types of mechanisms require old/used medium to be extracted from the vial while inserting new medium with new mixed gases in it, which can increase the chance of losing the embryos during the exchange. Therefore, the provision of new gases is performed by delivery mixed gases into the vials without the need to change the medium for it. In some embodiments, independently of the need of providing continuous replacement of gases, medium can be changed by taking out each vial and carefully changing the medium according to known techniques. In some embodiments, the rotating drum 546 is configured to be positioned in an angle, which allows the vials to have an angle with respect to the base on which the whole rotating module is standing. In some embodiments, the angle of from about 0 degrees (no angle—vials are kept on their side as shown for example in FIG. 44K) to about 45 degrees. In some embodiments, the angle is provided so a top of a vial is always in an upper position in relation to a bottom part of the vial. In some embodiments, the rotation of the rotating drum 546 is independent from the action of delivering mixed gases into the vials. In some embodiments, the rotating drum is configured to rotate at velocities of from about 1 rpm to about 100 rpm. In some embodiments, exiting gases from the rotating drum 546 are delivered to an outlet bottle 548 for gases. In some embodiments, the outlet bottle 548 acts as a pressure buffer for the system, which helps keeping a constant pressure throughout the system. In some embodiments, the incubator 510 comprises darkened walls, which allow keeping the samples in the dark. In some embodiments, the incubator 510 optionally comprises one or more cameras for monitoring the samples, for examples regular video cameras, IR cameras, night vision cameras, etc. In some embodiments, the incubator 510 comprises one or more heaters configured to keep the samples at a certain temperature. In some embodiments, the incubator 510 comprises one or more light sources, for example, white light, IR light, UV light and/or black light.

FIG. 44K shows an image of an exemplary rotating incubator module 510, according to some embodiments of the invention. FIG. 44L shows an image of exemplary containers (vials or bottles) having samples, according to some embodiments of the invention.

Exemplary Automated Fetal Incubation System

In some embodiments, the fetal incubation system as disclosed above, is connected to a master controller configured to perform automated actions according to predetermined protocols provided by a user. For example, a user programs the master controller to perform changes in the incubation chambers over a certain period of time. In some embodiments, the system will comprise electric valves overall the system, which will be activated/deactivated according to the programed protocols. In some embodiments, a potential advantage of utilizing automated systems is that it reduces the chances of human errors during the developments of the embryos. In some embodiments, optionally, the master controller provides periodic updates to a user to a PC or a mobile electronic device.

Exemplary General Information Related to the System

In general, a number of culture techniques have been proposed over the years since the 1930s by culturing the embryos in conventional static conditions, in rotating bottles on a drum (referred to as "roller culture systems") or on circulator platforms. These platforms remain highly inefficient for embryos survival and are limited to short periods of time, as the embryos begin to display developmental anomalies as early as 24 hours after culture initiation. Thus, stable and efficient protocols for extended culturing of pre-gastrulating mouse embryos all the way until advanced organogenesis stages were developed and are disclosed herein. In some embodiments, some of cell culture supplements or biomechanical principles newly established in stem cell research, were tested to assess if they could be helpful for keeping embryos alive (e.g. hyperbaric chambers, synthetic sera). In some embodiments, the "roller culture system" on a drum is used and it is integrated with a customized and in house developed electronic gas regulation module 502 that allowed precise control not only of $N_2$, $O_2$ and CO2 levels with high sensitivity, but also allowed controlling the atmospheric pressure. In some embodiments, sequential increases in the oxygen levels every 24 hours, starting from 5% $O_2$ at E7.5, 13% at E8.5, 18% at E9.5, and ending with 21% $O_2$ at E10.5 were applied and were found to be most optimal for the robust outcome reported herein. Additionally, when necessary, an increase in oxygen levels reached 95%. In addition, in some embodiments, maintaining a hyperbaric pressure of about 6.5 psi was found also critical for normal and efficient development of the embryos.

In some embodiments, the samples are kept in a static incubator. In some embodiments, the samples are kept in a dynamic incubator, for example a rotating incubator. In some embodiments, the samples are kept first in a static incubator and then moved to a dynamic incubator, or vice versa. In some embodiments, the samples are kept in a static incubator comprising, for example a rotating incubator inside of it. In some embodiments, when kept in a dynamic incubator the samples are kept in rotating bottles on a drum (referred to as "roller culture systems") or on circulator platforms.

In some embodiments, the embryos are kept on the rotating bottles culture unit inside a "precision" incubator system (For example the BTC01 model with gas bubbler kit—by B.T.C. Engineering,—Cullum Stan Precision Engineering Ltd—UK) during all the time of culture. In some embodiments, a 'rotator' culture method which provides continuous flow of oxygenating gas to cultures in rotating bottles was used and disclosed herein elsewhere (for example BTC Rotating Bottle Culture Unit BTCO2 model by B.T.C. Engineering,—Cullum Stan Precision Engineering Ltd—UK). In some embodiments, the culture bottles (Glass Bottles (Small) BTC 03 and Glass Bottles (Large) BTC 04) are plugged into the hollow rotating drum. In some embodiments, gas flows along the axis and is distributed to the culture bottles by a baffle plate within the drum. In some embodiments, the system maintains a stable pH, when compared to other systems with sealed culture bottles. In some embodiments, the rotator is supplied complete with gas filter, bubbler and leads by the manufacturer. In some embodiments, the BTC Precision Incubator uses a thyristor-controlled heater and high flow-rate fan to give a highly stable and uniform temperature throughout the easily accessible working volume. In some embodiments, the incubator has a working volume 370×350×200 mm high which is accessed through a hinged top. In some embodiments, the heater element is rated at 750 Watts. In some embodiments, Bung (Hole) BTC 06 is used to seal the bottles and Bung (Solid) BTC 07 is used to seal the drum (B.T.C. Engineering,—Cullum Starr Precision Engineering Ltd—UK).

In some embodiments, in order to achieve constant $O_2$ and $CO_2$ levels in the culture medium throughout the incubation period, the incubator module is linked to the gas and pressure control unit 502 (model #-HannaLab1; assembled and sold by Arad Technologies LTD, Ashdod, Israel). In some embodiments, carbon dioxide and oxygen concentration are regulated by specific controllers located on the gas and pressure control unit 502. In some embodiments, a pressure controller allows control of the gas pressure between 5 to 10 psi (positive pressure over ambient external atmospheric pressure). In some embodiments, nitrogen, $O_2$ and/or $CO_2$ are then injected into the gas mixer box at pressure of 6.5 psi which was found as the optimal level. In some embodiments, the mixing of the gases in the gas box is homogeneous and mixed by a centrifugal mixer blower. In some embodiments, the gases are injected into the incubator by a pump that builds pressure and sufficiency according to the count of air bubbles created in a water bottle, which is under the control of a one-way flow meter. In some embodiments, the bubble rate (which indicates the speed of gas flowing into the bottles) is be adjusted as needed by the user. In some embodiments, gas flows through the inlet into the water bottle, and the speed of gas flowing into the bottle is controlled with a valve. In some embodiments, humidified gas circulates to a glass test tube and then to the inside of the bottles in the rotating drum. In some embodiments, gas flow speed is monitored by the rate of bubbles created inside an outlet water-filled test tube. In some embodiments, the bottles with the samples are placed on the rotating bottle culture system, rotating at 30 revolutions per minute at 37° C., and continuously gassed with an atmosphere of, for example 5% $O_2$, 5% $CO_2$ at 6.5 pounds per square inch (psi), or for example 5% $O_2$, 5% $CO_2$ at 0.1 pounds per square inch (psi), or for example with a gas mixture of 13% $O_2$, 5% $CO_2$, or for example in a gas atmosphere of 18% $O_2$ and 5% $CO_2$, or for example with a gas supply of 21% $O_2$ and 5% $CO_2$. In some embodiments, for media exchange, culture media is pre-heated for at least an hour by placing it inside a glass bottle on the rotating culture with an adequate gas atmosphere depending on the stage of the cultured embryos. Exemplary methods related to the Fetal Incubation System Referring now to FIG. 44M, showing a flowchart of exemplary methods related to the fetal incubation system, according to some embodiments of the invention. In some embodiments, the user sets the desired levels of gas and pressure inside the incubator 550. For example 5% $CO_2$ and 10% $O_2$ at a pressure of 6.1 psi. In some embodiments, the gas and pressure controller activates the sensors in the gas mixing box to receive information about the actual levels of the gases in the gas mixing box 552. In some embodiments, the electric valves are opened to allow flow of gases from the gas sources, through the gas and pressure controller into the gas mixing box 554. In some embodiments, the gases are mixed inside the gas mixing box by activating a mixer blower 556. In some embodiments, the sensors in the gas mixing box are activated to monitor the levels of the gases inside until they reach the desired levels 558. In some embodiments, the mixed gases are extracted from the gas mixing box by activating a vacuum pump 560. In some embodiments, pressure of the extracted mixed gases are increased to a desired level by activating a pressure pump 562. In some embodiments, a unidirectional valve inside the incubator is opened to allow the pressurized mixed gases to flow into the incubator 564. In some embodiments, the pressurized mixed gases are passed through a humidifier 566. In some embodiments, the humidified pressurized mixed gases are delivered to the individual tubes containing the samples 568. In some embodiments, exiting gases are passed through an outlet tube before exiting the incubator 570.

According to specific embodiments, the methods further comprise isolating a cell, tissue or organ from the embryo following the culturing.

Non-limiting examples of such cells include stem cells [for example, but not limited to, embryonic stem cells, mesenchymal stem cells, neural stem cells, hematopoietic stem cells], blood cells, liver cells, insulin secreting pancreatic beta cells, muscle cells, lung epithelial cells, endothelial cells, glial cells.

These cells, tissue or organs may be used for example as a cell-based therapy, tissue replacement, organ or tissue implantation or for research purposes.

According to other specific embodiments, the methods further comprise transferring the synthetic embryo in-utero.

The established methods of generating synthetic embryos and methods and systems for culturing them ex utero as described herein may be further combined with e.g. genetic modification, chemical screens, tissue manipulation and microscopy methods and may constitute a powerful tool in basic research e.g. as a framework to investigate the emergence of cellular diversity, cell fate decisions and how tissues and organs emerge from a single totipotent cell; as well as a source of cells, tissue and organs for transplantation, generation of chimeric embryos, testing the effect of drugs on embryonic development (e.g. teratogenic effect) etc. Such methods are known in the art.

Thus, according to specific embodiments, the method comprises manipulating the synthetic embryo or the subpopulations of cells described herein.

According to specific embodiments, manipulating comprises introducing into the cells or the embryo a gene of interest.

According to specific embodiments, manipulating comprises introducing into the cells or embryo a polynucleotide of interest.

According to specific embodiments, manipulating comprises introducing into the cells or embryo a genome editing or RNA silencing agent.

According to specific embodiments, the manipulating comprises producing an embryo incompatible with life. Thus, for example, the manipulation may comprise knocking a selected gene to selectively perturb a certain organ, thus making the embryo with limited developmental potential and not being able to sustain viability, e.g. headless (e.g. deletion of Mesp 1 or NKX2-5) or heartless (e.g. deletion of Lim1), as further described in the Examples section which follows.

Thus, according to specific embodiments, the manipulating comprises introducing into the embryo a polynucleotide rendering an embryo incompatible with life.

Methods of designing, expressing and introducing a polynucleotide of interest such that it will be expressed in a cell of interest are well known in the art and further described herein above and below.

According to specific embodiments manipulating comprises microinjecting cells into the embryo to thereby obtain a chimeric embryo.

As used herein, the phrase "chimeric embryo" refers to an animal comprising cells of at least two genetically distinct individuals.

It is noted that the chimeric embryo can be composed of cells of two different individuals belonging to two different species, or to the same species.

According to some embodiments of the invention, the cells are allogeneic to the embryo.

According to some embodiments of the invention, the cells are xenogeneic to the embryo.

As used herein, the term "xenogeneic" refers to at least two individuals of different species.

According to specific embodiments, the cells are stem cells [for example, but not limited to, embryonic stem cells, mesenchymal stem cells, neural stem cells, hematopoietic stem cells, induced pluripotent stem cells (iPS)].

According to some embodiments of the invention, introducing the cells is performed ex vivo via direct injection or aggregation with the developing embryo.

According to specific embodiments, the manipulating comprises introducing into the cells or the embryo a drug of interest.

According to specific embodiments, the methods further comprise determining an effect of the manipulating on development of the embryo.

According to specific embodiments, any of the genes, polynucleotides, proteins, polypeptides and/or proteinaceous moieties described herein may have a sequence of a human gene, polynucleotide, protein, polypeptide and/or proteinaceous moiety or a functional fragment or homolog thereof which exhibit the desired activity as described herein.

According to specific embodiments, the gene, polynucleotide, protein, polypeptide and/or proteinaceous moiety is of a human origin.

According to other specific embodiments, the gene, polynucleotide, protein, polypeptide and/or proteinaceous moiety is a homolog of a human gene, polynucleotide, protein, polypeptide and/or proteinaceous moiety. Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the human sequence.

As used herein the term "about" refers to ±10% The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques.

Example 1

Figure 1:
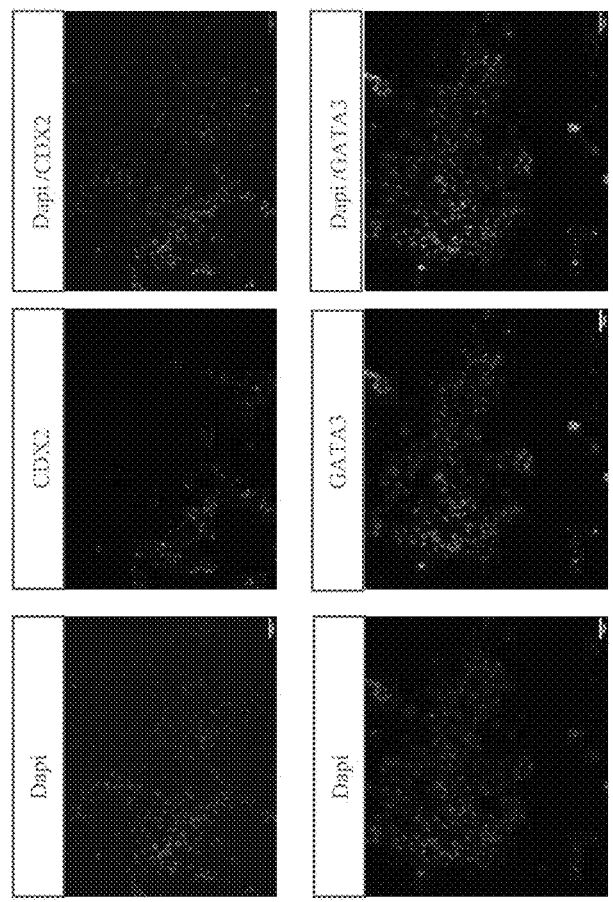

Aggregation of Mouse Naïve PSCs, TSCs and XENs does not Generate an Organized Embryo Materials and Methods Embryo derived Mouse TSC line #1 (mTSC #1)—was established according to previously described classical protocols (doi: 10.1126/science.282.5396.2072.). Briefly, TSCs were derived from E3.5 blastocysts flushed from the uterus of 5-weeks-old female CD1 mouse. The blastocysts were cultured on mitotically inactivated mouse MEF cells (feeder cells) with TSC culture medium: advanced RPMI 1640 (11875-093 Thermo Fisher Scientific or RPMI (Invitrogen) supplemented with 15-20 (v/v) FBS (Gibco, ES cell qualified; or Biological Industries), 1× GlutaMAX (35050061, Thermo Fisher Scientific; or Invitrogen), 0.1 mM β-mercaptoethanol (21985-023, Thermo Fisher Scientific; or Sigma), 1 mM sodium pyruvate (11360070, Thermo Fisher Scientific), 1% (v/v) penicillin—streptomycin (15140122, Thermo Fisher Scientific; or Biological Industries), 25 ng/ml recombinant human FGF4 (235-F4-125, R&D; or Peprotech), 1 µg/ml heparin (07980, Stem Cell; or Sigma) and 1× nonessential amino acids (Biological Industries). 25 ng/ml of FGF2 (Peprotech) was optionally added. DMEM can also be used instead of RPMI as typically practiced before in the field for making stable TSC lines. Until the outgrowth formed on day 4, the cells were subsequently disaggregated by incubated in 0.1% trypsin-EDTA for 5 minutes in the incubator. Mouse 70% embryonic fibroblast-conditioned medium containing FGF4 and heparin was added to stop the reaction and cells were returned to the incubator. Medium was replaced every other day until TS cell colonies were be observed (not before day 14—passage 3), and following the medium was changed to a TSC culture medium to maintain the cells. Immunostaining for TSC markers Cdx2, Gata3, TBR2, and TFAP2C and lack of Oct4 and Nanog pluripotency markers, confirmed TSC identity of this representative TSC line (FIGS. 1-2). The cells could be passaged for over 50 times while maintaining their morphology and markers.

Mouse ES derived Mouse TSC line #2 (mTSC #2)—was derived as previously established (PMID: 10742100) by inhibition of Oct4 together with transferring the cells in TSC media detailed above in mTSC #1. Briefly, the ZHBTC4 mouse ES line was used in which DOX induces inhibition of Oct4 shut down (Tet-off), and was passaged in TSC media together with DOX (PMID: 10742100). Immunostaining showed that while the parental ESC line is positive for the Oct4 pluripotency marker and negative for Cdx2 and Gata3 TSC markers (FIG. 3A); the established mTSC #2 line lacks Oct4 and Nanog pluripotency markers and stably expresses the TSC markers Cdx2, TBR2, Gata3 and TFAP2C (FIGS. 3B and 4), confirming the TSC identity of this representative TSC line. Further, the mTSC #2 line was maintained on MEFs and had a classical TSC colony morphology (doi: 10.1126/science.282.5396.2072.).

Mouse ES derived Mouse TSC line #3 (mTSC #3)—was derived as previously established (www(dot)doi(dot)org/10 (dot)1016/j(dot)cell(dot)2005(dot)08(dot)040) by transient overexpression of Cdx2 in mouse ESCs expanded in semi-primed FBS/LIF conditions with transferring the cells in TSC media detailed above in mTSC #1. Specifically, a previously described ICR mouse ES line (PMID: 19427283) was used in which Cdx2 was transiently transfected, and was passaged in TSC media. Following, TSC colonies were picked, passaged and validated. Immunostaining for TSC markers Cdx2 and Gata3 confirmed TSC identity of this representative TSC line (FIG. 5). Further, the mTSC #3 line was maintained on MEFs and had a classical TSC colony morphology.

Mouse XEN line #7 (XEN-ICR clone #7)—was established according to previously described classical protocols (doi: 10.1071/rd06125). Briefly, XEN cells were derived from E3.5 blastocysts flushed from the uterus of 5-weeks-old female ICR mouse using modified XEN conditions. Mouse blastocysts were cultured on feeder cells until they formed an outgrowth on day 4 that was subsequently disaggregated by incubation in 0.1% trypsin-EDTA for 5 minutes in the incubator. Fresh mouse ES (FBS-LIF based) was added to stop the trypsin reaction, and was replaced the medium every other day until XEN cell colonies could be observed. Following, XEN cell colonies were picked and maintained as lines with a standard XEN medium: advanced RPMI 1640 (11875-093, Thermo Fisher Scientific) or RPMI1640 (Gibco 11875085) supplemented with 15% (v/v) FBS (Gibco or Biological Industries) and 0.1 mM β-mercaptoethanol (21985-023, Thermo Fisher Scientific or Sigma), 1× Glutamax (Invitrogen), 1% penicillin—streptomycin (15140122, Thermo Fisher Scientific; or Biological Industries), 1× nonessential amino acids (Biological Industries) and 1 mM Sodium-pyruvate (BI 03-042-1B). It required at least 15 days and 3 passages to be able to establish individual early passage mouse XEN lines, as previously described (doi: 10.1071/rd06125). Immunostaining of early passage mouse XEN line clone 7 at passage 5, validated loss of the pluripotency markers Oct4 and Nanog as expected, and expression of the XEN markers Foxa2 and Gata4 (FIG. 6A). In addition, real-time PCR analysis demonstrated upregulation of expression of the XEN markers Gata6, PDGFRA, Sox17 and Gata4 (FIG. 6B), further confirming their identity (10.1371/journal.pone.0009794). Mouse naïve V6.5 naïve ESCs expanded in 2i-LIF condition were used as a reference control (value set as 1).

Mouse XEN line XEN-Prep1—was established as described for XEN line #7 (side by side). Real-time PCR analysis demonstrated upregulation of expression of the XEN markers Gata6, PDGFRA, Sox17 and Gata4 (FIG. 6B), confirming their identity (10.1371/journal-.pone.0009794). Mouse naïve V6.5 naïve ESCs expanded in 2i-LIF condition were used as a reference control (value set as 1).

Mouse naïve pluripotent stem cells (naïve PSCs) line—Pluripotent V6.5 GFP labeled mouse ES line (PMID: 19427283) was maintained and expanded in serum-free chemically defined N2B27-based media: 240 ml Neurobasal (ThermoFisher 21103049) and 240 ml of DMEM-F12 with HEPES (SIGMA D6421), 5 ml N2 supplement (Invitrogen; 17502048), 5-10 ml B27 supplement (Invitrogen; 17504044), 2 mM glutamine or 1 mM GLutamax (Invitrogen), 1% nonessential amino acids (Invitrogen), 0.1 mM β-mercaptoethanol (Sigma), 1% penicillin-streptomycin (Invitrogen). Optionally, the medium also included 5 mg/ml BSA (Sigma). Naïve 2i/LIF conditions for murine PSCs included 20 ng/ml recombinant human LIF (in-house made). Where indicated 2i was added: small-molecule inhibitors CHIR99021 (CH, 3 µM-Axon Medchem) and PD0325901 (PD, 1 µM—Axon Medchem 1408).

KH2-Gata4 Dox inducible cells (KH2-GATA4)—KH2-WT cell line is a v6.5 mouse ES line in which the Rosa26 locus was targeted to express M2Rtta, and the Col a1 Locus was modified to be receptive to a plasmid with TetOn promoter (PMID: 16400644) and an insert (in this case Gata4 gcccttttttgggttttttgttttgttttgttttgttttgat-ttttggtgacagttccgcacacccgcat-tctagttcttgtctgcctcgtgctcagagcttgg ggcgatgtaccaaagcctggc-catgccgccaaccacggcccccccgccggcgcctacgaagcaggtggccctg-gcgccttcatgcac agcgcgggcgccgcgtcctcgcccgtctacgtgcc-cactccgcgggtgccgtcctctgtgctgggcctgtcctacctgcagggcggtggc agtgccgctgcagctggaaccacctcgggtggcagctccggggccggcccgtcgggtgcagggcctgggacc-
cagcagggtagccct ggctggagccaagctggagccgagggagccgccta-
caccccgccgcccgtgtccccgcgcttctctttcccggggactactgggtccct
ggccggccgctgccgccgctgccgcagcccgggaagctgcagcc-
tacggcagtggccggcggggcggcgggcgctggtctggctggcc
gagagcagtacgggcgtccgggcttcgccggctcctactccagcccc-
tacccagcctacatggccgacgtgggagcatcctgggccgca
gccgctgccgcctctgccggccccttcgacagcccagtcctgcacagcctgcct-
ggacgggccaaccctggaagacaccccaatctcgt agatatgttt-
gatgacttctcagaaggcagagagtgtgtcaattgtggggccatgtccaccc-
cactctggaggcgagatgggacgggacac tacctgtgcaatgcctgtggcctc-
tatcacaagatgaacggcatcaaccggccctcattaagcctcagcgccgcctgt-
ccgcttcccgccg ggtaggcctctcctgtgccaactgccagactaccaccac-
cacgctgtggcgtcgtaatgccgagggtgagcctgtatgtaatgcctgccggc ctc-
tacatgaagctccatggggttccaggcctcttgcaatgcggaaggagggatt-
caaaccagaaaacggaagcccaagaacctgaat
aaatctaagacgccagcaggtcctgctggtga-
gaccctccctccctccagtggtgcctccagcggtaactccagcaatgc-
cactagcagca gcagcagcagtgaagagatgcgccccatcaa-
gacagagcccggctgtcatctcactatgggcacagcagctccatgtcccagacat-
tca
gtactgtgtccggccacgggccctccatccatccagtgctgtctgctct-
gaagctgtccccacaaggctatgcatctcctgtcactcagacat
cgcaggccagctccaagcaggactcttggaacagcctggtcctggctgacagt-
catggggacataatcaccgcgtaatcagcgccccc cttccctcttcaaat-
tcctgctcggacttgggacgtgggggccagcaaagtaaaaggctgggaagggc; SEQ ID NO: 1) which can be flipped in the collagen locus. Targeted colonies were subjected to hygromycin selection of 10 days, and individual ES colonies were selected for further analysis to generate KH2-Gata4 that overexpress Gata4 upon DOX addition (FIG. 8). Real Time PCR analysis and immunostaining confirmed that the clones showed DOX inducible overexpression of the Gata4 insert (FIGS. 9-10).

Aggregation media (AM)—240 ml Neurobasal (ThermoFisher 21103049) and 240 ml of DMEM-F12 (Thermo 21331-020 or SIGMA D6421), 5 ml N2 supplement (Invitrogen; 17502048), 10 ml B27 supplement (Invitrogen; 17504044), 2 mM glutamine or 1× GLutamax (Invitrogen), 1× nonessential amino acids (NEAA) (Invitrogen), 0.1 mM β-mercaptoethanol (GIBCO 31350-010), 1× penicillin-streptomycin (Invitrogen), 0.45% BSA (Sigma A7979), 1% Sodium-pyruvate (BI 03-042-1B). When indicated, serum was added to aggregation media at the indicated percentage and origin.

IVC1 media—Advanced DMEM/F12 (Gibco 12634010) supplemented with Glutamax 1×, Pen/Strep 1×, ITS-X 1× (Gibco 51500056), beta-Estradiol 8 nM, Progesterone 20 ng/ml, N-acetyl-L-cysteine 25 μM and FBS or HAS as indicated.

EUCM media (also referred to as EUCM1)—25% DMEM (GIBCO 11880) or Advanced DMEM/F12 (Thermo 12634010), 25% HAS (Human Adult Serum or Human umbilical cord serum), 50% Rat Serum (RAS), Glutamax 1× (GIBCO 35050038), HEPES 11 mM (GIBCO 15630056), Pen/Strep 1×. When indicated, the media was further supplemented with D-Glucose 4-12 mg/ml, sodium pyruvate 1 mM and/or non-essential amino acids (NEAA 1×). DMEM aliquots were stored at 4° C. and used within 2 months. Rat serum was stored at −80° C. and heat inactivated at 56° C. for half an hour and filtered through a 0.22 μm PVDF filter (Millipore; SLGV033RS) prior to use. HAS should be freshly thawed and used immediately before experimentation. Rat serum and HAS can be thawed/frozen once.

Aggregation plate preparation—To prepare the 24 well AggreWell 400 plate (STEMCELL Technologies 34415) or AggreWell 800 plate (STEMCELL Technologies), 500 ml of anti-adherence rinsing solution (STEMCELL Technologies 07010) was added to each well. The plate was then centrifuged at 2,000×g for 5 minutes and was incubated for 30 minutes at room temperature. Anti-adherence Rinsing solution (Stem Cell Technologies—#07010) was then aspirated from the well and 1 ml of PBS−/− was added to wash each well, and this PBS wash was repeated twice. The 500 ml of aggregation medium (AM) was added to each well after aspirating the PBS.

Co-aggregation and culture (FIG. 7A)—Co-aggregation was defined as time point 0 of the protocol and was made from three starting stem cell types:
1) V6.5-GFP (To give rise to embryo proper);
2) mouse XEN line #7 cells (expected to give rise to extraembryonic endoderm lineage); and
3) mouse TSC line #1 cells (expected to give rise to entire trophectoderm lineage). Cells were trypsinised with 0.05% trypsin-EDTA for 3-5 minutes followed by feeder depletion on gelatinized plates for 20 minutes at 37° C. (when MEFs were used). Following, cells were resuspended in aggregation media (AM) supplemented with Doxycycline (2 μg/ml final concentration). Following cell count, a total number of 18000 TSCs, 6000 XEN and 6000 v6.5-GFP WT cells were added per well in an AggreWell 400 Microwell 24 well plate. In 800 Microwell plates a total number of 4500 TSCs, 1500 XEN and 1500 V6.5 GFP cells were added per well in an AggreWell 24 well. The cell mixture was added as 1 ml per well (final volume of each well of 24 well is 1.5 ml), 25 cells/well.

Day 0—The plate was centrifuged at 100×g for 3 minutes and this was marked as day and then placed into static incubator at 37° C., 5% Co2 and 20% O2.

On Day 1, 1 ml of media was gently aspirated from each well and replaced with pre-warmed 1 ml of fresh AM+20% PBS+DOX as indicated in FIG. 7A.

On day 2, 1 ml of media was gently aspirated from each well and replaced with pre-warmed 1 ml of fresh AM+20% PBS as indicated in FIG. 7A.

On day 3, 1 ml of media was gently aspirated from each well and replaced with pre-warmed 1 ml of IVC1 media with 20% FBS as indicated in FIG. 7A.

On day 4, embryos were transferred with 3 ml Plastic Pasteur Pipette to a 15 ml falcon tubes, allowed to sit for 5 minutes, and most media was gently removed leaving embryos in ~1 ml media. The embryos were then moved with the pipette gently in petri dish (35 mm Corning 430588 plates) or (6 well plates Costar 3736) or iBidi plate with 4 ml of IVC1 media with 30% FBS, and were incubated on a rotating shaker 60 rpm in a static incubator (37° C., 20% O₂ and 5% Co2).

On day 5, 2-3 ml of media was gently aspirated with manual pipette and replaced with fresh IVC1 media with 30% HAS (bringing back to total volume of 4 ml) and incubated on a shaker (60 rpm) in a static incubator (37° C., 20% O₂ and 5% Co2).

From at day 6 and day 7—each day 2-3 ml of media was gently aspirated with manual pipette and replaced with fresh EUCM media supplemented with D-Glucose 4 mg/ml and sodium pyruvate 1 mM as indicated in FIG. 7A (bringing back to total volume of 4 ml).

At day 8 onwards, high quality embryos were selected and transferred into a previously described ex-utero roller culture system (Alejandro-Castrjon et al. Nature 2021) in fresh EUCM media supplemented with D-Glucose 4 mg/ml and sodium pyruvate 1 mM and incubated at 20% O₂, 5% Co2 and 6.5 Psi.

Co-aggregation and culture (FIG. 7D)—KH2-Gata4 Dox inducible cells expanded in 2i/LIF were used instead of XEN cells. To this end, KH2-GATA4 cells were subjected to DOX addition in 2i/LIf 12 hours prior to aggregation. Co-aggregation was defined as time point 0 of the protocol and was made from three starting stem cell types:
1) V6.5-GFP WT naïve ESCs (To give rise to embryo proper);
2) DOX pre-treated KH2 tetO-GATA4 naïve ESC (to give rise to extraembryonic endoderm lineage); and
3) TSCs (expected to give rise to entire trophectoderm lineage).

Cells were trypsinised with 0.05% trypsin-EDTA for 3-5 minutes followed by feeder depletion on gelatinized plates for 20 minutes at 37° C. (when MEFs were used). Following, cells were re-suspended in aggregation media (AM) supplemented with Doxycycline (2 μg/ml final concentration). Following cell count, a total number of 18000 TSCs, 6000 KH2-GATA4 and 6000 V6.5-GFP naïve ES cells were added per well in AggreWell 400 Microwell 24 well plate. In 800 Microwell plates a total number of 4500 TSCs, 1500 KH2-GATA4 and 1500 V6.5 GFP WT cells were added per well in AggreWell 24 well. The cell mixture was added as 1 ml per well (final volume of each well of 24 well is 1.5 ml), 25 cells/well.

Day 0—The plate was centrifuged at 100×g for 3 minutes and this was marked as day and then placed into static incubator at 37° C., 5% Co2 and 20% $O_2$.

On Day 1, 1 ml of media was gently aspirated from each well and replaced with pre-warmed 1 ml of fresh AM+20% FBS+DOX, as indicated in FIG. 7D.

On day 2, 1 ml of media was gently aspirated from each well and replaced with pre warmed 1 ml of fresh AM+20% FBS, as indicated in FIG. 7D.

On day 3, 1 ml of media was gently aspirated from each well and replaced with pre warmer 1 ml of IVC1 media with 20% FBS, as indicated in FIG. 7D.

On day 4, embryos were transferred with a 3 ml Plastic Pasteur Pipette to 15 ml falcon tubes, allowed to sit for 5 minutes, and most media was gently removed leaving embryos in ~1 ml media. The embryos were then moved with the pipette gently into petri dish (35 mm Corning 430588 plates) or (6 well plates Costar 3736) or iBidi plates with 4 ml of IVC1 media with 30% FBS (as indicated in FIG. 7D) and incubated on a shaker (60 rpm) in a static incubator (37° C., 20% $O_2$ and 5% Co2).

On day 5, 2-3 ml of media was gently aspirated with manual pipette and replaced with fresh IVC1 media with 30% KSR (Knockout serum replacement—Invitrogen, as indicated in FIG. 7D, bringing back to total volume of 4 ml) and kept on the shaker rotating at 60 rpm in the static incubator (37° C., 20% $O_2$ and 5% Co2).

From at day 6 and day 7—each day 2-3 ml of media was gently aspirated with a manual pipette and replaced with fresh EUCM media supplemented with D-Glucose 4 mg/ml and sodium pyruvate 1 mM, as indicated in FIG. 7D (bringing back to total volume of 4 ml).

At day 8 onwards, high quality embryos were selected and transferred into a previously described ex-utero roller culture system (Alejandro-Castrjon et al. Nature 2021) in fresh EUCM media supplemented with D-Glucose 4 mg/ml and sodium pyruvate 1 mM and incubated at 20% $O_2$, 5% Co2 and 6.5 Psi.

Whole-mount immunostaining of embryos—Embryos grown ex utero were dissected (with or without removing the yolk sac and amnion for E8.5 embryos), washed once with 1×PBS, then transferred to ibidi glass bottom 8-well slides (iBidi) and fixed with 4% PFA EM grade (Electron microscopy sciences, 15710) in PBS at 4° C. over-night. Embryos were then washed in PBS for 5 minutes 3 times, permeabilized in PBS with 0.5% Triton X-100/0.1 M glycine for 30 minutes, blocked with 10% normal donkey serum/0.1% Triton X-100 in PBS for 1 hour at room temperature (RT), and incubated over-night at 4° C. with primary antibodies, diluted in blocking solution. After, embryos were rinsed 3 times for 5 minutes each in PBS/0.2% TritonX-100, incubated for 2 hours at room temperature with secondary antibodies diluted 1:200 in blocking solution (all secondary antibodies were from Jackson ImmunoResearch), counterstained with DAPI (1 μg/ml in PBS) for 10 minutes, and washed with PBS for 5 minutes 3 times. If necessary, yolk sacs separated from the embryos were fixed and stained using this whole-mount immunostaining protocol. The following primary antibodies were used: Rabbit monoclonal anti-Brachyury (Cell Signaling, 81694) 1:100; Rabbit polyclonal anti-Cdx2 (Cell Signaling, 3977) 1:100; Mouse monoclonal anti-Cdx2 (Biogenex, AU392A-UC) 1:100; Goat polyclonal anti-Gata4 (Santa Cruz, SC-1237) 1:100; Rabbit polyclonal anti-Gata4 (Abcam, Ab84593) 1:100; Rabbit polyclonal anti-Foxa2 (Abcam, Ab40874) 1:100; Mouse monoclonal anti-Myosin Heavy Chain II (MF-20) (R&D, MAB4470) 1:100; Goat polyclonal anti-Otx2 (R&D, AF1979) 1:200; Rabbit polyclonal anti-Pax6 (Covance, PBR-278P) 1:100; Goat polyclonal anti-Sox2 (R&D, AF2018) 1:200; Rabbit polyclonal anti-Sox9 (Millipore, AB5535) 1:100; Goat polyclonal anti-Sox17 (R&D, AF1924) 1:100; Mouse monoclonal anti-Tuj1 (C-10) (Covance, MMS-435P) 1:200; Chicken polyclonal anti-GFP (Abcam, Ab13970) 1:250; Mouse monoclonal anti-Oct4 (Santa Cruz, SC-5279) 1:100; Goat polyclonal anti-Lefty 1 (R&D, AF746) 1:100, Goat polyclonal anti-mCherry/Tomato (SiCGEN, AB0040-200) 1:200.

Clearing of embryos from E9.5 to E11.5 was performed as follows: embryos were washed once with 1×PBS and fixed overnight at 4° C. with 4% PFA EM grade diluted in PBS. Samples were washed in PBS for 5 minutes three times, followed by sample pre-treatment without methanol, i.e.: Washed in PBS/0.2% TritonX-100 for 1 hour twice, then incubated in PBS/0.2% TritonX-100/20% DMSO at 37° C. overnight, then in PBS/0.1% Tween-20/0.1% TritonX-100/0.1% Deoxycholate/0.1% NP40/20% DMSO at 37° C. overnight, then washed in PBS/0.2% TritonX-100 for 1 hour twice. For immunostaining, embryos were permeabilized in PBS/0.2% TritonX-100/20% DMSO/0.3 M glycine at 37° C. overnight, and then blocked in PBS/0.2% TritonX-100/10% DMSO/6% Donkey Serum at 37° C. overnight. After blocking, embryos were incubated with primary antibodies diluted in PBS/0.2% Tween-20 with 10 μg/ml heparin (PTwH)/5% DMSO/3% Donkey Serum at 37° C. [E9.5/E10.5=24 hours; E11.5=48 hours (72 hours for Sox17 and Foxa2 antibodies)]. Afterwards, samples were washed in PTwH for 24 hours (15 minutes, 30 minutes, 1 hour, 2 hours, and overnight washes), and incubated with adequate secondary antibodies (1:200) diluted in PTwH/3% Donkey Serum at 37° C. for 48 hours.

For human cell specific NUMA staining (when used), donkey anti-rabbit Biotin and Streptavidin-Cy3 (each incubated overnight) were used for signal enhancement. After, embryos were incubated for 30 minutes with DAPI (1 μg/ml) diluted in PTwH, washed in PTwH for one day (5 minutes, 15 minutes, 30 minutes, 1 hour, 2 hours, and overnight washes) and dehydrated in methanol/$H_2O$ series (20%, 40%, 60%, 80%, 100%) 1 hour each at room temperature, and then incubated overnight in 100% methanol. Embryos were incubated in 66.6% DCM/33.3% methanol at room temperature on shaker for 3 hours, followed by 100% DCM (Sigma; 270997) for 5 minutes, and finally cleared and stored in Benzyl Ether (Sigma; 108014). The following primary antibodies were used: Rabbit monoclonal anti-Brachyury (Cell Signaling, 81694) 1:100; Rabbit polyclonal anti-Cdx2 (Cell Signaling, 3977) 1:100; Mouse monoclonal anti-Cdx2 (Biogenex, AU392A-UC) 1:100; Goat polyclonal anti-Gata4 (Santa Cruz, SC-1237) 1:100; Rabbit polyclonal anti-Gata4 (Abcam, Ab84593) 1:100; Rabbit polyclonal anti-Foxa2 (Abcam, Ab40874) 1:50; Mouse monoclonal anti-Myosin Heavy Chain II (MF-20) (R&D, MAB4470) 1:100; Goat polyclonal anti-Otx2 (R&D, AF1979) 1:200; Rabbit polyclonal anti-Pax6 (Covance, PBR-278P) 1:100; Goat polyclonal anti-Sox2 (R&D, AF2018) 1:200; Rabbit polyclonal anti-Sox9 (Millipore, AB5535) 1:100; Goat polyclonal anti-Sox17 (R&D, AF1924) 1:50; Mouse monoclonal anti-Tuj1 (C-10) (Covance, MMS-435P) 1:200; Chicken polyclonal anti-GFP (Abcam, Ab13970) 1:250, Goat polyclonal anti-mCherry/Tomato (SiCGEN, AB0040-200) 1:200; Rabbit polyclonal anti-human TEMEM119 (Invitrogen, PA562505) 1:100; Rabbit anti-hNUMA (Abcam, ab84680) 1:100.

Confocal Microscopy—Images were acquired with a Zeiss LSM 700 inverted confocal microscope (Carl Zeiss) equipped with 405 nm, 488 nm, 555 nm and 635 nm solid state lasers, using a Plan-Apochromat 20× air objective (numerical aperture 0.8) for E5.5/E6.5 embryos, and an EC Plan Neofluar 10× air objective (numerical aperture 0.3) for E7.5 to E11.5 embryos. Images were acquired at 1024×1024 resolution. All images were acquired within the following range of parameters: Laser power: 405 nm: 10-20%; 488 nm: 5-20%; 555 nm 10-40%; 635 nm: 30-80%. Gain ranged from 350 to 600. Pixel size was 1.25 μm with a z-step of 15 μm when using the 10× objective, or 0.5 μm with z-step of 5 μm when using the 20× objective. For confocal imaging, iDISCO cleared embryos were mounted in 35 mm glass bottom dishes (In Vitro Scientific, D35201.5N), employing ethyl cinnamate (Sigma, 112372) as imaging solution. For chimeric embryos, all parameters during image acquisition were compared to stained non-injected control embryos, imaged with equal parameters as the injected embryos. Images and maximum intensity projections were processed using Zen 2 blue edition software 2011 (Carl Zeiss) and Adobe Photoshop CS4.

Immunostaining of ES, TSC and XEN cell lines—Cells were grown on glass cover slips (13 mm 1.5H; Marienfeld, 0117530) fixed with 4% paraformaldehyde/phosphate buffer for 10 minutes at room temperature, washed three times with PBS, and permeabilized in PBS/0.1% Triton for 10 minutes. Cells were blocked with blocking solution (2% normal goat serum, 0.1% BSA in PBS/0.05% Tween) for 1 hour at RT and incubated with primary antibody diluted in blocking solution overnight at 4° C. (Antibodies in this study have all been validated in the literature and by ourselves). Cells were then washed three times with PBS/0.05% Tween, incubated with secondary antibodies for 1 hour at room temperature, washed in PBS/0.05% Tween, counterstained with DAPI (1 μg/ml), washed again three times with PBS/Tween 0.05% and mounted with Shandon Immu-Mount (Thermo Scientific, 9990412), and imaged. All comparative experiments were done simultaneously. All secondary antibodies were used from Jackson ImmunoResearch.

Real-Time PCR analysis—For RT-PCR total RNA was isolated using Trizol (Ambion Life Technologies), and 1 μg of total RNA was reverse transcribed using High-Capacity Reverse Transcription Kit (Applied Biosystems). Quantitative PCR analysis was performed with the SYBR™ Green PCR Master Mix (Applied Biosystems) using 10 ng of cDNA per reaction in a Viia7 platform (Applied Biosystems). Fold change was normalized to Gapdh and/or Actin expression as indicated per figure. The following primers were used:

```
Mouse Gapdh-Forward:
                                        (SEQ ID NO: 2)
AGTCAAGGCCGAGAATGGGAAG;

Mouse Gapdh-Reverse:
                                        (SEQ ID NO: 3)
AAGCAGTTGGTGGTGCAGGATG Mouse Oct4-Forward:
                                        (SEQ ID NO: 4)
AGAGGATCACCTTGGGGTACA;

Mouse Oct4-Reverse:
                                        (SEQ ID NO: 5)
CGAAGCGACAGATGGTGGTC;

Mouse Nanog-Forward:
                                        (SEQ ID NO: 6)
CTCAAGTCCTGAGGCTGACA;

Mouse Nanog-Reverse:
                                        (SEQ ID NO: 7)
TGAAACCTGTCCTTGAGTGC;

Mouse Sox2-Forward:
                                        (SEQ ID NO: 8)
TAGAGCTAGACTCCGGGCGATGA;

Mouse Sox2-Reverse:
                                        (SEQ ID NO: 9)
TTGCCTTAAACAAGACCACGAAA;

Mouse Klf4-Forward:
                                        (SEQ ID NO: 10)
GCACACCTGCGAACTCACAC;

Mouse Klf4-Reverse:
                                        (SEQ ID NO: 11)
CCGTCCCAGTCACAGTGGTAA;

Mouse Cdx2-Forward:
                                        (SEQ ID NO: 12)
GCGAAACCTGTGCGAGTGGATG;

Mouse Cdx2-Reverse:
                                        (SEQ ID NO: 13)
CGGTATTTGTCTTTTGTCCTGGTTTTCA;

Mouse Gata4-Forward:
                                        (SEQ ID NO: 14)
CACAAGATGAACGGCATCAACC;

Mouse Gata4-Reverse:
                                        (SEQ ID NO: 15)
CAGCGTGGTGGTAGTCTG;

Mouse Gata6-Forward:
                                        (SEQ ID NO: 16)
CTTGCGGGCTCTATATGAAACTCCAT;

Mouse Gata6-Reverse:
                                       ((SEQ ID NO: 17)
TAGAAGAAGAGGAAGTAGGAGTCATAGGGACA;

Mouse Brachyury(T)-Forward:
                                        (SEQ ID NO: 18)
CTGTGACTGCCTACCAGAATGAGGAG;
```

```
Mouse Brachyury(T)-Reverse:
                                          (SEQ ID NO: 19)
GGTCGTTTCTTTCTTTGGCATCAAG;

Mouse Otx2-Forward:
                                          (SEQ ID NO: 20)
CTTCGGGTATGGACTTGCTG Mouse Otx2-Reverse:
                                          (SEQ ID NO: 21)
CCTCATGAAGATGTCTGGGTAC;

Mouse Fgf5-Forward:
                                          (SEQ ID NO: 22)
CAAAGTCAATGGCTCCCACGAAG;

Mouse Fgf5-Reverse:
                                          (SEQ ID NO: 23)
CTACAATCCCCTGAGACACAGCAAATA;

Total (endogenous + exogenous) mouse Gata4
Forward:
                                          (SEQ ID NO: 24)
CCAGTGCTGTCTGCTCTGAA;

Total (endogenous + exogenous) mouse Gata4
Reverse:
                                          (SEQ ID NO: 25)
GCTGTTCCAAGAGTCCTGCT;

Total (endogenous + exogenous) mouse Cdx2
Forward:
                                          (SEQ ID NO: 26)
GCGAAACCTGTGCGAGTGGATG;

Total (endogenous + exogenous) mouse Cdx2
Reverse:
                                          (SEQ ID NO: 27)
CGGTATTTGTCTTTTGTCCTGGT;

Exogenous mouse Gata4 Forward:
                                          (SEQ ID NO: 28)
AAATTCCTGCTCGGACTTGGGAC;

Exogenous mouse Gata4 Reverse:
                                          (SEQ ID NO: 29)
GTGGTTTGTCCAAACTCATCAATGTATCTT;

Exogenous mouse Cdx2 Forward:
                                          (SEQ ID NO: 30)
GAGGGGTTTTAAACTCCACTGTCACC;

Exogenous mouse Cdx2 Reverse:
                                          (SEQ ID NO: 31)
GTGGTTTGTCCAAACTCATCAATGTATCTT;

Endogenous mouse Gata4 Forward:
                                          (SEQ ID NO: 32)
CACTGGAAAAGCCTGCGTTCTTACA;

Endogenous mouse Gata4 Reverse:
                                          (SEQ ID NO: 33)
AGAATAAGGAAGGAAGAAGTCTCTTGCCTC;

Endogenous mouse Cdx2 Forward:
                                          (SEQ ID NO: 34)
AATTATGGACCTCAGGGGAAGACATG;

Endogenous mouse Cdx2 Reverse:
                                          (SEQ ID NO: 35)
GCTGGCAGGAAGAGTCGGAATG.
```

Results

Co-aggregation of three starting cell types, namely a naïve mouse PSCs (V6.5-GFP), mouse XEN cells [mouse XEN line #7 cells or KH2-Gata4 Dox inducible cells) and mouse TSCs (mouse TSC line #1 cells) followed by ex-utero culturing (FIGS. 7A-F) did not lead to generation of an organized embryo. Specifically, at Day 4 of the protocol shown in FIG. 7A and days 5 and 6 of the protocol shown in FIG. 7D, trophoblast cells were aberrantly distributed in all regions of the embryos, and did not show the expected patters of being concentrated on the region opposite to the GFP+ epiblast (FIGS. 7B and 7E). At days 8 and 9, structures that lacked organized embryos in the yolk sac that did not show any sign of emergence of neural folds and cardiac regions were detected (FIGS. 7C and 7F).

Example 2

Aggregation of Three Mouse Naïve Pscs Subpopulations Generates an Organized Embryo Materials and Methods Mouse naïve pluripotent stem cells (naïve PSCs) line—As described in Example 1 hereinabove.

KH2-Gata4 Dox inducible naïve pluripotent stem cells (KH2-GATA4)—As described in Example 1 hereinabove.

KH2-Cdx2 Dox inducible naïve pluripotent stem cells (KH2-Cdx2)—As noted hereinabove, KH2-WT cell line is a v6.5 mouse ES line in which the Rosa26 locus was targeted to express M2Rtta, and the Cola1 Locus was modified to be receptive to a plasmid with TetOn promoter (PMID: 16400644) and an insert (in this case Cdx2: atgtacgtgagc-taccttctggacaaggacgtgagcatgtatcctagctccgtgcgc-cactccggcggcctgaacctggctccgcagaactt tgtcagtcctccgcagtacccggactacggtggttac-cacgtggcggccgcggcggctgctacggcgaacttggacagcgctcagtcccc agggccatcctggcccaccgcgtacggcgccctctccgcgaggactg-gaatggctacgcaccgggggcgctgcggcagccaacgc ggtagcc-cacggtctcaatggtggctcccggccgccgctatgggcta-cagcagccccgccgaataccacgcgcaccatcacccgcatc atcacccgcaccatccggccgcctcgccgtcctgcgcctccggcttgctgca-gacgctcaacctcggccccccggggcccgcagccacc gccgccgccgaacagctgtcccccagcggccagcggcgaaacctgtgcgagtg-gatgcgaagcccgcgcagcagtccctaggaag ccaagt-gaaaaccaggacaaaagacaaataccgggtggtgtacacagac-catcagcggctggagctggagaaggagtttcactttagtcg atacatcaccatcaggaggaaaagtgagctggctgc-cacacttgggctctccgagaggcaggttaaaatttggtttcagaaccgcagagcc aaggagaggaaaat-caagaagaagcagcagcagcaacagcagcagcagcaacaacagcctc-cacagccgccgccacaaccttccca gcctcagccgggtgccctgcg-gagcgtgcccgagcccttgagtcctgtgacctccttgcaaggctcagtgcctggtt-ctgtccctggggttc tggggccagctggaggggttttaaactccactgt-cacccagtga; SEQ ID NO: 36) which can be flipped in the collagen locus. Targeted colonies were subjected to hygromycin selection of 10 days, and individual ES colonies were selected for further analysis to generate KH2-Cdx2 that overexpress Cdx2 upon DOX addition (FIG. 11). Real Time PCR analysis and immunostaining confirmed that the clones showed DOX inducible overexpression of the Cdx2 insert (FIGS. 12-14).

Expansion and maintenance of naïve mouse PSCs—Three different mouse ES lines were separately expanded and maintained in mouse naïve N2B27 2iLIF conditions: KH2 ESC, KH2-Gata4 Dox inducible cells (KH2-GATA4) and KH2-Cdx2 Dox inducible cells (KH2-CDX2). Cells were expanded on gelatin or MEF coated plates in N2B27 2i/LIF medium for at least 3 passages (10-12 days) in order to become naïve (PMID 33915080; PMID 26860365; PMID: 26291026; PMID: 26076835; PMID 24172903; PMID 25569111) and competent to successfully execute the protocol delineated herein. Both 5% $O_2$ and 20% $O_2$ conditions were suitable (37° C. and 5% Co2).

N2B27 2i/LIF medium—240 ml Neurobasal (ThermoFisher 21103049) and 240 ml of DMEM-F12 (Thermo 21331-020 or SIGMA D6421), 5 ml N2 supplement (Invitrogen; 17502048), 10 ml B27 supplement (Invitrogen; 17504044), 2 mM glutamine or 1 mM GLutamax (Invitrogen), 1% nonessential amino acids (Invitrogen), 0.1 mM β-mercaptoethanol (Sigma), 1% penicillin-streptomycin (Invitrogen), 3 μM CHIR99021 (GSK3i—CH, Axon Medchem), 1 μM PD0325901 (MEK/ERKi, PD, Axon Medchem 1408) and recombinant LIF 20 ng/ml.

Aggregation media (AM)—As described in Example 1 hereinabove.

EUCM media (also referred to as EUCM1)—As described in Example 1 hereinabove.

EUCM2 media—CMRL (Gibco 11530037) or a 1:1 mix of CMRL and Advanced DMEM/F12 (Thermo 12634010), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 20% FBS.

EUCM3 media—CMRL (Gibco 11530037) or a 1:1 mix of CMRL and Advanced DMEM/F12 (Thermo 12634010), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% FBS.

EUCM4 media—CMRL (Gibco 11530037) or a 1:1 mix of CMRL and Advanced DMEM/F12 (Thermo 12634010), Glutamax 1×, Sodium pyruvate 1 mM, Pen/Strep 1×+NEAA 1×, D-Glucose 4 mg/mL, ITS-X 1× (Gibco 51500056), beta-Estradiol 8 nM, Progesterone 20 ng/ml, 30% HAS.

EUCM4* media—4:1 mix of CMRL (Gibco 11530037) and Advanced DMEM/F12 (Thermo 12634010), Glutamax 1×, Sodium pyruvate 0.5 mM, Pen/Strep 1×+NEAA 0.5×, +extra D-Glucose 3 mg/mL, ITS-X 1× (Gibco 51500056), beta-Estradiol 8 nM, Progesterone 20 ng/ml, 20% RAS, 10% HAS+HEPES 2 mM (GIBCO 15630056). When indicated, EUCM5 also contained 10% KSR.

EUCM5 media—4:1 mix of CMRL (Gibco 11530037) and Advanced DMEM/F12 (Thermo 12634010), Glutamax 1×, Sodium pyruvate 0.5 mM, Pen/Strep 1×+NEAA 0.5×, +extra D-Glucose 3 mg/mL, ITS-X 1× (Gibco 51500056), beta-Estradiol 8 nM, Progesterone 20 ng/ml, 30% RAS, 15% HAS, HEPES 2 mM (GIBCO 15630056). When indicated, EUCM5 also contained 5% KSR.

Optional short pre-aggregation Pre-Treatment—This optional step was applied where indicated for some of the donor naïve cells types already expanded in naïve N2B272i/LIF conditions for at least three passages, and were pre-treated for up to 48 hours prior to co-aggregation (defined as time 0) as indicated in the scheme. In this specific regimen (see e.g. FIGS. 15A, 17A, 19A, 20A, 21-22) naïve N2B27 2i/LIF media on KH2-Cdx2 was replaced for 48-12 hours prior to co-aggregation to AM+20% FBS+DOX; and naïve N2B27 2i/LIF media on KH2-Gata4 was replaced for 48-12 hours prior to co-aggregation to AM+20% FBS+DOX.

Aggregation plate preparation—As described in Example 1 hereinabove.

Co-aggregation and culture (FIG. 15A)—Co-aggregation was defined as time point 0 of the protocol and was made from three starting PSC cell types:
1) KH2 WT naïve ESCs (To give rise to embryo proper);
2) DOX pre-treated KH2-GATA4 naïve ES cells (to give rise to the entire extraembryonic endoderm lineage); and
3) DOX pre-treated KH2-CDX2 naïve ES cells (to give rise to entire trophectoderm lineage).

Cells were trypsinised with 0.05% trypsin-EDTA for 3-5 minutes followed by feeder depletion on gelatinized plates for 20 minutes at 37° C. (when MEFs were used). Cells were resuspended in aggregation media (AM) supplemented with Doxycycline (2 μg/ml final concentration). Following cell count, a total number of 18000 KH2-CDX2, 6000 KH2-GATA4 and 6000 KH2-WT (empty) cells were added per well in AggreWell 400 Microwell 24 well plates. In 800 Microwell plates, a total number of 4500 KH2-CDX2, 1500 KH2-GATA4 and 1500 KH2-WT (empty) cells were added per well in AggreWell 24 well. The cell mixture was added as 1 ml per well (final volume of each well of 24 well is 1.5 ml), 25 cells/well.

Day 0—The plate was centrifuged at 100×g for 3 minutes and this was marked as day 0, and then placed into static incubator at 37° C., 5% Co2 and 20% $O_2$.

On Day 1, 1 ml of media was gently aspirated from each well and replaced with pre-warmed 1 ml of fresh AM+20% FBS+DOX, as indicated in FIG. 15A.

On day 2, 1 ml of media was gently aspirated from each well and replaced with pre-warmed 1 ml of fresh AM+20% FBS, as indicated in FIG. 15A.

On day 3, 1 ml of media was gently aspirated from each well and replaced with pre-warmed 1 ml of EUCM2 (CMRL based) media with 20% FBS, as indicated in FIG. 15A.

On day 4, embryos were transferred with a 3 ml Plastic Pasteur Pipette to a 15 ml falcon tubes, allowed to sit for 5 minutes, and most media was gently removed leaving embryos in ~1 ml media. The embryos were then moved with the pipette gently in petri dish (35 mm Corning 430588 plates) or (6 well plates Costar 3736) with 4 ml of EUCM3 (CMRL based) media with 30% FBS (as indicated in Figure and incubated on a shaker at 60 rpm in a static incubator (37° C., 20% $O_2$ and 5% $CO_2$)].

On day 5, 2-3 ml of media was gently aspirated with a manual pipette and replaced with fresh EUCM4 (CMRL based) with 30% HAS, as indicated in FIG. 15A (bringing back to total volume of 4 ml), and kept on a shaker at 60 rpm in a static incubator (37° C., 20% O2 and 5% Co2).

On days 6 and 7—each day 2-3 ml of media was gently aspirated with a manual pipette and replaced with fresh EUCM media supplemented with D-Glucose 4 mg/ml and sodium pyruvate 1 mM, as indicated in FIG. 15A (bringing back to total volume of 4 ml).

On day 8 up to day 13—High quality embryos were selected and transferred into the previously described ex utero roller culture system (Alejandro-Castrjon et al. Nature 2021) in fresh EUCM media supplemented with D-Glucose 4 mg/ml and sodium-pyruvate 1 mM and incubated at 20% O2, 5% Co2 and 6.5 Psi, as indicated in FIG. 15A.

Co-aggregation and culture (FIG. 16A)—Co-aggregation was defined as time point 0 of the protocol and was made from three starting PSC cell types:
1) KH2 WT naïve ESC (To give rise to embryo proper);
2) KH2-GATA4 naïve ESCs (to give rise to the entire extraembryonic primitive endoderm (PRE) lineage); and
3) KH2-CDX2 naïve ESCs (to give rise to entire trophectoderm lineage).

Cells were trypsinised with 0.05% trypsin-EDTA for 3-5 minutes followed by feeder depletion on gelatinized plates for 20 minutes at 37° C. (when MEFs were used). Following, cells were resuspended in aggregation media (AM) supplemented with Doxycycline (2 μg/ml final concentration). Following cell count, a total number of 18000 KH2-CDX2, 6000 KH2-GATA4 and 6000 KH2-WT (empty) cells were added per well in in 400 Microwell AggreWell 24 well plate. In 800 Microwell plates a total number of 4500

KH2-CDX2, 1500 KH2-GATA4 and 1500 KH2-WT (empty) cells were added per well in AggreWell 24 well. The cell mixture was added as 1 ml per well (final volume of each well of 24 well is 1.5 ml), 25 cells/well.

Day 0—The plate was centrifuged at 100×g for 3 minutes and this was marked as day and then placed into a static incubator at 37° C., 5% Co2 and 20% O2.

On Day 1, 1 ml of media was gently aspirated from each well and replaced with pre-warmed 1 ml of fresh AM 20% FBS+DOX, as indicated in FIG. 16A.

On day 2, 1 ml of media was gently aspirated from each well and replaced with pre-warmed 1 ml of fresh AM+20% FBS+DOX, as indicated in FIG. 16A.

On day 3, 1 ml of media was gently aspirated from each well and replaced with pre-warmed 1 ml of EUCM2 (CMRL based) media with 20% FBS, as indicated in FIG. 16A.

On day 4, embryos were transferred with a 3 ml Plastic Pasteur Pipette to a 15 ml falcon tubes, allowed to sit for 5 minutes, and most media was gently removed leaving embryos in ~1 ml media. The embryos were then moved with the pipette gently into a petri dish (35 mm Corning 430588 plates) or 6 well plates (Costar 3736) or iBidi plates with 4 ml of EUCM3 (CMRL based) media with 30% FBS (as indicated in FIG. 16A) and incubated on a shaker at 60 rpm in a static incubator (37° C., 20% O2 and 5% Co2).

On day 5, 2-3 ml of media was gently aspirated with a manual pipette and replaced with fresh EUCM4 (CMRL based) medium with 30% HAS as indicated in FIG. 16A (bringing back to total volume of 4 ml) and kept on a shaker at 60 rpm in a static incubator (37° C., 20% O2 and 5% Co2).

At days 6 and 7—each day 2-3 ml of media was gently aspirated with a manual pipette and replaced with fresh EUCM media supplemented with D-Glucose 4 mg/ml and sodium-pyruvate 1 mM as indicated in FIG. 16A (bringing back to total volume of 4 ml).

At day 8 up to day 13—High quality embryos were selected and transferred into the previously described ex utero roller culture system (Alejandro-Castrejon et al. Nature 2021) in fresh EUCM media supplemented with D-Glucose 4 mg/ml and sodium-pyruvate 1 mM and incubated at 20% O2, 5% Co2 and 6.5 Psi, as indicated in FIG. 16A.

Co-aggregation and culture (FIG. 17A)—Co-aggregation was defined as time point 0 of the protocol and was made from three starting PSC cell types:

1) KH2 WT ESC (To give rise to embryo proper);
2) Dox pre-treated KH2-GATA4 (to give rise to extraembryonic primitive endoderm (PRE) lineage); and
3) Dox pre-treated KH2-CDX2 (to give rise to entire trophectoderm lineage).

Cells were trypsinised with 0.05% trypsin-EDTA for 3-5 minutes followed by feeder depletion on gelatinized plates for 20 minutes at 37° C. (when MEFs were used). Following, cells were resuspended in aggregation media (AM) supplemented with Doxycycline (2 µg/ml final concentration). Following cell count, a total number of 18000 KH2-CDX2, 6000 KH2-GATA4 and 6000 KH2-WT (empty) cells were added per well in 400 Microwell AggreWell 24 well plates. In 800 Microwell plates a total number of 4500 KH2-CDX2, 1500 KH2-GATA4 and 1500 KH2-WT (empty) cells were added per well in AggreWell 24 well. The cell mixture was added as 1 ml per well (final volume of each well of 24 well is 1.5 ml), 25 cells/well.

Day 0—The plate was centrifuged at 100×g for 3 minutes and this was marked as day and then placed into static incubator at 37% ° C., 5% Co2 and 20% O2.

On Day 1, 1 ml of media was gently aspirated from each well and replaced with pre-warmed 1 ml of fresh AM+20% FBS+DOX, as indicated in FIG. 17A.

On day 2, 1 ml of media was gently aspirated from each well and replaced with pre-warmed 1 ml of fresh AM+20% FBS, as indicated in FIG. 17A.

On day 3, 1 ml of media was gently aspirated from each well and replaced with pre-warmed 1 ml of EUCM2 (CMRL based) media with 20% FBS, as indicated in FIG. 17A.

On day 4, embryos were transferred with a 3 ml Plastic Pasteur Pipette to a 15 ml falcon tubes, allowed to sit for 5 minutes, and most media was gently removed leaving embryos in ~1 ml media. The embryos were then moved with the pipette gently into a petri dish (35 mm Corning 430588 plates) or 6 well plates (Costar 3736) or iBidi plates with 4 ml of EUCM3 (CMRL based) media with 30% FBS and incubated on a shaker rotating at 60 rpm in a static incubator (37° C., 20% O2 and 5% Co2), as indicated in FIG. 17A.

On day 5, 2-3 ml of media was gently aspirated with a manual pipette and replaced with fresh EUCM4 (CMRL based) with 30% HAS as indicated in FIG. 17A (bringing back to a total volume of 4 ml) and kept on the shaker at 60 rpm in a static incubator (37° C., 20% O2 and 5% Co2).

At days 6 and 7—each day 2-3 ml of media was gently aspirated with a manual pipette and replaced with fresh EUCM media supplemented with D-Glucose 4 mg/ml and sodium pyruvate 1 mM as indicated in FIG. 17A (bringing back to total volume of 4 ml).

At day 8 up to day 13—high quality embryos were selected and transferred into previously described ex utero roller culture system (Alejandro-Castrjon et al. Nature 2021) in fresh EUCM media supplemented with D-Glucose 4 mg/ml and sodium pyruvate 1 mM and incubated at 20% O2, 5% Co2 and 6.5 Psi, as indicated in FIG. 17A.

Co-aggregation and culture (FIG. 18A)—Co-aggregation was defined as time point 0 of the protocol and was made from three starting PSC cell types:

1) KH2 WT naïve ESC (To give rise to embryo proper);
2) KH2-GATA4 naïve ESC (to give rise to the entire extraembryonic primitive endoderm (PRE) lineage); and
3) KH2-CDX2 (to give rise to entire trophectoderm lineage).

Cells were trypsinised with 0.05% trypsin-EDTA for 3-5 min followed by feeder depletion on gelatinized plates for 20 min at 37 C (when MEFs were used). Cells were resuspended in aggregation media (AM) supplemented with Doxycycline (2 µg/ml final concentration). Following cell count, a total number of 18000 KH2-CDX2, 6000 KH2-GATA4 and 6000 KH2-WT (empty) cells were added per well in in 400 Microwell AggreWell 24 well plates. In 800 Microwell plates, a total number of 4500 KH2-CDX2, 1500 KH2-GATA4 and 1500 KH2-WT (empty) cells were added per well in AggreWell 24 well. The cell mixture was added as 1 ml per well (final volume of each well of 24 well is 1.5 ml), 25 cells/well.

Day 0—The plate was centrifuged at 100×g for 3 minutes and this was marked as day and then placed into static incubator at 37° C., 5% Co2 and 20% O2.

On Day 1, 1 ml of media was gently aspirated from each well and replaced with pre-warmed 1 ml of fresh AM+20% FBS+DOX, as indicated in FIG. 18A.

On day 2, 1 ml of media was gently aspirated from each well and replaced with pre-warmed 1 ml of fresh AM+20% FBS, as indicated in FIG. 18A.

On day 3, 1 ml of media was gently aspirated with from each well and replaced with pre-warmed 1 ml of EUCM2 (CMRL/advDMEM-F12 based) media with 20% FBS, as indicated in FIG. 18A.

On day 4, embryos were transferred with a 3 ml Plastic Pasteur Pipette to a 15 ml falcon tubes, allowed to sit for 5 minutes, and most media was gently removed leaving embryos in ~1 ml media. The embryos were then moved with the pipette gently into petri dish (35 mm Corning 430588 plates) or 6 well plates (Costar 3736) or iBidi plates with 4 ml of EUCM3 (CMRL/advDMEM-F12 based) media with 30% FBS and incubated on a shaker rotating at 60 rpm in a static incubator (37° C., 20% O2 and 5% Co2), as indicated in FIG. 18A.

On day 5, 2-3 ml of media was gently aspirated with a manual pipette and replaced with fresh EUCM4 (CMRL/advDMEM-F12 based) with 30% HAS, as indicated in FIG. 18A (bringing back to a total volume of 4 ml) and kept on the shaker at 60 rpm in a static incubator (37° C., 20% O2 and 5% Co2).

At days 6 and 7—each day 2-3 ml of media was gently aspirated with manual pipette and replaced with fresh EUCM media supplemented with D-Glucose 4 mg/ml and sodium-pyruvate 1 mM and 1× NEAA, as indicated in FIG. 18A (bringing back to a total volume of 4 ml).

At day 8 up to day 13—high quality embryos were selected and transferred into previously described ex utero roller culture system (Alejandro-Castrjon et al. Nature 2021) in fresh EUCM media supplemented with D-Glucose 4 mg/ml and sodium-pyruvate 1 mM and 1× NEAA and incubated at 20% O2, 5% Co2 and 6.5 Psi, as indicated in FIG. 18A.

Co-aggregation and culture (FIG. 19A)—Co-aggregation was defined as time point 0 of the protocol and was made from three starting PSC cell types:

KH2 WT naïve ESC (To give rise to embryo proper);

Dox pre-treated KH2-GATA4 naïve ESCs (to give rise to the entire extraembryonic primitive endoderm (PRE) lineage); and Dox pre-treated KH2-CDX2 (to give rise to entire extra-embryonic trophectoderm lineage).

Cells were trypsinised with 0.0 5% trypsin-EDTA for 3-5 minutes followed by feeder depletion on gelatinized plates for 20 minutes at 37° C. (when MEFs were used). Following, cells were resuspended in aggregation media (AM) supplemented with Doxycycline (2 µg/ml final concentration). Following cell count, a total number of 18000 KH2-CDX2, 6000 KH2-GATA4 and 6000 KH2-WT (empty) cells were added per well in 400 Microwell AggreWell 24 well plates. In 800 Microwell plates a total number of 4500 KH2-CDX2, 1500 KH2-GATA4 and 1500 KH2-WT (empty) cells were added per well in AggreWell 24 well. The cell mixture was added as 1 ml per well (final volume of each well of 24 well is 1.5 ml), 25 cells/well.

Day 0—The plate was centrifuged at 100×g for 3 minutes and this was marked as day and then placed into static incubator at 37° C., 5% Co2 and 20% O2.

On Day 1, 1 ml of media was gently aspirated from each well and replaced with pre-warmed 1 ml of fresh AM+20% FBS+DOX, as indicated in FIG. 19A.

On day 2, 1 ml of media was gently aspirated from each well and replaced with pre warmed 1 ml of fresh AM+20% FBS), as indicated in FIG. 19A.

On day 3, 1 ml of media was gently aspirated from each well and replaced with pre-warmed 1 ml of IVC1 media with 20% FBS, as indicated in FIG. 19A.

On day 4, embryos were transferred with a 3 ml Plastic Pasteur Pipette to a 15 ml falcon tubes, allowed to sit for 5 minutes, and most media was gently removed leaving embryos in ~1 ml media. The embryos were then moved with the pipette gently in petri dish (35 mm Corning 430588 plates) or 6 well plates (Costar 3736) or iBidi plates with 4 ml of IVC1 media with 30% FBS (as indicated in FIG. 19A) and incubated on a shaker rotating at 60 rpm in a static incubator (37° C., 20% O2 and 5% Co2).

On day 5, 2-3 ml of media was gently aspirated with manual pipette and replaced with fresh IVC1 media with 30% HAS, as indicated in FIG. 19A (bringing back to a total volume of 4 ml) and kept on the shaker at 60 rpm in a static incubator (37° C., 20% O2 and 5% Co2).

At days 6 and 7—each day 2-3 ml of media was gently aspirated with a manual pipette and replaced with fresh EUCM media supplemented with D-Glucose 4 mg/ml and sodium-pyruvate 1 mM as indicated in the FIG. 19A (bringing back to a total volume of 4 ml).

At day 8 up to day 13—high quality embryos were selected and transferred into previously described ex utero roller culture system (Alejandro-Castrjon et al. Nature 2021) in fresh EUCM media supplemented with D-Glucose 4 mg/ml and sodium-pyruvate 1 mM and incubated at 20% O2, 5% Co2 and 6.5 Psi, as indicated in FIG. 19A.

Co-aggregation and culture (FIG. 20A)—Co-aggregation was defined as time point 0 of the protocol and was made from three starting PSC cell types:

KH2 WT ESC (To give rise to embryo proper);

Dox pre-treated KH2-GATA4 (to give rise to extraembryonic primitive endoderm (Pre) lineage); and KH2-CDX2 naïve ESCs (to give rise to entire extraembryonic trophectoderm lineage) pre-treated with DOX, LPA (500 nM, 1-Oleoyl lysophosphatidic acid sodium salt: functions as a HIPPO pathway inhibitor and YAP translocator to the nucleus), FGF4 (25 ng/ml, Peprotech) and Heparin 0.2 unit/ml (Sigma H3149).

Cells were trypsinised with 0.05% trypsin-EDTA for 3-5 minutes followed by feeder depletion on gelatinized plates for 20 minutes at 37° C. (when MEFs were used). Cells were resuspended in aggregation media (AM) supplemented with Doxycycline (2 µg/ml final concentration). Following cell count, a total number of 18000 KH2-CDX2, 6000 KH2-GATA4 and 6000 KH2-WT (empty) cells were added per well in 400 Microwell AggreWell 24 well plates. In 800 Microwell plates, a total number of 4500 KH2-CDX2, 1500 KH2-GATA4 and 1500 KH2-WT (empty) cells were added per well in AggreWell 24 well. The cell mixture was added as 1 ml per well (final volume of each well of 24 well is 1.5 ml), 25 cells/well.

Day 0—The plate was centrifuged at 100×g for 3 minutes and this was marked as day and then placed into static incubator at 37° C., 5% Co2 and 20% O2.

On Day 1, 1 ml of media was gently aspirated from each well and replaced with pre-warmed 1 ml of fresh AM+20% FBS+DOX, as indicated in FIG. 20A.

On day 2, 1 ml of media was gently aspirated from each well and replaced with pre-warmed 1 ml of fresh AM+20% FBS, as indicated in FIG. 20A.

On day 3, 1 ml of media was gently aspirated from each well and replaced with pre-warmed 1 ml of EUCM2 (CMRL/advDMEM-F12 based) media with 20% FBS, as indicated in FIG. 20A.

On day 4, embryos were transferred with a 3 ml Plastic Pasteur Pipette to a 15 ml falcon tubes, allowed to sit for 5 minutes, and most media was gently removed leaving embryos in ~1 ml media. The embryos were then moved with the pipette gently into petri dish (35 mm Corning 430588 plates) or 6 well plates (Costar 3736) or iBidi plates with 4 ml of EUCM3 (CMRL/advDMEM-F12 based) media with 30% FBS (as indicated in FIG. 20A) and incubated on a shaker rotating at 60 rpm in a static incubator (37° C., 20% O2 and 5% Co2).

On day 5, 2-3 ml of media was gently aspirated with a manual pipette and replaced with fresh EUCM4 (CMRL/advDMEM-F12 based) with 30% HAS, as indicated in FIG. 20A (bringing back to a total volume of 4 ml) and kept on the shaker at 60 rpm in a static incubator (37° C., 20% O2 and 5% Co2).

At days 6 and 7—each day 2-3 ml of media was gently aspirated with a manual pipette and replaced with fresh EUCM media supplemented with D-Glucose 4 mg/ml and sodium-pyruvate 1 mM and 1× NEAA as indicated in FIG. 20A (bringing back to a total volume of 4 ml).

At day 8 up to day 13—high quality embryos were selected and transferred into previously described ex utero roller culture system (Alejandro-Castrjon et al. Nature 2021) in fresh EUCM media supplemented with D-Glucose 4 mg/ml, sodium-pyruvate 1 mM and 1× NEAA and incubated at 20% O2, 5% Co2 and 6.5 Psi, as indicated in FIG. 20A.

Co-aggregation and culture (FIGS. 21 and 22)—Co-aggregation was defined as time point 0 of the protocol and was made from three starting PSC cell types:

KH2 WT ESC (To give rise to embryo proper);
KH2-GATA4 (to give rise to extraembryonic endoderm lineage) pre-treated with Dox and CHIR99021; and
KH2-CDX2 (to give rise to entire trophectoderm lineage) pre-treated with DOX and LPA.

The protocols were as described hereinabove for e.g. FIG. 20A with the modifications as indicated in FIGS. 21 and 22, respectively.

Immunostaining and Microscopy—As described in Example 1 herein above.

Real-Time PCR analysis—As described in Example 1 herein above.

Results

The present inventors have devised a novel and inventive method to generate advanced synthetic embryos made solely from naïve ESCs or iPSCs, by transiently inducing overexpression of a factor that induces differentiation to extra embryonic primitive endodermal (Pre) cells such as Gata4 and/or Gata6 in a subpopulation of the naïve PSCs, transiently inducing overexpression of a factor that induces differentiation to trophectoderm cells such as Cdx2 and/or Gata3 and/or Gata2 and/or nuclear YAP in another subpopulation of the naïve PSCs and mixing and aggregating the two subpopulations with the same naïve PSCs that were not subjected to transient overexpression. Following, the generated aggregates may be grown ex utero to complete gastrulation and organogenesis or injected to the uterus to continue growth in-utero.

To this end, instead of using stable TSC lines made from the transgenic ESC lines described in Example 1 hereinabove and stabilized after several passages (at least 3 passages, 15 days), which might alter their characteristics, naïve mESCs that transiently overexpress Cdx2 upon addition of DOX in the early stages of embryo aggregation protocol were generated, in order to induce their rapid transition into early trophectoderm (TE). In addition, instead of using the blastocysts derived XEN cells described in Example 1 hereinabove, naïve niESCs that transiently overexpress Gata4 upon addition of DOX in the early stages of embryo aggregation protocol were generated, in order to induce their rapid transition into the extraembryonic primitive endoderm lineage.

Indeed, co-aggregation of these three stem cell populations, all originating from naïve ESCs/iPSCs as a starting material, followed by ex-utero culturing enabled generation of organized embryos, as exemplified in FIGS. 15A-23D). Interestingly, the equivalence between the culturing days and embryonic stages was as follows: Day 0—E3; Day 1—E3.5; Day 2—E4; Day 3—E4.5; Day 4—E5; Day 5—E6; Day 6—E7; Day 7—E8; Day 8—E9; Day 9—E10; Day 11—E12; Day 12—E13.

Real-time PCR analysis indicated that KH2-Gata4 cells significantly upregulate the endogenous extraembryonic ectoderm markers Gata4, Gata6 and PDGFRA following DOX induction in 2i/LIF (FIG. 24). Interestingly, while Dox treatment is stopped at day 2 of the culturing protocol (see e.g. FIG. 17A), embryos obtained at Day 4 of the protocol retain very high expression of endogenous extraembryonic ectoderm markers Gata4, Gata6 and PDGFRA (FIG. 24). In the same manner, real-time PCT analysis indicated that KH2-Cdx2 cells significantly upregulate the endogenous trophectoderm markers Elf5, Gata2, Gata3, Cdx2, Ap2gmma (also known as Tfap2c) and Hand1 (FIGS. 25-27). Interestingly, while Dox treatment is stopped at day 2 of the culturing protocol (see e.g. FIG. 17A), embryos obtained at Day 4 of the protocol retain very high expression of endogenous trophectoderm markers Elf5, Gata2, Gata3, Cdx2, Ap2gmma, EOMES, ETS2 and Hand1 (FIGS. 25-26).

Example 3

Aggregation of Three Mouse Naïve Pscs Subpopulations Generates an Organized Embryo Materials and Methods Animals—Natural in utero developed embryos were obtained from female mice 5-8 weeks old ICR or BDF1 mated with BDF1 male studs (Harlan). Insemination was verified the next morning by the presence of a copulatory plug, and this day was defined as embryonic day (E0.5). All animal experiments were performed according to the Animal Protection Guidelines of Weizmann Institute of Science and approved by relevant Weizmann Institute IACUC (#01390120-1, 01330120-2, 33520117-2). Mice were housed in a standard 12-hours light/12-hours dark cycle conditions in a specialized and certified animal facility.

Stem cell lines—The following mouse ES lines were used: WT V6.5 ESCs (C57B6/129sJae), BVSC ESC (Mixed BDF1×B6 background) and KH2-WT ESC line carrying both M2RtTa allele in the Rosa26 locus and a modified Col1 locus with an FRT site to efficiently insert Tet-ON regulated alleles as previously described (Hochedlinger et al., 2005). The previously described BVSC ESC lines (Hayashi et al., 2011) carries Blimp1-mVenus and Stella-Cfp (BVSC) reporter alleles which can be useful for tracking PGC formation.

Stem cells in vitro culture conditions—Golden stocks of mouse ESCs were cultured on feeder layer of irradiated mouse embryonic fibroblast (MEFs) and maintained (and gene targeted when relevant) in conventional mouse ES medium (Serum/LIF) composed of 1× DMEM (GIBCO 41965) supplemented with 20% FBS (heat inactivated and filtered), 1 mM GlutaMAX (GIBCO, 35050061), 1% penicillin streptomycin (Biological Industries—Sartorius 03-031-1B), 1% Sodium Pyruvate (Biological Industries—Sartorius 03-042-1B), 1% nonessential amino acids (Biological Industries—Sartorius 01-340-1B), 0.1 mM β-mercaptoethanol (Thermo 31350010), 10 ng/ml recombinant human LIF (in-house prepared).

To convert the cells into ground state naïve ESCs in 2i/LIF conditions, ESCs were maintained and expanded in serum-free chemically defined N2B27-based media: 240 ml Neurobasal (Thermo 21103049) and 240 ml of DMEM-F12 with HEPES (SIGMA D6421), 5 ml N2 supplement (Invitrogen; 17502048), 5 ml B27 supplement (Invitrogen; 17504044 or in house prepared), 1 mM GlutaMAX (GIBCO, 35050061), 1% nonessential amino acids (Biological Industries—Sartorius 01-340-1B), 0.1 mM β-mercaptoethanol (Thermo 31350010), 1% penicillin-streptomycin (Biological Industries—Sartorius 03-031-1B). Naïve 2i/LIF conditions for murine PSCs included 20 ng/ml recombinant human LIF (in-house made) and small-molecule inhibitors CHIR99021 (CHIR, 3 µM-Axon Medchem 1386) and PD0325901 (PD, 1 µM—Axon Medchem 1408) (referred to as 2i). Murine naïve ESCs were expanded on feeder layer (MEFs) or on 0.2% gelatin-coated plates. At least three passages in 2i/LIF conditions were applied before initiation of experimentation. Mouse naïve ESC lines were used up to 15 passages in 2i/LIF conditions. For maintenance ESCs were passaged with 0.25% trypsinization every 3-5 days.

KH2-Gata4 Dox inducible naïve pluripotent stem cells (KH2-GATA4)—As described in Example 1 hereinabove.

KH2-Cdx2 Dox inducible naïve pluripotent stem cells (KH2-Cdx2)—As described in Example 2 hereinabove.

Generation of ELF5 EYFP-NLS reporter on KH2-Cdx2 ESCs—iCdx2 (KH2-CDX2) validated clone 3 was used for CRISPR targeting EYFP in 3' end of mouse ELF5 gene. Cells we co-transfected with previously generated nuclear EYFP plasmid (Addgene #128833) and guide RNA plasmid (#128836). Following neomycin and ganciclovir antibiotic selection for 10 days, total clonal population was transfected with Cre and subcloned. Single cell clones were validated for correct insertion: at 3' end using forward ATGGTCCTGCTGGAGTTCGTGAC (SEQ ID NO: 37) and reverse TGGTCCATCTGCTTGTAGGCAAGA (SEQ ID NO: 38) primer pair, and at 5' end using forward TTCACCTTTGAAGCTAATCGTTTGAGG (SEQ ID NO: 39) and reverse AACTTGTGGCCGTTTACGTCGC (SEQ ID NO: 40) primer pair. Correctly targeted clones were further validated for off-target insertions by Southern blot analysis.

Generation of fluorescent labeled ESCs—KH2 WT ESCs, KH2-Gata4 clone 7 (iGata4) and KH2-Cdx2 clone 3 (iCdx2) were transduced with FUGW lentivirus particles constitutively expressing either fluorescent BFP, GFP or mCherry proteins, respectively. For the generation of lentivirus, HEK293T cells were plated in 10 ml DMEM, containing 10% FBS and Pen/Strep in cm dishes, in aliquots of 5.5 million cells per well. On the next day, cells were transfected with the third generation Addgene lentivirus vectors [0.8 µg of pRSV-Rev (Addgene 12253), 0.8 µg of pMDLg/pRRE (Addgene 12251), 1.6 µg of pMD2.G (Addgene12259)], using jetPEI™ transfection reagent, along with 16 µg of the target plasmid of each transduced fluorescent proteins BFP, GFP and mCherry. The supernatant containing the virus was collected 48 hours and 72 hours following transfection, filtered using 0.45 µm filter and freezed in −80° C. in 1 ml aliquots. ESCs were plated in FBS/Lif condition on gelatin coated 6-well plates at low density and transduced with lentivirus in the presence of protamine sulfate (8 µg/ml). 48 hours later the infected ESCs were expanded for 1-3 passages and sorted for positive population and further expanded for experimentation.

Isolation of human umbilical cord blood serum—Collection of human cord blood serum was done as described previously (Aguilera-Castrejon et al., 2021b) following the guidelines approved by Rambam Medical Center Helsinki committee (#RMB-0452-15). Healthy women over the age of 18 and under 40 who gave their consent and were scheduled for caesarian section delivery were eligible for cord blood collection. Blood was manually drawn by the obstetrician surgeon, using a large bore 14-gauge needle and a 50 mL syringe, directly from the umbilical cord. In brief, blood was collected and quickly distributed to ⅝ mL procoagulant sterile test tubes (Greiner Bio-One, Z Serum Sep Clot Activator, #456005) and cooled to 4° C. for 15 minutes, followed by centrifugation at 2500 G for 10 minutes at 4° C. Tubes showing signs of hemolysis were discarded. Serum was filtered through a 0.22 µM filter (Nalgene, Ref #565-0020), heat-inactivated at 55° C. in a water bath for 45 minutes and immediately aliquoted and stored at −80° C. for up to six months.

Co-aggregation and culture—AggreWell 24-well plate 400 (STEMCELL Technologies 34415), or AggreWell 24-well plate 800 (STEMCELL Technologies 34815) were used with equivalent outcome. AggreWell plate preparation was done according to manufacturer instructions. Briefly, 500 µl of anti-adherence rinsing solution (STEMCELL Technologies 07010) was added to each well. Plate was centrifuged at 2,000×g for 5 minutes and incubated 30 minutes at room temperature. After incubation, rinsing solution was removed and the plate was washed twice with PBS. 500 µl of aggregation media AM supplemented with DOX (2 µg/ml final concentration—Sigma D9891) and ROCKi Y27632 (5 nM final concentration—Axon Medchem 1683) was added to each well. The aggregation media contained: 1× DMEM (GIBCO-41965) supplemented with 20% FBS (GIBCO), 1 mM GlutaMAX (GIBCO, 35050061), 1% penicillin streptomycin (Biological Industries—Sartorius 03-031-1B), 1% Sodium Pyruvate (Biological Industries—Sartorius 03-042-1B), 1% nonessential amino acids (Biological Industries—Sartorius 01-340-1B) and 0.1 mM β-mercaptoethanol (Thermo 31350010).

To generate the synthetic embryos, referred to herein as "sEmbryo iCdx2", three starting PSC cell types were co-aggregated:
1) naïve WT ESCs (either KH2-WT, BVSC or V6.5 ESC) in 2i/LIF;
2) naïve iGata4 ESCs in 2i/LIF pre-treated with DOX (2 µg/ml-Sigma D9891) in 2iLIF media for 24 hours prior to the co-aggregation; and
3) naïve iCdx2 ESCs in 2i/LIF pretreated with DOX (2 µg/ml-Sigma D9891) for different time points (−1 day to −14 days prior to the co-aggregation) in TSC media (25 ng/ml FGF4 (Peprotech), 1µ/ml Heparin (Sigma)) supplemented with lysophosphatidic acid (LPA, a Hippo pathway inhibitor) 0.5-1 µM.

Co-Aggregation was Defined as Time Point 0 of the Protocol

At the day of aggregation (day 0), the three donor cell populations were trypsinized with 0.05% trypsin-EDTA solution (Biological Industries—Sartorius 03-053-1B) for 4 minutes at 37° C. Trypsin enzymatic reaction was stopped by adding aggregation media. Cells were centrifuged at 1200 rpm for 3 minutes and resuspended in aggregation medium with DOX (2 µg/ml-Sigma D9891) and ROCKi Y27632 (5 nM final concentration—Axon Medchem 1683). Following, cells were plated on gelatinized tissue culture plates for mouse embryonic fibroblast depletion for 20 minutes at 37° C. Supernatant was collected, centrifuged and cells were resuspended. The three cell fractions were counted and resuspended in aggregation media with DOX (2 µg/ml-Sigma D9891) and ROCKi Y27632 (5 nM—Axon Medchem 1683). A ratio of (1 WT-ESCs:1 iGata4 ESC:3.33 iCdx2 ESC) was maintained in aggregation experiments, as follows:

|  | Number of microwells per well in 24 well plate | Number of added cells per each well of a 24 well plate | # of Cells per single microwell |
|---|---|---|---|
| AggreWell 800 | 300 | 1-iCDX2: 5000 cells<br>2-iGATA4: 1500 cells<br>3-WT ESC 1500 cells | ~27 cells |
| AggreWell 400 | 1200 | 1-iCDX2: 20000 cells<br>2-iGATA4: 6000 cells<br>3-WT ESC 6000 cells | ~27 cells |

1 ml of cell-mix suspension was gently added drop wise to each well of the AggreWell plate followed by centrifugation at 700 rpm for 3 minutes and incubation at 37° C. (total end volume is 1.5 ml).

On the next day (day 1), 1 ml of media (out of total 1.5 ml) was gently removed from each well and replaced with 1 ml of preheated aggregation media with DOX (2 µg/ml-Sigma D9891).

On day 2, 1 ml of media was removed from each well and replaced with 1 ml of preheated aggregation media.

On day 3, 1 ml of media was removed from each well and replaced with 1 ml of preheated EUCM2 media. In this example, EUCM2 media refers to: Advanced DMEM/F12 (GIBCO 21331-020), 5 ml CMRL media (1% final concentration) as a supplement (5 ml GIBCO 11530037), extra added 1 mg/ml D(+)-Glucose Monohydrate (J. T. Baker—0113) (add 500 mg per 500 ml media), 100 nM T3 (3,3',5-Triiodo-L-thyronine sodium salt) (Sigma-Aldrich, T6397), 1 mM Sodium pyruvate (Sigma-Aldrich, S8636), 1 mM GlutaMAX (GIBCO, 35050061), 1% penicillin streptomycin (Biological Industries—Sartorius 03-031-1B), 1× of ITS-X supplement (Thermo Fisher Scientific 51500-056), 8 nM B-estradiol (Sigma-Aldrich, E8875), 200 ng/ml progesterone (Sigma-Aldrich, P0130), 25 µM N-acetyl-L-cysteine (Sigma-Aldrich, A7250)+20% FBS.

On day 4, the synthetic embryos were gently transferred to 6-well cell suspension culture plates (Greiner, 657185) with 5 ml of preheated EUCM3 media per well and placed on shaker rotation 60 rpm/min (Thermo 88881102+ 88881123). In this example, EUCM3 media refers to: Advanced DMEM/F12 (GIBCO 21331-020), 5 ml CMRL media (1% final concentration) as a supplement (5 ml GIBCO 11530037), extra added 1 mg/ml D(+)-Glucose Monohydrate (J. T. Baker—0113) (add 500 mg per 500 ml media), 100 nM T3 (3,3',5-Triiodo-L-thyronine sodium salt) (Sigma-Aldrich, T6397), 1 mM Sodium pyruvate (Sigma-Aldrich, S8636), 1 mM GlutaMAX (GIBCO, 35050061), 1% penicillin streptomycin (Biological Industries—Sartorius 03-031-1B), 1× of ITS-X supplement (Thermo Fisher Scientific 51500-056), 8 nM B-estradiol (Sigma-Aldrich, E8875), 200 ng/ml progesterone (Sigma-Aldrich, P0130), 25 µM N-acetyl-L-cysteine (Sigma-Aldrich, A7250)+30% FBS.

On day 5, egg cylinder shape sEmbryos were picked and transferred to glass culture bottles (50-30 embryos per bottle) containing 2 mL of EUCM media (the contents of which are described in Example 1 hereinabove). Following, the bottles were placed on the rolling culture system previously described electronically controlled roller culture platform (Aguilera-Castrejon et al., 2021a), rotating at 30 revolutions per minute at 37° C., and continuously gassed with an atmosphere of 21% $O_2$, 5% $CO_2$ at 7-8 pounds per square inch (psi). A black non-transparent cloth was used to cover the incubator from light during unit operation.

From day 6 to day 8, 1 ml of EUCM was replaced with preheated 1 ml of EUCM and kept on rolling culture system. Culture media was pre-heated for at least an hour by placing it inside a glass bottle on the rotating culture.

Whole-mount immunostaining—synthetic embryos grown ex utero and equivalent in utero controls were fixed with 4% PFA EM grade (Electron microscopy sciences, 15710) in PBS at 4° C. over-night. Natural embryos were dissected removing the Reichert's membrane for E6.5-E7.5 embryos, or the yolk sac and amnion for E8.5 embryos and washed once with 1×PBS before fixation. Synthetic embryos were then washed in PBS for 5 minutes 3 times, permeabilized in PBS with 0.5% Triton X-100/0.1 M glycine for 30 minutes, blocked with 10% normal donkey serum/0.1% Triton X-100 in PBS for 1 hour at room temperature (RT), and incubated over-night at 4° C. with primary antibodies, diluted in blocking solution. Following, embryos were rinsed 3 times for 5 minutes each in PBS/0.2% TritonX-100, incubated for 2 hours at room temperature with secondary antibodies diluted 1:200 in blocking solution (all secondary antibodies were from Jackson ImmunoResearch), counter-stained with DAPI (1 µg/ml in PBS) for 10 minutes, and washed with PBS for 5 minutes 3 times. Yolk sacs isolated from natural and synthetic embryos were fixed and stained following this protocol. The primary antibodies used were the following: Rabbit polyclonal anti-Gata4 (Abcam, Ab84593) 1:200; Rabbit polyclonal anti-Foxa2 (Abcam, Ab40874) 1:100; Goat polyclonal anti-Sox2 (R&D, AF2018) 1:200; monoclonal anti-Myosin Heavy Chain II (MF-20) (R&D, MAB4470) 1:200; Goat polyclonal anti-Sox17 (R&D, AF1924) 1:100; Rabbit monoclonal anti-Brachyury (Cell Signaling, 81694) 1:100; Rabbit polyclonal anti-Cdx2 (ab76541) 1:100; Mouse monoclonal anti-Oct4 (Santa Cruz, SC-5279) 1:100; Goat polyclonal anti-Otx2 (R&D, AF1979) 1:200; Goat polyclonal anti-TFAP2C/AP2γ (R&D, AF5059) 1:100; Goat polyclonal anti-Gata6 (R&D, AF1700) 1:100; Rabbit polyclonal anti-Eomes/Tbr2 (Abcam, Ab23345) 1:50; Rat Monoclonal anti-Cerberus 1 (R&D, MAB1986) 1:100; Rabbit polyclonal anti-Sox9 (Millipore, Ab5535) 1:100; Mouse monoclonal anti-Gata3 (Invitrogen, MA1-028) 1:100, Rabbit polyclonal anti-Nanog (Bethyl, A300-397A) 1:100; Goat polyclonal anti-Elf5 (Santa Cruz, sc9645) 1:100; Goat polyclonal anti-DKK1 (R&D, AF1096) 1:100 or Goat polyclonal anti-Brachyury (R&D, AF2085) 1:100.

Immunohistochemistry—For OCT-staining, on day 8 of the protocol, the synthetic embryos were fixed overnight in 4% PFA at 4° C., washed three times in PBS for 10 minutes each and submerged first in 15% Sucrose/PBS and then 30% sucrose overnight at 4° C. The day after, samples were subjected to increasing gradient of OCT concentration in Sucrose/PBS followed by embedding in OCT on dry ice and stored at −80° C. until further processing. Cryoblocks were cut with LEICA CM1950 and washed once with 1×PBS and incubated with 0.3% $H_2O_2$ for 20 minutes. Following permeabilization with 0.1% Triton X-100 in PBS for 10 minutes, slides were washed three times with 1×PBS for 2 minutes each and blocked in 10% normal donkey serum in PBS in humidified chamber for 20 minutes at room temperature. Slides were then incubated with a primary antibody diluted in antibody solution (1% BSA in 0.1% Triton X-100) at 4° C. overnight. Sections were then washed three times (5 minutes each) in 0.1% Triton X-100 in PBS, incubated with the appropriate secondary antibodies diluted in antibody solution at room temperature for 1 hour in the dark, counterstained with DAPI for 20 minutes and mounted with Shandon Immuno-Mount (Thermo Scientific, 9990412). The primary antibodies used were the following: Rabbit polyclonal anti-Gata4 (Abcam, Ab84593) 1:100; Rabbit polyclonal anti-Foxa2 (Abcam, Ab40874) 1:100; Goat polyclonal anti-Sox2 (R&D, AF2018) 1:100; Goat polyclonal anti-GATA6 (R&D, AF1700) 1:100; monoclonal anti-Myosin Heavy Chain II (MF-20) (R&D, MAB4470) 1:100 or Rabbit polyclonal NKX2.5 (Abcam, Ab97355) 1:100.

Confocal microscopy—Whole-mount immunofluorescence and immunohistochemistry images were acquired with a Zeiss LSM 700 inverted confocal microscope (Carl Zeiss) equipped with 405 nm, 488 nm, 555 nm and 635 nm solid state lasers, using a Plan-Apochromat 20× air objective (numerical aperture 0.8) for E5.5/E6.5 embryos, and an EC Plan Neofluar 10× air objective (numerical aperture 0.3) for synthetic embryos. Images were acquired at 1024×1024 resolution. All images were acquired within the following range of parameters: Laser power: 405 nm: 10-20%; 488 nm: 5-20%; 555 nm 10-40%; 635 nm: 30-80%. Gain ranged from 350 to 600. Pixel size was 1.25 µm with a z-step of 15 µm when using the 10× objective, or 0.5 µm with z-step of 5 µm when using the 20× objective. For confocal imaging synthetic embryos were mounted in 35 mm glass bottom dishes (In Vitro Scientific, D35201.5N). Images and maximum intensity projections were processed using Zen 2 blue edition software 2011 (Carl Zeiss) and Adobe Photoshop CS4.

Assessment of length—Morphometric measurements were performed using bright field images of synthetic embryos at the indicated time points. Length of the proximal-distal axis was measured for synthetic embryos at both day 4 and day 5. Antero-posterior axis was measured for synthetic embryos from day 8. Measurements were performed using the CellSens Entry software (Olympus). Length of in utero control natural embryos was used for comparison at matched embryonic stages as indicated.

Yolk sac erythroid progenitor staining—Synthetic embryos at day 8 of the protocol and natural E8.5 derived yolk sacs were dissected. Single cells flow cytometry staining was effected using MacsQuant VYB instrument (Miltenyi, Bergisch Gladbach, Germany). Data was analyzed with FlowJo. Staining was performed for 30 minutes at 4° C. in flow cytometry buffer (PBS, 10% fetal bovine serum and 0.02% azide). For erythroid progenitor staining, a biotinylated lineage cocktail of CD4, CD8, B22, CD11b, GR-1 and Ter119 (Miltenyi), together with anti-cKit APC (2B8), CD41 VG (MRW), CD45 PE (30-F11) (all from Biolegend) and CD34 PB (RAM34, eBioscience) was used, as previously described (Iturri et al., 2021). Streptavidin-PE-Cy7 (Biolegend) was used as a secondary conjugated antibody.

Erythroid colony forming assay—Harvested cells from day 8 or E8.5 yolk sacs were prepared as single cell suspension in Iscove's modified Dulbecco's medium supplemented with 2% FBS (GIBCO) and 1% penicillin streptomycin (Invitrogen). Isolated cells were plated in triplicate at a density of ($1\times10^6$) cells per 1.1 ml of Metho-Cult medium (Stem Cell Technologies,™ SF M3436) in 35-mm dish and maintained at 37° C. with 5% $CO_2$ for 12 days before being scored for primitive erythroid colonies. Colonies were visualized and validated with a bright field microscope A1 microscope (Zeiss).

RNA extraction & RT-PCR analysis—Total RNA was isolated using RNeasy mini kit (Qiagen) following manufacturer instructions. 1 µg of total RNA was reverse transcribed using a High-Capacity Reverse Transcription Kit (Applied Biosystems). RT-PCR was performed in triplicate using SYBR Green PCR Master Mix (QIAGEN) and run on Viia7 platform (Applied Biosystems). Values were normalization to ACTIN and/or GAPDH across all experiments, data is presented as fold difference compared reference sample set as 1. The following primers were used:

```
mGata3-Forward:
                                (SEQ ID NO: 41)
CTCGGCCATTCGTACATGGAA;

mGata3-Reverse:
                                (SEQ ID NO: 42)
GGATACCTCTGCACCGTAGC;

mGata2 Forward:
                                (SEQ ID NO: 43)
CACCCCGCCGTATTGAATG;

mGata2 Reverse:
                                (SEQ ID NO: 44)
CCTGCGAGTCGAGATGGTTG mElf5 Forward:
                                (SEQ ID NO: 45)
ATGTTGGACTCCGTAACCCAT;

mElf5-Reverse:
                                (SEQ ID NO: 46)
GCAGGGTAGTAGTCTTCATTGCT;

mHand1F:
                                (SEQ ID NO: 47)
GGCAGCTACGCACATCATCA;

mHand1 Reverse:
                                (SEQ ID NO: 48)
CCTGGCATCGGGACCATAG;

Total mCdx2 Forward:
                                (SEQ ID NO: 12)
GCGAAACCTGTGCGAGTGGATG;

Total mCdx2 Reverse:
                                (SEQ ID NO: 13)
CGGTATTTGTCTTTTGTCCTGGT;

mFgfr2 Forward:
                                (SEQ ID NO: 49)
GCCTCTCGAACAGTATTCTCCT;

mFgfr2 Reverse:
                                (SEQ ID NO: 50)
ACAGGGTTCATAAGGCATGGG;

Endogenous mGata4 Forward:
                                (SEQ ID NO: 32)
CACTGGAAAAGCCTGCGTTCTTACA;
```

Endogenous mGata4 Reverse:
(SEQ ID NO: 33)
AGAATAAGGAAGGAAGAAGTCTCTTGCCTC;

Endogenous mCdx2 Forward:
(SEQ ID NO: 34)
AATTATGGACCTCAGGGGAAGACATG;

Endogenous mCdx2 Reverse:
(SEQ ID NO: 35)
GCTGGCAGGAAGAGTCGGAATG;

mDppa1-Forward:
(SEQ ID NO: 51)
ATGATGTCCCTTCAAGTCCTCA;

mDppa1-Reverse:
(SEQ ID NO: 52)
TGTGTTGGGATCACTTCAGTGT;

Total mGata4-Forward:
(SEQ ID NO: 14)
CACAAGATGAACGGCATCAACC;

Total mGata4-Reverse:
(SEQ ID NO: 15)
CAGCGTGGTGGTAGTCTG;

mGata6-Forward
(SEQ ID NO: 53)
TCAGGGGTAGGGGCATCAG;

mGata6-Reverse:
(SEQ ID NO: 54)
GTAGAGGCCGTCTTGACCTG;

mGapdh-Forward:
(SEQ ID NO: 2)
AGTCAAGGCCGAGAATGGGAAG;

mGapdh-Reverse:
(SEQ ID NO: 3)
AAGCAGTTGGTGGTGCAGGATG;

mSox17-Forward:
(SEQ ID NO: 55)
AGCAGAACCCAGATCTGCAC;

mSox17-Reverse:
(SEQ ID NO: 56)
CGCCTTCCAAGACTTGCCTA;

mActin-Forward:
(SEQ ID NO: 57)
GATATCGCTGCGCTGGTCG;

mActin-Reverse:
(SEQ ID NO: 58)
CCACGATGGAGGGGAATACAG;

mHnf4a-Forward:
(SEQ ID NO: 59)
TGTTGCTAACACGATGCCCT;

mHnf4a-Forward:
(SEQ ID NO: 60)
GGCCACTCACACATCTGTCC;

Foxa2-Forward:
(SEQ ID NO: 61)
GCACTCGGCTTCCAGTATGC;

Foxa2-Reverse:
(SEQ ID NO: 62)
CGTAGTAGCTGCTCCAGTCG;

mPdgfra-Forward:
(SEQ ID NO: 63)
AGTGGCTACATCATCCCCCT;

mPdgfra-Reverse:
(SEQ ID NO: 64)
CCGAAGTCTGTGAGCTGTGT.

Bulk RNA-seq (Bulk MARS-seq)—RNA-seq libraries were prepared at the crown genomics institute of the Nancy and Stephen Grand Israel National Center for Personalized Medicine, Weizmann Institute of Science. A bulk adaptation of the MARS-Seq protocol (Keren-Shaul et al.) was used to generate RNA-Seq libraries for expression profiling different samples (3 biological replicates from each). Briefly, 60 ng of input RNA from each sample was barcoded during reverse transcription and pooled. Following Agencourct Ampure XP beads cleanup (Beckman Coulter), the pooled samples underwent second strand synthesis and were linearly amplified by T7 in vitro transcription. The resulting RNA was fragmented and converted into a sequencing-ready library by tagging the samples with Illumina sequences during ligation, RT, and PCR. Libraries were quantified by Qubit and TapeStation as previously described (Keren-Shaul et al.). Sequencing was done on a NovaSeq600 using an SP 100 cycles kit (Illumina).

Bulk RNA-seq analysis—Samples were analyzed using UTAP software. Reads were trimmed using CutAdapt (Martin 2011) (parameters: -a ADAPTER1 -a "A{10}" -a "T{10}" -A "A{10}" -A "T{10}" -times 2 -u 3 -u -3 -q 20 -m 25). Reads were mapped to genome mm10 using STAR v2.4.2a (parameters: -alignEndsType EndToEnd, -outFilter-MismatchNoverLmax 0.05, -twopassMode Basic—align-SoftClipAtReferenceEnds No).

Sample counting was done using STAR, quantifying mm10 RefSeq annotated genes. Further analysis was done for genes having a minimum of five reads in at least one sample. Normalization of the counts and differential expression analysis was performed using DESeq2 (Love et al. 2014) with the parameters betaPrior=true, cooksCutoff=false, and independentFiltering=false. Raw P-values were adjusted for multiple testing using the procedure of Benjamini and Hochberg. Hierarchical clustering was generated in UTAP software. Expression heatmap was generated using R pheatmap package.

10× single cell RNA-seq—E8.5 natural embryos and day 8 synthetic embryos were selected for single cell RNA-sequencing. Several samples were sequenced, one samples represents sEmbryo iCdx2 short term DOX induced (from Day-1 until Day +2) and two samples represent sEmbryo iCdx2 10 day dox induced (from Day −8 until Day +2). Moreover, to obtain sampling of single embryo based single cell RNA-seq (rather than relying only on pooled samples 2 embryos), a single sEmbryo from short term induced iCdx2 was processed and sequenced. All synethetic embryos samples were processed including extraembryonic compartments without any dissection. synthetic embryos were dissociated using Trypsin-EDTA solution A 0.25% (Biological Industries; 030501B). Trypsin was neutralized with media including 10% FBS and cells were washed and resuspended in 1× PBS with 400 μg/ml BSA. Cell suspension was filtered with a 100 μm cell strainer to remove cell clumps. A percentage of cell viability higher than 90% was determined by trypan blue staining. Cells were diluted at a final concentration of 1000 cells/scRNA-seq libraries were generated using the 10× Genomics Chromium v3 system (5000 cell target cell recovery) and sequenced on on Illumina NovaSeq 6000 platform according to the manufacturer's instructions.

10× Single cell RNA-seq analysis—10× Genomics data analysis was performed using Cell Ranger 7.0 software (10×

Genomics) for pre-processing of raw sequencing data, and Seurat 3.6.3 for downstream analysis. The mm10-3.0.0 gene set downloaded from 10× was used for gene reference requirements. To filter out low-expressing single cells, possible doublets produced during the 10× sample processing, or single cells with extensive mitochondrial expression, we filtered out cells with under 200 expressing genes, over 4,000 expressing genes and over 15% mitochondrial gene expression. Filtering reduced the cell count from overall 61,816 to 46,428 cells across all samples. Seurat integrated analysis and anchoring of all individual samples was performed and then normalized by log-normalization using a scale-factor of 10,000. The top 2,000 variable genes were identified by the variance stabilizing transformation method, and subsequently scaled and centered. Principal components analysis was performed for dimensional examination using the 'elbow' method. The first 15 dimensions showed the majority of data variability. Therefore, UMAP dimensional reduction was performed on the first 15 dimensions in all samples. Clusters were detected using Seurat FindClusters function, with resolution parameter=0.6.

For cluster annotation, the area under the curve (AUC) methodology was used to identify the enrichment of each annotated gene-set to each individual single cell. The annotations were based on published gene annotations (Ibarra-Soria et al., 2018), and performed using the R package AUCELL 1.8.035, using parameters: aucMaxRank=100 (5% of the total gene count) under the AUCell_calcAUC function. Each cell was then annotated to a single tissue based on its highest AUC score prediction. Each tissue was then cross-tabulated with each cluster to assess cluster-tissue overlap, and additionally normalized by z-score and ranged to 0-1 for plotting purposes. Next, to evaluate the probability of a certain cluster being enriched in a certain tissue, the annotated AUC predictions of each cell to a tissue was used to compare the observed cluster annotation of each cell, thus producing a P value based on Mann-Whitney U statistics. This was calculated using the R package verification—v1.42 roc. area function (CRAN.R-project(dot)org). Integration of both the predicted annotation overlap and its statistical enrichment to each duster resulted in a predicted tissue per cluster. T-Nest was used to assess significant changes in the proportional size of each cluster between natural and synthetic embryos. Expression pattern of selected genes was shown as two parameters: normalized mean expression, and enrichment of cells that express this gene (expression>0), among the specified cluster (either in natural or in synthetic originated cells).

Statistical analysis—All statistical analysis were performed using the GraphPad Prism 8 software (La Joya, California). Data on graphs indicates means plus s.e.m. of a minimum of three independent experiments, unless otherwise stated. Kolmogorov-Smirnov test was performed to check normal distribution of data before each statistical test. Significant difference between two samples was evaluated by unpaired two-sided Student's t-test if data was normally distributed or Mann-Whitney test for non-normally distributed data. p<0.05 was considered as statistically significant.

Results

As demonstrated in Example 2 hereinabove, co-aggregation of three stem cell populations, all originating from naïve ESCs/iPSCs as a starting material, followed by ex-utero culturing enabled generation of organized embryos.

Following, multiple rounds of testing and optimizations were conducted to determine the DOX pretreatment regimen compatible with a relatively more productive outcome, and to define optimal cell numbers and aggregation plates. The inventors also tested whether DOX continuation after co-aggregation of the three subpopulations (set as timepoint 0) could improve the experimental outcome.

The following conditions were selected and applied throughout Example 3 (FIG. 39A):

all steps of the protocol were done in 20% $O_2$ and 5% $CO_2$ conditions;

pre-induction of Gata4 for 24 hours in 2i/Lif conditions prior to co-aggregation;

pre-induction of Cdx2 for between 24 hours up to 14 days in TSC-LPA medium prior to co-aggregation;

400 or 800 micron AggreWell plates;

inclusion of DOX in the aggregation medium (AM) for the first 48 hours following aggregation.

a day 3, AM media was replaced by an EUCM2 which contained 20% FBS.

due to their increase in size, the aggregates were combined on day 4 and gently transferred to non-adherent tissue culture plates on a shaker placed inside a conventional tissue culture incubator and placed in EUCM3 which contained 30% FBS.

at day 5, egg-cylinder shaped embryos (FIG. 39B) were manually picked under the stereomicroscope and transferred to the ex utero roller culture system in EUCM conditions (FIG. 39C).

from day 5 to day 8 of the protocol, synthetic embryos continued to be grown in the roller culture system (20% $O_2$ plus 5% $CO_2$ and a pressure of 6.5-8 psi), and EUCM was refreshed daily. The roller culture—EUCM platform was essential for continuation of embryo development beyond day 5-6, as continuing only with the static conditions in these days yielded a detrimental outcome.

This 8 day protocol supported the self-organization and growth of naïve ESC derived aggregates into organogenesis stage synthetic embryos (also referred to herein as "sEmbryo iCdx2") that grow within extraembryonic membranes (FIGS. 39D-F), comparable to E8.5 in utero developed natural embryos as further described below.

Notably, synthetic embryos generated from the same iCdx2 and iGata4 ESCs but grown from day 4-7 in previous published IVC medium—static conditions based protocols (Bedzhov and Zernicka-Goetz, 2014; Harrison et al., 2017; Sozen et al., 2018), did not develop further than previously achieved (Amadei et al., 2021) and yielded empty yolk sacs that lack embryo proper structures (FIG. 39G).

Analysis of defined morphological traits during synthetic embryo growth were systematically compared to those classically well established in natural embryos at different time points in mouse embryogenesis (Dai et al., 2016; van Maele-Fabry et al., 1992; Mittenzweig et al., 2021; Ohinata et al., 2005; Parameswaran and Tam, 1995; Rossant and Tam, 2017; Schwarz and Hadjantonakis, 2020; Tam and Snow, 1980). The synthetic embryos originating from naïve ESCs starting populations faithfully resembled all stages of natural post-implantation development, going through luminogenesis, symmetry breaking and gastrulation, until early organ formation (FIG. 39B). Egg cylinder shape synthetic embryos start emerging on day 3 of the protocol, when aggregates start luminogenesis and an outer cell layer is formed, and without going through a blastocyst-like morphology in the earlier days. At day 4, the aggregates show similar morphology to an E5.5 embryo, with clear segregation into the epiblast (Epi) and extra-embryonic ectoderm (ExE) compartments surrounded by a layer of visceral endoderm (VE) cells (FIG. 39B). At day 5, the synthetic embryos closely resemble E6.5 in-utero embryos, showing a clear difference between the cup-shaped epiblast and the ExE, both enveloped by the VE. The Epi displays an expanded pro-amniotic cavity (PAC), and successfully break symmetry showing an incipient primitive streak in one side of the epiblast, adjacent to the ExE (FIG. 39B). After 6 days the synthetic embryos reach the neural plate stage. The amniotic folds have fused to form the amnion (Am) as expected, generating the amniotic (AC) and exocoelomic cavities (EC) (FIG. 39B), and an incipient allantoic bud (AB) can be observed in the ExE compartment at the opposite side of the neural plate. At day 7 there is a major expansion of the yolk sac (YS), which by then surrounds the embryo, mimicking what happens in natural in-utero embryos; while in the Epi compartment the anterior ectoderm begins to form a broad plate, the future neural groove, making evident the emergence of the head-to-tail axis (FIG. 39B). In the ventral part of the synthetic embryo at day 7, the migration of the primitive streak and the heart field are evident, and the foregut invagination starts to be seen, like E8.0 natural embryos (FIG. 39B). At day 8 the synthetic embryos closely resemble the morphology of E8.5 in utero embryos (FIGS. 39E-F). The dorso-ventral axis of the embryos is clearly seen by the neural folds facing the amnion dorsally versus the foregut facing the yolk sac ventrally (FIGS. 39E-F). The synthetic embryos continue growing completely enveloped inside the extra-embryonic membranes (yolk sac and amnion) and present an ectoplacental cone (EPC)-like structure in the opposite side of the embryo (FIG. 39E). The blood islands (BI) are clearly visible in the lateral sides of the yolk sac (FIG. 39E), and blood begins to circulate in the yolk sac vessels (vitelline circulation). The embryos display well-formed head folds, neural tube, invaginating foregut, beating heart, and between up to 4 pairs of somites, followed by the tail (FIG. 39F), demonstrating the complete establishment of the head-to-tail and dorso-ventral axis. The allantois extends from the posterior part of the embryo, connecting the tail to the EPC (FIG. 39E). Although there is a variation in size among adequately developed synthetic embryos at day 8, they were comparable to in utero developed natural E8.5 Embryos.

Using whole-mount immunofluorescence in natural embryos dissected at E5.5-E6.5, and in egg-cylinder synthetic embryos at day 3, 4 and 5, proper expression of canonical markers for the three cell lineages expected to be present in the mouse embryo at the egg cylinder-stage were corroborated: a cup-shaped epiblast positive for OCT4 and OTX2 (FIG. 40A); the extra-embryonic ectoderm (ExE) adjacent to the epiblast expressing CDX2, TFAP2C and EOMES (FIG. 40A); and the visceral endoderm (VE) positive for GATA4, GATA6, SOX17 and FOXA2 enveloping both compartments (FIG. 40A). OTX2 and EOMES were present also in the embryonic VE, as it occurs in natural embryos (FIG. 40A). SOX2 expression in the Epi compartment as well as the ExE was correctly recapitulated in synthetic embryos. Further, proper establishment and migration of the AVE from the distal part of the epiblast towards the future anterior part was evidenced by the staining for BMP antagonist CER1 and the WNT inhibitor DKK1 at day 4, either at the distal tip of the epiblast or asymmetrically located towards one side of the egg cylinder (FIG. 40B) similarly to as previously characterized in natural embryos and eTSC based day 4 synthetic embryos (Amadei et al., 2021). On day 5, a population of Brachyury$^+$ cells appeared at the posterior side of the epiblast near the ExE boundary, opposite to Cer 1 and DKK1, corroborating the appearance of the primitive streak and the onset of gastrulation in day 5 synthetic embryos (FIG. 40C). At day 6, the population of Brachyury$^+$ cells expanded and migrated towards the distal part of the Epi, between the VE and the Epiblast (FIG. 40D). Emergence of the axial mesoderm was evidenced by the presence of FOXA2/BRACHYURY+ cells at the distal tip of the primitive streak, as described for natural embryos at E7.5 (FIG. 40D). Similarly, definitive endoderm cells were identified in synthetic embryos at day 6 by co-staining of SOX17 and FOXA2, while a population of FOXA2+/SOX17-cells allocated along the distal tip of the egg-cylinder indicated the emerging midline of the embryo (FIG. 40E).

To analyze the emergence of primordial germ cells (PGCs) in the synthetic embryos the Blimp1-mVenus Stella-CFP reporter found in the BVSC ESC line (Hayashi et al., 2011) was used in the aggregation protocol alongside induction of Cdx2 and Gata4 cells. Activation of the Blimp1-mVenus fluorescent reporter was detected at day 5 by live imaging, specifically at the site of putative the primitive streak, in the boundaries of the Epi/ExE (FIG. 40F—Top row). Flow cytometry analysis confirmed the emergence of the initial PGC population in day 5 synthetic embryos which is known to originate first as Blimp1+Stella− cells in the developmentally equivalent natural E6.5 embryos (FIG. 40G) (Magnúsdóttir and Surani, 2014). Moreover, migration of PGC cells (Leitch et al., 2013) in synthetic embryos to the posterior ventral part of the embryos was observed at day 8 by SOX2 immunostaining, that were clearly separated from the neural tube SOX2+ population, indicating that PGC migration can be recapitulated as well in the synthetic embryos (FIG. 40F—Bottom row).

Following gastrulation, the developing embryo establishes its general body plan and displays multiple ectodermal, endodermal, and mesodermal-derived tissues. In addition to the morphological similarities observed between day 8 synthetic embryos and E8.5 natural in-utero embryos, proper differentiation and tissue morphogenesis were corroborated by assessing the expression of several lineage-specific markers by whole-mount immunofluorescence. The neural folds (NF) and neural tube (NT) derived from the epiblast ectoderm, presented strong Sox2 expression, properly allocated along the antero-posterior axis of the embryo (FIGS. 41A-B), while BRACHYURY+ cells were found along the embryonic midline, resembling the elongated notochord (Nc) and tail bud (FIG. 41B). The cardiac marker Myosin Heavy Chain II (MHC-II) was visible at the anterior ventral part of the embryo, specifically localized in the heart bud (FIG. 41A). OTX2 marks the embryonic forebrain and midbrain in the natural E8.5 embryo and was detected in the anterior part of the neural folds in the synthetic embryos (FIG. 41C). FOXA2, which is restricted to the notochord floor plate at the midline of the embryo, was also detected in day 8 syntheric embryos (FIG. 41C).

To further analyze the extent of tissue patterning, transversal plane cross-sectioning of the embryonic neural tube and heart was performed. SOX1 and FOXA2 staining indicated proper establishment of the dorso-ventral axis in the spinal cord, evidenced by the double positive cells specifically located at the ventral part, resembling the floor plate in natural embryos (FIG. 41D—yellow arrow and inset). Moreover, folding and complete closure of the proximal region of the neural tube was observed in day 8 synthetic embryos, which corresponds to what has been described in natural embryos (FIG. 41D—white arrow) (Massarwa and Niswander, 2013b; Nikolopoulou et al., 2017). Sectioning based analysis of the developing heart of the synthetic embryos at day 8 exhibited a remarkably similar morphology to the E8.5 natural embryo, suggesting proper recapitulation of heart morphogenesis. At E8.5, the primitive heart tube undergoes looping and develops into a chambered heart (Mandrycky et al., 2020). Formation of the chambers of the heart during cardiac looping (FIG. 41E), and emergence of functional heart beating that in turn propels blood circulation in the synthetic embryo (data not shown) were noted. Heart differentiation and patterning were further analyzed using four different markers of the developing heart (Gata4, Gata6, NKX2.5 and MHC-II), all of them showing proper expression in the heart tube of the synthetic embryos (FIG. 41E) in a comparable manner to equivalent E8.5 natural embryos. Altogether, these data suggest that the emergence and spatial-temporal organization of tissues derived from the three germ-layers of the mouse post-gastrulation embryo is recapitulated in the synthetic embryos described herein.

Development of the post-implantation mammalian embryo is highly dependent on the extraembryonic tissues, which are the main drivers for induction of symmetry breaking (AVE) at E5.5, and gastrulation together with formation of the primitive streak (ExE) at E6.5. As gastrulation proceeds, the mouse embryo becomes encapsulated by the rapidly enlarging extraembryonic tissues (e.g., yolk sac and amnion) (Pereira et al., 2011) (FIGS. 39B and 39E). However, currently there are no available stem cell based models that recapitulate this important process and the interactions involved in it. Remarkably, as shown in FIG. 39B, the formation and organization of extraembryonic tissues were properly recapitulated in the synethic embryos generated through the protocols described herein, based on anatomical and morphological analysis. Further, at day 7, the yolk sac starts to enlarge and engulf the embryo dorsally. Besides that, the amnion, ectoplacental cone, and yolk sac blood islands become evident (FIG. 42A). At day 8, the embryo develops completely within the yolk sac and amnion, with the amnion being the innermost membrane enveloping the embryo-proper from the dorsal part, surrounded by the vascularized yolk sac with the ectoplacental cone attached to it on the opposite side of the embryo (FIGS. 42A-B). Moreover, the presence and expression pattern of FOXA2 and SOX17 in yolk sacs and ectoplacental cones of day 8 synthetic embryos, following whole mount immunostaining, closely resembles that of natural in utero E8.5 embryonic extraembryonic compartment (FIG. 42C).

One of the important developmental events involving the extra-embryonic yolk sac, is the emergence of blood islands in the yolk sac (Yamane, 2018), which marks the first hematopoietic event during mammalian development (Nowotschin et al.; Pijuan-Sala et al., 2019). Blood islands were widely visible and abundant in developing yolk sacs (data not shown), and immunostaining of whole yolk-sacs for RUNX1 which marks these primitive hematopoietic progenitors, termed erythromyeloid progenitors (EMPs) (Iturri et al., 2021) confirmed their identity as similarly observed in natural embryos (FIG. 42D). EMPs are developmentally restricted blood progenitors the originate from the hemogenic endothelium of the yolk sac and have the potential to give rise to definitive hematopoietic cells from the erythroid and myeloid lineages. Recent studies have provided definitive surface markers that characterize the first primitive hematopoietic cells in E8-E8.75 mouse yolk sac (Iturri et al., 2021). FACS analysis confirmed authentic expression of defining surface markers delineating the different populations within the hematopoietic progenitors in the embryonic yolk sac compartment, as previously described in natural embryos, showing that LIN⁻ fraction contains double positive CD41±/cKit+ population, which can be subdivided into three subgroups based on CD34 and CD45 markers expression (FIG. 42E) (Iturri et al., 2021). Given that EMP based hematopoiesis supports embryo survival until birth through erythrocyte production, a methylcellulose based assay was used to validate erythroid functional colony forming and expansion potential from EMPs isolated from natural and synthetic yolk-sacs followed by in vitro incubation within the cytokine enriched methylcellulose culture plates (Iturri et al., 2021). Consistent with the authentic marker expression and subpopulation distribution observed (FIG. 42E), synthetic embryos derived blood progenitors robustly formed typical erythrocyte colonies with appropriate morphology in an identical manner to natural in utero derived yolk sacs derived EMPs (FIG. 42F). Of note, this latter experiment provides a proof of the ability to isolate and further in vitro expand properly differentiating cells from post-gastrulation synthetic embryos.

To characterize and annotate the various cell types present in the advanced synthetic embryos generated herein in a more quantitative and unbiased manner, and to identify to which extent the global transcriptional profile of lineages formed with synthetic embryos is like their natural counterparts, single cell RNA-sequencing (scRNA-seq) was performed using a 10× genomics platform. To this end, cells were collected from synthetic day 8 embryos with—E8.5 like morphology: 3 synthetic embryos that were developed from iCdx2 cells following brief 3 day DOX based induction (day −1 until day+2) and 4 embryos that were developed following iCdx2 cells following 10 day DOX based induction (day −7 until day+2) (FIGS. 43A-B). Clustering analysis based on differentially expressed genes revealed 22 different cell states (FIG. 43A). Subsequently, the identity of the clusters was annotated based on specific marker genes of the major cell lineages previously defined by single-cell transcriptomics of early mouse embryos (Pijuan-Sala et al., 2019). All three germ layers were represented, as well as all extraembryonic tissues, in one or more clusters, indicating the presence of different cell states within those lineages in a similar manner in both natural and synthetic embryos (FIGS. 43A-C). When examining synthetic embryo biological replicates, or when examining a single embryo based single cell RNA-seq sample (short iCdx2 induction), similar results were obtained (FIG. 43B).

Importantly, the profile of cell types found in the synthetic embryos developing ex utero was highly similar to natural embryos, demonstrating that lineage differentiation and commitment is faithfully recapitulated in the synthetic embryos at the single cell level (FIGS. 43B-C). This analysis confirmed that the composition of cell transcriptional states in the synthetic embryos developing ex utero until advanced organogenesis is equivalent to their natural counterparts. Comparison of the relative cell proportions of different cell types in synthetic and natural embryos showed no significant differences in the majority of clusters, while some moderate differences were found in only six of the cell clusters, including amnion and extra-embryonic endoderm (FIG. 43B). Transcriptionally, all cell clusters showed very high correlation (0.95-0.98) between synthetic and natural embryos (data not shown). In addition, specific markers for tissues that were validated above by morphological or immunostaining based analysis, such as somitic mesoderm, notochord, neural tube, and cardiac tissue were expressed specifically in their corresponding tissue cluster, both in synthetic and in natural embryos (data not shown). A similar conclusion could be reached when focusing on specific markers (Mittenzweig et al., 2021) for different extra-embryonic tissues (data not shown). Overall, these results prove that day 8 synthetic embryos are highly similar to their natural E8.5 counterparts.

Example 4

Generation of Human Naïve PSCs Transiently Expressing Gata4, Cdx2 and/or Gata3

Materials and Methods

Gata4, Cdx2, Gata3 inducible naïve human pluripotent stem cells—To generate human TetON inducible Gata4, Cdx2, Gata3 of Gata3-2A-Cdx2 overexpression inserts the present inventors designed targeting vectors for the safe harbor of the AAVS1 locus in human cells (10.1038/nbt.1927). WIBR3 human ESC s and JH22 human iPSC line were targeted with CRISPR and 2 targeting vectors—one introducing the M2Rtta allele (with neo selection) and the other including the transcriptional factor insert (TF) needed with a vector carrying puromycin selection. Electroporated cells were subjected to double antibiotic selection with puromycin and neomycin for 10-14 days, and clones were picked and validated for correct targeting and overexpression. The targeting schemes, designed plasmids and validation results are presented in FIGS. 28-37.

Expansion and maintenance of human naïve pluripotent cells—WIBR3-WT, WIBR3-TetOn-CDX2 and WIBR3-TetOn-Gata 4 were expanded in human naïve pluripotency conditions termed HENSM, as described in Bayerl et al. Cell Stem Cell 2021. Briefly, HENSM medium: 240 mL Neurobasal (ThermoFisher 21103049) and 240 mL of DMEM-F12 without HEPES (ThermoFisher 21331020), 5 mL N2 supplement (ThermoFisher 17502048 or in-house prepared), 5 mL (1×) GlutaMAX (ThermoFisher 35050061), 1% non-essential amino acids (BI 01-340-1B), 1% Penicillin-Streptomycin (BI 03-031-1B), 10 mL B27 supplement (Invitrogen 17504044), Geltrex (Invitrogen A1413202/A1413302—add 1 mL rapidly in media to obtain 0.2% final conc), 50 mg/ml Vitamin C (L-Ascorbic acid 2-phosphate sesquimagnesium salt hydrate—Sigma A8950), 20 ng/ml recombinant human LIF (Peprotech 300-05) and the following small molecule inhibitors: FGFRi/MEKi/ERKi (PD0325901 1.25 μM—Axon Medchem 1408); WNTi/TNKi (XAV939 2 μM—Sigma X3004 or Axon Medchem 1527); PKCi (Go6983 2 μM—Axon Medchem 2466), SRCi (CGP77675 1.2 μM—Axon Medchem 2097). Secondary boosting components: P38i/JNKi (BIRB0796 0.8 μM—Axon Medchem 1358), ROCKi Y27632 (1.2 μM—Axon Medchem 1683), and ACTIVIN A (ACT) 10 ng/ml. Cells in HENSM were grown on 1% Growth factor reduced Matrigel (BD FAL356231) or 1% GELTREX (ThermoFisher A1413202 or A1413302) or Biolaminin-511 (Biolamina Inc; including for HENSM-XF conditions) coated plates for at least 1 hour in 37° C. After at least 4 passages in HENSM lines acquired uniform human naïve pluripotency morphology and molecular validation as described in Bayerl et al. Cell Stem Cell 2021 and Gafni et al. *Nature* 2013.

Aggregation medium (AM)—1:1 DMEM-F12 (Thermo 11320033) & Neurobasal (Thermo 21103049), Glutamax 1×, Sodium pyruvate 1 mM, Pen/Strep 1×, NEAA 1×, N2 supplement 1× (Thermo 17502048), B27 supplement 1× (Thermo 17504044), beta-mercaptoethanol 0.1 mM (Thermo 31350010) and 0.45% BSA (SigmaAldrich A7979) (For 500 ml Total). The aggregation media was supplemented with Doxycycline (2 μg/ml final concentration) and 5 μM of Y27632 to increase cell survival for the first 24 hours.

Co-aggregation and culture—Co-aggregation was defined as time point 0 of the protocol and was made from three starting PSC cell types:
   WIBR3-WT naïve human ESCs (To give rise to embryo proper);
   Dox pre-treated (16 hours) WIBR3-TetOn-Gata4 naïve human ESCs (to give rise to extraembryonic primitive endoderm (Pre) lineage); and
   DOX pre-treated WIBR3-TetOn-CDX2 naïve human ESCs (to give rise to entire extraembryonic trophectoderm lineage).

Before harvesting cells were pretreated with 20 μM of ROCKi Y27632 to increase their survival after single cell passaging. Cells were dissociated into single cells with TryplE for 5 minutes at 37° C. Following, cells were resuspended in PBS, centrifuged, and rewashed with PBS and centrifuged again and PBS discarded, and resuspended in aggregation Media (AM). Following cell count, a total number of 36000 WIBR3-TetOn-Cdx2 and 12,000 WIBR3-TetOn-CDX2 human naïve ESCs and 12000 WIBR3-WT (empty) naïve human cells were added per well in 400 Microwell AggreWell 24 well plates. In 800 Microwell plates, 9000 WIBR3-TetOn-Cdx2 and 3000 WIBR3-TetOn-CDX2 human naïve ESCs and 3000 WIBR3-WT (empty) naïve human cells were added per well in AggreWell 24 well. The cell mixture was added as 1 ml per well (final volume of each well of 24 well is 1.5 ml).

Day 0—The plate was centrifuged at 100×g for 3 minutes and this was marked as day and then placed into static incubator at 37° C., 5% Co2 and 5% O2.
   On Day 1, 1 ml of media was gently aspirated from each well and replaced with pre-warmed 1 ml of fresh AM+DOX without ROCKi). This was repeated twice during that day to remove ROCKi.
   On Day2, 1 ml of media was gently aspirated from each well and replaced with pre-warmed 1 ml of fresh AM+DOX.
   On days 3 and 4, 1 ml of media was gently aspirated from each well and replaced with pre-warmed 1 ml of fresh AM.
   On days 5-8, 1 ml of media was gently aspirated from each well and replaced with pre-warmed 1 ml of fresh EUCM2 (CMRL/advDMEM-F12 based) media with 20% FBS and transfer plate into 5 Co2 and 20% O2.
   On days 9-11, 1 ml of media was gently aspirated from each well and replaced with pre-warmed 1 ml of EUCM2 (CMRL/advDMEM-F12 based) media with 30% FBS.
   At day 12, embryos were transferred into non-adherent 6 wells plate onto a rotating shaker in static conditions each well with 3 ml EUCM3 (CMRL/advDMEM-F12 based) media with 20% HAS and 20% KSR at 5% Co2 and 20% O2.
   On days 13-15, 1.5 ml of media was gently aspirated from each well and replaced with pre-warmed 1.5 ml of EUCM3 (CMRL/advDMEM-F12 based) media with 20% HAS and 20% KSR.
   On days 16-18, 1.5 ml of media was gently aspirated from each well and replaced with pre-warmed 1.5 ml of EUCM4 (CMRL/advDMEM-F12 based) media with 30% HAS and 20% KSR.
   On days 19-21, 1.5 ml of media was gently aspirated from each well and replaced with pre-warmed 1.5 ml of EUCM5 (CMRL/advDMEM-F12 based) media with 40% HAS and 20% KSR.
   At day 22 onwards—high quality embryos were selected and transferred into previously described ex utero roller culture system (Alejandro-Castrejon et al. Nature 2021) in fresh EUCM media supplemented with D-Glucose 4 mg/ml, sodium-pyruvate 1 mM and 1× NEAA and incubated at 20% O2, 5% Co2 and 6.5 Psi, with the change from mouse EUCM to human embryo EUCM is that the human optimized one contains 50% HAS and 25% KSR (and no RAS).

Results

Naïve human PSCs that transiently—overexpress Cdx2 upon addition of DOX in the early stages of embryo aggregation protocol were generated, in order to induce their rapid priming and transition towards early trophectoderm (FE). In addition, naïve human PSCs that transiently overexpress Gata4 upon addition of DOX in the early stages of embryo aggregation protocol were generated, in order to induce their rapid priming and transition towards the extraembryonic primitive endoderm lineage.

Following, co-aggregation of naïve human PSCs with these two stem cell populations followed by ex-utero culturing enabled generation of organized embryos, as exemplified in FIGS. 38A-B).

Example 5

Aggregation of Three Human Naïve Pscs Subpopulations Generates an Organized Embryo Materials and Methods Doxycycline inducible expression lines were generated by the PiggyBac approach for transient ectopic expression of CDX2 (inducing trophectoderm lineage specification) and GATA4 (inducing primitive endoderm differentiation), as explained in Example 4 hereinabove. Following, these lines were kept in HENSM medium (5 ng/ml activin) on mouse embryonic fibroblasts. Both generated lines and the wild type line were synchronized to reach confluence on the same day. 24 hours prior to aggregation the iCDX2 line was transferred into TIM (trophoblast inducing media—N2B27 supplemented with PD0325901, A-83, LIF, LPA, Y27632) plus Doxycycline. The iGata4 line was transferred to aggregation medium (1:1 ratio neurobasal DMEM f12, sodium pyruvate, GlutaMAX, penicillin streptomycin, N2 Supplement, B27 supplement, BSA and b-mercaptoethanol) plus Y27632 and Doxycycline. Following 24 hours of induction the three cell lines were harvested using TrypLE enzyme centrifuged and re-suspended in MEF medium (DMEM, sodium pyruvate, Penicillin Streptomycin, L-Glutamine and 20% FBS), posteriorly cells were plated on gelatin coated plates for 30 minutes to deplete MEFs. Afterwards cells in suspension were collected and passed through a 70 µm strainer and re-suspended in 1 ml for counting. Cells were plated in AggreWell 400 in concentrations of 36.9 iCDX2, 11.5 iGATA4, 11.5 naïve stem cells (also referred to as WT) per 400 µm microwell, on N2B27 medium supplemented with Y27632 (10 µm final concentration) and Doxycycline, cells were centrifuged to ensure dropping on the microwells. Plate was incubated in a 5% oxygen incubator. Next day the medium was exchanged for N2B27 Medium with Doxycycline and the following day to N2B27 alone. On day+3 aggregates were transferred to a non-adherent 6-well plate (2400 aggregates per well) on EUCM2+20% FBS medium (In this Example, EUCM2 refers to Advanced DMEM f12, T3, extra D-Glucose, 1% CMRL, ITSX, Penicillin Streptomycin, GlutaMAX, progesterone, b-estradiol, n-acetyl-n Cysteine with the indicated percentage of FBS) on day+4 FBS was increased to 30%, on day+5 to 50% and on day+6 to 75%. A schematic representation of the protocol is shown in FIG. 45A.

Results

Co-aggregation of the three stem cell populations, all originating from naïve ESCs/iPSCs as a starting material, followed by ex-utero culturing enabled generation of organized embryos, as exemplified in FIGS. 45A-E.

Specifically, during the second half of day 3 and day 4 (FIG. 45B) formation of the amniotic cavity characterized by a ring of columnar epithelium in the center of the aggregate with a cavity was identified. Immunohistochemistry demonstrated this ring comprises Oct4 positive cells and also showed a population of Gata4 positive cells predominantly in one side of the epiblast, a population forming the primitive endoderm.

On day+5 (FIG. 45C) the formation of two cavities was identified, the first surrounded by Oct4 cells (amniotic cavity) and the second one surrounded by Gata4 and Gata6 positive cells, giving rise to the yolk sac. Cells on the outer layer of the aggregates showed a strong staining for Gata3 forming the trophectoderm layer. On top of the Oct4 positive ring, a change of epithelium from a columnar to a squamous architecture losing the expression of Oct4 was evident, indicating the formation of the amnion. Also, some brachyury positive cells were also detected emerging from the posterior portion of the disc showing evidence of anterior/posterior symmetry breaking and formation of the extraembryonic mesoderm.

On Day +6 (FIG. 45D), a secondary yolk sac was evident by bright field imaging, starting to grow surrounding the bilaminar disc already formed leaving the disc hanging inside the cavity connected only by the connective stalk. Further, the extraembryonic mesoderm started to form a layer on the inner part of the secondary yolk sac characterized by brachyury expression.

On day+7 (FIG. 45E) the aggregates recapitulated a day post fertilization 14-15 human embryo. With bright field microscopy, the two cavities forming the bilaminar were identified, both of them connected by the epiblast and the formation the exocoelomic cavity was also evident.

Interestingly, the equivalence between the culturing days and embryonic stages was as follows: Day 0—PFDS; Day 1-PFD6; Day 2—PFD7; Day 3—PFD8; Day 4—PFD9; Day 5—PFD10; Day 6—PFD11; Day 7—PFD12; Day 8—PFD 13; Day 9—PFD14.

Example 6

Generation of Human Naïve PSCs Transiently Expressing Gata4, Cdx2 and/or Gata3

Materials and Methods

Gata4, Gata6, Cdx2, Gata3 inducible naïve human pluripotent stem cells—A PiggyBac plasmid expressing a cDNA insert of choice under the control of a doxycycline-inducible promotor was designed (FIG. 45F). The Piggybac vector used (www(dot)addgene(dot)org/104454/), carries M2Rtta and a site for cDNA insert of transcription factor of interest. This vector was used to generate 4 different plasmids: human CDX2 or Gata3 (to promote human PSC differentiation towards trophectoderm) and human GATA4 or GATA6 (to promote human primitive endoderm priming from human PSCs.

Expansion and maintenance of human naïve pluripotent cells—As described in Example 4 hereinabove.

Immunostaining—As described in Example 1 hereinabove. Antibodies used are shown in Table 1 herein below.

Results

Naïve human PSCs that transiently overexpress Cdx2 or Gata3 upon addition of DOX in the early stages of embryo aggregation protocol were generated, in order to induce their rapid priming and transition towards early trophectoderm (TE). In addition, naïve human PSCs that transiently overexpress Gata4 or GATA6 upon addition of DOX in the early stages of embryo aggregation protocol were generated, in order to induce their rapid priming and transition towards the extraembryonic primitive endoderm lineage. As shown in FIGS. 46A-C, CDX2, GATA4, GATA6 or GATA3 expression was specifically detected in the transduced cells only after DOX addition.

Example 7

Alternative Conditions for Obtaining Mouse Naïve PSCs as the Starting Population for Generating Embryos Alternative conditions to generate naïve PSCs as the starting population for generating organized embryos was were tested (FIGS. 47A-C). Under these conditions, naïve human PSCs that transiently overexpress Cdx2 upon addition of DOX and naïve human PSCs that transiently overexpress Gata4 upon addition of DOX were generated. Indeed, as explained in details hereinbelow, co-aggregation of the three stem cell populations, followed by ex-utero culturing enabled generation of organized embryos, as exemplified in FIGS. 47B-C.

FIG. 47A shows a schematic representation of the protocol.

WT ESCs were grown in one of the following media:

(i) N2B27 2i/LIF: serum-free chemically defined N2B27-based media: 240 ml Neurobasal (ThermoFisher 21103049) and 240 ml of DMEM-F12 with HEPES (SIGMA D6421), 5 ml N2 supplement (Invitrogen; 17502048), 5-10 ml B27 supplement (Invitrogen; 17504044), 2 mM glutamine or 1 mM GLutamax (Invitrogen), 1% nonessential amino acids (Invitrogen), 0.1 mM β-mercaptoethanol (Sigma), 1% penicillin-streptomycin (Invitrogen). Optionally, the medium also included 5 mg/ml BSA (Sigma). Naïve 2i/LIF conditions for murine PSCs included 20 ng/ml recombinant human LIF (in-house made). 2i was added: small-molecule inhibitors CHIR99021 (CH, 3 µM-Axon Medchem) and PD0325901 (PD, 11 µM—Axon Medchem 1408).

(ii) alternative 2i/LIF conditions (a2i or a2i-Lif conditions): serum-free chemically defined N2B27-based media: 240 ml Neurobasal (ThermoFisher 21103049) and 240 ml of DMEM-F12 with HEPES (SIGMA D6421), 5 ml N2 supplement (Invitrogen; 17502048), 5-10 ml B27 supplement (Invitrogen; 17504044), 2 mM glutamine or 1 mM GLutamax (Invitrogen), 1% nonessential amino acids (Invitrogen), 0.1 mM β-mercaptoethanol (Sigma), 1% penicillin-streptomycin (Invitrogen). Optionally, the medium also included 5 mg/ml BSA (Sigma). Naïve a2i/LIF conditions for murine PSCs included 20 ng/ml recombinant human LIF (in-house made). Small-molecule inhibitors CHIR99021 (CH, 3 µM-Axon Medchem) and SRCi CGP77675 1 microM, Axon 2097). This is an example of naïve PSCs conditions that do not involve inhibitors of the FGF/MEK/ERK pathway. Validation of this alternative condition to obtain naïve PSCs has been described in Choi, J., Huebner, A., Clement, K. et al. Nature 548, 219-223 (2017), www(dot)doi(dot)org/10.1038/nature23274.

(iii) Extended potential LCDM media [as described in Yang et al. Cell (2017) 169(2): 243-257, www(dot)cell (dot)com/fulltext/S0092-8674%2817%2930183-6].
Serum-free chemically defined N2B27-based media: 240 ml Neurobasal (ThermoFisher 21103049) and 240 ml of DMEM-F12 with HEPES (SIGMA D6421), 5 ml N2 supplement (Invitrogen; 17502048), 5-10 ml B27 supplement (Invitrogen; 17504044), 2 mM glutamine or 1 mM GLutamax (Invitrogen), 1% nonessential amino acids (Invitrogen), 0.1 mM β-mercaptoethanol (Sigma), 1% penicillin-streptomycin (Invitrogen). Optionally, the medium also included 5 mg/ml BSA (Sigma). LCDM (or also known as EPS) conditions for murine PSCs included 20 ng/ml recombinant human LIF (in-house made). Small-molecule inhibitors: CHIR 99021 (C, human: 1 mM, mouse: 3 mM; Tocris, 4423), (S)-(+)-Dimethindene maleate (D, 2 mM; Tocris, 1425) and Minocycline hydrochloride (M, 2 mM; Santa Cruz Biotechnology, sc-203339).

(iv) Serum/Lif (15% FBS/LIF (LIF 10 ng/ml) DMEM based conditions. 450 ml DMEM (TermmoFisher 241965-039), 2 mM glutamine or 1× GLutamax (Invitrogen), 1× nonessential amino acids (NEAA) (Invitrogen), 1× penicillin-streptomycin (Invitrogen), 1% Sodium-pyruvate (BI 03-042-1B), supplemented with 15% (v/v) FBS (Gibco or Biological Industries).

To generate the synthetic embryos, three starting PSC cell types were co-aggregated:

1) Naïve WT BVSC in either 2i/LIF, a2i/LIF, LCDM or serum/Lif conditions as indicated;

2) Naïve iGata4 ESCs in either 2i/LIF, a2i/LIF, LCDM or serum/Lif conditions as indicated, and pre-treated with DOX (2 µg/ml-Sigma D9891) in the same media for 24 hours prior to the co-aggregation; and 3) Naïve iCdx2 ESCs in either 2i/LIF, a2i/LIF, LCDM or serum/Lif conditions as indicated, pre-treated with DOX (2 µg/ml-Sigma D9891) for 24 hours prior to the co-aggregation (from day −1) in TSC media (25 ng/ml FGF4 (Peprotech), 1µ/ml Heparin (Sigma)) supplemented with lysophosphatidic acid (LPA, a Hippo pathway inhibitor) 01 µM.

Co-aggregation was defined as time point 0 of the protocol. At the day of aggregation (day 0), the three donor cell populations were trypsinized with 0.05% trypsin-EDTA solution (Biological Industries—Sartorius 03-053-1B) for 4 minutes at 37° C. Trypsin enzymatic reaction was stopped by adding aggregation media. Cells were centrifuged at 1200 rpm for 3 minutes and resuspended in aggregation medium with DOX (2 µg/ml-Sigma D9891) and ROCKi Y27632 (5 nM final concentration—Axon Medchem 1683). Following, cells were plated on gelatinized tissue culture plates for mouse embryonic fibroblast depletion for 20 minutes at 37° C. Supernatant was collected, centrifuged and cells were resuspended. The three cell fractions were counted and resuspended in aggregation media with DOX (2

μg/ml-Sigma D9891) and ROCKi Y27632 (5 nM—Axon Medchem 1683). A ratio of (1 WT-ESCs:1 iGata4 ESC:3.33 iCdx2 ESC) was maintained in aggregation experiments, as follows:

| | Number of microwells per well in 24 well plate | Number of added cells per each well of a 24 well plate | # of Cells per single microwell |
|---|---|---|---|
| AggreWell 800 | 300 | 1-iCDX2: 4800 cells<br>2-iGATA4: 1500 cells<br>3-WT ESC 1500 cells | ~27 cells |

1 ml of cell-mix suspension was gently added drop wise to each well of the AggreWell plate followed by centrifugation at 700 rpm for 3 minutes and incubation at 37° C. (total end volume is 1.5 ml).

On the next day (day 1), 1 ml of media (out of total 1.5 ml) was gently removed from each well and replaced with 1 ml of preheated aggregation media with DOX (2 μg/ml-Sigma D9891).

On day 2, 1 ml of media was removed from each well and replaced with 1 ml of preheated aggregation media.

On day 3, 1 ml of media was removed from each well and replaced with 1 ml of preheated EUCM2 media. In this example, EUCM2 media refers to: Advanced DMEM/F12 (GIBCO 21331-020), 5 ml CMRL media (1% final concentration) as a supplement (5 ml GIBCO 11530037), extra added 1 mg/ml D(+)-Glucose Monohydrate (J. T. Baker—0113) (add 500 mg per 500 ml media), 100 nM T3 (3,3',5-Triiodo-L-thyronine sodium salt) (Sigma-Aldrich, T6397), 1 mM Sodium pyruvate (Sigma-Aldrich, S8636), 1 mM GlutaMAX (GIBCO, 35050061), 1% penicillin streptomycin (Biological Industries—Sartorius 03-031-1B), 1× of ITS-X supplement (Thermo Fisher Scientific 51500-056), 8 nM B-estradiol (Sigma-Aldrich, E8875), 200 ng/ml progesterone (Sigma-Aldrich, P0130), 25 μM N-acetyl-L-cysteine (Sigma-Aldrich, A7250)+20% FBS.

On day 4, the synthetic embryos were gently transferred to 6-well cell suspension culture plates (Greiner, 657185) with 5 ml of preheated EUCM2 media which comprises 30% FBS per well and placed on shaker rotation 60 rpm/min (Thermo 88881102+88881123).

On day 5, egg cylinder shape sEmbryos were picked and transferred to glass culture bottles (50-30 embryos per bottle) containing 2 mL of EUCM media (the contents of which are described in Example 1 hereinabove). Following, the bottles were placed on the rolling culture system previously described electronically controlled roller culture platform (Aguilera-Castrejon et al., 2021a), rotating at 30 revolutions per minute at 37° C., and continuously gassed with an atmosphere of 21% O2, 5% $CO_2$ at 7-8 pounds per square inch (psi). A black non-transparent cloth was used to cover the incubator from light during unit operation.

From day 6 to day 8, 1 ml of EUCM was replaced with preheated 1 ml of EUCM and kept on rolling culture system. Culture media was pre-heated for at least an hour by placing it inside a glass bottle on the rotating culture.

As shown in FIGS. 47B-C, egg cylinder shaped embryos were obtained following the protocols comprising the different culturing conditions.

Example 8

A Two Steps Aggregation Protocol Enhances Efficiency of Embryos Formation

Materials and Methods

To generate the synthetic embryos, three starting PSC cell types were co-aggregated (FIG. 48):
 1) Naïve WT BVSC in 2i/LIF constitutively labeled with BFP (Blue) encoding lentivirus;
 2) Naïve iGata4 ESCs in 2i/LIF, labeled with GFP (Green) encoding lentivirus, pretreated with DOX (2 μg/ml-Sigma D9891) for 24 hours before aggregation (from day −1) in 2i/Lif media; and
 3) Naïve iCdx2 ESCs in 2i/LIF, labeled with RFP (Red) encoding lentivirus, pretreated with DOX (2 μg/ml-Sigma D9891) for 24 hours before aggregation (from day −1) in TSC media (25 ng/ml FGF4 (Peprotech), 1μ/ml Heparin (Sigma) supplemented with lysophosphatidic acid (LPA, a Hippo pathway inhibitor) 01 μM.

Co-aggregation was defined as time point 0 of the protocol.

At the day of aggregation (day 0) or one day later (day 1), either one or two or all three donor cell populations were trypsinized with 0.05% trypsin-EDTA solution (Biological Industries—Sartorius 03-053-1B) for 4 minutes at 37° C. Trypsin enzymatic reaction was stopped by adding aggregation media. Cells were centrifuged at 1200 rpm for 3 minutes and resuspended in aggregation medium with DOX (2 μg/ml-Sigma D9891) and ROCKi Y27632 (5 nM final concentration—Axon Medchem 1683). Following, cells were plated on gelatinized tissue culture plates for mouse embryonic fibroblast depletion for 20 minutes at 37° C. Supernatant was collected, centrifuged and cells were resuspended. The cell fractions were counted and resuspended in aggregation media with DOX (2 μg/ml-Sigma D9891) and ROCKi Y27632 (5 nM—Axon Medchem 1683). A ratio of 1 Blue BVSc ESCs:1 Green-iGata4 ESC:3.33 Red-iCdx2 ESC was maintained in aggregation experiments, as follows:

| | Number of microwells per well in 24 well plate | Number of added cells per each well of a 24 well plate | # of Cells per single microwell |
|---|---|---|---|
| AggreWell 800 | 300 | 1-Red-iCDX2: 4800 cells<br>2-Green-iGATA4: 1500 cells<br>3-Blue-WT ESC 1500 cells | ~27 cells |

1 ml of cell-mix suspension was gently added drop wise to each well of the AggreWell plate followed by centrifugation at 700 rpm for 3 minutes and incubation at 37° C. (total end volume is 1.5 ml).

On the next day (day 1), 1 ml of media (out of total 1.5 ml) was gently removed from each well and replaced with 1 ml of preheated aggregation media with DOX (2 μg/ml-Sigma D9891). When one or 2 of the cell fractions was added on day 1 instead of day 0, 1 ml of cell-mix suspension was gently added drop wise to each well of the AggreWell plate followed by centrifugation at 700 rpm for 3 minutes and incubation at 37° C. (total end volume is 1.5 ml).

On day 2, 1 ml of media was removed from each well and replaced with 1 ml of preheated aggregation media.

On day 3, 1 ml of media was removed from each well and replaced with 1 ml of preheated EUCM2 media. In this example, EUCM2 media refers to: Advanced DMEM/F12 (GIBCO 21331-020), 5 ml CMRL media (1% final concentration) as a supplement (5 ml GIBCO 11530037), extra added 1 mg/ml D(+)-Glucose Monohydrate (J. T. Baker—0113) (add 500 mg per 500 ml media), 100 nM T3 (3,3',5-Triiodo-L-thyronine sodium salt) (Sigma-Aldrich, T6397), 1 mM Sodium pyruvate (Sigma-Aldrich, S8636), 1 mM GlutaMAX (GIBCO, 35050061), 1% penicillin streptomycin (Biological Industries—Sartorius 03-031-1B), 1× of ITS-X supplement (Thermo Fisher Scientific 51500-056), 8 nM B-estradiol (Sigma-Aldrich, E8875), 200 ng/ml progesterone (Sigma-Aldrich, P0130), 25 µM N-acetyl-L-cysteine (Sigma-Aldrich, A7250)+20% FBS.

On day 4, the synthetic embryos were gently transferred to 6-well cell suspension culture plates (Greiner, 657185) with 5 ml of preheated EUCM3 media per well and placed on shaker rotation 60 rpm/min (Thermo 88881102+ 88881123). In this example, EUCM3 media here (EUCM2 media but with 30% FBS is also known as EUCM3) refers to: Advanced DMEM/F12 (GIBCO 21331-020), 5 ml CMRL media (1% final concentration) as a supplement (5 ml GIBCO 11530037), extra added 1 mg/ml D(+)-Glucose Monohydrate (J. T. Baker—0113) (add 500 mg per 500 ml media), 100 nM T3 (3,3',5-Triiodo-L-thyronine sodium salt) (Sigma-Aldrich, T6397), 1 mM Sodium pyruvate (Sigma-Aldrich, S8636), 1 mM GlutaMAX (GIBCO, 35050061), 1% penicillin streptomycin (Biological Industries—Sartorius 03-031-1B), 1× of ITS-X supplement (Thermo Fisher Scientific 51500-056), 8 nM B-estradiol (Sigma-Aldrich, E8875), 200 ng/ml progesterone (Sigma-Aldrich, P0130), 25 µM N-acetyl-L-cysteine (Sigma-Aldrich, A7250)+30% FBS.

On day 5, egg cylinder shape sEmbryos were picked and transferred to glass culture bottles (50-30 embryos per bottle) containing 2 mL of EUCM media (the contents of which are described in Example 1 hereinabove). Following, the bottles were placed on the rolling culture system previously described electronically controlled roller culture platform (Aguilera-Castrejon et al., 2021a), rotating at 30 revolutions per minute at 37° C., and continuously gassed with an atmosphere of 21% O2, 5% $CO_2$ at 6-8 pounds per square inch (psi). A black non-transparent cloth was used to cover the incubator from light during unit operation.

From day 6 to day 8, 1 ml of EUCM was replaced with preheated 1 ml of EUCM and kept on rolling culture system. Culture media was pre-heated for at least an hour by placing it inside a glass bottle on the rotating culture.

Results

Four different regimens for co-aggregating the three mouse stem cell populations, all originating from naïve ESCs/iPSCs as a starting material, followed by ex-utero culturing were evaluated (FIG. 48), basically assessing a 1-step aggregation protocol vs. a two steps aggregation protocol. sEmbryo formation efficiency of egg cylinder was evaluated on day 5. As shown in FIG. 48, adding iCDX2 ESCs at day 1, rather than at day 0, resulted in two-four times enhancement of normal egg-cylinder sEmbryo formation efficiency (highlighted with a blue arrow).

Example 9

Generation of Trophectoderm Primed Cells by Inducing Endogenous Expression of Differentiation Factors in Naïve PSCs Materials and Methods:

Generation of trophectoderm primed cells (FIGS. 49A-D)—Human naïve PSCs expanded in human HENSM conditions for at least 1 passage (4 days), which were plated on 1% 1% GELTREX (Thermo A1413202/A1413302) or Matrigel (BD) coated plates.

HENSM media:
Primary Cytokines+inhibitors:
1:1 mix of Neurobasal (Invitrogen 21103-049) and DMEM/F12 (Invitrogen 21331)—470 ml
Pen-strep 5 ml (Biological Industries 03-033-1B)
Glutamax—5 ml (Invitrogen 35050061)
NEAA—5 ml (Biological Industries 01-340-1B)
Sodium Pyruvate-5 ml (Biological Industries 03-042-1B)
10 ml B27 supplement: Invitrogen 17504-044 or Xenofree A1486701
L-ascorbic acid 2-phosphate (Sigma—A8960) (50 µg/ml final concentration) (1 vial)
Geltrex (Invitrogen A1413202/A1413302) or Matrigel—1 ml rapidly in media (0.2% final conc.)
5 ml Commercial N2 supplement (Invitrogen 17502048)
LIF (in house produced or Peprotech 300-05)—20 ng/ml final
WNTi-TNKi=XAV939 (Sigma X3004)—2 µM final
PKCi Go6983 (Axon 2466)—2 µM final
FGFRi—MEK1/2i—ERK1/2i—PD0325901 (Axon 1408)—1-1.211M final
SRCi CGP77675 (Axon 2097)—11 µM (1 vial=50 µL).
Optionally ACTIVIN A—(Peprotech 120-14E)—5 ng/ml final.
Optionally ROCKi Y27632 (Axon 1683)—11 µM.
Optionally BIRB796 P38i (0.4 µM)

A 3 days protocol for human trophoblast induction from human PSCs (using media adapted from Shingo Io et al. (2021) Cell Stem Cell, 28(6): 1023-1039 and Mitsuyoshi Amita et al. (2013) PNAS E1212-1221):

Step 1: In the first 24 hours (B)AP media was used:
1:1 mix of Neurobasal (Invitrogen 21103-049) and DMEM/F12 (Invitrogen 21331)—470 ml
Pen-strep 5 ml (Biological Industries 03-033-1B)
Glutamax—5 ml (Invitrogen 35050061)
NEAA—5 ml (Biological Industries 01-340-1B)
Sodium Pyruvate—5 ml (Biological Industries 03-042-1B)
10 ml B27 supplement: Invitrogen 17504-044 or Xeno-free A1486701
L-ascorbic acid 2-phosphate (Sigma—A8960) (50 µg/ml final concentration) (1 vial)
5 ml Commercial N2 supplement (Invitrogen 17502048)
(A) TGFRi A83-01-2 µM final concentration (Axon Medchem A83-01)
(P) FGFRi/MEKi/ERK PD0325901—2 µM final concentration (Axon Medchem 1408) [FGFRi PD173074 0.5-1 µM can be used instead]
(J) human recombinant BMP4 10 ng/ml was optionally included (Peprotech 120-05ET or 120-05).

Step 2: In the following 48 hours (from day 2-day 3 of pretreatment) AP(J) media was used:
1:1 mix of Neurobasal (Invitrogen 21103-049) and DMEM/F12 (Invitrogen 21331)—470 ml
Pen-strep 5 ml (Biological Industries 03-033-1B)
Glutamax—5 ml (Invitrogen 35050061)
NEAA—5 ml (Biological Industries 01-340-1B)
Sodium Pyruvate-5 ml (Biological Industries 03-042-1B)
10 ml B27 supplement: Invitrogen 17504-044 or Xeno-free A1486701
L-ascorbic acid 2-phosphate (Sigma—A8960) (50 µg/ml final concentration) (1 vial)

5 ml Commercial N2 supplement (Invitrogen 17502048)
(A) TGFRi A83-01-2 µM final concentration (Axon Medchem A83-01)
(P) FGFRi/MEKi/ERK PD0325901—2 µM final concentration (Axon Medchem 1408) [FGFRi PD173074 0.5-1 µM can be used instead]
(J) human JAK inhibitor I—1 µM final concentration was optionally included (Calbiochem 420099).

Gelatin/irradiated MEF coated plates or Merck Silk Laminin-511 (Dilute 1:200 in PBC to get working solution: 2.5 microg/ml) can be used instead of the coated Geltrex or Matrigel coated plates.

Immunostaining—As described in Example 1 hereinabove. Antibodies used are shown in Table 1 hereinbelow.

Gata3 inducible expression—A PiggyBac plasmid expressing a cDNA insert of choice under the control of a doxycycline-inducible promotor was designed (FIG. 45F). The Piggybac vector used (www(dot)addgene(dot)org/104454/), carries M2Rtta and a site for cDNA insert of transcription factor of interest. This vector was used to generate Gata3 (to promote human PSC differentiation towards trophectoderm and was introduced in human PSCs.

PCR—as described in in Example 1 hereinabove. List of primers is provided in Table 2 hereinbelow.

Results:

Examples 2-8 hereinabove describe generation of synthetic embryos by co-aggregation of three subpopulations of stem cells all originating from naïve PSCs. The trophectoderm primed cells were obtained by transient expression of exogenous CDX2 or Gata3. In the next step, the present inventors developed culturing conditions of naïve human PSCs allowing induced expression of endogenous differentiation factors leading to generation of the trophectoderm primed cells without the need for genetic modifications of the cells (FIGS. 49A-D).

Immunostaining characterization of the human trophectoderm primed cells induced according to the protocol described hereinabove demonstrated expression of known trophectoderm markers—CDX2, GATA2, Periostin, EOMES, CK7 and TFAP2C; and no expression of BST2, which marks extra-embryonic mesoderm and SYNDECAN1, which is known to emerge in later developed TSCs (FIG. 49B). Comparative analysis of 3 days trophectoderm primed cells with and without transgenic GATA3 overexpression. WT WIBR3 and iGATA3 WIBR3 naïve HPSCs were subjected side by side to the trophoblast induction protocol described hereinabove. Immunostaining characterization demonstrated that transgenic expression of GATA3 compromised the expression of the trophoblast markers TFAP2C and CK7, which was expressed only on some of the colonies of iGATA3 cells, while it was uniformly expressed on all WT cells (FIG. 49C). CDX2 expression level was much less abundant following ectopic expression of iGata3 cells compared to absence of ectopic exogenous GATA3 overexpression. RT PCR expression of different trophectoderm markers on the WT and iGATA3 WIBR3 cells isolated from experiment described in FIG. 49D. WT naïve TSCs were used as reference negative control (set as 1). WiBR3 derived TSC line was used as a reference control for some of the markers. Some samples included a regimen involved 3d expansion in Takashima differentiation protocol (Takashima protocol=the protocol described hereinabove; and then followed by 3 more days expansion in TSC media described in Example 13 hereinbelow). Most optimal results were obtained with WT donor naïve ESCs without overexpression of exogenous GATA3 (iG3). TE markers include: CDX2, GATA3, ENPEP, GATA2, TACSTD2, TFAP2C, ELF5 (and are SIGLEC6 negative).

Example 10

Generation of Extra Embryonic Primitive Endodermal Primed Cells by Inducing Endogenous Expression of Differentiation Factors in NaïVe Pscs Materials and Methods:

Generation of extra embryonic primitive endodermal primed cells (FIGS. 50A-D)—Previously, Josh Brickamn group has published a condition termed RACL that is able to induce primitive endoderm progenitor cells (PRE) at undefined efficiency from human naïve PSCs. FACS analysis for human PDGFRa, which marks PRE lineage, was used as an initial screen to see rapid and measure kinetics of PDGFRA induction levels (RnD systems AF-307-NA or FAB1062G). RACL media was assembled as previously published (www(dot)doi(dot)org/10.1242/dev(dot)180620) and contained: 480 ml RPMI media (21875-034 GIBCO Invitrogen), 10 ml B27 supplement (Invitrogen A18956-01 B27 without insulin), 1 mM GLutamax (Invitrogen), 1% nonessential amino acids (Invitrogen), 1% penicillin-streptomycin (Invitrogen), 100 ng/ml ActA, 3 µM CHIR99021 and 10 ng/ml LIF. An optimized RCL media which contained the same composition as RACL but without adding recombinant Activin was also used. Of note, the work of Brickman teaches away from RCL media, as it claims ACTIVIN is essential for PRE induction. Versions of RCL and RACL with B27 that was further supplemented with insulin (Invitrogen; 17504044) was also tested. Further, another version of the media tested was a N2B27 media not supplemented with CHIR99021 and LIF, making the media composed of:

1:1 mix of Neurobasal (Invitrogen 21103-049) and DMEM/F12 (Invitrogen 21331)—470 ml
Pen-strep 5 ml (Biological Industries 03-033-1B)
Glutamax—5 ml (Invitrogen 35050061)
NEAA—5 ml (Biological Industries 01-340-1B)
Sodium Pyruvate-5 ml (Biological Industries 03-042-1B)
10 ml B27 supplement: Invitrogen 17504-044 or Xenofree A1486701
5 ml Commercial N2 supplement (Invitrogen 17502048)

FACS analysis—Cell were immunostained with fluorescent labeled antibodies as indicated in Table 1 hereinbelow, washed with PBS and analyzed on FACS ARIA III and analyzed with a FACS DIVA software.

Immunostaining—As described in Example 1 hereinabove. Antibodies used are shown in Table 1 hereinbelow.

Gata6 inducible expression—As described in in Example 9 hereinabove but with Gata6 as an insert.

PCR—A described in Example 1 hereinabove. List of primed is provided in Table 2 hereinbelow.

Results:

Examples 2-8 hereinabove describe generation of synthetic embryos by co-aggregation of three subpopulations of stem cells all originating from naïve PSCs. The extra embryonic primitive endodermal primed cells (PRE) were obtained by transient expression of GATA4 or GATA6. In the next step, the present inventors developed culturing conditions of naïve human PSCs allowing induced expression of endogenous differentiation factors leading to generation of the extra embryonic primitive endodermal primed cells without the need for genetic modifications of the cells.

FACS analysis with an anti-PDGFRa antibody after 6 days of induction in the indicated media (some of which were divided into two phases of 3d and 3d sequential media, FIG. 50A) indicated that ACTIVIN supplementation decreases dramatically the efficiency of PRE cell induction. In addition, N2B27 media alone yielded a low fraction of PDGFRa positive cells, albeit at lower efficiency from RCL conditions. While using no insulin conditions yields better outcome over with insulin conditions, the effects were minimal. 3 days of RCL followed by 3 days of N2B27 also yielded excellent results, which were equivalent to these of 6 days RCL inductions (FIG. 50A). To test whether ectopic expression of GATA6 can yield better PRE induction results than those seen with WT WIBR3 cells, iGATA6 WIBR3 naïve cells originally expanded in HENSM conditions and including DOX in the Pre induction media were used as indicated (FIG. 50B). Overall, the results show, that RACL is inferior to RCL conditions. Ectopic GATA6 does not yield higher efficiencies of induction than for WT cells placed in RCL media (FIG. 50B). RT-PCR analysis was conducted to verify expression of PRE markers (PDGFRa, GATA4, GATA6, Nid2, SOX17) and confirm lower levels of definitive endoderm markers (Gsc and Foxa2) (FIG. 50C). The results confirm that without the need for ectopic expression of GATA6 transgenes WT cells expanded in RCL media for 6 days yield wanted optimal gene expression patterns confirming PRE identity, rather than definitive endoderm identity. Cells expanded in HENSM conditions were used a negative reference control. Immunostaining analysis of naïve WT WIBR3 and iGATA6 cells originally expanded in HENSM conditions for at least 2 passages, and then placed in PRE induction in RCL condition on MEFs for 6 days demonstrate that the cells express GATA4, GATA6, PDGFRa, Vim, NID2 and SOX17 which mark PRE cells. FOXa2 which marks definitive endoderm cells, rather than PRE was expressed at very low levels in these PRE induction settings as expected. DAPI counterstaining was used for reference control.

Example 11

GENERATION OF ORGANIZED SYNTHETIC HUMAN EMBRYOS

Materials and Methods:
Co-aggregation and culture (FIG. 51A)—Three starting cell types were co-aggregated:
1) Naïve WT cells cultured in HENSM medium.
2) For the primitive endoderm compartment—Naïve WT cells were plated on mouse embryonic fibroblast conditions on HENSM supplemented with ROCKi 10 µM (Axon Medchem 1683), next day medium was replaced by RCL medium, RCL was kept for 72 hours with 24-hour medium exchanges.
3) For the Trophectoderm lineage—Naïve WT cells were plated on feeder free conditions (Matrigel or laminin E8) on HENSM supplemented with ROCKi 10 µM, next day medium was replaced with (B)AP medium for 24 hours followed by medium replacement to AP(J) for another 48 hours.
  All three cell types were supplemented with 5 µM ROCKi Y27632 before harvesting for co-aggregation on the next day.
  Co-aggregation was defined as time point 0 of the protocol.
  At the day of aggregation (day 0), AggreWell plates 400, 24 wells (Stemcell technologies) were prepared according to manufacturer instructions and prefilled with 500 µL of N2B27 media and kept at 37° C. for medium equilibration.

The three cell populations were disaggregated with TrypLE (Thermo Fisher 12604054) for 3 minutes for the WT and Primitive endoderm cells and 5 minutes for the Trophectoderm cells at 37° C. Following, the enzyme was removed and cells were incubated for two minutes at room temperature, afterwards cells were collected with PBS. Cells were centrifuged at 1300 rpm for 3 minutes and resuspended in N2B27 ROCKi Y27632 (10 µM final concentration). Following, primitive endoderm cells were plated on gelatinized tissue culture plates for mouse embryonic fibroblast depletion for 30 minutes at 37° C. Supernatant was collected, and all three elements were centrifuged separately and cells were resuspended on N2B27 medium. The three cell fractions were counted and resuspended in N2B27 supplemented with ROCKi Y27632 (10 µl). A ratio of 1:1:3 (WT:PRE:TE) was maintained in aggregation experiments, as follows:

| | Number of microwells per well in 24 well plate | Number of added cells per each well of a 24 well plate | # of Cells per single microwell |
|---|---|---|---|
| AggreWell 400 | 1200 | 1-WT 27720 cells<br>2-PrE 27720 cells<br>3-TE 88560 cells | ~120 cells |

0.5 ml of cell-mix suspension was gently added drop wise to each well of the AggreWell plate followed by centrifugation at 700 rpm for 3 minutes and incubation at 37° C. 5% O2 (total end volume is 1 ml).

On the next day (day 1), 900 µL of medium were gently removed from each well and replaced with 1 ml of preheated N2B27 medium. The same procedure was repeated on day 2.

On day 3 aggregates were gently transferred to 6-well cell suspension culture plates (Greiner, 657185) with 3 ml of preheated EUCM2 (20%-30% FBs) media per well and placed on shaker rotation 60 rpm/min (Thermo 88881102+ 88881123). Plates were transferred to 21% O2 conditions.

On day 4, 2 ml of medium were gently removed per six-well and were placed with 2 ml of preheated EUCM2 (with 30% FBS). The same procedure was repeated on day 5

On day 6, 2 ml of medium were gently removed per six-well and were placed with 2 ml of preheated EUCM2 with 50% FBS. The same procedure was repeated on day 7.

Immunostaining—As described in Example 1 hereinabove. Antibodies used are shown in Table 1 hereinbelow.
Results:

Examples 2-8 hereinabove describe generation of synthetic embryos by co-aggregation of three subpopulations of stem cells all originating from naïve PSCs. The trophectoderm primed cells were obtained by transient expression of exogenous CDX2 or Gata3 and the extra embryonic primitive endodermal primed cells were obtained by transient expression of GATA4 or GATA6. Examples 9-10 hereinabove demonstrate culturing conditions of naïve PSCs developed by the present inventors allowing induced expression of endogenous differentiation factors leading to generation of the two primed populations without the need for genetic modifications of the cells.

As exemplified in FIGS. 51A-L, co-aggregation of the naïve PSCs with the two stem cell populations described in Examples 9-10, followed by ex-utero culturing enabled generation of organized embryos. FIG. 51B demonstrates progression of human sEmbryos from Day 4 to Day 8 following aggregation. As shown in the Figure, progression of days 4, 6 and 8 sEmbryos (top) correspond to 9-12 days post fertilization (dpf) of human embryos (schematically shown at the bottom). The top panel shows human days 4-8 sEmbryos immunostained for OCT4 (Cyan), SOX17 (Yellow) and CK7 (Magenta), which are markers for epiblast, hypoblast and trophoblast, respectively. All three lineages are represented in the right location. The epiblast (Cyan) is forming a compact layer and shows expansion of amniotic cavity through time. The hypoblast (Yellow) is closing to form the primary yolk sac lining the epiblast. The trophoblast is surrounding the SEM and is forming lacunae. A population of ExEM arises, here seen as DAPI cells under the PYS, forming a chorionic cavity by day 6. The chorionic cavity expands, creating a gap separating the epiblast and yolk sac from the surrounding trophoblast by day 8. The remodelling of the ExEM will partially pinch of the primary yolk sac to form the definitive yolk sac. FIG. 51C shows characterization of epiblast pluripotency in human sEmbryos. Immunostaining of Day 4 sEmbryos demonstrates strong expression of OCT4 and SOX2, while KLf17 is expressed at low levels at this stage. FIGS. 51D-E show apical cell polarity and lumenogenesis; and FIGS. 51F-G show Anterior-posterior symmetry breaking in the human D6 sEmbryos. Trophoblast compartment characterization (FIGS. 51H-J) indicates that all three trophoblast are present in Day 6 sEmbryos and form a surrounding layer covering the structure. Also evident are the membranes and syncytiotrophoblast with presence of cyto-(CK7+ only) and syn-cytiotrophoblast (CK7+ and HCGB+), formation of lacuna by syncytiotrophoblast and maximum projection shows that syncytiotrophoblast surround the whole structure. Extraembryonic mesoderm evaluation (FIGS. 51K-L) indicates presence of organized extraembryonic mesoderm cells invading the space between the yolk sac (SOX17+) and the outer trophoblast layer (DAPI, SOX17−, OCT4−, BST2−). Further, the extraembryonic mesoderm cells organize and form a cavity between PYS and trophoblast cells, indicating the formation of chorionic cavity.

Example 12

Generation of Organized Synthetic Rhesus Macaque Embryos

Materials and Methods:

Generation of naïve Rhesus Macaque PSCs—HENSM conditions made for human naïve ESCs, were adapted for Rhesus Macaque (RM) naïve ESC and iPSC line (RM1-ESC and RM1-iPSC lines), by reducing the SRCi concentration down from 1 µM to 0.33 µM. RM1-iPSc and RM1-ESC were expanded in primed FGF/TGF conditions on mouse irradiated MEFs or in TeSR primed conditions (stem cell technologies). Monkey naïve ESC and iPSC naïve lines were expanded for at least 3 passages in HENSM conditions either on plates coated with 1% GELTREX (Thermo A1413202/A1413302) or 1% Matrigel or Biolaminin511 (5 µg/ml) or MEF/gelatin coated plates. Of note, cells were expanded in 5% O2, but it is also possible in 20% O2.
MENSM—monkey naïve pluripotency media contained:
    1:1 mix of Neurobasal (Invitrogen 21103-049) and DMEM/F12 (Invitrogen 21331)—470 ml
    Pen-strep 5 ml (Biological Industries 03-033-1B)
    Glutamax—5 ml (Invitrogen 35050061)
    NEAA—5 ml (Biological Industries 01-340-1B)
    Sodium Pyruvate-5 ml (Biological Industries 03-042-1B)
    10 ml B27 supplement: Invitrogen 17504-044 or Xenofree A1486701
    L-ascorbic acid 2-phosphate (Sigma—A8960) (50 µg/ml final concentration) (1 vial)
    Optional: Geltrex (Invitrogen A1413202/A1413302) or Matrigel—1 ml rapidly in media (0.2% final conc.)
    5 ml Commercial N2 supplement (Invitrogen 17502048)
    LIF (in house produced or Peprotech 300-05)—20 ng/ml final
    WNTi-TNKi=XAV939 (Sigma X3004)—2 µM final
    PKCi Go6983 (Axon 2466)—2 µM final
    FGFRi—MEK1/2i—ERK1/2i—PD0325901 (Axon 1408)—1-1.2 µM final
    SRCi CGP77675 (Axon 2097)—0.33 µM
    Optional: ACTIVIN A—(Peprotech 120-14E)—5-10 ng/ml final.
    Optional: BIRB0796 P38i (0.4 µM)

Generation of trophectoderm primed cells and extra embryonic primitive endodermal primed cells (FIG. 53)—To generate non-human primate (NHP—Rhesus Macaque sEmbryos, three starting cell types were co-aggregated:

1) Naïve WT eSC/iPSc rhesus macaque cells cultured in MENSM medium.
2) For the primitive endoderm compartment—Naïve WT RM1 ESC/iPSC were plated on mouse embryonic fibroblast conditions on MENSM supplemented with ROCKi 10 µM (Axon Medchem 1683), next day medium was replaced by RCL medium, RCL was kept for 72 hours with 24-hour medium exchanges.
3) For the Trophectoderm lineage—Naïve WT RM1 ESC or RM1 iPSCs cells were plated on feeder free conditions (Matrigel or laminin E8) on MENSM supplemented with ROCKi 10 µM, next day medium was replaced with (B)AP medium for 24 hours, followed by medium replacement with AP(J) for another 48 hours.

Co-aggregation and culture (FIG. 53)—All three cell types were supplemented with 5 µM ROCKi Y27632 before harvesting for co-aggregation on the next day. Co-aggregation was defined as time point 0 of the protocol. At the day of aggregation (day 0), AggreWell plates 400, 24 wells (Stemcell technologies) were prepared according to manufacturer instructions and prefilled with 500 µL of N2B27 media and kept at 37° C. for medium equilibration. The three cell populations were disaggregated with TrypLE (Thermo Fisher 12604054) for 3 minutes for the WT and Primitive endoderm cells and 5 minutes for the Trophectoderm cells at 37° C. Following, the enzyme was removed and cells were incubated for two minutes at room temperature, afterwards cells were collected with PBS. Cells were centrifuged at 1300 rpm for 3 minutes and resuspended in N2B27 ROCKi Y27632 (10 µM final concentration). Following, primitive endoderm cells were plated on gelatinized tissue culture plates for mouse embryonic fibroblast depletion for 30 minutes at 37° C. Supernatant was collected, and all three elements were centrifuged separately and cells were resuspended on N2B27 medium. The three cell fractions were counted and resuspended in N2B27 supplemented with ROCKi Y27632 (10 µl). A ratio of 1:1:3 (WT:PRE:TE) was maintained in aggregation experiments, as follows:

| | Number of microwells per well in 24 well plate | Number of added cells per each well of a 24 well plate | # of Cells per single microwell |
|---|---|---|---|
| AggreWell 400 | 1200 | 1-WT 27720 cells<br>2-PrE 27720 cells<br>3-TE 88560 cells | ~120 cells |

0.5 ml of cell-mix suspension was gently added drop wise to each well of the AggreWell plate followed by centrifugation at 700 rpm for 3 minutes and incubation at 37° C. 5% O2 (total end volume is 1 ml).

On the next day (day 1), 900 µL of medium were gently removed from each well and replaced with 1 ml of preheated N2B27 medium. The same procedure was repeated on day 2.

On day 3, aggregates were gently transferred to 6-well cell suspension culture plates (Greiner, 657185) with 3 ml of preheated EUCM2 (20%-30% FBS) media per well and placed on shaker rotation 60 rpm/min (Thermo 88881102+88881123). Plates were transferred to 21% O2 conditions.

On day 4, 2 ml of medium were gently removed per six-well and were placed with 2 ml of preheated EUCM 2 (with 30% FBS). The same procedure was repeated on day 5.

On day 6, 2 ml of medium were gently removed per six-well and were placed with 2 ml of preheated EUCM2 with 50% FBS. The same procedure was repeated on day 7.

Results:

Naïve Rhesus Macaque (RM) PSCs were obtained. Phase Images show typical domed like morphology of RM1 naïve hESCs expanded in NENSM conditions at the indicated passages (FIG. 52A). Further, the cells were positive for all naïve pluripotency markers tested, namely DPPA3, TFCP2L1, KLF17 and NANOG (FIG. 52B).

Following, a subpopulation of naïve RM1 iPSCs and RM1 ESCs were cultured for 3 days in RCL condition to induce extra embryonic primitive endodermal signature, and a second subpopulation of naïve RM1 iPSCs and RM1 ESCs were cultured for 3 days in BAP-APJ protocol to induce trophectoderm signature (FIG. 53). Then, the three lineages were co-aggregated on Day 0 and the process of self-assembly of the RM sEmbryo started as indicated in the scheme including media compositions at each day.

As exemplified in FIG. 54, co-aggregation of the naïve PSCs with the two stem cell populations described, followed by ex-utero culturing enabled generation of organized embryos. The Figure demonstrates progression of RM sEmbryos from Day 6 following aggregation (on the left) corresponding to 9-12 days post fertilization (dpf) of RM embryos (schematically shown on the right). Immunostaining for OCT4, SOX17 and Gata3, markers for epiblast, hypoblast and trophoblast, respectively, indicated that all three lineages are represented in the right location. The epiblast is forming a compact layer and shows expansion of amniotic cavity through time. The hypoblast is closing to form the primary yolk sac lining the epiblast. The trophoblast is surrounding the SEM and is forming lacunae.

Example 13

Aggregation of Human NaïVe Pscs, Pre Cells and TSCs does not Generate an Organized Embryo Materials and Methods:

Derivation of a stable human TSC line from human naïve ESCs expanded in human naïve HENSM conditions—WIBR3 WT human female ESC line was expanded for at least 3 passages in HENSM media (as described in Example 9 hereinabove), either on plates coated with 1% GELTREX (Thermo A1413202/A1413302) or 1% Matrigel or Biolaminin511 (5 µg/ml) or MEF/gelatin coated plates. Cells were expanded in 5% O2, but it is also possible in 20% O2.

Generation of trophectoderm stem cells (TSC)—Human TSC line derived from WIBR3 naïve ESCs at (Passage 5). The latter was generated by transferring human naïve WIBR3 expanded in HENSM conditions into TSC media on MEF coated plates and serially passaged in TSC media and validated as TSC line. The TSC line was constitutively labeled with an RFP coding lentivirus (labeling it as RED). Human TSC media was previously described in Okae et al. (10.1016/j.stem.2017.11.004) with slight modifications:

DMEM/F12 (Invitrogen 21331)—470 ml 5 ml commercial N2 supplement (Invitrogen 17502048)

10 ml B27 supplement (Invitrogen 17504-044)

Sodium Pyruvate-5 ml (Biological Industries 03-042-1B)

Pen-strep 5 ml (Biological Industries 03-033-1B)

Glutamax—5 ml (Invitrogen 35050061)

NEAA—5 ml (Biological Industries 01-340-1B)

L-ascorbic acid 2-phosphate (Sigma—A8960) (50 µg/ml final concentration) (1 vial)

Human EGF 50 ng/ml final concentration (Peprotech—AF-100-15)

TGFRi A83-01-0.75—1 µM final concentration (Axon Medchem A83-01)

GSK3i CHIR99021—2 µM (Axon medchem 1386)

HDAC inhibitor—VPA 0.2 mM final concentration (WAKO #227-01071)

ROCKi Y27632 5 µM. (Axon 1683) (1 vial)

Of note, the medium described in Okae et al. comprises 1 ml of FBS to get 0.2% final FBS, and instead of N2 supplement they use ITS-X supplement and 4 times higher concertation of VPA).

Co-aggregation and culture—Three starting cell types were co-aggregated:

1) Naïve WT hESCs;

2) For the primitive endoderm compartment—Naïve WT cells were plated on mouse embryonic fibroblast conditions on HENSM supplemented with ROCKi 10 µM (Axon Medchem 1683), next day medium was replaced by RCL medium, RCL was kept for 72 hours with 24-hour medium exchanges; and 3) Human TSCs All three cell types were supplemented with 5 µM ROCKi Y27632 before harvesting for co-aggregation on the next day. Co-aggregation was defined as time point 0 of the protocol. At the day of aggregation (day 0), Aggrewell plates 400, 24 wells (Stemcell Technologies) were prepared according to manufacturer instructions and prefilled with 500 µL of N2B27 media and kept at 37° C. for medium equilibration. The three cell populations were disaggregated with TrypLE (Thermo Fisher 12604054) for 3 minutes for the WT and Primitive endoderm cells and 5 minutes for the TSC line cells at 37° C., next the enzyme was removed and cells were incubated for two minutes at room temperature, afterwards cells were collected with PBS. Cells were centrifuged at 1300 rpm for 3 minutes and resuspended in N2B27 ROCKi Y27632 (10 µM final concentration). Following, primitive endoderm cells were plated on gelatinized tissue culture plates for mouse embryonic fibroblast depletion for 30 minutes at 37° C. The supernatant was collected, and all three elements were centrifuged separately, and cells were resuspended on N2B27 medium. The three cell fractions were counted and resuspended in N2B27 supplemented with ROCKi Y27632 (10 µl). A ratio of 1:1:3 (WT:PRE:TE) was maintained in aggregation experiments, as follows:

| | Number of microwells per well in 24 well plate | Number of added cells per each well of a 24 well plate | # of Cells per single microwell |
|---|---|---|---|
| AggreWell 400 | 1200 | 1-WT 27720 cells<br>2-PrE 27720 cells<br>3-TSC 88560 cells | ~120 cells |

0.5 ml of cell-mix suspension was gently added drop wise to each well of the AggreWell plate followed by centrifugation at 700 rpm for 3 minutes and incubation at 37° C. 5% O2 (total end volume is 1 ml).

TSCs were introduced in day 0, day 1 and day 2 of the protocol, and protocol adjustment was done accordingly.

The next day (day1) 900 µL of medium were gently removed from each well and replaced with 1 ml of preheated N2B27 medium. Same procedure was repeated on day 2.

On day 3 aggregates were gently transferred to 6-well cell suspension culture plates (Greiner, 657185) with 3 ml of preheated EUCM2 (20%-30% FBs) media per well and placed on shaker rotation 60 rpm/min (Thermo 88881102+ 88881123). Plates were transferred to 21% O2 conditions.

On day 4, 2 ml of medium were gently removed per six-well and were placed with 2 ml of preheated EUCM 2 (with 30% FBS). Same procedure was repeated on day 5

On day 6, 2 ml of medium were gently removed per six-well and were placed with 2 ml of preheated EUCM2 with 50% FBS. Same procedure was repeated on day 7.

Immunostaining—As described in Example 1 hereinabove. Antibodies used are shown in Table 1 hereinbelow.

Results:

Human naïve WIBr3 ESCs expanded at least 3 passages in HENSM conditions were then transferred into TSC media, and after 3 passages a stable TSC line could be established and passaged for at least 70 more times. Cells were passaged every 5 days with TryplE. Immunostaining confirmed human TSC identity: human TSC cells were CDx2 negative, Cytokeratin7 (CK7) Positive and GATA3/ TFAP2C positive consistent with previous reports. 10.1016/ j.stem.2017.11.004 and 10.1016/j.stemcr.2022.09.008 (FIG. 55).

As shown in FIG. 56, co-aggregation of three starting cell types, namely naïve human ESCs PSCs, human TSCs and human PRE cells followed by ex-utero culturing did not lead to generation of an organized embryo. In all cases it could be appreciated that the cells co-localize in one side of the aggregate (as appreciated by their RED label) without surrounding the entire sEmbryo at Day 5, which does not correspond with the expected morphology and does not yield normally developed embryos that are surrounded by trophoblast lineage only on the outside periphery.

Example 14

Derivation of a Novel Mouse Extraembryonic Primitie Endodermal Primed Cell

Generation of extra embryonic primitive endodermal primed cells (PRE) originating from mouse naïve ESCs/ iPSCs which can be permanently expanded in culture— Previously PRE cells were described to be derived from mouse E3.5 blastocysts (and not from ESCs or iPSCs) (DOI: 10.1126/science.aay3325) and the media used was a commercial base whose base is not commercially disclosed (StemFit® Basic02 (Ajinomoto) supplemented with: CHIR99021 10 µM, FGF4 50 ng/ml, PDGF 25 ng/ml and Heparin 1 µg/ml) and 10 µM REPROCELL (Reprocell).

To derive PRE cells from in vitro expanded mouse ESCs and iPSCs that that can be permanently expanded in PRE media, three strategies were used (FIG. 57A).

In the top and middle panels of FIG. 57A, the PRE media used contained: serum-free chemically defined N2B27-based media: 240 ml Neurobasal (ThermoFisher 21103049) and 240 ml of DMEM-F12 with HEPES (SIGMA D6421), 5 ml N2 supplement (Invitrogen; 17502048), ml B27 supplement (Invitrogen; 17504044 with or without insulin), 2 mM glutamine or 1 mM GLutamax (Invitrogen), 1% nonessential amino acids (Invitrogen), 0.1 mM β-mercaptoethanol (Sigma), 1% penicillin-streptomycin (Invitrogen). Optionally, the medium also included 5 mg/ml BSA (Sigma). CHIR99021 10 µM, FGF4 50 ng/ml, PDGF 25 ng/ml and Heparin 1/ml). The medium did not contain REPROCELL (Reprocell).

When iGata4 cells were used (top panel of FIG. 57A), DOX was included only in the first 72 hours of the growth expansion protocol.

In both top and middle panels of FIG. 57A, the cells were maintained on MEFs in PRE media and passaged by TryplE every 4-5 days.

In the bottom panel of FIG. 57A, the RPE media used was an RPMI based media containing: 480 RPMI media (21875-034 GIBCO Invitrogen), 10 ml B27 supplement (Invitrogen; 17504044 with insulin or Invitrogen A18956-01 B27 without insulin), 1 mM GLutamax (Invitrogen), 1% nonessential amino acids (Invitrogen), 1% penicillin-streptomycin (Invitrogen), CHIR99021, 10 µM, FGF4 50 ng/ml, PDGF 25 ng/ml and Heparin 1/ml). The medium was devoid of REPROCELL (Reprocell) component.

In the bottom panel of FIG. 57A, WR CD1 iPSCs were passaged in the RPMI based PRE media, and were maintained on MEFs in PRE media and passaged by TryplE every 4-5 days.

Generation of synthetic embryos—To generate the synthetic embryos, three starting cell types were co-aggregated:
1) naïve WT BVSC in 2i/LIF, as indicated.
2) CD1 iPSc derived Pre cell line expanded in PRE media as described hereinabove.
3) naïve iCdx2 ESCs in 2i/LIF, pretreated with DOX (2 µg/ml-Sigma D9891) for 24 h before aggregation (from day -1) in TSC media (25 ng/ml FGF4 (Peprotech), 1µ/ml Heparin (Sigma)) supplemented with lysophosphatidic acid (LPA, a Hippo pathway inhibitor) 01 µM. Co-aggregation was defined as time point 0 of the protocol At the day of aggregation (day 0), the three donor cell populations were trypsinized with % trypsin-EDTA solution (Biological Industries—Sartorius 03-053-1B) for 4 minutes at 37° C. Trypsin enzymatic reaction was stopped by adding aggregation media. Cells were centrifuged at 1200 rpm for 3 minutes and resuspended in aggregation medium with DOX (2 µg/ml—Sigma D9891) and ROCKi Y27632 (5 nM final concentration—Axon Medchem 1683). Following, cells were plated on gelatinized tissue culture plates for mouse embryonic fibroblast depletion for 20 minutes at 37° C. Supernatant was collected, centrifuged and cells were resuspended. The three cell fractions were counted and resuspended in aggregation media with DOX (2 µg/ml-Sigma D9891) and ROCKi Y27632 (5 nM—Axon Medchem 1683). A ratio of (1 WT-ESCs:1 Pre cells:3.33 iCdx2 ESC) was maintained in aggregation experiments, as follows:

| | Number of microwells per well in 24 well plate | Number of added cells per each well of a 24 well plate | # of Cells per single microwell |
|---|---|---|---|
| AggreWell 800 | 300 | 1-iCDX2: 4800 cells<br>2-Pre cells: 1500 cells<br>3-WT ESC 1500 cells | ~27 cells |

1 ml of cell-mix suspension was gently added drop wise to each well of the AggreWell plate followed by centrifugation at 700 rpm for 3 minutes and incubation at 37° C. (total end volume is 1.5 ml).

On the next day (day 1), 1 ml of media (out of total 1.5 ml) was gently removed from each well and replaced with 1 ml of preheated aggregation media with DOX (2 μg/ml-Sigma D9891).

On day 2, 1 ml of media was removed from each well and replaced with 1 ml of preheated aggregation media.

On day 3, 1 ml of media was removed from each well and replaced with 1 ml of preheated EUCM2 media. In this example, EUCM2 media refers to: Advanced DMEM/F12 (GIBCO 21331-020), 5 ml CMRL media (1% final concentration) as a supplement (5 ml GIBCO 11530037), extra added 1 mg/ml D(+)-Glucose Monohydrate (J. T. Baker—0113) (add 500 mg per 500 ml media), 100 nM T3 (3,3',5-Triiodo-L-thyronine sodium salt) (Sigma-Aldrich, T6397), 1 mM Sodium pyruvate (Sigma-Aldrich, S8636), 1 mM GlutaMAX (GIBCO, 35050061), 1% penicillin streptomycin (Biological Industries—Sartorius 03-031-1B), 1× of ITS-X supplement (Thermo Fisher Scientific 51500-056), 8 nM B-estradiol (Sigma-Aldrich, E8875), 200 ng/ml progesterone (Sigma-Aldrich, P0130), 25 μM N-acetyl-L-cysteine (Sigma-Aldrich, A7250)+20% FBS.

On day 4, the synthetic embryos were gently transferred to 6-well cell suspension culture plates (Greiner, 657185) with 5 ml of preheated EUCM2 media containing 30% FBS per well and placed on shaker rotation 60 rpm/min (Thermo 88881102+88881123).

On day 5, egg cylinder shape sEmbryos were picked and transferred to glass culture bottles (50-30 embryos per bottle) containing 2 mL of EUCM media (the contents of which are described in Example 1 hereinabove). Following, the bottles were placed on the rolling culture system previously described electronically controlled roller culture platform (Aguilera-Castrejon et al., 2021a), rotating at 30 revolutions per minute at 37° C., and continuously gassed with an atmosphere of 21% O2, 5% $CO_2$ at 7-8 pounds per square inch (psi). A black non-transparent cloth was used to cover the incubator from light during unit operation.

From day 6 to day 8, 1 ml of EUCM was replaced with preheated 1 ml of EUCM and kept on rolling culture system. Culture media was pre-heated for at least an hour by placing it inside a glass bottle on the rotating culture.

FACS analysis—Cell were immunostained with fluorescent labeled antibodies as indicated in Table 1 hereinbelow, washed with PBS and analyzed on FACS ARIA III and analyzed with a FACS DIVA software.

Immunostaining—As described in Example 1 hereinabove.

Results:

The present inventors obtained novel extra embryonic primitive endodermal primed cells (PRE) originating from mouse naïve ESCs/iPSCs which can be permanently expanded in culture without losing their phenotype (FIG. 57A). FACS analysis demonstrated that these cells, but not parental ESC lines, express the PRE surface marker PDG-FRa (FIG. 57B). Immunostaining analysis demonstrated that these cells express the pluripotent marker Oct4 but not Nanog; the cells are also positive for Gata4 and Gata6 primitive endoderm markers and maintain E-cadherin expression (FIG. 57C). It is noted (as validated in literature DOI: 10.1126/science.aay3325) that XEN cells are negative for Oct4 which is a major difference between them and the obtained PRE cells; and mouse ESCs are positive for both Oct4 and Nanog, while the PRE cells are negative for Nanog and only positive for Oct4.

As exemplified in FIG. 58, co-aggregation of naïve mouse PSCs with this novel PRE cells and mouse iCDX2 trophectoderm primed cells, followed by ex-utero culturing enabled generation of organized embryos (FIG. 58). The Figure demonstrates generation of Day 8 mouse sEmbryos.

Example 15

Generation of Organized Synthetic Human Embryos

Materials and Methods:

Co-aggregation and culture (FIG. 59A)—Three starting cell types were co-aggregated:

4) Naïve WT PSC cells cultured in HENSM medium.

5) For the primitive endoderm compartment—Naïve WT cells were plated on mouse embryonic fibroblast conditions on HENSM supplemented with ROCKi 10 μM (Axon Medchem 1683), next day medium was replaced by RCL medium, RCL was kept for 72 h with 24-hour medium exchanges.

6) For the Trophectoderm lineage—Naïve WT cells were plated on feeder free conditions (Matrigel or laminin E8) on HENSM supplemented with ROCKi 10 μM, next day medium was replaced with (B)AP medium for 24 hours, next medium was replaced with AP(J) for another 48 hours.

All three cell types were supplemented with 5 μM ROCKi Y27632 before harvesting for co-aggregation on the next day. Co-aggregation was defined as time point 0 of the protocol. At the day of aggregation (day 0), Aggrewell plates 400, 24 wells (Stemcell Technologies) were prepared according to manufacturer instructions and prefilled with 500 μL of N2B27 media and kept at 37° C. for medium equilibration. The three cell populations were disaggregated with TrypLE (Thermo Fisher 12604054) for 3 minutes for the WT and Primitive endoderm cells and 5 minutes for the Trophectoderm cells at 37° C., next the enzyme was removed and cells were incubated for two minutes at room temperature, afterwards cells were collected with PBS. Cells were centrifuged at 1300 rpm for 3 minutes and resuspended in N2B27 ROCKi Y27632 (10 μM final concentration). Following, primitive endoderm cells were plated on gelatinized tissue culture plates for mouse embryonic fibroblast depletion for 30 minutes at 37° C. Supernatant was collected, and all three elements were centrifuged separately and cells were resuspended on N2B27 medium. The three cell fractions were counted and resuspended in N2B27 supplemented with ROCKi Y27632 (10 μl). A ratio of 1:1:3 (WT:PRE:TE) was maintained in aggregation experiments, as follows:

| | Number of microwells per well in 24 well plate | Number of added cells per each well of a 24 well plate | # of Cells per single microwell |
|---|---|---|---|
| AggreWell 400 | 1200 | 1-WT 27720 cells<br>2-PrE 27720 cells<br>3-TE 88560 cells | ~120 cells |

0.5 ml of cell-mix suspension was gently added drop wise to each well of the AggreWell plate followed by centrifugation at 700 rpm for 3 minutes and incubation at 37° C. 5% O2 (total end volume is 1 ml).

On the next day (day 1), 900 µL of medium were gently removed from each well and replaced with 1 ml of preheated N2B27 medium. Same procedure was repeated on day 2.

On day 3 aggregates were gently transferred to 6-well cell suspension culture plates (Greiner, 657185) with 3 ml of preheated EUCM2 (20%-30% FBs) media per well and placed on shaker rotation 60 rpm/min (Thermo 88881102+ 88881123). Plates were transferred to 21% O2 conditions.

On day 4, 2 ml of medium were gently removed per six-well and were placed with 2 ml of preheated EUCM 2 (with 30% FBS). The same procedure was repeated on day 5

On day 6, aggregates were collected and transferred into 4 ml of H-EUCM media and placed in Ex Utero electronically controlled Ex Utero Culture Device. Every 24 hours, aggregates were transferred into a new bottle with fresh 4 ml of HEUCM media until day 8 or later.

Electronically controlled ex utero roller culture platform (FIG. 59A)—Putative human sEmbryos were kept starting from Day 6 or later in the ex utero electronically controlled roller culture platform (Aguilera-Castrejon et al., 2021). A 'rotator' culture method provides continuous flow of oxygenating gas to cultures in rotating bottles. sEmbryos are kept on a rotating bottles culture unit inside a "precision" incubator system during all the time of culture. Glass culture bottles are plugged into the hollowed rotating drum. Oxygenating gas flows along the axis and is distributed to the culture bottles by a baffle plate within the drum (Aguilera-Castrejon et al., 2021). The rotator is supplied complete with gas filter, bubbler and leads by the manufacturer. The Incubator uses a thyristor-controlled heater and high flow-rate fan to give a highly stable and uniform temperature as previously described (Aguilera-Castrejon et al., 2021). The incubator has a working volume 370×350×200 mm high which is accessed through the hinged Perspex top. The heater element is rated at 750 Watts. Bung (Hole) is used to seal the bottles and Bung (Solid) is used to seal the drum (Aguilera-Castrejon et al., 2021). In order to achieve constant O2 and $CO_2$ levels in the culture medium throughout the incubation period, the incubator module was linked to an in-house designed and customized gas and pressure electronic control unit (models #-HannaLab1 or HannaLab1.2; designed by the Hanna lab (Aguilera-Castrejon et al., 2021). Carbon dioxide and oxygen concentration are regulated by specific controllers located inside the regulation module. A pressure transmitter allows precise and stable control of the gas pressure between 5 to 10 psi (positive pressure over ambient external atmospheric pressure), that is transmitted to the embryo bottle apparatus. Regulation of pressure generated by the pressure pump is done by setting the adequate voltage on the pressure transmitter. Oxygen and $CO_2$ are then injected into the gas mixer box. The mixing of the gases in the gas box is homogeneous and mixed by a centrifugal blower. The gases are injected into the incubator unit at pressure of 6.5-8 psi (as measured at the gas mixing box outlet) by a pump, which yields an effective pressure ~0.1-0.5 psi entering the rotating drum, reminiscnet of pressure values measured in amniotic fluid of early embryos in vivo (Sideris and Nicolaides, 1990).

Adequate and stable control of the pressure of the gas flowing from the mixing box outlet into the water bottle inside the incubator should be measured by using a pressure gauge before each experiment. The main components of the system are the following: Oxygen and $CO_2$ controller, pressure pump, vacuum pump, oxygen and $CO_2$ sensors, power supply, check valve, mix gas box, pressure transmitter, limit flow, adapter control for gases, 1 µm filters, centrifugal blower. Gas flows from the mix box through the inlet into the water bottle, and the speed of gas flowing into the bottle can be controlled with a valve on the lid of the water bottle. The bubble rate (which indicates the speed of gas flowing into the bottles) can be adjusted as needed by the user by closing/opening the valve. Ideally, the flow of bubbles should be such to allow formation of individual bubbles at a rate of 3-4 bubbles per second in the water-filled test tube outlet, or to the first point where continuous bubbling is observed. Humidified gas circulates to a glass test tube and then to the inside of the bottles in the rotating drum. Gas flow speed can be monitored by the rate of bubbles created inside the outlet water-filled test tube. A black nontransparent cloth is used cover the incubator to provide phototoxicity protection for the ex utero cultured embryos and sEmbryos.

H-EUCM is based on EUCM was previously established in Aguilera-Castrejon (Aguilera-Castrejon et al., 2021) for mouse embryos, with adaptation to be more suitable for human sEmbryos. Specifically, the H-EUCM is composed of:

1) 25% DMEM (GIBCO 11880—DMEM, low glucose, with pyruvate, no glutamine, no phenol red (and no HEPES)) or Advanced DMEM-F12 (Invitrogen 12634010) or CMRL (Invitrogen 11530037) or TCM199 media (Gibco 11150059 or Sigma M2520);

2) 50% Fetal Bovine Serum (FBS) (GIBCO) and 25% Human Umbilical Cord Blood Serum (HUS) (or Human Adult Blood Serum (HAS)) that is prepared in-house; and 3) supplemented with a final concentration of 1× GlutaMAX (GIBCO, 35,050,061), 50 units/ml penicillin— 50 mg/ml streptomycin (Biological industries, 030311B), extra added 1 mM sodium pyruvate (Biological industries, 030421B), extra added 4 mg/mL of D-glucose (J. T. Baker), and added HEPES (11 mM final concentration) (GIBCO 15630056).

Alternatively, EUCM2 media composed of 50% FBS or 50% FBs and 25% HAS could also be used in the roller culture on days 6 onwards.

Results:

Co-aggregation of the naïve PSCs with the two stem cell populations, followed by ex-utero culturing according to the protocols described hereinabove and in FIG. 59A enabled generation of organized embryos. As shown in FIG. 59B, the human sEmbryo shows bilaminar disc formation, amniotic cavity and yolk sac cavity, all surrounded by trophoblast compartment.

Example 16

Generation of Organized Synthetic Human Embryos

Materials and Methods:

Co-aggregation and culture (FIG. 60A)—Two starting cell types were co-aggregated:

1) Naïve WT PSC cells cultured in HENSM medium, which also give rise to primitive endoderm lineage once aggregation begins in N2B27 media; and 2) For the Trophectoderm lineage—Naïve WT cells were plated on feeder free conditions (Matrigel or laminin E8) on HENSM supplemented with ROCKi 10 µM, next day medium was replaced with (B)AP medium for 24 hours, next medium was replaced with AP(J) for another 48 hours.

Both cell types were supplemented with 5 µM ROCKi Y27632 before harvesting for co-aggregation on the next day. Co-aggregation was defined as time point 0 of the protocol. At the day of aggregation (day 0), Aggrewell plates 400, 24 wells (Stemcell Technologies) were prepared according to manufacturer instructions and prefilled with 500 µL of N2B27 media and kept at 37° C. for medium equilibration. The two cell populations were disaggregated with TrypLE (Thermo Fisher 12604054) for 3 minutes for the WT PSC cells and 5 minutes for the Trophectoderm cells at 37° C., next the enzyme was removed and cells were incubated for two minutes at room temperature, afterwards cells were collected with PBS. Cells were centrifuged at 1300 rpm for 3 minutes and resuspended in N2B27 ROCKi Y27632 (10 µM final concentration). The supernatant was collected, and all elements were centrifuged separately, and cells were resuspended on N2B27 medium. The two cell fractions were counted and resuspended in N2B27 supplemented with ROCKi Y27632 (10 µl). A ratio of 2:3 (WT:TE) was maintained in aggregation experiments, as follows:

| | Number of microwells per well in 24 well plate | Number of added cells per each well of a 24 well plate | # of Cells per single microwell |
|---|---|---|---|
| Aggre Well 400 | 1200 | 1-WT 55440 cells<br>2-TE 88560 cells | ~120 cells |

0.5 ml of cell-mix suspension was gently added drop wise to each well of the AggreWell plate followed by centrifugation at 700 rpm for 3 minutes and incubation at 37° C. 5% O2 (total end volume is 1 ml).

On the next day (day 1), 900 µL of medium were gently removed from each well and replaced with 1 ml of preheated N2B27 medium. The same procedure was repeated on day 2.

On day 3 aggregates were gently transferred to 6-well cell suspension culture plates (Greiner, 657185) with 3 ml of preheated EUCM2 (20%-30% FBs) media per well and placed on shaker rotation 60 rpm/min (Thermo 88881102+ 88881123). Plates were transferred to 21% O2 conditions.

On day 4, 2 ml of medium were gently removed per six-well and were placed with 2 ml of preheated EUCM 2 (with 30% FBS). The same procedure was repeated on day 5.

On day 6, aggregates were collected and transferred into 4 ml of H-EUCM media and placed in Ex Utero electronically controlled Ex Utero Culture Device. Every 24 hours, aggregates were transferred into a new bottle with fresh 4 ml of HEUCM media until day 8 or later.

Electronically controlled ex utero roller culture platform (FIG. 60A)—As described in Example 15 hereinabove and according to the scheme shown in FIG. 60A.

Results:

Co-aggregation of the naïve PSCs with the trophectoderm-primed population, followed by ex-utero culturing according to the protocols described hereinabove and in FIG. 60A enabled generation of organized embryos. As shown in FIG. 60B, the human sEmbryo shows bilaminar disc formation, amniotic cavity and yolk sac cavity, all surrounded by trophoblast compartment.

TABLE 1

Primary antibodies

| Ab name | Conc. | Volume | Aliquots | Cat no. | Type | Host | Company | Working dilution |
|---|---|---|---|---|---|---|---|---|
| Oct4 (C-10 clone) | 200 µg/ml | 100 µl | No | SC5279 | Monoclonal | Mouse | Santa cruz | 1:100 |
| E-cadherin [HECD-1] | 0.05 mg/ml | 500 µl | No | ab1416-500 | Monoclonal | Mouse | abcam | 1:200 |
| PDGFR-A | 0.5 mg/ml | 100 µl | No | 14-140-182 | Monoclonal | Rat | eBioscience | |
| Gata4 | 1 mg/ml | 100 µl | 5 µl | ab84593 | Polyclonal | Rabbit | abcam | 1:100/1:200 |
| CDX2 | 0.1 mg/ml | 100 µl | | #3977 | Polyclonal | Rabbit | Cell signaling | 1:100/1:200 |
| GFP | ND | 50 µl | 10 µl | ab290 | Polyclonal | Rabbit | abcam | 1:250-1:500 |
| GFP | 1 mg/ml | 100 µl | 10 µl | ab6673 | Polyclonal | Goat | abcam | 1:250 |
| MF 20-s (myosin) | 26 µg/ml | 1 ml | 100 µl | | monoclonal | Hybridoma | DHSB | 1:250 |
| human/mouse CDX2 | 50 mg/ml | 1 ml | 50 µl | AU392A-UC | monoclonal | mouse | Biogenex | 1:100 |
| mSox2 | 0.2 mg/ml | 100 µl | 25 µl | AF2018 | polyclonal | Goat | R&D | 1:200 |
| Gata4 | 0.2 mg/ml | 1 ml | No | sc-1237 | polyclonal | Goat | Santa Cruz | 1:200 |
| Nanog | 0.5 mg/ml | | 8 µl | 14-5761 | polyclonal | Rat | eBioscience | 1:250-1:500 |
| SOX9 | 1 mg/ml | 100 ug | No | ab5535 | polyclonal | Rabbit | Millipore | 1:100-1:200 |
| Anti-PKC ζ (H-1) | 0.2 mg/ml | 1 ml | N/A | sc-17781 | Monoclonal | Mouse | Santa Cruz | |
| Anti-AP-2α (3B5) | 0.2 mg/ml | 1 ml | N/A | sc-12726 | Monoclonal | Mouse | Santa Cruz | |
| Gata4 | 0.2 mg/ml | 1 ml | | sc-25310 | Monoclonal | Mouse | Santa Cruz | 1:100 |
| Gata4 | 0.5 mg/ml | 100 ug | | 14-9980-82 | Monoclonal | Rat | invitrogen | |
| Anti-PKC ζ (H-1) | 0.2 mg/ml | 1 ml | N/A | sc-17781 | Monoclonal | Mouse | Santa Cruz | |
| Anti-TFAP2a (AP-2α) (3B5) | 0.2 mg/ml | 1 ml | N/A | sc-12726 | Monoclonal | Mouse | Santa Cruz | |
| Human Otx2 | 0.2 mg/ml | 500 µl | 20 µl | AF1979 | Polyclonal | Goat | R&D | 1:200 |
| Pax6 | 2 mg/ml | 100 µl | not aliquoted | Poly901301 | Polyclonal | Rabbit | Biolegend | 1:100 |

TABLE 1-continued

| Primary antibodies | | | | | | | | |
|---|---|---|---|---|---|---|---|---|
| Ab name | Conc. | Volume | Aliquots | Cat no. | Type | Host | Company | Working dilution |
| TUJ1 | 1 mg/ml | 250 ul | not aliquoted | 801202 | monoclonal | Mouse | Biolegend | 1:100 |
| FOXA2 | ND | 100 μl | 10 ul | ab108422 | Monoclonal | Rabbit | abcam | 1:100 |
| TBR2 (EOMES) | 1 mg/ml | 100 μl | 8 μl | AB2283 | Polyclonal | Rabbit | millipore | 1:50 Low signal |
| Sox17 | 0.2 mg/ml | 100 μl | 10 μl | AF1924 | Polyclonal | Goat | R&D | 1:100-1:50 |
| Lefty | 1 mg/ml | 100 μl | 10 μl | ab22569 | Polyclonal | Rabbit | abcam | 1:100 |
| Brachyury(D2Z3J) mAb | | 100 μl | | #81694 | monoclonal | Rabbit | Cell signaling | 1:100 |
| Human KLF17 [N-terminus 2-51 aa] | 0.5 mg/ml | 100 μl | 10 μl | ab84196 | Polyclonal | Rabbit | abcam | |
| Human KLF17 [C-terminus 250-279 aa] (KLF17 C) | | 400 μl | 20 μl | ab174956 | Polyclonal | Rabbit | abcam | |
| Human KLF17 | 0.6 mg/ml | 100 ul | | HPA024629 | Polyclonal | Rabbit | sigma | |
| TFAP2c (AP2γ) | | | | #2320 | Polyclonal | rabbit | cell signaling | Middle background |
| Myosin heavy chain (clone MF20) | 0.2 mg/ml | 500 μl | 20 μl | MAB470 | monoclonal | mouse | R&D | 1:250 |
| CK8 Cytokeratin 8 | 1 mg/ml | 100 ul | | MABT329 | monoclonal | Rat | Millipore | |
| Lefty | 0.2 mg/ml | 500 μl | 20 μl | AF746 | polyclonal | Goat | R&D | 1:100 |
| mCHERRY/tdTomato | | | 10 ul | AB0040200 | polyclonal | Goat | SICGEN ANTIBODIES | 1:200 |
| TBR2/Eomes | 1 mg/ml | 100 ul | 5 ul | ab23345 | Polyclonal | Rabbit | abcam | 1:50/1:100 |
| Cdx2 | 1 mg/ml | 100 ul | 5 ul | ab76541 | Monoclonal | Rabbit | abcam | 1:200/1:500 |
| DKK1 | 0.2 mg/ml | 500 ul | 20 ul | AF1096 | Polyclonal | Goat | R&D | 1:100 |
| AP2gamma (Tfap2c) | 0.2 mg/ml | 500 ul | 10 ul | AF5059 | monoclonal | Goat | R&D | 1:100/1:200 |
| cytokeratin7 CK7 | | 100 ul | 9 ul | ab181598 | Monoclonal | Rabbit | abcam | 1:200 |
| NR2F2 | | 100 ul | 9 ul | ab211776 | Monoclonal | Rabbit | abcam | |
| nanog | | 100 ul | 9 ul | ab109250 | Monoclonal | Rabbit | abcam | |
| TBX3 | | 100 ul | 9 ul | ab99302 | Monoclonal | Rabbit | abcam | |
| Mouse Anti-Zo-1 | 0.5 mg/mL | 100 ul | | Zy-339100 | Monoclonal | Mouse | invitrogen | 1:200 |
| Brachyury | 0.2 mg/ml | 100 μl | 10 μl | AF2085 | Polyclonal | Goat | R&D | 1:100 |
| Lefty | 0.2 mg/ml | 500 μl | 20 μl | AF746 | polyclonal | Goat | R&D | 1:100 |
| RUNX1/AML1 [clone EPR23044-100] | | 100 ul | 5 ul | ab240639 | Monoclonal | Rabbit | Abcam | 1:100 |
| HOXB4 [clone EPR1917] | | 100 ul | 5 ul | ab133521 | Monoclonal | Rabbit | Abcam | 1:100 |
| FoxG1 (clone EPR18987) | 0.57 mg/ml | 100 ul | 6 ul | ab196868 | Monoclonal | Rabbit | abcam | 1:100 |
| GATA3 | | | | AF2605 | Polyclonal | Goat | R&D | 1:200 |
| GATA3 | | | | MA1-028 | monoclonal | Mouse | invitrogen | 1:200 |
| Anti hCG beta | 0.2 mg/ml | 100 ul | 10 ul | ab9582 | Monoclonal | Mouse | abcam | 1:200 |
| Anti-PKC ζ (H-1) | 0.2 mg/ml | 1 ml | N/A | sc-17781 | Monoclonal | Mouse | Santa Cruz | |
| Anti-AP-2α (3B5) | 0.2 mg/ml | 1 ml | N/A | sc-12726 | Monoclonal | Mouse | Santa Cruz | |
| Cerberus 1 | 0.2 mg/ml | 200 ul | 7.5 ul | AF1075 | Polyclonal | Goat | R&D | |
| TROP-2 [Clone 77220] | 0.2 mg/ml | 200 ul | 7.5 ul | MAB650 | Polyclonal | Goat | R&D | |
| Gata6 (clone D61E4) | | 100 ul | Not aliquoted | #5951 | Monoclonal | Rabbit | Cell Signaling | |
| Blimp1/PDRI-BF1 [Clone C14A4] | | 100 ul | Not aliquoted | #9115 | Monoclonal | Rabbit | Cell Signaling | |
| E-Cadherin [Clone 24E10] | | 100 ul | Not aliquoted | #3195 | Monoclonal | Rabbit | Cell Signaling | |
| Collagen VI | | 100 ul | 7 ul | ab6588 | Polyclonal | Rabbit | Abcam | |
| Wnt5a [Clone 24E10] | | 100 ul | 7 ul | ab235966 | Polyclonal | Rabbit | Abcam | |
| Cytokeratin 7 [EPR1619Y] | | 100 ul | 7 ul | ab68459 | Monoclonal | Rabbit | Abcam | 1:200 |
| FoxA1 [clone 1B1] | 1 mg/ml | 200 ul | 7.5 ul | ab55178 | Monoclonal | Mouse | Abcam | |
| VEGFR2/KDR/Flk-1 | 0.2 mg/ml | 200 ul | 10 ul | AF357 | Polyclonal | Goat | R&D | |
| Oct3/4 | 0.2 mg/ml | 200 ul | 7.5 ul | AF1759 | Polyclonal | Goat | R&D | |
| Gata6 | 0.2 mg/ml | 500 ul | 10 ul | AF1700 | Polyclonal | Goat | R&D | |
| Syndecan1 [EPR6454] | | 100 ul | 5.5 ul | ab128936 | Monoclonal | Rabbit | Abcam | 1:250/1:500 |
| Islet1 [EP4182] | | 100 ul | 5.5 ul | ab109517 | Monoclonal | Rabbit | Abcam | |
| PDGFR-alpha | | 100 ul | 5.5 ul | ab230457 | Polyclonal | Rabbit | Abcam | |
| PDGFR-alpha [EPR5480] | | 100 ul | 5.5 ul | ab134123 | Monoclonal | Rabbit | Abcam | |
| MIXL1 | | 100 ul | 5.5 ul | HPA005662 | Polyclonal | Rabbit | SIGMA | |
| Nidogen-2 | | 100 ul | 5.5 ul | AF3385 | Polyclonal | Goat | R&D | |
| GABRP | 0.5 mg/ml | 100 ul | 6.5 ul | PA5-46830 | Polyclonal | Rabbit | Invitrogen | |
| Hesx1 | | 100 ul | 6.5 ul | ab246949 | Polyclonal | Rabbit | Abcam | |

TABLE 1-continued

| Primary antibodies | | | | | | | | |
|---|---|---|---|---|---|---|---|---|
| Ab name | Conc. | Volume | Aliquots | Cat no. | Type | Host | Company | Working dilution |
| Periostin | 0.5 mg/ml | 100 ul | 10 ul | ab14041 | Polyclonal | Rabbit | Abcam | |
| Vimentin [RV202] | 1 mg/ml | 100 ul | 10 ul | ab8978 | Monoclonal | Mouse | Abcam | |
| Tetherin/BTS2 [EPR20202] | 0.75 mg/ml | 100 ul | 10 ul | ab243230 | Monoclonal | Rabbit | Abcam | |
| GATA2 [EPR2822] | 0.325 mg/ml | 100 ul | 10 ul | ab109241 | Monoclonal | Rabbit | Abcam | |

TABLE 2

List of primers:

| Primer | Sequence | SEQ ID NO: |
|---|---|---|
| Primer: human GATA2 (Forward): | ACTGACGGAGAGCATGAAGAT | 131 |
| Primer: human GATA2 (Reverse): | CCGGCACATAGGAGGGGTA | 132 |
| Primer: human GATA3 (Forward): | GCCCCTCATTAAGCCCAAG | 133 |
| Primer: human GATA3 (Reverse): | TTGTGGTGGTCTGACAGTTCG | 134 |
| Primer: human ENPEP (Forward): | TCCCAAAGAATACGGAGCACT | 135 |
| Primer: human ENPEP (Reverse): | TCATGGGGACAGACTTCTCAA | 136 |
| Primer: human ELF5 (Forward): | TAGGGAACAAGGAATTTTTCGGG | 137 |
| Primer: human ELF5 (Reverse): | GTACACTAACCTTCGGTCAACC | 138 |
| Primer: human DAB2 (Forward): | ACCACCCTTTCACAAGCAAC | 139 |
| Primer: human DAB2 (Reverse): | TGTGCCCATTTGCAATTCTA | 140 |
| Primer: human TACSTD2 (Forward): | ACAACGATGGCCTCTACGAC | 141 |
| Primer: human TACSTD2 (Reverse): | AGTTCACGCACCAGCACAC | 142 |
| Primer: human TFAP2A (Forward): | GTTACCCTGCTCACATCACTAG | 143 |
| Primer: human TFAP2A (Reverse): | TCTTGTCACTTGCTCATTGGG | 144 |
| Primer: human SIGLEC6 (Forward): | TCACAACCCTGGTTTTCCTC | 145 |
| Primer: human SIGLEC6 (Reverse): | CTGTCTGGAACTGGTGCTGA | 146 |
| Primer: human CDX2-F (Forward): | TCACCATCCGGAGGAAAGCC | 147 |
| Primer: human CDX2-R (Reverse): | CTCTCCTTTGCTCTGCGGTT | 148 |
| Primer: human HAND1 (Forward): | CCAAGGATGCACAGTCTGG | 149 |
| Primer: human HAND1 (Reverse): | AGGAGGAAAACCTTCGTGCTG | 150 |
| Primer: human TFAP2C (Forward): | ACGAAATGAGATGGCAGCTAGGAAGA | 151 |
| Primer: human TFAP2C (Reverse): | TGTCCGGTCTTGGCTGAGAAGTTC | 152 |
| Primer: human ABCG2 (Forward): | ACG AAC GGA TTA ACA GGG TCA | 153 |
| Primer: human ABCG2 (Reverse): | CCT CCA GAC ACA CCA CGG ATA | 154 |
| Primer: human KRT19 (Forward): | ACC TGG AGA TGC AGA TCG AA | 155 |

TABLE 2-continued

List of primers:

| Primer | Sequence | SEQ ID NO: |
|---|---|---|
| Primer: human KRT19 (Reverse): | AAT CCA CCT CCA CAC TGA CC | 156 |
| Primer: human VGLL1 (Forward): | TGC CTC CCG GCT CAG TTC ACT | 157 |
| Primer: human VGLL1 (Reverse): | CCC AGT GGT TTG GTG GTG TA | 158 |
| Primer: human NR2F2 (Forward): | GCC ATA GTC CTG TTC ACC TCA | 159 |
| Primer: human NR2F2 (Reverse): | AAT CTC GTC GGC TGG TTG | 160 |
| Primer: human SOX17 (Forward): | TGG CGC AGC AGA ATC CAG AC | 161 |
| Primer: human SOX17 (Reverse) | TTG GGG TGG TCC TGC ATG TG | 162 |
| Primer: human PDGFR-alpha (Forward): | TGC CTG ACA TTG ACC CTG T | 163 |
| Primer: human PDGFR-alpha (Reverse): | CCG TCT CAA TGG CAC TCT C | 164 |
| Primer: human CXCR4 (Forward): | CCT GCC TGG TAT TGT CAT CC | 165 |
| Primer: human CXCR4 (Reverse): | GAT GGG GAT GAT TGT GGT CT | 166 |
| Primer: human HHEX1 (Forward): | GCG GAC GGT GAA CGA CTA | 167 |
| Primer: human HHEX1 (Reverse): | GGC CGC CTT TCC TTT TAT | 168 |
| Primer: human GSC (Forward): | CCT CCG CGA GGA GAA AGT | 169 |
| Primer: human GSC (Reverse): | CGT TCT CCG ACT CCT CTG AT | 170 |
| Primer: human Nidogen-2 (Forward): | GTG TCA GGC TTG AGG TGG AG | 171 |
| Primer: human Nidogen-2 (Reverse): | TGC CTG ACA TTG ACC CTG T | 172 |
| Primer: human GATA6 (Forward): | GCGGGCTCTACAGCAAGAT | 173 |
| Primer: human GATA6 (Reverse): | TGGCACAGGACAATCCAAG | 174 |
| Primer: human GATA4 (Forward): | GGAAGCCCAAGAACCTGAAT | 175 |
| Primer: human GATA4 (Reverse): | GTTGCTGGAGTTGCTGGAA | 176 |
| Primer: human FOXA2 (Forward): | TGAAGATGGAAGGGCACGAGC | 177 |
| Primer: human FOXA2 (Reverse): | CCGACATGCTCATGTACGTGTTCAT | 178 |
| Primer: human VIM (Forward): | AGTCCACTGAGTACCGGAGAC | 179 |
| Primer: human VIM (Reverse): | CATTTCACGCATCTGGCGTTC | 180 |
| Primer: human GAPDH (Forward): | AGGGCTGCTTTTAACTCTGGT | 181 |
| Primer: human GAPDH (Reverse): | CCCCACTTGATTTTGGAGGGA | 182 |
| Primer: human ACTIN (Forward): | CCACGAAACTACCTTCAACTCC | 183 |
| Primer: human ACTIN (Reverse): | GTGATCTCCTTCTGCATCCTGT | 184 |
| Primer: human PSG3 (Forward): | TCG TAA AGC GAG GTG ATG GG | 185 |
| Primer: human PSG3 (Reverse): | AAG CTC ACA GCC TCC ATG TC | 186 |
| Primer: human EGFR (Forward): | AAC TGT GAG GTG GTC CTT GG | 187 |
| Primer: human EGFR (Reverse): | GTT GAG GGC AAT GAG GAC AT | 188 |
| Primer: human DPP4 (Forward): | TGG TCT CCA AAC GGC ACT TT | 189 |
| Primer: human DPP4 (Reverse): | AAC TGT GAG GTG GTC CTT GG | 190 |

TABLE 2-continued

List of primers:

| Primer | Sequence | SEQ ID NO: |
|---|---|---|
| Primer: human CGA (Forward): | CAC TCC ACT AAG GTC CAA GAA GA | 191 |
| Primer: human CGA (Reverse): | CCG TGT GGT TCT CCA CTT TGA | 192 |
| Primer: human CDH10 (Forward): | AGA TGC CGA TGA CCC TTC ATA | 193 |
| Primer: human CDH10 (Reverse): | TGT TCG GTA AAG CAG TCC TGA | 194 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of generating a synthetic embryo, the method comprising:
   (a) inducing expression of an endogenous factor that induces differentiation to trophectoderm cells in a subpopulation of naïve pluripotent stem cells (PSCs) to obtain trophectoderm primed cells;
   (b) inducing expression of an endogenous factor that induces differentiation to extra embryonic primitive endodermal cells in a second subpopulation of naïve PSCs to obtain extra embryonic primitive endodermal primed cells;
   (c) mixing said trophectoderm primed cells and said extra embryonic primitive endodermal primed cells with naïve PSCs under conditions that allow formation of aggregated cells; and
   (d) ex-utero culturing said aggregated cells following said (c) in a static culture followed by a dynamic culture,
   wherein said (a) comprises culturing said subpopulation of naïve PSCs with a factor selected from the group consisting of a TGFR inhibitor, a FGFR inhibitor, a MEK/ERK inhibitor, a BMP4, a JAK inhibitor, a ROCK pathway inhibitor, FGF4, FGF2, heparin, a SUMOylation inhibitor, a Histone Deacetylase inhibitor, a HIPPO signaling pathway inhibitor, and a factor that induces YAP nuclear translocation, under conditions enabling expression of said endogenous factor, starting within 6 days—6 hours prior to said mixing, and wherein said (b) comprises culturing said second subpopulation of naïve PSCs with a factor selected from the group consisting of a GSK-3 inhibitor, WNT ligand, heparin, FGF2, FGF4, PDGF, leukemia inhibitory factor (LIF), and insulin, under conditions enabling expression of said endogenous factor, starting within 6-6 hours prior to said mixing,
   thereby generating the synthetic embryo.

2. The method of claim 1, wherein said mixing said naïve PSCs, said trophectoderm primed cells and said extra embryonic primitive endodermal primed cells is effected concomitantly.

3. The method of claim 1, wherein said mixing said naïve PSCs and said extra embryonic primitive endodermal primed cells is effected prior to said mixing with said trophectoderm primed cells.

4. The method of claim 1, wherein said trophectoderm cells and/or said extra embryonic primitive endodermal primed cells express a pluripotency marker at said mixing.

5. The method of claim 1, wherein said trophectoderm primed cells express a trophectoderm marker at said mixing.

6. The method of claim 1, wherein said extra embryonic endodermal primed cells express an extra embryonic primitive endoderm marker at said mixing.

7. The method of claim 1, wherein said endogenous factor that induces differentiation to extra embryonic primitive endodermal cells comprises Gata4, Gata6 and/or SOX17.

8. The method of claim 1, wherein said endogenous factor that induces differentiation to trophectoderm cells is selected from the group consisting of Cdx2, Gata3 and Gata2.

9. The method of claim 1, wherein said inducing said expression of said endogenous factor starts about 3 days prior to said mixing.

10. The method of claim 1, wherein a ratio between said naïve PSCs and said trophectoderm primed cells is between 1:1 and 1:5.

11. The method of claim 1, wherein a ratio between said naïve PSCs and said primitive endodermal primed cells is between 1:1 and 2:1.

12. The method of claim 1, wherein said static culture is effected until said embryo reaches at least an early post-implantation egg-cylinder or bilaminar disc stage.

13. The method of claim 1, wherein said dynamic culture starts the latest when said embryo reaches an early somite stage.

14. The method of claim 1, wherein said dynamic culture comprises a shaker culture, a roller culture or a sequential combination thereof.

15. The method of claim 1, wherein said dynamic culture is effected under a hyperbaric pressure of more than 0.05 and less than 10.2 pounds per square inch (psi).

16. The method of claim 1, wherein said culturing is effected in an atmosphere comprising 10-40% oxygen.

17. The method of claim 1, wherein said cells are mammalian cells.

18. The method of claim 17, wherein said mammalian cells are mouse cells, human cells or non-human primate cells.

* * * * *

UNITED STATES PATENT AND TRADEMARK OFFICE
CERTIFICATE OF CORRECTION

PATENT NO. : 11,959,097 B2
APPLICATION NO. : 18/226877
DATED : April 16, 2024
INVENTOR(S) : Yaqub Hanna et al.

It is certified that error appears in the above-identified patent and that said Letters Patent is hereby corrected as shown below:

In the Claims

In Claim 1, Column 230 at Line 41, "within 6-6 hours prior in mid mixing" should be changed to --within 6 days-6 hours prior to said mixing --.

Signed and Sealed this
First Day of October, 2024

Katherine Kelly Vidal
*Director of the United States Patent and Trademark Office*

SEQUENCE LISTING

```
Sequence total quantity: 199
SEQ ID NO: 1            moltype = DNA  length = 1515
FEATURE                 Location/Qualifiers
misc_feature            1..1515
                        note = Gata 4 insert
source                  1..1515
                        mol_type = other DNA
                        organism = synthetic construct
SEQUENCE: 1
gcccttttg ggttttgtt ttgttttgtt ttgttttgat ttttggtgac agttccgcac    60
acccgcattc tagttcttgt ctgcctcgtg ctcagagctt ggggcgatgt accaaagcct   120
ggccatggcc gccaaccacg gcccccgcc cggcgcctac gaagcaggtg gccctggcgc   180
cttcatgcac agcgcgggcg ccgcgtcctc gcccgtctac gtgccactc cgcgggtgcc   240
gtcctctgtg ctgggcctgt cctacctgca gggcggtggc agtgccgctg cagctggaac   300
cacctcgggt ggcagctccg gggccggccc gtcgggtgca gggcctggga cccagcaggg   360
tagccctggc tggagccaag ctggagccga gggagccgca tacaccccgc cgcccgtgtc   420
cccgcgcttc tctttccccgg ggactactgg gtccctggcg gccgctgccg ccgctgccgc   480
agcccgggaa gctgcagcct acggcagtgg cggcggggcg gcgggcgctg gtctggctgg   540
ccgagagcag tacgggcgtc cgggcttcgc cggctcctac tccagccct acccagccta   600
catggccgac gtgggagcat cctgggccgc agccgctgcc gcctctgccg gccccttcga   660
cagcccagtc ctgcacagcc tgcctggacg ggccaacct ggaagacacc ccaatctcgt   720
agatatgttt gatgacttct cagaaggcag agagtgtgtc aattgtgggg ccatgtccac   780
cccactctgg aggcgagatg ggacgggaca ctacctgtgc aatgcctgtg gcctctatca   840
caagatgaac ggcatcaacc ggccctcat taagcctcag cgccgcctgt ccgcttcccg   900
ccgggtaggc ctctcctgtg ccaactgcca gactaccacc accacgctgt ggcgtcgtaa   960
tgccgaggt gagcctgtat gtaatgcctg cggcctctac atgaagctcc atgggggttcc  1020
caggcctctt gcaatgcgga aggaggggat tcaaaccaga aaacggaagc ccaagaacct  1080
gaataaatct aagacgccag caggtcctgc tggtgagacc ctcccctcct ccagtggtgc  1140
ctccagcggt aactccagca atgccactag cagcagcagc agcagtgaag agatgcgccc  1200
catcaagaca gagcccgggc tgtcatctca ctatgggcac agcagctcca tgtcccagac  1260
attcagtact gtgtccggcc acgggccctc catccatcca gtgctgtctg ctctgaagct  1320
gtccccacaa ggctatgcat ctcctgtcac tcagacatcg caggccagct ccaagcagga  1380
ctcttggaac agcctggtcc tggctgacag tcatggggac ataatcaccg cgtaatcagc  1440
gccccccctt ccctcttcaa attcctgctc ggacttggga cgtggggcc agcaaagtaa  1500
aaggctggga aggggc                                                  1515

SEQ ID NO: 2            moltype = DNA  length = 22
FEATURE                 Location/Qualifiers
misc_feature            1..22
                        note = Single strand DNA oligonucleotide
source                  1..22
                        mol_type = other DNA
                        organism = synthetic construct
SEQUENCE: 2
agtcaaggcc gagaatggga ag                                            22
```

-continued

```
SEQ ID NO: 3            moltype = DNA   length = 22
FEATURE                 Location/Qualifiers
misc_feature            1..22
                        note = Single strand DNA oligonucleotide
source                  1..22
                        mol_type = other DNA
                        organism = synthetic construct
SEQUENCE: 3
aagcagttgg tggtgcagga tg                                                22

SEQ ID NO: 4            moltype = DNA   length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 4
agaggatcac cttggggtac a                                                 21

SEQ ID NO: 5            moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 5
cgaagcgaca gatggtggtc                                                   20

SEQ ID NO: 6            moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 6
ctcaagtcct gaggctgaca                                                   20

SEQ ID NO: 7            moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 7
tgaaacctgt ccttgagtgc                                                   20

SEQ ID NO: 8            moltype = DNA   length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 8
tagagctaga ctccgggcga tga                                               23

SEQ ID NO: 9            moltype = DNA   length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 9
ttgccttaaa caagaccacg aaa                                               23

SEQ ID NO: 10           moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 10
gcacacctgc gaactcacac                                                   20
```

```
SEQ ID NO: 11              moltype = DNA   length = 21
FEATURE                    Location/Qualifiers
misc_feature               1..21
                           note = Single strand DNA oligonucleotide
source                     1..21
                           mol_type = other DNA
                           organism = synthetic construct
SEQUENCE: 11
ccgtcccagt cacagtggta a                                               21

SEQ ID NO: 12              moltype = DNA   length = 22
FEATURE                    Location/Qualifiers
misc_feature               1..22
                           note = Single strand DNA oligonucleotide
source                     1..22
                           mol_type = other DNA
                           organism = synthetic construct
SEQUENCE: 12
gcgaaacctg tgcgagtgga tg                                              22

SEQ ID NO: 13              moltype = DNA   length = 28
FEATURE                    Location/Qualifiers
misc_feature               1..28
                           note = Single strand DNA oligonucleotide
source                     1..28
                           mol_type = other DNA
                           organism = synthetic construct
SEQUENCE: 13
cggtatttgt cttttgtcct ggttttca                                        28

SEQ ID NO: 14              moltype = DNA   length = 22
FEATURE                    Location/Qualifiers
misc_feature               1..22
                           note = Single strand DNA oligonucleotide
source                     1..22
                           mol_type = other DNA
                           organism = synthetic construct
SEQUENCE: 14
cacaagatga acggcatcaa cc                                              22

SEQ ID NO: 15              moltype = DNA   length = 18
FEATURE                    Location/Qualifiers
misc_feature               1..18
                           note = Single strand DNA oligonucleotide
source                     1..18
                           mol_type = other DNA
                           organism = synthetic construct
SEQUENCE: 15
cagcgtggtg gtagtctg                                                   18

SEQ ID NO: 16              moltype = DNA   length = 26
FEATURE                    Location/Qualifiers
misc_feature               1..26
                           note = Single strand DNA oligonucleotide
source                     1..26
                           mol_type = other DNA
                           organism = synthetic construct
SEQUENCE: 16
cttgcgggct ctatatgaaa ctccat                                          26

SEQ ID NO: 17              moltype = DNA   length = 32
FEATURE                    Location/Qualifiers
misc_feature               1..32
                           note = Single strand DNA oligonucleotide
source                     1..32
                           mol_type = other DNA
                           organism = synthetic construct
SEQUENCE: 17
tagaagaaga ggaagtagga gtcataggga ca                                   32

SEQ ID NO: 18              moltype = DNA   length = 26
FEATURE                    Location/Qualifiers
misc_feature               1..26
                           note = Single strand DNA oligonucleotide
source                     1..26
                           mol_type = other DNA
                           organism = synthetic construct
SEQUENCE: 18
```

-continued

```
ctgtgactgc ctaccagaat gaggag                                          26

SEQ ID NO: 19          moltype = DNA   length = 25
FEATURE                Location/Qualifiers
misc_feature           1..25
                       note = Single strand DNA oligonucleotide
source                 1..25
                       mol_type = other DNA
                       organism = synthetic construct
SEQUENCE: 19
ggtcgtttct ttctttggca tcaag                                           25

SEQ ID NO: 20          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 20
cttcgggtat ggacttgctg                                                 20

SEQ ID NO: 21          moltype = DNA   length = 22
FEATURE                Location/Qualifiers
misc_feature           1..22
                       note = Single strand DNA oligonucleotide
source                 1..22
                       mol_type = other DNA
                       organism = synthetic construct
SEQUENCE: 21
cctcatgaag atgtctgggt ac                                              22

SEQ ID NO: 22          moltype = DNA   length = 23
FEATURE                Location/Qualifiers
misc_feature           1..23
                       note = Single strand DNA oligonucleotide
source                 1..23
                       mol_type = other DNA
                       organism = synthetic construct
SEQUENCE: 22
caaagtcaat ggctcccacg aag                                             23

SEQ ID NO: 23          moltype = DNA   length = 27
FEATURE                Location/Qualifiers
misc_feature           1..27
                       note = Single strand DNA oligonucleotide
source                 1..27
                       mol_type = other DNA
                       organism = synthetic construct
SEQUENCE: 23
ctacaatccc ctgagacaca gcaaata                                         27

SEQ ID NO: 24          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 24
ccagtgctgt ctgctctgaa                                                 20

SEQ ID NO: 25          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 25
gctgttccaa gagtcctgct                                                 20

SEQ ID NO: 26          moltype = DNA   length = 22
FEATURE                Location/Qualifiers
misc_feature           1..22
                       note = Single strand DNA oligonucleotide
source                 1..22
                       mol_type = other DNA
                       organism = synthetic construct
```

```
SEQUENCE: 26
gcgaaacctg tgcgagtgga tg                                              22

SEQ ID NO: 27           moltype = DNA  length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 27
cggtatttgt cttttgtcct ggt                                             23

SEQ ID NO: 28           moltype = DNA  length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 28
aaattcctgc tcggacttgg gac                                             23

SEQ ID NO: 29           moltype = DNA  length = 30
FEATURE                 Location/Qualifiers
misc_feature            1..30
                        note = Single strand DNA oligonucleotide
source                  1..30
                        mol_type = other DNA
                        organism = synthetic construct
SEQUENCE: 29
gtggtttgtc caaactcatc aatgtatctt                                      30

SEQ ID NO: 30           moltype = DNA  length = 26
FEATURE                 Location/Qualifiers
misc_feature            1..26
                        note = Single strand DNA oligonucleotide
source                  1..26
                        mol_type = other DNA
                        organism = synthetic construct
SEQUENCE: 30
gagggttttt aaactccact gtcacc                                          26

SEQ ID NO: 31           moltype = DNA  length = 30
FEATURE                 Location/Qualifiers
misc_feature            1..30
                        note = Single strand DNA oligonucleotide
source                  1..30
                        mol_type = other DNA
                        organism = synthetic construct
SEQUENCE: 31
gtggtttgtc caaactcatc aatgtatctt                                      30

SEQ ID NO: 32           moltype = DNA  length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 32
cactggaaaa gcctgcgttc ttaca                                           25

SEQ ID NO: 33           moltype = DNA  length = 30
FEATURE                 Location/Qualifiers
misc_feature            1..30
                        note = Single strand DNA oligonucleotide
source                  1..30
                        mol_type = other DNA
                        organism = synthetic construct
SEQUENCE: 33
agaataagga aggaagaagt ctcttgcctc                                      30

SEQ ID NO: 34           moltype = DNA  length = 26
FEATURE                 Location/Qualifiers
misc_feature            1..26
                        note = Single strand DNA oligonucleotide
source                  1..26
                        mol_type = other DNA
```

```
                            organism = synthetic construct
SEQUENCE: 34
aattatggac ctcaggggaa gacatg                                         26

SEQ ID NO: 35           moltype = DNA   length = 22
FEATURE                 Location/Qualifiers
misc_feature            1..22
                        note = Single strand DNA oligonucleotide
source                  1..22
                        mol_type = other DNA
                        organism = synthetic construct
SEQUENCE: 35
gctggcagga agagtcggaa tg                                             22

SEQ ID NO: 36           moltype = DNA   length = 936
FEATURE                 Location/Qualifiers
misc_feature            1..936
                        note = Cdx2 insert
source                  1..936
                        mol_type = other DNA
                        organism = synthetic construct
SEQUENCE: 36
atgtacgtga gctaccttct ggacaaggac gtgagcatgt atcctagctc cgtgcgccac    60
tccggcggcc tgaacctggc tccgcagaac tttgtcagtc ctccgcagta cccggactac   120
ggtggttacc acgtggcggc cgcggcggct gctacggcga acttggacag cgctcagtcc   180
ccagggccat cctggcccac cgcgtacggc gcccctctcg gcgaggactg gaatggctac   240
gcacccgggg gcgctgcggc agccaacgcg gtagcccacg gtctcaatgg tggctccccg   300
gccgccgcta tgggctacag cagccccgcc gaataccacg cgcaccatca cccgcatcat   360
cacccgcacc atccggccgc ctcgccgtcc tgcgcctccg gcttgctgca gacgctcaac   420
ctcggcccca cggggcccgc agccaccgcc gccgccgaac agctgtcccc cagccgccag   480
cggcgaaacc tgtgcgagtg gatgcggaag cccgcgcagc agtccctagg aagccaagtg   540
aaaaccagga caaagacaa ataccgggtg gtgtacacag accatcagcg gctggagctg   600
gagaaggagt ttcactttag tcgatacatc accatcagga ggaaaagtga gctggctgcc   660
acacttgggc tctccgagag gcaggttaaa atttggttc agaaccgcag agccaaggag   720
aggaaaatca agaagaagca gcagcagcaa cagcagcagc agcaacaaca gcctccacag   780
ccgccgccac aaccttccca gcctcagccg ggtgccctgc ggagcgtgcc cgagcccttg   840
agtcctgtga cctccttgca aggctcagtg cctggttctg tccctggggt tctggggcca   900
gctggagggg ttttaaactc cactgtcacc cagtga                             936

SEQ ID NO: 37           moltype = DNA   length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 37
atggtcctgc tggagttcgt gac                                            23

SEQ ID NO: 38           moltype = DNA   length = 24
FEATURE                 Location/Qualifiers
misc_feature            1..24
                        note = Single strand DNA oligonucleotide
source                  1..24
                        mol_type = other DNA
                        organism = synthetic construct
SEQUENCE: 38
tggtccatct gcttgtaggc aaga                                           24

SEQ ID NO: 39           moltype = DNA   length = 27
FEATURE                 Location/Qualifiers
misc_feature            1..27
                        note = Single strand DNA oligonucleotide
source                  1..27
                        mol_type = other DNA
                        organism = synthetic construct
SEQUENCE: 39
ttcacctttg aagctaatcg tttgagg                                        27

SEQ ID NO: 40           moltype = DNA   length = 22
FEATURE                 Location/Qualifiers
misc_feature            1..22
                        note = Single strand DNA oligonucleotide
source                  1..22
                        mol_type = other DNA
                        organism = synthetic construct
SEQUENCE: 40
aacttgtggc cgtttacgtc gc                                             22
```

```
SEQ ID NO: 41            moltype = DNA  length = 21
FEATURE                  Location/Qualifiers
misc_feature             1..21
                         note = Single strand DNA oligonucleotide
source                   1..21
                         mol_type = other DNA
                         organism = synthetic construct
SEQUENCE: 41
ctcggccatt cgtacatgga a                                                  21

SEQ ID NO: 42            moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 42
ggatacctct gcaccgtagc                                                    20

SEQ ID NO: 43            moltype = DNA  length = 19
FEATURE                  Location/Qualifiers
misc_feature             1..19
                         note = Single strand DNA oligonucleotide
source                   1..19
                         mol_type = other DNA
                         organism = synthetic construct
SEQUENCE: 43
caccccgccg tattgaatg                                                     19

SEQ ID NO: 44            moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 44
cctgcgagtc gagatggttg                                                    20

SEQ ID NO: 45            moltype = DNA  length = 21
FEATURE                  Location/Qualifiers
misc_feature             1..21
                         note = Single strand DNA oligonucleotide
source                   1..21
                         mol_type = other DNA
                         organism = synthetic construct
SEQUENCE: 45
atgttggact ccgtaaccca t                                                  21

SEQ ID NO: 46            moltype = DNA  length = 23
FEATURE                  Location/Qualifiers
misc_feature             1..23
                         note = Single strand DNA oligonucleotide
source                   1..23
                         mol_type = other DNA
                         organism = synthetic construct
SEQUENCE: 46
gcagggtagt agtcttcatt gct                                                23

SEQ ID NO: 47            moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 47
ggcagctacg cacatcatca                                                    20

SEQ ID NO: 48            moltype = DNA  length = 19
FEATURE                  Location/Qualifiers
misc_feature             1..19
                         note = Single strand DNA oligonucleotide
source                   1..19
                         mol_type = other DNA
                         organism = synthetic construct
SEQUENCE: 48
cctggcatcg ggaccatag                                                     19
```

```
SEQ ID NO: 49          moltype = DNA  length = 22
FEATURE                Location/Qualifiers
misc_feature           1..22
                       note = Single strand DNA oligonucleotide
source                 1..22
                       mol_type = other DNA
                       organism = synthetic construct
SEQUENCE: 49
gcctctcgaa cagtattctc ct                                              22

SEQ ID NO: 50          moltype = DNA  length = 21
FEATURE                Location/Qualifiers
misc_feature           1..21
                       note = Single strand DNA oligonucleotide
source                 1..21
                       mol_type = other DNA
                       organism = synthetic construct
SEQUENCE: 50
acagggttca taaggcatgg g                                               21

SEQ ID NO: 51          moltype = DNA  length = 22
FEATURE                Location/Qualifiers
misc_feature           1..22
                       note = Single strand DNA oligonucleotide
source                 1..22
                       mol_type = other DNA
                       organism = synthetic construct
SEQUENCE: 51
atgatgtccc ttcaagtcct ca                                              22

SEQ ID NO: 52          moltype = DNA  length = 22
FEATURE                Location/Qualifiers
misc_feature           1..22
                       note = Single strand DNA oligonucleotide
source                 1..22
                       mol_type = other DNA
                       organism = synthetic construct
SEQUENCE: 52
tgtgttggga tcacttcagt gt                                              22

SEQ ID NO: 53          moltype = DNA  length = 19
FEATURE                Location/Qualifiers
misc_feature           1..19
                       note = Single strand DNA oligonucleotide
source                 1..19
                       mol_type = other DNA
                       organism = synthetic construct
SEQUENCE: 53
tcagggtag gggcatcag                                                   19

SEQ ID NO: 54          moltype = DNA  length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 54
gtagaggccg tcttgacctg                                                 20

SEQ ID NO: 55          moltype = DNA  length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 55
agcagaaccc agatctgcac                                                 20

SEQ ID NO: 56          moltype = DNA  length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 56
```
cgccttccaa gacttgccta                                                20

SEQ ID NO: 57          moltype = DNA   length = 19
FEATURE                Location/Qualifiers
misc_feature           1..19
                       note = Single strand DNA oligonucleotide
source                 1..19
                       mol_type = other DNA
                       organism = synthetic construct
SEQUENCE: 57
gatatcgctg cgctggtcg                                                 19

SEQ ID NO: 58          moltype = DNA   length = 21
FEATURE                Location/Qualifiers
misc_feature           1..21
                       note = Single strand DNA oligonucleotide
source                 1..21
                       mol_type = other DNA
                       organism = synthetic construct
SEQUENCE: 58
ccacgatgga ggggaataca g                                              21

SEQ ID NO: 59          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 59
tgttgctaac acgatgccct                                                20

SEQ ID NO: 60          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 60
ggccactcac acatctgtcc                                                20

SEQ ID NO: 61          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 61
gcactcggct tccagtatgc                                                20

SEQ ID NO: 62          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 62
cgtagtagct gctccagtcg                                                20

SEQ ID NO: 63          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 63
agtggctaca tcatccccct                                                20

SEQ ID NO: 64          moltype = DNA   length = 20
FEATURE                Location/Qualifiers
misc_feature           1..20
                       note = Single strand DNA oligonucleotide
source                 1..20
                       mol_type = other DNA
                       organism = synthetic construct

```
SEQUENCE: 64
ccgaagtctg tgagctgtgt                                              20

SEQ ID NO: 65           moltype = DNA  length = 203
FEATURE                 Location/Qualifiers
misc_feature            1..203
                        note = 203bp amplicon covering human XIST transcription
                         start site
source                  1..203
                        mol_type = other DNA
                        organism = synthetic construct
SEQUENCE: 65
gggtaaattt tgaaccaacc aaatcacaaa gatgtccggc tttcaatctt ctaggccacg   60
cctcttatgc tctctccgcc ctcagccccc ccttcagttc ttaaagcgct gcaattcgct  120
gctgcagcca tatttcttac tctctcgggg ctggaagctt cctgactgaa gatctgttct  180
agaaagaacc ccaagtgcag aga                                          203

SEQ ID NO: 66           moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 66
agggagcagt ttgccctact                                              20

SEQ ID NO: 67           moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 67
cacatgcagc gtggtatctt                                              20

SEQ ID NO: 68           moltype = AA  length = 313
FEATURE                 Location/Qualifiers
source                  1..313
                        mol_type = protein
                        organism = Homo sapiens
SEQUENCE: 68
MYVSYLLDKD VSMYPSSVRH SGGLNLAPQN FVSPPQYPDY GGYHVAAAAA AAANLDSAQS   60
PGPSWPAAYG APLREDWNGY APGGAAAAAN AVAHGLNGGS PAAAMGYSSP ADYHPHHHPH  120
HHHPHHPAAAP SCASGLLQTL NPGPPGPAAT AAAEQLSPGG QRRNLCEWMR KPAQQSLGSQ  180
VKTRTKDKYR VVYTDHQRLE LEKEFHYSRY ITIRRKAELA ATLGLSERQV KIWFQNRRAK  240
ERKINKKKLQ QQQQQQPPQP PPPPPQPPQP QPGPLRSVPE PLSPVSSLQA SVPGSVPGVL  300
GPTGGVLNPT VTQ                                                     313

SEQ ID NO: 69           moltype =    length =
SEQUENCE: 69
000

SEQ ID NO: 70           moltype = DNA  length = 3448
FEATURE                 Location/Qualifiers
source                  1..3448
                        mol_type = genomic DNA
                        organism = Homo sapiens
mRNA                    1..3448
SEQUENCE: 70
aatcacggaa ggccgccggc ctggggctcc gcacgccagc ctgtggcggg tcttccccgc   60
ctctgcagcc tagtgggaag gaggtgggag gaaagaagga agaaagggag ggagggagga  120
ggcaggccag agggagggac cgcctcggag gcagaaggcc cgcggaggcc cagcggagca  180
ccgcggggctg gggcgcagcc acccgccgct cctcgagtcc cctcgcccct ttcccttcgt  240
gccccccggc agcctccagc gtcggtcccc aggcagcatg gtgaggtctg ctcccggacc  300
ctcgccacca tgtacgtgag ctacctcctg gacaaggacg tgagcatgta ccctagctcc  360
gtgcgccact ctggcggcct caacctggcg ccgcagaact tcgtcagccc ccgcagtac  420
ccggactacg gcggttacca cgtggcggcc gcagctgcag cggcagcgaa cttggacagc  480
gcgcagtccc cggggccatc ctggccggca cgtatggcg ccccactccg ggaggactgg  540
aatggctacg cgcccggagg cgccgcggcc gccgccaacg ccgtggctca cggcctcaac  600
ggtggctccc cggccgcagc catgggctac agcagccccg cagactacca tccgcaccac  660
cacccgcatc accacccgca ccaccgcc gccgcgcctt cctgcgcttc tgggctgctg  720
caaacgctca accccggccc ctctgggccc gccgccacg ctgccggcga cttgacagc  780
cccggcggcc agcggcggaa cctgtgcgag tggatgcgga agccggcgca gcagtccctc  840
ggcagccaag tgaaaaccag gacgaaagac aaatatcgag tggtgtacac ggaccaccag  900
cggctggagc tggagaagga gtttcactac agtcgctaca tcaccatccg gaggaaagcc  960
gagctagccg ccacgctggg gctctctgag aggcaggtta aaatctggtt tcagaaccgc 1020
agagcaaagg agaggaaaat caacaagaag aagttgcagc agcaacagca gcagcagcca 1080
```

-continued

```
ccacagccgc ctccgccgcc accacagcct ccccagcctc agccaggtcc tctgagaagt    1140
gtcccagagc ccttgagtcc ggtgtcttcc ctgcaagcct cagtgcctgg ctctgtccct    1200
ggggttctgg ggccaactgg gggggtgcta aaccccaccg tcacccagtg acccaccggg    1260
ttctgcagcg gcagagcaat tccaggctga gccatgagga gcgtggactc tgctagactc    1320
ctcaggagag acccctcccc tcccacccac agccatgacc ctacagacct ggctctcaga    1380
ggaaaaatgg gagccaggag taagacaagt gggatttggg gcctcaagaa atatactctc    1440
ccagattttt acttttccc atctggcttt tctgccact gaggagacag aaagcctccg     1500
ctgggcttca ttccggactg gcagaagcat tgcctggact gaccacacca accaggcctt    1560
catcctcctc cccagctctt ctcttcctag atctgcaggc tgcacctctg gctagagccg    1620
aggggagaga gggactcaag ggaaaggcaa gcttgaggcc aagatggctg ctgcctgctc    1680
atggccctcg gaggtccagc tgggcctcct gcctccgggc aggcaaggtt tacactgcgg    1740
aagccaaagg cagctaagat agaaagctgg actgaccaaa gactgcagaa cccccaggtg    1800
gcctgcgtct ttttctctt cccttcccag accaggaaag gcttggctgg tgtatgcaca    1860
gggtgtggta tgaggggtg gttattggac tccaggcctg accaggggc ccgaacaggg      1920
acttgtttag agagcctgtc accagagctt ctctgggctg aatgtatgtc agtgctataa    1980
atgccagagc caacctggac ttcctgtcat tttcacaatc ttggggctga tgaagaaggg    2040
ggtgggggga gtttgtgttg ttgttgctgc tgtttgggtt gttggtctgt gtaacatcca    2100
agccagagtt tttaaagcct tctgatcca tggggggaga agtgatatgg tgaagggaag     2160
tggggagtat ttgaacacag ttgaattttt tctaaaaaga aaaagagata aatgagcttt    2220
ccagatttca gattctgtat ttatcttcag attttgtctg caactatttt ttatttttta    2280
aagaaatgaa atatcttctc tgcttgcaag ctgatttgga aaattcagag agggagtgga    2340
gattatctgg acagcctcat tttacccag agcatccagaa gccaggttctg              2400
agaccttccc tgcccccaag cctgagccca gccttggaat gcgtggctct cctgggggtg    2460
cctttgggca aatgcacat ctgaatggcc aggtgcttcc cagcagtcag aaattatggg     2520
gggtgggggt gagagggccc cctcatagca tctcaccaaa tccacatgga ggcttttgtc    2580
aaacagcagg cagttccctt ctgcagtgac tccctcctaa ggcagccca caacccagct     2640
agttaaacgt gagcattaaa ttttttttaa aaaaaatccc cctagtttcc caagacagca    2700
tttccatgaa tttagtcttc tgtaaatcac tgggcatttc cgtagagcct ttctgcctcc    2760
actctcttct ctgtctttgc agtttcctta tccccgaccg cgcccccct tccaacccaa     2820
tcaccccaca aacaagattt ctagcccaca tataaaatga tccttttagt gacagttttct   2880
tgttatctgg ccgatccact ggggaccggg ctgcagcctt taaaatttt gatcctggag     2940
gccgccgagc tgaactttcc ggcaggacc gggcgagggg gcttagccc ttcgtttcga      3000
tcttcccacc aacatccgag agcctaatca gcgcgcccac ggaggcgcct taagggcagt    3060
tggggaagat gagcagagcc gggaaacagc aagaggtata agccctctgc agcacctctg    3120
caattccgcg gcccttccgg gtggcgtata cagctccagg attgggaaag gggctccggt    3180
ggcccggccc gcgggcgcct ggcctcgaag ccagagggag gagtgcgggg cgtggggtcg    3240
gggggtgccg ggcagaggag gaagccgtgt ccgggtccgc tgggcgaggg gtcctgggtc    3300
agggggtcctg ggtcagggcc ggtctgagcc ccggtgcccc gcaggtctcc ccgcgcccg    3360
gccgcgccca caggcccgcc ccctagccgc cggggttgct atgcgttgcc gtgaaacgcc    3420
tgtcaataaa ccctgtttgg acagtgga                                       3448

SEQ ID NO: 71          moltype =    length =
SEQUENCE: 71
000

SEQ ID NO: 72          moltype = AA   length = 311
FEATURE                Location/Qualifiers
source                 1..311
                       mol_type = protein
                       organism = Mus musculus
SEQUENCE: 72
MYVSYLLDKD VSMYPSSVRH SGGLNLAPQN FVSPPQYPDY GGYHVAAAAA ATANLDSAQS     60
PGPSWPTAYG APLREDWNGY APGGAAAANA VAHGLNGGSP AAAMGYSSPA EYHAHHHPHH    120
HPHHPAASPS CASGLLQTLN LGPPGPAATA AAEQLSPSGQ RRNLCEWMRK PAQQSLGSQV    180
KTRTKDKYRV VYTDHQRLEL EKEFHFSRYI TIRRKSELAA TLGLSERQVK IWFQNRRAKE    240
RKIKKKQQQQ QQQQQQQPPQ PPPQPSQPQP GALRSVPEPL SPVTSLQGSV PGSVPGVLGP    300
AGGVLNSTVT Q                                                         311

SEQ ID NO: 73          moltype = DNA  length = 2145
FEATURE                Location/Qualifiers
source                 1..2145
                       mol_type = genomic DNA
                       organism = Mus musculus
SEQUENCE: 73
tccgcgagcc aacctgcggc gggtcatccc cgcctctaca gcttactggc aaggaggtgg     60
gaggaaagaa ggaagagagg ggaggaggca ggacggaggg aggagctgcc gggaggcag    120
aagctctgca aggagccgac ggagcaccgt gggctgaggt gcagccagct accttttatct  180
ctagccccct gcgcctcgcg cctctggcag ccttcaacgt ttgtcccag acagcatggt    240
gaggtctgct ctgggtccct cgccaccatg tacgtgagct acctctgga caaggacgtg    300
agcatgtatc ctagctccgt gcgccactcc ggcggcctga acctggctcc gcagaacttt    360
gtcagtcctc cgcagtaccc ggactacggt ggttaccacg tggcggccgc ggcggctgct    420
acggcgaact tggacagcgc tcagtcccca gggccatcct ggccaccgc gtacggcgcc    480
cctctccgcg aggactggaa tggctacgca ccgggggcg ctgcggcagc caacgcggta    540
gcccacggc tcaatggtgg ctcccggcc tgctatgg gctacagcag ccccgccgaa       600
taccacgcgc accatcaccc gcatcatcac ccgcaccatc cggccgcctc ccgtcctgc    660
gcctccggct tgctgcagac gctcaacctc gcccccgg gcccgcagc caccgcc         720
gccgaacagc tgtcccccag cggccagcgg cgaaacctgt gcgagtggat gcggaagccc    780
gcgcagcagt ccctaggaag ccaagtgaaa accaggacaa aagacaaata ccgggtggtg    840
tacacagacc atcagcggct ggagctggag aaggagtttc actttagtcg atacatcacc    900
```

-continued

```
atcaggagga aaagtgagct ggctgccaca cttgggctct ccgagaggca ggttaaaatt   960
tggtttcaga accgcagagc caaggagagg aaaatcaaga agaagcagca gcagcaacag  1020
cagcagcagc aacaacagcc tccacagccg ccgccacaac cttcccagcc tcagccgggt  1080
gccctgcgga gcgtgcccga gcccttgagt cctgtgacct ccttgcaagg ctcagtgcct  1140
ggttctgtcc ctgggttct ggggccagct ggaggggttt taaactccac tgtcacccag  1200
tgaccctcc cgtggtctga agcggcggcg gcacagcaat cccaggctga gccatgagga  1260
gtatggacgc tgcgagaatc ctcagaagag attcctctcc tcctacccac gaacagcatc  1320
tactgatgga gattgaggac agaagatgag tggaattatg acctcaggg gaagacatgg  1380
tttagatttt ttttttcttt ttaacttttc ccattccgac tcttcctgcc agcaacgaca  1440
aacgaagtga ttcctgggc ttcttcgttc atgctctttg ccaggactga ctaccgacat  1500
gaagctatca gcctctttg ccccagctct ttgcctctct gtatttctgt gtggagctga  1560
ggagagagtg agactggatg gggtgggggt agcaatactt gagccaaggt ggctgtttcc  1620
tgctgactgc tttctgagaa ccagctggcc gtcctgcctc cgggcaggg actattcaaa  1680
ctacaggagc cagaggcagc taagatagct ggactgaccg aagtctgcag aacctccccc  1740
accaggtggt ctgggctttc ttctccacaa atcaggaagg ggtggtgggt tcaggggctg  1800
cggtgagagg gggttggtta gccaacgcca ggccccgcg acaagggctt gtttagaaag  1860
cctgtcacca gagctgctgt aggcggaatg tatgtctgtg ttgtaaatgc cagagccaac  1920
ctggacttcc tgtcccttcc ctcgtctttg gctgaagaag accggaattg tttgctgctg  1980
ttcgagtcac tgatctgtgt aacgagccaa acaagccttt taaaaagcct tcttgatcca  2040
tgggtagaga agttgtatgg tgaagggaag tcgggagggg gggaagggga tccgaacaca  2100
gttgactttt attttgtaaa aagacaaaga taaacgaact ttaac                 2145
```

| SEQ ID NO: 74 | moltype = AA  length = 444 |
|---|---|
| FEATURE | Location/Qualifiers |
| source | 1..444 |
| | mol_type = protein |
| | organism = Homo sapiens |

SEQUENCE: 74
```
MEVTADQPRW VSHHHPAVLN GQHPDTHHPG LSHSYMDAAQ YPLPEEVDVL FNIDGQGNHV   60
PPYYGNSVRA TVQRYPPTHH GSQVCRPPHL HGSLPWLDGG KALGSHHTAS PWNLSPFSKT  120
SIHHGSPGPL SVYPPASSSS LSGGHASPHL FTFPPTPPKD VSPDPSLSTP GSAGSARQDE  180
KECLKYQVPL PDSMKLESSH SRGSMTALGG ASSSTHHPIT TYPPYVPEYS SGLFPPSSLL  240
GGSPTGFGCK SRPKARSSTE GRECVNCGAT STPLWRRDGT GHYLCNACGL YHKMNGQNRP  300
LIKPKRRLSA ARRAGTSCAN CQTTTTTLWR RNANGDPVCN ACGLYYKLHN INRPLTMKKE  360
GIQTRNRKMS SKSKKCKKVH DSLEDFPKNS SFNPAALSRH MSSLSHISPF SHSSHMLTTP  420
TPMHPPSSLS FGPHHPSSMV TAMG                                        444
```

| SEQ ID NO: 75 | moltype =  length = |
|---|---|

SEQUENCE: 75
000

| SEQ ID NO: 76 | moltype = AA  length = 443 |
|---|---|
| FEATURE | Location/Qualifiers |
| source | 1..443 |
| | mol_type = protein |
| | organism = Mus musculus |

SEQUENCE: 76
```
MEVTADQPRW VSHHHPAVLN GQHPDTHHPG LGHSYMEAQY PLTEEVDVLF NIDGQGNHVP   60
SYYGNSVRAT VQRYPPTHHG SQVCRPPLLH GSLPWLDGGK ALSSHHTASP WNLSPFSKTS  120
IHHGSPGPLS VYPPASSSSL AAGHSSPHLF TFPPTPPKDV SPDPSLSTPG SAGSARQDEK  180
ECLKYQVQLP DSMKLETSHS RGSMTTLGGA SSSAHHPITT YPPYVPEYSS GLFPPSSLLG  240
GSPTGFGCKS RPKARSSTEG RECVNCGATS TPLWRRDGTG HYLCNACGLY HKMNGQNRPL  300
IKPKRRLSAA RRAGTSCANC QTTTTTLWRR NANGDPVCNA CGLYYKLHNI NRPLTMKKEG  360
IQTRNRKMSS KSKKCKKVHD ALEDFPKSSS FNPAALSRHM SSLSHISPFS HSSHMLTTPT  420
PMHPPSGLSF GPHHPSSMVT AMG                                         443
```

| SEQ ID NO: 77 | moltype = AA  length = 442 |
|---|---|
| FEATURE | Location/Qualifiers |
| source | 1..442 |
| | mol_type = protein |
| | organism = Mus musculus |

SEQUENCE: 77
```
MEVTADQPRW VSHHHPAVLN GQHPDTHHPG LGHSYMEAQY PLTEEVDVLF NIDGQGNHVP   60
SYYGNSVRAT VQRYPPTHHG SQVCRPPLLH GSLPWLDGGK ALSSHHTASP WNLSPFSKTS  120
IHHGSPGPLS VYPPASSSSL AAGHSSPHLF TFPPTPPKDV SPDPSLSTPG SAGSARQDEK  180
ECLKYQVQLP DSMKLETSHS RGSMTTLGGA SSSAHHPITT YPPYVPEYSS GLFPPSSLLG  240
GSPTGFGCKS RPKARSSTGR ECVNCGATST PLWRRDGTGH YLCNACGLYH KMNGQNRPLI  300
KPKRRLSAAR RAGTSCANCQ TTTTTLWRRN ANGDPVCNAC GLYYKLHNIN RPLTMKKEGI  360
QTRNRKMSSK SKKCKKVHDA LEDFPKSSSF NPAALSRHMS SLSHISPFSH SSHMLTTPTP  420
MHPPSGLSFG PHHPSSMVTA MG                                          442
```

| SEQ ID NO: 78 | moltype = AA  length = 366 |
|---|---|
| FEATURE | Location/Qualifiers |
| source | 1..366 |
| | mol_type = protein |
| | organism = Mus musculus |

SEQUENCE: 78
```
MEVTADQPRW VSHHHPAVLN GQHPDTHHPG LGHSYMEAQY PLTEEVDVLF NIDGQGNHVP   60
SYYGNSVRAT VQRYPPTHHG SQVCRPPLLH GSLPWLDGGK ALSSHHTASP WNLSPFSKTS  120
```

```
IHHGSPGPLS VYPPASSSSL AAGHSSPHLF TFPPTPPKDV SPDPSLSTPG SAGSARQDEK    180
ECLKYQVQLP DSMKLETSHS RGSMTTLGGA SSSAHHPITT YPPYVPEYSS GLFPPSSLLG    240
GSPTGFGCKS RPKARSSTEG RECVNCGATS TPLWRRDGTG HYLCNACGLY HKMNGQNRPL    300
IKPKRRLSAA RRAGTSCANC QTTTTTLWRR NANGDPVCNA CGLYYKLHNT PDYEERRHPD    360
PKPEDV                                                              366

SEQ ID NO: 79           moltype = AA   length = 365
FEATURE                 Location/Qualifiers
source                  1..365
                        mol_type = protein
                        organism = Mus musculus
SEQUENCE: 79
MEVTADQPRW VSHHPAVLN GQHPDTHHPG LGHSYMEAQY PLTEEVDVLF NIDGQGNHVP     60
SYYGNSVRAT VQRYPPTHHG SQVCRPPLLH GSLPWLDGGK ALSSHHTASP WNLSPFSKTS    120
IHHGSPGPLS VYPPASSSSL AAGHSSPHLF TFPPTPPKDV SPDPSLSTPG SAGSARQDEK    180
ECLKYQVQLP DSMKLETSHS RGSMTTLGGA SSSAHHPITT YPPYVPEYSS GLFPPSSLLG    240
GSPTGFGCKS RPKARSSTGR ECVNCGATST PLWRRDGTGH YLCNACGLYH KMNGQNRPLI    300
KPKRRLSAAR RAGTSCANCQ TTTTTLWRRN ANGDPVCNAC GLYYKLHNTP DYEERRHPDP    360
KPEDV                                                               365

SEQ ID NO: 80           moltype = DNA   length = 3257
FEATURE                 Location/Qualifiers
source                  1..3257
                        mol_type = genomic DNA
                        organism = Mus musculus
SEQUENCE: 80
agctgtctgc gaacactgag ctgcctggcg ccgtcttgat agtttcagaa agaatgcatt     60
ccctgtaaaa aaaaaatact gagagaggga gaggagaaag agagagagac tgagagagcg    120
agacatagag agctacgcaa tctgaccggg caggtcacac gcctcctcct cctcctctac    180
gctccttgct actcaggtga tcggaagagc aaccgtctct gagcgccaag gaatcagtgt    240
gcagtgtggt cacactcgga ttcctctctc cctcctttt ttttttttt ttttgacccc     300
tttattcctc cgtgtctgct tttttttgg gggggggat cgccctcatt cttttctttt     360
tcttctttcc cttcctttct tttgctaaac tatcccgcaa agattttct ttcctcccta    420
aaccctcctt tttgctctcc ttttctatac ccttaactgc aaacaaacca ttaaacgacc    480
cctctcctgg gcctccgacg gcaggagtcc gcggacctcc caggccgaca gccctccctc    540
tacccgcgag ggtccgggc cgggcgagag ggcgcgagca cagccgagga catgggagtg    600
actgcggacc agccgcgctg ggtgagccac catcaccccg cggtcctcaa cggtcagcac    660
ccagacacgc accaccggg cctcggccat tcgtacatgg aagctcagta tccgctgacg    720
gaagagggtgg acgtacttt taacatcgat ggtcaaggca accacgtccc gtcctactac    780
ggaaactccg tcagggctac ggtgcagagg tatcctccga cccaccacgg gagccaggta    840
tgccgcccgc ctctgctgca cggatctctg ccctggctgg atggcggcaa agccctgagc    900
agccaccaca ccgcctcgcc ctggaacctc agccccttct ccaagacgtc catccaccac    960
ggctcctccg ggcctctgtc cgtttaccct ccggcttcat cctcttctct ggcggccggc   1020
cactccagtc ctcatctctt caccttcccg cccacccccgc cgaaagacgt ctccccgac   1080
ccgtcgctgt ccaccccggg atccgccggg tcggccaggc aagatgagaa agagtgcctc   1140
aagtatcagg tgcagctgcc agatagcatg aagctggaga cgtctcactc tcgaggcagc   1200
atgaccaccc tgggtgggc ctcatcctca gcccaccacc tcattaccac ctatccgccc   1260
tatgtgcccg agtacagctc tggactcttc ccacccagca gcctgctggg aggatcccct   1320
accgggttcg gatgtaagtc gaggcccaag gcacgatcca gcacagaagg cagggagtgt   1380
gtgaactgcg gggcaacctc taccccactg tggcggcgag atggtaccgg gcactacctt   1440
tgcaatgcct gcggactcta ccataaaatg aatgggcaga accggcccct tatcaagccc   1500
aagcgaaggc tgtcggcagc aaggagagca gggacatcct gcgcgaactg tcagaccacc   1560
accaccaccc tctggaggag gaacgctaat ggggacccgg tctgcaatgc ctgtgggctg   1620
tactacaagc ttcataatat taacagaccc ctgactatga agaagaagg catccagacc   1680
cgaaaccgga agatgtctag caaatgcaaa aagtgcaaaa aggtgcatga cgcgctggag   1740
gacttcccca agagcagctc cttcaacccg gccgctctct ccagacacat gtcatccctg   1800
agccacatct ctcccttcag ccactccagc cacatgctga ccacaccgac gcccatgcat   1860
ccgcctccg gcctctcctt cggacctcac caccttcca gcatggtcac cgccatgggt   1920
tagagaggca gagccctgct ccacatgcgt gaggagtctc caagtgtgcg aagagttcct   1980
ccgaccccctt ctacttgcgt ttttcgcagg agcagtatca tgaagcccga aagcgacaga   2040
tctgtgtttt tgaaggcaga aagcaaaatg tttgcttctt ttttcaaagg agctcgaggt   2100
ggtgtctgca ttccaaccac tgaatccgga tccatttgt gaataagcca ttcagactca   2160
tattcccctat ttaacagggt ctctagtgct gtgaaaaaaa tattgctgaa cattgcatat   2220
aacttatatt gtaagaaata ctgtacattt gaggaagact ttattgtacc tggatagctg   2280
taagaaaggc atgaaggacg ccaagagttt taaggaatat aggggggatta aagtatggag   2340
atacagaaga aaccactaag tctgatgtcc aaatgggcac actgtcagtt ttgtttccct   2400
tcagttgttt gatgcattta aaaaaaaaaa aagaaagaa aaagaaaaaa aggggggggg     2460
gggagaaaaa aataaattaa aaaaaaaaaa aaaaaaagaa aagaaagaaa aatctaagaa   2520
aaaaaaaaaa aaggttgtag gcaaatcatt tgttccaggc tgtgagcctg tgcaaaagag   2580
atttcagatc tgggcaatgg gtgtgtgatc tcacccactg aagatctgag aatgtcatgg   2640
ctaggcctac atgctctgtg aatcagtccc tgtaattgtt gtttgtatgt ataattcaga   2700
agcaccaaaa taagaaaaga tgtagattta tttcatcata ttatacagac tgaattgttg   2760
tataaattta tttactgcta gtgttaggaa ctgctttttt tttttttttt ggttttaatg   2820
tttttttttt tgttgtttt tcttttttct ctggattttt tggttgaata                2880
aactagattg ctttcagttg acttaaggtg gatgtactct ggaggggttta tttttccttt   2940
tattattatt tttgatggta tttattaaat agcttctatg ggcccggcgg tacctgtctt   3000
tttcgtcact tttcttgcag cctaaactat gaaggtagca gcgtaccagc taccaacatg   3060
catgtcagag acccggccac tcacaggcct ggtcctgaga gccaccggc tgactgttag   3120
ccctgtgtgt ttctgtatta gtgatcactg cctttaaaca gtctgttgga ataatactat   3180
```

```
aaaaataata ataaagttaa aatattttaa aacaaaaaaa aaaaaaaaaa aaaaaaaaaa    3240
aaaaaaaaaa aaaaaa                                                   3257

SEQ ID NO: 81           moltype = DNA   length = 3212
FEATURE                 Location/Qualifiers
source                  1..3212
                        mol_type = genomic DNA
                        organism = Mus musculus
SEQUENCE: 81
agctgtctgc gaacactgag ctgcctggcg ccgtcttgat agtttcagaa agaatgcatt     60
ccctgtaaaa aaaaaatact gagagaggga gaggagaaag agagagagac tgagagagcg    120
agacatagag agctacgcaa tctgaccggg caggtcacac gctcctcct cctcctctac     180
gctccttgct actcaggtga tcggaagagc aaccgtctct gagcgccaag gaatcagtgt    240
gcagtgtggt cacactcgga ttcctctctc cctccttttt ttttttttt ttttgacccc    300
tttattcctc cgtgtctgct ttttttttgg ggggggggat cgccctcatt cttttctttt    360
tcttctttcc cttcctttct tttgctaaac tatcccgcaa agattttct ttcctccta     420
aaccctcctt tttgctctcc ttttctatac ccttaactgc aaacaaacca ttaaacgacc    480
cctctcctgg gcctccgacg gcaggagtcc gcggacctcc caggccgaca gccctccctc    540
tacccgcgag ggttccgggc cgggcgagag ggcgcgagca cagccgagga catggaggtg    600
actgcggacc agccgcgctg ggtgagccac catcaccccg cggtcctcaa cggtcagcac    660
ccagacacgc accacccggg cctcggccat tcgtacatgg aagctcagta tccgctgacg    720
gaagaggtgg acgtacttt taacatcgat ggtcaaggca accacgtccc gtcctactac     780
ggaaactccg tcagggctac ggtgcagagg tatcctccga cccaccacgg gagccaggta    840
tgccgcccgc ctctgctgca cggatctctg ccctggctgg atggcggcaa agccctgagc    900
agccaccaca ccgcctcgcc ctggaacctc agccccttct ccaagacgtc catccaccac    960
ggctctccgg ggcctctgtc cgtttaccct ccggcttcat cctcttctct ggcggccggc   1020
cactccagtc ctcatctctt caccttcccg cccaccccgc cgaaagacgt ctccccagac   1080
ccgtcgctgt ccaccccggg atccgccggg tcggccaggc aagatgagaa agagtgcctc   1140
aagtatcagg tgcagctgcc agatagcatg aagctggaga cgtctcactc tcgaggcagc   1200
atgaccaccc tgggtggggc ctcatcctca gcccaccacc ccattaccac ctatccgccc   1260
tatgtgcccg agtacagctc tggactcttc ccacccagca gcctgctggg aggatcccct   1320
accgggttcg gatgtaagtc gaggcccaag gcacgatcca gcacaggcag ggagtgtgtg   1380
aactgcgggg caacctctac cccactgtgg cggcgagatg gtaccgggca ctacctttgc   1440
aatgcctgcg gactctacca taaatgaat gggcagaacc ggccccttat caagcccaag   1500
cgaaggctgt cggcagcaag gagagcaggg acatcctgcg cgaactgtca gaccaccacc   1560
accaccctct ggaggaggaa cgctaatggg gacccggtct gcaatgcctg tgggctgtac   1620
tacaagcttc ataatattaa cagacccctg actatgaaga aagaaggcat ccagacccga   1680
aaccggaaga tgtctagcaa atcgaaaaag tgcaaaaagg tgcatgacgc gctggaggac   1740
ttccccaaga gcagctcctt caacccggcc gctctctcca gcacacgtc atccctgagc    1800
cacatctctc ccttcagcca ctccagccac atgctgacca caccgacgcc catgcatccg   1860
ccctccggcc tctccttcgg acctcaccac ccttccagca tggtcaccgc catgggttag   1920
agaggcagag ccctgctcca catgcgtgag gagtctccaa gtgtgcgaag agttcctccg   1980
acccccttcta cttgcgtttt tcgcaggagc agtatcatga agcccgaaag cgacagatct   2040
gtgttttttga aggcagaaag caaaatgttt gcttcttttt tcaaaggagc tcgaggtggt   2100
gtctgcattc caaccactga atccggatcc catttgtgaa taagccattc agactcatat   2160
tccctattta acagggtctc tagtgctgtg aaaaaaatat tgctgaacat tgcatataac   2220
ttatattgta agaaatactg tacatttgag gaagacttta ttgtacctgg atagctgtaa   2280
gaaaggcatg aaggacgcca agagttttaa ggaatatagg gggattaaag tatggagata   2340
cagaagaaac cactaagtct gatgtccaaa tgggcacact gtcagtttg tttcccttca    2400
gttgtttgat gcatttaaaa aaaaaaaaaa gaaagaaaaa gaaaaaagg ggggggggg    2460
agaaaaaaat aaattaaaaa aaagaaaaaa aaagaaaat ctaagaaaaa                2520
aaaaaaaaag gttgtaggca aatcatttgt tccaggctgt gagcctgtgc aaaagagatt    2580
tcagatctgg gcaatgggtg tgtgatctca cccactgaag atctgagaat gtcatggcta    2640
ggcctacatg ctctgtgaat cagtccctgt aattgttgtt tgtatgtata attcagaagc    2700
accaaaataa gaaaagatgt agatttattt catcatatta tacagactga attgttgtat    2760
aaatttattt actgctagtg ttaggaactg ctttttttt tttttttggt tttaatgttt    2820
tttttttttt tgtttttgt tttttttttt ctttctctct ggattttgg ttgaataaac    2880
tagattgctt tcagttgact taaggtggat gtactctgga gggtttattt ttccttttat   2940
tattatttt gatggtattt attaaatagc ttctatggg ccggcggtac ctgtcttttt     3000
cgtcacttt cttgcagcct aaactgaaa ggtagcagca taccagctac caacatgcat    3060
gtcagagacc cggccactca caggcctggt cctgagagcc acctggctga ctgttagccc    3120
ctgtgtgttc tgtattagtg atcactgcct ttaaacagtc tgttggaata atactataaa   3180
aataataata aagttaaaat attttaaaac aa                                 3212

SEQ ID NO: 82           moltype = DNA   length = 3207
FEATURE                 Location/Qualifiers
source                  1..3207
                        mol_type = genomic DNA
                        organism = Mus musculus
SEQUENCE: 82
agctgtctgc gaacactgag ctgcctggcg ccgtcttgat agtttcagaa agaatgcatt     60
ccctgtaaaa aaaaaatact gagagaggga gaggagaaag agagagagac tgagagagcg    120
agacatagag agctacgcaa tctgaccggg caggtcacac gctcctcct cctcctctac     180
gctccttgct actcaggtga tcggaagagc aaccgtctct gagcgccaag gaatcagtgt    240
gcagtgtggt cacactcgga ttcctctctc cctccttttt ttttttttt ttttgacccc    300
tttattcctc cgtgtctgct ttttttttgg ggggggggat cgccctcatt cttttctttt    360
tcttctttcc cttcctttct tttgctaaac tatcccgcaa agattttct ttcctccta     420
aaccctcctt tttgctctcc ttttctatac ccttaactgc aaacaaacca ttaaacgacc    480
cctctcctgg gcctccgacg gcaggagtcc gcggacctcc caggccgaca gccctccctc    540
```

```
tacccgcgag ggttccgggc cgggcgagag ggcgcgagca cagccgagga catggaggtg    600
actgcggacc agccgcgctg ggtgagccac catcaccccg cggtcctcaa cggtcagcac    660
ccagacacgc accacccggg cctcggccat tcgtacatgg aagctcagta tccgctgacg    720
gaagaggtga acgtactttt taacatcgat ggtcaaggca accacgtccc gtcctactac    780
ggaaactccg tcagggctac ggtgcagagg tatcctccga cccaccacgg gagccaggta    840
tgccgcccgc ctctgctgca cggatctctg ccctggctgg atggcggcaa agccctgagc    900
agccaccaca ccgcctcgcc ctggaacctc agcccttct ccaagacgtc catccaccac    960
ggctctccgg ggcctctgtc cgtttaccct ccggcttcat cctcttctct ggcggccggc   1020
cactccagtc ctcatctctt caccttcccg cccacccgc cgaaagacgt ctccccagac   1080
ccgtcgctgt ccaccccggg atccgccggg tcggccaggc aagatgagaa agagtgcctc   1140
aagtatcagg tgcagctgcc agatagcatg aagctggaga cgtctcactc tcgaggcagc   1200
atgaccaccc tgggtggggc ctcatcctca gcccaccacc ccattaccac ctatccgccc   1260
tatgtgcccg agtacagctc tggactcttc ccacccagca gcctgctggg aggatcccct   1320
accgggttcg gatgtaagtc gaggcccaag gcacgatcca gcacaggcag caggagtgt   1380
gtgaactgcg gggcaacctc taccccactg tggcggcgag atggtaccgg gcactacttt   1440
tgcaatgcct gcggactcta ccataaaatg aatgggcaga accggcccct tatcaagccc   1500
aagcgaaggc tgtcggcagc aaggagagca gggacatcct gcgcgaactg tcagaccacc   1560
accaccaccc tctggaggag aacgctaat ggggacccgg tctgcaatgc ctgtgggctg   1620
tactacaagc ttcataatac ccctgactat gaagaaagaa ggcatccaga cccgaaaccg   1680
gaagatgtct agcaaatcga aaagtgcaa aaaggtgcat gacgcgctgg aggacttccc   1740
caagagcagc tccttcaacc cggccgctct ctccagacac atgtcatccc tgagccacat   1800
ctctccctc agccactcca gccacatgct gaccacaccg acgccatgc atccgccctc   1860
cggcctctcc ttcggacctc accaccttc cagcatggtc accgccatgg gttagagagg   1920
cagagccctg ctccacatgc gtgaggagtc tccaagtgtg cgaagagttc ctccgacccc   1980
ttctactgg gttttcgca ggagcagtat catgaagccc gaaagcgaca gatctgtgtt   2040
tttgaaggca gaaagcaaaa tgtttgcttc tttttcaaa ggagctcgag gtggtgtctg   2100
cattccaacc actgaatccg gatcccattt gtgaataagc cattcagact catattccct   2160
atttaacagg gtctctagtg ctgtgaaaaa aatattgctg aacattgcat ataacttata   2220
ttgtaagaaa tactgtacat ttgaggaaga ctttattgta cctggatagc tgtaagaaag   2280
gcatgaagga cgccaagagt tttaaggaat atagggggat taaagtatgg agatacagaa   2340
gaaaccacta agtctgatgt ccaaatgggc acactgtcag ttttgtttcc cttcagttgt   2400
ttgatgcatt taaaaaaaaa aaaagaaag aaaagaaaa aaggggggg ggggagaaa   2460
aaaataaatt aaaaaaaaa aaaaaaag aaagaaaga aaatctaag aaaaaaaaaa   2520
aaaaggttgt aggcaaatca tttgttccag gctgtgagcc tgtgcaaaag agatttcaga   2580
tctgggcaat gggtgtgtga tctcacccac tgaagatctg agaatgtcat ggctaggcct   2640
acatgctctg tgaatcagtc cctgtaattg ttgtttgtat gtataattca gaagcaccaa   2700
aataagaaaa gatgtagatt tatttcatca tattatacag actgaattgt tgtataaatt   2760
tatttactgc tagtgttagg aactgctttt ttttttttt ttggttttaa tgttttttt   2820
tttttgttt tttgttttt tttttcttc tctctggatt tttggttgaa taaactagat   2880
tgctttcagt tgacttaagg tggatgtact ctggagggtt tatttttcct tttattatta   2940
ttttgatgg tatttattaa atagcttcta tgggcccggc ggtacctgtc tttttcgtca   3000
cttttcttgc agcctaaact atgaaggtag cagcgtacca gctaccaaca tgcatgtcag   3060
agacccggcc actcacaggc ctggtcctga gagccacctg gctgactgtt agccctgtg   3120
tgttctgtat tagtgatcac tgcctttaaa cagtctgttg gaataatact ataaaataa   3180
taataaagtt aaaatattt aaaacaa                                       3207

SEQ ID NO: 83        moltype = DNA   length = 3204
FEATURE              Location/Qualifiers
source               1..3204
                     mol_type = genomic DNA
                     organism = Mus musculus
SEQUENCE: 83
agctgtctgc gaacactgag ctgcctggcg ccgtcttgat agtttcagaa agaatgcatt     60
ccctgtaaaa aaaaaatact gagagaggga gaggagaaag agagagagac tgagagagcg    120
agacatagag agctacgcaa tctgaccggg caggtcacac gcctcctcct cctcctctac    180
gctccttgct actcaggtga tcggaagaga aaccgtctct gagcgccaag gaatcagtgt    240
gcagtgtggt cacactcgga ttcctctctc cctccttttt ttttttttt ttttgacccc    300
tttattcctc cgtgtctgct tttttttgg ggggggat cgccctcatt cttttctttt    360
tcttctttcc cttcctttct tttgctaaac tatcccgcaa agatttttct ttcctcccta    420
aaccctcctt tttgctctcc ttttctatac ccttaactgc aaacaaacca ttaaacgacc    480
cctctcctgg gcctccgacg gcaggagtcc gcggacctcc caggccgaca gccctccctc    540
tacccgcgag ggttccgggc cgggcgagag ggcgcgagca cagccgagga catggaggtg    600
actgcggacc agccgcgctg ggtgagccac catcaccccg cggtcctcaa cggtcagcac    660
ccagacacgc accaccgggg cctcggccat tcgtacatgg aagctcagta tccgctgacg    720
gaagaggtgg acgtactttt taacatcgat ggtcaaggca accacgtccc gtcctactac    780
ggaaactccg tcagggctac ggtgcagagg tatcctccga cccaccacgg gagccaggta    840
tgccgcccgc ctctgctgca cggatctctg ccctggctgg atggcggcaa agccctgagc    900
agccaccaca ccgcctcgcc ctggaacctc agcccttct ccaagacgtc catccaccac    960
ggctctccgg ggcctctgtc cgtttaccct ccggcttcat cctcttctct ggcggccggc   1020
cactccagtc ctcatctctt caccttcccg cccacccgc cgaaagacgt ctccccagac   1080
ccgtcgctgt ccaccccggg atccgccggg tcggccaggc aagatgagaa agagtgcctc   1140
aagtatcagg tgcagctgcc agatagcatg aagctggaga cgtctcactc tcgaggcagc   1200
atgaccaccc tgggtggggc ctcatcctca gcccaccacc ccattaccac ctatccgccc   1260
tatgtgcccg agtacagctc tggactcttc ccacccagca gcctgctggg aggatcccct   1320
accgggttcg gatgtaagtc gaggcccaag gcacgatcca gcacaggcag gagtgtgtg   1380
aactgcgggg caacctctac cccactgtgg cggcgagatg gtaccgggca ctacctttgc   1440
aatgcctgcg gactctacca taaaatgaat gggcagaacc ggccccttat caagcccaag   1500
cgaaggctgt cggcagcaag gagagcaggg acatcctgcg cgaactgtca gaccaccacc   1560
accaccctct ggaggaggaa cgctaatggg gacccggtct gcaatgcctg tgggctgtac   1620
```

```
tacaagcttc ataataccco tgactatgaa gaaagaaggc atccagaccc gaaaccggaa    1680
gatgtctagc aaatcgaaaa agtgcaaaaa ggtgcatgac gcgctggagg acttccccaa    1740
gagcagctcc ttcaacccgg ccgctctctc cagacacatg tcatccctga gcccacatctc   1800
tcccttcagc cactccagcc acatgctgac cacaccgacg cccatgcatc cgccctccgg    1860
cctctcottc ggacctcacc acccttccag catggtcacc gccatgggtt agagaggcag    1920
agccctgctc cacatgcgtg aggagtctcc aagtgtgcga agagttcctc cgacccctttc   1980
tacttgcgtt tttcgcagga gcagtatcat gaagcccgaa agcgacagat ctgtgttttt    2040
gaaggcagaa agcaaaatgt ttgcttcttt tttcaaagga gctcgaggtg gtgtctgcat    2100
tccaaccact gaatccggat cccattttgtg aataagccat tcagactcat attccctatt    2160
taacagggtc tctagtgctg tgaaaaaaat attgctgaac attgcatata acttatattg    2220
taagaaatac tgtacatttg aggaagactt tattgtacct ggatagctgt aagaaaggca    2280
tgaaggacgc caagagtttt aaggaatata gggggattaa agtatggaga tacagaagaa    2340
accactaagt ctgatgtcca aatgggcaca ctgtcagttt tgtttccctt cagttgtttg    2400
atgcatttaa aaaaaaaaa aagaaaaaa agaaaaaaa ggagaaaaaa                  2460
ataaattaaa aaaaaaaaa aaaaagaaa agaaagaaaa atcctaagaa aaaaaaaaaa      2520
aggttgtagg caaatcattt gttccaggct gtgagcctgt gcaaaagaga tttcagatct    2580
gggcaatggg tgtgtgatct cacccactga agatctgaga atgtcatggc taggcctaca    2640
tgctctgtga atcagtccct gtaattgttg tttgtatgta taattcagaa gcaccaaaat    2700
aagaaaagat gtagatttat ttcatcatat tatacagact gaattgttgt ataaatttat    2760
ttactgctag tgttaggaac tgctttttttt ttttttttg gttttaatgt tttttttttt   2820
tttgttttt gttttttttt ttcttctct ctggattttt ggttgaataa actagattgc     2880
tttcagttga cttaaggtgg atgtactctg gaggggtttat ttttccttt attattattt    2940
ttgatggtat ttattaaata gcttctatgg gcccggcggt acctgtcttt ttcgtcactt    3000
ttcttgcagc ctaaactatg aaggtagcag cgtaccagct accaacatgc atgtcagaga    3060
cccggccact cacaggcctg gtcctgagag ccacctggct gactgttagc ccctgtgtgt    3120
tctgtattag tgatcactgc cttttaaacag tctgttggaa taatactata aaaataataa   3180
taaagttaaa atatttttaaa acaa                                          3204

SEQ ID NO: 84              moltype = AA  length = 480
FEATURE                    Location/Qualifiers
source                     1..480
                           mol_type = protein
                           organism = Homo sapiens
SEQUENCE: 84
MEVAPEQPRW MAHPAVLNAQ HPDSHHPGLA HNYMEPAQLL PPDEVDVFFN HLDSQGNPYY     60
ANPAHARARV SYSPAHARLT GGQMCRPHLL HSPGLPWLDG GKAALSAAAA HHHNPWTVSP   120
FSKTPLHPSA AGGPGGPLSV YPGAGGGSGG GSGSSVASLT PTAAHSGSHL FGFPPTPPKE   180
VSPDPSTTGA ASPASSSAGG SAARGEDKDG VKYQVSLTES MKMESGSPLR PGLATMGTQP   240
ATHHPIPTYP SYVPAAAHDY SSGLFHPGGF LGGPASSFTP KQRSKARSCS EGRECVNCGA   300
TATPLWRRDG TGHYLCNACG LYHKMNGQNR PLIKPKRRLS AARRAGTCCA NCQTTTTTLW   360
RRNANGDPVC NACGLYYKLH NVNRPLTMKK EGIQTRNRKM SNKSKKSKKG AECFEELSKC   420
MQEKSSPFSA AALAGHMAPV GHLPPFSHSG HILPTPTPIH PSSSLSFGHP HPSSMVTAMG   480

SEQ ID NO: 85              moltype = AA  length = 466
FEATURE                    Location/Qualifiers
source                     1..466
                           mol_type = protein
                           organism = Homo sapiens
SEQUENCE: 85
MEVAPEQPRW MAHPAVLNAQ HPDSHHPGLA HNYMEPAQLL PPDEVDVFFN HLDSQGNPYY     60
ANPAHARARV SYSPAHARLT GGQMCRPHLL HSPGLPWLDG GKAALSAAAA HHHNPWTVSP   120
FSKTPLHPSA AGGPGGPLSV YPGAGGGSGG GSGSSVASLT PTAAHSGSHL FGFPPTPPKE   180
VSPDPSTTGA ASPASSSAGG SAARGEDKDG VKYQVSLTES MKMESGSPLR PGLATMGTQP   240
ATHHPIPTYP SYVPAAAHDY SSGLFHPGGF LGGPASSFTP KQRSKARSCS EGRECVNCGA   300
TATPLWRRDG TGHYLCNACG LYHKMNGQNR PLIKPKRRLS TTTTLWRRNA NGDPVCNACG   360
LYYKLHNVNR PLTMKKEGIQ TRNRKMSNKS KKSKKGAECF EELSKCMQEK SSPFSAAALA   420
GHMAPVGHLP PFSHSGHILP TPTPIHPSSS LSFGHPHPSS MVTAMG                  466

SEQ ID NO: 86              moltype = AA  length = 480
FEATURE                    Location/Qualifiers
source                     1..480
                           mol_type = protein
                           organism = Homo sapiens
SEQUENCE: 86
MEVAPEQPRW MAHPAVLNAQ HPDSHHPGLA HNYMEPAQLL PPDEVDVFFN HLDSQGNPYY     60
ANPAHARARV SYSPAHARLT GGQMCRPHLL HSPGLPWLDG GKAALSAAAA HHHNPWTVSP   120
FSKTPLHPSA AGGPGGPLSV YPGAGGGSGG GSGSSVASLT PTAAHSGSHL FGFPPTPPKE   180
VSPDPSTTGA ASPASSSAGG SAARGEDKDG VKYQVSLTES MKMESGSPLR PGLATMGTQP   240
ATHHPIPTYP SYVPAAAHDY SSGLFHPGGF LGGPASSFTP KQRSKARSCS EGRECVNCGA   300
TATPLWRRDG TGHYLCNACG LYHKMNGQNR PLIKPKRRLS AARRAGTCCA NCQTTTTTLW   360
RRNANGDPVC NACGLYYKLH NVNRPLTMKK EGIQTRNRKM SNKSKKSKKG AECFEELSKC   420
MQEKSSPFSA AALAGHMAPV GHLPPFSHSG HILPTPTPIH PSSSLSFGHP HPSSMVTAMG   480

SEQ ID NO: 87              moltype = DNA  length = 3383
FEATURE                    Location/Qualifiers
source                     1..3383
                           mol_type = genomic DNA
                           organism = Homo sapiens
SEQUENCE: 87
```

```
gagagagagg cagcgtgagc gccaggaagg tagcgaggcc agcgtcgccc cgggactcgc    60
tgctcaagtc tgtctattgc ctgccgccac atccatccta gcagggcccc gtcgcccacc   120
aggcggacaa aagcggtccg ctgaacacca tgccggccgct cggcgtgccg cccaggctct  180
gctggtgagc gccgccaccc cgcgcccagg tcccgcgagc ccgcctgccg cgcacctcgc   240
cctgctccca gctctactcc aggccccgtc cgcccgggcc cgcgcccac cgcgcctcgc    300
tcgggccgtt gccgtctgca cccagacccc gagccgccgc cgccggccat ggaggtggcg   360
cccgagcagc cgcgctggat ggcgcacccg gccgtgctga atgcgcagca ccccgactca   420
caccacccgg gcctggcgca caactacatg aacccgcgc agctgctgcc tccagacgag    480
gtggacgtct tcttcaatca cctcgactcg cagggcaacc cctactatcg caacccccgct  540
cacgcgcggg cgcgcgtctc ctacagcccc gcgcacgccc gcctgaccgg aggccagatg   600
tgccgcccac acttgttgca cagcccgggt tgcccctggc tggacggggg caaagcagcc   660
ctctctgccg ctgcggccca ccaccacaac ccctggaccg tgagccccctt ctccaagacg   720
ccactgcacc cctcagctgc tggaggccct ggaggcccac tctctgtgta cccaggggct   780
gggggtggga gcgggggagg cagcgggagc tcagtggcct ccctcacccc tacagcagcc   840
cactctggct cccaccttt cggcttccca cccacgccac ccaaagaagt gtctcctgac    900
cctagcacca cggggctgc gtctccagcc tcatcttccg cggggggtag tgcagcccga    960
ggagaggaca aggacggcgt caagtaccag gtgtcactga cggagagcat gaagatggaa   1020
agtggcagtc ccctgcgccc aggctagct actatgggca ccagcctgc tacacaccac    1080
cccatcccca cctaccccc ctatgtgccg gcggctgccc acgactacag cagcggactc    1140
ttccacccg gaggcttcct ggggggaccg gcctccagct tcaccctaa gcagcgcagc     1200
aaggctcgtt cctgttcaga aggccggag tgtgtcaact gtgggccac agccacccct    1260
ctctggcgga gggacggcac cggccactac ctgtgcaatg cctgtgggcct ctaccacaag  1320
atgaatgggc agaaccgacc actcatcaag cccaagcgaa gactgtccgg cgccagaaga   1380
gccggcacct gttgtgcaaa ttgtcagacg acaaccacca cctttatgcg ccgaaacgcc    1440
aacgggacc ctgtctgcaa cgcctgtggc ctctactaca gctgcacaa tgttaacagg    1500
ccactgacca tgaagaagga aggatccag actcggaacc ggaagatgtcc caacaagtcc   1560
aagaagagca agaaaggggc ggagtgcttc gaggagctgt caaagtgcat gcaggagaag   1620
tcatccccct tcagtgcagc tgccctggct ggacacatgg cacctgtggg ccacctcccg   1680
ccccttcagcc actccggaca catcctgccc actccgacgc ccatccaccc ctcctccagc   1740
ctctccttcg gccacccca cccgtccagc atggtgaccg ccatgggcta gggaacagat   1800
ggacgtcgag gaccgggcac tcccgggatg ggtggaccaa acccttagca gcccagcatt   1860
tcccgaaggc cgacaccact cctgccagcc cggctcggcc cagcacccc tctcctggag    1920
ggcgcccagc agcctgccag cagttactgt gaatgttccc caccgctgag aggctgcctc   1980
cgcacctgac cgctgcccag gtggggttc ctgcatggac agttgtttgg agaacaacaa   2040
ggacaacttt atgtagagaa aaggagggga cgggacaagc gaaggcaacc attttaagaa   2100
ggaaaaagga ttaggcaaaa ataatttatt ttgctcttgt ttctaacaag gacttggaga   2160
cttggtggtc tgagctgtcc caagtcctcc ggttcttcct cgggattggc gggtccactt   2220
gccagggctc tgggggcaga tttgtgggga cctcagcctg caccctcttc tcctctggct   2280
tccctctctg aaatagccga actccaggct gggctgccag aaagccagag tggccacggc   2340
ccagggaggg tgagctggtg cctgctttga cgggccaggc cctggagggc agagacaatc   2400
acgggcggtc ctgcacagat tcccaggcca gggctgggtc acaggaagga aacaacattt    2460
tcttgaaagg ggaaacgtct cccagatcgc tcccttggct ttgaggccga agctgctgtg   2520
actgtgtccc cttactgagc gcaagccaca gcctgtcttg ccctgtaaata             2580
catccttttt ctgctaaccc ttcaacccc tcgcctccta ctctgagaca aaagaaaaaa    2640
tattaaaaaa atgcataggc ttaactgct gatgagttaa ttgtttttatt tttaaactct   2700
ttttgggtcc agttgattgt acgtagccac aggagccctg ctatgaaagg aataaaacct   2760
acacacaagg ttgagctttt gcaattcttt ttggaaaaga gggatcc cacagcccta     2820
gtatgaaagc tgggggtggg gaggggcctt tgctgccctt ggtttctggg ggctggttgg   2880
catttgctgg cctggcaggg ggtgaaggca ggagttgggg gcaggtcagg accaggaccc   2940
agggagaggc tgtgtccctg ctgggtctc aggtccagct ttactgtggc tgtctggatc    3000
cttcccaagg tacagctgta tataaacgtg tcccgagctt agattctgta tgcggtgacg   3060
gcggggtgtg gtggcctgtg aggggcccct ggcccaggag gaggattgtg ctgatgtagt   3120
gaccaagtgc aatatgggcg ggcagtcgct gcagggagca ccacgccag aagtaactta    3180
ttttgtacta gtgtccgcat aagaaaaaga atcggcagta ttttctgttt ttatgtttta   3240
tttggcttgt ttattttgg attagtgaac taagttattg ttaattatgt acaacattta    3300
tatattgtct gtaaaaaatg tatgctatcc tcttattcct ttaaagtgag tactgttaag   3360
aataataaaa tacttttgt gaa                                            3383
```

SEQ ID NO: 88      moltype = DNA   length = 3470
FEATURE             Location/Qualifiers
source              1..3470
                     mol_type = genomic DNA
                     organism = Homo sapiens
SEQUENCE: 88

```
actgggtcaa gcacagccct gagcggccgc gtgtccgagg cccaggtgcc ctctagagcc    60
ctgtagttcc tgccctctc tgccctctc ggctcctgct gttccgccgc tgtcgtccga    120
accatcccaa cccccagtcc acccagacag cgcccgagct aggggaggga acggtctggg   180
agtcggcagc tggcgccagg gcggccggag gatgccgagg ggcggagcc ggagggccc    240
gaggccgagg cgcactctac ccccagctcc taccctgtaa gccccgccag gctccggacg   300
tgctgtccct gggccgtcg ccctcggggc tcccgccgga actccttcac tctcagaggc   360
cgagtccctc ccctccccac ggctgcgtgt ggccgttgcc gtctgcaccc agaccctgag   420
ccgccgccgc cggccatgga ggtggcgccc gagcagccgc gctggatggc gcaccccgcc   480
gtgctgaatg cgcagcaccc cgactcacac caccccggc tggcgcacaa ctacatggaa   540
cccgcgcagc tgctgcctcc agacgaggtg gacgtcttct tcaatcacct cgactcgcag   600
ggcaaccct actatcgccaa cccgctcac gcgcgggcgc gtctcctac agccccgcg    660
cacgcccgcc tgaccggagg ccagatgtgc cgcccacact tgttgcacag cccgggtttg   720
ccctggctga cgggggcaa agcagccctc tctgccgctg cggccaccac ccacaacccc   780
tggaccgtga gccccttctc caagacgcca ctgcaccct cagctgctgg aggccctgga   840
ggcccactct ctgtgtaccc aggggctggg ggtgggagcg gggaggcag cgggagctca   900
```

```
gtggcctccc tcacccctac agcagcccac tctggctccc acctttcgg cttcccaccc   960
acgccaccca aagaagtgtc tcctgaccct agcaccacgg gggctgcgtc tccagcctca  1020
tcttccgcgg ggggtagtgc agcccgagga gaggacaagg acggcgtcaa gtaccaggtg  1080
tcactgacgg agagcatgaa gatggaaagt ggcagtcccc tgcgcccagg cctagctact  1140
atgggcaccc agcctgctac acaccacccc atcccacct accctccta tgtgccggcg   1200
gctgcccacg actacagcag cggactcttc caccccggag gcttcctggg gggaccggcc  1260
tccagcttca cccctaagca gcgcagcaag gctcgttcct gttcagaagg ccgggagtgt  1320
gtcaactgtg gggccacagc cacccctctc tggcggcggg acggcaccgg ccactacctg  1380
tgcaatgcct gtggcctcta ccacaagatg aatgggcaga accgaccact catcaagcct  1440
aagcgaagac tgtcggccgc cagaagagcc ggcacctgtt gtgcaaattg tcagacgaca  1500
accaccacct tatggcgccg aaacgccaac ggggaccctg tctgcaacgc ctgtggcctc  1560
tactacaagc tgcacaatgt taacaggcca ctgaccatga agaaggaagg gatccagact  1620
cggaaccgga agatgtccaa caagtccaag aagagcaaga aaggggcgga gtgcttcgag  1680
gagctgtcaa agtgcatgca ggagaagtca tcccccttca gtcgactgc cctggctgga   1740
cacatggcac ctgtgggcca cctcccgccc ttcagccact ccggacacat cctgcccact  1800
ccgacgccca tccaccctc ctccagcctc tccttcggcc accccacc gtccagcatg    1860
gtgaccgcca tgggctaggg aacagatgga cgtcgaggac cgggcactcc cgggatgggt  1920
ggaccaaaacc cttagcagcc cagcatttcc cgaaggccga caccactcct gccagcccgg  1980
ctcggcccag cacccctct cctgagggc gcccagcagc ctgccagcag ttactgtgaa    2040
tgttccccac cgctgagagg ctgcctccgc acctgaccgc tgcccaggtg gggtttcctg  2100
catgacagt tgtttggaga acaacaagga caactttatg tagagaaaag gaggggacgg   2160
gacagacgaa ggcaaccatt tttagaagga aaaaggatta ggcaaaaata atttattttg  2220
ctcttgtttc taacaaggac ttggagactt ggtggtctga gctgtcccaa gtcctccggt  2280
tcttcctcgg gattggcggg tccacttgcc agggctctgg gggcagattt gtggggacct  2340
cagcctgcac cctcttctcc tctggcttcc ctctctgaaa tagccgaact ccaggctggg  2400
ctgagccaaa gccagagtgg ccacgcccca gggagggtgga gctggtgcct gctttgacgg  2460
gccaggccct ggagggcaga gacaatcacg ggcggtcctg cacagattcc caggccaggg  2520
ctgggtcaca ggaaggaaac aacattttct tgaaagggga aacgtctccc agatcgctcc  2580
cttggctttg aggccgaagc tgctgtgact gtgtcccctt actgagcgca agccacagcc  2640
tgtcttgtca ggtgaccct gtaaatacat ccttttctg ctaaccctc gaccccctcg     2700
cctcctactc tgagacaaaa gaaaaaatat taaaaaatg cataggctta actcgctgat   2760
gagttaattg ttttattttt aaactctttt tgggtccagt tgattgtacg tagccacagg  2820
agccctgcta tgaaaggaat aaaacctaca cacaaggttg gagctttgca attctttttg  2880
gaaaagagct gggatcccac agccctagta tgaaagctgg gggtggggag gggccttgtc  2940
tgccttggt ttctgggggc tggttggcat ttgctgggct ggcaggggtt gaaggcagga   3000
gttgggggca ggtcaggacc aggacccagg gagaggctgt gtccctgctg gggtctcagg  3060
tccagcttta ctgtggctgt ctggatcctt cccaaggtac agctgtatat aaacgtgtcc  3120
cgagcttaga ttctgtatgc ggtgacgcg gggtgtggtg gcctgtgagg ggccctggc    3180
ccaggaggag gattgtgctg atgtagtgac caagtgcaat atgggcgggc agtcgctgca  3240
gggagcacca cggccagaag taacttattt tgtactagtg tccgcataag aaaaagaatc  3300
ggcagtattt tctgttttta tgttttattt ggcttgtttt attttggatt agtgaactaa  3360
gttattgtta attatgtaca acatttatat attgtctgta aaaatgtat gctatcctct   3420
tattcctta aagtgagtac tgttaagaat aataaaaatac ttttttgtgaa            3470

SEQ ID NO: 89          moltype = DNA   length = 3263
FEATURE                Location/Qualifiers
source                 1..3263
                       mol_type = genomic DNA
                       organism = Homo sapiens
SEQUENCE: 89
gagtcggcag ctggcgccag ggcggccgga ggatgccgag gggccggagc cggagggcc    60
cgaggccgag gcgcactcta ccccagctc ctaccctgta agccccgcca gcctccggac   120
gtgctgtccc tgggccgtc gcctcgggg ctccgccgg aactccttca ctctcagagg    180
ccgagtccct cccctcccca cggctgcgtg tggccgttgc cgtctgcacc cagaccctga   240
gccgccgccg ccggccatgg aggtggcgcc cgagcagccc cgctgatgg cgcacccggc   300
cgtgctgaat gcgcagcacc ccgactcaca ccacccgggc ctggcgcaca actacatgga   360
acccgcgcag ctgctgcctc cagacgaggt ggacgtcttc ttcaatcacc tgactcgca    420
gggcaacccc tactatgcca accccgctca cgcgcgggcg cgcgtctcct acagccccgc   480
gcacgcccgc ctgaccggag gccagatgtg ccgcccacac ttgttgcaca gcccgggttt   540
gccctggctg gacgggggca aagcagccct ctctgccgct gcgggcccac caccacaacc   600
ctggaccgtg agcccttct ccaagacgcc actgcacccc tcagctgctg gaggccctgg   660
aggcccactc tctgtgtacc caggggctgg gggtgggagc ggggaggca gcgggagctc    720
agtggcctcc ctcaccccta cagcagccca ctctggctcc acctttcg gcttcccacc    780
cacgccaccc aagaagtgt ctcctgaccc tagcaccagg gggctgcgtc ctccagcctca   840
atcttccgcg gggggtagtg cagcccgagg agaggacaag gacggcgtca agtaccaggt   900
gtcactgacg gagagcatga agatggaaag tggcagtccc ctgcgcccag gcctagctac   960
tatgggcacc cagcctgcta cacaccaccc catcccacc taccctcct atgtgccggc    1020
ggctgcccac gactacagca gcggactctt caccccgga gcttcctgg gggaccggc     1080
ctccagcttc accctaagc agcgcagcaa ggctcgttcc tgttcagaag ccgggagtgt   1140
tgtcaactgt ggggccacag ccacccctct ctggcggcgg gacggcaccg gccactacct  1200
gtgcaatgcc tgtggcctct accacaagat gaatgggcag aaccgaccac tcatcaagcc  1260
caagcgaaga ctgacgacaa ccaccacctt atggcgccga aacgccaacg ggaccctgt   1320
ctgcaacgcc tgtggcctct actacaagct gcacaatgtt aacaggccac tgaccatgaa  1380
gaaggaaggg atccagactc ggaaccgaa agatgtccaa caagtccaaga agagcaagaa  1440
aggggcggag tgcttcgagg agctgtcaaa gtgcatgcag gagaagtcat cccccttcag  1500
tgcagctgcc ctggctggac acatggcacc tgtgggccac ctcccgccct tcagccactc  1560
cggacacatc ctgcccactc cgacgccat ccacccctcc tccagcctct ccttcggcca    1620
cccccacccg tccagcatgg tgaccgccat gggctaggga acagatggac gtcgaggacc  1680
gggcactccc gggatgggtg gaccaaaccc ttagcagccc agcattccc gaaggccgac   1740
```

```
accactcctg ccagcccggc tcggcccagc accccctctc ctggagggcg cccagcagcc    1800
tgccagcagt tactgtgaat gttccccacc gctgagaggc tgcctccgca cctgaccgct    1860
gcccaggtgg ggtttcctgc atggacagtt gtttggagaa caacaaggac aactttatgt    1920
agagaaaagg aggggacggg acagacgaag gcaaccattt ttagaaggaa aaaggattag    1980
gcaaaaataa tttattttgc tcttgtttct aacaaggact tggagacttg gtggtctgag    2040
ctgtcccaag tcctccggtt cttcctcggg attggcgggt ccacttgcca gggctctggg    2100
ggcagatttg tggggacctc agcctgcacc ctcttctcct ctggcttccc tctctgaaat    2160
agccgaactc caggctgggc tgagccaaag ccagagtggc cacggcccag ggagggtgag    2220
ctggtgcctg ctttgacggg ccaggccctg gagggcagag acaatcacgg gcggtcctgc    2280
acagattccc aggccagggc tgggtcacag gaaggaaaca acattttctt gaaaggggaa    2340
acgtctccca gatcgctccc ttggctttga ggccgaagct gctgtgactg tgtcccctta    2400
ctgagcgcaa gccacagcct gtcttgtcag gtggaccctg taaatacatc ttttctgc     2460
taaccccttca accccctcgc ctcctactct gagacaaaag aaaaaatatt aaaaaaatgc    2520
ataggcttaa ctcgctgatg agttaattgt tttattttta aactcttttt gggtccagtt    2580
gattgtacgt agccacagga gccctgctat gaaaggaata aaacctacac acaaggttgg    2640
agctttgcaa ttcttttttgg aaaagagctg ggatcccaca gccctagtat gaaagctggg    2700
ggtgggggagg ggcctttgct gcccttggtt tctgggggct ggttggcatt tgctggcctg    2760
gcagggggtg aaggcaggag ttgggggcag gtcaggacca ggacccaggg agaggctgtg    2820
tccctgctgg ggtctcaggt ccagcttttac tgtggctgtc tggatccttc ccaaggtaca    2880
gctgtatata aacgtgtccc gagcttagat tctgtatgcg gtgacggcgg ggtgtggtgg    2940
cctgtgaggg gcccctggcc caggaggagg attgtgctga tgtagtgacc aagtgcaata    3000
tgggcgggca gtcgctgcag ggagcaccac ggccagaagt aacttatttt gtactagtgt    3060
ccgcataaga aaaagaatcg gcagtatttt ctgttttttat gttttatttg gcttgtttta    3120
ttttggatta gtgaactaag ttattgttaa ttatgtacaa catttatata ttgtctgtaa    3180
aaaatgtatg ctatcctctt attcctttaa agtgagtact gttaagaata ataaaatact    3240
ttttgtgaat gcccaaaaaa aaa                                           3263

SEQ ID NO: 90          moltype = AA   length = 480
FEATURE                Location/Qualifiers
source                 1..480
                       mol_type = protein
                       organism = Mus musculus
SEQUENCE: 90
MEVAPEQPRW MAHPAVLNAQ HPDSHHPGLA HNYMEPAQLL PPDEVDVFFN HLDSQGNPYY     60
ANPAHARARV SYSPAHARLT GGQMCRPHLL HSPGLPWLDG GKAALSAAAA HHHSPWTVSP    120
FSKTPLHPSA AGAPGGPLSV YPGAAGGSGG GSGSSVASLT PTAAHSGSHL FGFPPTPPKE    180
VSPDPSTTGA ASPASSSAGG SVARGEDKDG VKYQVSLSES MKMEGGSPLR PGLATMGTQP    240
ATHHPIPTYP SYVPAAAHDY GSSLFHPGGF LGGPASSFTP KQRSKARSCS EGRECVNCGA    300
TATPLWRRDG TGHYLCNACG LYHKMNGQNR PLIKPKRRLS AARRAGTCCA NCQTTTTTLW    360
RRNANGDPVC NACGLYYKLH NVNRPLTMKK EGIQTRNRKM SSKSKKSKKG AECFEELSKC    420
MQEKSPPFSA AALAGHMAPV GHLPPFSHSG HILPTPTPIH PSSSLSFGHP HPSSMVTAMG    480

SEQ ID NO: 91          moltype = AA   length = 480
FEATURE                Location/Qualifiers
source                 1..480
                       mol_type = protein
                       organism = Mus musculus
SEQUENCE: 91
MEVAPEQPRW MAHPAVLNAQ HPDSHHPGLA HNYMEPAQLL PPDEVDVFFN HLDSQGNPYY     60
ANPAHARARV SYSPAHARLT GGQMCRPHLL HSPGLPWLDG GKAALSAAAA HHHSPWTVSP    120
FSKTPLHPSA AGAPGGPLSV YPGAAGGSGG GSGSSVASLT PTAAHSGSHL FGFPPTPPKE    180
VSPDPSTTGA ASPASSSAGG SVARGEDKDG VKYQVSLSES MKMEGGSPLR PGLATMGTQP    240
ATHHPIPTYP SYVPAAAHDY GSSLFHPGGF LGGPASSFTP KQRSKARSCS EGRECVNCGA    300
TATPLWRRDG TGHYLCNACG LYHKMNGQNR PLIKPKRRLS AARRAGTCCA NCQTTTTTLW    360
RRNANGDPVC NACGLYYKLH NVNRPLTMKK EGIQTRNRKM SSKSKKSKKG AECFEELSKC    420
MQEKSPPFSA AALAGHMAPV GHLPPFSHSG HILPTPTPIH PSSSLSFGHP HPSSMVTAMG    480

SEQ ID NO: 92          moltype = DNA   length = 3258
FEATURE                Location/Qualifiers
source                 1..3258
                       mol_type = genomic DNA
                       organism = Mus musculus
SEQUENCE: 92
gtctgtgcag gagtcggcag ctggcgccag ggcggccgga ggatgcagag gggccggagc      60
cgggcgggcc ggaggccgag acgcgcgctg tcccccaccc ctatcccgtg aatccgccgg     120
ccctggaacg cgctgtcgct ggcccgccg taccccgggct ctcctggtgt ctcttactct     180
ctactgctga gccctcccct tcccgcgccg ctgcagtgg ccgccccacc ttcgcctggt     240
tcccaagaca cagtagtgga ccatggaggt ggcgcctgag cagcctcgct ggatggcgca     300
ccccgccgta ttgaatgcgc agcacccccga ctcgcaccat ccgggcctgg cgcataacta     360
catggagcca gcacagctgc tgcctcccga cgaggtggat gtcttcttca accatctcga     420
ctcgcagggc aacccttact acgccaaccc ggccacgcg cgcgcgcgcg tttcctacag     480
cccgcgcat gcccgtctca ccggaggcca gatgtgccga ccacttgt tgcacagccc     540
aggcttgccg tggctggacg ggggcaaagc agctctctct gccgccgctg cccatcacca     600
cagtccctgg accgtcagcc cgttctccaa gaccccgctg cacccctcag cctgctggag     660
acccggaggg cctctgtctg tttacccagg ggctgcgggt gggagcgggg gaggcagtgg     720
gagctccgtg gcctccctca ccccactgc agcccactcg ggctcccatc tcttcggctt     780
cccacccacg ccacccaaag aagtgtctcc agacccagc acaacaggag ctgcttcccc     840
ggcctcttct tctgcagggg gtagtgtagc ccggggtgag acaaggatg gcgtcaagta     900
ccaagtgtca ctctccgaga gcatgaagat ggaaggcgg agtcccctgc gcccgggcct     960
```

```
agctaccatg ggcacccagc ctgcaacaca ccaccegata cccacctatc cctcctatgt   1020
gcccgccgca gctcatgact atggcagcag tctcttccat ccaggaggct tcctgggtgg   1080
ccccgcctcc agcttcaccc ctaagcagag aagcaaggct cgctcctgct cagaaggccg   1140
ggagtgtgtc aactgtggtg ccacagccac ccctctctgg cgacgagatg gcacgggcca   1200
ctacctgtgc aatgcctgtg ggctctacca caagatgaat ggacagaacc ggccgctcat   1260
caagcccaag cggaggctgt ctgctgccaa aagagcgggc acctgttgtg caaattgtca   1320
gacgacaacc accaccttat ggcgccggaa cgccaacggg gaccctgtgt gcaacgcctg   1380
tggcctctac tacaagctgc acaatgttaa caggccactg accatgaaga aggaagggat   1440
ccagacccgg aatcggaaga tgtccagcaa atccaagaag agcaagaaag gggctgaatg   1500
tttcgaggag ctctccaagt gcatgcaaga gaagtcaccg cccttcagtg cggctgccct   1560
ggctggacac atggcacctg tgggacacct cccacctttt agtcactctg gacacatcct   1620
acccacgccc acgcctatcc acccttcctc cagtctctct tttggccacc cccaccegtc   1680
cagcatggtg actgccatgg gctaggcaag cctcccactg gacagacatg gacatcaagg   1740
gtggtttggc agaaccagag cgaggctggg cactcccagg atgggtggaa catactcttg   1800
gctcccgccc atcccaagag acccacttcc tcctgccagc ctagcctggc cgaagccacc   1860
tctccttgga ggactcccag ccttgtgccg ccattactgt gaatatttct aactgggctg   1920
cagctcgcgt gtgcccgggg tgctgcccag aaaagtgttt tcacggagag tgtttgtttg   1980
gagagcaaaa tggacaggtt tacagattta tagcaagaag agactgggga tagaaaaatg   2040
aaaccttttt ttttctttt cttttttct tcttctgttt tatttttttg atggagaaag    2100
gagtaggcaa aagaaaaat aatttatttt gctcttattt cttacaagaa cgtgaagaca    2160
tggaggcgtg tgctatttgt gttcttgggg tccttctttg ggacctcctg ccaccagtca   2220
gggctctcgg gggcagactt agaggtcctc agcctgcctc tccttcaccc cagcctgcct   2280
gcagggtagc ccctgccctg acgcagccct agagggcaga gacaattgca ggcggtcctg   2340
cgcagattcc caggccaggg ctgggtcaca ggaaggaaac attctctgga aaggggaaac   2400
gtctcccaga tcattcccct ggcttccaga ggccaaagct ggtgtgaccc aaatgggcca   2460
gagctgcagc ctgtgctcta ggccagtcgg acccctgtaa atacaacctt ctttctgct    2520
aaacctcgg ccccctcccc ctctaagata aataagaaaa tactcaaagc gaaaaccaaa    2580
ctgcataagc ttaacccgct gatgagtggt tttattttga aactcgtttt ttgggtccag   2640
tcaattgtac gttgccacag aagcccgct atggaaaaaa ataaataaa cctacaaacc     2700
aggcctggac ttcacagtcc tttgagtggt tcttgggtct cacagccctg gcagggggcct  2760
cgggacaagg gggaatctta tgctcttggt ttctgggaga caggggggcag gcaggcagtg  2820
gccctgtgat cccaggcttc tgttctgctg tggctggctg aatccttcaa ggtacagttg   2880
tacataaaaa gtgtcccaag cttcgattct gtgtgtggtg gtggcagtgg tgcagcagcc   2940
agcaaggggg cccccgagtga gcccagggag acgattgtgc tgagtcaacc aagtgcaata  3000
tcggttcca gttgctgcag agcaccctaa ccggaagtaa cttattttgt gctagtaccc    3060
gcataagaga agaatcggca gtattttctg ttttttatgtt ttgggcttgt tttattttga  3120
attagtgacc taagttattg ttaactgtgt acaacattta aatattgtct gtaaaaattg   3180
tatgctaccc tcttattcct ttaaagtgaa tactgttaaa aataataaaa tacttttgt    3240
gaaaaaaaaa aaaaaaa                                                  3258

SEQ ID NO: 93          moltype = DNA    length = 3150
FEATURE                Location/Qualifiers
source                 1..3150
                       mol_type = genomic DNA
                       organism = Mus musculus
SEQUENCE: 93
gcggccgcgc tgactcccgc gggccgacca gccacgccgc tcacaccgct gcctccctgc   60
tgagccctgg ccgtggccgc ccgagggcgc cgcccaccgc gccgcagtcg ggccgcccca   120
ccttcgcctg gttcccaaga cacagtagtg gaccatggag gtggcgcctg agcagcctcg   180
ctggatggcc caccccgccg tattgaatgc gcagcacccc gactcgcacc atccgggcct   240
ggcgcataac tacatggagc cagcacagct gctgcctccc gacgaggtgg atgtcttctt   300
caaccatctc gactcgcagg gcaaccctta ctacgccaac ccggcccacg cgcgcgcgcg   360
cgttcctac agcccggcgc atgcccgtct caccggaggc cagatgtgcc gaccacactt   420
gttgcacagc ccaggcttgc cgtggctgga cgggggcaaa gcagctctct ctgccgccgc   480
tgcccatcac cacagtccct ggaccgtcag cccgttctcc aagacccgc tgcaccccte    540
agctgctgga gcaccggag ggcctctgtc tgtttaccca ggggctgcgg gtgggagcgg    600
gggaggcagt gggagctccg tggcctcct caccccact gcagcccact cgggctccca    660
tctcttcggc ttcccaccca cgccaccaa agaagtgtct ccagacccca gcacaacagg    720
agctgcttcc ccggcctctt cttctgcagg gggtagtgta gccgggggtg aggacaagga   780
tggcgtcaag taccaagtgt cactcctcga gagcatgaag atggaaggcg gcagtcccct   840
gcgcccgggc ctagctacca tgggcaccca gcctgcaaca caccaccgga tacccaccta   900
tccctcctat gtgcccgccg cagctcatga ctatggcagc agtctcttcc atccaggagg   960
cttcctgggt ggccccgcct ccagcttcac ccctaagcag agaagcaagg ctcgctcctg   1020
ctcagaaggc cgggagtgtg tcaactgtgg tgccacagcc accectctct ggcgacgaga   1080
tggcacgggc cactacctgt gcaatgcctg tgggctctac acaagatga atggacagaa    1140
ccggccgctc atcaagccca gcggaggct gtctgctgcc agaagagcgg gcacctgttg    1200
tgcaaattgt cagacgacaa ccaccacctt atggcgccgg aacgccaacg ggaccctgt    1260
gtgcaacgcc tgtggcctct actacaagct gcacaatgtt aacaggccac tgaccatgaa   1320
gaaggaaggg atccagaccc ggaatcggaa gatgtccagc aaatccaaga agagcaagaa   1380
aggggctgaa tgtttcgagg agctctccaa gtgcatgcaa gagaagtcac cgcccttcag   1440
tgcggctgcc ctggctggac acatggcacc tgtgggacac ctcccacctt ttagtcactc   1500
tggacacatc ctacccacgc ccacgcctat ccacccttcc tccagtctct cttttggcca   1560
cccccacccg tccagcatgg tgactgccat gggctaggca agcctcccac tggacagaca   1620
tggacatcaa gggtggtttg gcagaaccag acgaggctg ggcacccctg ggatgggtgg    1680
aacatactct tggctcccgc ccatcccaag agacccactt cctcctgcca gctagcctg    1740
gccgaagcca cctctccttg gaggactccc agccttgtgc cgccattact gtgaatattt   1800
ctaactggc tgcagctcgc gtgtgcccgg ggtgctgccc agaaaagtgt tcacggag     1860
agtgtttgtt tggagagcaa aatggacagg tttacagatt tatagcaaga agagactggg   1920
gatagaaaaa tgaaaccttt tttttctttt ttctttttt cttcttctgt ttatttttt    1980
```

```
tgatggagaa aggagtaggc aagaagaaaa ataatttatt ttgctcttat ttcttacaag  2040
aacgtgaaga catggaggcg tgtgctattt gtgttcttgg ggtccttctt tgggacctcc  2100
tgccaccagt cagggctctc gggggcagac ttagaggtcc tcagcctgag cctccttcac  2160
cccagcctgc ctgcagggta gcccctgccc tgacgcagcc ctagagggca gagacaattg  2220
caggcggtcc tgcgcagatt cccaggccag ggctggctgc caggaaggaa acattctctg  2280
gaaaggggaa acgtctccca gatcattccc ctggcttcca gaggccaaag ctggtgtgac  2340
ccaaatgggc cagagctgca gcctgtgctc taggccagtc ggaccctgt aaatacaacc  2400
ttcttttctg ctaaaccctc ggcccoctcc ccctctaaga taaataagaa aatactcaaa  2460
gcgaaaacca aactgcataa gcttaacccg ctgatgagtg gttttatttt gaaactcgtt  2520
ttttgggtcc agtcaattgt acgttgccac agaagcccg ctatggaaaa aaataaataa  2580
aacctacaaa ccaggcctga gcttcacagt cctttgagtg gttcttgggt cccacagccc  2640
tggcaggggg ctcgggacaa ggggaatct tatgctcttg gtttctggga cagggggc    2700
aggcaggcag tggccctgtg atcccaggct tctgttctgc tgtggctggc tgaatccttc  2760
aaggtacagt tgtacataaa aagtgtccca agcttcgatt ctgtgttgg tggtggcagt  2820
ggtgcagcag ccagcaaggg ggccccgagt gagcccaggg agacgattgt gctgagtcaa  2880
ccaagtgcaa tatcggtgtc cagttgctgc agagcacct aaccgaagt aacttatttt  2940
gtgctagtac ccgcataaga gaagaatcgg cagtattttc tgttttatg ttttgggctt  3000
gttttatttt gaattagtga cctaagttat tgttaactgt gtacaacatt taaatattgt  3060
ctgtaaaaat tgtatgctac cctcttattc cttaaagtg aatactgtta aaaataataa  3120
aatactttt gtgaaaaaaa aaaaaaaaaa                                    3150

SEQ ID NO: 94            moltype = AA   length = 206
FEATURE                  Location/Qualifiers
source                   1..206
                         mol_type = protein
                         organism = Homo sapiens
SEQUENCE: 94
MSGPGTAAVA LLPAVLLALL APWAGRGGAA APTAPNGTLE AELERRWESL VALSLARLPV   60
AAQPKEAAVQ SGAGDYLLGI KRLRRLYCNV GIGFHLQALP DGRIGGAHAD TRDSLLELSP  120
VERGVVSIFG VASRFFVAMS SKGKLYGSPF FTDECTFKEI LLPNNYNAYE SYKYPGMFIA  180
LSKNGKTKKG NRVSPTMKVT HFLPRL                                      206

SEQ ID NO: 95            moltype = DNA   length = 3165
FEATURE                  Location/Qualifiers
source                   1..3165
                         mol_type = genomic DNA
                         organism = Homo sapiens
SEQUENCE: 95
ctggcgctca gggaggcgcg cactgctcct cagagtccca gctccagccg cgcgcttttcc  60
gcccggctcg ccgctccatg cagccggggt agagcccggc gcccggggc cccgtcgctt  120
gcctcccgca cctcctcggt tgcgcactcc tgcccgaggt cggccgtgcg ctcccgcggg  180
acgccacagg cgcagctctg cccccagct tcccgggcgc actgaccgcc tgaccgacgc  240
acggcctcg ggccggatg tcggggcccg ggacggcgc ggtagcgctg ctcccgccgg  300
tcctgctggc cttgctggcg ccctgggcgg gccgaggggg cgccgccgca cccactgcac  360
ccaacggcac gctggaggcc gagctggagc gccgctggga gagcctggtg gcgctctcgt  420
tggcgcgcct gccggtggca gcgcagccca aggaggcgg cgtccagagc ggcgccggcg  480
actacctgct gggcatcaag cggctggcggc ggctctactg caacgtgggc atcgggcttcc  540
accctccaggc gctccccgac ggccgcatcg gcggcgcgca gcggacacc cgcgacagcc  600
tgctggagct ctcgcccgtg gagcggggcg tggtgagcat cttcggcgtg gccagccggt  660
tcttcgtggc catgagcagc aagggcaagc tctatggctc gccttcttc accgatgagt  720
gcacgttcaa ggagattctc cttcccaaca actacaacgc ctacgagtcc tacaagtacc  780
ccggcatgtt catcgccctg agcaagaatg ggaagaccaa gaaggggaac cgagtgtcgc  840
ccaccatgaa ggtcacccac ttcctcccca ggctgtgacc ctccagagga cccttgcctc  900
agcctcggga agccctggg agggcagtgc cgagggtcac cttggtgcac tttcttcgga  960
tgaagagttt aatgcaagag taggtgtaag atatttaagt taattattta aatgtgtata 1020
tattgccacc aaattattta tagttctgcg ggtgtgtttt ttaattttct gggggaaaaa 1080
aaagacaaaa caaaaaacca actctgactt ttctggtgca acagtggaga atcttaccat 1140
tggatttctt taacttgtca aaagttgtca cgagtgtgct gctattctgt gttttaaaaa 1200
aaggtgacat tggattccga tgtcatcccc tgtagtatgg cgtgagcat ctctgtctgg 1260
aaaggcccgc ctgaggcttg ggcagccagt tcagggagct ccaggcttg gctctcggct 1320
agcatcctca gaggccccact cccttttgtgc cctgttgcta ttaatcggga catatcggtt 1380
tacttcgggt acagaaagtg cggtgttgaa gtcctcgctg ccactctgtt tttagatctg 1440
ccaagactga cctttgaact ttcctgtagt caatcttcct cgatctacca gatggagag 1500
acccttggac aactttataa actcctgttt gccttttttg gatcagcgac agccccatc  1560
gctgtgacta ttggggaaaa gacgaagctc tttcataaat tccatggaga ggaatcaata 1620
tcccactgga aggctagaaa tggacaagat agtgtatttg caatcacaaa caaacccta  1680
gtgatgaaaa ataaatttgtg atggcagatg cttctgatgg tgtgatagaa tatgttttttg 1740
aaaacaaacc atcgaaccc ccgccccacc cccaaaacgg gcttccctgt gtttagggag 1800
ctttgggcta gaactagctca cgattttttag gtgaaatgct cttgtaattg tacaaagcac 1860
ttggtgcagt gtttgcgtgg agcagcctgc tgctttctga tgcattccct gtttaagtgc 1920
gtttaacatc tacctcacaa gccctgaaac cccaggcaaa acccacagaa agctcatacc 1980
cggtgcagga gtttgccatc ccaagtggct ttttttccat atgtagccaa aaaggattgc 2040
agatagcgtc ggtgcgtccc attcgaacct tgtcacgttt gagctatctt taccctgtga 2100
tttacttta gtaaggtga tcatggtgaa atatttgca gacagctgtt acagtacact 2160
atatggtcac caagtaaacct tatatttttc tttatatatt ttacaaatgt aacccctgtc 2220
attgaagcaa ccgtggaaga ggcagggtcg gtgatgttta aaaaaagttc cgaggtgatg 2280
gcaaacattt aattttaatg aatgactttt tagagtttat acaaaatgac cttagcttgc 2340
taccagaaat gctccgaatg tttcgtcaag actttaatac tctcctagga tgtttctgaa 2400
ctgtctcccg aattaacttt atgggagtct acagacagca agactggaaa atctgattgg 2460
```

```
agttttttgtc tttcacattc cttttgaaaa ctctttgttc gaatgcaaat catcgactta    2520
aaatactatt cttaaccaag gcctggaaga aagaagacac ttgcaaagcc gctaagacag    2580
gaccacacat cttaaactgc tgttcctacc atgcactaaa ctgttttttaa gttttaaacc   2640
acaccctagg ctccaggagt gttcaggaaa gatggtgttt gtaggtctcc atgctgtttg    2700
gcgttggggg gtgtggaggg atcatccgtc gactttctga attttaatgt attcacttag    2760
taacaaacca tgattgtctt aaatgcctta aattattatg agatttcttg tctcagagcc    2820
caatcagatt gtcaggaatt aacatgtgtt aggtttgatc acccttgacc acttcttata    2880
gatatttctt caacaaatca tgtgtgatgc ctgtaggaac acaactgtac cttttaaaata  2940
ttgttttcat attgctgtga tggggattcg aggttcctgt atgtgccact gttttcagaa    3000
tctgtagttt tatacaggtg ccgaccctcg ttgtgatgta tgtgctgtgc acattgacat    3060
gctgaccgac aatgataagc gtttatcgtg tataaaaaga caccactgga ctggatgtac    3120
acaactggga aaggaattaa aagctattaa aattgtgcct tgaaa                    3165

SEQ ID NO: 96          moltype = AA   length = 202
FEATURE                Location/Qualifiers
source                 1..202
                       mol_type = protein
                       organism = Mus musculus
SEQUENCE: 96
MAKRGPTTGT LLPRVLLALV VALADRGTAA PNGTRHAELG HGWDGLVARS LARLPVAAQP     60
PQAAVRSGAG DYLLGLKRLR RLYCNVGIGF HLQVLPDGRI GGVHADTRDS LLELSPVQRG   120
VVSIFGVASR FFVAMSSRGK LFGVPFFTDE CKFKEILLPN NYNAYESYAY PGMFMALSKN   180
GRTKKGNRVS PTMKVTHFLP RL                                            202

SEQ ID NO: 97          moltype = DNA   length = 3032
FEATURE                Location/Qualifiers
source                 1..3032
                       mol_type = genomic DNA
                       organism = Mus musculus
SEQUENCE: 97
gcgcggggac tatcccgcca ccgttgcgtc cctatttgct ctcgctactt aggtctgtgc     60
gcagcactca ccgaactcac ggcccgcagc tcgaactcac gcacggcccg cgggccggga   120
tggcgaaacg cgggccgacc acagggacgc tgctgcccag gtcctgctg gccctggtgg    180
tggccctggc ggaccgaggg accgccgcac ccaacggcac gcggcacgca gaattggggc   240
acggctggga cggcttggtg gcccgctcgc tggcacgcct gccggtggcc gcgcagccgc   300
cgcaggcgga ggtccgcagc ggcgcagggg actacctgct gggcctcaaa aggcttcggc   360
ggctctactg caacgtgggc atcggattcc acctgcaggt gctgcccgac ggccgcatcg   420
gtggtgtgca cgcagacacg agggacagtc ttctggagct ctctccggtg cagcgaggcg   480
tggtgagcat cttcggagtg gccagccggt tcttcgtggc catgagcagc aggggcaagc   540
tcttcggtgt gcctttcttt accgacgagt gtaaattcaa agaaatactt ctgcccaaca   600
actacaacgc ctacgaatcc tacgcgtacc cggtatgtt catggccctc agtaagaacg    660
gcggaccaa gagggaac cgagtgtcgc ctaccatgaa ggtaacccac ttccttccta      720
gactggtacc ctccggaagcc ctgcctcagc ctcggaagca caccctaccc ctcaggaagta 780
gcactttctc tcgatggaga attgtttgca aaaaaactgg tctaagatat ttaaattatt   840
taaatatgta tatatggacg cccaattatt tataatttta tgtattctca tttttcgggg   900
gggggatatg accaaaagaa caaacaaatt gcagctcaga cctctttgga atagcggaac   960
agacttcttt cttcactatc aaagatatgg gtgtgatgct gtttcatgtg tgcctctaaa  1020
acttggtgac atcagttttcc aagggtgcct ggcctgtaac tggaaaggcc tgcctggac   1080
ctctgaggca gtgagaagga ccctgagcgt tcccgatcgg gagcattctg ccgtcgccgc  1140
tccctctgct tcctttggta tgaacccgtt cggatcggtt tactccaggg acagaagtcc  1200
tcccgcctct gttttttagat ctccaagact gatctttgaa ctctcttgca gtcaatcatc 1260
ttcttggacc taccggatag gagacccttga cacaactttta taaactcctg tttgccattt 1320
ttggactggc caacagggca cgttgcttgt agccactgga actttgcttt tctggagagg  1380
aactaggat ggacaagagg gtgtgtgcgc tcgccacaac tcaaaactct ggggatgaaa   1440
ttctgtttg tgatagagga tgatttgttg ggatataaca atgtatttg caagaatcaa    1500
actgagaaaa acaggcttcc ctgaatatgg gaagctttgt gctggaactc cataaattaa  1560
gggtgagctg cccttttccca ccccaggcag cctttatgca ggcagactgc aggagtccga 1620
attccggtgc tgcccaaagg tgaaggaatt ctatccccat ctacctcaga gttcctgaga  1680
ccctggtgac taagctggag gctctgctgg gtgcatctgc ctgcttctct tccacatgta  1740
gtatctggac ccttgtcacg ttccagctat ctttacccaa tgatttactt ttagtaaggga 1800
gtattcatgg tgaaaatatg cacgaccagc tgtcggagtg cactatatgg tcaccaagtc  1860
aagtaaccct tatattttc tttatatatt ttacgaatgt aaccctgtc actgagacca    1920
aaatggaaga gcagggtcgg tggcatttaa aaaaagggc tgaggtgagg agaacaatt    1980
aattttaatg aatgactttg gagtttatac aaaatgacct tagctcgctt caggaatgc    2040
ttctccccaa gatgttaaga ctctgctggg agacttctga gcaacctccc gaattaactt   2100
tatgggaggc tacagacagc aagactgaa aatctcattg gcatttttt tttttgtctt    2160
tcacattcct ttagaaaact ctttgttttgg atgctaatgg gatacttaaa atactattct  2220
gtaccacagc ccaagatgga agaagccaca cccaaagtgg gaggtgggag ctcctcccaa  2280
acttcctttc tgtctggtgg ctcacaggac aataagattt tgtgttttttt aaatccaggc 2340
cctaggctcc aagagtgttg gggagaagac agttgaaatg tcttttcttc ttgttatttt  2400
ctaaaagacg gtctcatagc ccaggctgta cctgaacttg ctatgtcact aaagatgacc  2460
ttgaattctct gatcctcttg ccccatttcc tagtgctaag gttacaggca ttgcccacca  2520
cgcccactcc ttaggtgctg ggaattgaaa tcaagtgcct gccaggccac tccacagaga  2580
taggcctccc tctttttttgt gggggaggaa atgtggggtc ttactctgta gccaaggctg  2640
gcctactgct tgagcccaag tgttgagact acaggtagaa ggcactgcc ctgttctgat   2700
gggattctct gcagctatgt tgcttcaggc aggctgtggt cctacctgac acctattacc  2760
tgtttcttca gccagctagc tccctttcct gcgcccaggg acaagactgt atctttgaa   2820
ttttgttacc agaatgggtt tgatgtttct gctctgtatc tgccactgtt accgagtcgg  2880
tctgtagtta ctacaggtgt cgacccagag atagtatgtg ctatgcacac tggatgctcc  2940
```

```
atccaaagag aagcattcaa tcatgtatag acagccccat ggactgatgg gaatgattgg   3000
gagagatatt aaaatgacaa acgtgtctgc aa                                 3032

SEQ ID NO: 98           moltype = AA   length = 288
FEATURE                 Location/Qualifiers
source                  1..288
                        mol_type = protein
                        organism = Homo sapiens
SEQUENCE: 98
MVGVGGGDVE DVTPRPGGCQ ISGRGARGCN GIPGAAAWEA ALPRRRPRRH PSVNPRSRAA    60
GSPRTRGRRT EERPSGSRLG DRGRGRALPG GRLGGRGRGR APERVGGRGR GRGTAAPRAA   120
PAARGSRPGP AGTMAAGSIT TLPALPEDGG SGAFPPGHFK DPKRLYCKNG GFFLRIHPDG   180
RVDGVREKSD PHIKLQLQAE ERGVVSIKGV CANRYLAMKE DGRLLASKCV TDECFFFERL   240
ESNNYNTYRS RKYTSWYVAL KRTGQYKLGS KTGPGQKAIL FLPMSAKS                288

SEQ ID NO: 99           moltype = AA   length = 155
FEATURE                 Location/Qualifiers
source                  1..155
                        mol_type = protein
                        organism = Homo sapiens
SEQUENCE: 99
MAAGSITTLP ALPEDGGSGA FPPGHFKDPK RLYCKNGGFF LRIHPDGRVD GVREKSDPHI    60
KLQLQAEERG VVSIKGVCAN RYLAMKEDGR LLASKCVTDE CFFFERLESN NYNTYRSRKY   120
TSWYVALKRT GQYKLGSKTG PGQKAILFLP MSAKS                              155

SEQ ID NO: 100          moltype = DNA   length = 6801
FEATURE                 Location/Qualifiers
source                  1..6801
                        mol_type = genomic DNA
                        organism = Homo sapiens
SEQUENCE: 100
gtggccgaac cgccgaactc agaggccggc cccagaaaac ccgagcgagt aggggcggc     60
gcgcaggagg gaggagaact gggggcgcgg gaggctggtg ggtgtggggg gtggagatgt   120
agaagatgtg acgccgcggc ccggcgggtg ccagattagc ggacgcggtg cccgcggttg   180
caacgggatc ccgggcgctg cagcttggga ggcggctctc cccaggcggc gtccgcggaa   240
acacccatcc gtgaacccca ggtcccgggc cgccggctcg ccgcgcacca ggggccggcg   300
gacagaagag cggccgagcg gctcgaggct ggggggaccgc gggcgcggcc gcgcgctgcc   360
gggcggggagg ctggggggcc ggggccgggg ccgtgccccg gagcgggtcg gaggccgggg   420
ccggggcggg gggacgagcgg ctcccgcgc ggctccacgg gctcggggat cccggccggg   480
ccccgcaggg accatggcag ccgggagcat caccacgctg cccgccttgc ccgaggatgg   540
cggcagcgggc gccttcccgc ccggccactt caaggacccc aagcggctgt actgcaaaaa   600
cgggggcttc ttcctgcgca tccacccgga cggccgagtt gacggggtcc gggagaagag   660
cgaccctcac atcaagctac aacttcaagc agaagagga ggatgttgt ctatcaaggg   720
agtgtgtgct aaccgttacc tggctatgaa ggaagatgga agattactgg cttctaaatg   780
tgttacggat gagtgtttct ttttgaacg attggaatct aataactaca atacttaccg   840
gtcaaggaaa tacaccagtt ggtatgtggc actgaaacga actgggcagt ataaacttgg   900
atccaaaaca ggacctgggc agaaaagctat acttttttct ccaatgtctg ctaagagctg   960
attttaatgg ccacatctaa tctcatttca catgaaagaa gaagtatatt ttagaaattt  1020
gttaatgaga gtaaaagaaa ataaatgtgt atagctcagt ttggataatt ggtcaaacaa  1080
ttttttatcc agtagtaaaa tatgtaacca ttgtcccagt aaagaaaaat aacaaaagtt  1140
gtaaaatgta tattctccct tttatattgc atctgctgtt acccagtgaa gcttacctag  1200
agcaatgatc ttttttcacgc atttgcttta ttcgaaaaga ggcttttaaa atgtgcatgt  1260
ttagaaacaa aatttcttca tggaaatcat atacattaga aaatcacagt cagatgttta  1320
atcaatccaa aatgtccact atttcttatg tcattcgtta gtctacatgt ttctaaacat  1380
ataaatgtga atttaatcaa ttcctttcat agttttataa ttctctggca gttccttatg  1440
atagagttta taaacagtc ctgtgtaaac tgctggaagt tcttccacag tcaggtcaat  1500
tttgtcaaac ccttctctgt acccatacag cagcagccta gcaactctgc tggtgatggg  1560
agttgtattt tcagtcttcg ccaggtcatt gagatccatc cactcacatc ttaagcattc  1620
ttcctggcaa aaatttatgg tgaatgaata tggctttagg cggcagatga tatacatatc  1680
tgacttccca aaagctccag gatttgtgtg ctgttgccga atactcagga cggacctgaa  1740
ttctgatttt ataccagtct cttcaaaaac ttctcgaacc gctgtgtctc ctacgtaaaa  1800
aaagagatgt acaaatcaat aataattaca cttttagaaa ctgtatcatc aaagatttttc  1860
agttaaagta gcattatgta aaggctcaaa acattaccct aacaaagtaa agttttcaat  1920
acaaattctt tgccttgtgg atatcaagaa atcccaaaat attttcttac cactgtaaat  1980
tcaagaagct tttgaaatgc tgaatatttc tttggctgct acttggaggc ttatctacct  2040
gtacattttt ggggtcagct cttttaact tcttgctgct ctttttccca aaaggtaaaa  2100
atatagattg aaaagttaaa acattttgca tggctgcagt tcctttgttt cttgagataa  2160
gattccaaag aacttagatt catttcttca acaccgaaat gctggaggtg tttgatcagt  2220
tttcaagaaa cttggaatat aaataatttt ataattcaac aaaggttttc acattttata  2280
aggttgattt ttcaattaaa tgcaaatttg tgtggcagga ttttattgc cattaacata  2340
ttttttgtggc tgctttttct acacatccag atgtcccctc taactgggct ttctctaatt  2400
ttgtgatgtt ctgtcattgt ctcccaaagt atttaggaga agccctttaa aaagctgcct  2460
tcctctacca ctttgctgga aagcttcaca attgtcacag acaaagattt ttgttccaat  2520
actcgttttg cctctatttt tcttgtttgt caaatagtaa atgatatttg ccctttgcagt  2580
aattctactg tgaaaaaaca tgcaagaag aggaagtcac agaaacatgt ctcaattccc  2640
atgtgctgtg actgtagact gtcttaccat agactgtctt acccatcccc tggatatgct  2700
cttgttttt ccctctaata gctatggaaa gatgcataga aagagtataa tgttttaaaa  2760
cataaggcat ttgtctgcca ttttcaatt acatgctgac ttcccttaca attgagattt  2820
gcccataggt taaacatggt tagaaacaac tgaaagcata aagaaaaat ctaggccggg  2880
```

```
tgcagtggct catgcctata ttccctgcac tttgggaggc caaagcagga ggatcgcttg    2940
agcccaggag ttcaagacca acctggtgaa acccgtctc tacaaaaaaa cacaaaaaat     3000
agccaggcat ggtggcgtgt acatgtggtc tcagatactt gggaggctga ggtgggaggg    3060
ttgatcactt gaggctgaga ggtcaaggtt gcagtgagcc ataatcgtgc cactgcagtc    3120
cagcctaggc aacagagtga gacttttgtct caaaaaaaga gaaatttcc ttaataagaa    3180
aagtaatttt tactctgatg tgcaatacat ttgttattaa atttattatt taagatggta    3240
gcactagtct taaattgtat aaaatatccc ctaacatgtt taaatgtcca tttttattca    3300
ttatgctttg aaaaataatt atggggaaat acatgtttgt tattaaattt attattaaag    3360
atagtagcac tagtcttaaa tttgatataa catctcctaa cttgttttaaa tgtccatttt    3420
tattctttat gttgaaaat aaattatggg gatcctattt agctcttagt accactaatc    3480
aaaagttcgg catgtagctc atgatctatg ctgtttctat gtcgtggaag cactggatgg    3540
gggtagtgag caaatctgcc ctgctcagca gtcaccatag cagctgactg aaaatcagca    3600
ctgcctgagt agtttttgatc agtttaactt gaatcactaa ctgactgaaa attgaatggg    3660
caaataagtg cttttgtctc cagatatgc gggagaccct tccacctcaa gatggatatt    3720
tcttccccaa ggatttcaag atgaattgaa atttttaatc aagatagtgt gcttatcct    3780
gttgtatttt ttattatttt aatatactgt aagccaaact gaaataacat ttgctgtttt    3840
ataggtttga agaacatagg aaaaactaag aggttttgtt tttatttttg ctgatgaaga    3900
gatatgttta aatatgttgt attgttttgt ttagttacag gacaataagt aaatggagtt    3960
tatatttgtt atttctattt tgttatattt aataatagaa ttagattgaa ataaaatata    4020
atgggaaata atctgcagaa tgtgggtttt cctggtgttt ccctctgact ctagtgcact    4080
gatgatctct gataaggctc agctgcttta tagttctctg gctaatgcag cagatactct    4140
tcctgccagt ggtaatacga ttttttaaga aggcagtttg tcaattttaa tcttgtggat    4200
accttatac tcttaggta ttattttata caaaagcctt gaggattgca ttctatttc       4260
tatatgaccc tcttgatatt taaaaaacac tatggataac aattcttcat ttacctagta    4320
ttatgaaaga atgaaggagt tcaaacaaat gtgtttccca gttaactagg gtttactgtt    4380
tgagccaata taaatgttta actgtttgtg atggcagtat tcctaaagta cattgcatgt    4440
tttcctaaat acagagttta aataatttca gtaattctta gatgattcag cttcatcatt    4500
aagaatatct tttgtttat gttgagttag aaatgccttc atatagacat agtctttcag    4560
acctctactg tcagttttca tttctagctg cttttcagggt tttatgaatt tcaggcaaa    4620
gcttaattt acactaagct taggaagtat ggctaatgcc aacggcagtt tttttcttct    4680
taattccaca tgactgaggc atatatgatc tctgggtagg tgagttgttg tgacaaccac    4740
aagcactttt tttttttta aagaaaaaaa ggtagtgaat ttaatcat ctggacttta      4800
agaaggattc tggagtatac ttaggcctga aattatat atttggcttg gaaatgtgtt      4860
tttcttcaat tacatctaca agtaagtaca gctgaaattc agaggaccca taagagttca    4920
catgaaaaaa atcaatttat ttgaaaaggc aagatgcagg agagaggaag ccttgcaaac    4980
ctgcagactg cttttgccc aatatagatt gggtaaggct gcaaaacata agcttaatta    5040
gctcacatgc tctgctctca cgtggcacca gtggatagtg tgagagaatt aggctgtaga    5100
acaaatggcc ttctctttca gcattcacac cactacaaaa tcatcttta tatcaacaga    5160
agaataagca taaactaagc aaaaggtcaa taagtacctg aaaccaagat tggctagaga    5220
tatatcttaa tgcaatccat tttctgatgg attgttacga gttggctata taatgatgt    5280
atggtatttt gatttgtgta aaagttttaa aaatcaagct ttaagtacat ggacatttt     5340
aaataaaata tttaaagaca atttagaaaa ttgccttaat atcattgttg gctaaataga    5400
atagggaaca tgcatattaa ggaaaaggtc atggagaaat aatattggta tcaaacaaat    5460
acattgattt gtcatgatac acattgaatt tgatccaata gtttaaggaa taggtaggaa    5520
aatttggttc ctatttttcg atttcctgta aatcagtgac ataaataatt cttagcttat    5580
tttatatttc cttgtcttaa atactgagct cagtaagttg tgttagggga ttatttctca    5640
gttgagactt tcttatatga cattttacta tgttttgact acctgactat taaaaataaa    5700
tagtagatac aatttttcata aagtgaagaa ttatataatc actgctttat aactgacttt    5760
attatattta tttcaaagtt catttaaagg ctactattca tcctctgtga tggaatggtc    5820
aggaatttgt tttctcatag tttaattcca acaacaatat tagtcgtatc caaaataacc    5880
tttaatgcta aactttactg atgtatatcc aaagcttctc attttcagac agattaatc    5940
agaagcagtc ataaacagaa gaataggtgg tatgttccta atgatattat ttctactaat    6000
ggaataaact gtaatattag aaattatgct gctaattata tcagctctga ggtaatttct    6060
gaaatgttca gactcagtcg gaacaaattg gaaaatttaa atttttattc ttagctataa    6120
agcaagaaag taaacacatt aaatttcctca acattttaa gccaattaaa aatataaaag    6180
atacacacca atatcttctt caggctctga caggcctcct ggaaacttcc acatatttt    6240
caactgcagt ataagtcag aaaataaagt taacataact ttcactaaca cacacatatg    6300
tagatttcac aaaatccacc tataattggt caaagtggtt gagaatatat ttttagtaa    6360
ttgcatgcaa aattttttcta gcttccatcc ttttctccctc gtttcttctt tttttggggg    6420
agctggtaac tgatgaaatc ttttcccacc ttttctcttc aggaaatata agtggttttg    6480
tttggttaac gtgatacatt ctgtatgaat gaaacattgg agggaaacat ctactgaatt    6540
tctgtaattt aaaatatttt gctgctagtt aactatgaac agatagaaga atcttacaga    6600
tgctgctata aataagtaga aaatataaat ttcatcacta aaatatgcta ttttaaaatc    6660
tatttcctat attgtatttc taatcagatg tattactctt attatttcta ttgtatgtgt    6720
taatgatttt atgtaaaaat gtaattgctt ttcatgagta gtatgaataa aattgattag    6780
tttgtgtttt cttgtctccc a                                              6801

SEQ ID NO: 101      moltype = DNA   length = 6652
FEATURE             Location/Qualifiers
source              1..6652
                    mol_type = genomic DNA
                    organism = Homo sapiens
SEQUENCE: 101
gccagattag cggacgcggt gcccgcggtt gcaacgggat cccgggcgct gcagcttggg     60
aggcggctct cccccaggcgg cgtccgcgga gacaccatcc cgtgaacccc aggtcccggg   120
ccgccggctc gccgcgcacc aggggccggg ggacagaaga gcggccgagc ggctcgagcc   180
tgggggaccg cggcgcggc cgcgcgctgc cgggcgggag gctgggggc cggggccggg     240
gccgtgcccc ggagcgggtc ggaggccggg gccggggccg gggacggcg ctccccgcg     300
cggctccagc ggctcgggga tcccggccgg gccccgcagg gaccatggca gccgggagca   360
```

```
tcaccacgct gcccgccttg cccgaggatg gcggcagcgg cgccttcccg cccggccact   420
tcaaggaccc caagcggctg tactgcaaaa acggggcctt cttcctgcgc atccaccccg   480
acggccgagt tgacggggtc cgggagaaga gcgaccctca catcaagcta caacttcaag   540
cagaagagag aggagttgtg tctatcaaag gagtgtgtgc taaccgttac ctggctatga   600
aggaagatgg aagattactg gcttctaaat gtgttacgga tgagtgtttc ttttttgaac   660
gattggaatc taataactac aatacttacc ggtcaaggaa ataccaccagt tggtatgtgg   720
cactgaaacg aactgggcag tataaacttg gatccaaaac aggacctggg cagaaagcta   780
tacttttct tccaatgtct gctaagagct gattttaatg gccacatcta atctcatttc   840
acatgaaaga agaagtatat tttagaaatt tgttaatgag agtaaaagaa aataaatgtg   900
tatagctcag tttggataat tggtcaaaca atttttttatc cagtagtaaa atatgtaacc   960
attgtcccag taaagaaaaa taacaaaagt tgtaaaatgt atattctccc ttttatattg  1020
catctgctgt tacccagtga agcttaccta gagcaatgat cttttttcacg catttgcttt  1080
attcgaaaag aggcttttaa aatgtgcatg tttagaaaca aaatttcttc atggaaatca  1140
tatacattag aaaatcacag tcagatgttt aatcaatcca aaatgtccac tatttcttat  1200
gtcattcgtt agtctacatg tttctaaaca tataaatgtg aatttaatca attcctttca  1260
tagttttata attctctggc agttccttat gatagagttt ataaaacagt cctgtgtaaa  1320
ctgctggaag ttcttccaca gtcaggtcaa ttttgtcaaa cccttctctg tacccataca  1380
gcagcagcct agcaactctg ctggtgatgg gagttgtatt ttcagtcttc gccaggtcat  1440
tgagatccat ccactcacat cttaagcatt cttcctggca aaaatttatg gtgaatgaat  1500
atggctttag gcggcagatg atatacatat ctgacttccc aaaagctcca ggatttgtgt  1560
gctgttgccg aatactcagg acggacctga attctgattt tataccagtc tcttcaaaaa  1620
cttctcgaac cgctgtgtct cctactgtaaa aaaagagatg tacaaatcaa taataattac  1680
acttttagaa actgtatcat caaagatttt cagttaaagt agcattatgt aaaggctcaa  1740
aacattaccc taacaaagta aagttttcaa tacaaattct ttgccttgtg gatatcaaga  1800
aatcccaaaa tattttctta ccactgtaaa ttcaagaagc ttttgaaatg ctgaatattt  1860
ctttggctgc tacttggagg cttatctacc tgtacatttt tgggggtcagc tcttttttaac  1920
ttcttgctgc tcttttttccc aaaaggtaaa aatatagatt gaaaagttaa aacattttgc  1980
atggctgcag ttcctttgtt tcttgagata agattccaaa gaacttagat tcatttcttc  2040
aacaccgaaa tgctggaggt gtttgatcag ttttcaagaa acttggaata taaataattt  2100
tataattcaa caaaggtttt cacatttttat aaggttgatt tttcaattaa atgcaaattt  2160
gtgtggcagg attttttattg ccattaacat attttttgtgg ctgcttttttc tacacatcca  2220
gatggtccct ctaactgggc tttctctaat tttgtgatgt tctgtcattg tctcccaaag  2280
tatttaggag aagcccttta aaaagctgcc ttcctctacc actttgctgg aaagcttcac  2340
aattgtcaca gacaaagatt tttgttccaa tactcgtttt gcctctattt ttcttgtttg  2400
tcaaatagta aatgatattt gcccttgcag taattctact ggtgaaaaac atgcaaagaa  2460
gaggaagtca cagaaacatg tctcaattcc catgtgctgt gactgtagac tgtcttacca  2520
tagactgtct tacccatccc ctggatatgc tcttgttttt tccctctaat agctatggaa  2580
agatgcatag aaagagtata atgttttaaa acataaggca tttgtctgcc atttttcaat  2640
tacatgctga cttccccttac aattgagatt tgcccatagg ttaacatgg ttagaaacaa  2700
ctgaaagcat aaaagaaaaa tctaggccgg gtgcagtggc tcatgcctat attccctgca  2760
ctttgggagg ccaaagcagg aggatcgctt gagcccagga gttcaagacc aacctggtga  2820
aacccccgtct ctacaaaaaa acacaaaaaa tagccaggca tggtggcgtg tacatgtggt  2880
ctcagatact tgggaggctg aggtgggagg gttgatcact tgaggctgag aggtcaaggt  2940
tgcagtgagc cataatcgtg ccactgcagt ccagcctagg caacagagtg agactttgtc  3000
tcaaaaaaag agaatttttc cttaataaga aaagtaattt ttactctgat gtgcaataca  3060
tttgttatta aatttattat ttaagatggt agcactagtc ttaaattgta taaaatatcc  3120
cctaacatgt ttaaatgtcc atttttattc attatgcttt gaaaaaataat tatggggaaa  3180
tacatgtttg ttattaaatt tattattaaa gatagtagca ctagtcttaa atttgatata  3240
acatctccta acttgtttaa atgtccattt ttattcttta tgtttgaaaa taaattatgg  3300
ggatcctatt tagctcttag taccactaat caaaagttcg gcatgtagct catgatctat  3360
gctgttttcta tgtcgtggaa gcactggatg ggggtagtga gcaaatctgc cctgctcagt  3420
agtcaccata gcagctgact gaaaatcagc actgcctgag tagttttgat cagtttaact  3480
tgaatcacta actgactgaa aattgaatgg gcaaataagt gcttttgtct ccagagtatg  3540
cgggagaccc ttccacctca agatggatat ttcttcccca aggatttcaa gatgaattga  3600
aattttttaat caagatagtg tgcttttattc tgttgtattt tttatttattt taatatactg  3660
taagccaaac tgaaataaca tttgctgttt tataggtttg aagaacatag gaaaaactaa  3720
gaggttttgt ttttattttt gctgatgaag agatatgttt aaatatgttg tattgttttg  3780
tttagttaca ggacaataat gaaatggagt ttatatttgt tatttctatt tgttatatt  3840
taataataga attagattga aataaaaatat aatgggaaat aatctgcaga atgtgggttt  3900
tcctggtgtt tccctctgac tctagtgcac tgatgatctc tgataaggct cagctgcttt  3960
atagttctct ggctaatgca gcagatactc ttcctgccag tggtaatacg atttttttaag  4020
aaggcagttt gtcaatttta atcttgtgga tacctttata ctcttagggt attatttttat  4080
acaaaagcct tgaggattgc attctatttt ctatatgacc ctcttgatat ttaaaaaaca  4140
ctatggataa caattcttca ttttacctagt attatgaaag aatgaaggag ttcaaacaaa  4200
tgtgtttccc agttaactag ggtttactgt ttgagccaat ataaatgttt aactgtttgt  4260
gatggcagta ttcctaaagt acattgcatg ttttttcctaaa tacagagttt aaataatttc  4320
agtaattctt agatgattca gcttcatcat taagaatatc ttttgtttta tgttgagtta  4380
gaaatgcctt catatagaca tagtctttca gacctctact gtcagttttc attttctagct  4440
gctttcaggg tttttatgaat tttcaggcaa agctttaatt tacactaagc ttaggaagta  4500
tggctaatgc caacggcagt tttttttcttc ttaattccac atgactgagg catatatgat  4560
ctctgggtag gtgagttgtt gtgacaacca caagcacttt tttttttttt aaagaaaaaa  4620
aggtagtgaa ttttttaatca tctggacttt aagaaggatt ctggagtata cttaggcctg  4680
aaattatata tatttggctt ggaaatgtgt tttttcttcaa ttacatctac aagtaagtac  4740
aatttaattta agctgaaatt cagaggaccc ataagagttc acatgaaaaa aatcaattta  4800
tttgaaaagg
caagatgcag gagagaggaa gccttgcaaa cctgcagact gctttttgcc caatatagat  4860
tgggtaaggc tgcaaaacat aagcttaatt agctcacatg ctctgctctc acgtggcacc  4920
agtggatagt gtgagagaat taggctgtag aacaaatggc cttctctttc agcattcaca  4980
ccactacaaa atcatctttt atatcaacag aagaataagc ataaactaag caaaaggtca  5040
ataagtacct gaaaccaaga ttggctagag atatatctta atgcaatcca ttttctgatg  5100
```

```
gattgttacg agttggctat ataatgtatg tatggtattt tgatttgtgt aaaagttttta    5160
aaaatcaagc tttaagtaca tggacatttt taaataaaat atttaaagac aatttagaaa    5220
attgccttaa tatcattgtt ggctaaatag aatagggggac atgcatatta aggaaaaggt    5280
catggagaaa taatattggt atcaaacaaa tacattgatt tgtcatgata cacattgaat    5340
ttgatccaat agtttaagga ataggtagga aaatttgatt tctattttc gattcctgt     5400
aaatcagtga cataaataat tcttagctta ttttatattt ccttgtctta aatactgagc    5460
tcagtaagtt gtgttagggg attatttctc agttgagact ttcttatatg acattttact    5520
atgttttgac tacctgacta ttaaaaataa atagtagata caattttcat aaagtgaaga    5580
attatataat cactgcttta taactgactt tattatattt atttcaaagt tcatttaaag    5640
gctactattc atcctctgtg atggaatggt caggaatttg ttttctcata gtttaattcc    5700
aacaacaata ttagtcgtat ccaaaataac ctttaatgct aaactttact gatgtatatc    5760
caaagcttct cattttcaga cagattaatc cagaagcagt cataaacaga gaataggtg    5820
gtatgttcct aatgatatta tttctactaa tggaataaac tgtaataaaa gaaattatgc    5880
tgctaattat atcagctctg aggtaatttc tgaaatgttc agactcagtc ggaacaaatt    5940
ggaaaattta aatttttatt cttagctata aagcaagaaa gtaaacacat taatttcctc    6000
aacatttta agccaattaa aaatataaaaa gatacacacc aatatcttct tcaggctctg    6060
acaggcctcc tggaaacttc cacatatttt tcaactgcag tataaagtca gaaaataaag    6120
ttaacataac tttcactaac acacacatat gtagatttca caaaatccac ctataattgg    6180
tcaaagtggt tgagaatata ttttttagta attgcatgca aaattttct agcttccatc     6240
cttctccct cgtttcttct ttttttgggg gagctggtaa ctgatgaaat cttttcccac    6300
cttttctctt caggaaatat aagtggtttt gtttggttaa cgtgatacat tctgtatgaa    6360
tgaaacattg gagggaaaca tctactgaat ttctgtaatt taaaatattt tgctgctagt    6420
taactatgaa cagatagaag aatcttacag atgctgctat aaaataagtag aaaatataaa    6480
tttcatcact aaaatatgct atttttaaaat ctatttccta tattgtattt ctaatcagat    6540
gtattactct tattatttct attgtatgtg ttaatgattt tatgtaaaaaa tgtaattgct    6600
tttcatgagt agtatgaata aaattgatta gtttgtgttt tcttgtctcc ca            6652

SEQ ID NO: 102          moltype = AA   length = 154
FEATURE                 Location/Qualifiers
source                  1..154
                        mol_type = protein
                        organism = Mus musculus
SEQUENCE: 102
MAASGITSLP ALPEDGGAAF PPGHFKDPKR LYCKNGGFFL RIHPDGRVDG VREKSDPHVK     60
LQLQAEERGV VSIKGVCANR YLAMKEDGRL LASKCVTEEC FFFERLESNN YNTYRSRKYS    120
SWYVALKRTG QYKLGSKTGP GQKAILFLPM SAKS                                154

SEQ ID NO: 103          moltype = DNA   length = 695
FEATURE                 Location/Qualifiers
source                  1..695
                        mol_type = genomic DNA
                        organism = Mus musculus
SEQUENCE: 103
ggccccgggc cgttgtacac tcaagggggct ctctcggctt caggaagagt ccggctgcac     60
tgggctggga gccggcgggg acacggactg ggaggctggc agcccgcggg cgagccgcgc    120
tggggggccg aggccgggt cggggccggg gagcccaag agctgccaca gcggggtccc     180
ggggccggcg aagggccatg gctgccagcg gcatcacctc gcttcccgca ctgccggagg    240
acggcggcgc cgccttccca ccaggccact tcaaggaccc caagcggctc tactgcaaga    300
acggcggctt cttcctgcgc atccatcccg acggccgcgt ggatggcgtc cgcgagaaga    360
gcgacccaca cgtcaaacta caactccaag cagaagagag aggagttgtg tctatcaagg    420
gagtgtgtgc caaccggtac cttgctatga aggaagatgg acggctgctg gcttctaagt    480
gtgttacaga agagtgtttc ttctttgaac gactggaatc taataactac aatacttacc    540
ggtcacggaa atactccagt tggtatgtgg cactgaaacg aactgggcag tataaactcg    600
gatccaaaac gggacctgga cagaaggcca tactgtttct tccaatgtct gctaagagct    660
gactcacttt tgacactgtc actgagacac tgtca                              695

SEQ ID NO: 104          moltype = AA   length = 443
FEATURE                 Location/Qualifiers
source                  1..443
                        mol_type = protein
                        organism = Homo sapiens
SEQUENCE: 104
MYQSLAMAAN HGPPPGAYEA GGPGAFMHGA GAASSPVYVP TPRVPSSVLG LSYLQGGGAG     60
SASGGASGGS SGGAASGAGP GTQQGSPGWS QAGADGAAYT PPPVSPRFSF PGTTGSLAAA    120
AAAAAAREAA AYSSGGGAAG AGLAGREQYG RAGFAGSYSS PYPAYMADVG ASWAAAAAAS    180
AGPFDSPVLH SLPGRANPAA RHPNLVDMFD DFSEGRECVN CGAMSTPLWR RDGTGHYLCN    240
ACGLYHKMNG INRPLIKPQR RLSASRRVGL SCANCQTTTT TLWRRNAEGE PVCNACGLYM    300
KLHGVPRPLA MRKEGIQTRK RKPKNLNKSK TPAAPSGSES LPPASGASSN SSNATTSSSE    360
EMRPIKTEPG LSSHYGHSSS VSQTFSVSAM SGHGPSIHPV LSALKLSPQG YASPVSQSPQ    420
TSSKQDSWNS LVLADSHGDI ITA                                            443

SEQ ID NO: 105          moltype = AA   length = 236
FEATURE                 Location/Qualifiers
source                  1..236
                        mol_type = protein
                        organism = Homo sapiens
SEQUENCE: 105
MFDDFSEGRE CVNCGAMSTP LWRRDGTGHY LCNACGLYHK MNGINRPLIK PQRRLSASRR     60
VGLSCANCQT TTTTLWRRNA EGEPVCNACG LYMKLHGVPR PLAMRKEGIQ TRKRKPKNLN    120
```

```
KSKTPAAPSG SESLPPASGA SSNSSNATTS SSEEMRPIKT EPGLSSHYGH SSSVSQTFSV     180
SAMSGHGPSI HPVLSALKLS PQGYASPVSQ SPQTSSKQDS WNSLVLADSH GDIITA        236

SEQ ID NO: 106            moltype = AA  length = 442
FEATURE                   Location/Qualifiers
source                    1..442
                          mol_type = protein
                          organism = Homo sapiens
SEQUENCE: 106
MYQSLAMAAN HGPPPGAYEA GGPGAFMHGA GAASSPVYVP TPRVPSSVLG LSYLQGGGAG     60
SASGGASGGS SGGAASGAGP GTQQGSPGWS QAGADGAAYT PPPVSPRFSF PGTTGSLAAA    120
AAAAAAREAA AYSSGGGAAG AGLAGREQYG RAGFAGSYSS PYPAYMADVG ASWAAAAAAS    180
AGPFDSPVLH SLPGRANPAA RHPNLDMFDD FSEGRECVNC GAMSTPLWRR DGTGHYLCNA    240
CGLYHKMNGI NRPLIKPQRR LSASRRVGLS CANCQTTTTT LWRRNAEGEP VCNACGLYMK    300
LHGVPRPLAM RKEGIQTRKR KPKNLNKSKT PAAPSGSESL PPASGASSNS SNATTSSSEE    360
MRPIKTEPGL SSHYGHSSSV SQTFSVSAMS GHGPSIHPVL SALKLSPQGY ASPVSQSPQT    420
SSKQDSWNSL VLADSHGDII TA                                            442

SEQ ID NO: 107            moltype = AA  length = 236
FEATURE                   Location/Qualifiers
source                    1..236
                          mol_type = protein
                          organism = Homo sapiens
SEQUENCE: 107
MFDDFSEGRE CVNCGAMSTP LWRRDGTGHY LCNACGLYHK MNGINRPLIK PQRRLSASRR     60
VGLSCANCQT TTTTLWRRNA EGEPVCNACG LYMKLHGVPR PLAMRKEGIQ TRKRKPKNLN    120
KSKTPAAPSG SESLPPASGA SSNSSNATTS SSEEMRPIKT EPGLSSHYGH SSSVSQTFSV    180
SAMSGHGPSI HPVLSALKLS PQGYASPVSQ SPQTSSKQDS WNSLVLADSH GDIITA        236

SEQ ID NO: 108            moltype = AA  length = 194
FEATURE                   Location/Qualifiers
source                    1..194
                          mol_type = protein
                          organism = Homo sapiens
SEQUENCE: 108
MFDDFSEGRE CVNCGAMSTP LWRRDGTGHY LCNACGLYHK MNGINRPLIK PQRRLVPRPL     60
AMRKEGIQTR KRKPKNLNKS KTPAAPSGSE SLPPASGASS NSSNATTSSS EEMRPIKTEP    120
GLSSHYGHSS SVSQTFSVSA MSGHGPSIHP VLSALKLSPQ GYASPVSQSP QTSSKQDSWN    180
SLVLADSHGD IITA                                                     194

SEQ ID NO: 109            moltype = DNA  length = 3419
FEATURE                   Location/Qualifiers
source                    1..3419
                          mol_type = genomic DNA
                          organism = Homo sapiens
SEQUENCE: 109
ggggacttgg aggcggccgg cgcaggggcc gcgagaggct tcgtcgccgc tgcagctccg     60
gggggctccca ggggagcgtg cgcggaacct ccaggcccag caggacccccg gctgcgcgcga   120
ggaggaagga gccagcctag cagcttctgc gcctgtggcc gcgggtgtcc tggaggcctc    180
tcggtgtgac gagtggggga cccgaaggct cgtgcgccac ctccaggcct ggacgctgcc    240
ctccgtcttc tgccccaat aggtgcgccg gaccttcagg ccctggggtg aattcagctg    300
ctcctacatc agcttccgga accaccaaaa attcaaattg ggattttccg gagtaaacaa    360
gagcctagag ccctttgctc aatgctggat ttaaatacgta tatatttttta agcgagttgg  420
ttttttcccc tttgattttt gatcttcgcg acagttcctc ccacgcatat tatcgttgtt    480
gccgtcgttt tctctcccg cgtggctcct tgacctgcgg gggagagaga ggacaccgaa    540
gccgggagct cgcagggacc atgtatcaga gcttggccat ggccgccaac cacgggccgc    600
cccccggtgc ctacgaggcg ggcggccccg gcgccttcat gcacggcgcg ggcgccgcgt    660
cctcgccagt ctacgtgccc acaccgcggg tgccctcctc cgtgctgggc ctgtcctacc    720
tccagggcgg aggcgcgggc tctgcgtccg gaggcgcctc gggcggcagc tccggtgggg    780
ccgcgtctgg tgcggggccc gggacccagc agggcagccc gggatggagc caggcgggag    840
ccgacggagc cgcttacacc ccgccgccgg tgtccgccgc cttctccttc ccggggacca    900
ccgggtccct ggcggccgcc gccgcgctg ccgcgggccg ggaagctgcg gcctacagca    960
gtggcggcgg agcggcgggt gcgggcctgg cgggccgcga gcagtacggg cgcgccggct   1020
tcgcgggctc ctactccagc ccctaccccg cttacatggc ggacgtgggc gcctccggg   1080
ccgcagccgc cgccgcctcc gccggccccct tcgacagccc ggtcctgcac agcctgcccg   1140
gccgggccaa cccggccgcc cgacacccca atctcgtaga tatgtttgac gacttctcag   1200
aaggcagaga gtgtgtcaac tgtgggggcta tgtccaccccc gctctggagg cgagatggga   1260
cgggtcacta tctgtgcaac gcctgcgggc tctaccacaa gatgaacggc atcaaccggc   1320
cgctcatcaa gcctcagcgc cggctgtccg cctcccgccg agtgggcctc tcctgtgcca   1380
actgccagac caccaccacc acgctgtggc gccgcaatgc ggagggcgag cctgtgtgca   1440
atgcctgcgg cctctacatg aagctccacg gggtccccag gcctcttgca atgcggaaag   1500
agggggatcca aaccagaaaa cggaagccca agaacctgaa taaatctaag acaccagcag   1560
ctccttcagg cagtgagagc cttcctcccg ccagcggtgc ttcagcaac tccagcaacg   1620
ccaccaccag ctccagcgag gagatgcgtc ccatcaagac ggagcctggc ctgtcatctc   1680
actacgggca cagcagctcc gtgtcccaga cgttctcagt cagtgcgatg tctggccatg   1740
ggccctccat ccaccctgtc ctctcggccc tgaagctctc cccacaaggc tatgcgtctc   1800
ccgtcagcca gtcccacag accagctcca gcaggactc ttggaacagc ctggtcttgg   1860
ccgacagtca cggggacata atcactgcgt aatcttccct cttcccctct caaattcctg   1920
cacggacctg ggacttggag gatagcaaag aaggaggccc tgggctccca ggggccggcc   1980
```

-continued

```
tcctctgcct ggtaatgact ccagaacaac aactgggaag aaacttgaag tcgacaatct    2040
ggttagggga agcgggtgtt ggattttctc agatgccttt acacgctgat gggactggag    2100
ggagcccacc cttcagcacg agcacactgc atctctcctg tgagttggag acttctttcc    2160
caagatgtcc ttgtccctg cgttccccac tgtggcctag accgtgggtt ttgcattgtg     2220
tttctagcac cgaggatctg agaacaagcg gagggccggg ccctgggacc cctgctccag    2280
cccgaatgac ggcatctgtt tgccatgtac ctggatgcga cgggcccctg gggacaggcc    2340
cttgccccat ccatccgctt gaggcatggc accgccctgc atccctaata ccaaatctga    2400
ctccaaaatt gtggggtgtg acatacaagt gactgaacac ttcctgggga gctacagggg    2460
cacttaaccc accacagcac agcctcatca aaatgcagct ggcaacttct ccccaggtg     2520
ccttccccct gctgccggcc tttgctcctt cacttccaac atctctcaaa ataaaaatcc    2580
ctcttcccgc tctgagcgat tcagctctgc ccgcagcttg tacatgtctc tccctggca    2640
aaacaagagc tgggtagttt agccaaacgg caccccctcg agttcactgc agacccttcg    2700
ttcaccgtgt cacacataga ggggttctga gtaagaacaa aacgttctgc tgctcaagcc    2760
agtctggcaa gcactcagcc cagcctcgag gtccttctgg ggagagtgta agtggacaga    2820
gtcctggtca gggggcagga gtgtcccaag ggctggccca cctgctgtct gtctgctcct    2880
cctagcccct ggtcagatgg cagccagagt ccctcaggac ctgcagcctc gccccggcag    2940
aagtcttttg tccaggaggc aaaaagccag agattctgca acacgaattc gaagcaaaca    3000
aacacaacac aacagaattc ctggaaagaa gacgactgct aagacacggc agggggcct    3060
ggagggagcc tccgactctg agctgctccg ggatctgccg cgttctcctc tgcacattgc    3120
tgtttctgcc cctgatgctg gagctcaagg agactccttc ctctttctca gcagagctgt    3180
agctgactgt ggcattacta cgcctcccca cacgcccaga cccctcactc caaaatccta    3240
ctggctgtag cagagaatac cttttgaacca agattctgtt ttaatcatca tttacattgt    3300
tttcttccaa aggccccctc gtatacccct cctaacccac aaacctgtta acattgtctt    3360
aaggtgaaat ggctggaaaa tcagtattta actaataaat ttatctgtat tcctctttc    3419

SEQ ID NO: 110         moltype = DNA  length = 2640
FEATURE                Location/Qualifiers
source                 1..2640
                       mol_type = genomic DNA
                       organism = Homo sapiens
SEQUENCE: 110
agagggagct gggagacacg gctcacaacg tctccctccc acccggctga gaacagcctg    60
gaatccctgt gcagagtttg cctcacacca ggccttgagc agccgcaggg acgccgctcc    120
ccaccgcggg gacgcatcct gctctgcacc ctggttctcg gcgctgcgcc cgcggaggct    180
cgtgcgcggg aggctgcccg tgcgggtgag gactgagtgc cgcgcaggga aggagtatcg    240
cagaccggcg cccaggccca gcgggggaat ccaaggggcg tgttgcagga ctcggcattc    300
gttctgcgcg ggtcaccttg aatgtctgtc cggatccctc gcggcagggc cgcagaggcg    360
cgtccatatc ttggaggaat tcgttccata gaatgagtag atatgtttga cgacttctca    420
gaaggcagag agtgtgtcaa ctgtggggct atgtccaccc cgctctggag gcagatgggt    480
acgggtcact atctgtgcaa cgcctgcggc ctctaccaca agatgaacgg catcaaccgg    540
ccgctcatca agcctcagcg ccggctgtcc gcctcccgcc gagtgggcct ctcctgtgcc    600
aactgccaga ccaccaccac cacgctgtgg cgccgcaatg cggagggcga gcctgtgtgc    660
aatgcctgcg gcctctacat gaagctccac ggggtccgcg ggcctcttgc aatgcggaaa    720
gaggggatcc aaaccagaaa acggaagccc aagaacctga taaatctaa gacaccagca     780
gctccttcag gcagtgagag ccttcctccc gccagcggtg cttccagcaa ctccagcaac    840
gccaccacca gcagcagcga ggagatgcgt cccatcaaga cggagcctgg cctgtcatct    900
cactacgggc acagcactc cgtgtcccag acgttctcag tcagtcgcgat gtctggccat    960
gggccctcca tccaccctgt cctctcggcc ctgaagctct cccacacaag ctatgcgtct    1020
cccgtcagcc agtctccaca gaccagctcc aagcaggact cttggaacag cctggtcttg    1080
gccgacagtc acgggacat aatcactgcg taatcttccc tcttccctcc tcaaattcct    1140
gcacggacct gggacttgga ggatagcaaa gaaggaggcc ctgggctccc aggggccggc    1200
ctcctctgcc tggtaatgac tccagaacaa caactgggaa gaaacttgaa gtcgacaatc    1260
tggttagggg aagcgggtgt tggattttct cagatgcctt tacacgctga tgggactgga    1320
gggagcccac cttcagcac gagcacactg catctctcct gtgagttgga gacttctttc     1380
ccaagatgtc cttgtcccct gcgttcccca ctgtggccta gaccgtgggt tttgcattgt    1440
gtttctagca ccgaggatct gagaacaagc ggagggccgg ccctgggacc cctgctcca     1500
gcccgaatga cggcatctgt ttgccatgta cctggatgcg acgggcccct ggggacaggc    1560
ccttgcccca tccatccgct tgaggcatgg caccgccctg catccctaat accaaatctg    1620
actccaaaat tgtggggtgt gacatacaag tgactgaaca cttcctgggg agctacaggg    1680
gcacttaacc caccacagca cagcctcatc aaaatgcagc tggcaacttc tccccaggt     1740
gccttccccc tgctgccggc ctttgctcct tcacttccaa catctctcaa ataaaaatc     1800
cctcttcccg ctctgagcga ttcagctctg ccgcagctt gtacatgtct ctccctggc      1860
aaaacaagag ctgggtagtt tagccaaacg gcaccccctc gagttcactg cagacccttc    1920
gttcaccgtg tcacacatag aggggttctg agtaagaaca aacgttctgc tgctcaagc     1980
cagtctggca agcactcagc ccagcctcga ggtccttctg ggagagtgt aagtggacag     2040
agtcctggtc agggggcagg agtgtcccaa gggctggccc acctgctgtc tgtctgctcc    2100
tcctagcccc tggtcagatg gcagccagag tccctcagga cctgcagcct cgccccggca    2160
gaagtcttt gtcaggagg caaaaagcca gagattctgc aacacgaatt cgaagcaaac      2220
aaacacaaca caacagaatt cctggaaaga gacgactgc taagacacgg cagggggcc      2280
tggagggagc ctccgactct gagctgctcc gggatctgcc gcgttctcct ctgcacattg    2340
ctgtttctgc ccctgatgct ggagctcaag gagactcctt ctctttctc agcagagctg     2400
tagctgactg tggcattact acgcctcccc acacgcccag acccctcact ccaaaatcct    2460
actggctgta gcagagaata ccttttgaacc aagattctgt ttaatcatc atttacattg    2520
ttttcttcca aaggccccct cgtataccct cctaaccca aaacctgtt aacattgtct      2580
taaggtgaaa tggctggaaa atcagtattt aactaataaa tttatctgta ttcctctttc    2640

SEQ ID NO: 111         moltype = DNA  length = 3416
FEATURE                Location/Qualifiers
source                 1..3416
```

```
                    mol_type = genomic DNA
                    organism = Homo sapiens
SEQUENCE: 111
ggggacttgg aggcggccgg cgcaggggcc gcgagaggct tcgtcgccgc tgcagctccg     60
ggggctccca ggggagcgtg cgcggaacct ccaggcccag caggacccg gctgcggcga    120
ggaggaagga gccagcctag cagcttctgc gcctgtggcc gcgggtgtcc tggaggcctc    180
tcggtgtgac gagtggggga cccgaaggct cgtgcgccac ctccaggcct ggacgctgcc    240
ctccgtcttc tgccccaat aggtgcgccg gaccttcagg ccctggggtg aattcagctg    300
ctcctacatc agcttccgga accaccaaaa attcaaattg ggattttccg gagtaaacaa    360
gagcctagag cccttgctc aatgctggat ttaatacgta tatatttta agcgagttgg    420
tttttccc tttgattttt gatcttcgcg acagttcctc ccacgcatat tatcgttgtt    480
gccgtcgttt tctctccccg cgtggctcct tgacctgcga gggagagaga ggacaccgaa    540
gccgggagct cgcagggacc atgtatcaga gcttggccat ggccgccaac cacgggccgc    600
ccccggtgc ctacgaggcg ggcggccccg gcgccttcat ggccgcgcg ggcgccgcgt    660
cctcgccagt ctacgtgccc acaccgcggg tgccctcctc cgtgctgggc ctgtcctacc    720
tccaggcgg aggcgcgggc tctgcgtccg gaggcgcctc gggcggcagc tccggtgggg    780
ccgcgtctgt tgcggggccc gggacccagc agggcagccc gggatggagc caggcgggag    840
ccgacggagc cgcttacacc ccgcgcccgg tgtcgccgcg cttctccttc ccggggacca    900
ccgggtccct ggcggccgcc gccgccgctg ccgcggcccg ggaagctgcg gcctacagca    960
gtggcggcgg agcggcgggt gcgggcctgg cgggccgcga gcagtacggg cgcgccggct   1020
tcgcgggctc ctactccagc ccctaccgg cttacatggc cgacgtgggc gcgtcctggg   1080
ccgcagccgc cgcgcctcc gccggccct tcgacacgcc ggtcctgcac agcctgcccg   1140
gccgggccaa cccggccgcc cgacacccca atctcgatat gtttgacgac ttctcagaag   1200
gcagagagtg tgtcaactgt ggggctatgt ccacccgct ctggaggcga gatgggacgg   1260
gtcactatct gtgcaacgcc tgcggcctct accacaagat gaacggcatc aaccggccgc   1320
tcatcaagcc tcagcgccgg ctgtccgcct cccgccagt gggcctctc tgtgccaact   1380
gccagaccac caccaccacg ctgtggcgcc gcaatgcgga gggcgagcct gtgtgcaatg   1440
cctgcggcct ctacatgaag ctccacgggg tccccaggcc tcttgcaatg cggaaagagg   1500
ggatccaaac cagaaaacgg aagcccaaga acctgaataa atctaagaca ccagcagctc   1560
cttcaggcag tgagagcctt cctcccgcca gcggtgcttc cagcaactcc agcaacgcca   1620
ccaccagcag cagcgaggag atgcgtccca tcaagacgag gcctggcctg tcatctcact   1680
acgggcacag cagctccgtg tcccagacgt tctcagtcag tgcgatgtct ggccatgggc   1740
cctccatcca ccctgtcctc tcggccctga agctctcccc acaaggctat gcgtctcccg   1800
tcagccagtc tccacagacc agctccaagc aggactcttg gaacagcctg gtcttggcgg   1860
acagtcacgg gacataatc actgcgtaat cttccctctt ccctcctcaa attcctgcac   1920
ggacctggga cttggaggat agcaaagaag gaggccctgg gctcccaggg gccggcctcc   1980
tctgcctggt aatgactcca gaacaacaac tgggaagaaa cttgaagtcg acaatctggt   2040
taggggaagc gggtgttgga ttttctcaga tgcctttaca cgctgatggg actggaggga   2100
gcccacccctt cagcacgagc acactgcatc tctcctgtga gttggagact tcttcccaaa   2160
gatgtccttg tcccctgcgt tccccactgt ggcctagacc gtgggttttg cattgtgttt   2220
ctagcaccga ggatctgaga acaagcggag ggccgggccc tgggacccct gctccagccc   2280
gaatgacggc atctgtttgc catgtacctg gatgcgacgg gccctgggg acaggccctt   2340
gcccatcca tccgctgag gcatggcacc gcctgcatc cctaataca aatctgactc   2400
caaaattgtg gggtgtgaca tacaagtgac tgaacacttc ctggggagct acaggggcac   2460
ttaacccacc acagcacagc ctcatcaaaa tgcagctggc aacttctccc ccaggtgcct   2520
tcccctgct gccggccttt gctccttcac ttccaacatc tctcaaaata aaaatccctc   2580
ttcccgctct gagcgattca gctctgcccg cagcttgtac atgtctctcc cctggcaaaa   2640
caagagctgg gtagtttagc caaacgcac ccctcgagt tcactgcaga cccttcgttc   2700
accgtgtcac acatagaggg gttctgagta agaacaaaac gttctgctgc tcaagccagt   2760
ctggcaagca ctcagcccag cctcgaggtc cttctgggga gagtgtaagt ggacagagtc   2820
ctggtcaggg ggcaggagtg tcccaagggc tggcccacct gctgtctgtc tgctcctcct   2880
agcccttggt cagatggcag ccagagtccc tcaggacctg cagcctcgcc ccggcagaag   2940
tcttttgtcc aggaggcaaa aagccagaga ttctgcaaca cgaattcgaa gcaaacaaac   3000
acaacacaac agaattcctg gaaagaagac gactgctaag acacggcagg ggggcctgga   3060
gggagcctcc gactctgagc tgctccggga tctgccggct tctccctctgc acattgctgt   3120
ttctgccct gatgctggag ctcaaggaga ctccttcctc tttctcagca gagctgtagc   3180
tgactgtggc attactacgc ctccccacac gcccagaccc ctcactccaa aatcctactg   3240
gctgtagcag agaatacctt tgaaccaaga ttctgttta atcatcattt acattgtttt   3300
cttccaaagg ccccctcgta taccctccct aaccacaaa cctgttaaca ttgtcttaag   3360
gtgaaatggc tggaaaatca gtatttaact aataaattta tctgtattcc tctttc        3416

SEQ ID NO: 112        moltype = DNA   length = 2343
FEATURE               Location/Qualifiers
source                1..2343
                      mol_type = genomic DNA
                      organism = Homo sapiens
SEQUENCE: 112
ggggacttgg aggcggccgg cgcaggggcc gcgagaggct tcgtcgccgc tgcagctccg     60
ggggctccca ggggagcgtg cgcggaacct ccaggcccag cagatatgtt tgacgacttc    120
tcagaaggca gagagtgtgt caactgtggg gctatgtcca cccgctctg gaggcgagat    180
gggacgggtc actatctgtg caacgcctgc ggcctctacc acaagatgaa cggcatcaac    240
cggccgctca tcaagcctca gcgccggctg tccgcctccc gccagtggg cctctcctgt    300
gccaactgcc agaccaccac caccacgctg tggcgccgca atgcggaggg cgagcctgtg    360
tgcaatgcc tgcggcctcta catgaagctc cacggggtcc ccaggcctct tgcaatgcgg    420
aaagagggga tccaaccag aaaacgaag cccaagaacc tgaataaatc taagacacca    480
gcagctcctt caggcagtga gagccttcct cccgccagcg tgcttccag caactccagc    540
aacgccacca ccagcagcag cgaggagatg cgtcccatca gacggagcc tggcctgtca    600
tctcactacg gcacagcag ctccgtgtcc cagacgttct cagtcagtgc gatgtctggc    660
catgggccct ccatccaccc tgtcctctcg gccctgaagc tctccccaca aggctatgcg    720
```

```
tctcccgtca gccagtctcc acagaccagc tccaagcagg actcttggaa cagcctggtc    780
ttggccgaca gtcacgggga cataatcact gcgtaatctt ccctcttccc tcctcaaatt    840
cctgcacgga cctgggactt ggaggatagc aaagaaggag gccctgggct cccaggggcc    900
ggcctcctct gcctggtaat gactccgaaa caacaactgg gaagaaactt gaagtcgaca    960
atctggttag gggaagcggg tgttggattt tctcagatgc ctttacacgc tgatgggact   1020
ggagggagcc caccttcag cacgagcaca ctgcatctct cctgtgagtt ggagacttcc   1080
ttcccaagat gtccttgtcc cctgcgttcc ccactgtggc ctagaccgtg ggttttgcat   1140
tgtgtttcta gcaccgagga tctgagaaca agcggagggc cgggccctgg gaccccctgct   1200
ccagcccgaa tgacggcatc tgtttgccat gtacctggat gcgacgggcc cctgggaca   1260
ggcccttgcc ccatccatcc gcttgaggca tggcaccgcc ctgcatccct aataccaaat   1320
ctgactccaa aattgtgggg tgtgacatac aagtgactga acacttcctg gggagctaca   1380
ggggcactta acccaccaca gcacagcctc atcaaaatgc agctggcaac ttctccccca   1440
ggtgccttcc ccctgctgcc ggcctttgct ccttcacttc caacatctct caaaataaaa   1500
atccctcttc ccgctctgag cgattcagct ctgcccgcag cttgtacatg tctctcccct   1560
ggcaaaacaa gagctgggta gtttagccaa acggcacccc ctcgagttca ctgcagaccc   1620
ttcgttcacc gtgtcacaca tagaggggtt ctgagtaaga acaaaacgtt ctgctgctca   1680
agccagtctg gcaagcactc agcccagcct cgaggtcctt ctggggagag tgtaagtgga   1740
cagagtcctg gtcaggggc aggagtgtcc caagggctgg cccacctgct gtctgtctgc   1800
tcctcctagc ccttggtcag atggcagcca gagtccctca ggacctgcag cctcgccccg   1860
gcagaagtct tttgtccagg aggcaaaaag ccagagattc tgcaacacga attcgaagca   1920
aacaaacaca acacaacaga attcctggaa agaagcgac tgctaagaca cggcaggggg   1980
gcctggaggg agcctccgac tctgagctgc tccgggatct gccgcgttct cctctgcaca   2040
ttgctgtttc tgcccctgat gctggagctc aaggagactc cttcctcttt ctcagcagag   2100
ctgtagctga ctgtggcatt actacgcctc cccacgccc cagaccctc actccaaaat   2160
cctactggct gtagcagaga ataccttga accaagattc tgttttaatc atcatttaca   2220
ttgtttttctt ccaaaggccc cctcgtatac cctcctaac ccacaaacct gttaacattg   2280
tcttaaggtg aaatggctgg aaaatcagta tttaactaat aaatttatct gtattcctct   2340
ttc                                                                2343

SEQ ID NO: 113         moltype = DNA  length = 2376
FEATURE                Location/Qualifiers
source                 1..2376
                       mol_type = genomic DNA
                       organism = Homo sapiens
SEQUENCE: 113
ggggacttgg aggcggccgg cgcaggggcc gcgagaggct tcgtcgccgc tgcagctccg     60
ggggctccca ggggagcgtg cgcggaacct ccaggcccag caggaccccg gctgcggcga    120
ggaggaagga gccagcctag cagcttctgc gcctgtggcc gcgggtgtcc tggaggcctc    180
tcggtgtgac gagtggggga cccgaaggct cgtgcgccac ctccaggcct ggacgctgcc    240
ctccgtcttc tgcccccaat agatatgttt gacgacttct cagaaggcag agagtgtgtc    300
aactgtgggg ctatgtccac cccgctctgg aggcagatg ggacgggtca ctatctgtgc    360
aacgcctgcg gcctctacca caagatgaac ggcatcaacc ggccgctcat caagcctcag    420
cgccggctgg tccccaggcc tctttgcaatg cggaaagagg ggatccaaac cagaaaacgg    480
aagcccaaga acctgaataa atctaagaca ccagcagctc cttcaggcag tgagagcctt    540
cctcccgcca gcgtgcttc cagcaactcc agcaacgcca ccaccagcag cagcgaggag    600
atgcgtccca tcaagacgga gcctggcctg tcatctcact acgggcacag cagctccgtg    660
tcccagacgt tctcagtcag tgcgatgtct ggccatgggc ctccatcca ccctgtcctc    720
tcggccctga agctctccccc acaaggctat gcgtctcccg tcagccagtc tccacagacc    780
agctccaagc aggactcttg gaacagcctg gtcttggccg acagtcacgg ggacataatc    840
actgcgtaat cttcccctctt ccctcctcaa attcctgcac ggacctggga cttggaggat    900
agcaaagaag gaggccctgg gctcccaagg gccggcctcc tctgcctggt aatgactcca    960
gaacaacaac tgggaagaaa cttgaagtcg acaatctggt tagggaagc gggtgttgga   1020
ttttctcaga tgcctttaca cgctgatggg actggaggga gccacccctt cagcacgagc   1080
acactgcatc tctcctgtga gttggagact cttttcccaa gatgtccttg tccctgcgt   1140
tccccactgt ggcctagacc gtgggttttg catttgtgttt ctagcaccga ggatctgaga   1200
acaagcggag ggccgggccc tgggaccct gctccagccc gaatgacggc atctgtttgc   1260
catgtacctg gatgcgacgg gcccctgggg acaggccctt gccccatcca tccgcttgag   1320
gcatggcacc gccctgcatc cctaatacca aatctgactc caaaattgtg gggtgtgaca   1380
tacaagtgac tgaacacttc ctggggagct acaggggcac ttaacccacc acagcacaga   1440
ctcatcaaaa tgcagctggc aacttctccc ccaggtgcct tccccctgct gccggccttt   1500
gctccttcac ttccaacatc tctcaaaata aaaatccctc ttcccgctct gagcgattca   1560
gctctgcccg cagcttgtac atgtctctcc cctggcaaaa caagagctgg gtagtttagc   1620
caaacggcac cccctcgagt tcactgcaga cccttcgttc accgtgtcac acatagaggg   1680
gttctgagta agaacaaaac gttctgctgc tcaagccagt ctggcaagca ctcagcccag   1740
cctcgaggtc cttctgggga gagtgtaagt ggacagagtc ctggtcaggg gcaggagtg   1800
tcccaagggc tggcccacct gctgtctgtc tgctcctcct agcccttggt cagatggcag   1860
ccagagtccc tcaggacctg cagcctcgcc ccggcagaag tcttttgtcc aggaggcaaa   1920
aagccagaga ttctgcaaca cgaattcgaa gcaaacaaca acaacacaac agaattcctg   1980
gaaagaagac gactgctaag acacggcagg ggggcctgga gggagcctcc gactctgagc   2040
tgctccggga tctgccgcgt tctcctctgc acattgctgt ttctgcccct gatgctggag   2100
ctcaaggaga ctccttcctc tttctcagca gagctgtagc tgactgtggc attactacgc   2160
ctccccacac gcccagaccc ctcactccaa aatcctactg gctgtagcag agaataccttt   2220
tgaaccaaga ttctgtttta atcatcattt acattgtttt cttccaaagg cccccctcgta   2280
taccctcct aaacccacaaa cctgttaaca ttgtcttaag gtgaaatggc tggaaaatca   2340
gtatttaact aataaattta tctgtattcc ctttc                              2376

SEQ ID NO: 114         moltype = AA   length = 442
FEATURE                Location/Qualifiers
source                 1..442
```

```
                        mol_type = protein
                        organism = Mus musculus
SEQUENCE: 114
MYQSLAMAAN HGPPPGAYEA GGPGAFMHSA GAASSPVYVP TPRVPSSVLG LSYLQGGGSA    60
AAAGTTSGGS SGAGPSGAGP GTQQGSPGWS QAGAEGAAYT PPPVSPRFSF PGTTGSLAAA   120
AAAAAAREAA AYGSGGGAAG AGLAGREQYG RPGFAGSYSS PYPAYMADVG ASWAAAAAAS   180
AGPFDSPVLH SLPGRANPGR HPNLVDMFDD FSEGRECVNC GAMSTPLWRR DGTGHYLCNA   240
CGLYHKMNGI NRPLIKPQRR LSASRRVGLS CANCQTTTTT LWRRNAEGEP VCNACGLYMK   300
LHGVPRPLAM RKEGIQTRKR KPKNLNKSKT PAGPAGETLP PSSGASSGNS SNATSSSSSS   360
EEMRPIKTEP GLSSHYGHSS SMSQTFSTVS GHGPSIHPVL SALKLSPQGY ASPVTQTSQA   420
SSKQDSWNSL VLADSHGDII TA                                           442

SEQ ID NO: 115          moltype = AA   length = 441
FEATURE                 Location/Qualifiers
source                  1..441
                        mol_type = protein
                        organism = Mus musculus
SEQUENCE: 115
MYQSLAMAAN HGPPPGAYEA GGPGAFMHSA GAASSPVYVP TPRVPSSVLG LSYLQGGGSA    60
AAAGTTSGGS SGAGPSGAGP GTQQGSPGWS QAGAEGAAYT PPPVSPRFSF PGTTGSLAAA   120
AAAAAAREAA AYGSGGGAAG AGLAGREQYG RPGFAGSYSS PYPAYMADVG ASWAAAAAAS   180
AGPFDSPVLH SLPGRANPGR HPNLDMFDDF SEGRECVNCG AMSTPLWRRD GTGHYLCNAC   240
GLYHKMNGIN RPLIKPQRRL SASRRVGLSC ANCQTTTTTL WRRNAEGEPV CNACGLYMKL   300
HGVPRPLAMR KEGIQTRKRK PKNLNKSKTP AGPAGETLPP SSGASSGNSS NATSSSSSSE   360
EMRPIKTEPG LSSHYGHSSS MSQTFSTVSG HGPSIHPVLS ALKLSPQGYA SPVTQTSQAS   420
SKQDSWNSLV LADSHGDIIT A                                             441

SEQ ID NO: 116          moltype = DNA   length = 3405
FEATURE                 Location/Qualifiers
source                  1..3405
                        mol_type = genomic DNA
                        organism = Mus musculus
SEQUENCE: 116
gcgccgggag caggggacaa gccggaggcc cgcagagtgg ccgcccgagg ctcagccgca    60
gttgcagctc cgcggactca cggagatcgc gccggttttc tgggaaactg gagctggcca   120
ggactgccgc ttcgcttcga agggaccggg ccctctttgt cattcttcgc tggagccgct   180
ctggagctag cagctgcgcc tgggtgtgta gcaggcagaa agcaaggact aggcttcttt   240
agccggtggg tgatccgaag gcctgctcag ggtgttcgag accagcctgg actgcgtctg   300
ggcacctcca gcctctgggc cctggaataa gtccgcgcct cccgcacgat ttctggagca   360
accgcaaatc caatttggga tttttctttt cctgagcaaa ccagagccta gaggtttctg   420
ctttgatgct ggatttaatt cgtatatatt ttgagcgagt tgggcctctc ctcgtttttt   480
gatctccggt tgttttttt tgggggggg ggttagtttt tgggttttg ttttgttttg     540
ttttgtttg atttttggtg acagttccgc acacccgcat tctagtttctt gtctgcctcg   600
tgctcagagc ttggggcgat gtaccaaagc ctggccatgg ccgccaacca cggcccccg    660
cccggcgcct acgaagcagg tggccctggc gccttcatgc acagcgcggg cgccgcgtcc   720
tcgcccgtct acgtgcccac tccgcgggtg ccgtcctctg tgctgggcct gtcctacctg   780
cagggcggtg gcagtgccgc tgcagctgga accacctgcg gtgccagctc cggggccggc   840
ccgtcgggtg cagggcctgg gacccagcag ggtagccctg gctggagcca agctggagcc   900
gagggagccg cctacacccc gccgccgtc tcccgcgct tctctttccc ggggactact      960
gggtccctgc cggccgctgc cgccgctgcc gcagcccggg aagctgcagc ctacggcagt  1020
ggcggggggc cggcggggcgc tggtctggct ggccgagagc agtacgggcg tccgggcttc  1080
gccggctcct actccagccc ctacccagcc tacatggccg acgtgggagc atcctgggcc  1140
gcagccgctg ccgcctctgc cggccccttc gacagcccag tcctgcacag cctgcctgga  1200
cgggccaacc ctgaagacac cccaatctc gatatgtttg atgactttc agaaggcaga    1260
gagtgtgtca attgtggggc catgtccacc ccactctgga ggcgagatgg gacgggacac  1320
tacctgtgca atgcctgtgg cctctatcac aagatgaacg gcatcaaccg gcccctcatt  1380
aagcctcagc gccgcctgtc cgcttccgc cgggtaggcc tctcctgtgc caactgccag    1440
actaccacca ccacgctgtg gcgtcgtaat ccgagggtg agcctgtatg taatgcctgc    1500
ggcctctaca tgaagctcca tgggttcca aggcctcttg caatgcgcag ggagggatt    1560
caaaccagaa aacggaagcc caagaacctg aataaatcta agacgccagc aggtcctgct  1620
ggtgagaccc tccctccctc cagtggtgcc tccagcggta actccagcaa tgccactagc  1680
agcagcagca gcagtgaaga gatgcgcccc atcaagacag agcccgggct gtcatctcac  1740
tatgggcaca gcagctccat gtcccagaca ttcagtactg tgtccggcca cgggccctcc  1800
atccatccag tgctgtctgc tctgaagctg tccccacaag tgggctacgc tcctgtcact  1860
cagacatcgc aggccagctc caagcaggac tcttggaaca gcctggtcct ggctgacagt  1920
catggggaca taatcaccgc gtaatcagcg ccccccttc cctcttcaaa ttcctgctcg   1980
gacttgggac gtggggcca gcaaagtaaa aggctgggc accttggcc agcccctttg     2040
tctgggaaca actcctgaag aacaactggg tagaacttga agttgttgac aatcacttag  2100
ggatatgggt gttccgggtt gttcaaacac ctttcaggt ggacgcactg aaaagctcag    2160
gttcttacag agaagcccac cttggctgca agcacagcac agtgaggcaa gagacttctt  2220
ccttccttat tctccacctg cctgtccagg acagacacat aatctccttc accccagctc  2280
cccaccagt tgtggtggtg gttttcctt tgtgatccta gagtggctgt aggggcggag     2340
gcttcaagac accatctaca gtctgagcag ggtgtctact tgttgtagac tagacataga  2400
agccctgtgg ttgtccaaca ctcccctgc ttgaggcatg gcacatctca gtcttggcact   2460
taccagatct gactccaaag tgctgggttc aatgcagatg ttactgaatg cttcctgggg  2520
agattaggtg aggggaaggc acatcaccca tcacacagaa tagcttcatc aaatcgcagc  2580
ctggccatgg tgccttccct tcctctccca ggaacatcaa ccccttgct ctccagcctg    2640
aacatctacc ctctgcaaaa gtagagccca gttgtgcagc taatgccact aggtgctata  2700
tcccagcatc cttttcaccc cttcacacac aggggttcca aggaggaaca aaacctgcta  2760
```

-continued

```
ccaaagcagc cttggtgact atggctcatc tgcacctcag gggggtgggggg agggccctct  2820
ggaggttgtg tctacagcac aatactgttc ccaggactct agcttgcttg ccccgagcct  2880
gccaagccaa gccctcttaa gtcagacagt tacctggctc tgggactttc tccagcacag  2940
atcctttgtc tagaaaatac agactgtttg caaaataaat tcaaagcaga aacaactaaa  3000
ggaaatttgt gaaaggacaa aggtgataga cgggagaaga tgtccccagg gctggcggga  3060
cagtcatgat agcagctgtc ctaggattgg cctccctccc atctcccacc attactgggg  3120
ctcccagaga ttcttccttg tcctcatcac ccacagagct gtagccaact gtggcattac  3180
tttattttac ccaaaattcc cagccccacc cctaaacctt actggccgta gcagagaata  3240
gcttcgaacc aagattctgt tgtaatcatt ttcgctgttt ctccctcaag gccgccttcc  3300
ccatgcctgc ccctcctcca caaccgtta acattgtctt aaggtgaaat ggctgtaaaa  3360
tcagtattta actaataaat ttatctgtat tcctgtttcc tccga                   3405

SEQ ID NO: 117         moltype = DNA  length = 3408
FEATURE                Location/Qualifiers
source                 1..3408
                       mol_type = genomic DNA
                       organism = Mus musculus
SEQUENCE: 117
gcgccgggag caggggacaa gccggaggcc cgcagagtgg ccgcccgagg ctcagccgca    60
gttgcagctc cgcggactca cggagatcgc gccggttttc tgggaaactg gagctggcca  120
ggactgccgc ttcgcttcga agggaccggg ccctctttgt cattcttcgc tggagccgct  180
ctggagctag cagctgcgcc tgggtgtgta gcaggcagaa agcaaggact aggcttcttt  240
agccggtggg tgatccgaag gcctgctcag ggtgttcgag accagcctgg actgcgtctg  300
ggcacctcca gcctctgggc cctggaatag agtccgccct cccgcacgat ttctggagca  360
accgcaaatc caatttggga ttttcttttt cctgagcaaa ccagagccta gaggtttctg  420
ctttgatgct ggatttaatt cgtatatatt ttgagcgagt tggcctctc ctcgttttt    480
gatctccggt tgtttttttt ttggggggggg ggttagtttt tgggttttttg ttttgttttg  540
ttttgttttg attttggtg acagttccgc acacccgcat tctagttctt gtctgcctcg   600
tgctcagagc ttggggcgat gtaccaaagc ctggccatgg ccgccaacca cggcccccccg  660
cccggccgct acgaagcagg tggccctggc gccttcctgc acagccgcgg agccgcgtcc   720
tcgcccgtct acgtgcccac tccgcgggtg ccgtcctctg tgctgggcct gtcctacctg   780
cagggcggtg gcagtgccgc tgcagctgga accacctcgg gtggcagctc cggggccggc  840
ccgtcgggtg cagggcctgg gacccagcag ggtagccctg gctggagcca agctggagcc   900
gagggagccg cctacacccc gccgcccgtg tccccgcgct tctctttccc gggggactact  960
gggtccctgg cggccgctgc cgcgcgtgcc gcagcccgcg ggg aagctgcagc ctacggcagt 1020
ggcggccggg cggcgggcgc tggtctggct ggccgagagc agtacgggcg tccgggcttc  1080
gccggctcct actccagccc ctacccagcc tacatggccg acgtgggagc atcctgggcc  1140
gcagccgctg ccgcctctgc cggcccctcc gacagcccag tcctgcacag cctgcctgga  1200
cgggccaacc ctggaagaca cccccaatctc gtagatatgt ttgatgactt ctcagaaggc  1260
agagagtgtg tcaattgtgg ggccatgtcc acccccactct ggaggcgaga tgggacggga  1320
cactacctgt gcaatgcctg tggcctctat acaagatga acggcatcaa ccggcccctc   1380
attaagcctc agcgccgcct gtccgcttcc cgccgggtag gcctctcctg tgccaactgc  1440
cagactacca ccaccacgct gtggcgtcgt aatgccgagg gtgagcctgt atgtaatgcc   1500
tgcggcctct acatgaagct ccatgggggtt cccaggcctc ttgcaatgcg aaggagggg   1560
attcaaacca gaaaacggaa gcccaagaac ctgaataaat ctaagacgcc agcaggtcct  1620
gctggtgaga ccctccctcc ctccagtggt gcctccagcg gtaactccag caatgccact   1680
agcagcagca gcagcagtga agagatgcgc ccatccagca cagagccgg gctgtcatct  1740
cactatgggc acagcagctc catgtcccag acattcagta ctgtgtccgg ccacgggccc  1800
tccatccatc cagtgctgtc tgctctgaag ctgtccccac aaggctatgc atctcctgtc  1860
actcagacat cgcaggccag ctccaagcag gactcttgga acagcctggt cctggctgac  1920
agtcatgggg acataatcac cgcgtaatca gcgcccccccc ttccctcttc aaattcctgc  1980
tcggacttgg gacgtggggg ccagcaaagt aaaaggctgg ggcacccttg gccagccct   2040
ttgtctggga acaactcctg aagaacaact gggtagaact tgaagttgtt gacaatcact  2100
tagggatatg ggtgttccgg gttgttcaaa caccttttcca ggtggagcac tggaaaagcc  2160
tgcgttctta cagagaagcc caccttggct gcaagcacag cacagtgagg caagagactt  2220
cttccttcct tattctccac ctgcctgtcc aggacagaca cataatctcc ttcaccccag   2280
ctccccaccc agttgtggtg gtgggttttt ctttgtgatc ctagagtggc tgtaggggcg  2340
gaggcttcaa gacaccatct acagtctgag cagggtgtct acttgttgta gactagacat  2400
agaagccctg ccccttgtcca acactccccct tgcttgaggc atggcacatc tctgcatgtc  2460
ccataccaga tctgactcca aagtgctggg ttcaatgcag atgttactga atgcttcctg  2520
gggagattag gtgagggaa ggcacatcac ccatcacaca gaatagcttc atcaaatcgc   2580
agcctggcca tggtgccttc ccttcctctc ccaggaacat caaaccccctt gctctccagc  2640
ctgaacatct accctctgca aaagtagagc ccagttgtgc agctaatgcc actaggtgct  2700
atatcccagc atcctttttca cccccttcaca cacaggggtt ccaaggagga acaaaacctgg  2760
ctaccaaagc agccttggtg actatggctc atctgcacct caggggggtgg gggagggccc  2820
tctgaggtt gtgtctacag cacaatactg ttccaggac tctagcttgc ttgccccgag  2880
cctgccaagc caagccctct taagtcagac agttacctgg ctctgggact ttctccagca  2940
cagatccttt gtctagaaaa tacagactgt ttgcaaaata aattcaaagc agaaacaact  3000
aaaggaaatt tgtgaaagga caaaggtgat agacggggaa agatgtcccc agggctggcg  3060
ggacagtcat gatagcagct gtcctaggat tggcctccct cccatctccc accattactg  3120
gggctcccag agattcttcc ttgtcctcat cacccacaga gctgtagcca actgtggcat  3180
tactttattt tacccaaaat tcccagcccc acccctaaac cttactggcc gtagcagaga  3240
atagcttcga accaagattc tgttgtaatc attttcgctg tttctccctc aaggccgcct  3300
tccccatgcc tgcccctcct ccacaaacccg ttaaccattgt cttaaggtga aatggctgta  3360
aaaatcagtat ttaactaata aatttatctg tattcctgtt tcctccga                3408

SEQ ID NO: 118         moltype = AA   length = 595
FEATURE                Location/Qualifiers
source                 1..595
```

```
                            mol_type = protein
                            organism = Homo sapiens
SEQUENCE: 118
MALTDGGWCL PKRFGAAGAD ASDSRAFPAR EPSTPPSPIS SSSSSCSRGG ERGPGGASNC    60
GTPQLDTEAA AGPPARSLLL SSYASHPFGA PHGPSAPGVA GPGGNLSSWE DLLLFTDLDQ   120
AATASKLLWS SRGAKLSPFA PEQPEEMYQT LAALSSQGPA AYDGAPGGFV HSAAAAAAAA   180
AAASSPVYVP TTRVGSMLPG LPYHLQGSGS GPANHAGGAG AHPGWPQASA DSPPYGSGGG   240
AAGGGAAGPG GAGSAAAHVS ARFPYSPSPP MANGAAREPG GYAAAGSGGA GGVSGGGSSL   300
AAMGGREPQY SSLSAARPLN GTYHHHHHHH HHHPSPYSPY VGAPLTPAWP AGPFETPVLH   360
SLQSRAGAPL PVPRGPSADL LEDLSESREC VNCGSIQTPL WRRDGTGHYL CNACGLYSKM   420
NGLSRPLIKP QKRVPSSRRL GLSCANCHTT TTTLWRRNAE GEPVCNACGL YMKLHGVPRP   480
LAMKKEGIQT RKRKPKNINK SKTCSGNSNN SIPMTPTSTS SNSDDCSKNT SPTTQPTASG   540
AGAPVMTGAG ESTNPENSEL KYSGQDGLYI GVSLASPAEV TSSVRPDSWC ALALA        595

SEQ ID NO: 119          moltype = AA   length = 358
FEATURE                 Location/Qualifiers
source                  1..358
                        mol_type = protein
                        organism = Homo sapiens
SEQUENCE: 119
MGDWSFLGNF LEEVHKHSTV VGKVWLTVLF IFRMLVLGTA AESSWGDEQA DFRCDTIQPG    60
CQNVCYDQAF PISHIRYWVL QIIFVSTPSL VYMGHAMHTV RMQEKRKLRE AERAKEVRGS   120
GSYEYPVAEK AELSCWEEGN GRIALQGTLL NTYVCSILIR TTMEVGFIVG QYFIYGIFLT   180
TLHVCRRSPC PHPVNCYVSR PTEKNVFIVF MLAVAALSLL LSLAELYHLG WKKIRQRFVK   240
PRQHMAKCQL SGPSVGIVQS CTPPPDFNQC LENGPGGKFF NPFSNNMASQ QNTDNLVTEQ   300
VRGQEQTPGE GFIQVRYGQK PEVPNGVSPG HRLPHGYHSD KRRLSKASSK ARSDDLSV    358

SEQ ID NO: 120          moltype = AA   length = 589
FEATURE                 Location/Qualifiers
source                  1..589
                        mol_type = protein
                        organism = Mus musculus
SEQUENCE: 120
MALTDGGWCL PKRFGAAAAD AGDSGPFPAR EPSSPLSPIS SSSSSCSRGG DRGPCGASNC    60
RTPQLDAEAV AGPPGRSLLL SPYASHPFAA AHGAAAPGVA GPGSALSTWE DLLLFTDLDQ   120
AATASKLLWS SRGAKLSPFA AEQPEEMYQT LAALSSQGPA AYDGAPGGFV HSAAAAAAAA   180
AAASSPVYVP TTRVGSMLSG LPYLQGAGSG PSNHAGGAGA HPGWSQASAD SPPYGGGGAA   240
GGGAAGPGGA GSATAHASAR FPYSPSPPMA NGAARDPGGY VAAGGTGAGS VSGGGGSLAA   300
MGGREHQYSS LSAARPLNGT YHHHHHHHPT YSPYMAAPLT PAWPAGPFET PVLHSLQGRA   360
GAPLPVPRGP STDLLEDLSE SRECVNCGSI QTPLWRRDGT GHYLCNACGL YSKMNGLSRP   420
LIKPQKRVPS SRRLGLSCAN CHTTTTTLWR RNAEGEPVCN ACGLYMKLHG VPRPLAMKKE   480
GIQTRKRKPK NINKSKACSG NSSGSVPMTP TSSSSNSDDC TKNTSPSTQA TTSGVGASVM   540
SAVGENANPE NSDLKYSGQD GLYIGVSLSS PAEVTSSVRQ DSWCALALA              589

SEQ ID NO: 121          moltype = DNA   length = 3194
FEATURE                 Location/Qualifiers
source                  1..3194
                        mol_type = genomic DNA
                        organism = Mus musculus
SEQUENCE: 121
cccacagcct ggcaccctcc ggctagcgct gtttgtttag ggctcggtga gtccaatcag    60
gagcgcaggc tgcagttttc cggcagagca gtaagaggcg cctcctctct cctttttatt   120
caccagcagc gactagcaga ccccggactc tcgctctccc gccggcgccc tccgcctctc   180
tccgcgcccc ggagcaccct cggtcgcggc cgttcttctc gcacatcgct cgaggaatca   240
aaagtcaggt tggagtagcg ccggacagtg gatggccttg actgacggcg gctggtgcct   300
gccaaagcgt ttcggggctg ctgctgcgga cgccggcgac tccgggccct ttccagcgcg   360
ggagccctcc tcgccgcttt cccccatctc gtcttcgtcc tcctcctgct cccggggcgg   420
ggatcgcggt ccctgcggcg ccagcaactg caggacgccg cagctcgacg ccgaggcggt   480
ggcgggacct ccgggccgct cgctcttgct cagcccctac gcctcgcatc ccttcgccgc   540
tgcccacgga gccgcgcgc cggggtcgc aggcccggg agcgccctgt cgacttggga   600
ggacctgttg ctcttcactg acctcgatca ggccgcgacc gccagcaagc tgttgtggtc   660
cagccggggc gccaaactga gcccctttcgc ggccgagcag ccgaggaaa tgtaccagac   720
cctcgccgcc ctgtccagcc aggggcccgc cgcttacgac ggcgcgcccg gcggcttcgt   780
gcactccgca gcggcggcgg ccgctgccgc gccggcagcc agctccccgg tctacgtccc   840
caccacgcgc gtgggctcca tgctgtccgg cctgccctac cttaaggggc gggcagcgg   900
gcccagcaat cacgcgggcg gagcgggtgc ccacccagcc tggtcccagg cctccgcgga   960
cagcccccg tatggcgggg gtggcgcagc cggcggcggc gcggccggac ctggaggtgc  1020
gggatcggct acggccacg cctctgcacg ctttcccctac tcgcccagcc cgcccatggc  1080
caacgggcc gcgcgagacc ccgggggcta cgtggctgcg ggcggcacgg gcgcaggcag  1140
tgtgagtgga ggtggcggca gcctggcggc catgggtggc cgggagcacc agtacagctc  1200
gctgtccgca gctcggccgc tgaacggaac gtaccaccac caccatcacc atcacccgac  1260
ctactcgccc tacatggccg caccgctgac tcctgcctgg ccagcaggac ccttcgaaac  1320
gccggtgctc cacagcttac agggccgcgc gggagctcca ctcccggtgc cacggggccc  1380
cagcacagac ctgttgaggg acctgtcgga gagccgcgag tgcgtgaact gcggctccat  1440
ccagacgcca ctgtggagac gagacggcac cggtcattac ctgtgcaatg catgcggtct  1500
ctacagcaag atgaatggcc tcagcaggcc cctcatcaag ccacagaagc gcgtgccttc  1560
atcacgcgcg cttggactgt cctgtgccaa ctgtcacacc acaaccacta ccttatggcg  1620
tagaaatgct gagggtgagc ctgtgtgcaa tgcttgcggg ctctatatga aactccatgg  1680
ggtgcctcga ccacttgcta tgaaaaaaga aggaattcaa accaggaaac gaaaacctaa  1740
```

-continued

```
aaatataaat aagtcaaaag cttgctccgg taacagcagt ggctctgtcc ctatgactcc    1800
tacttcctct tcttctaatt cagatgactg caccaaaaat acttctcctt ctacacaagc    1860
gaccacctca ggggtagggg catcagtgat gtctgcagtg ggagaaaacg ccaaccccga    1920
gaacagtgac ctcaagtatt caggtcaaga cggcctctac ataggtgtca gtctgtcctc    1980
ccctgccgaa gtcacatcct ccgtgcgaca ggattcttgg tgtgctctgg ccctggcctg    2040
agctggtgct accaagaggc aaggagggct ctgaaggcct cataccactt gtgtctgata    2100
ttgtccagca gtccagatgg cagcaaaaat gcagacataa cattccttcg atgcgtgatt    2160
tctgtgcctt tgttttgaaa gagatatatt tctcaagaag cttactgaag taagaagaga    2220
tgggcttttg caggaagggc cagcaccgtg ggcatgtggc ctgctcctgc cagcctgggc    2280
tgcttcctgc ctctgactct gccccatacc agtgggagaa actgtgacaa tgaccgtgga    2340
cttgtctgct aaggaagatt gagagattta agagaaaatg tttgtgtatt gctccaaatc    2400
atgtgcttct tgtgatcaac ctcggttatc ccagaaccca ttcatcccg accaccgtgc     2460
acatttcaca agcgttcgtg gagaggagca ctgggagcca tttggtctat cctggaggcg    2520
gagtgcattc ctggggtctc aacaagaata ttaatttgac agattgcatc atgacagaca    2580
ctgactgact tatctcaacg ttcatcgtaa cgtggctgat ctgaggtcac ttggaatttg    2640
taaacagggt agcaaacaag atatttttct tccatgtaca caataatttt tttaagtgca    2700
atttgcgttg cagcaatcag tgttaaatca tttgcataag atttaacagc atttttataa    2760
tgaatgtaaa cattttaact taatggtact taaaataatt taaaaaaaag ttaactttag    2820
acatatgctt cttacactca cagcccactt ctgtgttccc aattgtttaa agaaaaaaa     2880
aaaagatttc aagaacaaat cttctctcag gaaattgcct tttctccatt tatgaatttt    2940
tatacaagaa caccaacaca gtcccgttc ttttactgag gaaaaagtgc tggaaattgc      3000
aacaaacctt tactacctag agaatagcat ttgtaaatat tctaagtatc tgtaacactc    3060
ttgacgcctg taccacgtga ccaacccaca ggttggttta cattattatt tttttaatg     3120
ggatatcata tggaaaccta tttcaccaga gttttaaaaa ataaaagggt tattgtttg      3180
tgttctgtac agtg                                                     3194

SEQ ID NO: 122          moltype = AA    length = 433
FEATURE                 Location/Qualifiers
source                  1..433
                        mol_type = protein
                        organism = Homo sapiens
SEQUENCE: 122
MSGRPRTTSF AESCKPVQQP SAFGSMKVSR DKDGSKVTTV VATPGQGPDR PQEVSYTDTK     60
VIGNGSFGVV YQAKLCDSGE LVAIKKVLQD KRFKNRELQI MRKLDHCNIV RLRYFFYSSG    120
EKKDEVYLNL VLDYVPETVY RVARHYSRAK QTLPVIYVKL YMYQLFRSLA YIHSFGICHR    180
DIKPQNLLLD PDTAVLKLCD FGSAKQLVRG EPNVSYICSR YYRAPELIFG ATDYTSSIDV    240
WSAGCVLAEL LLGQPIFPGD SGVDQLVEII KVLGTPTREQ IREMNPNYTE FKFPQIKAHP    300
WTKDSSGTGH FTSGVRVFRP RTPPEAIALC SRLLEYTPTA RLTPLEACAH SFFDELRDPN    360
VKLPNGRDTP ALFNFTTQEL SSNPPLATIL IPPHARIQAA ASTPTNATAA SDANTGDRGQ    420
TNNAASASAS NST                                                      433

SEQ ID NO: 123          moltype = AA    length = 420
FEATURE                 Location/Qualifiers
source                  1..420
                        mol_type = protein
                        organism = Homo sapiens
SEQUENCE: 123
MSGRPRTTSF AESCKPVQQP SAFGSMKVSR DKDGSKVTTV VATPGQGPDR PQEVSYTDTK     60
VIGNGSFGVV YQAKLCDSGE LVAIKKVLQD KRFKNRELQI MRKLDHCNIV RLRYFFYSSG    120
EKKDEVYLNL VLDYVPETVY RVARHYSRAK QTLPVIYVKL YMYQLFRSLA YIHSFGICHR    180
DIKPQNLLLD PDTAVLKLCD FGSAKQLVRG EPNVSYICSR YYRAPELIFG ATDYTSSIDV    240
WSAGCVLAEL LLGQPIFPGD SGVDQLVEII KVLGTPTREQ IREMNPNYTE FKFPQIKAHP    300
WTKVFRPRTP PEAIALCSRL LEYTPTARLT PLEACAHSFF DELRDPNVKL PNGRDTPALF    360
NFTTQELSSN PPLATILIPP HARIQAAAST PTNATAASDA NTGDRGQTNN AASASASNST    420

SEQ ID NO: 124          moltype = AA    length = 88
FEATURE                 Location/Qualifiers
source                  1..88
                        mol_type = protein
                        organism = Homo sapiens
SEQUENCE: 124
MKVLAAVHSP GGAVPQQPGQ AMWPQRDGLP ALPRQRHGEG QAGGAVPHSR VPWHLPGQHH     60
PGPEDPQPQC PQPPQQAQRH RRHPARPP                                        88

SEQ ID NO: 125          moltype = AA    length = 379
FEATURE                 Location/Qualifiers
source                  1..379
                        mol_type = protein
                        organism = Homo sapiens
SEQUENCE: 125
MAAAAAQGGG GGEPRRTEGV GPGVPGEVEM VKGQPFDVGP RYTQLQYIGE GAYGMVSSAY     60
DHVRKTRVAI KKISPFEHQT YCQRTLREIQ ILLRFRHENV IGIRDILRAS TLEAMRDVYI    120
VQDLMETDLY KLLKSQQLSN DHICYFLYQI LRGLKYIHSA NVLHRDLKPS NLLINTTCDL    180
KICDFGLARI ADPEHDHTGF LTEYVATRWY RAPEIMLNSK GYTKSIDIWS VGCILAEMLS    240
NRPIFPGKHY LDQLNHILGI LGSPSQEDLN CIINMKARNY LQSLPSKTKV AWAKLFPKSD    300
SKALDLLDRM LTFNPNKRIT VEEALAHPYL EQYYDPTDEP VAEEPFTFAM ELDDLPKERL    360
KELIFQETAR FQPGVLEAP                                                379

SEQ ID NO: 126          moltype = AA    length = 357
```

```
FEATURE                 Location/Qualifiers
source                  1..357
                        mol_type = protein
                        organism = Homo sapiens
SEQUENCE: 126
MAAAAAQGGG GGEPRRTEGV GPGVPGEVEM VKGQPFDVGP RYTQLQYIGE GAYGMVSSAY   60
DHVRKTRVAI KKISPFEHQT YCQRTLREIQ ILLRFRHENV IGIRDILRAS TLEAMRDVYI  120
VQDLMETDLY KLLKSQQLSN DHICYFLYQI LRGLKYIHSA NVLHRDLKPS NLLINTTCDL  180
KICDFGLARI ADPEHDHTGF LTEYVATRWY RAPEIMLNSK GYTKSIDIWS VGCILAEMLS  240
NRPIFPGKHY LDQLNHILGI LGSPSQEDLN CIINMKARNY LQSLPSKTKV AWAKLFPKSD  300
SKALDLLDRM LTFNPNKRIT VEEALAHPYL EQYYDPTDEV GQSPAAVGLG AGEQGGT     357

SEQ ID NO: 127          moltype = AA  length = 335
FEATURE                 Location/Qualifiers
source                  1..335
                        mol_type = protein
                        organism = Homo sapiens
SEQUENCE: 127
MAAAAAQGGG GGEPRRTEGV GPGVPGEVEM VKGQPFDVGP RYTQLQYIGE GAYGMVSSAY   60
DHVRKTRVAI KKISPFEHQT YCQRTLREIQ ILLRFRHENV IGIRDILRAS TLEAMRDVYI  120
VQDLMETDLY KLLKSQQLSN DHICYFLYQI LRGLKYIHSA NVLHRDLKPS NLLINTTCDL  180
KICDFGLARI ADPEHDHTGF LTEYVATRWY RAPEIMLNSK GYTKSIDIWS VGCILAEMLS  240
NRPIFPGKHY LDQLNHILAL DLLDRMLTFN PNKRITVEEA LAHPYLEQYY DPTDEPVAEE  300
PFTFAMELDD LPKERLKELI FQETARFQPG VLEAP                             335

SEQ ID NO: 128          moltype = DNA  length = 1745
FEATURE                 Location/Qualifiers
source                  1..1745
                        mol_type = genomic DNA
                        organism = Homo sapiens
SEQUENCE: 128
ccccgtagaa ccgagggggt gggcccgggg gtcccggggg aggtggagat ggtgaagggg   60
cagccgttcg acgtgggccc gcgctacacg cagttgcagt acatcggcga gggcgcgtac  120
ggcatggtca gctcggccta tgaccacgtg cgcaagactc gcgtggccat caagaagatc  180
agcccttcg aacatcagac ctactgccag cgcacgctcc gggagatcca gatcctgctg  240
cgcttccgcc atgagaatgt catcggcatc cgagacattc tgcgggcgtc cacccctgga  300
gccatgagag atgtctacat tgtgcaggac ctgatggaga ctgacctgta caagttgctg  360
aaaagccagc agctgagcaa tgaccatatc tgctacttcc tctaccagat cctgcgcggc  420
ctcaagtaca tccactccgc caacgtgctc accgagatc taaagcccatc caacctgctc  480
atcaacacca cctgcgacct taagatttgt gatttcggcc tggcccggat tgccgatcct  540
gagcatgacc acaccggctt cctgacggag tatgtggcta cgcgctggta ccgggcccca  600
gagatcatgc tgaactccaa gggctatacc aagtccatcg acatctggtc tgtgggctgc  660
attctggctg agatgctctc taaccggccc atcttccctg gcaagcacta cctggatcag  720
ctcaaccaca ttctgggcat cctgggctcc ccatcccagg aggacctgaa ttgtatcatc  780
aacatgaagg cccgaaacta cctacagtct ctgccctcca agaccaaggt ggcttgggcc  840
aagctttttcc ccaagtcaga ctccaaagcc cttgacctgc tggaccggat gttaaccttt  900
aaccccaata aacggatcac agtggaggaa gcgctgaccc accctaccct ggagcagtac  960
tatgacccga cggatgagcc agtggccgag gagcccttca ccttcgccat ggagctggat 1020
gacctaccta aggagcggct gaaggagctc atcttccagg agacagcacg cttccagccc 1080
ggagtgctgg aggcccccta gcccagacag acatctctgc accctgggc ctggacctgc  1140
ctcctgcctg ccctctccc gccagactgt tagaaaatgg acactgtgcc cagcccggc  1200
cttggcagcc caggccgggg tggagcatgg gcctggccac ctctctcctt tgctgaggcc 1260
tccagcttca ggcaggccaa ggttctcct ccccacccgc cctccccacg ggcctcggga 1320
cctcaggtgg gcccagttca atctcccgct gctgctgctg cgcccttacc ttccccagcg 1380
tcccagtctc tggcagtttt ggaatggaag ggttctggct gccccaacct gctgaagggc 1440
agaggtggag ggtgggggc gctgagtagg gactcacggc catgcctgcc ccctctcatct 1500
cattcaaacc ccaccctagt ttccctgaag gaacattcct tagtctcaag gctagcatc  1560
cctgaggagc caggccgggc cgaatcccct ccctgtcaaa gctgtcactt cgcgtgccct 1620
cgctgcttct gtgtgtggtg agcagaagtg gagctggggg gcgtggagag cccggctgcc 1680
cctgccacct ccctgacccg tctaatatat aaatatagag atgtgtctat ggctgaaaaa 1740
aaaaa                                                              1745

SEQ ID NO: 129          moltype = AA  length = 360
FEATURE                 Location/Qualifiers
source                  1..360
                        mol_type = protein
                        organism = Homo sapiens
SEQUENCE: 129
MAAAAAAGAG PEMVRGQVFD VGPRYTNLSY IGEGAYGMVC SAYDNVNKVR VAIKKISPFE   60
HQTYCQRTLR EIKILLRFRH ENIIGINDII RAPTIEQMKD VYIVQDLMET DLYKLLKTQH  120
LSNDHICYFL YQILRGLKYI HSANVLHRDL KPSNLLLNTT CDLKICDFGL ARVADPDHDH  180
TGFLTEYVAT RWYRAPEIML NSKGYTKSID IWSVGCILAE MLSNRPIFPG KHYLDQLNHI  240
LGILGSPSQE DLNCIINLKA RNYLLSLPHK NKVPWNRLFP NADSKALDLL DKMLTFNPHK  300
RIEVEQALAH PYLEQYYDPS DEPIAEAPFK FDMELDDLPK EKLKELIFEE TARFQPGYRS  360

SEQ ID NO: 130          moltype = AA  length = 360
FEATURE                 Location/Qualifiers
source                  1..360
                        mol_type = protein
```

-continued

```
                      organism = Homo sapiens
SEQUENCE: 130
MAAAAAAGAG PEMVRGQVFD VGPRYTNLSY IGEGAYGMVC SAYDNVNKVR VAIKKISPFE    60
HQTYCQRTLR EIKILLRFRH ENIIGINDII RAPTIEQMKD VYIVQDLMET DLYKLLKTQH   120
LSNDHICYFL YQILRGLKYI HSANVLHRDL KPSNLLLNTT CDLKICDFGL ARVADPDHDH   180
TGFLTEYVAT RWYRAPEIML NSKGYTKSID IWSVGCILAE MLSNRPIFPG KHYLDQLNHI   240
LGILGSPSQE DLNCIINLKA RNYLLSLPHK NKVPWNRLFP NADSKALDLL DKMLTFNPHK   300
RIEVEQALAH PYLEQYYDPS DEPIAEAPFK FDMELDDLPK EKLKELIFEE TARFQPGYRS   360

SEQ ID NO: 131          moltype = DNA  length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 131
actgacggag agcatgaaga t                                              21

SEQ ID NO: 132          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 132
ccggcacata ggaggggta                                                 19

SEQ ID NO: 133          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 133
gcccctcatt aagcccaag                                                 19

SEQ ID NO: 134          moltype = DNA  length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 134
ttgtggtggt ctgacagttc g                                              21

SEQ ID NO: 135          moltype = DNA  length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 135
tcccaaagaa tacggagcac t                                              21

SEQ ID NO: 136          moltype = DNA  length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 136
tcatggggac agacttctca a                                              21

SEQ ID NO: 137          moltype = DNA  length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 137
tagggaacaa ggaattttc ggg                                             23
```

```
SEQ ID NO: 138           moltype = DNA  length = 22
FEATURE                  Location/Qualifiers
misc_feature             1..22
                         note = Single strand DNA oligonucleotide
source                   1..22
                         mol_type = other DNA
                         organism = synthetic construct
SEQUENCE: 138
gtacactaac cttcggtcaa cc                                              22

SEQ ID NO: 139           moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 139
accacccttt cacaagcaac                                                 20

SEQ ID NO: 140           moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 140
tgtgcccatt tgcaattcta                                                 20

SEQ ID NO: 141           moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 141
acaacgatgg cctctacgac                                                 20

SEQ ID NO: 142           moltype = DNA  length = 19
FEATURE                  Location/Qualifiers
misc_feature             1..19
                         note = Single strand DNA oligonucleotide
source                   1..19
                         mol_type = other DNA
                         organism = synthetic construct
SEQUENCE: 142
agttcacgca ccagcacac                                                  19

SEQ ID NO: 143           moltype = DNA  length = 22
FEATURE                  Location/Qualifiers
misc_feature             1..22
                         note = Single strand DNA oligonucleotide
source                   1..22
                         mol_type = other DNA
                         organism = synthetic construct
SEQUENCE: 143
gttaccctgc tcacatcact ag                                              22

SEQ ID NO: 144           moltype = DNA  length = 21
FEATURE                  Location/Qualifiers
misc_feature             1..21
                         note = Single strand DNA oligonucleotide
source                   1..21
                         mol_type = other DNA
                         organism = synthetic construct
SEQUENCE: 144
tcttgtcact tgctcattgg g                                               21

SEQ ID NO: 145           moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 145
tcacaaccct ggttttcctc                                                 20
```

```
SEQ ID NO: 146          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 146
ctgtctggaa ctggtgctga                                               20

SEQ ID NO: 147          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 147
tcaccatccg gaggaaagcc                                               20

SEQ ID NO: 148          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 148
ctctcctttg ctctgcggtt                                               20

SEQ ID NO: 149          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 149
ccaaggatgc acagtctgg                                                19

SEQ ID NO: 150          moltype = DNA  length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 150
aggaggaaaa ccttcgtgct g                                             21

SEQ ID NO: 151          moltype = DNA  length = 26
FEATURE                 Location/Qualifiers
misc_feature            1..26
                        note = Single strand DNA oligonucleotide
source                  1..26
                        mol_type = other DNA
                        organism = synthetic construct
SEQUENCE: 151
acgaaatgag atggcagcta ggaaga                                        26

SEQ ID NO: 152          moltype = DNA  length = 24
FEATURE                 Location/Qualifiers
misc_feature            1..24
                        note = Single strand DNA oligonucleotide
source                  1..24
                        mol_type = other DNA
                        organism = synthetic construct
SEQUENCE: 152
tgtccggtct tggctgagaa gttc                                          24

SEQ ID NO: 153          moltype = DNA  length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 153
```

```
acgaacggat taacagggtc a                                              21

SEQ ID NO: 154         moltype = DNA   length = 21
FEATURE                Location/Qualifiers
misc_feature           1..21
                       note = Single strand DNA oligonucleotide
source                 1..21
                       mol_type = other DNA
                       organism = synthetic construct
SEQUENCE: 154
cctccagaca caccacggat a                                              21

SEQ ID NO: 155         moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 155
acctggagat gcagatcgaa                                                20

SEQ ID NO: 156         moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 156
aatccacctc cacactgacc                                                20

SEQ ID NO: 157         moltype = DNA   length = 21
FEATURE                Location/Qualifiers
misc_feature           1..21
                       note = Single strand DNA oligonucleotide
source                 1..21
                       mol_type = other DNA
                       organism = synthetic construct
SEQUENCE: 157
tgcctcccgg ctcagttcac t                                              21

SEQ ID NO: 158         moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 158
cccagtggtt tggtggtgta                                                20

SEQ ID NO: 159         moltype = DNA   length = 21
FEATURE                Location/Qualifiers
misc_feature           1..21
                       note = Single strand DNA oligonucleotide
source                 1..21
                       mol_type = other DNA
                       organism = synthetic construct
SEQUENCE: 159
gccatagtcc tgttcacctc a                                              21

SEQ ID NO: 160         moltype = DNA   length = 18
FEATURE                Location/Qualifiers
misc_feature           1..18
                       note = Single strand DNA oligonucleotide
source                 1..18
                       mol_type = other DNA
                       organism = synthetic construct
SEQUENCE: 160
aatctcgtcg gctggttg                                                  18

SEQ ID NO: 161         moltype = DNA   length = 20
FEATURE                Location/Qualifiers
misc_feature           1..20
                       note = Single strand DNA oligonucleotide
source                 1..20
                       mol_type = other DNA
                       organism = synthetic construct
```

```
SEQUENCE: 161
tggcgcagca gaatccagac                                               20

SEQ ID NO: 162          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 162
ttggggtggt cctgcatgtg                                               20

SEQ ID NO: 163          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 163
tgcctgacat tgaccctgt                                                19

SEQ ID NO: 164          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 164
ccgtctcaat ggcactctc                                                19

SEQ ID NO: 165          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 165
cctgcctggt attgtcatcc                                               20

SEQ ID NO: 166          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 166
gatggggatg attgtggtct                                               20

SEQ ID NO: 167          moltype = DNA  length = 18
FEATURE                 Location/Qualifiers
misc_feature            1..18
                        note = Single strand DNA oligonucleotide
source                  1..18
                        mol_type = other DNA
                        organism = synthetic construct
SEQUENCE: 167
gcggacggtg aacgacta                                                 18

SEQ ID NO: 168          moltype = DNA  length = 18
FEATURE                 Location/Qualifiers
misc_feature            1..18
                        note = Single strand DNA oligonucleotide
source                  1..18
                        mol_type = other DNA
                        organism = synthetic construct
SEQUENCE: 168
ggccgccttt ccttttat                                                 18

SEQ ID NO: 169          moltype = DNA  length = 18
FEATURE                 Location/Qualifiers
misc_feature            1..18
                        note = Single strand DNA oligonucleotide
source                  1..18
                        mol_type = other DNA
```

```
                        organism = synthetic construct
SEQUENCE: 169
cctccgcgag gagaaagt                                                     18

SEQ ID NO: 170          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 170
cgttctccga ctcctctgat                                                   20

SEQ ID NO: 171          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 171
gtgtcaggct tgaggtggag                                                   20

SEQ ID NO: 172          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 172
tgcctgacat tgaccctgt                                                    19

SEQ ID NO: 173          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 173
gcgggctcta cagcaagat                                                    19

SEQ ID NO: 174          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 174
tggcacagga caatccaag                                                    19

SEQ ID NO: 175          moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 175
ggaagcccaa gaacctgaat                                                   20

SEQ ID NO: 176          moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 176
gttgctggag ttgctggaa                                                    19

SEQ ID NO: 177          moltype = DNA  length = 21
FEATURE                 Location/Qualifiers
misc_feature            1..21
                        note = Single strand DNA oligonucleotide
source                  1..21
```

```
                    mol_type = other DNA
                    organism = synthetic construct
SEQUENCE: 177
tgaagatgga agggcacgag c                                              21

SEQ ID NO: 178      moltype = DNA   length = 25
FEATURE             Location/Qualifiers
misc_feature        1..25
                    note = Single strand DNA oligonucleotide
source              1..25
                    mol_type = other DNA
                    organism = synthetic construct
SEQUENCE: 178
ccgacatgct catgtacgtg ttcat                                          25

SEQ ID NO: 179      moltype = DNA   length = 21
FEATURE             Location/Qualifiers
misc_feature        1..21
                    note = Single strand DNA oligonucleotide
source              1..21
                    mol_type = other DNA
                    organism = synthetic construct
SEQUENCE: 179
agtccactga gtaccggaga c                                              21

SEQ ID NO: 180      moltype = DNA   length = 21
FEATURE             Location/Qualifiers
misc_feature        1..21
                    note = Single strand DNA oligonucleotide
source              1..21
                    mol_type = other DNA
                    organism = synthetic construct
SEQUENCE: 180
catttcacgc atctggcgtt c                                              21

SEQ ID NO: 181      moltype = DNA   length = 21
FEATURE             Location/Qualifiers
misc_feature        1..21
                    note = Single strand DNA oligonucleotide
source              1..21
                    mol_type = other DNA
                    organism = synthetic construct
SEQUENCE: 181
agggctgctt ttaactctgg t                                              21

SEQ ID NO: 182      moltype = DNA   length = 21
FEATURE             Location/Qualifiers
misc_feature        1..21
                    note = Single strand DNA oligonucleotide
source              1..21
                    mol_type = other DNA
                    organism = synthetic construct
SEQUENCE: 182
ccccacttga ttttggaggg a                                              21

SEQ ID NO: 183      moltype = DNA   length = 22
FEATURE             Location/Qualifiers
misc_feature        1..22
                    note = Single strand DNA oligonucleotide
source              1..22
                    mol_type = other DNA
                    organism = synthetic construct
SEQUENCE: 183
ccacgaaact accttcaact cc                                             22

SEQ ID NO: 184      moltype = DNA   length = 22
FEATURE             Location/Qualifiers
misc_feature        1..22
                    note = Single strand DNA oligonucleotide
source              1..22
                    mol_type = other DNA
                    organism = synthetic construct
SEQUENCE: 184
gtgatctcct tctgcatcct gt                                             22

SEQ ID NO: 185      moltype = DNA   length = 20
FEATURE             Location/Qualifiers
misc_feature        1..20
                    note = Single strand DNA oligonucleotide
```

```
source                      1..20
                            mol_type = other DNA
                            organism = synthetic construct
SEQUENCE: 185
tcgtaaagcg aggtgatggg                                                   20

SEQ ID NO: 186              moltype = DNA  length = 20
FEATURE                     Location/Qualifiers
misc_feature                1..20
                            note = Single strand DNA oligonucleotide
source                      1..20
                            mol_type = other DNA
                            organism = synthetic construct
SEQUENCE: 186
aagctcacag cctccatgtc                                                   20

SEQ ID NO: 187              moltype = DNA  length = 20
FEATURE                     Location/Qualifiers
misc_feature                1..20
                            note = Single strand DNA oligonucleotide
source                      1..20
                            mol_type = other DNA
                            organism = synthetic construct
SEQUENCE: 187
aactgtgagg tggtccttgg                                                   20

SEQ ID NO: 188              moltype = DNA  length = 20
FEATURE                     Location/Qualifiers
misc_feature                1..20
                            note = Single strand DNA oligonucleotide
source                      1..20
                            mol_type = other DNA
                            organism = synthetic construct
SEQUENCE: 188
gttgagggca atgaggacat                                                   20

SEQ ID NO: 189              moltype = DNA  length = 20
FEATURE                     Location/Qualifiers
misc_feature                1..20
                            note = Single strand DNA oligonucleotide
source                      1..20
                            mol_type = other DNA
                            organism = synthetic construct
SEQUENCE: 189
tggtctccaa acggcacttt                                                   20

SEQ ID NO: 190              moltype = DNA  length = 20
FEATURE                     Location/Qualifiers
misc_feature                1..20
                            note = Single strand DNA oligonucleotide
source                      1..20
                            mol_type = other DNA
                            organism = synthetic construct
SEQUENCE: 190
aactgtgagg tggtccttgg                                                   20

SEQ ID NO: 191              moltype = DNA  length = 23
FEATURE                     Location/Qualifiers
misc_feature                1..23
                            note = Single strand DNA oligonucleotide
source                      1..23
                            mol_type = other DNA
                            organism = synthetic construct
SEQUENCE: 191
cactccacta aggtccaaga aga                                               23

SEQ ID NO: 192              moltype = DNA  length = 21
FEATURE                     Location/Qualifiers
misc_feature                1..21
                            note = Single strand DNA oligonucleotide
source                      1..21
                            mol_type = other DNA
                            organism = synthetic construct
SEQUENCE: 192
ccgtgtggtt ctccactttg a                                                 21

SEQ ID NO: 193              moltype = DNA  length = 21
FEATURE                     Location/Qualifiers
misc_feature                1..21
```

```
                       note = Single strand DNA oligonucleotide
source                 1..21
                       mol_type = other DNA
                       organism = synthetic construct
SEQUENCE: 193
agatgccgat gacccttcat a                                               21

SEQ ID NO: 194         moltype = DNA  length = 21
FEATURE                Location/Qualifiers
misc_feature           1..21
                       note = Single strand DNA oligonucleotide
source                 1..21
                       mol_type = other DNA
                       organism = synthetic construct
SEQUENCE: 194
tgttcggtaa agcagtcctg a                                               21

SEQ ID NO: 195         moltype = AA  length = 408
FEATURE                Location/Qualifiers
source                 1..408
                       mol_type = protein
                       organism = Homo sapiens
SEQUENCE: 195
MIPGNRMLMV VLLCQVLLGG ASHASLIPET GKKKVAEIQG HAGGRRSGQS HELLRDFEAT      60
LLQMFGLRRR PQPSKSAVIP DYMRDLYRLQ SGEEEEEQIH STGLEYPERP ASRANTVRSF     120
HHEEHLENIP GTSENSAFRF LFNLSSIPEN EVISSAELRL FREQVDQGPD WERGFHRINI     180
YEVMKPPAEV VPGHLITRLL DTRLVHHNVT RWETFDVSPA VLRWTREKQP NYGLAIEVTH     240
LHQTRTHQGQ HVRISRSLPQ GSGNWAQLRP LLVTFGHDGR GHALTRRRRA KRSPKHHSQR     300
ARKKNKNCRR HSLYVDFSDV GWNDWIVAPP GYQAFYCHGD CPFPLADHLN STNHAIVQTL     360
VNSVNSSIPK ACCVPTELSA ISMLYLDEYD KVVLKNYQEM VVEGCGCR                  408

SEQ ID NO: 196         moltype = AA  length = 408
FEATURE                Location/Qualifiers
source                 1..408
                       mol_type = protein
                       organism = Mus musculus
SEQUENCE: 196
MIPGNRMLMV VLLCQVLLGG ASHASLIPET GKKKVAEIQG HAGGRRSGQS HELLRDFEAT      60
LLQMFGLRRR PQPSKSAVIP DYMRDLYRLQ SGEEEEEQS QGTGLEYPER PASRANTVRS     120
FHHEEHLENI PGTSESSAFR FLFNLSSIPE NEVISSAELR LFREQVDQGP DWEQGFHRIN     180
IYEVMKPPAE MVPGHLITRL LDTRLVHHNV TRWETFDVSP AVLRWTREKQ PNYGLAIEVT     240
HLHQTRTHQG QHVRISRSLP QGSGDWAQLR PLLVTFGHDG RGHTLTRRRA KRSPKHHPQR     300
SRKKNKNCRR HSLYVDFSDV GWNDWIVAPP GYQAFYCHGD CPFPLADHLN STNHAIVQTL     360
VNSVNSSIPK ACCVPTELSA ISMLYLDEYD KVVLKNYQEM VVEGCGCR                  408

SEQ ID NO: 197         moltype = AA  length = 414
FEATURE                Location/Qualifiers
source                 1..414
                       mol_type = protein
                       organism = Homo sapiens
SEQUENCE: 197
MSSPDAGYAS DDQSQTQSAL PAVMAGLGPC PWAESLSPIG DMKVKGEAPA NSGAPAGAAG      60
RAKGESRIRR PMNAFMVWAK DERKRLAQQN PDLHNAELSK MLGKSWKALT LAEKRPFVEE     120
AERLRVQHMQ DHPNYKYRPR RRKQVKRLKR VEGGFLHGLA EPQAAALGPE GGRVAMDGLG     180
LQFPEQGFPA GPPLLPPHMG GHYRDCQSLG APPLDGYPLP TPDTSPLDGV DPDPAFFAAP     240
MPGDCPAAGT YSYAQVSDYA GPPEPPAGPM HPRLGPEPAG PSIPGLLAPP SALHVYYGAM     300
GSPGAGGGRG FQMQPHQHQ HQHQHHPPGP GQPSPPPEAL PCRDGTDPSQ PAELLGEVDR     360
TEFEQYLHFV CKPEMGLPYQ GHDSGVNLPD SHGAISSVVS DASSAVYYCN YPDV           414

SEQ ID NO: 198         moltype = DNA  length = 2346
FEATURE                Location/Qualifiers
source                 1..2346
                       mol_type = genomic DNA
                       organism = Homo sapiens
SEQUENCE: 198
gcagtgtcac taggccggct gggggccctg ggtacgctgt agaccagacc gcgacaggcc      60
agaacacggg cggcggcttc gggccgggag acccgcgcag ccctcggggc atctcagtgc     120
ctcactcccc acccccctccc ccgggtcggg ggaggcggcg cgtccggcgg agggttgagg    180
ggagccggag aggcctggag cgccatgagc agcccggatg cgggatacgc cagtgacgac     240
cagagccaga cccagagcgc gctgcccgcg gtgatggccg gctgggccc ctgcccctgg      300
gccgagtcgc tgagccccat cggggacatg aaggtgaagg gcgaggcgcc ggcgaacagc     360
ggagccaccg ccggggccgc gggccgagcc aagggcgagt cccgtatccg gcggccgatg     420
aacgctttca tggtgtgggc taaggacgag cgcaagcggc tggcgcagca gaatccggac     480
ctgcacaacg ccgagttgag caagatgctg ggcaagtcgt ggaagcgcct gaccgccgag     540
gagaagcggc ccttcgtgga ggaggcagag cggctgcgcg tgcagcacat gcaggaccac     600
cccaactaca agtaccggcc gcggcggcgc aagcaggtga gcggctgaa gcgggtggag      660
ggcggcttcc tgcacgggct ggctgagccg caggcggccg cgctgggccc cgagggcggc     720
cgcgtggcca tggacggcct gggcctccag ttccccgagc agggcttccc cgccggcccg     780
ccgctgctgc ctccgcacat gggcggccac taccgcgact gccagagtct gggcgcgcct     840
```

```
ccgctcgacg gctacccgtt gcccacgccc gacacgtccc cgctggacgg cgtggacccc    900
gacccggctt tcttcgccgc cccgatgccc ggggactgcc cggcggccgg cacctacagc    960
tacgcgcagg tctcggacta cgctggcccc ccggagcctc ccgccggtcc catgcacccc   1020
cgactcggcc cagagcccgc gggtccctcg attccgggcc tcctggcgcc acccagcgcc   1080
cttcacgtgt actacggcgc gatgggctcg cccggggcgg gcggcgggcg cggcttccag   1140
atgcagccgc aacaccagca ccagcaccag caccagccac acccccgggg ccccggacag   1200
ccgtcgcccc ctccggaggc actgccctgc cgggacggca cggaccccag tcagcccgcc   1260
gagctcctcg gggaggtgga ccgcacggaa tttgaacagt atctgcactt cgtgtgcaag   1320
cctgagatgg gcctcccccta ccaggggcat gactccggtg tgaatctccc cgacagccac   1380
ggggccattt cctcggtggt gtccgacgcc agctccgcgg tatattactg caactatcct   1440
gacgtgtgac aggtccctga tccgccccag cctgcaggcc agaagcagtg ttacacactt   1500
cctggaggag ctaaggaaat cctcagactc ctgggttttt gttgttgctg ttgttgtttt   1560
ttaaaaggtg tgttggcata taatttatgg taatttattt tgtctgccac ttgaacagtt   1620
tgggggggtg aggtttcatt taaaatttgt tcagagattt gtttcccata gttggattgt   1680
caaaaccccta tttccaagtt caagttaact agctttgaat gtgtcccaaa acagcttcct   1740
ccatttcctg aaagtttatt gatcaaagaa atgttgtcct gggtgtgttt tttcaatctt   1800
ctaaaaaata aaatctggaa tcctgctttt ttgctctact agtacctctg tcacactagt   1860
cttatcaaaa accagttctt aagatcaatg ttaagtttat tagttaatgt aaatttctca   1920
tcctcgaaaa gggtgaacat aaatgccttt aaggagtata tctaaaaata aacattagga   1980
tatctaagtt tgatgtaatt gtttcaggaa ggaaaaaaga aaagcattct ggaatgagcc   2040
tacttcaagt aatcttagtt tctaaaacta acagttaata ttttcaattc cagtatatca   2100
ctttaagtag aaggggatgt ccaagtaatt ttggtttttct aactgttgaa tcataagctt   2160
gacctgcccc cagaggcttt ttggatgttt ttatctgtgt tttgccatct ctttacactc   2220
ctcgacattc agtttacctt aatcttcaca tttttacacc ttgggaagtg gcaagcatcg   2280
ctgggtttaa gataaaggag tcacaaaaac taatcaaaat aaaatttgca ttatgacaac   2340
ttttaa                                                             2346

SEQ ID NO: 199        moltype = AA  length = 419
FEATURE               Location/Qualifiers
source                1..419
                      mol_type = protein
                      organism = Mus musculus
SEQUENCE: 199
MSSPDAGYAS DDQSQPRSAQ PAVMAGLGPC PWAESLSPLG DVKVKGEVVA SSGAPAGTSG     60
RAKAESRIRR PMNAFMVWAK DERKRLAQQN PDLHNAELSK MLGKSWKALT LAEKRPFVEE    120
AERLRVQHMQ DHPNYKYRPR RRKQVKRMKR VEGGFLHALV EPQAGALGPE GGRVAMDGLG    180
LPFPEPGYPA GPPLMSPHMG PHYRDCQGLG APALDGYPLP TPDTSPLDGV EQDPAFFAAP    240
LPGDCPAAGT YTYAPVSDYA VSVEPPAGPM RVGPDPSGPA MPGILAPPSA LHLYYGAMGS    300
PAASAGRGFH AQPQQPLQPQ APPPPPQQQH PAHGPGQPSP PPEALPCRDG TESNQPTELL    360
GEVDRTEFEQ YLPFVYKPEM GLPYQGHDCG VNLSDSHGAI SSVVSDASSA VYYCNYPDI    419
```